(12) United States Patent
Doucette-Stamm et al.

(10) Patent No.: US 6,617,156 B1
(45) Date of Patent: Sep. 9, 2003

(54) **NUCLEIC ACID AND AMINO ACID SEQUENCES RELATING TO *ENTEROCOCCUS FAECALIS* FOR DIAGNOSTICS AND THERAPEUTICS**

(76) Inventors: Lynn A. Doucette-Stamm, 14 Flanagan Dr., Framingham, MA (US) 01701; David Bush, 205 Holland St., Somerville, MA (US) 02144

( * ) Notice: Subject to any disclaimer, the term of this patent is extended or adjusted under 35 U.S.C. 154(b) by 0 days.

(21) Appl. No.: 09/134,000

(22) Filed: Aug. 13, 1998

Related U.S. Application Data
(60) Provisional application No. 60/055,778, filed on Aug. 15, 1997.

(51) Int. Cl.[7] ................. C12N 15/31; C12N 15/63; C12N 1/13; C12Q 1/68
(52) U.S. Cl. ............. 435/320.1; 536/23.7; 536/24.32; 435/252.3; 435/69.1; 435/6
(58) Field of Search .............. 536/23.7, 24.32; 435/320.1, 252.3, 6, 69.1, 69.3

(56) References Cited

U.S. PATENT DOCUMENTS

| | | | | |
|---|---|---|---|---|
| 4,835,256 A | * | 5/1989 | Taniguchi et al. | 530/351 |
| 5,417,971 A | * | 5/1995 | Potter et al. | 424/256.1 |
| 5,459,034 A | * | 10/1995 | Tabaqchali et al. | 435/6 |
| 5,624,816 A | * | 4/1997 | Carraway et al. | 435/69.1 |

FOREIGN PATENT DOCUMENTS

| | | | |
|---|---|---|---|
| WO | 9850555 | 11/1998 | |
| WO | 98/80554 | * 11/1998 | C12N/15/31 |

OTHER PUBLICATIONS

Frere et al. J. Basic Microbiol. 36(5):305–310, 1996.*
Tanaka et al. Molecular and Cellular Biology 9(2):757–768, 1989.*
Bugert et al. Molecular Microbiology 15(5):917–933, 1995.*
Mason et al. Journal of Bacteriology 175(9):2632–2639, 1993.*
Wagner et al. Journal of Bacteriology 177(21):6144–6152, 1995.*
Chen et al. Yeast 7:287–299, 1991.*

* cited by examiner

*Primary Examiner*—Mary E. Mosher
(74) *Attorney, Agent, or Firm*—Genome Therapeutics Corporation

(57) ABSTRACT

The invention provides isolated polypeptide and nucleic acid sequences derived from *Enterococcus faecalis* that are useful in diagnosis and therapy of pathological conditions; antibodies against the polypeptides; and methods for the production of the polypeptides. The invention also provides methods for the detection, prevention and treatment of pathological conditions resulting from bacterial infection.

19 Claims, No Drawings

NUCLEIC ACID AND AMINO ACID SEQUENCES RELATING TO *ENTEROCOCCUS FAECALIS* FOR DIAGNOSTICS AND THERAPEUTICS

This application claims priority of U.S. Provisional application No. 60/055,778, filed Aug. 15, 1997, all of which is hereby incorporated herein by reference in its entirety.

FIELD OF THE INVENTION

The invention relates to isolated nucleic acids and polypeptides derived from *Enterococcus faecalis* that are useful as molecular targets for diagnosis, prophylaxis and treatment of pathological conditions, as well as materials and methods for the diagnosis, prevention, and amelioration of pathological conditions resulting from bacterial infection.

BRIEF DESCRIPTION OF THE SEQUENCE LISTING

Incorporated herein by reference in its entirety is a Sequence Listing, comprising SEQ ID NO: 1 to SEQ ID NO: 6812. The Sequence Listing is contained on a CD-ROM, three copies of which are filed, the Sequence Listing being in a computer-readable ASCII file named "GTC005.pto", created on Sep. 6, 2001 and of 10.3 megabytes in size, in Windows NT 4.0, ASCII text format.

BACKGROUND OF THE INVENTION

*Enterococcus faecalis* (*E. faecalis*) is a gram-positive, facultative, anaerobic cocci, that is widely distributed in nature, animals, and humans. Enterococci are part of the normal gastrointestinal and genital tract flora, and among the 17 known species, *E. faecalis* is dominant in humans, accounting for 80–90% of clinically isolated specimens, and it exhibits increasing levels of multidrug resistance (Kaufhold, A and Klein, R (1995) *Zentralblatt fuer Bakteriologie* 282 (4): 507–518; and Svec, P, Sedlacek, I, and Pakrova, E (1996) *Epidemiologie Mikrobiologie Imunologie* 45: 153–157). *E. faecalis* infections include urinary tract infections (UTI), bacteremia, endocarditis, and wound and abdominal-pelvic infections, accounting for 16% of all UTIs, and 8% of all becteremias (Ardino, R C, and Murray, B E (1990) Principles and Practice of Infectious Diseases, 3rd ed., Mandell et al, eds., Update Vol. 2, No. 4).

Vancomycin resistant enterococci (VRE) have emerged in the midst of high level resistance to penicillin and aminoglycosides (Centers for Disease Control and Prevention (1993) *MMWR* 42:597–599; and Handwerger, S, et al (1993) *Clin Infect Dis* 16:750–755). Resistance can be intrinsic (chromosomally mediated), or acquired (plasmid or transposon mediated), with higher levels of resistance in acquired. VRE are characterized by resistance to virtually all available antibiotics, including vancomycin, considered the "last resort" antibiotic effective against gram-positive bacteria. Treatment options for physicians are limited, with the latest strategy being combinations of antimicrobials or the use of new unproven compounds (Moellering, R C Jr. (1991) *J Antimicrob Chemother* 28: 1–12; and Hayden, M K et al (1994) *Antimicrob Agents Chemother* 38 1225–1229; and Mobarakai, N et al (1994) *J Antimicrob Chemother* 33: 319–321). From 1989 through 1993, the percentage of nosocomial (hospital incurred) infections by VRE increased from 0.3% to 7.9% (Centers for Disease Control and Prevention (1993) *MMWR* 42:597–599). There was a 34-fold increase in ICU patients, and a increasing trend among non-ICU patients (Centers for Disease Control and Prevention (1993) *MMWR* 42:597–599). These numbers may not be an accurate reflection of the actual total, as clinical identification of vancomycin resistance is not consistently detected, especially in the VanB phenotype which confers moderate resistance (Tenover, F C (1993) *J Clin Microbiol* 31:1695–1699; and Sahm, D F (1990) *Antimicrob Agents Chemother* 34: 1846–1848; and Zabransky, R J (1994) *Microbiol Infect Dis* 20:113–116). Patients can be colonized and carry VRE without symptoms, with chief areas of colonization being anus, axilla, stool, perineal, umbilicus, wounds, foley catheters, and colostomy sites.

Epidemiology of *E. faecalis* is not completely understood, but it is thought that most infections and colonizations are a result of the patient's endogenous flora (Murray, B E (1990) *Clin Microbiol Rev* 3:46–65). Recent evidence suggests that *E. faecalis* can be spread by direct contact with other infected patients, indirect transmission from hospital personnel (Boyce, J M et al (1994) *J Clin Microbiol* 32:1148–53; and Rhineheart, E et al (1990) *N Engl J Med* 323:1814–1818), or from contaminated hospital surfaces and equipment (Karanfil, L V et al (1992) *Infect Control Hosp Epidemiol* 13:195–200; and Boyce, J M et al (1994) *J Clin Microbiol* 32:1148–53; and Livornese, L L Jr. (1992) *Ann Intern Med* 117:112–116). Increased risk for the critically ill, those with underlying disease of immunosuppression (i.e. ICU, oncology, and transplant patients), cardiothoracic/intraabdominal surgical patients and those with urinary or central venous catheters has been demonstrated. In addition, risk for *E. faecalis* infection increases for patients with long hospital stays or previous multiantimicrobial or vancomycin treatments (Boyce, J M et al (1994) *J Clin Microbiol* 32:1148–1153; Boyle, J F et al (1993) *J Clin Microbiol* 31:1280–1285; Karanfil, L V et al (1992) *Infect Control Hosp Epidemiol* 13:195–200; Handwerger, S et al (1993) *Clin Infect Dis* 16:750–755; Montecalvo, M A et al (1994) *Antimicrob Agents Chemother* 38:1363–1367).

Additional concern stems from the ability of the *E. faecalis* plasmid borne VanA gene, which confers high level vancomycin resistance, to transfer in vitro to several gram positive microorganisms such as *Staphylococcus aureus* (Leclercq, R et al (1989) *Antimicrob Agents Chemother* 33:10–15; and Noble, W C, et al (1992) *FEMS Microbiology Letters* 72:195–198). To date, no clinical isolates of *S. aureus* or *S. epidermidis* have shown vancomycin resistance conferred by plasmid transfer, but clinically isolated strains of *S. haemolyticus* have (Degner, J E, et al (1994) *J Clin Microbiol* 32:2260–2265; and Veach, L A, et al (1990) *J Clin Microbiol* 28:2064–2068).

These concerns point to the need for diagnostic tools and therapeutics aimed at proper identification of strain and eradication of virulence. The design of vaccines that will limit the spread of infection and halt transfer of resistance factors is very desirable.

SUMMARY OF THE INVENTION

The present invention fulfills the need for diagnostic tools and therapeutics by providing bacterial-specific compositions and methods for detecting, treating, and preventing bacterial infection, in particular *E. faecalis* infection.

The present invention encompasses isolated nucleic acids and polypeptides derived from *E. faecalis* that are useful as reagents for diagnosis of bacterial disease, components of effective antibacterial vaccines, and/or as targets for antibacterial drugs, including anti-*E. faecalis* drugs. They can also be used to detect the presence of *E. faecalis* and other Enterococcus species in a sample; and in screening compounds for the ability to interfere with the *E. faecalis* life cycle or to inhibit *E. faecalis* infection. They also has use as biocontrol agents for plants.

The present invention also provides a genome-wide comparison by FASTA of the predicted amino acid sequences of several *E. faecalis* open reading frames (ORFs) with the predicted amino acid sequence of several *E. faecium* ORFs (Table 3). Together, *E. faecalis* and *E. faecium* account for >95% of all VRE infections. Genomic comparison of *E. faecalis* with *E. faecium* at the sequence, open reading frame (ORF), and gene level provides valuable information on shared targets, which can be exploited in designing diagnostics and therapeutics for VRE. Identifying common essential genes through sequencing and analysis of both genomes provides a much quicker route to these targets, and speeds the progress of probe design for identification of VRE infection, and vaccine compositions for protection from and treatment of these infections.

More specifically, this invention features compositions of nucleic acids corresponding to entire coding sequences of *E. faecalis* proteins, including surface or secreted proteins or parts thereof, nucleic acids capable of binding mRNA from *E. faecalis* proteins to block protein translation, and methods for producing *E. faecalis* proteins or parts thereof using peptide synthesis and recombinant DNA techniques. This invention also features antibodies and nucleic acids useful as probes to detect *E. faecalis* infection. In addition, vaccine compositions and methods for the protection or treatment of infection by *E. faecalis* are within the scope of this invention.

The nucleotide sequences provided in SEQ ID NO: 1–SEQ ID NO: 3405, a fragment thereof, or a nucleotide sequence at least 99.5% identical to a sequence contained within SEQ ID NO: 1–SEQ ID NO: 3405 may be "provided" in a variety of medias to facilitate use thereof. As used herein, "provided" refers to a manufacture, other than an isolated nucleic acid molecule, which contains a nucleotide sequence of the present invention, i.e., the nucleotide sequence provided in SEQ ID NO: 1–SEQ ID NO: 3405, a fragment thereof, or a nucleotide sequence at least 99.5% identical to a sequence contained within SEQ ID NO: 1–SEQ ID NO: 3405. Uses for and methods for providing nucleotide sequences in a variety of media is well known in the art (see e.g., EPO Publication No. EP 0 756 006).

In one application of this embodiment, a nucleotide sequence of the present invention can be recorded on computer readable media. As used herein, "computer readable media" refers to any media which can be read and accessed directly by a computer. Such media include, but are not limited to: magnetic storage media, such as floppy discs, hard disc storage media, and magnetic tape; optical storage media such as CD-ROM; electrical storage media such as RAM and ROM; and hybrids of these categories such as magnetic/optical storage media. A person skilled in the art can readily appreciate how any of the presently known computer readable media can be used to create a manufacture comprising computer readable media having recorded thereon a nucleotide sequence of the present invention.

As used herein, "recorded" refers to a process for storing information on computer readable media. A person skilled in the art can readily adopt any of the presently known methods for recording information on computer readable media to generate manufactures comprising the nucleotide sequence information of the present invention.

A variety of data storage structures are available to a person skilled in the art for creating a computer readable media having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable media. The sequence information can be represented in a word processing text file, formatted in commercially-available software such as WordPerfect and Microsoft Word, or represented in the form of an ASCII file, stored in a database application, such as DB2, Sybase, Oracle, or the like. A person skilled in the art can readily adapt any number of data processor structuring formats (e.g. text file or database) in order to obtain computer readable media having recorded thereon the nucleotide sequence information of the present invention.

By providing the nucleotide sequences of SEQ ID NO: 1–SEQ ID NO: 3405, a fragment thereof, or a nucleotide sequence at least 99.5% identical to SEQ ID NO: 1–SEQ ID NO: 3405 in computer readable form, a person skilled in the art can routinely access the coding sequence information for a variety of purposes. Computer software is publicly available which allows a person skilled in the art to access sequence information provided in a computer readable media. Examples of such computer software include programs of the "Staden Package", "DNA Star", "MacVector", GCG "Wisconsin Package" (Genetics Computer Group, Madison, Wis.) and "NCBI Toolbox" (National Center For Biotechnology Information).

Computer algorithms enable the identification of open reading frames (ORFs) within SEQ ID NO: 1–SEQ ID NO: 3405 which contain homology to ORFs or proteins from other organisms. Examples of such similarity-search algorithms include the BLAST [Altschul et al., J. Mol. Biol. 215:403–410 (1990)] and Smith-Waterman [Smith and Waterman (1981) Advances in Applied Mathematics, 2:482–489] search algorithms. These algorithms are utilized on computer systems as exemplified below. The ORFs so identified represent protein encoding fragments within the *E. faecalis* genome and are useful in producing commercially important proteins such as enzymes used in fermentation reactions and in the production of commercially useful metabolites.

The present invention further provides systems, particularly computer-based systems, which contain the sequence information described herein. Such systems are designed to identify commercially important fragments of the *E. faecalis* genome. As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A person skilled in the art can readily appreciate that any one of the currently available computer-based systems is suitable for use in the present invention. The computer-based systems of the present invention comprise a data storage means having stored therein a nucleotide sequence of the present invention and the necessary hardware means and software means for supporting and implementing a search means. As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of the *E. faecalis* genome which are similar to, or "match", a particular target sequence or target motif. A variety of known algorithms are known in the art and have been disclosed publicly, and a variety of commercially available software for conducting homology-based similarity searches are available and can be used in the computer-based systems of the present invention. Examples of such software includes, but is not limited to, FASTA (GCG Wisconsin Package), Bic_SW (Compugen Bioccelerator), BLASTN2, BLASTP2, BLASTX2 (NCBI) and Motifs (GCG). A person skilled in the art can readily recognize that any one of the available algorithms or implementing software packages for conducting homology searches can be adapted for use in the present computer-based systems.

As used herein, a "target sequence" can be any DNA or amino acid sequence of six or more nucleotides or two or more amino acids. A person skilled in the art can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that many genes are longer than 500 amino acids, or 1.5 kb in length, and that commercially important fragments of the *E. faecalis* genome, such as sequence fragments involved in gene expression and protein processing, will often be shorter than 30 nucleotides.

As used herein, "a target structural motif," or "target motif," refers to any rationally selected sequence or combination of sequences in which the sequence(s) are chosen based on a specific functional domain or three-dimensional configuration which is formed upon the folding of the target polypeptide. There are a variety of target motifs known in the art. Protein target motifs include, but are not limited to, enzymatic active sites, membrane spanning regions, and signal sequences. Nucleic acid target motifs include, but are not limited to, promoter sequences, hairpin structures and inducible expression elements (protein binding sequences).

A variety of structural formats for the input and output means can be used to input and output the information in the computer-based systems of the present invention. A preferred format for an output means ranks fragments of the *E. faecalis* genome possessing varying degrees of homology to the target sequence or target motif. Such presentation provides a person skilled in the art with a ranking of sequences which contain various amounts of the target sequence or target motif and identifies the degree of homology contained in the identified fragment.

A variety of comparing means can be used to compare a target sequence or target motif with the data storage means to identify sequence fragments of the *E. faecalis* genome. In the present examples, implementing software which implement the BLASTP2 and bic_SW algorithms (Altschul et al., J Mol. Biol. 215:403–410 (1990); Compugen Biocellerator) was used to identify open reading frames within the *E. faecalis* genome. A person skilled in the art can readily recognize that any one of the publicly available homology search programs can be used as the search means for the computer-based systems of the present invention.

The invention features *E. faecalis* polypeptides, preferably a substantially pure preparation of an *E. faecalis* polypeptide, or a recombinant *E. faecalis* polypeptide. In preferred embodiments: the polypeptide has biological activity; the polypeptide has an amino acid sequence at least 60%, 70%, 80%, 90%, 95%, 98%, or 99% identical to an amino acid sequence of the invention contained in the Sequence Listing, preferably it has about 65% sequence identity with an amino acid sequence of the invention contained in the Sequence Listing, and most preferably it has about 92% to about 99% sequence identity with an amino acid sequence of the invention contained in the Sequence Listing; the polypeptide has an amino acid sequence essentially the same as an amino acid sequence of the invention contained in the Sequence Listing; the polypeptide is at least 5, 10, 20, 50, 100, or 150 amino acid residues in length; the polypeptide includes at least 5, preferably at least 10, more preferably at least 20, more preferably at least 50, 100, or 150 contiguous amino acid residues of the invention contained in the Sequence Listing. In yet another preferred embodiment, the amino acid sequence which differs in sequence identity by about 7% to about 8% from the *E. faecalis* amino acid sequences of the invention contained in the Sequence Listing is also encompassed by the invention.

In preferred embodiments: the *E. faecalis* polypeptide is encoded by a nucleic acid of the invention contained in the Sequence Listing, or by a nucleic acid having at least 60%, 70%, 80%, 90%, 95%, 98%, or 99% homology with a nucleic acid of the invention contained in the Sequence Listing.

In a preferred embodiment, the subject *E. faecalis* polypeptide differs in amino acid sequence at 1, 2, 3, 5, 10 or more residues from a sequence of the invention contained in the Sequence Listing. The differences, however, are such that the *E. faecalis* polypeptide exhibits an *E. faecalis* biological activity, e.g., the *E. faecalis* polypeptide retains a biological activity of a naturally occurring *E. faecalis* enzyme.

In preferred embodiments, the polypeptide includes all or a fragment of an amino acid sequence of the invention contained in the Sequence Listing; fused, in reading frame, to additional amino acid residues, preferably to residues encoded by genomic DNA 5' or 3' to the genomic DNA which encodes a sequence of the invention contained in the Sequence Listing.

In yet other preferred embodiments, the *E. faecalis* polypeptide is a recombinant fusion protein having a first *E. faecalis* polypeptide portion and a second polypeptide portion, e.g., a second polypeptide portion having an amino acid sequence unrelated to *E. faecalis*. The second polypeptide portion can be, e.g., any of glutathione-S-transferase, a DNA binding domain, or a polymerase activating domain. In preferred embodiment the fusion protein can be used in a two-hybrid assay.

Polypeptides of the invention include those which arise as a result of alternative transcription events, alternative RNA splicing events, and alternative translational and postrans-lational events.

In a preferred embodiment, the encoded *E. faecalis* polypeptide differs (e.g., by amino acid substitution, addition or deletion of at least one amino acid residue) in amino acid sequence at 1, 2, 3, 5, 10 or more residues, from a sequence of the invention contained in the Sequence Listing. The differences, however, are such that: the *E. faecalis* encoded polypeptide exhibits a *E. faecalis* biological activity, e.g., the encoded *E. faecalis* enzyme retains a biological activity of a naturally occurring *E. faecalis*.

In preferred embodiments, the encoded polypeptide includes all or a fragment of an amino acid sequence of the invention contained in the Sequence Listing; fused, in reading frame, to additional amino acid residues, preferably to residues encoded by genomic DNA 5' or 3' to the genomic DNA which encodes a sequence of the invention contained in the Sequence Listing.

The *E. faecalis* strain, from which the nucleotide sequences have been sequenced, was deposited on Jun. 26, 1997 in the American Type Culture Collection (ATCC # 55986) as strain 14336.

Included in the invention are: allelic variations; natural mutants; induced mutants; proteins encoded by DNA that hybridize under high or low stringency conditions to a nucleic acid which encodes a polypeptide of the invention contained in the Sequence Listing (for definitions of high and low stringency see Current Protocols in Molecular Biology, John Wiley & Sons, New York, 1989, 6.3.1–6.3.6, hereby incorporated by reference); and, polypeptides specifically bound by antisera to *E. faecalis* polypeptides, especially by antisera to an active site or binding domain of *E. faecalis* polypeptide. The invention also includes fragments, preferably biologically active fragments. These and other polypeptides are also referred to herein as *E. faecalis* polypeptide analogs or variants.

The invention further provides nucleic acids, e.g., RNA or DNA, encoding a polypeptide of the invention. This includes double stranded nucleic acids as well as coding and antisense single strands.

In preferred embodiments, the subject *E. faecalis* nucleic acid will include a transcriptional regulatory sequence, e.g. at least one of a transcriptional promoter or transcriptional enhancer sequence, operably linked to the *E. faecalis* gene sequence, e.g., to render the *E. faecalis* gene sequence suitable for expression in a recombinant host cell.

In yet a further preferred embodiment, the nucleic acid which encodes an *E. faecalis* polypeptide of the invention, hybridizes under stringent conditions to a nucleic acid probe corresponding to at least 8 consecutive nucleotides of the invention contained in the Sequence Listing; more preferably to at least 12 consecutive nucleotides of the invention contained in the Sequence Listing; more preferably to at least 20 consecutive nucleotides of the invention contained in the Sequence Listing; more preferably to at least 40 consecutive nucleotides of the invention contained in the Sequence Listing.

In another aspect, the invention provides a substantially pure nucleic acid having a nucleotide sequence which encodes an *E. faecalis* polypeptide. In preferred embodiments: the encoded polypeptide has biological activity; the encoded polypeptide has an amino acid sequence at least 60%, 70%, 80%, 90%, 95%, 98%, or 99% homologous to an amino acid sequence of the invention contained in the Sequence Listing; the encoded polypeptide has an amino acid sequence essentially the same as an amino acid sequence of the invention contained in the Sequence Listing; the encoded polypeptide is at least 5, 10, 20, 50, 100, or 150 amino acids in length; the encoded polypeptide comprises at least 5, preferably at least 10, more preferably at least 20, more preferably at least 50, 100, or 150 contiguous amino acids of the invention contained in the Sequence Listing.

In another aspect, the invention encompasses: a vector including a nucleic acid which encodes an *E. faecalis* polypeptide or an *E. faecalis* polypeptide variant as described herein; a host cell transfected with the vector; and a method of producing a recombinant *E. faecalis* polypeptide or *E. faecalis* polypeptide variant; including culturing the cell, e.g., in a cell culture medium, and isolating the *E. faecalis* or *E. faecalis* polypeptide variant, e.g., from the cell or from the cell culture medium.

One embodiment of the invention is directed to substantially isolated nucleic acids. Nucleic acids of the invention include sequences comprising at least about 8 nucleotides in length, more preferably at least about 12 nucleotides in length, even more preferably at least about 15–20 nucleotides in length, that correspond to a subsequence of any one of SEQ ID NO: 1–SEQ ID NO: 3405 or complements thereof. Alternatively, the nucleic acids comprise sequences contained within any ORF (open reading frame), including a complete protein-coding sequence, of which any of SEQ ID NO: 1–SEQ ID NO: 3405 forms a part. The invention encompasses sequence-conservative variants and function-conservative variants of these sequences. The nucleic acids may be DNA, RNA, DNA/RNA duplexes, protein-nucleic acid (PNA), or derivatives thereof.

In another aspect, the invention features, a purified recombinant nucleic acid having at least 50%, 60%, 70%, 80%, 90%, 95%, 98%, or 99% homology with a sequence of the invention contained in the Sequence Listing. The invention also encompasses recombinant DNA (including DNA cloning and expression vectors) comprising these *E. faecalis*-derived sequences; host cells comprising such DNA, including fungal, bacterial, yeast, plant, insect, and mammalian host cells; and methods for producing expression products comprising RNA and polypeptides encoded by the *E. faecalis* sequences. These methods are carried out by incubating a host cell comprising a *E. faecalis*-derived nucleic acid sequence under conditions in which the sequence is expressed. The host cell may be native or recombinant. The polypeptides can be obtained by (a) harvesting the incubated cells to produce a cell fraction and a medium fraction; and (b) recovering the *E. faecalis* polypeptide from the cell fraction, the medium fraction, or both. The polypeptides can also be made by in vitro translation.

In another aspect, the invention features nucleic acids capable of binding mRNA of *E. faecalis*. Such nucleic acid is capable of acting as antisense nucleic acid to control the translation of mRNA of *E. faecalis*. A further aspect features a nucleic acid which is capable of binding specifically to an *E. faecalis* nucleic acid. These nucleic acids are also referred to herein as complements and have utility as probes and as capture reagents.

In another aspect, the invention features an expression system comprising an open reading frame corresponding to *E. faecalis* nucleic acid. The nucleic acid further comprises a control sequence compatible with an intended host. The expression system is useful for making polypeptides corresponding to *E. faecalis* nucleic acid.

In another aspect, the invention encompasses: a vector including a nucleic acid which encodes a *E. faecalis* polypeptide or a *E. faecalis* polypeptide variant as described herein; a host cell transfected with the vector; and a method of producing a recombinant *E. faecalis* polypeptide or *E. faecalis* polypeptide variant; including culturing the cell, e.g., in a cell culture medium, and isolating the *E. faecalis* or *E. faecalis* polypeptide variant, e.g., from the cell or from the cell culture medium.

In yet another embodiment, the invention encompasses reagents for detecting bacterial infection, including *E. faecalis* infection, which comprise at least one *E. faecalis*-derived nucleic acid defined by any one of SEQ ID NO: 1–SEQ ID NO: 3405, or sequence-conservative or function-conservative variants thereof. Alternatively, the diagnostic reagents comprise polypeptide sequences that are contained within any open reading frames (ORFs), including complete protein-coding sequences, contained within any of SEQ ID NO: 1–SEQ ID NO: 3405, or polypeptide sequences contained within any of SEQ ID NO: 3406–SEQ ID NO: 6810, or polypeptides of which any of the above sequences forms a part, or antibodies directed against any of the above peptide sequences or function-conservative variants and/or fragments thereof.

The invention further provides antibodies, preferably monoclonal antibodies, which specifically bind to the polypeptides of the invention. Methods are also provided for producing antibodies in a host animal. The methods of the invention comprise immunizing an animal with at least one E. faecalis-derived immunogenic component, wherein the immunogenic component comprises one or more of the polypeptides encoded by any one of SEQ ID NO: 1–SEQ ID NO: 3405 or sequence-conservative or function-conservative variants thereof; or polypeptides that are contained within any ORFs, including complete protein-coding sequences, of which any of SEQ ID NO: 1–SEQ ID NO: 3405 forms a part; or polypeptide sequences contained within any of SEQ ID NO: 3406–SEQ ID NO: 6810; or polypeptides of which any of SEQ ID NO: 3406–SEQ ID NO: 6810 forms a part. Host animals include any warm blooded animal, including without limitation mammals and birds. Such antibodies have utility as reagents for immunoassays to evaluate the abundance and distribution of E. faecalis-specific antigens.

In yet another aspect, the invention provides diagnostic methods for detecting E. faecalis antigenic components or anti-E. faecalis antibodies in a sample. E. faecalis antigenic components are detected by a process comprising: (i) contacting a sample suspected to contain a bacterial antigenic component with a bacterial-specific antibody, under conditions in which a stable antigen-antibody complex can form between the antibody and bacterial antigenic components in the sample; and (ii) detecting any antigen-antibody complex formed in step (i), wherein detection of an antigen-antibody complex indicates the presence of at least one bacterial antigenic component in the sample. In different embodiments of this method, the antibodies used are directed against a sequence encoded by any of SEQ ID NO: 1–SEQ ID NO: 3405 or sequence-conservative or function-conservative variants thereof, or against a polypeptide sequence contained in any of SEQ ID NO: 3406–SEQ ID NO: 6810 or function-conservative variants thereof.

In yet another aspect, the invention provides a method for detecting antibacterial-specific antibodies in a sample, which comprises: (i) contacting a sample suspected to contain antibacterial-specific antibodies with a E. faecalis antigenic component, under conditions in which a stable antigen-antibody complex can form between the E. faecalis antigenic component and antibacterial antibodies in the sample; and (ii) detecting any antigen-antibody complex formed in step (i), wherein detection of an antigen-antibody complex indicates the presence of antibacterial antibodies in the sample. In different embodiments of this method, the antigenic component is encoded by a sequence contained in any of SEQ ID NO: 1–SEQ ID NO: 3405 or sequence-conservative and function-conservative variants thereof, or is a polypeptide sequence contained in any of SEQ ID NO: 3406–SEQ ID NO: 6810 or function-conservative variants thereof.

In another aspect, the invention features a method of generating vaccines for immunizing an individual against E. faecalis. The method includes: immunizing a subject with an E. faecalis polypeptide, e.g., a surface or secreted polypeptide, or a combination of such peptides or active portion(s) thereof, and a pharmaceutically acceptable carrier. Such vaccines have therapeutic and prophylactic utilities.

In another aspect, the invention features a method of evaluating a compound, e.g. a polypeptide, e.g., a fragment of a host cell polypeptide, for the ability to bind an E. faecalis polypeptide. The method includes: contacting the Enterococcus compound with an E. faecalis polypeptide and determining if the compound binds or otherwise interacts with an E. faecalis polypeptide. Compounds which bind E. faecalis are candidates as activators or inhibitors of the bacterial life cycle. These assays can be performed in vitro or in vivo.

In another aspect, the invention features a method of evaluating a compound, e.g. a polypeptide, e.g., a fragment of a host cell polypeptide, for the ability to bind an E. faecalis nucleic acid, e.g., DNA or RNA. The method includes: contacting the Enterococcus compound with an E. faecalis nucleic acid and determining if the compound binds or otherwise interacts with an E. faecalis polypeptide. Compounds which bind E. faecalis are candidates as activators or inhibitors of the bacterial life cycle. These assays can be performed in vitro or in vivo.

A particularly preferred embodiment of the invention is directed to a method of screening test compounds for anti-bacterial activity, which method comprises: selecting as a target a bacterial specific sequence, which sequence is essential to the viability of a bacterial species; contacting a test compound with said target sequence; and selecting those test compounds which bind to said target sequence as potential anti-bacterial candidates. In one embodiment, the target sequence selected is specific to a single species, or even a single strain, i.e., the E. faecalis strain 14336. In a second embodiment, the target sequence is common to at least two species of bacteria. In a third embodiment, the target sequence is common to a family of bacteria. The target sequence may be a nucleic acid sequence or a polypeptide sequence. Methods employing sequences common to more than one species of microorganism may be used to screen candidates for broad spectrum anti-bacterial activity.

The invention also provides methods for preventing or treating disease caused by certain bacteria, including E. faecalis, which are carried out by administering to an animal in need of such treatment, in particular a warm-blooded vertebrate, including but not limited to birds and mammals, a compound that specifically inhibits or interferes with the function of a bacterial polypeptide or nucleic acid. In a particularly preferred embodiment, the mammal to be treated is human.

DETAILED DESCRIPTION OF THE INVENTION

The sequences of the present invention include the specific nucleic acid and amino acid sequences set forth in the Sequence Listing that forms a part of the present specification, and which are designated SEQ ID NO: 1–SEQ ID NO: 6810. Use of the terms "SEQ ID NO: 1–SEQ ID NO: 3405", "SEQ ID NO: 3406–SEQ ID NO: 6810", "the sequences depicted in Table 2", etc., is intended, for convenience, to refer to each individual SEQ ID NO individually, and is not intended to refer to the genus of these sequences. In other words, it is a shorthand for listing all of these sequences individually. The invention encompasses each sequence individually, as well as any combination thereof.

Definitions

"Nucleic acid" or "polynucleotide" as used herein refers to purine- and pyrimidine-containing polymers of any length, either polyribonucleotides or polydeoxyribonucleotides or mixed polyribo-polydeoxyribo nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases.

A nucleic acid or polypeptide sequence that is "derived from" a designated sequence refers to a sequence that corresponds to a region of the designated sequence. For nucleic acid sequences, this encompasses sequences that are homologous or complementary to the sequence, as well as "sequence-conservative variants" and "function-conservative variants." For polypeptide sequences, this encompasses "function-conservative variants." Sequence-conservative variants are those in which a change of one or more nucleotides in a given codon position results in no alteration in the amino acid encoded at that position. Function-conservative variants are those in which a given amino acid residue in a polypeptide has been changed without altering the overall conformation and function of the native polypeptide, including, but not limited to, replacement of an amino acid with one having similar physico-chemical properties (such as, for example, acidic, basic, hydrophobic, and the like). "Function-conservative" variants also include any polypeptides that have the ability to elicit antibodies specific to a designated polypeptide.

An "*E. faecalis*-derived" nucleic acid or polypeptide sequence may or may not be present in other bacterial species, and may or may not be present in all *E. faecalis* strains. This term is intended to refer to the source from which the sequence was originally isolated. Thus, a *E. faecalis*-derived polypeptide, as used herein, may be used, e.g., as a target to screen for a broad spectrum antibacterial agent, to search for homologous proteins in other species of bacteria or in eukaryotic organisms such as fungi and humans, etc.

A purified or isolated polypeptide or a substantially pure preparation of a polypeptide are used interchangeably herein and, as used herein, mean a polypeptide that has been separated from other proteins, lipids, and nucleic acids with which it naturally occurs. Preferably, the polypeptide is also separated from substances, e.g., antibodies or gel matrix, e.g., polyacrylamide, which are used to purify it. Preferably, the polypeptide constitutes at least 10, 20, 50 70, 80 or 95% dry weight of the purified preparation. Preferably, the preparation contains: sufficient polypeptide to allow protein sequencing; at least 1, 10, or 100 mg of the polypeptide.

A purified preparation of cells refers to, in the case of plant or animal cells, an in vitro preparation of cells and not an entire intact plant or animal. In the case of cultured cells or microbial cells, it consists of a preparation of at least 10% and more preferably 50% of the subject cells.

A purified or isolated or a substantially pure nucleic acid, e.g., a substantially pure DNA, (are terms used interchangeably herein) is a nucleic acid which is one or both of the following: not immediately contiguous with both of the coding sequences with which it is immediately contiguous (i.e., one at the 5' end and one at the 3' end) in the naturally-occurring genome of the organism from which the nucleic acid is derived; or which is substantially free of a nucleic acid with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant DNA which is part of a hybrid gene encoding additional *E. faecalis* DNA sequence.

A "contig" as used herein is a nucleic acid representing a continuous stretch of genomic sequence of an organism.

An "open reading frame", also referred to herein as ORF, is a region of nucleic acid which encodes a polypeptide. This region may represent a portion of a coding sequence or a total sequence and can be determined from a stop to stop codon or from a start to stop codon.

As used herein, a "coding sequence" is a nucleic acid which is transcribed into messenger RNA and/or translated into a polypeptide when placed under the control of appropriate regulatory sequences. The boundaries of the coding sequence are determined by a translation start codon at the five prime terminus and a translation stop code at the three prime terminus. A coding sequence can include but is not limited to messenger RNA, synthetic DNA, and recombinant nucleic acid sequences.

A "complement" of a nucleic acid as used herein refers to an anti-parallel or antisense sequence that participates in Watson-Crick base-pairing with the original sequence.

A "gene product" is a protein or structural RNA which is specifically encoded by a gene.

As used herein, the term "probe" refers to a nucleic acid, peptide or other chemical entity which specifically binds to a molecule of interest. Probes are often associated with or capable of associating with a label. A label is a chemical moiety capable of detection. Typical labels comprise dyes, radioisotopes, luminescent and chemiluminescent moieties, fluorophores, enzymes, precipitating agents, amplification sequences, and the like. Similarly, a nucleic acid, peptide or other chemical entity which specifically binds to a molecule of interest and immobilizes such molecule is referred herein as a "capture ligand". Capture ligands are typically associated with or capable of associating with a support such as nitro-cellulose, glass, nylon membranes, beads, particles and the like. The specificity of hybridization is dependent on conditions such as the base pair composition of the nucleotides, and the temperature and salt concentration of the reaction. These conditions are readily discernable to one of ordinary skill in the art using routine experimentation.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

Nucleic acids are hybridizable to each other when at least one strand of a nucleic acid can anneal to the other nucleic acid under defined stringency conditions. Stringency of hybridization is determined by: (a) the temperature at which hybridization and/or washing is performed; and (b) the ionic strength and polarity of the hybridization and washing solutions. Hybridization requires that the two nucleic acids contain complementary sequences; depending on the stringency of hybridization, however, mismatches may be tolerated. Typically, hybridization of two sequences at high stingency (such as, for example, in a solution of 0.5×SSC, at 65° C.) requires that the sequences be essentially completely homologous. Conditions of intermediate stringency (such as, for example, 2×SSC at 65° C.) and low stringency (such as, for example 2×SSC at 55° C.), require correspondingly less overall complementarity between the hybridizing sequences. (1×SSC is 0.15 M NaCl, 0.015 M Na citrate).

The terms peptides, proteins, and polypeptides are used interchangeably herein.

As used herein, the term "surface protein" refers to all surface accessible proteins, e.g. inner and outer membrane proteins, proteins adhering to the cell wall, and secreted proteins.

A polypeptide has E. faecalis biological activity if it has one, two and preferably more of the following properties: (1) if when expressed in the course of an E. faecalis infection, it can promote, or mediate the attachment of E. faecalis to a cell; (2) it has an enzymatic activity, structural or regulatory function characteristic of an E. faecalis protein; (3) or the gene which encodes it can rescue a lethal mutation in an E. faecalis gene. A polypeptide has biological activity if it is an antagonist, agonist, or super-agonist of a polypeptide having one of the above-listed properties.

A biologically active fragment or analog is one having an in vivo or in vitro activity which is characteristic of the E. faecalis polypeptides of the invention contained in the Sequence Listing, or of other naturally occurring E. faecalis polypeptides, e.g., one or more of the biological activities described herein. Especially preferred are fragments which exist in vivo, e.g., fragments which arise from post transcriptional processing or which arise from translation of alternatively spliced RNA's. Fragments include those expressed in native or endogenous cells as well as those made in expression systems, e.g., in CHO cells. Because peptides such as E. faecalis polypeptides often exhibit a range of physiological properties and because such properties may be attributable to different portions of the molecule, a useful E. faecalis fragment or E. faecalis analog is one which exhibits a biological activity in any biological assay for E. faecalis activity. Most preferably the fragment or analog possesses 10%, preferably 40%, more preferably 60%, 70%, 80% or 90% or greater of the activity of E. faecalis, in any in vivo or in vitro assay.

Analogs can differ from naturally occurring E. faecalis polypeptides in amino acid sequence or in ways that do not involve sequence, or both. Non-sequence modifications include changes in acetylation, methylation, phosphorylation, carboxylation, or glycosylation. Preferred analogs include E. faecalis polypeptides (or biologically active fragments thereof) whose sequences differ from the wild-type sequence by one or more conservative amino acid substitutions or by one or more non-conservative amino acid substitutions, deletions, or insertions which do not substantially diminish the biological activity of the E. faecalis polypeptide. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be made in view of the table below.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

As used herein, the term "fragment", as applied to an E. faecalis analog, will ordinarily be at least about 20 residues, more typically at least about 40 residues, preferably at least about 60 residues in length. Fragments of E. faecalis polypeptides can be generated by methods known to those skilled in the art. The ability of a candidate fragment to exhibit a biological activity of E. faecalis polypeptide can be assessed by methods known to those skilled in the art as described herein. Also included are E. faecalis polypeptides containing residues that are not required for biological activity of the peptide or that result from alternative mRNA splicing or alternative protein processing events.

An "immunogenic component" as used herein is a moiety, such as an E. faecalis polypeptide, analog or fragment thereof, that is capable of eliciting a humoral and/or cellular immune response in a host animal.

An "antigenic component" as used herein is a moiety, such as an E. faecalis polypeptide, analog or fragment thereof, that is capable of binding to a specific antibody with sufficiently high affinity to form a detectable antigen-antibody complex.

The term "antibody" as used herein is intended to include fragments thereof which are specifically reactive with E. faecalis polypeptides.

As used herein, the term "cell-specific promoter" means a DNA sequence that serves as a promoter, i.e., regulates expression of a selected DNA sequence operably linked to the promoter, and which effects expression of the selected DNA sequence in specific cells of a tissue. The term also covers so-called "leaky" promoters, which regulate expression of a selected DNA primarily in one tissue, but cause expression in other tissues as well.

Misexpression, as used herein, refers to a non-wild type pattern of gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of increased expression (as compared with wild type) in a predetermined cell type or tissue type; a pattern of expression that differs from wild type in terms of the splicing size, amino acid sequence, post-translational modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

As used herein, "host cells" and other such terms denoting microorganisms or higher eukaryotic cell lines cultured as unicellular entities refers to cells which can become or have been used as recipients for a recombinant vector or other transfer DNA, and include the progeny of the original cell which has been transfected. It is understood by individuals skilled in the art that the progeny of a single parental cell may not necessarily be completely identical in genomic or total DNA compliment to the original parent, due to accident or deliberate mutation.

As used herein, the term "control sequence" refers to a nucleic acid having a base sequence which is recognized by the host organism to effect the expression of encoded sequences to which they are ligated. The nature of such control sequences differs depending upon the host organism; in prokaryotes, such control sequences generally include a promoter, ribosomal binding site, terminators, and in some cases operators; in eukaryotes, generally such control sequences include promoters, terminators and in some instances, enhancers. The term control sequence is intended to include at a minimum, all components whose presence is necessary for expression, and may also include additional components whose presence is advantageous, for example, leader sequences.

As used herein, the term "operably linked" refers to sequences joined or ligated to function in their intended manner. For example, a control sequence is operably linked to coding sequence by ligation in such a way that expression of the coding sequence is achieved under conditions compatible with the control sequence and host cell.

The "metabolism" of a substance, as used herein, means any aspect of the expression, function, action, or regulation of the substance. The metabolism of a substance includes modifications, e.g., covalent or non-covalent modifications of the substance. The metabolism of a substance includes modifications, e.g., covalent or non-covalent modification, the substance induces in other substances. The metabolism of a substance also includes changes in the distribution of the substance. The metabolism of a substance includes changes the substance induces in the distribution of other substances.

A "sample" as used herein refers to a biological sample, such as, for example, tissue or fluid isloated from an individual (including without limitation plasma, serum, cerebrospinal fluid, lymph, tears, saliva and tissue sections) or from in vitro cell culture constituents, as well as samples from the environment.

Technical and scientific terms used herein have the meanings commonly understood by one of ordinary skill in the art to which the present invention pertains, unless otherwise defined. Reference is made herein to various methodologies known to those of skill in the art. Publications and other materials setting forth such known methodologies to which reference is made are incorporated herein by reference in their entireties as though set forth in full. The practice of the invention will employ, unless otherwise indicated, conventional techniques of chemistry, molecular biology, microbiology, recombinant DNA, and immunology, which are within the skill of the art. Such techniques are explained fully in the literature. See e.g., Sambrook, Fritsch, and Maniatis, *Molecular Cloning: Laboratory Manual* 2nd ed. (1989); *DNA Cloning,* Volumes I and II (D. N Glover ed. 1985); *Oligonucleotide Synthesis* (M. J. Gait ed, 1984); *Nucleic Acid Hybridization* (B. D. Hames & S. J. Higgins eds. 1984); the series, *Methods in Enzymology* (Academic Press, Inc.), particularly Vol. 154 and Vol. 155 (Wu and Grossman, eds.); *PCR—A Practical Approach* (McPherson, Quirke, and Taylor, eds., 1991); *Immunology,* 2d Edition, 1989, Roitt et al., C. V. Mosby Company, and New York; *Advanced Immunology,* 2d Edition, 1991, Male et al., Grower Medical Publishing, New York.; *DNA Cloning: A Practical Approach,* Volumes I and II, 1985 (D. N. Glover ed.); *Oligonucleotide Synthesis,* 1984, (M. L. Gait ed); *Transcription and Translation,* 1984 (Hames and Higgins eds.); *Animal Cell Culture,* 1986 (R. I. Freshney ed.); *Immobilized Cells and Enzymes,* 1986 (IRL Press); Perbal, 1984, *A Practical Guide to Molecular Cloning;* and *Gene Transfer Vectors for Mammalian Cells,* 1987 (J. H. Miller and M. P. Calos eds., Cold Spring Harbor Laboratory);

Any suitable materials and/or methods known to those of skill can be utilized in carrying out the present invention: however preferred materials and/or methods are described. Materials, reagents and the like to which reference is made in the following description and examples are obtainable from commercial sources, unless otherwise noted.

*E. faecalis* Genomic Sequence

This invention provides nucleotide sequences of the genome of *E. faecalis* which thus comprises a DNA sequence library of *E. faecalis* genomic DNA. The detailed description that follows provides nucleotide sequences of *E. faecalis*, and also describes how the sequences were obtained and how ORFs and protein-coding sequences were identified. Also described are methods of using the disclosed *E. faecalis* sequences in methods including diagnostic and therapeutic applications. Furthermore, the library can be used as a database for identification and comparison of medically important sequences in this and other strains of *E. faecalis*.

To determine the genomic sequence of *E. faecalis*, DNA from strain 14336 of *E. faecalis* was isolated after Zymolyase digestion, sodium dodecyl sulfate lysis, potassium acetate precipitation, phenol:chloroform extractionand ethanol precipitation (Soll, D. R., T. Srikantha and S. R. Lockhart: Characterizing Developmentally Regulated Genes in *E. faecalis*. In Microbial Genome Methods. K. W. Adolph, editor. CRC Press. New York. p 17–37.). DNA was sheared hydrodynamically using an HPLC (Oefner, et. al., 1996) to an insert size of 2000–3000 bp. After size fractionation by gel electrophoresis the fragments were blunt-ended, ligated to adapter oligonucleotides and cloned into the pGTC (Thomann) vector to construct a "shotgun" subclone library.

DNA sequencing was achieved using established ABI sequencing methods on ABI377 automated DNA sequencers. The cloning and sequencing procedures are described in more detail in the Exemplification.

Individual sequence reads were assembled using PHRAP (P. Green, Abstracts of DOE Human Genome Program Contractor-Grantee Workshop V, January 1996, p. 157). The average contig length was about 3–4 kb.

All subsequent steps were based on sequencing by ABI377 automated DNA sequencing methods. The cloning and sequencing procedures are described in more detail in the Exemplification.

A variety of approaches are used to order the contigs so as to obtain a continuous sequence representing the entire *E. faecalis* genome. Synthetic oligonucleotides are designed that are complementary to sequences at the end of each contig. These oligonucleotides may be hybridized to libaries of *E. faecalis* genomic DNA in, for example, lambda phage vectors or plasmid vectors to identify clones that contain sequences corresponding to the junctional regions between individual contigs. Such clones are then used to isolate template DNA and the same oligonucleotides are used as primers in polymerase chain reaction (PCR) to amplify junctional fragments, the nucleotide sequence of which is then determined.

The *E. faecalis* sequences were analyzed for the presence of open reading frames (ORFs) comprising at least 180 nucleotides. As a result of the analysis of ORFs based on stop-to-stop codon reads, it should be understood that these ORFs may not correspond to the ORF of a naturally-occurring *E. faecalis* polypeptide. These ORFs may contain start codons which indicate the initiation of protein synthesis of a naturally-occurring *E. faecalis* polypeptide. Such start codons within the ORFs provided herein can be identified by those of ordinary skill in the relevant art, and the resulting ORF and the encoded *E. faecalis* polypeptide is within the scope of this invention. For example, within the ORFs a codon such as AUG or GUG (encoding methionine or valine) which is part of the initiation signal for protein synthesis can be identified and the portion of an ORF to corresponding to a naturally-occurring *E. faecalis* polypeptide can be recognized. The predicted coding regions were defined by evaluating the coding potential of such sequences with the program GENEMARK™ (Borodovsky and McIninch, 1993, *Comp.* 17:123).

Each predicted ORF amino acid sequence was compared with all sequences found in current GENBANK, SWISS-PROT, and PIR databases using the BLAST algorithrn. BLAST identifies local alignments occurring by chance between the ORF sequence and the sequence in the databank (Altschal et al., 1990, L Mol. Biol. 215:403–410). Homologous ORFs (probabilities less than $10^{-5}$ by chance) and ORF's that are probably non-homologous (probabilities greater than $10^{-5}$ by chance) but have good codon usage were identified. Both homologous, sequences and non-homologous sequences with good codon usage, are likely to encode proteins and are encompassed by the invention.

*E. faecalis* Nucleic Acids

The present invention provides a library of *E. faecalis*-derived nucleic acid sequences. The libraries provide probes, primers, and markers which are used as markers in epidemiological studies. The present invention also provides a library of *E. faecalis*-derived nucleic acid sequences which comprise or encode targets for therapeutic drugs.

The nucleic acids of this invention may be obtained directly from the DNA of the above referenced *E. faecalis* strain by using the polymerase chain reaction (PCR). See "*PCR, A Practical Approach*" (McPherson, Quirke, and Taylor, eds., IRL Press, Oxford, UK, 1991) for details about the PCR. High fidelity PCR can be used to ensure a faithful DNA copy prior to expression. In addition, the authenticity of amplified products can be verified by conventional sequencing methods. Clones carrying the desired sequences described in this invention may also be obtained by screening the libraries by means of the PCR or by hybridization of synthetic oligonucleotide probes to filter lifts of the library colonies or plaques as known in the art (see, e.g., Sambrook et al., *Molecular Cloning, A Laboratory Manual* 2nd edition, 1989, Cold Spring Harbor Press, NY).

It is also possible to obtain nucleic acids encoding *E. faecalis* polypeptides from a cDNA library in accordance with protocols herein described. A cDNA encoding an *E. faecalis* polypeptide can be obtained by isolating total mRNA from an appropriate strain. Double stranded cDNAs can then be prepared from the total mRNA. Subsequently, the cDNAs can be inserted into a suitable plasmid or viral (e.g., bacteriophage) vector using any one of a number of known techniques. Genes encoding *E. faecalis* polypeptides can also be cloned using established polymerase chain reaction techniques in accordance with the nucleotide sequence information provided by the invention. The nucleic acids of the invention can be DNA or RNA. Preferred nucleic acids of the invention are contained in the Sequence Listing.

The nucleic acids of the invention can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

In another example, DNA can be chemically synthesized using, e.g., the phosphoramidite solid support method of Matteucci et al., 1981, *J. Am. Chem. Soc.* 103:3185, the method of Yoo et al., 1989, *J. Biol. Chem.* 764:17078, or other well known methods. This can be done by sequentially linking a series of oligonucleotide cassettes comprising pairs of synthetic oligonucleotides, as described below.

Nucleic acids isolated or synthesized in accordance with features of the present invention are useful, by way of example, without limitation, as probes, primers, capture ligands, antisense genes and for developing expression systems for the synthesis of proteins and peptides corresponding to such sequences. As probes, primers, capture ligands and antisense agents, the nucleic acid normally consists of all or part (approximately twenty or more nucleotides for specificity as well as the ability to form stable hybridization products) of the nucleic acids of the invention contained in the Sequence Listing. These uses are described in further detail below.

Probes

A nucleic acid isolated or synthesized in accordance with the sequence of the invention contained in the Sequence Listing can be used as a probe to specifically detect *E. faecalis*. With the sequence information set forth in the present application, sequences of twenty or more nucleotides are identified which provide the desired inclusivity and exclusivity with respect to *E. faecalis*, and extraneous nucleic acids likely to be encountered during hybridization conditions. More preferably, the sequence will comprise at least twenty to thirty nucleotides to convey stability to the hybridization product formed between the probe and the intended target molecules.

Sequences larger than 1000 nucleotides in length are difficult to synthesize but can be generated by recombinant DNA techniques. Individuals skilled in the art will readily recognize that the nucleic acids, for use as probes, can be provided with a label to facilitate detection of a hybridization product.

Nucleic acid isolated and synthesized in accordance with the sequence of the invention contained in the Sequence Listing can also be useful as probes to detect homologous regions (especially homologous genes) of other Enterococcus species using appropriate stringency hybridization conditions as described herein.

Capture Ligand

For use as a capture ligand, the nucleic acid selected in the manner described above with respect to probes, can be readily associated with a support. The manner in which nucleic acid is associated with supports is well known. Nucleic acid having twenty or more nucleotides in a sequence of the invention contained in the Sequence Listing have utility to separate E. faecalis nucleic acid from one strain from the nucleic acid of other another strain as well as from other organisms. Nucleic acid having twenty or more nucleotides in a sequence of the invention contained in the Sequence Listing can also have utility to separate other Enterococcus species from each other and from other organisms. Preferably, the sequence will comprise at least twenty nucleotides to convey stability to the hybridization product formed between the probe and the intended target molecules. Sequences larger than 1000 nucleotides in length are difficult to synthesize but can be generated by recombinant DNA techniques.

Primers

Nucleic acid isolated or synthesized in accordance with the sequences described herein have utility as primers for the amplification of E. faecalis nucleic acid. These nucleic acids may also have utility as primers for the amplification of nucleic acids in other Enterococcus species. With respect to polymerase chain reaction (PCR) techniques, nucleic acid sequences of >10–15 nucleotides of the invention contained in the Sequence Listing have utility in conjunction with suitable enzymes and reagents to create copies of E. faecalis nucleic acid. More preferably, the sequence will comprise twenty or more nucleotides to convey stability to the hybridization product formed between the primer and the intended target molecules. Binding conditions of primers greater than 100 nucleotides are more difficult to control to obtain specificity. High fidelity PCR can be used to ensure a faithful DNA copy prior to expression. In addition, amplified products can be checked by conventional sequencing methods.

The copies can be used in diagnostic assays to detect specific sequences, including genes from E. faecalis and/or other Enterococcus species. The copies can also be incorporated into cloning and expression vectors to generate polypeptides corresponding to the nucleic acid synthesized by PCR, as is described in greater detail herein. The nucleic acids of the present invention find use as templates for the recombinant production of E. faecalis-derived peptides or polypeptides.

Antisense

Nucleic acid or nucleic acid-hybridizing derivatives isolated or synthesized in accordance with the sequences described herein have utility as antisense agents to prevent the expression of E. faecalis genes. These sequences also have utility as antisense agents to prevent expression of genes of other Enterococcus species.

In one embodiment, nucleic acid or derivatives corresponding to E. faecalis nucleic acids is loaded into a suitable carrier such as a liposome or bacteriophage for introduction into bacterial cells. For example, a nucleic acid having twenty or more nucleotides is capable of binding to bacteria nucleic acid or bacteria messenger RNA. Preferably, the antisense nucleic acid is comprised of 20 or more nucleotides to provide necessary stability of a hybridization product of non-naturally occurring nucleic acid and bacterial nucleic acid and/or bacterial messenger RNA. Nucleic acid having a sequence greater than 1000 nucleotides in length is difficult to synthesize but can be generated by recombinant DNA techniques. Methods for loading antisense nucleic acid in liposomes is known in the art as exemplified by U.S. Pat. No. 4,241,046 issued Dec. 23, 1980 to Papahadjopoulos et al.

The present invention encompasses isolated polypeptides and nucleic acids derived from E. faecalis that are useful as reagents for diagnosis of bacterial infection, components of effective anti-bacterial vaccines, and/or as targets for anti-bacterial drugs, including anti-E. faecalis drugs.

The present invention also provides a genome-wide comparison by FASTA of the predicted amino acid sequences of several E. faecalis open reading frames (ORFs) with the predicted amino acid sequence of several E. faecium ORFs (Table 3). Together, E. faecalis and E. faecium account for >95% of all VRE infections. Genomic comparison of E. faecalis ORFs with E. faecium ORFs at the amino acid sequence level provides valuable information on shared targets, which can be exploited in designing diagnostics and therapeutics for VRE. Identifying common essential genes through sequencing and analysis of both genomes provides a much quicker route to these targets, and speeds the progress of (1) probe design for identification of VRE infection, (2) identification of vaccine compositions for protection from and treatment of these infections, and (3) development of screening assays for inhibitors of gene products common to both organisms. In all cases, the homology relationships described in Table 3 are highly significant. The percentage identity between the ORFs of the two organisms shown in Table 3 ranges from about 18% up to 100%. Approximately 800 ORFs show complete amino acid sequence identity between the two organisms. Many ORFs do not share significant amino acid sequence identity between these two species, and they are not shown in Table 3. Therefore, Table 3 represents a useful listing of some gene targets common in the two species.

Expression of E. faecalis Nucleic Acids

Table 2, which is appended herewith and which forms part of the present specification, provides a list of open reading frames (ORFs) in both strands and a putative identification of the particular function of a polypeptide which is encoded by each ORF, based on the homology match (determined by the BLAST algorithm) of the predicted polypeptide with known proteins encoded by ORFs in other organisms. An ORF is a region of nucleic acid which encodes a polypeptide. This region may represent a portion of a coding sequence or a total sequence and was determined from stop to stop codons. The first column contains a designation for the contig from which each ORF was identified (numbered arbitrarily). Each contig represents a continuous stretch of the genomic sequence of the organism. The second column lists the ORF designation. The third and fourth columns list the SEQ ID numbers for the nucleic acid and amino acid sequences corresponding to each ORF, respectively. The fifth and sixth columns list the length of the nucleic acid ORF and the length of the amino acid ORF, respectively. The nucleotide sequence corresponding to each ORF begins at the first nucleotide immediately following a stop codon and ends at the nucleotide immediately preceding the next downstream stop codon in the same reading frame. It will be recognized by one skilled in the art that the natural translation initiation sites will correspond to ATG, GTG, or TTG codons located within the ORFs. The natural initiation sites depend not only on the sequence of a start codon but also on the context of the DNA sequence adjacent to the start codon. Usually, a recognizable ribosome binding site is found within 20 nucleotides upstream from the initiation codon. In some cases where genes are translationally coupled and coordinately expressed together in "operons", ribosome binding sites are not present, but the initiation codon of a downstream gene may occur very close to, or overlap, the stop codon of the an upstream gene in the same operon. The correct start codons can be generally identified without undue experimentation because only a few codons need be tested. It is recognized that the translational machinery in bacteria initiates all polypeptide chains with the amino acid methionine, regardless of the sequence of the start codon. In some cases, polypeptides are post-translationally modified, resulting in an N-terminal amino acid other than methionine in vivo. The seventh and eighth columns in Table 2 provide metrics for assessing the likelihood of the homology match (determined by the BLASTP2 algorithm), as is known in the art, to the genes indicated in the ninth column. Specifically, the seventh column represents the "score" for the match (a higher score is a better match), and the eighth column represents the "P-value" for the match (the probability that such a match could have occurred by chance; the lower the value, the more likely the match is valid). If a BLASP2 score of less than 46 was obtained, no value is reported in the table. The ninth column provides, where available, the accession number (AC) or the Swissprot accession number (SP), the organism (OR), the gene name (GN), the product name (PN), and the description (DE) or notes (NT) for each ORF. This information allows one of ordinary skill in the art to determine a potential use for each identified coding sequence and, as a result, allows to use the polypeptides of the present invention for commercial and industrial purposes consistent with the type of putative identification of the polypeptide.

Using the information provided in SEQ ID NO: 1–SEQ ID NO: 3405 and in Table 2 together with routine cloning and sequencing methods, one of ordinary skill in the art will be able to clone and sequence all the nucleic acid fragments of interest including open reading frames (ORFs) encoding a large variety proteins of E. faecalis.

Nucleic acid isolated or synthesized in accordance with the sequences described herein have utility to generate polypeptides. The nucleic acid of the invention exemplified in SEQ ID NO: 1–SEQ ID NO: 3405 and in Table 2 or fragments of said nucleic acid encoding active portions of E. faecalis polypeptides can be cloned into suitable vectors or used to isolate nucleic acid. The isolated nucleic acid is combined with suitable DNA linkers and cloned into a suitable vector.

The function of a specific gene or operon can be ascertained by expression in a bacterial strain under conditions where the activity of the gene product(s) specified by the gene or operon in question can be specifically measured. Alternatively, a gene product may be produced in large quantities in an expressing strain for use as an antigen, an industrial reagent, for structural studies, etc. This expression can be accomplished in a mutant strain which lacks the activity of the gene to be tested, or in a strain that does not produce the same gene product(s). This includes, but is not limited to, Eucaryotic species such as the yeast *Saccharomyces cerevisiae,* Methanobacterium strains or other Archaea, and Eubacteria such as *E. coli, B. Subtilis, S. Aureus, S. Pneumonia* or *Pseudomonas putida.* In some cases the expression host will utilize the natural E. faecalis promoter whereas in others, it will be necessary to drive the gene with a promoter sequence derived from the expressing organism (e.g., an E. coli beta-galactosidase promoter for expression in E. coli).

To express a gene product using the natural E. faecalis promoter, a procedure such as the following can be used. A restriction fragment containing the gene of interest, together with its associated natural promoter element and regulatory sequences (identified using the DNA sequence data) is cloned into an appropriate recombinant plasmid containing an origin of replication that functions in the host organism and an appropriate selectable marker. This can be accomplished by a number of procedures known to those skilled in the art. It is most preferably done by cutting the plasmid and the fragment to be cloned with the same restriction enzyme to produce compatible ends that can be ligated to join the two pieces together. The recombinant plasmid is introduced into the host organism by, for example, electroporation and cells containing the recombinant plasmid are identified by selection for the marker on the plasmid. Expression of the desired gene product is detected using an assay specific for that gene product.

In the case of a gene that requires a different promoter, the body of the gene (coding sequence) is specifically excised and cloned into an appropriate expression plasmid. This subcloning can be done by several methods, but is most easily accomplished by PCR amplification of a specific fragment and ligation into an expression plasmid after treating the PCR product with a restriction enzyme or exonuclease to create suitable ends for cloning.

A suitable host cell for expression of a gene can be any procaryotic or eucaryotic cell. Suitable methods for transforming host cells can be found in Sambrook et al. (*Molecular Cloning: A Laboratory Manual,* 2nd Edition, Cold Spring Harbor Laboratory press (1989)), and other laboratory textbooks.

For example, a host cell transfected with a nucleic acid vector directing expression of a nucleotide sequence encoding an E. faecalis polypeptide can be cultured under appropriate conditions to allow expression of the polypeptide to occur. Suitable media for cell culture are well known in the art. Polypeptides of the invention can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such polypeptides. Additionally, in many situations, polypeptides can be produced by chemical cleavage of a native protein (e.g., tryptic digestion) and the cleavage products can then be purified by standard techniques.

In the case of membrane bound proteins, these can be isolated from a host cell by contacting a membrane-associated protein fraction with a detergent forming a solubilized complex, where the membrane-associated protein is no longer entirely embedded in the membrane fraction and is solubilized at least to an extent which allows it to be chromatographically isolated from the membrane fraction. Chromatographic techniques which can be used in the final purification step are known in the art and include hydrophobic interaction, lectin affinity, ion exchange, dye affinity and immunoaffinity.

One strategy to maximize recombinant E. faecalis peptide expression in E. coli is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy would be to alter the nucleic acid encoding an E. faecalis peptide to be inserted into an expression vector so that the individual codons for each amino acid would be those preferentially utilized in highly expressed *E. coli* proteins (Wada et al., (1992) *Nuc. Acids Res.* 20:2111–2118). Such alteration of nucleic acids of the invention can be carried out by standard DNA synthesis techniques.

The nucleic acids of the invention can also be chemically synthesized using standard techniques. Various methods of chemically synthesizing polydeoxynucleotides are known, including solid-phase synthesis which, like peptide synthesis, has been fully automated in commercially available DNA synthesizers (See, e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

The present invention provides a library of *E. faecalis*-derived nucleic acid sequences. The libraries provide probes, primers, and markers which can be used as markers in epidemiological studies. The present invention also provides a library of *E. faecalis*-derived nucleic acid sequences which comprise or encode targets for therapeutic drugs.

Nucleic acids comprising any of the sequences disclosed herein or sub-sequences thereof can be prepared by standard methods using the nucleic acid sequence information provided in SEQ ID NO: 1–SEQ ID NO: 3405. For example, DNA can be chemically synthesized using, e.g., the phosphoramidite solid support method of Matteucci et al., 1981, *J. Am. Chem. Soc.* 103:3185, the method of Yoo et al., 1989, *J. Biol. Chem.* 764:17078, or other well known methods. This can be done by sequentially linking a series of oligonucleotide cassettes comprising pairs of synthetic oligonucleotides, as described below.

Of course, due to the degeneracy of the genetic code, many different nucleotide sequences can encode polypeptides having the amino acid sequences defined by SEQ ID NO: 3406–SEQ ID NO: 6810 or sub-sequences thereof. The codons can be selected for optimal expression in prokaryotic or eukaryotic systems. Such degenerate variants are also encompassed by this invention.

Insertion of nucleic acids (typically DNAs) encoding the polypeptides of the invention into a vector is easily accomplished when the termini of both the DNAs and the vector comprise compatible restriction sites. If this cannot be done, it may be necessary to modify the termini of the DNAs and/or vector by digesting back single-stranded DNA overhangs generated by restriction endonuclease cleavage to produce blunt ends, or to achieve the same result by filling in the single-stranded termini with an appropriate DNA polymerase.

Alternatively, any site desired may be produced, e.g., by ligating nucleotide sequences (linkers) onto the termini. Such linkers may comprise specific oligonucleotide sequences that define desired restriction sites. Restriction sites can also be generated by the use of the polymerase chain reaction (PCR). See, e.g., Saiki et al., 1988, *Science* 239:48. The cleaved vector and the DNA fragments may also be modified if required by homopolymeric tailing.

The nucleic acids of the invention may be isolated directly from cells. Alternatively, the polymerase chain reaction (PCR) method can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

The nucleic acids of the present invention may be flanked by natural *E. faecalis* regulatory sequences, or may be associated with heterologous sequences, including promoters, enhancers, response elements, signal sequences, polyadenylation sequences, introns, 5'- and 3'-noncoding regions, and the like. The nucleic acids may also be modified by many means known in the art. Non-limiting examples of such modifications include methylation, "caps", substitution of one or more of the naturally occurring nucleotides with an analog, internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. PNAs are also included. The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

The invention also provides nucleic acid vectors comprising the disclosed *E. faecalis*-derived sequences or derivatives or fragments thereof. A large number of vectors, including plasmid and bacterial vectors, have been described for replication and/or expression in a variety of eukaryotic and prokaryotic hosts, and may be used for cloning or protein expression.

The encoded *E. faecalis* polypeptides may be expressed by using many known vectors, such as pUC plasmids, pET plasmids (Novagen, Inc., Madison, Wis.), or pRSET or pREP (Invitrogen, San Diego, Calif.), and many appropriate host cells, using methods disclosed or cited herein or otherwise known to those skilled in the relevant art. The particular choice of vector/host is not critical to the practice of the invention.

Recombinant cloning vectors will often include one or more replication systems for cloning or expression, one or more markers for selection in the host, e.g. antibiotic resistance, and one or more expression cassettes. The inserted *E. faecalis* coding sequences may be synthesized by standard methods, isolated from natural sources, or prepared as hybrids, etc. Ligation of the *E. faecalis* coding sequences to transcriptional regulatory elements and/or to other amino acid coding sequences may be achieved by known methods. Suitable host cells may be transformed/transfected/infected as appropriate by any suitable method including electroporation, $CaCl_2$ mediated DNA uptake, bacterial infection, microinjection, microprojectile, or other established methods.

Appropriate host cells include bacteria, archebacteria, fungi, especially yeast, and plant and animal cells, especially mammalian cells. Of particular interest are *E. faecalis, E. coli, B. Subtilis, Saccharomyces cerevisiae, Saccharomyces carlsbergensis, Schizosaccharomyces pombi,* SF9 cells, C129 cells, 293 cells, Neurospora, and CHO cells, COS cells, HeLa cells, and immortalized mammalian myeloid and lymphoid cell lines. Preferred replication systems include M13, ColE1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc.

are known in the art. Under appropriate expression conditions, host cells can be used as a source of recombinantly produced E. faecalis-derived peptides and polypeptides.

Advantageously, vectors may also include a transcription regulatory element (i.e., a promoter) operably linked to the E. faecalis portion. The promoter may optionally contain operator portions and/or ribosome binding sites. Non-limiting examples of bacterial promoters compatible with E. coli include: b-lactamase (penicillinase) promoter; lactose promoter; tryptophan (trp) promoter; araBAD (arabinose) operon promoter; lambda-derived $P_1$ promoter and N gene ribosome binding site; and the hybrid tac promoter derived from sequences of the trp and lac UV5 promoters. Non-limiting examples of yeast promoters include 3-phosphoglycerate kinase promoter, glyceraldehyde-3-phosphate dehydrogenase (GAPDH) promoter, galactokinase (GAL1) promoter, galactoepimerase promoter, and alcohol dehydrogenase (ADH) promoter. Suitable promoters for mammalian cells include without limitation viral promoters such as that from Simian Virus 40 (SV40), Rous sarcoma virus (RSV), adenovirus (ADV), and bovine papilloma virus (BPV). Mammalian cells may also require terminator sequences, polyA addition sequences and enhancer sequences to increase expression. Sequences which cause amplification of the gene may also be desirable. Furthermore, sequences that facilitate secretion of the recombinant product from cells, including, but not limited to, bacteria, yeast, and animal cells, such as secretory signal sequences and/or prohormone pro region sequences, may also be included. These sequences are well described in the art.

Nucleic acids encoding wild-type or variant E. faecalis-derived polypeptides may also be introduced into cells by recombination events. For example, such a sequence can be introduced into a cell, and thereby effect homologous recombination at the site of an endogenous gene or a sequence with substantial identity to the gene. Other recombination-based methods such as nonhomologous recombinations or deletion of endogenous genes by homologous recombination may also be used.

The nucleic acids of the present invention find use as templates for the recombinant production of E. faecalis-derived peptides or polypeptides.

Identification and Use of E. faecalis Nucleic Acid Sequences

The disclosed E. faecalis polypeptide and nucleic acid sequences, or other sequences that are contained within ORFs, including complete protein-coding sequences, of which any of the disclosed E. faecalis-specific sequences forms a part, are useful as target components for diagnosis and/or treatment of E. faecalis-caused infection.

It will be understood that the sequence of an entire protein-coding sequence of which each disclosed nucleic acid sequence forms a part can be isolated and identified based on each disclosed sequence. This can be achieved, for example, by using an isolated nucleic acid encoding the disclosed sequence, or fragments thereof, to prime a sequencing reaction with genomic E. faecalis DNA as template; this is followed by sequencing the amplified product. The isolated nucleic acid encoding the disclosed sequence, or fragments thereof, can also be hybridized to E. faecalis genomic libraries to identify clones containing additional complete segments of the protein-coding sequence of which the shorter sequence forms a part. Then, the entire protein-coding sequence, or fragments thereof, or nucleic acids encoding all or part of the sequence, or sequence-conservative or function-conservative variants thereof, may be employed in practicing the present invention.

Preferred sequences are those that are useful in diagnostic and/or therapeutic applications. Diagnostic applications include without limitation nucleic-acid-based and antibody-based methods for detecting bacterial infection. Therapeutic applications include without limitation vaccines, passive immunotherapy, and drug treatments directed against gene products that are both unique to bacteria and essential for growth and/or replication of bacteria.

Identification of Nucleic Acids Encoding Vaccine Components and Targets for Agents Effective against E. faecalis The disclosed E. faecalis genome sequence includes segments that direct the synthesis of ribonucleic acids and polypeptides, as well as origins of replication, promoters, other types of regulatory sequences, and intergenic nucleic acids. The invention encompasses nucleic acids encoding immunogenic components of vaccines and targets for agents effective against E. faecalis. Identification of said immunogenic components involved in the determination of the function of the disclosed sequences, which can be achieved using a variety of approaches. Non-limiting examples of these approaches are described briefly below.

Homology to Known Sequences

Computer-assisted comparison of the disclosed E. faecalis sequences with previously reported sequences present in publicly available databases is useful for identifying functional E. faecalis nucleic acid and polypeptide sequences. It will be understood that protein-coding sequences, for example, may be compared as a whole, and that a high degree of sequence homology between two proteins (such as, for example, >80–90%) at the amino acid level indicates that the two proteins also possess some degree of functional homology, such as, for example, among enzymes involved in metabolism, DNA synthesis, or cell wall synthesis, and proteins involved in transport, cell division, etc. In addition, many structural features of particular protein classes have been identified and correlate with specific consensus sequences, such as, for example, binding domains for nucleotides, DNA, metal ions, and other small molecules; sites for covalent modifications such as phosphorylation, acylation, and the like; sites of protein:protein interactions, etc. These consensus sequences may be quite short and thus may represent only a fraction of the entire protein-coding sequence. Identification of such a feature in an E. faecalis sequence is therefore useful in determining the function of the encoded protein and identifying useful targets of antibacterial drugs.

Of particular relevance to the present invention are structural features that are common to secretory, transmembrane, and surface proteins, including secretion signal peptides and hydrophobic transmembrane domains. E. faecalis proteins identified as containing putative signal sequences and/or transmembrane domains are useful as immunogenic components of vaccines.

Targets for therapeutic drugs according to the invention include, but are not limited to, polypeptides of the invention, whether unique to E. faecalis or not, that are essential for growth and/or viability of E. faecalis under at least one growth condition. Polypeptides essential for growth and/or viability can be determined by examining the effect of deleting and/or disrupting the genes, i.e., by so-called gene "knockout". Alternatively, genetic footprinting can be used (Smith et al., 1995, Proc. Natl. Acad. Sci. USA 92:5479–6433; Published International Application WO 94/26933; U.S. Pat. No. 5,612,180). Still other methods for assessing essentiality includes the ability to isolate conditional lethal mutations in the specific gene (e.g., temperature sensitive mutations). Other useful targets for therapeutic drugs, which include polypeptides that are not essential for growth or viability per se but lead to loss of viability of the cell, can be used to target therapeutic agents to cells.

Strain-specific Sequences

Because of the evolutionary relationship between different *E. faecalis* strains, it is believed that the presently disclosed *E. faecalis* sequences are useful for identifying, and/or discriminating between, previously known and new *E. faecalis* strains. It is believed that other *E. faecalis* strains will exhibit at least 70% sequence homology with the presently disclosed sequence. Systematic and routine analyses of DNA sequences derived from samples containing *E. faecalis* strains, and comparison with the present sequence allows for the identification of sequences that can be used to discriminate between strains, as well as those that are common to all *E. faecalis* strains. In one embodiment, the invention provides nucleic acids, including probes, and peptide and polypeptide sequences that discriminate between different strains of *E. faecalis*. Strain-specific components can also be identified functionally by their ability to elicit or react with antibodies that selectively recognize one or more *E. faecalis* strains.

In another embodiment, the invention provides nucleic acids, including probes, and peptide and polypeptide sequences that are common to all *E. faecalis* strains but are not found in other bacterial species.

*E. faecalis* Polypeptides

This invention encompasses isolated *E. faecalis* polypeptides encoded by the disclosed *E. faecalis* genomic sequences, including the polypeptides of the invention contained in the Sequence Listing. Polypeptides of the invention are preferably at least 5 amino acid residues in length. Using the DNA sequence information provided herein, the amino acid sequences of the polypeptides encompassed by the invention can be deduced using methods well-known in the art. It will be understood that the sequence of an entire nucleic acid encoding an *E. faecalis* polypeptide can be isolated and identified based on an ORF that encodes only a fragment of the cognate protein-coding region. This can be achieved, for example, by using the isolated nucleic acid encoding the ORF, or fragments thereof, to prime a polymerase chain reaction with genomic *E. faecalis* DNA as template; this is followed by sequencing the amplified product.

The polypeptides of the present invention, including function-conservative variants of the disclosed ORFs, may be isolated from wild-type or mutant *E. faecalis* cells, or from heterologous organisms or cells (including, but not limited to, bacteria, fungi, insect, plant, and mammalian cells) including *E. faecalis* into which a *E. faecalis*-derived protein-coding sequence has been introduced and expressed. Furthermore, the polypeptides may be part of recombinant fusion proteins.

*E. faecalis* polypeptides of the invention can be chemically synthesized using commercially automated procedures such as those referenced herein, including, without limitation, exclusive solid phase synthesis, partial solid phase methods, fragment condensation or classical solution synthesis. The polypeptides are preferably prepared by solid phase peptide synthesis as described by Merrifield, 1963, *J. Am. Chem. Soc.* 85:2149. The synthesis is carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the *E. faecalis* protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against a *E. faecalis* protein or against peptides derived therefrom can be used as purification reagents. Other purification methods are possible.

The present invention also encompasses derivatives and homologues of *E. faecalis*-encoded polypeptides. For some purposes, nucleic acid sequences encoding the peptides may be altered by substitutions, additions, or deletions that provide for functionally equivalent molecules, i.e., function-conservative variants. For example, one or more amino acid residues within the sequence can be substituted by another amino acid of similar properties, such as, for example, positively charged amino acids (arginine, lysine, and histidine); negatively charged amino acids (aspartate and glutamate); polar neutral amino acids; and non-polar amino acids.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

To identify *E. faecalis*-derived polypeptides for use in the present invention, essentially the complete genomic sequence of a virulent, methicillin-resistant isolate of *Enterococcus faecalise* isolate was analyzed. While, in very rare instances, a nucleic acid sequencing error may be revealed, resolving a rare sequencing error is well within the art, and such an occurrence will not prevent one skilled in the art from practicing the invention.

Also encompassed are any *E. faecalis* polypeptide sequences that are contained within the open reading frames (ORFs), including complete protein-coding sequences, of which any of SEQ ID NO: 1–SEQ ID NO: 3405 forms a part. Table 2, which is appended herewith and which forms part of the present specification, provides a putative identification of the particular function of a polypeptide which is encoded by each ORF, based on the homology match (determined by the BLAST algorithm) of the predicted polypeptide with known proteins encoded by ORFs in other organisms. As a result, one skilled in the art can use the polypeptides of the present invention for commercial and industrial purposes consistent with the type of putative identification of the polypeptide.

The present invention provides a library of *E. faecalis*-derived polypeptide sequences, and a corresponding library of nucleic acid sequences encoding the polypeptides, wherein the polypeptides themselves, or polypeptides contained within ORFs of which they form a part, comprise sequences that are contemplated for use as components of vaccines. Non-limiting examples of such sequences are listed by SEQ ID NO in Table 2, which is appended herewith and which forms part of the present specification.

The present invention also provides a library of *E. faecalis*-derived polypeptide sequences, and a corresponding library of nucleic acid sequences encoding the polypeptides, wherein the polypeptides themselves, or polypeptides contained within ORFs of which they form a part, comprise sequences lacking homology to any known prokaryotic or eukaryotic sequences. Such libraries provide probes, primers, and markers which can be used to diagnose *E. faecalis* infection, including use as markers in epidemiological studies. Non-limiting examples of such sequences are listed by SEQ ID NO in Table 2, which is appended.

The present invention also provides a library of *E. faecalis*-derived polypeptide sequences, and a corresponding library of nucleic acid sequences encoding the polypeptides, wherein the polypeptides themselves, or polypeptides contained within ORFs of which they form a part, comprise targets for therapeutic drugs.

Specific Example: Determination of Enterococcus Protein Antigens for Antibody and Vaccine Development The selection of Enterococcus protein antigens for vaccine development can be derived from the nucleic acids encoding *E. faecalis* polypeptides. First, the ORF's can be analyzed for homology to other known exported or membrane proteins and analyzed using the discriminant analysis described by Klein, et al. (Klein, P., Kanehsia, M., and DeLisi, C. (1985) *Biochimica et Biophysica Acta* 815, 468–476) for predicting exported and membrane proteins.

Homology searches can be performed using the BLAST algorithm contained in the Wisconsin Sequence Analysis Package (Genetics Computer Group, University Research Park, 575 Science Drive, Madison, Wis. 53711) to compare each predicted ORF amino acid sequence with all sequences found in the current GenBank, SWISS-PROT and PIR databases. BLAST searches for local alignments between the ORF and the databank sequences and reports a probability score which indicates the probability of finding this sequence by chance in the database. ORF's with significant homology (e.g. probabilities lower than $1\times10^{-6}$ that the homology is only due to random chance) to membrane or exported proteins represent protein antigens for vaccine development. Possible functions can be provided to *E. faecalis* genes based on sequence homology to genes cloned in other organisms.

Discriminant analysis (Klein, et al. supra) can be used to examine the ORF amino acid sequences. This algorithm uses the intrinsic information contained in the ORF amino acid sequence and compares it to information derived from the properties of known membrane and exported proteins. This comparison predicts which proteins will be exported, membrane associated or cytoplasmic. ORF amino acid sequences identified as exported or membrane associated by this algorithm are likely protein antigens for vaccine development.

Production of Fragments and Analogs of *E. faecalis* Nucleic Acids and Polypeptides Based on the discovery of the *E. faecalis* gene products of the invention provided in the Sequence Listing, one skilled in the art can alter the disclosed structure (of *E. faecalis* genes), e.g., by producing fragments or analogs, and test the newly produced structures for activity. Examples of techniques known to those skilled in the relevant art which allow the production and testing of fragments and analogs are discussed below. These, or analogous methods can be used to make and screen libraries of polypeptides, e.g., libraries of random peptides or libraries of fragments or analogs of cellular proteins for the ability to bind *E. faecalis* polypeptides. Such screens are useful for the identification of inhibitors of *E. faecalis*.

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Alteration of Nucleic Acids and Polypeptides: Random Methods

Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein).

PCR Mutagenesis

In PCR mutagenesis, reduced Taq polymerase fidelity is used to introduce random mutations into a cloned fragment of DNA (Leung et al., 1989, *Technique* 1:11–15). The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, S A (1983) *Tetrahedron* 39:3; Itakura et al. (1981) *Recombinant DNA, Proc 3rd Cleveland Sympos. Macromolecules,* ed. A G Walton, Amsterdam: Elsevier pp273–289; Itakura et al. (1984) *Annu. Rev. Biochem.* 53:323; Itakura et al. (1984) *Science* 198:1056; Ike et al.

(1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Alteration of Nucleic Acids and Polypeptides: Methods for Directed Mutagenesis

Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci. USA*, 75: 5765 [1978]).

Cassette Mutagenesis

Another method for preparing variants, cassette mutagenesis, is based on the technique described by Wells et al. (*Gene,* 34:315[1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants (Ladner et al., WO 88/06630). In this method, the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Other Modifications of *E. faecalis* Nucleic Acids and Polypeptides

It is possible to modify the structure of an *E. faecalis* polypeptide for such purposes as increasing solubility, enhancing stability (e.g., shelf life ex vivo and resistance to proteolytic degradation in vivo). A modified *E. faecalis* protein or peptide can be produced in which the amino acid sequence has been altered, such as by amino acid substitution, deletion, or addition as described herein.

An *E. faecalis* peptide can also be modified by substitution of cysteine residues preferably with alanine, serine, threonine, leucine or glutamic acid residues to minimize dimerization via disulfide linkages. In addition, amino acid side chains of fragments of the protein of the invention can be chemically modified. Another modification is cyclization of the peptide.

In order to enhance stability and/or reactivity, an *E. faecalis* polypeptide can be modified to incorporate one or more polymorphisms in the amino acid sequence of the protein resulting from any natural allelic variation. Additionally, D-amino acids, non-natural amino acids, or non-amino acid analogs can be substituted or added to produce a modified protein within the scope of this invention. Furthermore, an *E. faecalis* polypeptide can be modified using polyethylene glycol (PEG) according to the method of A. Sehon and co-workers (Wie et al., supra) to produce a protein conjugated with PEG. In addition, PEG can be added during chemical synthesis of the protein. Other modifications of *E. faecalis* proteins include reduction/alkylation (Tarr, *Methods of Protein Microcharacterization,*

J. E. Silver ed., Humana Press, Clifton N.J. 155–194 (1986)); acylation (Tarr, supra); chemical coupling to an appropriate carrier (Mishell and Shiigi, eds, *Selected Methods in Cellular Immunology,* WH Freeman, San Francisco, Calif. (1980), U.S. Pat. No. 4,939,239; or mild formalin treatment (Marsh, (1971) *Int. Arch. of Allergy and Appl. Immunol.,* 41: 199–215).

To facilitate purification and potentially increase solubility of an *E. faecalis* protein or peptide, it is possible to add an amino acid fusion moiety to the peptide backbone. For example, hexa-histidine can be added to the protein for purification by immobilized metal ion affinity chromatography (Hochuli, E. et al., (1988) *Bio/Technology,* 6: 1321–1325). In addition, to facilitate isolation of peptides free of irrelevant sequences, specific endoprotease cleavage sites can be introduced between the sequences of the fusion moiety and the peptide.

To potentially aid proper antigen processing of epitopes within an *E. faecalis* polypeptide, canonical protease sensitive sites can be engineered between regions, each comprising at least one epitope via recombinant or synthetic methods. For example, charged amino acid pairs, such as KK or RR, can be introduced between regions within a protein or fragment during recombinant construction thereof. The resulting peptide can be rendered sensitive to cleavage by cathepsin and/or other trypsin-like enzymes which would generate portions of the protein containing one or more epitopes. In addition, such charged amino acid residues can result in an increase in the solubility of the peptide.

Primary Methods for Screening Polypeptides and Analogs

Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case, binding to *E. faecalis* polypeptide or an interacting protein, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid assays such as the system described below (as with the other screening methods described herein), can be used to identify polypeptides, e.g., fragments or analogs of a naturally-occurring *E. faecalis* polypeptide, e.g., of cellular proteins, or of randomly generated polypeptides which bind to an *E. faecalis* protein. (The *E. faecalis* domain is used as the bait protein and the library of variants are expressed as prey fusion proteins.) In an analogous fashion, a two hybrid assay (as with the other screening methods described herein), can be used to find polypeptides which bind a *E. faecalis* polypeptide.

Display Libraries

In one approach to screening assays, the Enterococcus peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, a detectably labeled ligand can be used to score for potentially functional peptide homologs. Fluorescently labeled ligands, e.g., receptors, can be used to detect homologs which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd., and fl are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:4457–4461).

A common approach uses the maltose receptor of *E. coli* (the outer membrane protein, LamB) as a peptide fusion partner (Charbit et al. (1986) *EMBO* 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) *Vaccines* 91, pp. 387–392), PhoE (Agterberg, et al. (1990) *Gene* 88, 37–45), and PAL (Fuchs et al. (1991) *Bio/Tech.* 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) *Appl. Environ. Microbiol.* 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of many peptide copies on the host cells (Kuwajima et al. (1988) *Bio/Tech.* 6, 1080–1083). Surface proteins of other bacterial species have also served as peptide fusion partners. Examples include the Staphylococcus protein A and the outer membrane IgA protease of Neisseria (Hansson et al. (1992) *J. Bacteriol.* 174, 4239–4245 and Klauser et al. (1990) *EMBO J.* 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) *PNAS USA* 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stablely associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. U.S.A.* 89–1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are under-represented in the libraries (Gallop et al. (1994) *J. Med. Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro method based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem.* 204,357–364). To identify the sequences of the active peptides one sequences the DNA produced by the phagemid host.

Secondary Screening of Polypeptides and Analogs

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of interest is identified, it is routine for one skilled in the art to obtain analogs and fragments.

Peptide Mimetics of *E. faecalis* Polypeptides

The invention also provides for reduction of the protein binding domains of the subject *E. faecalis* polypeptides to generate mimetics, e.g. peptide or non-peptide agents. The peptide mimetics are able to disrupt binding of a polypeptide to its counter ligand, e.g., in the case of an *E. faecalis* polypeptide binding to a naturally occurring ligand. The critical residues of a subject *E. faecalis* polypeptide which are involved in molecular recognition of a polypeptide can be determined and used to generate *E. faecalis*-derived peptidomimetics which competitively or noncompetitively inhibit binding of the *E. faecalis* polypeptide with an interacting polypeptide (see, for example, European patent applications EP-412,762A and EP-B31,080A).

For example, scanning mutagenesis can be used to map the amino acid residues of a particular *E. faecalis* polypeptide involved in binding an interacting polypeptide, peptidomimetic compounds (e.g. diazepine or isoquinoline derivatives) can be generated which mimic those residues in binding to an interacting polypeptide, and which therefore can inhibit binding of an *E. faecalis* polypeptide to an interacting polypeptide and thereby interfere with the function of *E. faecalis* polypeptide. For instance, nonhydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), b-turn dipeptide cores (Nagai et al. (1985) *Tetrahedron Lett* 26:647; and Sato et al. (1986) *J Chem Soc Perkin Trans* 1:1231), and b-aminoalcohols (Gordon et al. (1985) *Biochem Biophys Res Commun* 126:419; and et al. (1986) *Biochem Biophys Res Commun* 134:71).

Vaccine Formulations for *E. faecalis* Nucleic Acids and Polypeptides

This invention also features vaccine compositions for protection against infection by *E. faecalis* or for treatment of *E. faecalis* infection, a gram-positive bacterium. In one embodiment, the vaccine compositions contain one or more immunogenic components such as a surface protein from *E. faecalis*, or portion thereof, and a pharmaceutically acceptable carrier. Nucleic acids within the scope of the invention are exemplified by the nucleic acids of the invention contained in the Sequence Listing which encode *E. faecalis* surface proteins. Any nucleic acid encoding an immunogenic *E. faecalis* protein, or portion thereof, which is capable of expression in a cell, can be used in the present invention. These vaccines have therapeutic and prophylactic utilities.

One aspect of the invention provides a vaccine composition for protection against infection by *E. faecalis* which contains at least one immunogenic fragment of an *E. faecalis* protein and a pharmaceutically acceptable carrier. Preferred fragments include peptides of at least about 10 amino acid residues in length, preferably about 10–20 amino acid residues in length, and more preferably about 12–16 amino acid residues in length.

Immunogenic components of the invention can be obtained, for example, by screening polypeptides recombinantly produced from the corresponding fragment of the nucleic acid encoding the full-length *E. faecalis* protein. In addition, fragments can be chemically synthesized using techniques known in the art such as conventional Merrifield solid phase f-Moc or t-Boc chemistry.

In one embodiment, immunogenic components are identified by the ability of the peptide to stimulate T cells. Peptides which stimulate T cells, as determined by, for example, T cell proliferation or cytokine secretion are defined herein as comprising at least one T cell epitope. T cell epitopes are believed to be involved in initiation and perpetuation of the immune response to the protein allergen which is responsible for the clinical symptoms of allergy. These T cell epitopes are thought to trigger early events at the level of the T helper cell by binding to an appropriate HLA molecule on the surface of an antigen presenting cell, thereby stimulating the T cell subpopulation with the relevant T cell receptor for the epitope. These events lead to T cell proliferation, lymphokine secretion, local inflammatory reactions, recruitment of additional immune cells to the site of antigen/T cell interaction, and activation of the B cell cascade, leading to the production of antibodies. A T cell epitope is the basic element, or smallest unit of recognition by a T cell receptor, where the epitope comprises amino acids essential to receptor recognition (e.g., approximately 6 or 7 amino acid residues). Amino acid sequences which mimic those of the T cell epitopes are within the scope of this invention.

Screening immunogenic components can be accomplished using one or more of several different assays. For example, in vitro, peptide T cell stimulatory activity is assayed by contacting a peptide known or suspected of being immunogenic with an antigen presenting cell which presents appropriate MHC molecules in a T cell culture. Presentation of an immunogenic *E. faecalis* peptide in association with appropriate MHC molecules to T cells in conjunction with the necessary co-stimulation has the effect of transmitting a signal to the T cell that induces the production of increased levels of cytokines, particularly of interleukin-2 and interleukin-4. The culture supernatant can be obtained and assayed for interleukin-2 or other known cytokines. For example, any one of several conventional assays for interleukin-2 can be employed, such as the assay described in *Proc. Natl. Acad. Sci USA*, 86: 1333 (1989) the pertinent portions of which are incorporated herein by reference. A kit for an assay for the production of interferon is also available from Genzyme Corporation (Cambridge, Mass.).

Alternatively, a common assay for T cell proliferation entails measuring tritiated thymidine incorporation. The proliferation of T cells can be measured in vitro by determining the amount of $^3$H-labeled thymidine incorporated into the replicating DNA of cultured cells. Therefore, the rate of DNA synthesis and, in turn, the rate of cell division can be quantified.

Vaccine compositions of the invention containing immunogenic components (e.g., *E. faecalis* polypeptide or fragment thereof or nucleic acid encoding an *E. faecalis* polypeptide or fragment thereof) preferably include a pharmaceutically acceptable carrier. The term "pharmaceutically acceptable carrier" refers to a carrier that does not cause an allergic reaction or other untoward effect in patients to whom it is administered. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the antibody. For vaccines of the invention containing *E. faecalis* polypeptides, the polypeptide is co-administered with a suitable adjuvant.

It will be apparent to those of skill in the art that the therapeutically effective amount of DNA or protein of this invention will depend, inter alia, upon the administration schedule, the unit dose of antibody administered, whether the protein or DNA is administered in combination with other therapeutic agents, the immune status and health of the patient, and the therapeutic activity of the particular protein or DNA.

Vaccine compositions are conventionally administered parenterally, e.g., by injection, either subcutaneously or intramuscularly. Methods for intramuscular immunization are described by Wolff et al. (1990) *Science* 247: 1465–1468 and by Sedegah et al. (1994) *Immunology* 91: 9866–9870. Other modes of administration include oral and pulmonary formulations, suppositories, and transdermal applications. Oral immunization is preferred over parenteral methods for inducing protection against infection by *E. faecalis*. Cain et. al. (1993) *Vaccine* 11: 637–642. Oral formulations include such normally employed excipients as, for example, pharmaceutical grades of mannitol, lactose, starch, magnesium stearate, sodium saccharine, cellulose, magnesium carbonate, and the like.

The vaccine compositions of the invention can include an adjuvant, including, but not limited to aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphos-phoryloxy)-ethylamine (CGP 19835A, referred to a MTP-PE); RIBI, which contains three components from bacteria; monophosphoryl lipid A; trehalose dimycoloate; cell wall skeleton (MPL+TDM+CWS) in a 2% squalene/Tween 80 emulsion; and cholera toxin. Others which may be used are non-toxic derivatives of cholera toxin, including its B subunit, and/or conjugates or genetically engineered fusions of the *E. faecalis* polypeptide with cholera toxin or its B subunit, procholeragenoid, fungal polysaccharides, including schizophyllan, muramyl dipeptide, muramyl dipeptide derivatives, phorbol esters, labile toxin of *E. coli*, non-*E. faecalis* bacterial lysates, block polymers or saponins.

Other suitable delivery methods include biodegradable microcapsules or immuno-stimulating complexes (ISCOMs), cochleates, or liposomes, genetically engineered attenuated live vectors such as viruses or bacteria, and recombinant (chimeric) virus-like particles, e.g., bluetongue. The amount of adjuvant employed will depend on the type of adjuvant used. For example, when the mucosal adjuvant is cholera toxin, it is suitably used in an amount of 5 mg to 50 mg, for example 10 mg to 35 mg. When used in the form of microcapsules, the amount used will depend on the amount employed in the matrix of the microcapsule to achieve the desired dosage. The determination of this amount is within the skill of a person of ordinary skill in the art.

Carrier systems in humans may include enteric release capsules protecting the antigen from the acidic environment of the stomach, and including *E. faecalis* polypeptide in an insoluble form as fusion proteins. Suitable carriers for the vaccines of the invention are enteric coated capsules and polylactide-glycolide microspheres. Suitable diluents are 0.2 N NaHCO3 and/or saline.

Vaccines of the invention can be administered as a primary prophylactic agent in adults or in children, as a secondary prevention, after successful eradication of *E. faecalis* in an infected host, or as a therapeutic agent in the aim to induce an immune response in a susceptible host to prevent infection by *E. faecalis*. The vaccines of the invention are administered in amounts readily determined by persons of ordinary skill in the art. Thus, for adults a suitable dosage will be in the range of 10 mg to 10 g, preferably 10 mg to 100 mg. A suitable dosage for adults will also be in the range of 5 mg to 500 mg. Similar dosage ranges will be applicable for children. Those skilled in the art will recognize that the optimal dose may be more or less depending upon the patient's body weight, disease, the route of administration, and other factors. Those skilled in the art will also recognize that appropriate dosage levels can be obtained based on results with known oral vaccines such as, for example, a vaccine based on an *E. coli* lysate (6 mg dose daily up to total of 540 mg) and with an enterotoxigenic *E. coli* purified antigen (4 doses of 1 mg) (Schulman et al., *J. Urol.* 150:917–921 (1993); Boedecker et al., *American Gastroenterological Assoc.* 999:A-222 (1993)). The number of doses will depend upon the disease, the formulation, and efficacy data from clinical trials. Without intending any limitation as to the course of treatment, the treatment can be administered over 3 to 8 doses for a primary immunization schedule over 1 month (Boedeker, *American Gastroenterological Assoc.* 888:A-222 (1993)).

In a preferred embodiment, a vaccine composition of the invention can be based on a killed whole *E. coli* preparation with an immunogenic fragment of an *E. faecalis* protein of the invention expressed on its surface or it can be based on an *E. coli* lysate, wherein the killed *E. coli* acts as a carrier or an adjuvant.

It will be apparent to those skilled in the art that some of the vaccine compositions of the invention are useful only for preventing *E. faecalis* infection, some are useful only for treating *E. faecalis* infection, and some are useful for both preventing and treating *E. faecalis* infection. In a preferred embodiment, the vaccine composition of the invention provides protection against *E. faecalis* infection by stimulating humoral and/or cell-mediated immunity against *E. faecalis*. It should be understood that amelioration of any of the symptoms of *E. faecalis* infection is a desirable clinical goal, including a lessening of the dosage of medication used to treat *E. faecalis*-caused disease, or an increase in the production of antibodies in the serum or mucous of patients.

Antibodies Reactive with *E. faecalis* Polypeptides

The invention also includes antibodies specifically reactive with the subject *E. faecalis* polypeptide. Anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide. Techniques for conferring immunogenicity on a protein or peptide include conjugation to carriers or other techniques well known in the art. An immunogenic portion of the subject *E. faecalis* polypeptide can be administered in the presence of adjuvant. The progress of immunization can be monitored by detection of antibody titers in plasma or serum. Standard ELISA or other immunoassays can be used with the immunogen as antigen to assess the levels of antibodies.

In a preferred embodiment, the subject antibodies are immunospecific for antigenic determinants of the *E. faecalis* polypeptides of the invention, e.g. antigenic determinants of a polypeptide of the invention contained in the Sequence Listing, or a closely related human or non-human mammalian homolog (e.g., 90% homologous, more preferably at least 95% homologous). In yet a further preferred embodiment of the invention, the anti-*E. faecalis* antibodies do not substantially cross react (i.e., react specifically) with a protein which is for example, less than 80% percent homologous to a sequence of the invention contained in the Sequence Listing. By "not substantially cross react", it is meant that the antibody has a binding affinity for a non-homologous protein which is less than 10 percent, more preferably less than 5 percent, and even more preferably less than 1 percent, of the binding affinity for a protein of the invention contained in the Sequence Listing. In a most preferred embodiment, there is no cross-reactivity between bacterial and mammalian antigens.

The term antibody as used herein is intended to include fragments thereof which are also specifically reactive with *E. faecalis* polypeptides. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the invention is further intended to include bispecific and chimeric molecules having an anti-*E. faecalis* portion.

Both monoclonal and polyclonal antibodies (Ab) directed against *E. faecalis* polypeptides or *E. faecalis* polypeptide variants, and antibody fragments such as Fab' and F(ab')$_2$, can be used to block the action of *E. faecalis* polypeptide and allow the study of the role of a particular *E. faecalis* polypeptide of the invention in aberrant or unwanted intracellular signaling, as well as the normal cellular function of the *E. faecalis* and by microinjection of anti-*E. faecalis* polypeptide antibodies of the present invention.

Antibodies which specifically bind *E. faecalis* epitopes can also be used in immunohistochemical staining of tissue samples in order to evaluate the abundance and pattern of expression of *E. faecalis* antigens. Anti *E. faecalis* polypeptide antibodies can be used diagnostically in immunoprecipitation and immuno-blotting to detect and evaluate *E. faecalis* levels in tissue or bodily fluid as part of a clinical testing procedure. Likewise, the ability to monitor *E. faecalis* polypeptide levels in an individual can allow determination of the efficacy of a given treatment regimen for an individual afflicted with such a disorder. The level of an *E. faecalis* polypeptide can be measured in cells found in bodily fluid, such as in urine samples or can be measured in tissue, such as produced by gastric biopsy. Diagnostic assays using anti-*E. faecalis* antibodies can include, for example, immunoassays designed to aid in early diagnosis of *E. faecalis* infections. The present invention can also be used as a method of detecting antibodies contained in samples from individuals infected by this bacterium using specific *E. faecalis* antigens.

Another application of anti-*E. faecalis* polypeptide antibodies of the invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a subject *E. faecalis* polypeptide can then be detected with antibodies, as, for example, reacting nitrocellulose filters lifted from infected plates with anti-*E. faecalis* polypeptide antibodies. Phage, scored by this assay, can then be isolated from the infected plate. Thus, the presence of *E. faecalis* gene homologs can be detected and cloned from other species, and alternate isoforms (including splicing variants) can be detected and cloned.

Kits Containing Nucleic Acids, Polypeptides or Antibodies of the Invention

The nucleic acid, polypeptides and antibodies of the invention can be combined with other reagents and articles to form kits. Kits for diagnostic purposes typically comprise the nucleic acid, polypeptides or antibodies in vials or other suitable vessels. Kits typically comprise other reagents for performing hybridization reactions, polymerase chain reactions (PCR), or for reconstitution of lyophilized components, such as aqueous media, salts, buffers, and the like. Kits may also comprise reagents for sample processing such as detergents, chaotropic salts and the like. Kits may also comprise immobilization means such as particles, supports, wells, dipsticks and the like. Kits may also comprise labeling means such as dyes, developing reagents, radioisotopes, fluorescent agents, luminescent or chemiluminescent agents, enzymes, intercalating agents and the like. With the nucleic acid and amino acid sequence information provided herein, individuals skilled in art can readily assemble kits to serve their particular purpose. Kits further can include instructions for use.

Drug Screening Assays Using *E. faecalis* Polypeptides

By making available purified and recombinant *E. faecalis* polypeptides, the present invention provides assays which can be used to screen for drugs which are either agonists or antagonists of the normal cellular function, in this case, of the subject *E. faecalis* polypeptides, or of their role in intracellular signaling. Such inhibitors or potentiators may be useful as new therapeutic agents to combat *E. faecalis* infections in humans. A variety of assay formats will suffice and, in light of the present inventions, will be comprehended by the person skilled in the art.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target. Accordingly, in an exemplary screening assay of the present invention, the compound of interest is contacted with an isolated and purified *E. faecalis* polypeptide.

Screening assays can be constructed in vitro with a purified *E. faecalis* polypeptide or fragment thereof, such as an *E. faecalis* polypeptide having enzymatic activity, such that the activity of the polypeptide produces a detectable reaction product. The efficacy of the compound can be assessed by generating dose response curves from data obtained using various concentrations of the test compound. Moreover, a control assay can also be performed to provide a baseline for comparison. Suitable products include those with distinctive absorption, fluorescence, or chemiluminescence properties, for example, because detection may be easily automated. A variety of synthetic or naturally occurring compounds can be tested in the assay to identify those which inhibit or potentiate the activity of the *E. faecalis* polypeptide. Some of these active compounds may directly, or with chemical alterations to promote membrane permeability or solubility, also inhibit or potentiate the same activity (e.g., enzymatic activity) in whole, live *E. faecalis* cells.

Overexpression Assays

Overexpression assays are based on the premise that overproduction of a protein would lead to a higher level of resistance to compounds that selectively interfere with the function of that protein. Overexpression assays may be used to identify compounds that interfere with the function of virtually any type of protein, including without limitation enzymes, receptors, DNA- or RNA-binding proteins, or any proteins that are directly or indirectly involved in regulating cell growth.

Typically, two bacterial strains are constructed. One contains a single copy of the gene of interest, and a second contains several copies of the same gene. Identification of useful inhibitory compounds of this type of assay is based on a comparison of the activity of a test compound in inhibiting growth and/or viability of the two strains. The method involves constructing a nucleic acid vector that directs high level expression of a particular target nucleic acid. The vectors are then transformed into host cells in single or multiple copies to produce strains that express low to moderate and high levels of protein encoding by the target sequence (strain A and B, respectively). Nucleic acid comprising sequences encoding the target gene can, of course, be directly integrated into the host cell.

Large numbers of compounds (or crude substances which may contain active compounds) are screened for their effect on the growth of the two strains. Agents which interfere with an unrelated target equally inhibit the growth of both strains. Agents which interfere with the function of the target at high concentration should inhibit the growth of both strains. It should be possible, however, to titrate out the inhibitory effect of the compound in the overexpressing strain. That is, if the compound is affecting the particular target that is being tested, it should be possible to inhibit the growth of strain A at a concentration of the compound that allows strain B to grow.

Alternatively, a bacterial strain is constructed that contains the gene of interest under the control of an inducible promoter. Identification of useful inhibitory agents using this type of assay is based on a comparison of the activity of a test compound in inhibiting growth and/or viability of this strain under both inducing and non-inducing conditions. The method involves constructing a nucleic acid vector that directs high-level expression of a particular target nucleic acid. The vector is then transformed into host cells that are grown under both non-inducing and inducing conditions (conditions A and B, respectively).

Large numbers of compounds (or crude substances which may contain active compounds) are screened for their effect on growth under these two conditions. Agents that interfere with the function of the target should inhibit growth under both conditions. It should be possible, however, to titrate out the inhibitory effect of the compound in the overexpressing strain. That is, if the compound is affecting the particular target that is being tested, it should be possible to inhibit growth under condition A at a concentration that allows the strain to grow under condition B.

Ligand-binding Assays

Many of the targets according to the invention have functions that have not yet been identified. Ligand-binding assays are useful to identify inhibitor compounds that interfere with the function of a particular target, even when that function is unknown. These assays are designed to detect binding of test compounds to particular targets. The detection may involve direct measurement of binding. Alternatively, indirect indications of binding may involve stabilization of protein structure or disruption of a biological function. Non-limiting examples of useful ligand-binding assays are detailed below.

A useful method for the detection and isolation of binding proteins is the Biomolecular Interaction Assay (BIAcore) system developed by Pharmacia Biosensor and described in the manufacturer's protocol (LKB Pharmacia, Sweden). The BIAcore system uses an affinity purified anti-GST antibody to immobilize GST-fusion proteins onto a sensor chip. The sensor utilizes surface plasmon resonance which is an optical phenomenon that detects changes in refractive indices. In accordance with the practice of the invention, a protein of interest is coated onto a chip and test compounds are passed over the chip. Binding is detected by a change in the refractive index (surface plasmon resonance).

A different type of ligand-binding assay involves scintillation proximity assays (SPA, described in U.S. Pat. No. 4,568,649).

Another type of ligand binding assay, also undergoing development, is based on the fact that proteins containing mitochondrial targeting signals are imported into isolated mitochondria in vitro (Hurt et al., 1985, Embo J. 4:2061–2068; Eilers and Schatz, Nature, 1986, 322:228–231). In a mitochondrial import assay, expression vectors are constructed in which nucleic acids encoding particular target proteins are inserted downstream of sequences encoding mitochondrial import signals. The chimeric proteins are synthesized and tested for their ability to be imported into isolated mitochondria in the absence and presence of test compounds. A test compound that binds to the target protein should inhibit its uptake into isolated mitochondria in vitro.

Another ligand-binding assay is the yeast two-hybrid system (Fields and Song, 1989, Nature 340:245–246). The yeast two-hybrid system takes advantage of the properties of the GAL4 protein of the yeast Saccharomyces cerevisiae. The GAL4 protein is a transcriptional activator required for the expression of genes encoding enzymes of galactose utilization. This protein consists of two separable and functionally. essential domains: an N-terminal domain which binds to specific DNA sequences ($UAS_G$); and a C-terminal domain containing acidic regions, which is necessary to activate transcription. The native GAL4 protein, containing both domains, is a potent activator of transcription when yeast are grown on galactose media. The N-terminal domain binds to DNA in a sequence-specific manner but is unable to activate transcription. The C-terminal domain contains the activating regions but cannot activate transcription because it fails to be localized to $UAS_G$. In the two-hybrid system, a system of two hybrid proteins containing parts of GAL4: (1) a GAL4 DNA-binding domain fused to a protein 'X' and (2) a GAL4 activation region fused to a protein 'Y'. If X and Y can form a protein-protein complex and reconstitute proximity of the GAL4 domains, transcription of a gene regulated by $UAS_G$ occurs. Creation of two hybrid proteins, each containing one of the interacting proteins X and Y, allows the activation region of $UAS_G$ to be brought to its normal site of action.

The binding assay described in Fodor et al., 1991, Science 251:767–773, which involves testing the binding affinity of test compounds for a plurality of defined polymers synthesized on a solid substrate, may also be useful.

Compounds which bind to the polypeptides of the invention are potentially useful as antibacterial agents for use in therapeutic compositions.

Pharmaceutical formulations suitable for antibacterial therapy comprise the antibacterial agent in conjunction with one or more biologically acceptable carriers. Suitable biologically acceptable carriers include, but are not limited to, phosphate-buffered saline, saline, deionized water, or the like. Preferred biologically acceptable carriers are physiologically or pharmaceutically acceptable carriers.

The antibacterial compositions include an antibacterial effective amount of active agent. Antibacterial effective amounts are those quantities of the antibacterial agents of the present invention that afford prophylactic protection against bacterial infections or which result in amelioration or cure of an existing bacterial infection. This antibacterial effective amount will depend upon the agent, the location and nature of the infection, and the particular host. The amount can be determined by experimentation known in the art, such as by establishing a matrix of dosages and frequencies and comparing a group of experimental units or subjects to each point in the matrix.

The antibacterial active agents or compositions can be formed into dosage unit forms, such as for example, creams, ointments, lotions, powders, liquids, tablets, capsules, suppositories, sprays, aerosols or the like. If the antibacterial composition is formulated into a dosage unit form, the dosage unit form may contain an antibacterial effective amount of active agent. Alternatively, the dosage unit form may include less than such an amount if multiple dosage unit forms or multiple dosages are to be used to administer a total dosage of the active agent. Dosage unit forms can include, in addition, one or more excipient(s), diluent(s), disintegrant(s), lubricant(s), plasticizer(s), colorant(s), dosage vehicle(s), absorption enhancer(s), stabilizer(s), bactericide(s), or the like.

For general information concerning formulations, see, e.g., Gilman et al. (eds.), 1990, *Goodman and Gilman's: The Pharmacological Basis of Therapeutics,* 8th ed., Pergamon Press; and *Remington's Pharmaceutical Sciences,* 17th ed., 1990, Mack Publishing Co., Easton, Pa.; Avis et al. (eds.), 1993, *Pharmaceutical Dosage Forms: Parenteral Medications,* Dekker, New York; Lieberman et al (eds.), 1990, *Pharmaceutical Dosage Forms: Disperse Systems,* Dekker, New York.

The antibacterial agents and compositions of the present invention are useful for preventing or treating *E. faecalis* infections. Infection prevention methods incorporate a prophylactically effective amount of an antibacterial agent or composition. A prophylactically effective amount is an amount effective to prevent *E. faecalis* infection and will depend upon the specific bacterial strain, the agent, and the host. These amounts can be determined experimentally by methods known in the art and as described above.

*E. faecalis* infection treatment methods incorporate a therapeutically effective amount of an antibacterial agent or composition. A therapeutically effective amount is an amount sufficient to ameliorate or eliminate the infection. The prophylactically and/or therapeutically effective amounts can be administered in one administration or over repeated administrations. Therapeutic administration can be followed by prophylactic administration, once the initial bacterial infection has been resolved.

The antibacterial agents and compositions can be administered topically or systemically. Topical application is typically achieved by administration of creams, ointments, lotions, or sprays as described above. Systemic administration includes both oral and parental routes. Parental routes include, without limitation, subcutaneous, intramuscular, intraperitoneal, intravenous, transdermal, inhalation and intranasal administration.

EXEMPLIFICATION

Cloning and Sequencing *E. faecalis* Genomic Sequence

This invention provides nucleotide sequences of the genome of *E. faecalis* which thus comprises a DNA sequence library of *E. faecalis* genomic DNA. The detailed description that follows provides nucleotide sequences of *E. faecalis*, and also describes how the sequences were obtained and how ORFs (Open Reading Frames) and protein-coding sequences can be identified. Also described are methods of using the disclosed *E. faecalis* sequences in methods including diagnostic and therapeutic applications. Furthermore, the library can be used as a database for identification and comparison of medically important sequences in this and other strains of *E. faecalis* as well as other species of Enterococcus.

Chromosomal DNA from strain14336 of *E. faecalis* was isolated after Zymolyase digestion, sodium dodecyl sulfate lysis, potassium acetate precipitation, phenol:chloroform extraction and ethanol precipitation (Soll, D. R., T. Srikantha and S. R. Lockhart: Characterizing Developmentally Regulated Genes in *E. faecalis*. In Microbial Genome Methods. K. W. Adolph, editor. CRC Press. New York. p 17–37.). Genomic *E. faecalis* DNA was hydrodynamically sheared in an HPLC and then separated on a standard 1% agarose gel. Fractions corresponding to 2500–3000 bp in length were excised from the gel and purifed by the GeneClean procedure (Bio101, Inc.).

The purified DNA fragments were then blunt-ended using T4 DNA polymerase. The healed DNA was then ligated to unique BstXI-linker adapters (5'-GTCTTCACCACGGGG-3' and 5'-GTGGTGAAGAC-3' (SEQ ID NOS: 6811 and 6812) in 100–1000 fold molar excess). These linkers are complimentary to the BstXI-cut pGTC vector, while the overhang is not self-complimentary. Therefore, the linkers will not concatermerize nor will the cut-vector religate itself easily. The linker-adapted inserts were separated from the unincorporated linkers on a 1% agarose gel and purified using GeneClean. The linker-adapted inserts were then ligated to BstXI-cut vector to construct a "shotgun" sub-lclone libraries.

Only major modifications to the protocols are highlighted. Briefly, the library was then transformed into DH5á competent cells (Gibco/BRL, DH5á transformation protocol). It was assessed by plating onto antibiotic plates containing ampicillin and IPTG/Xgal. The plates were incubated overnight at 37° C. Transformants were then used for plating of clones and picking for sequencing. The cultures were grown overnight at 37° C. DNA was purified using a silica bead DNA preparation (Engelstein, 1996) method. In this manner, 25 $\mu$g of DNA was obtained per clone.

These purified DNA samples were then sequenced using primarily ABI dye-terminator chemistry. All subsequent steps were based on sequencing by ABI377 automated DNA sequencing methods. The ABI dye terminator sequence reads were run on ABI377 machines and the data was transferred to UNIX machines following lane tracking of the gels. Base calls and quality scores were determined using the program PHRED (Ewing et al., 1998, Genome Res. 8: 175–185; Ewing and Green, 1998, Genome Res. 8: 685–734). Reads were assembled using PHRAP (P. Green, Abstracts of DOE Human Genome Program Contractor—Grantee Workshop V, January 1996, p.157) with default program parameters and quality scores. The initial assembly was done at 2.3-fold coverage and yielded 712 contigs.

Finishing can follow the initial assembly. Missing mates (sequences from clones that only gave reads from one end of the Enterococcus DNA inserted in the plasmid) can be identified and sequenced with ABI technology to allow the identification of additional overlapping contigs.

End-sequencing of randomly picked genomic lambda was also performed. Sequencing on a both sides was done for all lambda sequences. The lambda library backbone helped to verify the integrity of the assembly and allowed closure of some of the physical gaps. Primers for walking off the ends of contigs would be selected using pick_primer (a GTC program) near the ends of the clones to facilitate gap closure. These walks can be sequenced using the selected clones and primers. These data are then reassembled with PHRAP. Additional sequencing using PCR-generated templates and screened and/or unscreened lambda templates can be done in addition.

To identify *E. faecalis* polypeptides the complete genomic sequence of *E. faecalis* were analyzed essentially as follows: First, all possible stop-to-stop open reading frames (ORFs) greater than 180 nucleotides in all six reading frames were translated into amino acid sequences. Second, the identified ORFs were analyzed for homology to known (archeabacter, prokaryotic and eukaryotic) protein sequences. Third, the coding potential of non-homologous sequences were evaluated with the program GENEMARK™ (Borodovsky and McIninch, 1993, Comp. Chem. 17:123).

Identification, Cloning and Expression of E. faecalis Nucleic Acids

Expression and purification of the E. faecalis polypeptides of the invention can be performed essentially as outlined below.

To facilitate the cloning, expression and purification of membrane and secreted proteins from E. faecalis, a gene expression system, such as the pET System (Novagen), for cloning and expression of recombinant proteins in E. coli, is selected. Also, a DNA sequence encoding a peptide tag, the His-Tag, is fused to the 3' end of DNA sequences of interest in order to facilitate purification of the recombinant protein products. The 3' end is selected for fusion in order to avoid alteration of any 5' terminal signal sequence.

PCR Amplification and Cloning of Nucleic Acids Containing ORF's Encoding Enzymes Nucleic acids chosen (for example, from the nucleic acids set forth in SEQ ID NO: 1–SEQ ID NO: 3405) for cloning from the 14336 strain of E. faecalis are prepared for amplification cloning by polymerase chain reaction (PCR). Synthetic oligonucleotide primers specific for the 5' and 3' ends of open reading frames (ORFs) are designed and purchased from GibcoBRL Life Technologies (Gaithersburg, Md., USA). All forward primers (specific for the 5' end of the sequence) are designed to include an NcoI cloning site at the extreme 5' terminus. These primers are designed to permit initiation of protein translation at a methionine residue followed by a valine residue and the coding sequence for the remainder of the native E. faecalis DNA sequence. All reverse primers (specific for the 3' end of any E. faecalis ORF) include a EcoRI site at the extreme 5' terminus to permit cloning of each E. faecalis sequence into the reading frame of the pET-28b. The pET-28b vector provides sequence encoding an additional 20 carboxy-terminal amino acids including six histidine residues (at the extreme C-terminus), which comprise the His-Tag.

Genomic DNA prepared from the 14336 strain of E. faecalis is used as the source of template DNA for PCR amplification reactions (Current Protocols in Molecular Biology, John Wiley and Sons, Inc., F. Ausubel et al., eds., 1994). To amplify a DNA sequence containing an E. faecalis ORF, genomic DNA (50 nanograms) is introduced into a reaction vial containing 2 mM $MgCl_2$, 1 micromolar synthetic oligonucleotide primers (forward and reverse primers) complementary to and flanking a defined E. faecalis ORF, 0.2 mM of each deoxynucleotide triphosphate; dATP, dGTP, dCTP, dTTP and 2.5 units of heat stable DNA polymerase (Amplitaq, Roche Molecular Systems, Inc., Branchburg, N.J., USA) in a final volume of 100 microliters.

Upon completion of thermal cycling reactions, each sample of amplified DNA is washed and purified using the Qiaquick Spin PCR purification kit (Qiagen, Gaithersburg, Md., USA). All amplified DNA samples are subjected to digestion with the restriction endonucleases, e.g., NcoI and EcoRI (New England BioLabs, Beverly, Mass., USA) (Current Protocols in Molecular Biology, John Wiley and Sons, Inc., F. Ausubel et al., eds., 1994). DNA samples are then subjected to electrophoresis on 1.0% NuSeive (FMC BioProducts, Rockland, Me. USA) agarose gels. DNA is visualized by exposure to ethidium bromide and long wave uv irradiation. DNA contained in slices isolated from the agarose gel is purified using the Bio 101 GeneClean Kit protocol (Bio 101 Vista, Calif., USA).

Cloning of E. faecalis Nucleic Acids into an Expression Vector

The pET-28b vector is prepared for cloning by digestion with endonucleases, e.g., NcoI and EcoRI (Current Protocols in Molecular Biology, John Wiley and Sons, Inc., F. Ausubel et al., eds., 1994). The pET-28a vector, which encodes a His-Tag that can be fused to the 5' end of an inserted gene, is prepared by digestion with appropriate restriction endonucleases.

Following digestion, DNA inserts are cloned (Current Protocols in Molecular Biology, John Wiley and Sons, Inc., F. Ausubel et al., eds., 1994) into the previously digested pET-28b expression vector. Products of the ligation reaction are then used to transform the BL21 strain of E. coli (Current Protocols in Molecular Biology, John Wiley and Sons, Inc., F. Ausubel et al., eds., 1994) as described below.

Transformation of Competent Bacteria with Recombinant Plasmids

Competent bacteria, E coli strain BL21 or E. coli strain BL21 (DE3), are transformed with recombinant pET expression plasmids carrying the cloned E. faecalis sequences according to standard methods (Current Protocols in Molecular, John Wiley and Sons, Inc., F. Ausubel et al., eds., 1994). Briefly, 1 microliter of ligation reaction is mixed with 50 microliters of electrocompetent cells and subjected to a high voltage pulse, after which, samples are incubated in 0.45 milliliters SOC medium (0.5% yeast extract, 2.0% tryptone, 10 mM NaCl, 2.5 mM KCl, 10 mM MgCl2, 10 mM MgSO4 and 20, mM glucose) at 37° C. with shaking for 1 hour. Samples are then spread on LB agar plates containing 25 microgram/ml kanamycin sulfate for growth overnight. Transformed colonies of BL21 are then picked and analyzed to evaluate cloned inserts as described below.

Identification of Recombinant Expression Vectors with E. faecalis Nucleic Acids

Individual BL21 clones transformed with recombinant pET-28b E. faecalis ORFs are analyzed by PCR amplification of the cloned inserts using the same forward and reverse primers, specific for each E. faecalis sequence, that were used in the original PCR amplification cloning reactions. Successful amplification verifies the integration of the E. faecalis sequences in the expression vector (Current Protocols in Molecular Biology, John Wiley and Sons, Inc., F. Ausubel et al., eds., 1994).

Isolation and Preparation of Nucleic Acids from Transformants

Individual clones of recombinant pET-28b vectors carrying properly cloned E. faecalis ORFs are picked and incubated in 5 mls of LB broth plus 25 microgram/ml kanamycin sulfate overnight. The following day plasmid DNA is isolated and purified using the Qiagen plasmid purification protocol (Qiagen Inc., Chatsworth, Calif., USA).

Expression of Recombinant E. faecalis Sequences in E. coli

The pET vector can be propagated in any E. coli K-12 strain e.g. HMS174, HB101, JM109, DH5, etc. for the purpose of cloning or plasmid preparation. Hosts for expression include E. coli strains containing a chromosomal copy of the gene for T7 RNA polymerase. These hosts are lysogens of bacteriophage DE3, a lambda derivative that carries the lacI gene, the lacUV5 promoter and the gene for T7 RNA polymerase. T7 RNA polymerase is induced by addition of isopropyl-B-D-thiogalactoside (IPTG), and the T7 RNA polymerase transcribes any target plasmid, such as pET-28b, carrying its gene of interest. Strains used include: BL21(DE3) (Studier, F. W., Rosenberg, A. H., Dunn, J. J., and Dubendorff, J. W. (1990) Meth. Enzymol. 185, 60–89).

To express recombinant E. faecalis sequences, 50 nanograms of plasmid DNA isolated as described above is used to transform competent BL21(DE3) bacteria as described above (provided by Novagen as part of the pET expression system kit). The lacZ gene (beta-galactosidase) is expressed in the pET-System as described for the *E. faecalis* recombinant constructions. Transformed cells are cultured in SOC medium for 1 hour, and the culture is then plated on LB plates containing 25 micrograms/ml kanamycin sulfate. The following day, bacterial colonies are pooled and grown in LB medium containing kanamycin sulfate (25 micrograms/ml) to an optical density at 600 nM of 0.5 to 1.0 O.D. units, at which point, 1 millimolar IPTG was added to the culture for 3 hours to induce gene expression of the *E. faecalis* recombinant DNA constructions.

After induction of gene expression with IPTG, bacteria are pelleted by centrifugation in a Sorvall RC-3B centrifuge at 3500×g for 15 minutes at 4° C. Pellets are resuspended in 50 milliliters of cold 10 mM Tris-HCl, pH 8.0, 0.1 M NaCl and 0.1 mM EDTA (STE buffer). Cells are then centrifuged at 2000×g for 20 min at 4° C. Wet pellets are weighed and frozen at −80° C. until ready for protein purification.

A variety of methodologies known in the art can be utilized to purify the isolated proteins. (Current Protocols in Protein Science, John Wiley and Sons, Inc., J. E. Coligan et al., eds., 1995). For example, the frozen cells are thawed, resupended in buffer and ruptured by several passages through a small volume microfluidizer (Model M-110S, Microfluidics International Corporation, Newton, Mass.). The resultant homogenate is centrifuged to yield a clear supernatant (crude extract) and following filtration the crude extract is fractionated over columns. Fractions are monitored by absorbance at $OD_{280}$ nm. and peak fractions may analyzed by SDS-PAGE.

The concentrations of purified protein preparations are quantified spectrophotometrically using absorbance coefficients calculated from amino acid content (Perkins, S. J. 1986 Eur. J. Biochem. 157, 169–180). Protein concentrations are also measured by the method of Bradford, M. M. (1976) Anal. Biochem. 72, 248–254, and Lowry, O. H., Rosebrough, N., Farr, A. L. & Randall, R. J. (1951) J. Biol. Chem. 193, pages 265–275, using bovine serum albumin as a standard.

SDS-polyacrylamide gels of various concentrations are purchased from BioRad (Hercules, Calif., USA), and stained with Coomassie blue. Molecular weight markers may include rabbit skeletal muscle myosin (200 kDa), *E. coli* (-galactosidase (116 kDa), rabbit muscle phosphorylase B (97.4 kDa), bovine serum albumin (66.2 kDa), ovalbumin (45 kDa), bovine carbonic anhydrase (31 kDa), soybean trypsin inhibitor (21.5 kDa), egg white lysozyme (14.4 kDa) and bovine aprotinin (6.5 kDa).

EQUIVALENTS

Those skilled in the art will recognize, or be able to ascertain using no more than routine experimentation, many equivalents to the specific embodiments and methods described herein. The specific embodiments described herein are offered by way of example only, and the invention is to limited only by the terms of the appended claims, along with the full scope of equivalents to which such claims are entitled.

TABLE 2

| Contig | Orf | NT Seq Id | AA Seq ID | NT Orf Length | AA Orf Length | Score | Probability | Description |
|---|---|---|---|---|---|---|---|---|
| contig100 | 35409705_f3_1 | 1 | 3406 | 918 | 305 | 437 | 2.40E-41 | SP:P77327] [OR:*ESCHERICHIA COLI*] [GN:PROY] [DE:PROLINE SPECIFIC PERMEASE PROY] |
| contig101 | 31647702_f1_1 | 2 | 3407 | 738 | 246 | 619 | 1.20E-60 | SP:P46338] [OR:*BACILLUS SUBTILIS*] [GN:YQGG] [DE:REGION PRECURSOR (ORF108)] |
| contig102 | 32602186_c2_2 | 3 | 3408 | 627 | 208 | 245 | 5.30E-21 | [AC:D90783] [OR:*Escherichia coli*] [PN:Spermidine/putrescine transport ATP-binding] [NT:ORF_ID] |
| contig103 | 35160251_f1_1 | 4 | 3409 | 534 | 178 | 501 | 4.00E-48 | SP:P54548] [OR:*BACILLUS SUBTILIS*] [GN:YOJK] [DE:HYPOTHETICAL 34.0 KD PROTEIN IN GLNQ-ANSR INTERGENIC REGION] |
| contig104 | 781525_c1_3 | 5 | 3410 | 651 | 216 | 527 | 7.00E-51 | SP:P44697] [OR:*HAEMOPHILUS INFLUENZAE*] [GN:HI0416] [DE:HYPOTHETICAL PROTEIN HI0416] |
| contig105 | 24430340_c3_4 | 6 | 3411 | 510 | 169 | 55 | 0.84 | [AC:M30560] [OR:*Mus musculus*] [NT:Ig mu-chain V-D-J region] |
| contig105 | 2232162_c2_3 | 7 | 3412 | 555 | 184 | 83 | 0.14 | SP:P37467] [OR:*BACILLUS SUBTILIS*] [GN:XPAC] [DE:XPAC PROTEIN] |
| contig106 | 5132942_f2_2 | 8 | 3413 | 255 | 85 | 160 | 7.10E-11 | [AC:D86418] [OR:*Bacillus subtilis*] [PN:Yfnl] |
| contig107 | 16302276_f1_1 | 9 | 3414 | 372 | 123 | 197 | 6.50E-16 | SP:P54452] [OR:*BACILLUS SUBTILIS*] [GN:YOEG] [DE:HYPOTHETICAL 20.1 KD PROTEIN IN NUCB-AROD INTERGENIC REGION] |
| contig107 | 19726707_f3_2 | 10 | 3415 | 366 | 121 | 265 | 4.10E-23 | SP:P54453] [OR:*BACILLUS SUBTILIS*] [GN:YOEH] [DE:HYPOTHETICAL 41.0 KD PROTEIN IN NUCB-AROD INTERGENIC REGION] |
| contig108 | 33690625_c3_11 | 11 | 3416 | 591 | 197 | 264 | 5.20E-23 | SP:P45691] [OR:*ESCHERICHIA COLI*] [GN:YHCS] [DE:(O309)] |
| contig108 | 35651090_f1_1 | 12 | 3417 | 213 | 70 | 53 | 0.69 | SP:P10713] [OR:*NEUROSPORA CRASSA*] [GN:CON-10] [DE:CONIDIATION-SPECIFIC PROTEIN 10] |
| contig108 | 2551651_c2_9 | 13 | 3418 | 366 | 121 | 84 | 0.0049 | [AC:U53885] [OR:*Mycobacterium avium*] [PN:fibronectin attachment protein] [GN:FAP-A] |
| contig109 | 17162_f3_2 | 14 | 3419 | 324 | 107 | 172 | 6.90E-13 | SP:P75942] [OR:*ESCHERICHIA COLI*] [GN:FLGJ] [DE:FLAGELLAR PROTEIN FLGJ] |
| contig109 | 14954677_f1_1 | 15 | 3420 | 654 | 218 | 84 | 0.82 | SP:P22382] [OR:SIMIAN IMMUNODEFICIENCY VIRUS] [GN:POL] [DE:TRANSCRIPTASE;; RIBONUCLEASE H.] |
| contig11 | 35677382_f1_1 | 16 | 3421 | 690 | 229 | 638 | 1.90E-62 | SP:P41972] [OR:*STAPHYLOCOCCUS AUREUS*] [GN:ILES] [DE:(ILERS)] |
| contig110 | 33400061_c2_6 | 17 | 3422 | 963 | 321 | 445 | 3.40E-42 | [AC:D50098] [OR:*Bacillus subtilis*] [PN:multidrug transporter] [GN:bmr3] |
| contig110 | 19817885_c2_5 | 18 | 3423 | 405 | 134 | 562 | 1.40E-54 | SP:P54419] [OR:*BACILLUS SUBTILIS*] [GN:METK] [DE:ADENOSYLTRANSFERASE) (ADOMET SYNTHETASE)] |
| contig111 | 3994212_f3_3 | 19 | 3424 | 192 | 63 | 89 | 0.00066 | [AC:M32103] [OR:*Staphylococcus aureus*] [NT:ORF-27] |
| contig111 | 22151437_f1_1 | 20 | 3425 | 540 | 179 | 223 | 1.10E-18 | [AC:M32103] [OR:*Staphylococcus aureus*] [NT:ORF-27] |
| contig112 | 26589762_f2_2 | 21 | 3426 | 396 | 131 | 337 | 1.40E-30 | SP:P23240] [OR:*VIBRIO CHOLERAE*] [GN:ALDA] [DE:ALDEHYDE DEHYDROGENASE.] |
| contig112 | 25485887_c2_4 | 22 | 3427 | 369 | 122 | 378 | 4.30E-35 | SP:P00343] [OR:*LACTOBACILLUS CASEI*] [DE:L-LACTATE DEHYDROGENASE.] |
| contig113 | 594567_f1_1 | 23 | 3428 | 273 | 90 | 330 | 5.30E-30 | SP:P07842] [OR:*BACILLUS STEAROTHERMOPHILUS*] [GN:RPSI] [DE:30S RIBOSOMAL PROTEIN S9 (BS10)] |
| contig113 | 14501449_c1_5 | 24 | 3429 | 588 | 195 | 125 | 2.00E-06 | SP:P20709] [OR:BACTERIOPHAGE L54A] [GN:INT] [DE:INTEGRASE] |
| contig114 | 5910137_f3_2 | 25 | 3430 | 756 | 251 | 384 | 1.00E-35 | [AC:U36837] [OR:*Lactococcus lactis*] [PN:ORFU] |

TABLE 2-continued

| Contig | Orf | NT Seq Id | AA Seq ID | NT Orf Length | AA Orf Length | Score | Probability | Description |
|---|---|---|---|---|---|---|---|---|
| contig114 | 4486088_f1_1 | 26 | 3431 | 198 | 65 | 56 | 0.43 | [AC:PS0274] [OR:*Parechinus angulosus*] [PN:homeotic protein box6] [GN:box6] |
| contig115 | 22382306_c3_3 | 27 | 3432 | 843 | 281 | 1090 | 1.50E-110 | [AC:U72720] [OR:*Streptococcus pneumoniae*] [PN:heat shock protein 70] [GN:dnaK] [NT:HSP70; partial peptide sequencing was also done] |
| contig116 | 253181_f1_1 | 28 | 3433 | 717 | 238 | 849 | 5.30E-85 | [AC:M92842] [OR:*Listeria monocytogenes*] [GN:prs] |
| contig117 | 14660938_c3_3 | 29 | 3434 | 1338 | 446 | 129 | 1.00E-05 | [SP:P55140] [OR:*ESCHERICHIA COLI*] [GN:YGCG] [DE:HYPOTHETICAL 34.9 KD PROTEIN IN CYSJ-ENO INTERGENIC REGION (O313)] |
| contig118 | 7082011_f2_1 | 30 | 3435 | 504 | 167 | 168 | 7.70E-13 | [AC:Z82987] [OR:*Bacillus subtilis*] [PN:unknown, highly similar to *E. coli* YecD] [GN:ywoC] |
| contig118 | 14625627_c3_4 | 31 | 3436 | 282 | 93 | 189 | 4.60E-15 | [AC:Z75208] [OR:*Bacillus subtilis*] [PN:hypothetical protein] [GN:ysbB] [NT:homology to ywbG of *Bacillus subtilis*; putative] |
| contig119 | 23861675_c2_3 | 32 | 3437 | 720 | 240 | 690 | 3.70E-68 | [SP:P23630] [OR:*BACILLUS SUBTILIS*] [GN:LYSA] [DE:DIAMINOPIMELATE DECARBOXYLASE, (DAP DECARBOXYLASE)] |
| contig12 | 25551286_c1_1 | 33 | 3438 | 570 | 189 | 608 | 1.80E-59 | [SP:P77834] [OR:*BACILLUS STEAROTHERMOPHILUS*] [GN:DEOD] [DE:(PNP)] |
| contig120 | 30712532_f3_2 | 34 | 3439 | 501 | 166 | 250 | 1.60E-21 | [SP:P39787] [OR:*BACILLUS SUBTILIS*] [GN:DNAD] [DE:DNA REPLICATION PROTEIN DNAD] |
| contig120 | 34648427_f2_1 | 35 | 3440 | 555 | 185 | 423 | 7.30E-40 | [SP:P39788] [OR:*BACILLUS SUBTILIS*] [GN:NTH] [DE:APYRIMIDINIC SITE) LYASE] |
| contig121 | 24069450_c3_4 | 36 | 3441 | 819 | 273 | 338 | 7.50E-31 | [AC:U64312] [OR:*Bacillus firmus*] [PN:amidase] |
| contig122 | 34084442_f1_1 | 37 | 3442 | 621 | 206 | 447 | 2.10E-42 | [AC:Z75208] [OR:*Bacillus subtilis*] [PN:trigger factor] [GN:tig] [NT:homology to trigger factor of Haemophilus] |
| contig122 | 6148577_f3_3 | 38 | 3443 | 540 | 179 | 480 | 6.70E-46 | [SP:P19775] [OR:*STAPHYLOCOCCUS AUREUS*] [GN:TNP] [DE:TRANSPOSASE FOR INSERTION SEQUENCE ELEMENT IS256 IN TRANSPOSON TN4001] |
| contig123 | 22460816_c2_3 | 39 | 3444 | 318 | 105 | | | |
| contig123 | 33203387_f3_1 | 40 | 3445 | 678 | 225 | 142 | 2.70E-07 | [AC:AB001488] [OR:*Bacillus subtilis*] [GN:ydeE] [NT:SIMILAR TO ORF16 OF *ENTEROCOCCUS FAECALIS*] |
| contig124 | 976590_f1_1 | 41 | 3446 | 1230 | 410 | 352 | 2.40E-32 | [AC:D90009] [OR:Synechocystis sp.] [PN:hypothetical protein] [NT:ORF_ID] |
| contig125 | 1268806_f3_1 | 42 | 3447 | 408 | 135 | 63 | 0.999 | [AC:D87601] [OR:Measles virus] [PN:fusion protein] |
| contig125 | 3945468_f3_2 | 43 | 3448 | 423 | 141 | 174 | 1.00E-12 | [SP:P54389] [OR:*BACILLUS SUBTILIS*] [GN:YPIA] [DE:HYPOTHETICAL 48.3 KD PROTEIN IN QCRA 5'REGION] |
| contig126 | 6929630_f1_1 | 44 | 3449 | 195 | 64 | 69 | 0.52 | [AC:U59323] [OR:*Homo sapiens*] [PN:homolog of yeast UPF1] [GN:HUPF1] [NT:putative Zn Knuckle; type 1 RNA helicase region; |
| contig126 | 36142138_f2_2 | 45 | 3450 | 393 | 130 | 123 | 4.50E-08 | [SP:P05706] [OR:*ESCHERICHIA COLI*] [GN:SRLB] [DE:II, A COMPONENT), (EIII-GUT)] |
| contig127 | 4100463_c1_2 | 46 | 3451 | 471 | 156 | 382 | 6.30E-40 | [SP:P37455] [OR:*BACILLUS SUBTILIS*] [GN:SSB] [DE:SINGLE-STRAND BINDING PROTEIN (SSB) (HELIX-DESTABILIZING PROTEIN)] |
| contig127 | 992176_c3_3 | 47 | 3452 | 234 | 77 | 66 | 0.41 | [SP:P47254] [OR:*MYCOPLASMA GENITALIUM*] [GN:THDF] [DE:POSSIBLE THIOPHENE AND FURAN OXIDATION PROTEIN THDF] |
| contig128 | 35162513_c2_6 | 48 | 3453 | 435 | 145 | 60 | 0.25 | [AC:U42580] [OR:*Paramecium bursaria* Chlorella virus 1] [GN:a269R] |
| contig128 | 4328591_c2_5 | 49 | 3454 | 735 | 244 | 111 | 0.00041 | [SP:Q58207] [OR:*METHANOCOCCUS JANNASCHII*] [GN:MJ0797] [DE:HYPOTHETICAL PROTEIN MJ0797] |

TABLE 2-continued

| Contig | Orf | NT Seq Id | AA Seq ID | NT Orf Length | AA Orf Length | Score | Probability | Description |
|---|---|---|---|---|---|---|---|---|
| contig129 | 36207812_c1_6 | 50 | 3455 | 204 | 68 | 81 | 0.0029 | [SP:P80239] [OR:*BACILLUS SUBTILIS*] [GN:AHPC] [DE:PROTEIN 22] |
| contig129 | 24645438_c1_5 | 51 | 3456 | 801 | 266 | 523 | 1.90E-50 | [AC:X99710] [OR:*Lactococcus lactis*] [PN:methyltransferase] [NT:homology with (D64004)] |
| contig129 | 24506253_c3_7 | 52 | 3457 | 207 | 68 | 55 | 0.52 | [AC:U19586] [OR:*Kluyveromyces lactis*] [NT:similar to *Saccharomyces cerevisiae* KIN28,] |
| contig13 | 21973437_c2_4 | 53 | 3458 | 369 | 123 | 132 | 8.20E-08 | [SP:P47473] [OR:*MYCOPLASMA GENITALIUM*] [GN:NRDE] [DE:(RIBONUCLEOTIDE REDUCTASE)] |
| contig13 | 4688465_c3_5 | 54 | 3459 | 258 | 85 | 166 | 1.80E-11 | [SP:P50620] [OR:*BACILLUS SUBTILIS*] [GN:NRDE] [DE:(RIBONUCLEOTIDE REDUCTASE)] |
| contig13 | 16597525_f2_2 | 55 | 3460 | 222 | 73 | 50 | 0.9999 | [AC:L76581] [OR:*Escherichia coli*] [PN:unknown] |
| contig130 | 35316275_f2_2 | 56 | 3461 | 189 | 62 | 68 | 0.03 | [OR:*Mycoplasma hyopneumoniae*] [PN:hypothetical protein] |
| contig130 | 35194512_c3_3 | 57 | 3462 | 489 | 162 | 654 | 2.40E-64 | [SP:P12047] [OR:*BACILLUS SUBTILIS*] [GN:PURB] [DE:ADENYLOSUCCINATE LYASE, (ADENYLOSUCCINASE) (ASL)] |
| contig131 | 782751_f2_2 | 58 | 3463 | 504 | 168 | 51 | 0.92 | [SP:P07367] [OR:*RHODOBACTER CAPSULATUS*] [GN:PUCA] [DE:PIGMENT PROTEIN, ALPHA CHAIN] |
| contig132 | 26209843_f2_2 | 59 | 3464 | 798 | 265 | 844 | 1.80E-84 | [AC:U51115] [OR:*Bacillus subtilis*] [PN:GMP synthetase] [GN:guaA] |
| contig133 | 4801442_c3_5 | 60 | 3465 | 741 | 246 | 521 | 3.00E-50 | [AC:Z94043] [OR:*Bacillus subtilis*] [PN:hypothetical protein] [GN:yvdM] [NT:putative beta-phosphoglucomutase] |
| contig133 | 10573524_c1_3 | 61 | 3466 | 351 | 116 | 152 | 1.30E-09 | [SP:Q10850] [OR:*MYCOBACTERIUM TUBERCULOSIS*] [GN:MTCY39.11C] [DE:HYPOTHETICAL 145.8 KD PROTEIN CY39.11C] |
| contig134 | 19823425_f3_2 | 62 | 3467 | 717 | 238 | 488 | 9.50E-47 | [SP:P43440] [OR:*ENTEROCOCCUS HIRAE*] [GN:NTPJ] [DE:TRANSLOCATING ATPASE SUBUNIT J] |
| contig134 | 35183438_f2_1 | 63 | 3468 | 348 | 115 | 214 | 2.80E-17 | [SP:P26235] [OR:*ENTEROCOCCUS HIRAE*] [GN:NAPA] [DE:NA(+)/H(+) ANTIPORTER] |
| contig135 | 5910176_f3_2 | 64 | 3469 | 186 | 61 | 102 | 2.00E-05 | [SP:P44865] [OR:*HAEMOPHILUS INFLUENZAE*] [GN:GPMA] [DE:(BPG-DEPENDENT PGAM)] |
| contig135 | 34171792_f2_1 | 65 | 3470 | 585 | 194 | 655 | 1.90E-64 | [SP:P44865] [OR:*HAEMOPHILUS INFLUENZAE*] [GN:GPMA] [DE:(BPG-DEPENDENT PGAM)] |
| contig135 | 11931254_c1_4 | 66 | 3471 | 621 | 206 | 557 | 4.60E-54 | [SP:Q04944] [OR:*CLOSTRIDIUM ACETOBUTYLICUM*] [GN:BDHA] [DE:NADH-DEPENDENT BUTANOL DEHYDROGENASE A, (BDH I)] |
| contig136 | 34179767_c2_3 | 67 | 3472 | 1047 | 348 | 171 | 2.40E-10 | [AC:AE000125] [OR:*Escherichia coli*] [PN:hypothetical protein in hemL-pfs intergenic] [GN:yadQ] [NT:o473; 100 pct identical to YADQ_ECOLI SW] |
| contig137 | 35406287_f1_1 | 68 | 3473 | 1110 | 369 | 1036 | 8.10E-105 | [AC:D78193] [OR:*Bacillus subtilis*] [GN:yydE] |
| contig137 | 2923202_c3_2 | 69 | 3474 | 228 | 75 | 65 | 0.22 | [SP:Q28233] [OR:*CERVUS ELAPHUS*] [GN:IL12A] [DE:MATURATION FACTOR 35 KD SUBUNIT] (CLMF P35)] |
| contig138 | 24823512_c3_3 | 70 | 3475 | 480 | 159 | 348 | 6.50E-32 | [AC:AB002150] [OR:*Bacillus subtilis*] [PN:YbbK] |
| contig138 | 24328187_f1_1 | 71 | 3476 | 324 | 108 | 65 | 0.93 | [AC:M95596] [OR:*Oryctolagus cuniculus*] [PN:titin] |
| contig139 | 14101442_f3_1 | 72 | 3477 | 1035 | 344 | 1360 | 3.70E-139 | [SP:P39815] [OR:*BACILLUS SUBTILIS*] [GN:GID] [DE:GID PROTEIN (FRAGMENT)] |
| contig14 | 12146825_f2_1 | 73 | 3478 | 183 | 60 | 72 | 0.034 | [SP:P46378] [OR:*RHODOCOCCUS FASCIANS*] [GN:FAS6] [DE:HYPOTHETICAL 21.1 KD PROTEIN IN FASCIATION LOCUS (ORF6)] |
| contig14 | 11931555_c3_3 | 74 | 3479 | 279 | 92 | 304 | 3.00E-27 | [SP:P54537] [OR:*BACILLUS SUBTILIS*] [GN:YQIZ] [DE:INTERGENIC REGION] |

TABLE 2-continued

| Contig | Orf | NT Seq Id | AA Seq ID | NT Orf Length | AA Orf Length | Score | Probability | Description |
|---|---|---|---|---|---|---|---|---|
| contig140 | 34064712_c1_4 | 75 | 3480 | 243 | 81 | 61 | 0.47 | [AC:U22157] [OR:*Methanosarcina thermophila*] [PN:beta-type proteasome subunit] [GN:psmB] |
| contig140 | 1073426_c1_3 | 76 | 3481 | 810 | 269 | 66 | 0.24 | [SP:Q01049] [OR:*HERPESVIRUS SAIMIRI*] [GN:53] [DE:PUTATIVE MEMBRANE PROTEIN 53] |
| contig140 | 12579377_c2_5 | 77 | 3482 | 396 | 131 | 164 | 1.60E-11 | [AC:L16534] [OR:*Rhodococcus corallinus*] [PN:N-ethylammeline chlorohydrolase] [GN:trzA] |
| contig141 | 4961528_c2_5 | 78 | 3483 | 333 | 111 | 181 | 3.30E-14 | [SP:P39803] [OR:*BACILLUS SUBTILIS*] [GN:YITT] [DE:HYPOTHETICAL 30.5 KD PROTEIN IN IPI 5'REGION (ORF1)] |
| contig141 | 6292137_f1_1 | 79 | 3484 | 258 | 85 | 61 | 0.994 | [SP:P32745] [OR:*HOMO SAPIENS*] [GN:SSTR3] [DE:SOMATOSTATIN RECEPTOR TYPE 3 (SS3R) (SSR-28)] |
| contig141 | 16611010_f3_3 | 80 | 3485 | 531 | 176 | 521 | 3.00E-50 | [AC:Y09476] [OR:*Bacillus subtilis*] [PN:YitK] [NT:putative - Some homology with HI1034 (H.] |
| contig142 | 289688_c1_4 | 81 | 3486 | 414 | 137 | 175 | 4.30E-13 | [SP:Q38653] [OR:BACTERIOPHAGE A511] [GN:PLY511] [DE:ENDOLYSIN, (N-ACETYLMURAMOYL-L-ALANINE AMIDASE] |
| contig142 | 23476577_c3_5 | 82 | 3487 | 198 | 65 | 52 | 0.92 | [SP:P46079] [OR:ANABAENA SP] [DE:HYPOTHETICAL 13.8 KD PROTEIN IN FRAC 3'REGION] |
| contig142 | 25583436_f2_1 | 83 | 3488 | 243 | 81 | 50 | 0.99 | [AC:Z79753] [OR:*Caenorhabditis elegans*] [PN:F35E12.8] |
| contig143 | 3611001_f1_1 | 84 | 3489 | 252 | 83 | 51 | 0.85 | [OR:*Presbytis entellus*] [PN:MHC class II histocompatibility antigen DQ alpha chain 1] |
| contig143 | 23377_f2_3 | 85 | 3490 | 942 | 313 | 278 | 1.70E-24 | [AC:D37826] [OR:*Photobacterium damsela* subsp. *piscicida*] [PN:PP-FLO] |
| contig144 | 34617817_f1_1 | 86 | 3491 | 993 | 330 | 228 | 3.40E-19 | [SP:P44869] [OR:*HAEMOPHILUS INFLUENZAE*] [GN:HI0767] [DE:HYPOTHETICAL PROTEIN HI0767] |
| contig144 | 6281316_f2_2 | 87 | 3492 | 276 | 92 | 173 | 2.30E-13 | [SP:P23875] [OR:*ESCHERICHIA COLI*] [GN:KDTB] [DE:LIPOPOLYSACCHARIDE CORE BIOSYNTHESIS PROTEIN KDTB] |
| contig145 | 36133462_f3_1 | 88 | 3493 | 462 | 153 | 61 | 0.51 | [AC:Z75208] [OR:*Bacillus subtilis*] [PN:hypothetical protein] [GN:yshA] [NT:unknown function; putative] |
| contig145 | 11181916_c1_2 | 89 | 3494 | 201 | 66 | 66 | 0.11 | [AC:L25385] [OR:*Chloroplast Phragmites australis*] [PN:RNA polymerase beta-subunit] [GN:rpoC2] |
| contig147 | 24252326_f1_1 | 90 | 3495 | 303 | 100 | 67 | 0.9999 | [AC:U64198] [OR:*Homo sapiens*] [PN:II-12 receptor beta2] |
| contig147 | 36126057_c1_5 | 91 | 3496 | 474 | 157 | 338 | 7.50E-31 | [SP:P33385] [OR:*LISTERIA MONOCYTOGENES*] [DE:(ORFZ)] |
| contig147 | 26596327_c1_4 | 92 | 3497 | 195 | 64 | 113 | 5.20E-07 | [SP:P54173] [OR:*BACILLUS SUBTILIS*] [GN:YPIQ] [DE:HYPOTHETICAL 19.9 KD PROTEIN IN ILVD-THYB INTERGENIC REGION] |
| contig148 | 25423317_f2_2 | 93 | 3498 | 1299 | 432 | 79 | 0.15 | [OR:*Rattus norvegicus*] [PN:protein kinase C substrate, 80K] |
| contig149 | 16406308_f3_4 | 94 | 3499 | 351 | 116 | 76 | 0.22 | [SP:P15994] [OR:*PODOSPORA ANSERINA*] [DE:ATP SYNTHASE A CHAIN, (PROTEIN 6)] |
| contig149 | 2742882_f2_3 | 95 | 3500 | 471 | 157 | 208 | 4.40E-17 | [AC:Y09476] [OR:*Bacillus subtilis*] [PN:YisV] [NT:putative] |
| contig15 | 3360312_f1_1 | 96 | 3501 | 459 | 152 | 516 | 1.00E-49 | [AC:Z93937] [OR:*Bacillus subtilis*] [PN:unknown] [GN:yufQ] |
| contig150 | 10010957_c1_4 | 97 | 3502 | 408 | 136 | 289 | 1.20E-24 | [SP:Q54089] [OR:*STREPTOCOCCUS EQUISIMILIS*] [GN:RELA] [DE:PROTEIN] |
| contig150 | 444662_c3_6 | 98 | 3503 | 261 | 86 | 235 | 6.10E-20 | [SP:P54461] [OR:*BACILLUS SUBTILIS*] [GN:YOEU] [DE:HYPOTHETICAL 28.8 KD PROTEIN IN DNAJ-RPSU INTEREGENIC REGION] |
| contig150 | 24042813_c3_5 | 99 | 3504 | 192 | 63 | 128 | 3.30E-08 | [SP:P54461] [OR:*BACILLUS SUBTILIS*] [GN:YOEU] [DE:HYPOTHETICAL 28.8 KD PROTEIN IN DNAJ-RPSU INTEREGENIC REGION] |

TABLE 2-continued

| Contig | Orf | NT Seq Id | AA Seq ID | NT Orf Length | AA Orf Length | Score | Probability | Description |
|---|---|---|---|---|---|---|---|---|
| contig151 | 4710963_f3_1 | 100 | 3505 | 603 | 200 | 59 | 0.63 | [SP:P72851] [OR:SYNECHOCYSTIS SP] [GN:RPMB] [DE:50S RIBOSOMAL PROTEIN L28] |
| contig151 | 24390927_c2_4 | 101 | 3506 | 186 | 61 | 65 | 0.15 | [SP:P01365] [OR:SACCHAROMYCES CEREVISIAE] [GN:MATAL1] [DE:MATING-TYPE PROTEIN ALPHA-1] |
| contig152 | 5334552_f1_1 | 102 | 3507 | 291 | 96 | 242 | 1.10E-20 | [SP:P55873] [OR:BACILLUS SUBTILIS] [GN:RPLT] [DE:50S RIBOSOMAL PROTEIN L20] |
| contig152 | 12923552_c1_4 | 103 | 3508 | 387 | 128 | 228 | 3.40E-19 | [SP:P37507] [OR:BACILLUS SUBTILIS] [GN:YAQ] [DE:HYPOTHETICAL 13.9 KD PROTEIN IN COTF-TETB INTERGENIC REGION] |
| contig152 | 31438465_f3_3 | 104 | 3509 | 204 | 67 | | | |
| contig153 | 24636010_f2_2 | 105 | 3510 | 240 | 79 | 235 | 6.10E-20 | [SP:P37807] [OR:BACILLUS SUBTILIS] [GN:RPMB] [DE:RIBOSOMAL PROTEIN L28] |
| contig153 | 5370716_c3_3 | 106 | 3511 | 510 | 169 | 50 | 0.9995 | [AC:Y14082] [OR:Bacillus subtilis] [PN:hypothetical protein] [GN:yhdS] [NT:Similarity to a hypothetical protein, YF18, from] |
| contig154 | 24015950_c3_5 | 107 | 3512 | 309 | 102 | 53 | 0.86 | [OR:Entamoeba histolytica] [PN:amoebapore B] |
| contig154 | 6928125_f3_4 | 108 | 3513 | 402 | 134 | 139 | 9.10E-10 | [AC:Y14081] [OR:Bacillus subtilis] [PN:hypothetical protein] [GN:yhjE] [NT:Similarity to hypothetical protein yqeD from] |
| contig155 | 6095133_f1_1 | 109 | 3514 | 513 | 170 | | | |
| contig155 | 19687530_f2_3 | 110 | 3515 | 312 | 103 | 51 | 0.98 | [AC:Z84823] [OR:Nicotiana tabacum] [PN:phospholipase D] [NT:5' fragment] |
| contig155 | 21724200_f1_2 | 111 | 3516 | 456 | 151 | 75 | 0.83 | [AC:749968] [OR:Caenorhabditis elegans] [NT:similarity to the Drosophila disabled protein; cDNA] |
| contig156 | 259825_c3_5 | 112 | 3517 | 234 | 78 | 55 | 0.52 | [SP:P51415] [OR:MYCOPLASMA CAPRICOLUM] [GN:RPMG] [DE:50S RIBOSOMAL PROTEIN L33] |
| contig156 | 23955562_c3_4 | 113 | 3518 | 546 | 181 | 325 | 1.80E-29 | [SP:P54475] [OR:BACILLUS SUBTILIS] [GN:YQFR] [DE:PROBABLE RNA HELICASE IN CCCA-SODA INTERGENIC REGION] |
| contig157 | 14665802_f3_1 | 114 | 3519 | 804 | 268 | 910 | 1.80E-91 | [SP:Q53727] [OR:STAPHYLOCOCCUS AUREUS] [GN:PCRA] [DE:ATP-DEPENDENT HELICASE PCRA.] |
| contig158 | 207340_f3_2 | 115 | 3520 | 1059 | 352 | 343 | 2.20E-31 | [SP:P44550] [OR:HAEMOPHILUS INFLUENZAE] [GN:HI0172] [DE:HYPOTHETICAL PROTEIN HI0172] |
| contig158 | 25880002_c2_3 | 116 | 3521 | 270 | 89 | 55 | 0.999 | [AC:Z86089] [OR:Mycobacterium tuberculosis] [PN:unknown] [GN:MTCY0A4.04c] [NT:MTCY0A4.04c, 381 aa, some similarity to] |
| contig159 | 16611577_f3_3 | 117 | 3522 | 501 | 166 | 488 | 9.50E-47 | [SP:P42923] [OR:BACILLUS SUBTILIS] [GN:RPLJ] [DE:50S RIBOSOMAL PROTEIN L10 (BL5)] |
| contig16 | 7082035_f2_1 | 118 | 3523 | 966 | 322 | 853 | 2.00E-85 | [SP:Q24803] [OR:ENTAMOEBA HISTOLYTICA] [GN:ADH2] [DE:ALCOHOL DEHYDROGENASE 2.] |
| contig160 | 2601444_c1_1 | 119 | 3524 | 327 | 108 | 255 | 4.80E-21 | [AC:L26286] [OR:Schistosoma mansoni] [PN:SMDR1] |
| contig161 | 19729692_f3_2 | 120 | 3525 | 414 | 137 | 407 | 3.60E-38 | [SP:P37887] [OR:BACILLUS SUBTILIS] [GN:CYSK] [DE:(O-ACETYL)SERINE (THIOL)-LYASE (CSASE)] |
| contig161 | 23469005_f2_1 | 121 | 3526 | 591 | 196 | 468 | 1.20E-44 | [SP:P37887] [OR:BACILLUS SUBTILIS] [GN:CYSK] [DE:(O-ACETYL)SERINE (THIOL)-LYASE (CSASE)] |
| contig162 | 14582001_f1_1 | 122 | 3527 | 876 | 292 | 303 | 1.00E-25 | [SP:Q10850] [OR:MYCOBACTERIUM TUBERCULOSIS] [GN:MTCY39.11C] [DE:HYPOTHETICAL 145.8 KD PROTEIN CY39.11C] |
| contig163 | 24331561_c2_5 | 123 | 3528 | 1023 | 341 | 1046 | 7.00E-106 | [SP:Q00752] [OR:STREPTOCOCCUS MUTANS] [GN:MSMK] [DE:MULTIPLE SUGAR-BINDING TRANSPORT ATP-BINDING PROTEIN MSMK] |

TABLE 2-continued

| Contig | Orf | NT Seq Id | AA Seq ID | NT Orf Length | AA Orf Length | Score | Probability | Description |
|---|---|---|---|---|---|---|---|---|
| contig164 | 35957051_f1_1 | 124 | 3529 | 495 | 164 | 298 | 1.30E-26 | [SP:P33661] [OR:*CLOSTRIDIUM ACETOBUTYLICUM*] [DE:HYPOTHETICAL 15.2 KD PROTEIN IN SIGG 3'REGION (ORF V)] |
| contig164 | 2242937_f1_2 | 125 | 3530 | 309 | 102 | 129 | 9.30E-08 | [SP:P07908] [OR:*BACILLUS SUBTILIS*] [GN:DNAB] [DE:REPLICATION INITIATION AND MEMBRANE ATTACHMENT PROTEIN] |
| contig165 | 35410177_f1_1 | 126 | 3531 | 489 | 162 | 53 | 0.97 | [SP:P00840] [OR:*ZEA MAYS*] [GN:ATP9] [DE:PROTEIN] |
| contig165 | 6542687_f1_2 | 127 | 3532 | 321 | 107 | 213 | 3.20E-17 | [SP:P37112] [OR:*BACILLUS STEAROTHERMOPHILUS*] [GN:AMA] [DE:N-ACYL-L-AMINO ACID AMIDOHYDROLASE, (AMINOACYLASE)] |
| contig166 | 34197182_c3_3 | 128 | 3533 | 720 | 239 | 733 | 1.00E-72 | [SP:P35159] [OR:*BACILLUS SUBTILIS*] [GN:YPUL] [DE:HYPOTHETICAL 26.0 KD PROTEIN IN SPMB-AROC INTERGENIC REGION (ORFX13)] |
| contig167 | 26220638_c1_4 | 129 | 3534 | 306 | 102 | 119 | 2.00E-07 | [OR:*Methanococcus jannaschii*] [PN:hypothetical protein MJ1163] |
| contig167 | 12535400_c1_3 | 130 | 3535 | 501 | 166 | 120 | 1.00E-06 | [OR:*Streptomyces coelicolor*] [PN:acVA-1 protein] |
| contig168 | 24628186_c2_4 | 131 | 3536 | 666 | 221 | 595 | 4.40E-58 | [AC:D83026] [OR:*Bacillus subtilis*] [GN:cydD] [NT:homologous to many ATP-binding transport proteins;] |
| contig168 | 36140775_c1_3 | 132 | 3537 | 213 | 70 | 64 | 0.12 | [SP:P47579] [OR:*MYCOPLASMA GENITALIUM*] [GN:MG337] [DE:HYPOTHETICAL PROTEIN MG337] |
| contig169 | 14114030_f3_1 | 133 | 3538 | 876 | 291 | 258 | 2.20E-22 | [AC:Y09476] [OR:*Bacillus subtilis*] [PN:DegA] |
| contig169 | 24401533_c3_5 | 134 | 3539 | 384 | 127 | | | |
| contig17 | 5117318_f2_1 | 135 | 3540 | 786 | 261 | 422 | 9.40E-40 | [AC:U51911] [OR:*Bacillus subtilis*] [PN:unknown] [GN:ykrA] [NT:similar in C-terminus to partial sequence of orf1] |
| contig170 | 24425150_f3_1 | 136 | 3541 | 609 | 202 | 60 | 0.5 | [OR:*Homo sapiens*] [PN:Sm protein G] |
| contig170 | 13148452_f3_2 | 137 | 3542 | 240 | 80 | 74 | 0.096 | [AC:Y10304] [OR:*Bacillus subtilis*] [GN:priA] |
| contig171 | 5098212_f1_1 | 138 | 3543 | 570 | 189 | 128 | 6.40E-07 | [SP:Q03158] [OR:*STREPTOCOCCUS PNEUMONIAE*] [GN:ENDA] [DE:DNA-ENTRY NUCLEASE (COMPETENCE-SPECIFIC NUCLEASE)] |
| contig171 | 23629682_f2_2 | 139 | 3544 | 267 | 89 | 78 | 0.019 | [AC:U88907] [OR:*Pseudomonas wisconsinensis*] [PN:lipase helper protein] [GN:lpwB] [NT:LpwB; necessary for activation of LpwA] |
| contig172 | 16800967_f1_1 | 140 | 3545 | 1638 | 545 | 434 | 5.00E-41 | [AC:U67998] [OR:*Sinorhizobium meliloti*] [PN:cyclic beta-1,2-glucan modification protein] [GN:cgmA] [NT:ORF2; with similarity to rkpI gene product encoded] |
| contig173 | 7071877_f1_1 | 141 | 3546 | 852 | 283 | 751 | 1.30E-74 | [SP:P43472] [OR:*PEDIOCOCCUS PENTOSACEUS*] [GN:SCRR] [DE:SUCROSE (SCR) OPERON REPRESSOR] |
| contig174 | 1300800_c2_3 | 142 | 3547 | 738 | 245 | 566 | 5.10E-55 | [SP:P54521] [OR:*BACILLUS SUBTILIS*] [GN:YQIB] [DE:VII LARGE SUBUNIT] |
| contig175 | 6350408_f2_2 | 143 | 3548 | 375 | 124 | 330 | 5.30E-30 | [SP:P39796] [OR:*BACILLUS SUBTILIS*] [GN:TRER] [DE:TREHALOSE OPERON TRANSCRIPTIONAL REPRESSOR] |
| contig175 | 35360936_f3_3 | 144 | 3549 | 690 | 229 | 52 | 0.999 | [AC:M55534] [OR:*Rattus norvegicus*] [PN:alpha(B)-crystallin] [NT:ORF2] |
| contig176 | 4070317_f1_1 | 145 | 3550 | 213 | 70 | 56 | 0.43 | [AC:Z66494] [OR:*Caenorhabditis elegans*] [PN:T01B7.1] |
| contig176 | 26306587_c2_6 | 146 | 3551 | 495 | 164 | 66 | 0.997 | [AC:U38915] [OR:*Synechocystis sp.*] [PN:hypothetical transposase] [NT:C-terminal part of the truncated hypothetical] |
| contig176 | 16212837_c3_7 | 147 | 3552 | 720 | 239 | 607 | 2.30E-59 | [SP:P31458] [OR:*ESCHERICHIA COLI*] [GN:YIDU] [DE:HYPOTHETICAL 64.0 KD PROTEIN IN IBPA-GYRB INTERGENIC REGION] |
| contig177 | 13861532_c2_4 | 148 | 3553 | 813 | 270 | 52 | 0.78 | [AC:X92955] [OR:*Brassica oleracea*] [PN:pollen coat protein] [NT:putative] |

TABLE 2-continued

| Contig | Orf | NT Seq Id | AA Seq ID | NT Orf Length | AA Orf Length | Score | Probability | Description |
|---|---|---|---|---|---|---|---|---|
| contig177 | 26839662_c3_5 | 149 | 3554 | 615 | 204 | 54 | 0.7 | [AC:JH0658] [OR:*Chlamydia psittaci*] [PN:histone H1-like protein] |
| contig178 | 26578936_f1_1 | 150 | 3555 | 243 | 80 | 191 | 3.40E-15 | [SP:P54530] [OR:*BACILLUS SUBTILIS*] [GN:YQIS] [DE:(PHOSPHOTRANSBUTYRYLASE)] |
| contig178 | 22870312_f1_2 | 151 | 3556 | 696 | 232 | 627 | 1.80E-61 | [OR:*Clostridium acetobutylicum*] [PN:butyrate kinase] |
| contig179 | 6523282_f1_1 | 152 | 3557 | 450 | 149 | | | |
| contig179 | 20078317_f3_3 | 153 | 3558 | 528 | 175 | 199 | 8.30E-15 | [AC:Y14078] [OR:*Bacillus subtilis*] [PN:Hypothetical protein] [GN:yhaN] [NT:similarity to orfX from *Staphylococcus aureus*] |
| contig18 | 25414063_f3_1 | 154 | 3559 | 801 | 267 | 310 | 8.70E-28 | [AC:D90905] [OR:*Synechocystis sp.*] [PN:hypothetical protein] [NT:ORF_ID] |
| contig180 | 3907966_f3_1 | 155 | 3560 | 579 | 192 | 267 | 2.50E-23 | [AC:AB001488] [OR:*Bacillus subtilis*] [GN:ydgI] [NT:SIMILAR TO NITROREDUCTASE.] |
| contig181 | 20507325_f1_1 | 156 | 3561 | 546 | 181 | 485 | 2.00E-46 | [AC:U57759] [OR:*Streptococcus gordonii*] [PN:intrageneric coaggregation-relevant adhesin] |
| contig181 | 34275682_f2_3 | 157 | 3562 | 780 | 259 | 78 | 0.997 | [SP:P26027] [OR:*BRADYRHIZOBIUM JAPONICUM*] [GN:NODU] [DE:NODULATION PROTEIN U.] |
| contig181 | 4875063_c2_4 | 158 | 3563 | 318 | 105 | 207 | 5.70E-17 | [AC:U51115] [OR:*Bacillus subtilis*] [PN:unknown] [NT:yeebF] |
| contig182 | 1052192_c2_5 | 159 | 3564 | 246 | 82 | 98 | 2.00E-05 | [SP:P23884] [OR:*ESCHERICHIA COLI*] [GN:GCVH] [DE:GLYCINE CLEAVAGE SYSTEM H PROTEIN] |
| contig182 | 24808067_c3_7 | 160 | 3565 | 384 | 127 | 120 | 9.40E-08 | [SP:P54503] [OR:*BACILLUS SUBTILIS*] [GN:YOGZ] [DE:HYPOTHETICAL 14.8 KD PROTEIN IN SODA-COMGA INTERGENIC REGION] |
| contig182 | 31855510_c3_6 | 161 | 3566 | 687 | 228 | 196 | 3.20E-15 | [SP:P39604] [OR:*BACILLUS SUBTILIS*] [GN:YWCF] [DE:HYPOTHETICAL 43.3 KD PROTEIN IN QOXD-VPR INTERGENIC REGION] |
| contig183 | 35290627_f2_1 | 162 | 3567 | 510 | 169 | 67 | 0.088 | [AC:Z81331] [OR:*Mycobacterium tuberculosis*] [PN:unknown] [GN:MTCY16B7.35c] [NT:MTCY16B7.35c, unknown, len] |
| contig183 | 25680250_f2_2 | 163 | 3568 | 945 | 315 | 724 | 9.30E-72 | [SP:P54460] [OR:*BACILLUS SUBTILIS*] [GN:YQET] [DE:HYPOTHETICAL 34.6 KD PROTEIN IN DNAJ-RPSU INTEREGENIC REGION] |
| contig184 | 34632787_f3_3 | 164 | 3569 | 372 | 123 | 53 | 0.84 | [AC:L47974] [OR:*Bos taurus*] [PN:TATA-box binding protein] |
| contig184 | 34586007_c1_4 | 165 | 3570 | 387 | 128 | | | |
| contig184 | 401683_c3_5 | 166 | 3571 | 306 | 101 | 175 | 4.30E-13 | [AC:U19620] [OR:*Agrobacterium tumefaciens*] [PN:MocD] [GN:mocD] |
| contig185 | 11832325_f2_2 | 167 | 3572 | 849 | 282 | 811 | 5.60E-81 | [AC:AF000658] [OR:*Streptococcus pneumoniae*] [PN:putative serine protease] [GN:sphtra] [NT:SPHtra] |
| contig185 | 14272500_c2_4 | 168 | 3573 | 366 | 121 | 219 | 4.50E-17 | [SP:P43820] [OR:*HAEMOPHILUS INFLUENZAE*] [GN:PHET] [DE:TRNA LIGASE BETA CHAIN] (PHERS)] |
| contig186 | 36026883_f1_1 | 169 | 3574 | 372 | 123 | 164 | 2.00E-12 | [SP:P54519] [OR:*BACILLUS SUBTILIS*] [GN:YOHY] [DE:HYPOTHETICAL 14.7 KD PROTEIN IN ACCC-FOLD INTERGENIC REGION] |
| contig186 | 14501578_f2_3 | 170 | 3575 | 531 | 177 | 210 | 2.20E-16 | [SP:P47609] [OR:*MYCOPLASMA GENITALIUM*] [GN:MG369] [DE:HYPOTHETICAL PROTEIN MG369] |
| contig187 | 24742937_c1_5 | 171 | 3576 | 885 | 295 | 647 | 1.30E-63 | [SP:Q46171] [OR:*CLOSTRIDIUM PERFRINGENS*] [GN:ARCC] [DE:CARBAMATE KINASE.] |
| contig187 | 35253525_c2_6 | 172 | 3577 | 654 | 217 | 179 | 3.00E-13 | [SP:P37489] [OR:*BACILLUS SUBTILIS*] [GN:YBO] [DE:HYPOTHETICAL 48.2 KD PROTEIN IN COTF-TETB INTERGENIC REGION] |
| contig188 | 6350281_f1_1 | 173 | 3578 | 1086 | 362 | 631 | 6.70E-62 | [SP:Q53727] [OR:*STAPHYLOCOCCUS AUREUS*] [GN:PCRA] [DE:ATP-DEPENDENT HELICASE PCRA.] |

TABLE 2-continued

| Contig | Orf | NT Seq Id | AA Seq ID | NT Orf Length | AA Orf Length | Score | Probability | Description |
|---|---|---|---|---|---|---|---|---|
| contig189 | 34252285_c2_3 | 174 | 3579 | 864 | 288 | 686 | 9.90E-68 | [SP:Q46807] [OR:ESCHERICHIA COLI] [GN:YQEA] [DE:CARBAMATE KINASE-LIKE PROTEIN 1] |
| contig189 | 973278_c3_4 | 175 | 3580 | 300 | 99 | 65 | 0.9991 | [SP:P24588] [OR:HOMO SAPIENS] [DE:REGULATORY SUBUNIT II HIGH AFFINITY BINDING PROTEIN] |
| contig19 | 32657757_c2_1 | 176 | 3581 | 543 | 181 | 492 | 3.60E-47 | [SP:P54476] [OR:BACILLUS SUBTILIS] [GN:YQFS] [DE:PROBABLE ENDONUCLEASE IV, (ENDODEOXYRIBONUCLEASE IV)] |
| contig19 | 4790931_c3_2 | 177 | 3582 | 327 | 108 | 68 | 0.992 | [AC:AB000622] [OR:Enterobacter cloacae] [PN:MelY] [GN:melY] |
| contig19 | 29392275_f2_2 | 178 | 3583 | 279 | 92 | 67 | 0.21 | [SP:P43013] [OR:HAEMOPHILUS INFLUENZAE] [GN:HI1366] [DE:HYPOTHETICAL PROTEIN HI1366 (ORF3)] |
| contig190 | 26570830_c1_6 | 179 | 3584 | 690 | 229 | 418 | 2.50E-39 | [OR:Methanococcus jannaschii] [PN:ABC transporter probable ATP-binding subunit homolog] |
| contig190 | 14631452_c3_7 | 180 | 3585 | 219 | 72 | 53 | 0.89 | [SP:P42618] [OR:ESCHERICHIA COLI] [GN:YQJE] [DE:HYPOTHETICAL 15.1 KD PROTEIN IN EXUR-TDCC INTERGENIC REGION] |
| contig191 | 24728386_c3_4 | 181 | 3586 | 732 | 244 | 538 | 7.90E-52 | [AC:Z75208] [OR:Bacillus subtilis] [PN:hypothetical protein] [GN:yshD] [NT:shows homology to mutS of Thermus aquaticus;] |
| contig191 | 20523312_c2_3 | 182 | 3587 | 543 | 180 | 356 | 8.40E-32 | [AC:Z75208] [OR:Bacillus subtilis] [PN:hypothetical protein] [GN:yshD] [NT:shows homology to mutS of Thermus aquaticus;] |
| contig192 | 24656655_f2_3 | 183 | 3588 | 291 | 96 | 169 | 6.00E-13 | [SP:P07472] [OR:HALOPHILIC EUBACTERIUM NRCC 41227] [GN:RPL1] [DE:50S RIBOSOMAL PROTEIN L7/L12 ('A' TYPE)] |
| contig192 | 33867817_f1_1 | 184 | 3589 | 198 | 65 | 54 | 0.96 | [OR:Mus musculus] [PN:corticosteroid-binding globulin] |
| contig192 | 19726550_c2_4 | 185 | 3590 | 438 | 145 | 71 | 0.37 | [OR:Arabidopsis thaliana] [PN:V-type proton-ATPase] |
| contig193 | 7032562_f1_1 | 186 | 3591 | 945 | 314 | 1203 | 1.60E-122 | [OR:Bacillus subtilis] [PN:recE protein] [GN:recE] |
| contig193 | 630301_c3_4 | 187 | 3592 | 183 | 60 | | | |
| contig194 | 1953142_f1_1 | 188 | 3593 | 522 | 173 | 298 | 1.30E-26 | [AC:U73111] [OR:Salmonella typhimurium] [PN:high-affinity periplasmic glutamine binding] |
| contig194 | 32226087_f2_2 | 189 | 3594 | 852 | 284 | 275 | 3.50E-24 | [SP:P10344] [OR:ESCHERICHIA COLI] [GN:GLNH] [DE:GLUTAMINE-BINDING PERIPLASMIC PROTEIN PRECURSOR (GLNBP)] |
| contig195 | 4884708_c3_3 | 190 | 3595 | 1245 | 415 | 861 | 2.80E-86 | [AC:Y08559] [OR:Bacillus subtilis] [PN:Unknown] [GN:ywnE] [NT:Product similar to Escherichia coli cardiolipin] |
| contig196 | 22270327_f3_4 | 191 | 3596 | 183 | 60 | 58 | 0.29 | [SP:P13308] [OR:BACTERIOPHAGE T4] [GN:Y06C] [DE:HYPOTHETICAL 8.5 KD PROTEIN IN TK-VS INTERGENIC REGION] |
| contig196 | 30578406_c3_6 | 192 | 3597 | 216 | 71 | 83 | 0.0045 | [OR:Bacillus amyloliquefaciens] [PN:probable phosphotransferase system enzyme II, fructose-specific] |
| contig196 | 23906264_c1_5 | 193 | 3598 | 1392 | 463 | 616 | 2.60E-60 | [SP:P23387] [OR:RHODOBACTER CAPSULATUS] [GN:FRUA] [DE:(EC 2.7.1.69) (EII-FRU)] |
| contig197 | 21680187_f2_2 | 194 | 3599 | 735 | 244 | 223 | 1.10E-18 | [AC:AB002150] [OR:Bacillus subtilis] [PN:YbbH] |
| contig198 | 3915192_c2_3 | 195 | 3600 | 957 | 319 | 89 | 0.15 | [SP:P00551] [OR:Escherichia coli] [NT:phosphotransferase (AA 1-271)] |
| contig199 | 24329703_c3_4 | 196 | 3601 | 603 | 200 | 219 | 3.00E-18 | [SP:P75144] [OR:MYCOPLASMA PNEUMONIAE] [GN:MGPA] [DE:MGPA PROTEIN] |
| contig2 | 23646932_f2_1 | 197 | 3602 | 285 | 95 | 140 | 7.10E-10 | [AC:L29324] [OR:Streptococcus pneumoniae] [PN:repressor protein] [NT:ORF3] |
| contig20 | 23632010_f3_1 | 198 | 3603 | 462 | 153 | 321 | 6.70E-28 | [SP:P55465] [OR:RHIZOBIUM SP] [GN:Y4GI] [DE:HYPOTHETICAL 102.8 KD PROTEIN Y4GI] |
| contig20 | 32429577_f3_2 | 199 | 3604 | 387 | 128 | | | |

TABLE 2-continued

| Contig | Orf | NT Seq Id | AA Seq ID | NT Orf Length | AA Orf Length | Score | Probability | Description |
|---|---|---|---|---|---|---|---|---|
| contig200 | 16143807_f3_2 | 200 | 3605 | 201 | 66 | 94 | 0.00063 | [OR:*Craterostigma plantagineum*] [PN:transketolase, 3] |
| contig200 | 29579660_f2_1 | 201 | 3606 | 837 | 278 | 926 | 3.70E-93 | [AC:Z73234] [OR:*Bacillus subtilis*] [PN:transketolase] [GN:tktA] |
| contig200 | 2460378_c3_7 | 202 | 3607 | 507 | 168 | 98 | 0.0001 | [AC:AF000352] [OR:*Escherichia coli*] [NT:o305; This 305 aa orf is 20 pct identical (9 gaps)] |
| contig201 | 10664542_f3_3 | 203 | 3608 | 999 | 332 | 400 | 2.00E-37 | [AC:U29454] [OR:*Staphylococcus aureus*] [PN:penicillin binding protein 4] [GN:pbpD] [NT:PBP4; low molecular weight PBP; Method |
| contig202 | 34084415_f3_3 | 204 | 3609 | 192 | 63 | 133 | 4.30E-09 | [OR:*Methanococcus jannaschii*] [PN:hypothetical protein MJ1163] |
| contig202 | 3945463_f3_4 | 205 | 3610 | 1329 | 442 | 139 | 4.80E-07 | [SP:Q57647] [OR:*METHANOCOCCUS JANNASCHII*] [GN:MJ0188] [DE:HYPOTHETICAL PROTEIN MJ0188] |
| contig202 | 32242840_f1_1 | 206 | 3611 | 231 | 77 | 129 | 4.70E-08 | [SP:P75144] [OR:*MYCOPLASMA PNEUMONIAE*] [GN:MGPA] [DE:MGPA PROTEIN] |
| contig203 | 22868761_f1_1 | 207 | 3612 | 417 | 138 | 372 | 1.90E-34 | [SP:P42085] [OR:*BACILLUS SUBTILIS*] [GN:XPT] [DE:XANTHINE PHOSPHORIBOSYLTRANSFERASE,] |
| contig203 | 25676592_f3_2 | 208 | 3613 | 666 | 222 | 422 | 9.40E-40 | [SP:P42086] [OR:*BACILLUS SUBTILIS*] [GN:PBUX] [DE:XANTHINE PERMEASE] |
| contig204 | 3946941_c1_3 | 209 | 3614 | 399 | 132 | 110 | 1.10E-06 | [SP:P33645] [OR:*ESCHERICHIA COLI*] [GN:CHPA] [DE:PEMK-LIKE PROTEIN 1 (MAZF PROTEIN)] |
| contig204 | 7244062_c3_4 | 210 | 3615 | 249 | 82 | 61 | 0.89 | [AC:U24188] [OR:*Lilium longiflorum*] [GN:CCaMK] [NT:serine/threonine kinase; binds to calcium and |
| contig205 | 5132817_f2_1 | 211 | 3616 | 894 | 297 | 184 | 4.40E-13 | [SP:P39074] [OR:*BACILLUS SUBTILIS*] [GN:BMRU] [DE:BMRU PROTEIN] |
| contig206 | 19728452_c2_8 | 212 | 3617 | 822 | 274 | 84 | 0.76 | [AC:U97189] [OR:*Caenorhabditis elegans*] [GN:C48B6.7] |
| contig206 | 9870317_c2_7 | 213 | 3618 | 183 | 60 | 59 | 0.24 | [AC:Z82015] [OR:*Bacillus subtilis*] [GN:yukI] [NT:yukI is new name for yuxI] |
| contig206 | 167176_c3_9 | 214 | 3619 | 429 | 142 | 50 | 0.997 | [AC:U67984] [DE:HYPOTHETICAL PROTEIN MJECL24] |
| contig206 | 25445312_c1_6 | 215 | 3620 | 558 | 185 |  |  | [AC:U67984] [OR:*Pongo pygmaeus*] [PN:Charcot-Leyden crystal protein] [NT:contains carbohydrate recognition domain.] |
| contig207 | 36375811_f1_1 | 216 | 3621 | 801 | 266 | 775 | 3.70E-77 | [AC:U28137] [OR:*Lactobacillus casei*] [PN:Ccpa protein] [GN:ccpA] |
| contig207 | 23957837_c2_3 | 217 | 3622 | 621 | 206 | 132 | 5.00E-09 | [AC:X81089] [OR:*Lactococcus lactis*] [NT:ORF2] |
| contig208 | 969452_c3_3 | 218 | 3623 | 723 | 241 | 248 | 2.60E-21 | [SP:Q60283] [OR:*METHANOCOCCUS JANNASCHII*] [GN:MJECL24] [DE:HYPOTHETICAL PROTEIN MJECL24] |
| contig209 | 35406412_f2_1 | 219 | 3624 | 537 | 178 | 135 | 2.40E-09 | [AC:D90768] [OR:*Escherichia coli*] [PN:Immunity repressor protein.] [GN:yqjC] [NT:ORF_ID] |
| contig209 | 22526950_f3_2 | 220 | 3625 | 384 | 127 | 302 | 4.90E-27 | [SP:P45171] [OR:*HAEMOPHILUS INFLUENZAE*] [GN:POTA] [DE:SPERMIDINE/PUTRESCINE TRANSPORT ATP-BINDING PROTEIN POTA] |
| contig209 | 24414127_f3_3 | 221 | 3626 | 225 | 74 | 156 | 5.00E-11 | [SP:P44531] [OR:*HAEMOPHILUS INFLUENZAE*] [GN:HI0126] [DE:HYPOTHETICAL ABC TRANSPORTER ATP-BINDING PROTEIN HI0126] |
| contig209 | 3907127_f3_4 | 222 | 3627 | 216 | 72 | 176 | 4.60E-13 | [SP:P23858] [OR:*ESCHERICHIA COLI*] [GN:POTA] [DE:SPERMIDINE/PUTRESCINE TRANSPORT ATP-BINDING PROTEIN POTA] |
| contig21 | 4328382_c3_1 | 223 | 3628 | 459 | 152 | 228 | 3.40E-19 | [OR:*Bacillus megaterium*] [PN:hypothetical protein 2] |
| contig210 | 32221951_c3_1 | 224 | 3629 | 708 | 235 | 549 | 3.30E-53 | [SP:P19210] [OR:*BACILLUS FIRMUS*] [GN:MUTM] [DE:GLYCOSYLASE] |
| contig211 | 14648452_c2_6 | 225 | 3630 | 687 | 229 | 70 | 0.74 | [AC:M61022] [OR:*Mus musculus*] [PN:immunoglobulin heavy chain VDJ region] |
| contig212 | 19579212_c3_1 | 226 | 3631 | 360 | 119 | 300 | 7.90E-27 | [OR:*Streptococcus thermophilus*] [PN:transposase] |

TABLE 2-continued

| Contig | Orf | NT Seq Id | AA Seq ID | NT Orf Length | AA Orf Length | Score | Probability | Description |
|---|---|---|---|---|---|---|---|---|
| contig213 | 1208316_f2_1 | 227 | 3632 | 762 | 253 | 87 | 0.12 | [SP:P39787] [OR:*BACILLUS SUBTILIS*] [GN:DNAD] [DE:DNA REPLICATION PROTEIN DNAD] |
| contig213 | 26776567_f2_2 | 228 | 3633 | 333 | 110 | 78 | 0.0075 | [SP:P32529] [OR:*SACCHAROMYCES CEREVISIAE*] [GN:RPA12] [DE:(A12.2)] |
| contig214 | 26384681_f3_3 | 229 | 3634 | 432 | 143 | 497 | 1.10E-47 | [AC:U39612] [OR:*Streptococcus mutans*] [PN:formyl-tetrahydrofolate synthetase] [GN:fhs] [NT:formyl-tetrahydrofolate ligase; ATP-dependant] |
| contig214 | 5164025_f1_1 | 230 | 3635 | 903 | 300 | 989 | 7.70E-100 | [AC:U39612] [OR:*Streptococcus mutans*] [PN:formyl-tetrahydrofolate synthetase] [GN:fhs] [NT:formyl-tetrahydrofolate ligase; ATP-dependant] |
| contig215 | 22535885_c3_2 | 231 | 3636 | 708 | 236 | 347 | 8.30E-32 | [SP:P54176] [OR:*BACILLUS CEREUS*] [DE:HEMOLYSIN III] |
| contig215 | 25667192_f1_1 | 232 | 3637 | 369 | 123 | 263 | 6.60E-23 | [AC:ZI6422] [OR:*Staphylococcus aureus*] [PN:unknown] [GN:ORF2] |
| contig216 | 24025151_c2_3 | 233 | 3638 | 918 | 305 | 586 | 3.90E-57 | [SP:P09374] [OR:*ESCHERICHIA COLI*] [GN:PFLA] [DE:PYRUVATE FORMATE-LYASE 1 ACTIVATING ENZYME.] |
| contig216 | 20488149_c1_2 | 234 | 3639 | 435 | 144 | 344 | 1.70E-31 | [SP:P37836] [OR:*CHLAMYDOMONAS REINHARDTII*] [GN:PF1] [DE:(FRAGMENT)] |
| contig217 | 651708_f3_3 | 235 | 3640 | 279 | 92 | 115 | 1.20E-06 | [SP:P33566] [OR:*NEISSERIA GONORRHOEAE*] [GN:PILD] [DE:TYPE 4 PREPILIN-LIKE PROTEIN SPECIFIC LEADER PEPTIDASE.] |
| contig217 | 24317803_c2_5 | 236 | 3641 | 297 | 98 | 73 | 0.086 | [SP:P44493] [OR:*HAEMOPHILUS INFLUENZAE*] [GN:AMIB] [DE:PROBABLE N-ACETYLMURAMOYL-L-ALANINE AMIDASE PRECURSOR.] |
| contig217 | 10743932_c3_6 | 237 | 3642 | 399 | 132 | 431 | 1.00E-40 | [AC:U81957] [OR:*Streptococcus gordonii*] [PN:RNA polymerase beta' subunit] [GN:rpoC] |
| contig218 | 34570202_f3_1 | 238 | 3643 | 924 | 308 | 582 | 2.80E-63 | [AC:D64005] [OR:*Synechocystis sp.*] [PN:cadmium-transporting ATPase] [GN:cadA] [NT:ORF_ID] |
| contig219 | 16853152_f2_2 | 239 | 3644 | 1305 | 435 | 277 | 4.80E-24 | [OR:*Saccharopolyspora erythraea*] [PN:glutamate transport protein homolog] [GN:hgtA] |
| contig22 | 23457281_f3_1 | 240 | 3645 | 867 | 288 | 905 | 6.10E-91 | [SP:P04077] [OR:*BACILLUS CALDOTENAX*] [GN:TYRS] [DE:TYROSYL-TRNA SYNTHETASE, (TYROSINE--TRNA LIGASE) (TYRRS)] |
| contig220 | 17002213_c1_3 | 241 | 3646 | 417 | 138 | 257 | 2.90E-22 | [SP:P39667] [OR:*BACILLUS SUBTILIS*] [GN:YRXA] [DE:HYPOTHETICAL 19.7 KD PROTEIN IN PHEA-NIFS INTERGENIC REGION (ORF1)] |
| contig220 | 25679500_c3_4 | 242 | 3647 | 645 | 214 | 318 | 9.80E-29 | [SP:P77791] [OR:*ESCHERICHIA COLI*] [GN:YLAD] [DE:20.0 KD PROTEIN IN TESB-HHA INTERGENIC REGION] |
| contig221 | 4039802_f2_1 | 243 | 3648 | 843 | 280 | 144 | 4.50E-08 | [AC:JC6007] [OR:*Bacillus thuringiensis*] [PN:transcriptional activator plcR] [GN:plcR] |
| contig221 | 34195262_f3_2 | 244 | 3649 | 510 | 169 | 142 | 2.70E-09 | [AC:U65015] [OR:*Vibrio furnissii*] [PN:GlcNAc 6-P deacetylase] [GN:manD] [NT:ManD] |
| contig222 | 12218900_f2_2 | 245 | 3650 | 312 | 103 | 136 | 8.90E-09 | [SP:Q38653] [OR:BACTERIOPHAGE A511] [GN:PLY511] [DE:ENDOLYSIN, (N-ACETYLMURAMOYL-L-ALANINE AMIDASE)] |
| contig222 | 16822026_f3_3 | 246 | 3651 | 822 | 273 | 266 | 3.20E-23 | [SP:Q38653] [OR:BACTERIOPHAGE A511] [GN:PLY511] [DE:ENDOLYSIN, (N-ACETYLMURAMOYL-L-ALANINE AMIDASE)] |
| contig222 | 30078177_f3_4 | 247 | 3652 | 567 | 188 | 328 | 8.60E-30 | [SP:P74696] [OR:*SYNECHOCYSTIS SP*] [GN:TRUB] [DE:TRNA PSEUDOURIDINE 55 SYNTHASE (PS155 SYNTHASE)] |
| contig223 | 33400316_c2_5 | 248 | 3653 | 396 | 132 | 212 | 1.70E-17 | [OR:*Streptococcus salivarius*] [PN:hypothetical protein] |

TABLE 2-continued

| Contig | Orf | NT Seq Id | AA Seq ID | NT Orf Length | AA Orf Length | Score | Probability | Description |
|---|---|---|---|---|---|---|---|---|
| contig223 | 864187_c2_4 | 249 | 3654 | 663 | 220 | 62 | 0.9998 | [AC:U93364] [OR:*Lactococcus lactis cremoris*] [PN:EpsR] [GN:epsR] |
| contig224 | 23523557_c1_5 | 250 | 3655 | 252 | 84 | 65 | 0.64 | [AC:U86345] [OR:*Trypanosoma brucei rhodesiense*] [PN:GP63-1 surface protease homolog] [GN:gp63-1] [NT:homolog of Leishmania GP63 surface protease;] |
| contig224 | 20820886_c1_4 | 251 | 3656 | 234 | 77 | 55 | 0.94 | [AC:AB001488] [OR:*Bacillus subtilis*] [GN:ydE] [NT:FUNCTION UNKNOWN.] |
| contig224 | 6739062_c3_7 | 252 | 3657 | 948 | 315 | 545 | 8.70E-53 | [SP:P42015] [OR:*BACILLUS STEAROTHERMOPHILUS*] [GN:PTSG] [DE:COMPONENT), (EII-GLC/EIII-GLC) (FRAGMENT)] |
| contig225 | 35394531_f2_1 | 253 | 3658 | 684 | 227 | 293 | 4.40E-26 | [SP:P26212] [OR:*BACILLUS SUBTILIS*] [GN:SACT] [DE:SACPA OPERON ANTITERMINATOR] |
| contig225 | 33396937_f2_2 | 254 | 3659 | 615 | 204 | 321 | 8.50E-29 | [AC:U65014] [OR:*Vibrio furnissii*] [PN:PTS permease for N-acetylglucosamine and] [GN:nagE] [NT:PTS enzyme IINag] |
| contig226 | 7146942_c1_5 | 255 | 3660 | 609 | 202 | 128 | 5.50E-07 | [SP:P45544] [OR:*ESCHERICHIA COLI*] [GN:YHFR] [DE:(O265)] |
| contig226 | 4808462_f3_3 | 256 | 3661 | 192 | 63 | 55 | 0.84 | [SP:P45710] [OR:*BACILLUS SUBTILIS*] [GN:YOXI] [DE:HYPOTHETICAL 18.1 KD PROTEIN IN CCDA 3'REGION] |
| contig226 | 5109387_f1_1 | 257 | 3662 | 264 | 87 | 51 | 0.9995 | [OR:*Aspergillus fumigatus*] [PN:chs A protein] |
| contig227 | 20898510_f2_1 | 258 | 3663 | 1062 | 354 | 1820 | 6.70E-188 | [OR:*Enterococcus faecalis*] [PN:cylM protein] |
| contig228 | 33672192_f2_1 | 259 | 3664 | 1230 | 409 | 878 | 4.50E-88 | [AC:Y08559] [OR:*Bacillus subtilis*] [PN:Unknown] [GN:ywnE] [NT:Product similar to *Escherichia coli* cardiolipin] |
| contig229 | 158568_f1_1 | 260 | 3665 | 846 | 281 | 53 | 0.997 | [SP:P38636] [OR:*SACCHAROMYCES CEREVISIAE*] [GN:ATX1] [DE:METAL HOMEOSTASIS FACTOR ATX1] |
| contig23 | 26179687_c3_5 | 261 | 3666 | 387 | 129 | 138 | 1.20E-09 | [AC:AB001488] [OR:*Bacillus subtilis*] [GN:ydeP] [NT:FUNCTION UNKNOWN, SIMILAR PRODUCT IN *E. COLI*, H.] |
| contig23 | 494557_c3_4 | 262 | 3667 | 387 | 128 | 172 | 2.90E-13 | [OR:*Streptococcus mutans*] [PN:orf X 5' of lacR] |
| contig230 | 33401717_c1_3 | 263 | 3668 | 1194 | 398 | 459 | 1.10E-42 | [AC:D90911] [OR:*Synechocystis sp.*] [PN:cation-transporting ATPase PacL] [GN:pacL] [NT:ORF_ID] |
| contig231 | 31678968_f3_2 | 264 | 3669 | 726 | 241 | 101 | 0.002 | [AC:Z50854] [OR:*Enterococcus hirae*] [GN:orf] |
| contig231 | 24644013_f3_3 | 265 | 3670 | 252 | 83 | 60 | 0.36 | [AC:U41518] [OR:*Homo sapiens*] [PN:channel-like integral membrane protein] [GN:AQP-1] [NT:aquaporin-1] |
| contig232 | 14652268_c2_2 | 266 | 3671 | 858 | 285 | 364 | 4.00E-33 | [SP:Q02469] [OR:*SHEWANELLA PUTREFACIENS*] [DE:(FLAVOCYTOCHROME C)] |
| contig233 | 11116326_f2_1 | 267 | 3672 | 861 | 286 | 355 | 1.20E-32 | [AC:D83026] [OR:*Bacillus subtilis*] [GN:yxkD] [NT:homologous to jojC gene product (*B. subtilis*;] |
| contig234 | 22474077_c1_3 | 268 | 3673 | 822 | 274 | 537 | 3.20E-56 | [SP:P39046] [OR:*ENTEROCOCCUS HIRAE*] [DE:(MURAMIDASE 2)] |
| contig234 | 22464077_f1_1 | 269 | 3674 | 348 | 116 | 154 | 1.30E-10 | [AC:AB001488] [OR:*Bacillus subtilis*] [GN:ydeR] [NT:PROBABLE INTEGRAL MEMBRANE PROTEIN, SIMILAR TO] |
| contig235 | 30642252_f3_3 | 270 | 3675 | 1704 | 567 | 94 | 0.36 | [AC:D90906] [OR:*Synechocystis sp.*] [PN:DNA helicase II] [GN:uvrD] [NT:ORF_ID] |
| contig236 | 9932836_c1_3 | 271 | 3676 | 495 | 164 | 180 | 4.10E-14 | [OR:*Listeria monocytogenes*] [PN:probable transport protein arpJ] |
| contig236 | 14567268_c1_2 | 272 | 3677 | 309 | 102 |  |  | |
| contig237 | 25439437_c3_7 | 273 | 3678 | 750 | 250 | 288 | 1.50E-25 | [SP:P45170] [OR:*HAEMOPHILUS INFLUENZAE*] [GN:POTB] [DE:SPERMIDINE/PUTRESCINE TRANSPORT SYSTEM PERMEASE PROTEIN POTB] |
| contig237 | 10632837_c3_6 | 274 | 3679 | 453 | 150 | 75 | 0.77 | [SP:P50591] [OR:*HOMO SAPIENS*] [DE:TNF-RELATED APOPTOSIS INDUCING LIGAND (TRAIL) (APO-2 LIGAND)] |
| contig238 | 26424437_f1_1 | 275 | 3680 | 759 | 252 | 258 | 2.20E-22 | [AC:AE000310] [OR:*Escherichia coli*] [GN:yojL] [NT:f351; Residues 1–121 are 100 pct identical to] |

TABLE 2-continued

| Contig | Orf | NT Seq Id | AA Seq ID | NT Orf Length | AA Orf Length | Score | Probability | Description |
|---|---|---|---|---|---|---|---|---|
| contig238 | 33261461_f2_3 | 276 | 3681 | 675 | 224 | 227 | 4.30E-19 | [SP:P31465] [OR:ESCHERICHIA COLI] [GN:YIEF] [DE:HYPOTHETICAL 20.4 KD PROTEIN IN TNAB-BGLB INTERGENIC REGION] |
| contig238 | 6923441_f2_4 | 277 | 3682 | 297 | 99 | 124 | 3.50E-08 | [SP:P31465] [OR:ESCHERICHIA COLI] [GN:YIEF] [DE:HYPOTHETICAL 20.4 KD PROTEIN IN TNAB-BGLB INTERGENIC REGION] |
| contig239 | 7082001_f1_1 | 278 | 3683 | 201 | 66 | 214 | 1.00E-17 | [SP:P39788] [OR:BACILLUS SUBTILIS] [GN:NTH] [DE:APYRIMIDINIC SITE) LYASE)] |
| contig239 | 35979692_f3_2 | 279 | 3684 | 699 | 232 | 258 | 2.20E-22 | [SP:P39796] [OR:BACILLUS SUBTILIS] [GN:TRER] [DE:TREHALOSE OPERON TRANSCRIPTIONAL REPRESSOR] |
| contig24 | 15026400_c1_3 | 280 | 3685 | 681 | 226 | 91 | 0.083 | [SP:Q09251] [OR:CAENORHABDITIS ELEGANS] [GN:C16C10.5] [DE:HYPOTHETICAL 47.6 KD PROTEIN C16C10.5 IN CHROMOSOME III] |
| contig240 | 20000332_c3_6 | 281 | 3686 | 1302 | 433 | 1201 | 2.60E-122 | [SP:P22326] [OR:BACILLUS SUBTILIS] [GN:TYRS] [DE:(TYRRS)] |
| contig241 | 16532892_f2_3 | 282 | 3687 | 276 | 91 | 154 | 4.40E-11 | [SP:P28635] [OR:ESCHERICHIA COLI] [GN:YAEC] [DE:PRECURSOR] |
| contig241 | 23992175_f1_2 | 283 | 3688 | 849 | 282 | 550 | 2.60E-53 | [SP:Q55482] [OR:SYNECHOCYSTIS SP] [GN:SLL0506] [DE:HYPOTHETICAL 28.8 KD PROTEIN SLL0506] |
| contig241 | 29306955_f3_4 | 284 | 3689 | 195 | 65 | 97 | 0.0062 | [AC:AB001488] [OR:Bacillus subtilis] [GN:ydcM] [NT:SIMILAR TO IMMUNITY REGION PROTEIN IN BACTERIOPHAGE] |
| contig242 | 4431426_f1_1 | 285 | 3690 | 1044 | 347 | | | |
| contig242 | 807688_f2_2 | 286 | 3691 | 399 | 133 | 402 | 1.20E-37 | [AC:AB001488] [OR:Bacillus subtilis] [GN:ydcL] [NT:PROBABLE INTEGRASE.] |
| contig243 | 1370311_f2_1 | 287 | 3692 | 1089 | 362 | | | |
| contig244 | 1222061_f2_2 | 288 | 3693 | 306 | 101 | 183 | 2.20E-13 | [AC:L49336] [OR:Clostridium longisporum] [PN:PTS-dependent enzyme II] [GN:abgF] |
| contig244 | 14629663_f1_1 | 289 | 3694 | 1479 | 492 | 1067 | 4.20E-108 | [SP:P42403] [OR:BACILLUS SUBTILIS] [GN:YCKE] [DE:(BETA-D-GLUCOSIDE GLUCOHYDROLASE) (AMYGDALASE)] |
| contig245 | 12895913_f2_1 | 290 | 3695 | 402 | 133 | 66 | 0.9999 | [AC:U41224] [OR:Trypanosoma brucei rhodesiense] [GN:expression site-associated gene Id] |
| contig245 | 16609682_f2_2 | 291 | 3696 | 228 | 75 | 79 | 0.0093 | [OR:Trypanosoma cruzi] [PN:repetitive protein antigen 3] |
| contig245 | 16485885_f2_3 | 292 | 3697 | 240 | 79 | 108 | 7.80E-06 | [AC:Z94043] [OR:Bacillus subtilis] [PN:hypothetical protein] [GN:yvcJ] [NT:similar to hypothetical MTCY21B4] |
| contig246 | 35391578_f2_2 | 293 | 3698 | 627 | 208 | 545 | 8.70E-53 | [SP:P04067] [OR:STREPTOMYCES PLICATUS] [DE:ACETYLCHITOBIOSYL BETA-N-ACETYLGLUCOSAMINIDASE H) (ENDO H)] |
| contig247 | 30565805_f3_2 | 294 | 3699 | 1209 | 402 | 75 | 0.89 | [SP:Q06242] [OR:ENTEROCOCCUS FAECIUM] [DE:VANZ PROTEIN] |
| contig248 | 24501538_f1_1 | 295 | 3700 | 792 | 263 | 93 | 0.00028 | [SP:P35838] [OR:CLOSTRIDIUM ACETOBUTYLICUM] [DE:HYPOTHETICAL PROTEIN IN LYC 5REGION (FRAGMENT)] |
| contig248 | 507187_f1_2 | 296 | 3701 | 210 | 70 | 52 | 0.78 | [SP:P00023] [OR:CROTALUS ATROX] [DE:CYTOCHROME C] |
| contig249 | 4804703_c3_8 | 297 | 3702 | 456 | 151 | 310 | 6.90E-28 | [AC:D84432] [OR:Bacillus subtilis] [PN:BiD] |
| contig249 | 25680332_c3_7 | 298 | 3703 | 258 | 85 | 70 | 0.026 | [AC:U53154] [OR:Caenorhabditis elegans] [GN:C33G8.3] |
| contig249 | 30272056_c2_6 | 299 | 3704 | 498 | 165 | 205 | 9.30E-17 | [OR:Methanococcus jannaschii] [PN:hypothetical protein homolog MJ0531] |
| contig25 | 6257627_f1_1 | 300 | 3705 | 576 | 191 | 392 | 1.40E-36 | [SP:P39605] [OR:BACILLUS SUBTILIS] [GN:YWCG] [DE:HYPOTHETICAL 28.3 KD PROTEIN IN QOXD-VPR |

TABLE 2-continued

| Contig | Orf | NT Seq Id | AA Seq ID | NT Orf Length | AA Orf Length | Score | Probability | Description |
|---|---|---|---|---|---|---|---|---|
| contig250 | 13923401_c3_5 | 301 | 3706 | 1170 | 389 | 983 | 3.30E-99 | INTERGENIC REGION] [OR:*Bacillus subtilis*] [PN:hisC homolog] |
| contig250 | 129032_c2_4 | 302 | 3707 | 243 | 80 | 57 | 0.36 | [AC:U31743] [OR:*Homo sapiens*] [PN:HLA-DMB variant] |
| contig250 | 24710428_c1_3 | 303 | 3708 | 183 | 60 | 51 | 0.85 | [AC:L19118] [OR:*Rattus norvegicus*] [PN:complement receptor type 1] [GN:CR1] |
| contig251 | 34414724_c1_4 | 304 | 3709 | 1434 | 478 | 401 | 6.00E-37 | [SP:P37710] [OR:*ENTEROCOCCUS FAECALIS*] [DE:AUTOLYSIN, (N-ACETYLMURAMOYL-L-ALANINE AMIDASE)] |
| contig252 | 10157842_c1_4 | 305 | 3710 | 492 | 163 | 64 | 0.15 | [AC:U56077] [OR:*Pseudomonas aeruginosa*] [PN:periplasmic glucosidase] [NT:*Escherichia coli* BglX homolog] |
| contig252 | 26260912_f2_1 | 306 | 3711 | 474 | 157 | 232 | 1.30E-19 | [SP:Q59384] [OR:*ESCHERICHIA COLI*] [GN:GLOA] [DE:(ALDOKETOMUTASE) (GLYOXALASE 1)] |
| contig252 | 6064443_f3_3 | 307 | 3712 | 441 | 147 | 314 | 2.60E-28 | [SP:P22347] [OR:*LACTOCOCCUS LACTIS*] [DE:HYPOTHETICAL 18.7 KD PROTEIN IN PEPX 3'REGION (ORF3)] |
| contig253 | 34179786_c2_2 | 308 | 3713 | 828 | 276 | 375 | 8.90E-35 | [SP:Q57664] [OR:*METHANOCOCCUS JANNASCHII*] [GN:MJ0211] [DE:GALACTOSE 4-EPIMERASE] |
| contig253 | 860636_c3_3 | 309 | 3714 | 537 | 178 | 75 | 0.32 | [SP:P45145] [OR:*HAEMOPHILUS INFLUENZAE*] [GN:HI1297] [DE:HYPOTHETICAL PROTEIN HI1297] |
| contig254 | 33243877_f3_6 | 310 | 3715 | 375 | 124 | 208 | 6.90E-17 | [SP:P40410] [OR:*BACILLUS SUBTILIS*] [GN:FEUB] [DE:IRON-UPTAKE SYSTEM PROTEIN FEUB] |
| contig254 | 14667842_f2_5 | 311 | 3716 | 873 | 291 | 372 | 1.90E-34 | [SP:P49937] [OR:*BACILLUS SUBTILIS*] [GN:FHUG] [DE:FERRICHROME TRANSPORT PERMEASE PROTEIN FHUG] |
| contig255 | 21490957_c3_4 | 312 | 3717 | 243 | 80 | 50 | 0.93 | [AC:Z72843] [OR:*Saccharomyces cerevisiae*] [NT:ORF YGR057c] |
| contig255 | 22470386_f2_2 | 313 | 3718 | 426 | 142 | 52 | 0.96 | [AC:X61517] [OR:*Mycoplasma genitalium*] [NT:random genomic sequence MG08; open reading frame] |
| contig256 | 38557_f2_2 | 314 | 3719 | 615 | 204 | 522 | 2.40E-50 | [AC:D90907] [OR:*Synechocystis sp.*] [PN:amidase] [NT:ORF_ID] |
| contig256 | 33802182_f1_1 | 315 | 3720 | 801 | 266 | 899 | 2.70E-90 | [SP:Q45486] [OR:*BACILLUS SUBTILIS*] [GN:YZDD] [DE:PET112-LIKE PROTEIN] |
| contig257 | 7070428_c3_3 | 316 | 3721 | 468 | 155 | 70 | 0.87 | [SP:P48923] [OR:*CANDIDA PARAPSILOSIS*] [GN:ND6] [DE:NADH-UBIQUINONE OXIDOREDUCTASE CHAIN 6,] |
| contig257 | 6692125_f3_1 | 317 | 3722 | 234 | 77 | 68 | 0.081 | [AC:U02510] [OR:Ovine respiratory syncytial virus] [PN:M2 (22K) protein] |
| contig257 | 24300674_c1_2 | 318 | 3723 | 636 | 211 | 1069 | 2.60E-108 | [SP:P19775] [OR:*STAPHYLOCOCCUS AUREUS*] [GN:TNP] [DE:TRANSPOSASE FOR INSERTION SEQUENCE ELEMENT IS256 IN TRANSPOSON TN4001] |
| contig258 | 12219781_f3_3 | 319 | 3724 | 837 | 278 | 500 | 5.10E-48 | [AC:D84648] [OR:*Bacillus stearothermophilus*] [PN:exo-alpha-1,4-glucosidase] |
| contig258 | 210962_f1_1 | 320 | 3725 | 489 | 162 | 240 | 1.30E-19 | [SP:P29094] [OR:*BACILLUS THERMOGLUCOSIDASIUS*] [DE:DEXTRINASE (ISOMALTASE) (DEXTRIN 6-ALPHA-D-GLUCANOHYDROLASE)] |
| contig258 | 23604838_f2_2 | 321 | 3726 | 276 | 91 | 217 | 2.70E-17 | [SP:P51184] [OR:*STAPHYLOCOCCUS XYLOSUS*] [GN:SCRA] [DE:(EC 2.7.1.69) (EII-SCR)] |
| contig259 | 1172752_f2_3 | 322 | 3727 | 213 | 70 | 58 | 0.51 | [SP:P19746] [OR:*CAPRIPOXVIRUS*] [DE:PROTEIN F7] |
| contig259 | 423125_f1_1 | 323 | 3728 | 768 | 255 | 276 | 2.80E-24 | [AC:X98110] [OR:*Streptococcus gordonii*] [PN:response regulator] [GN:comE2] |
| contig259 | 4814625_f2_4 | 324 | 3729 | 759 | 252 | 186 | 9.50E-15 | [AC:L13334] [OR:*Staphylococcus lugdunensis*] |
| contig26 | 23647555_c1_3 | 325 | 3730 | 720 | 239 | 335 | 1.60E-30 | [SP:P50726] [OR:*BACILLUS SUBTILIS*] [GN:YPAA] [DE:HYPOTHETICAL 20.5 KD PROTEIN IN SERA-FER |

TABLE 2-continued

| Contig | Orf | NT Seq Id | AA Seq ID | NT Orf Length | AA Orf Length | Score | Probability | Description |
|---|---|---|---|---|---|---|---|---|
| contig260 | 14220443_f1_1 | 326 | 3731 | 639 | 212 | 286 | 2.40E-25 | INTERGENIC REGION] [AC:D90779] [OR:*Escherichia coli*] [PN:Acyl carrier protein phosphodiesterase (ACP) [NT:ORF_ID] |
| contig260 | 25651702_c3_6 | 327 | 3732 | 1185 | 394 | 418 | 2.50E-39 | [AC:X99400] [OR:*Streptococcus pneumoniae*] [PN:membrane protein] |
| contig261 | 781432_f3_1 | 328 | 3733 | 900 | 300 | 444 | 1.40E-41 | [SP:P08716] [OR:*ESCHERICHIA COLI*] [GN:HLYB] [DE:HEMOLYSIN SECRETION ATP-BINDING PROTEIN, PLASMID] |
| contig261 | 33292342_c3_2 | 329 | 3734 | 207 | 68 | 52 | 0.999 | [SP:P20296] [OR:*PYROCOCCUS WOESEI*] [DE:HYPOTHETICAL 24.7 KD PROTEIN IN GAPDH 5'REGION (ORF A)] |
| contig262 | 15710913_f3_2 | 330 | 3735 | 1257 | 418 | 385 | 7.80E-36 | [SP:Q48460] [OR:*KLEBSIELLA PNEUMONIAE*] [DE:PROBABLE CPS BIOSYNTHESIS GLYCOSYLTRANSFERASE, (ORF14)] |
| contig263 | 4688263_f1_1 | 331 | 3736 | 624 | 208 | 228 | 1.50E-18 | [AC:U61539] [OR:*Bacillus firmus*] [PN:Na+/H+ antiporter] [GN:nhaC] [NT:NahC] |
| contig264 | 7082026_f1_1 | 332 | 3737 | 885 | 295 | 192 | 9.50E-14 | [SP:Q05587] [OR:*SALMONELLA TYPHIMURIUM*] [GN:POCR] [DE:REGULATORY PROTEIN POCR] |
| contig265 | 29392933_f1_1 | 333 | 3738 | 1146 | 382 | 763 | 6.90E-76 | [AC:D78016] [OR:*Enterococcus faecalis*] [PN:TRAC] [GN:traC] [NT:ORF3; replication related gene] |
| contig266 | 26023917_f1_1 | 334 | 3739 | 528 | 175 | 270 | 1.60E-33 | [AC:Z94864] [OR:*Schizosaccharomyces pombe*] [PN:unknown] [GN:SPAC57A10.03] [NT:SPAC57A10.03, cyclophilin-related, len] |
| contig266 | 36147192_f3_3 | 335 | 3740 | 231 | 76 | 61 | 0.69 | [AC:U00033] [OR:*Caenorhabditis elegans*] [GN:F37C12.2] |
| contig266 | 21679664_c2_5 | 336 | 3741 | 378 | 125 | 321 | 4.70E-29 | [SP:Q08432] [OR:*BACILLUS SUBTILIS*] [GN:PAIB] [DE:PUTATIVE AMINOTRANSFERASE B.] |
| contig267 | 2757327_c1_3 | 337 | 3742 | 1005 | 335 | 340 | 4.60E-31 | [AC:U77778] [OR:*Staphylococcus epidermidis*] [PN:putative membrane protein] [GN:epiH] [NT:EpiH] |
| contig267 | 12673385_f3_2 | 338 | 3743 | 216 | 71 | 64 | 0.078 | [SP:P26886] [OR:*EUPLOTES RAIKOVI*] [GN:MAT2,MAT9] [DE:MATING PHEROMONE ER-2/ER-9 PRECURSOR (EUPLOMONE R2/R9)] |
| contig267 | 4886018_f1_1 | 339 | 3744 | 285 | 95 | 91 | 0.00059 | [SP:Q05624] [OR:*CLOSTRIDIUM ACETOBUTYLICUM*] [GN:PTB] [DE:PHOSPHATE BUTYRYLTRANSFERASE, (PHOSPHOTRANSBUTYRYLASE)] |
| contig268 | 14875000_f1_1 | 340 | 3745 | 1620 | 540 | 273 | 1.30E-20 | [AC:M81736] [OR:*Staphylococcus aureus*] [PN:collagen adhesin] [GN:cna] |
| contig269 | 3917842_c3_9 | 341 | 3746 | 516 | 171 | 498 | 8.30E-48 | [SP:P32393] [OR:*BACILLUS SUBTILIS*] [GN:COMEB] [DE:COME OPERON PROTEIN 2] |
| contig269 | 23691187_c1_5 | 342 | 3747 | 681 | 226 | 327 | 1.10E-29 | [SP:P39694] [OR:*BACILLUS SUBTILIS*] [GN:COMEA] [DE:COME OPERON PROTEIN 1] |
| contig269 | 29785134_c2_6 | 343 | 3748 | 1095 | 364 | 136 | 4.30E-06 | [OR:*Methanococcus jannaschii*] [PN:hypothetical protein MJ1318] |
| contig27 | 36366450_f2_1 | 344 | 3749 | 543 | 181 | | | |
| contig270 | 35407675_f2_2 | 345 | 3750 | 1416 | 471 | 1252 | 1.00E-127 | [AC:D88802] [OR:*Bacillus subtilis*] [GN:ydiF] [NT:*H. influenzae* hypothetical ABC transporter; P44808] |
| contig271 | 34661566_c2_4 | 346 | 3751 | 336 | 111 | 111 | 3.70E-06 | [SP:P29823] [OR:*AGROBACTERIUM RADIOBACTER*] [GN:LACF] [DE:LACTOSE TRANSPORT SYSTEM PERMEASE PROTEIN LACF] |
| contig271 | 26250012_c3_5 | 347 | 3752 | 1221 | 406 | 375 | 1.30E-59 | [SP:P75264] [OR:*MYCOPLASMA PNEUMONIAE*] [DE:HYPOTHETICAL ABC TRANSPORTER ATP-BINDING PROTEIN MG187 HOMOLOG] |
| contig272 | 209811_f1_1 | 348 | 3753 | 732 | 243 | 201 | 2.50E-16 | [SP:P77728] [OR:*ESCHERICHIA COLI*] [GN:APBA] [DE:APBA PROTEIN] |
| contig272 | 21978881_c1_2 | 349 | 3754 | 1080 | 359 | 710 | 2.80E-70 | [SP:P54459] [OR:*BACILLUS SUBTILIS*] [GN:YQEN] |

TABLE 2-continued

| Contig | Orf | NT Seq Id | AA Seq ID | NT Orf Length | AA Orf Length | Score | Probability | Description |
|---|---|---|---|---|---|---|---|---|
| contig273 | 2444525_f3_1 | 350 | 3755 | 1032 | 343 | 250 | 3.70E-21 | [DE:HYPOTHETICAL 40.5 KD PROTEIN IN COMEC-RPST INTERGENIC REGION] |
| contig273 | 2676025O_c1_2 | 351 | 3756 | 276 | 91 | 62 | 0.34 | [AC:U66880] [OR:Staphylococcus simulans] [PN:FemA] [GN:femA] [AC:D90900] [OR:Synechocystis sp.] [PN:shikimate kinase] [GN:aroK] [NT:ORF_ID] |
| contig274 | 969092_f2_1 | 352 | 3757 | 768 | 255 | 72 | 0.039 | [AC:M29955] [OR:Escherichia coli] [NT:ltrA gene product (5' end put.); putative] |
| contig274 | 21519813_f2_2 | 353 | 3758 | 228 | 75 | 58 | 0.57 | [AC:Z81030] [OR:Caenorhabditis elegans] [PN:C01G10.4] |
| contig275 | 26377340_c3_4 | 354 | 3759 | 747 | 249 | 176 | 4.20E-12 | [SP:P44180] [OR:HAEMOPHILUS INFLUENZAE] [GN:HI1405] [DE:HYPOTHETICAL PROTEIN HI1405] |
| contig275 | 7245326_c3_3 | 355 | 3760 | 228 | 75 | 79 | 0.0085 | [AC:D90907] [OR:Synechocystis sp.] [PN:hypothetical protein] [NT:ORF_ID] |
| contig275 | 4042878_c2_2 | 356 | 3761 | 330 | 109 | 53 | 0.74 | [AC:U68241] [OR:Carassius auratus] [PN:twiggy-winkle hedgehog] |
| contig276 | 14954143_c2_8 | 357 | 3762 | 432 | 144 | 501 | 4.00E-48 | [SP:P54689] [OR:HAEMOPHILUS INFLUENZAE] [GN:ILVE] [DE:BRANCHED-CHAIN AMINO ACID AMINOTRANSFERASE,] |
| contig276 | 23445432_c1_5 | 358 | 3763 | 477 | 158 | 291 | 7.10E-26 | [AC:AB001488] [OR:Bacillus subtilis] [GN:ydaT] [NT:FUNCTION UNKNOWN.] |
| contig277 | 6736631_f3_2 | 359 | 3764 | 1092 | 363 | 707 | 5.90E-70 | [SP:P12045] [OR:BACILLUS SUBTILIS] [GN:PURK] [DE:(AIR CARBOXYLASE) (AIRC)] |
| contig277 | 5116543_f3_3 | 360 | 3765 | 393 | 130 | 502 | 3.10E-48 | [SP:P12047] [OR:BACILLUS SUBTILIS] [GN:PURB] [DE:ADENYLOSUCCINATE LYASE, (ADENYLOSUCCINASE) (ASL)] |
| contig278 | 31461062_c3_2 | 361 | 3766 | 1089 | 362 | 353 | 1.90E-32 | [SP:P44720] [OR:HAEMOPHILUS INFLUENZAE] [GN:HI0457] [DE:HYPOTHETICAL PROTEIN HI0457] |
| contig279 | 26282885_f3_5 | 362 | 3767 | 1548 | 515 | 281 | 6.50E-32 | [SP:P13398] [OR:PSEUDOMONAS SP] [GN:NYLA] [DE:DEGRADING ENZYME EI) |
| contig279 | 14663938_f1_2 | 363 | 3768 | 183 | 60 | 58 | 0.29 | [OR:Bos primigenius taurus] [PN:bactenecin 5] |
| contig28 | 253886_f1_1 | 364 | 3769 | 438 | 145 | 248 | 2.60E-21 | [AC:L16975] [OR:Lactococcus lactis] [NT:ORF1] |
| contig28 | 5197813_f1_2 | 365 | 3770 | 453 | 151 | 227 | 4.30E-19 | [SP:P54390] [OR:BACILLUS SUBTILIS] [GN:YPIB] |
| contig280 | 12188261_f1_1 | 366 | 3771 | 447 | 148 | 161 | 1.60E-10 | [DE:HYPOTHETICAL 21.4 KD PROTEIN IN QCRA 5'REGION] [SP:P13267] [OR:BACILLUS SUBTILIS] [GN:POLC] [DE:DNA POLYMERASE III, ALPHA CHAIN.] |
| contig280 | 24406282_f3_4 | 367 | 3772 | 219 | 72 | 60 | 0.81 | [OR:Methanococcus jannaschii] [PN:acetylpolyamine aminohydolase] |
| contig280 | 24414042_f2_3 | 368 | 3773 | 306 | 101 | 58 | 0.29 | |
| contig281 | 29882092_c3_7 | 369 | 3774 | 201 | 66 | 58 | 0.29 | [AC:X53324] [OR:group G streptococcus] [PN:Protein G'] [GN:Protein G gene] [NT:Truncated gene] |
| contig281 | 56552_f3_1 | 370 | 3775 | 858 | 286 | 101 | 0.0077 | [SP:P25551] [OR:ESCHERICHIA COLI] [GN:RBSR] [DE:RIBOSE OPERON REPRESSOR] |
| contig282 | 245962_c3_4 | 371 | 3776 | 879 | 292 | 398 | 3.30E-37 | [AC:D90905] [OR:Synechocystis sp.] [PN:hypothetical protein] [NT:ORF_ID] |
| contig282 | 19688909_c2_3 | 372 | 3777 | 222 | 73 | 110 | 1.70E-06 | [AC:D32253] [OR:Magnetospirillum sp.] [NT:putative protein highly homologous to E. coli RNase] |
| contig283 | 25820313_f1_1 | 373 | 3778 | 648 | 215 | 100 | 0.0059 | [AC:D90905] [OR:Methanococcus jannaschii] [PN:hypothetical protein MJ0798] |
| contig283 | 16443905_c2_5 | 374 | 3779 | 555 | 184 | 867 | 6.50E-87 | [AC:L35659] [OR:Streptococcus bovis] [PN:malic enzyme] [NT:Malic enzyme (S)-malate] |
| contig284 | 902187_c3_7 | 375 | 3780 | 777 | 258 | 178 | 1.30E-12 | [SP:P26833] [OR:CLOSTRIDIUM PERFRINGENS] [DE:HYPOTHETICAL 31.2 KD PROTEIN IN NAGH 5'REGION (ORFB)] |
| contig284 | 24643812_f2_2 | 376 | 3781 | 765 | 254 | 338 | 7.50E-31 | [AC:D90816] [OR:Escherichia coli] [GN:ydjC] [NT:ORF_ID] |

TABLE 2-continued

| Contig | Orf | NT Seq Id | AA Seq ID | NT Orf Length | AA Orf Length | Score | Probability | Description |
|---|---|---|---|---|---|---|---|---|
| contig285 | 9767842_c3_6 | 377 | 3782 | 237 | 79 | 141 | 5.00E-09 | [AC:Y13308] [OR:Yersinia enterocolitica] [PN:sulfate permease] [NT:ORF3] |
| contig285 | 29390711_c2_4 | 378 | 3783 | 966 | 321 | 274 | 4.50E-24 | [SP:P33019] [OR:ESCHERICHIA COLI] [GN:YEIH] [DE:HYPOTHETICAL 36.9 KD PROTEIN IN LYSP-NFO INTERGENIC REGION] |
| contig285 | 2056268_c3_5 | 379 | 3784 | 375 | 124 | 50 | 0.99 | [AC:U51793] [OR:Hepatitis C virus] [PN:envelope glycoprotein E2] [NT:hypervariable region 1] |
| contig285 | 9881557_f2_3 | 380 | 3785 | 240 | 80 | 62 | 0.69 | [AC:Y08256] [OR:Sulfolobus solfataricus] [GN:orf c02005] |
| contig286 | 963342_c1_3 | 381 | 3786 | 1200 | 399 | 791 | 7.40E-79 | [SP:Q01444] [OR:MYCOPLASMA MYCOIDES] [DE:HYPOTHETICAL PROTEIN IN FFH 5'REGION (FRAGMENT)] |
| contig287 | 20745436_f3_2 | 382 | 3787 | 876 | 291 | 145 | 4.50E-08 | [SP:P54721] [OR:BACILLUS SUBTILIS] [GN:YFIE] [DE:HYPOTHETICAL 31.5 KD PROTEIN IN GLVBC 3'REGION] |
| contig287 | 93757_f3_3 | 383 | 3788 | 477 | 159 | 133 | 2.40E-08 | [AC:D86380] [OR:Bacillus cereus] [PN:Alkaline D-peptidase] [GN:adp] |
| contig288 | 25673900_f3_1 | 384 | 3789 | 684 | 227 | 74 | 0.57 | [AC:U47096] [OR:Daucus carota] [NT:a LEA protein] |
| contig288 | 24242056_c3_5 | 385 | 3790 | 477 | 158 | 341 | 3.60E-31 | [SP:P19219] [OR:BACILLUS SUBTILIS] [GN:ADAA] [DE:METHYLPHOSPHOTRIESTER-DNA ALKYLTRANSFERASE] |
| contig289 | 7082027_f1_1 | 386 | 3791 | 1200 | 400 | 86 | 0.53 | [AC:U33332] [OR:Human cytomegalovirus] [NT:orf UL154] |
| contig29 | 13006930_f2_1 | 387 | 3792 | 336 | 111 | 220 | 9.90E-18 | [SP:P37466] [OR:BACILLUS SUBTILIS] [GN:YABE] [DE:HYPOTHETICAL 47.7 KD PROTEIN IN METS-KSGA INTERGENIC REGION] |
| contig29 | 13711592_f2_2 | 388 | 3793 | 504 | 168 | 91 | 0.034 | [SP:Q49857] [OR:MYCOBACTERIUM LEPRAE] [GN:B229_C1_170] [DE:HYPOTHETICAL 38.0 KD PROTEIN B229_C1_170 PRECURSOR] |
| contig290 | 26808211_f3_3 | 389 | 3794 | 1347 | 448 | 667 | 1.00E-65 | [AC:D86418] [OR:Bacillus subtilis] [PN:YfnA] |
| contig290 | 24875093_f1_1 | 390 | 3795 | 240 | 80 | 248 | 2.50E-20 | [SP:P37465] [OR:BACILLUS SUBTILIS] [GN:METS] [DE:(METRS)] |
| contig291 | 12508578_f2_1 | 391 | 3796 | 1452 | 483 | 132 | 3.30E-05 | [AC:Z83107] [OR:Caenorhabditis elegans] [PN:F11C3.3] [NT:similar to myosin heavy chain; cDNA EST CESAB82R] |
| contig291 | 26282182_f2_2 | 392 | 3797 | 405 | 134 | 67 | 0.99995 | [SP:Q13620] [OR:HOMO SAPIENS] [GN:CUL4B] [DE:CULLIN HOMOLOG 4B (CUL-4B) (FRAGMENT)] |
| contig292 | 3928318_f1_1 | 393 | 3798 | 603 | 200 | 746 | 4.30E-74 | [AC:294043] [OR:Bacillus subtilis] [PN:hypothetical protein] [GN:yvdN] [NT:similar to CLPP_ECOLI ATP-dependent clp protease] |
| contig292 | 34187592_c2_3 | 394 | 3799 | 543 | 180 | 91 | 0.027 | [AC:Y11777] [OR:Rickettsia prowazekii] [PN:outer membrane protein] [GN:com1] |
| contig293 | 24431562_c2_4 | 395 | 3800 | 585 | 194 | 439 | 1.50E-41 | [SP:P42020] [OR:LACTOCOCCUS LACTIS] [GN:PEPT] [DE:PEPTIDASE T, (AMINOTRIPEPTIDASE) (TRIPEPTIDASE)] |
| contig293 | 24413142_c2_3 | 396 | 3801 | 546 | 181 | 246 | 2.60E-20 | [OR:Enterococcus faecalis] [PN:probable pheromone binding protein/pheromone responsive gene Z protein] [GN:prgZ] |
| contig294 | 22400450_f3_2 | 397 | 3802 | 1758 | 585 | 1364 | 1.40E-139 | [SP:P21458] [OR:BACILLUS SUBTILIS] [GN:SPOIIIE] [DE:STAGE III SPORULATION PROTEIN E] |
| contig295 | 2656418_f2_1 | 398 | 3803 | 774 | 257 | 518 | 6.30E-50 | [SP:P54470] [OR:BACILLUS SUBTILIS] [GN:YOFL] [DE:HYPOTHETICAL 30.3 KD PROTEIN IN GLYS-DNAG/DNAE INTERGENIC REGION] |
| contig295 | 24619703_c1_3 | 399 | 3804 | 816 | 271 | 679 | 5.50E-67 | [SP:P72535] [OR:STREPTOCOCCUS PNEUMONIAE] [GN:THRB] [DE:HOMOSERINE KINASE, (HK)] |
| contig295 | 22925961_c3_5 | 400 | 3805 | 351 | 116 | 113 | 3.10E-06 | [SP:P09123] [OR:BREVIBACTERIUMBACILLUS SP] [GN:THRC] [DE:THREONINE SYNTHASE,] |
| contig296 | 14142542_f3_3 | 401 | 3806 | 324 | 107 | 121 | 2.30E-07 | [SP:P42902] [OR:ESCHERICHIA COLI] [GN:AGAR] |

TABLE 2-continued

| Contig | Orf | NT Seq Id | AA Seq ID | NT Orf Length | AA Orf Length | Score | Probability | Description |
|---|---|---|---|---|---|---|---|---|
| contig296 | 34063527_f2_1 | 402 | 3807 | 966 | 321 | 332 | 3.20E-30 | [DE:PUTATIVE AGA OPERON TRANSCRIPTIONAL REPRESSOR] [SP:P23391] [OR:*LACTOCOCCUS LACTIS*] [GN:LACC] |
| contig297 | 5161663_f1_1 | 403 | 3808 | 1791 | 596 | 1557 | 5.00E-160 | [DE:TAGATOSE-6-PHOSPHATE KINASE, (PHOSPHOTAGATOKINASE)] [AC:Z94043] [OR:*Bacillus subtilis*] [PN:hypothetical protein] [GN:yvdK] [NT:similar to trembl] |
| contig298 | 25678562_c1_2 | 404 | 3809 | 321 | 107 | 415 | 5.20E-39 | [OR:*Enterococcus faecalis*] [PN:probable pheromone-responsive regulatory protein R] [GN:prgR] |
| contig298 | 22359627_f3_1 | 405 | 3810 | 183 | 60 | 51 | 0.85 | [AC:U02259] [OR:*Mycoplasma genitalium*] [NT:Homology to initiation factor DnaA J01602] |
| contig299 | 4798587_f3_1 | 406 | 3811 | 1734 | 578 | 1349 | 5.50E-138 | [AC:L76359] [OR:*Streptomyces peucetius*] [PN:daunorubicin resistance protein] [GN:drrC] |
| contig3 | 24410169_c1_1 | 407 | 3812 | 429 | 142 | 639 | 9.50E-63 | [OR:*ENTEROCOCCUS FAECALIS*] [GN:EBSA] [DE:PORE FORMING PROTEIN EBSA] |
| contig30 | 33861563_c1_4 | 408 | 3813 | 1035 | 345 | 293 | 4.40E-26 | SP:P39074] [OR:*BACILLUS SUBTILIS*] [GN:BMRU] [DE:BMRU PROTEIN] |
| contig300 | 10353950_f2_2 | 409 | 3814 | 1008 | 335 | 506 | 1.20E-48 | [SP:Q10449] [OR:*SCHIZOSACCHAROMYCES POMBE*] [GN:SPAC12B10.16C] [DE:HYPOTHETICAL 57.2 KD PROTEIN C12B10.16C IN CHROMOSOME 1] |
| contig300 | 35432011_f1_1 | 410 | 3815 | 390 | 129 | 243 | 1.40E-19 | [AC:AE000176] [OR:*Escherichia coli*] [GN:ybgB] [NT:o877; 100 pct identical to the first 86 residues of] |
| contig300 | 10007652_f3_3 | 411 | 3816 | 207 | 68 | 52 | 0.95 | [OR:*Brassica napus*] [PN:3-oxoacyl-[acyl-carrier-protein] |
| contig301 | 2675006_f2_1 | 412 | 3817 | 1290 | 429 | 307 | 1.30E-26 | [AC:L25426] [OR:*Staphylococcus aureus*] [PN:penicillin-binding protein 2] [GN:pbp2] |
| contig301 | 2625187_f2_2 | 413 | 3818 | 189 | 62 | 63 | 0.27 | [AC:JH0240] [OR:*Mus musculus*] [PN:aspartic proteinase,] |
| contig302 | 36223418_f3_2 | 414 | 3819 | 645 | 214 | 910 | 1.80E-91 | [AC:U74322] [OR:*Lactococcus lactis*] [PN:6-phosphogluconate dehydrogenase] |
| contig302 | 15117317_f1_1 | 415 | 3820 | 555 | 184 | 272 | 7.40E-24 | [AC:D64002] [OR:*Synechocystis sp.*] [PN:regulatory components of sensory transduction] [NT:ORF_ID] |
| contig303 | 21875903_f3_3 | 416 | 3821 | 486 | 161 | 130 | 1.00E-08 | [SP:P37958] [OR:*BACILLUS SUBTILIS*] [GN:MECA] [DE:NEGATIVE REGULATOR OF GENETIC COMPETENCE MECA] |
| contig303 | 4884838_f2_2 | 417 | 3822 | 846 | 281 | 407 | 3.60E-38 | [AC:X99710] [OR:*Lactococcus lactis*] [PN:transcription factor] [NT:weak homology with vsf-1 gene (X73635)] |
| contig304 | 21971918_c2_4 | 418 | 3823 | 246 | 81 | 64 | 0.89 | [SP:Q09630] [OR:*CAENORHABDITIS ELEGANS*] [GN:ZC506.4] [DE:PROBABLE METABOTROPIC GLUTAMATE RECEPTOR ZC506.4] |
| contig304 | 6285250_c3_3 | 419 | 3824 | 750 | 249 | 654 | 2.40E-64 | [AC:D88802] [OR:*Bacillus subtilis*] [GN:ydhR] [NT:*S. mutans* fructokinase; Q07211 (665)] |
| contig305 | 31533516_c3_6 | 420 | 3825 | 1227 | 408 | 1077 | 3.60E-109 | [SP:P12039] [OR:*BACILLUS SUBTILIS*] [GN:PURD] [DE:RIBONUCLEOTIDE SYNTHETASE) (PHOSPHORIBOSYLGLYCINAMIDE SYNTHETASE)] |
| contig306 | 26383507_c3_9 | 421 | 3826 | 849 | 283 | 216 | 6.30E-18 | [AC:U87792] [OR:*Bacillus subtilis*] [PN:unknown] [NT:ORF307; hypothetical 34.7 kd protein] |
| contig306 | 4343752_f3_6 | 422 | 3827 | 279 | 92 | 66 | 0.68 | [AC:D64005] [OR:*Synechocystis sp.*] [PN:hypothetical protein] [NT:ORF_ID] |
| contig307 | 14537691_f2_2 | 423 | 3828 | 294 | 97 | 135 | 3.70E-09 | [AC:AE000181] [OR:*Escherichia coli*] [NT:o234; This 234 aa orf is 26 pct identical (15 gaps)] |

TABLE 2-continued

| Contig | Orf | NT Seq Id | AA Seq ID | NT Orf Length | AA Orf Length | Score | Probability | Description |
|---|---|---|---|---|---|---|---|---|
| contig307 | 35937841_c1_4 | 424 | 3829 | 1149 | 382 | 182 | 1.00E-13 | [AC:Y14082] [OR:Bacillus subtilis] [PN:hypothetical protein] [GN:yhdW] [NT:Similarity to glycerol diester phosphodiesterase] |
| contig308 | 16506875_c2_5 | 425 | 3830 | 1134 | 377 | 158 | 2.40E-15 | [SP:P29240] [OR:DISCOPYGE OMMATA] [DE:5'-NUCLEOTIDASE PRECURSOR, (ECTO-NUCLEOTIDASE)] |
| contig309 | 13183591_f3_4 | 426 | 3831 | 288 | 95 | 57 | 0.36 | [AC:U37208] [OR:Simian immunodeficiency virus] [PN:envelope glycoprotein] [GN:env] |
| contig309 | 34100687_f2_3 | 427 | 3832 | 663 | 220 | 274 | 4.50E-24 | [AC:Y09476] [OR:Bacillus subtilis] [PN:YisX] [NT:putative] |
| contig309 | 12150313_c3_6 | 428 | 3833 | 246 | 81 | 69 | 0.54 | [SP:Q00099] [OR:ICTALURID HERPESVIRUS 1] [GN:56] [DE:HYPOTHETICAL GENE 56 PROTEIN] |
| contig31 | 24687678_c3_4 | 429 | 3834 | 255 | 85 | 62 | 0.12 | [SP:Q05360] [OR:LUCILIA CUPRINA] [GN:W] [DE:WHITE PROTEIN (FRAGMENT)] |
| contig310 | 15120887_f2_1 | 430 | 3835 | 1335 | 444 | 1354 | 1.60E-138 | [SP:P20964] [OR:BACILLUS SUBTILIS] [GN:OBG] [DE:SPO0B-ASSOCIATED GTP-BINDING PROTEIN] |
| contig311 | 36329057_f1_1 | 431 | 3836 | 876 | 291 | 683 | 2.10E-67 | [SP:P26946] [OR:BACILLUS FIRMUS] [DE:HYPOTHETICAL ABC TRANSPORTER ATP-BINDING PROTEIN] |
| contig311 | 5271078_f2_2 | 432 | 3837 | 249 | 82 | 92 | 0.00077 | [AC:Y14078] [OR:Bacillus subtilis] [PN:Hypothetical protein] [GN:yhaP] [NT:aa 1–147 show similarity to putative] |
| contig312 | 1283452_f2_2 | 433 | 3838 | 1659 | 552 | 68 | 0.31 | [AC:S79441] [OR:Bacillus sp.] [NT:Description] |
| contig313 | 5975890_f1_1 | 434 | 3839 | 192 | 63 | 64 | 0.97 | [AC:L35928] [OR:Streptococcus salivarius] [PN:glucosyltransferase] [GN:gtfm] |
| contig313 | 3955336_f1_2 | 435 | 3840 | 210 | 69 | 58 | 0.61 | [SP:Q05966] [OR:BRASSICA NAPUS] [GN:GRP10] [DE:GLYCINE-RICH RNA-BINDING PROTEIN 10] |
| contig313 | 6048562_c1_4 | 436 | 3841 | 255 | 84 | 58 | 0.999 | [SP:P32899] [OR:SACCHAROMYCES CEREVISIAE] [GN:YHR148W] [DE:PUTATIVE 40S RIBOSOMAL PROTEIN YHR148W] |
| contig314 | 4720463_c1_3 | 437 | 3842 | 369 | 123 | 66 | 0.048 | [AC:L47607] [OR:Picea glauca] [PN:late embryogenesis abundant protein] [GN:EMB15] [NT:ABA-responsive and embryogenesis-associated gene] |
| contig315 | 16839086_f2_2 | 438 | 3843 | 465 | 154 | 87 | 0.0003 | [SP:P00323] [OR:DESULFOVIBRIO VULGARIS] [DE:FLAVODOXIN] |
| contig315 | 5196062_f3_3 | 439 | 3844 | 438 | 145 | 120 | 2.60E-07 | [SP:P25983] [OR:BACILLUS SUBTILIS] [GN:PYRDII] [DE:DIHYDROOROTATE DEHYDROGENASE ELECTRON TRANSFER SUBUNIT] |
| contig315 | 16979712_f1_1 | 440 | 3845 | 210 | 70 | 111 | 2.70E-06 | [OR:Methanococcus jannaschii] [PN:cytochrome-c3 hydrogenase gamma chain homolog] |
| contig316 | 34157952_c1_3 | 441 | 3846 | 723 | 241 | 201 | 2.50E-16 | [AC:Z56283] [OR:Lactobacillus helveticus] [GN:orf2] |
| contig316 | 207811_c2_4 | 442 | 3847 | 801 | 266 | 239 | 8.30E-20 | [AC:Z56283] [OR:Lactobacillus helveticus] [GN:orf1] |
| contig317 | 1220462_f2_1 | 443 | 3848 | 1671 | 556 | 1226 | 5.90E-125 | [AC:U16134] [OR:Synechococcus sp.] [PN:ClpC] [GN:clpC] |
| contig318 | 11754215_f2_1 | 444 | 3849 | 1356 | 451 | 964 | 3.40E-97 | [SP:P17894] [OR:BACILLUS SUBTILIS] [GN:RECN] [DE:DNA REPAIR PROTEIN RECN (RECOMBINATION PROTEIN N)] |
| contig319 | 25442657_f3_2 | 445 | 3850 | 783 | 260 | 85 | 0.18 | [OR:Saccharomyces cerevisiae] [PN:HSH49 protein] [GN:HSH49] |
| contig319 | 4876643_c2_3 | 446 | 3851 | 324 | 107 | 70 | 0.98 | [AC:U30821] [OR:Cyanelle Cyanophora paradoxa] [PN:DnaK] [GN:dnaK-A] |
| contig319 | 2932937_c3_4 | 447 | 3852 | 222 | 73 | 195 | 1.10E-15 | [AC:L36907] [OR:Lactococcus lactis] [PN:ATP-dependent protease] [GN:clpA] [NT:ORF137; putative] |
| contig32 | 3735793_f3_2 | 448 | 3853 | 1188 | 396 | 1291 | 7.70E-132 | [SP:P09373] [OR:ESCHERICHIA COLI] [GN:PFLB] [DE:FORMATE ACETYLTRANSFERASE 1, (PYRUVATE FORMATE-LYASE 1)] |
| contig320 | 14187801_f2_4 | 449 | 3854 | 219 | 72 | 101 | 9.20E-05 | [SP:Q50739] [OR:MYCOBACTERIUM TUBERCULOSIS] |

TABLE 2-continued

| Contig | Orf | NT Seq Id | AA Seq ID | NT Orf Length | AA Orf Length | Score | Probability | Description |
|---|---|---|---|---|---|---|---|---|
| contig320 | 13001076_c1_13 | 450 | 3855 | 255 | 84 | 65 | 0.9 | [GN:MTCY9C4.09] [DE:HYPOTHETICAL 47.5 KD PROTEIN CY9C4.09] [AC:Z81317] [OR:Schizosaccharomyces pombe] [PN:unknown] [GN:SPAC6G9.04] [NT:SPAC6G9.04, unknown, len] |
| contig320 | 33835942_f3_8 | 451 | 3856 | 213 | 70 | 218 | 3.90E-18 | [OR:Methanococcus jannaschii] [PN:hypothetical protein homolog MJ0531] |
| contig320 | 4695187_f2_7 | 452 | 3857 | 516 | 171 | | | |
| contig321 | 25430443_c3_4 | 453 | 3858 | 1002 | 333 | 428 | 1.40E-48 | [SP:Q24803] [OR:ENTAMOEBA HISTOLYTICA] [DE:ALCOHOL DEHYDROGENASE 2.] [GN:ADH2] |
| contig321 | 29773438_f3_3 | 454 | 3859 | 261 | 87 | 54 | 0.6 | [AC:AF003525] [OR:Mus musculus] [PN:beta-defensin 1] |
| contig322 | 35839066_c2_3 | 455 | 3860 | 396 | 132 | 208 | 7.70E-17 | [SP:Q47898] [OR:FLAVOBACTERIUM MENINGOSEPTICUM] [DE:(GLYCOSYLASPARAGINASE) (ASPARTYLGLUCOSAMINIDASE) (AGA)] |
| contig322 | 24394206_c1_2 | 456 | 3861 | 1278 | 425 | 358 | 4.00E-54 | [AC:D90901] [OR:Bacillus stearothermophilus] [PN:hypothetical protein 1] |
| contig323 | 25858967_c2_5 | 457 | 3862 | 195 | 65 | 66 | 0.28 | [AC:D90901] [OR:Synechocystis sp.] [PN:hypothetical protein] [NT:ORF_ID] |
| contig323 | 23548427_c2_4 | 458 | 3863 | 948 | 315 | 63 | 0.5 | [OR:Macaca mulatta] [GN:TPH] [NT:Description] |
| contig323 | 12401075_c1_3 | 459 | 3864 | 216 | 71 | 55 | 0.52 | [AC:Y08631] [OR:Human astrovirus] [PN:capsid protein precursor] [GN:ORF2] |
| contig324 | 33395317_c3_11 | 460 | 3865 | 840 | 280 | 843 | 2.30E-84 | [AC:U58210] [OR:Streptococcus thermophilus] [PN:tetrahydrofolate dehydrogenase/cyclohydrolase] [GN:folD] |
| contig324 | 9923452_c2_10 | 461 | 3866 | 489 | 162 | 283 | 5.00E-25 | [SP:P54520] [OR:BACILLUS SUBTILIS] [GN:YOHZ] [DE:N UTILIZATION SUBSTANCE PROTEIN B HOMOLOG (NUSB PROTEIN)] |
| contig324 | 10724144_c1_8 | 462 | 3867 | 480 | 159 | 215 | 8.10E-18 | [SP:P54519] [OR:BACILLUS SUBTILIS] [GN:YOHY] [DE:HYPOTHETICAL 14.7 KD PROTEIN IN ACCC-FOLD INTERGENIC REGION] |
| contig325 | 25977343_c3_10 | 463 | 3868 | 780 | 259 | 299 | 1.00E-26 | [AC:U75471] [OR:Streptococcus mutans] [PN:high affinity branched chain amino acid] [GN:ilvG] |
| contig325 | 24803800_c1_7 | 464 | 3869 | 912 | 303 | 127 | 8.20E-06 | [AC:D90794] [OR:Escherichia coli] [PN:L-arabinose transport system permease protein] [GN:araH] [NT:ORF_ID] |
| contig326 | 30562806_f3_2 | 465 | 3870 | 1815 | 604 | 136 | 2.70E-05 | [SP:P54334] [OR:BACILLUS SUBTILIS] [GN:XKDO] [DE:PHAGE-LIKE ELEMENT PBSX PROTEIN XKDO] |
| contig327 | 198302_f2_2 | 466 | 3871 | 1923 | 640 | 1409 | 2.40E-144 | [AC:U21932] [OR:Bacillus subtilis] [PN:L-glutamine-D-fructose-6-phosphate] [GN:gcaA] |
| contig327 | 34652213_c1_6 | 467 | 3872 | 285 | 94 | | | |
| contig327 | 24805317_c2_8 | 468 | 3873 | 261 | 86 | | | |
| contig328 | 6445250_f1_1 | 469 | 3874 | 1314 | 437 | 676 | 1.10E-66 | [SP:P46317] [OR:BACILLUS SUBTILIS] [GN:CELB] [DE:PERMEASE IIC COMPONENT) (PHOSPHOTRANSFERASE ENZYME II, C COMPONENT)] |
| contig328 | 24265702_c2_8 | 470 | 3875 | 264 | 87 | 63 | 0.996 | [AC:Z96800] [OR:Mycobacterium tuberculosis] [PN:hypothetical protein MTCY63.10c] [GN:PPE-family] [NT:MTCY63.10c. len] |
| contig328 | 4098527_f2_2 | 471 | 3876 | 309 | 102 | 77 | 0.087 | [AC:Z71264] [OR:Caenorhabditis elegans] [PN:K07G5.1] [NT:protein predicted using Genefinder; Weak similarity] |
| contig328 | 4882827_f3_6 | 472 | 3877 | 243 | 80 | 145 | 1.30E-09 | [SP:P13254] [OR:PSEUDOMONAS PUTIDA] [DE:METHIONINE GAMMA-LYASE, (L-METHIONINASE)] |
| contig329 | 23636086_f2_1 | 473 | 3878 | 888 | 295 | 62 | 0.56 | [OR:Homo sapiens] [PN:alpha-actinin] |
| contig329 | 1050900_c1_2 | 474 | 3879 | 345 | 114 | 89 | 0.00053 | [OR:Haemophilus influenzae] [PN:hypothetical protein HI0522] |
| contig33 | 33237700_c2_2 | 475 | 3880 | 555 | 185 | 79 | 0.99 | [AC:U97014] [OR:Caenorhabditis elegans] [GN:T05E8.3] [NT:strong |

TABLE 2-continued

| Contig | Orf | NT Seq Id | AA Seq ID | NT Orf Length | AA Orf Length | Score | Probability | Description |
|---|---|---|---|---|---|---|---|---|
| contig330 | 4414768_f1_1 | 476 | 3881 | 354 | 117 | 80 | 0.25 | similarity to the 'DEAH' subfamily of the [AC:U83113] [OR:Homo sapiens] [PN:INS-1 winged-helix homolog] [NT:similar to human putative M phase phosphoprotein 2] |
| contig330 | 25675312_f1_2 | 477 | 3882 | 444 | 147 | 390 | 2.30E-36 | [SP:P44551] [OR:HAEMOPHILUS INFLUENZAE] [GN:HI0174] [DE:HYPOTHETICAL PROTEIN HI0174] |
| contig330 | 25430391_f1_3 | 478 | 3883 | 600 | 200 | 470 | 7.70E-45 | [SP:P25745] [OR:ESCHERICHIA COLI] [GN:YCFB] [DE:HYPOTHETICAL PROTEIN IN PURB 5'REGION (ORF-15) (FRAGMENT)] |
| contig330 | 24348577_c2_6 | 479 | 3884 | 1347 | 448 | 1359 | 4.80E-139 | [OR:Corynebacterium glutamicum] [PN:glutamate dehydrogenase (NADP+).] |
| contig331 | 19582805_f2_5 | 480 | 3885 | 801 | 267 | 183 | 9.50E-14 | [AC:D64004] [OR:Synechocystis sp.] [PN:hypothetical protein] [NT:ORF_ID] |
| contig332 | 15625013_f1_1 | 481 | 3886 | 216 | 71 | 52 | 0.95 | [OR:Staphylococcus sp.] [PN:fobB protein] |
| contig332 | 94063_c3_7 | 482 | 3887 | 945 | 314 | 966 | 2.10E-97 | [AC:U09352] [OR:Streptococcus pyogenes] [PN:67 kDa Myosin-crossreactive streptococcal] [NT:ORF2] |
| contig333 | 35401562_c2_4 | 483 | 3888 | 375 | 125 | 163 | 2.60E-12 | [SP:Q00053] [OR:LACTOBACILLUS HELVETICUS] [GN:GALM] [DE:ALDOSE 1-EPIMERASE, (MUTAROTASE) (FRAGMENT)] |
| contig333 | 10801250_c1_3 | 484 | 3889 | 696 | 231 | 720 | 2.50E-71 | [AC:Z70730] [OR:Lactococcus lactis] [PN:beta-phosphoglucomutase] |
| contig333 | 985383_c3_5 | 485 | 3890 | 387 | 128 | 372 | 1.40E-33 | [AC:Z94043] [OR:Bacillus subtilis] [PN:hypothetical protein] [GN:yvdK] [NT:similar to tremb1] |
| contig334 | 26384567_f1_1 | 486 | 3891 | 540 | 179 | 80 | 0.54 | [SP:P07908] [OR:BACILLUS SUBTILIS] [GN:DNAB] [DE:REPLICATION INITIATION AND MEMBRANE ATTACHMENT PROTEIN] |
| contig334 | 26603431_f3_4 | 487 | 3892 | 936 | 311 | 613 | 5.40E-60 | [SP:P06567] [OR:BACILLUS SUBTILIS] [GN:DNAI] [DE:PRIMOSOMAL PROTEIN DNAI] |
| contig335 | 9766068_f1_1 | 488 | 3893 | 1419 | 472 | 1695 | 1.20E-174 | [AC:Z67739] [OR:Streptococcus pneumoniae] [PN:DNA topoisomerase IV] [GN:parE] [NT:ParE subunit] |
| contig336 | 26572687_f2_2 | 489 | 3894 | 1341 | 446 | 644 | 2.80E-63 | [OR:Bacillus subtilis] [PN:DNA-directed DNA polymerase, III chain dnaX] [GN:dnaX] |
| contig336 | 36189717_f1_1 | 490 | 3895 | 327 | 109 | 178 | 6.70E-14 | [SP:P24281] [OR:BACILLUS SUBTILIS] [GN:YAAK] [DE:HYPOTHETICAL 11.8 KD PROTEIN IN DNAZ-RECR INTERGENIC REGION] |
| contig337 | 4118938_f3_1 | 491 | 3896 | 471 | 156 | 493 | 2.80E-47 | [SP:P80239] [OR:BACILLUS SUBTILIS] [GN:AHPC] [DE:PROTEIN 22] |
| contig337 | 24430287_f3_2 | 492 | 3897 | 987 | 329 | 727 | 4.50E-72 | [SP:P52213] [OR:CLOSTRIDIUM LITORALE] [GN:TRXB] [DE:THIOREDOXIN REDUCTASE.] |
| contig338 | 6539712_c1_5 | 493 | 3898 | 657 | 218 | 91 | 0.025 | [SP:P17418] [OR:BACTEROIDES NODOSUS] [GN:FIMC] [DE:POSSIBLE FIMBRIAL ASSEMBLY PROTEIN FIMC (SEROGROUP D)] |
| contig338 | 16907312_f2_2 | 494 | 3899 | 207 | 68 | 66 | 0.62 | [OR:Saccharomyces cerevisiae] [PN:probable membrane protein YPR185w] |
| contig338 | 6929713_f2_3 | 495 | 3900 | 390 | 129 | | | |
| contig339 | 33361378_f3_6 | 496 | 3901 | 228 | 75 | 59 | 0.95 | [OR:Saccharomyces cerevisiae] [PN:probable membrane protein YLR360w] |
| contig339 | 19723451_c2_7 | 497 | 3902 | 1491 | 496 | 984 | 2.60E-99 | [SP:P39883] [OR:BACTEROIDES NODOSUS] [GN:PRFC] [DE:PEPTIDE CHAIN RELEASE FACTOR 3 (RF-3)] |
| contig34 | 4867943_c2_3 | 498 | 3903 | 528 | 175 | 448 | 1.60E-42 | [SP:P07672] [OR:ESCHERICHIA COLI] [GN:APT] [DE:ADENINE PHOSPHORIBOSYLTRANSFERASE, (APRT)] |
| contig340 | 79806_f2_1 | 499 | 3904 | 438 | 145 | 259 | 1.80E-22 | [SP:P26646] [OR:ESCHERICHIA COLI] [GN:YHDH] [DE:(O324)] |

TABLE 2-continued

| Contig | Orf | NT Seq Id | AA Seq ID | NT Orf Length | AA Orf Length | Score | Probability | Description |
|---|---|---|---|---|---|---|---|---|
| contig340 | 52318_f2_2 | 500 | 3905 | 789 | 262 | 132 | 2.50E-06 | [OR:*Methanococcus jannaschii*] [PN:pantothenate metabolism flavoprotein] |
| contig341 | 31773887_c1_3 | 501 | 3906 | 1665 | 555 | 257 | 2.90E-19 | [SP:P23545] [OR:*BACILLUS SUBTILIS*] [GN:PHOR] [DE:ALKALINE PHOSPHATASE SYNTHESIS SENSOR PROTEIN PHOR,] |
| contig341 | 11896090_c2_4 | 502 | 3907 | 393 | 130 | 331 | 4.10E-30 | [SP:P13792] [OR:*BACILLUS SUBTILIS*] [GN:PHOP] [DE:PHOP] |
| contig342 | 31742010_f3_1 | 503 | 3908 | 1341 | 446 | 633 | 4.10E-62 | [SP:P30336] [OR:*BACILLUS FIRMUS*] [GN:CADA] [DE:ATPASE] |
| contig343 | 21769802_f3_2 | 504 | 3909 | 234 | 77 | 131 | 2.10E-08 | [SP:P54721] [OR:*BACILLUS SUBTILIS*] [GN:YfIE] |
| contig343 | 1208443_f3_3 | 505 | 3910 | 768 | 255 | 446 | 2.70E-42 | [DE:HYPOTHETICAL 31.5 KD PROTEIN IN GLVBC 3REGION] [AC:Z83337] [OR:*Bacillus subtilis*] [GN:ywpI] [NT:highly similar to phosphotransferase system] |
| contig343 | 4730340_f3_4 | 506 | 3911 | 276 | 92 | 67 | 0.34 | [SP:P39918] [OR:*COXIELLA BURNETII*] [DE:HYPOTHETICAL 49.9 KD PROTEIN IN SPOIIIE-SERS INTERGENIC REGION] |
| contig344 | 23494127_c1_3 | 507 | 3912 | 861 | 287 | 238 | 2.60E-19 | [SP:Q09320] [OR:*CAENORHABDITIS ELEGANS*] [GN:F40B5.2] [DE:HYPOTHETICAL 69.0 KD PROTEIN F40B5.2 IN CHROMOSOME X] |
| contig344 | 36070188_c2_4 | 508 | 3913 | 618 | 205 | 55 | 0.94 | [SP:P45628] [OR:*LEIURUS QUINQUESTRIATUS HEBRAEUS*] [DE:CHARYBDOTOXIN 2 (CHTX-LQ2) (TOXIN 18-2) (LQH 18-2)] |
| contig344 | 23849218_c3_5 | 509 | 3914 | 663 | 220 | 53 | 0.995 | [SP:P13832] [OR:*Rattus norvegicus*] [NT:myosin regulatory light chain (582 is 1st base in] |
| contig345 | 34550000_c3_3 | 510 | 3915 | 894 | 297 | 366 | 8.00E-34 | [OR:*Methanococcus jannaschii*] [PN:N-ethylammeline chlorohydrolase homolog] |
| contig345 | 4571905_c2_1 | 511 | 3916 | 255 | 84 | 102 | 0.0001 | [SP:P39761] [OR:*BACILLUS SUBTILIS*] [GN:ADEC] [DE:ADENINE DEAMINASE, (ADENASE) (ADENINE AMINASE)] |
| contig346 | 7089212_c3_4 | 512 | 3917 | 198 | 65 | 63 | 0.93 | [AC:D09910] [OR:*Synechocystis sp.*] [PN:sensory transduction histidine kinase] [NT:ORF_ID] |
| contig346 | 34566502_f3_2 | 513 | 3918 | 273 | 90 | | | |
| contig346 | 4901587_f2_1 | 514 | 3919 | 342 | 113 | 73 | 0.51 | [OR:*Campylobacter jejuni*] [PN:cell binding factor 2] |
| contig347 | 7126_c2_7 | 515 | 3920 | 465 | 155 | 98 | 0.00031 | [SP:P10051] [OR:*CITROBACTER DIVERSUS*] [DE:AMINOGLYCOSIDE N6-ACETYLTRANSFERASE, (AAC(6'))] |
| contig347 | 6690753_c2_6 | 516 | 3921 | 204 | 67 | 59 | 0.24 | [SP:P34279] [OR:*CAENORHABDITIS ELEGANS*] [GN:C02F5.2] [DE:HYPOTHETICAL 9.4 KD PROTEIN C02F5.2 IN CHROMOSOME III] |
| contig347 | 26766903_f2_2 | 517 | 3922 | 630 | 209 | 155 | 1.80E-11 | [SP:P45544] [OR:*Methanococcus jannaschii*] [PN:mutator protein mutT] |
| contig347 | 24398507_c1_5 | 518 | 3923 | 402 | 133 | 687 | 7.80E-68 | [SP:P37061] [OR:*ENTEROCOCCUS FAECALIS*] [GN:NOX] [DE:NADH OXIDASE, (NOXASE)] |
| contig348 | 12303138_f1_1 | 519 | 3924 | 189 | 62 | 58 | 0.31 | [SP:P06385] [OR:*MARCHANTIA POLYMORPHA*] [GN:RPL20] [DE:CHLOROPLAST 50S RIBOSOMAL PROTEIN L20] |
| contig348 | 4961578_c3_6 | 520 | 3925 | 774 | 257 | 686 | 9.90E-68 | [SP:P42423] [OR:*BACILLUS SUBTILIS*] [GN:YXDL] [DE:HYPOTHETICAL ABC TRANSPORTER ATP-BINDING PROTEIN IN IDH 3REGION] |
| contig348 | 9772555_c3_5 | 521 | 3926 | 756 | 251 | 173 | 8.20E-13 | [SP:P45544] [OR:*ESCHERICHIA COLI*] [GN:YHFR] [DE:(O265)] |
| contig349 | 24306712_f3_2 | 522 | 3927 | 969 | 322 | 189 | 7.50E-13 | [AC:L37338] [OR:*Streptomyces peucetius*] [PN:putative repressor] [GN:dnrO] [NT:putative] |
| contig349 | 5088212_c1_3 | 523 | 3928 | 294 | 97 | 201 | 1.00E-15 | [AC:Z81451] [OR:*Mycobacterium tuberculosis*] [PN:unknown] [GN:MTCY428.20] [NT:MTCY428.20, len] |
| contig349 | 29735006_c3_5 | 524 | 3929 | 279 | 92 | 281 | 8.60E-25 | [AC:X92418] [OR:*Streptococcus thermophilus*] [PN:gamma-glutamyl phosphate reductase] [GN:proA] |
| contig35 | 26753941_c1_3 | 525 | 3930 | 894 | 298 | 86 | 0.42 | [AC:U30873] [OR:*Bacillus subtilis*] [PN:NatB] [GN:natB] |

TABLE 2-continued

| Contig | Orf | NT Seq Id | AA Seq ID | NT Orf Length | AA Orf Length | Score | Probability | Description |
|---|---|---|---|---|---|---|---|---|
| contig350 | 4111032_f2_2 | 526 | 3931 | 348 | 115 | 63 | 0.098 | [AC:M63929] [OR:Human immunodeficiency virus type 1] [GN:vpu] |
| contig350 | 2767891_c2_5 | 527 | 3932 | 369 | 122 | 68 | 0.992 | [OR:Coxiella burnetii] [PN:mucZ protein] [GN:mucZ] |
| contig350 | 23355443_f3_4 | 528 | 3933 | 684 | 227 | 442 | 7.10E-42 | [SP:P54596] [OR:BACILLUS SUBTILIS] [GN:YHCL] [DE:HYPOTHETICAL 49.0 KD PROTEIN IN CSPB-GLPP INTERGENIC REGION] |
| contig351 | 23438438_c3_6 | 529 | 3934 | 222 | 73 | 66 | 0.28 | [AC:D70843] [OR:Bacillus stearothermophilus] [PN:heme O synthetase] [GN:ctaB] |
| contig351 | 33252217_c1_5 | 530 | 3935 | 687 | 228 | 354 | 1.50E-32 | [SP:P54168] [OR:BACILLUS SUBTILIS] [GN:YPGQ] [DE:HYPOTHETICAL 23.1 KD PROTEIN IN BSAA-ILVD INTERGENIC REGION] |
| contig351 | 16932962_c1_4 | 531 | 3936 | 525 | 174 | 269 | 1.50E-23 | [SP:P05100] [OR:ESCHERICHIA COLI] [GN:TAG] [DE:GLYCOSYLASE I, CONSTITUTIVE] (TAG I) |
| contig352 | 24727050_c2_9 | 532 | 3937 | 252 | 83 | 52 | 0.78 | [AC:U42580] [OR:Paramecium bursaria Chlorella virus 1] [GN:a371R] |
| contig352 | 9766376_f1_1 | 533 | 3938 | 279 | 92 | 83 | 0.0031 | [SP:P25385] [OR:SACCHAROMYCES CEREVISIAE] [GN:BOS1] [DE:VESICULAR TRANSPORT PROTEIN BOS1] |
| contig352 | 976582_f2_3 | 534 | 3939 | 348 | 115 | 67 | 0.89 | [OR:Vibrio cholerae] [PN:hypothetical protein] |
| contig352 | 672081_f3_4 | 535 | 3940 | 414 | 137 | 59 | 0.38 | [OR:Phasianus colchicus] [PN:Major Histocompatibility Complex class IIB] |
| contig352 | 26384687_f3_5 | 536 | 3941 | 675 | 224 | 89 | 0.27 | [OR:Kluyveromyces marxianus var. lactis] [PN:DNA-binding protein RAP1 homolog] |
| contig353 | 26567068_f1_1 | 537 | 3942 | 363 | 120 | 152 | 8.70E-11 | [AC:Z79580] [OR:Bacillus subtilis] [GN:putative ORF] |
| contig353 | 14898587_f2_3 | 538 | 3943 | 915 | 304 | 637 | 1.50E-62 | [AC:Y11213] [OR:Streptococcus thermophilus] [PN:hypothetical protein] [GN:ORF 1] |
| contig353 | 24782806_f3_4 | 539 | 3944 | 612 | 204 | 195 | 1.10E-15 | [AC:Y11213] [OR:Streptococcus thermophilus] [PN:hypothetical protein] [GN:ORF 2] |
| contig354 | 31735783_f3_2 | 540 | 3945 | 582 | 193 | 414 | 6.60E-39 | [AC:P44634] [OR:HAEMOPHILUS INFLUENZAE] [GN:HI0315] [DE:HYPOTHETICAL PROTEIN HI0315] |
| contig354 | 35820387_f1_1 | 541 | 3946 | 489 | 162 | 156 | 1.70E-09 | [AC:AB001488] [OR:Bacillus subtilis] [GN:ydfL] [NT:PROBABLE REGULATORY PROTEIN, SIMILAR TO] |
| contig355 | 15079207_f1_1 | 542 | 3947 | 840 | 279 | | | |
| contig355 | 22459375_f2_2 | 543 | 3948 | 183 | 60 | 83 | 0.23 | [AC:X95984] [OR:Solanum berthaultii] [PN:glutamic acid-rich protein] |
| contig355 | 16959327_f3_3 | 544 | 3949 | 603 | 201 | 379 | 1.70E-44 | [AC:AE000219] [OR:Escherichia coli] [PN:hypothetical protein in pth-pts intergenic] [GN:ychM] [NT:f550; 98 pct identical to fragment YCHM_ECOLI SW] |
| contig356 | 25673900_f2_2 | 545 | 3950 | 1311 | 436 | | | |
| contig357 | 11002_c3_6 | 546 | 3951 | 1275 | 425 | 797 | 1.70E-79 | [SP:P50852] [OR:BACILLUS STEAROTHERMOPHILUS] [GN:MTLA] [DE:(EC 2.7.1.69) (EII-MTL)] |
| contig358 | 30566880_f3_3 | 547 | 3952 | 642 | 213 | 278 | 1.70E-24 | [AC:Y08498] [OR:Lactobacillus gasseri] [PN:aggregation promoting protein] [GN:apfA] |
| contig358 | 5102312_c2_5 | 548 | 3953 | 387 | 128 | 218 | 3.90E-18 | [SP:P14205] [OR:BACILLUS SUBTILIS] [GN:COMAB] [DE:COMA OPERON PROTEIN 2] |
| contig358 | 26053762_f2_2 | 549 | 3954 | 381 | 126 | 296 | 2.10E-26 | [SP:P23966] [OR:BACILLUS SUBTILIS] [GN:MENB] [DE:(DHNA SYNTHETASE)] |
| contig358 | 35738752_f1_1 | 550 | 3955 | 189 | 62 | 153 | 4.80E-11 | [SP:P23966] [OR:BACILLUS SUBTILIS] [GN:MENB] [DE:(DHNA SYNTHETASE)] |
| contig359 | 23439707_c1_4 | 551 | 3956 | 654 | 218 | 103 | 0.0091 | [SP:P32896] [OR:SACCHAROMYCES CEREVISIAE] [GN:PDC2] [DE:PDC2 PROTEIN] |
| contig359 | 35344432_c1_3 | 552 | 3957 | 648 | 215 | 84 | 0.42 | [SP:P22865] [OR:LACTOCOCCUS LACTIS] [GN:USP45] |

TABLE 2-continued

| Contig | Orf | NT Seq Id | AA Seq ID | NT Orf Length | AA Orf Length | Score | Probability | Description |
|---|---|---|---|---|---|---|---|---|
| contig36 | 14648432_c1_1 | 553 | 3958 | 240 | 79 | 62 | 0.62 | [DE:SECRETED 45 KD PROTEIN PRECURSOR] [OR:Saccharomyces cerevisiae] [PN:hypothetical protein YPR128c] |
| contig36 | 33242125_c2_2 | 554 | 3959 | 390 | 129 | 93 | 6.80E-05 | [AC:AB001488] [OR:Bacillus subtilis] [GN:ydcN] [NT:PROBABLE REPRESSOR PROTEIN.] |
| contig360 | 5910087_f1_1 | 555 | 3960 | 228 | 75 | 120 | 1.10E-07 | [AC:AE000139] [OR:Escherichia coli] [NT:o201; This 201 aa orf is 28 pct identical (6 gaps)] |
| contig360 | 35595177_f1_2 | 556 | 3961 | 1236 | 411 | 500 | 5.10E-48 | [AC:AE000139] [OR:Escherichia coli] [NT:o460; This 460 aa orf is 23 pct identical (24 gaps)] |
| contig361 | 22459375_c2_5 | 557 | 3962 | 1128 | 375 | 658 | 9.20E-65 | [AC:U81166] [OR:Lactococcus lactis cremoris] [PN:histidine kinase LlkinA] [GN:llkinA] |
| contig361 | 234812_c1_4 | 558 | 3963 | 249 | 82 | 56 | 0.45 | [AC:L05017] [OR:Streptococcus pyogenes] [PN:M-like protein] |
| contig362 | 6347031_f2_3 | 559 | 3964 | 537 | 178 | 113 | 3.30E-05 | [AC:U25682] [OR:Pasteurella haemolytica] [PN:Lpp38] [NT:38 kDa lipoprotein] |
| contig362 | 10759680_f1_1 | 560 | 3965 | 477 | 158 | 218 | 3.30E-17 | [SP:P39761] [OR:BACILLUS SUBTILIS] [GN:ADEC] [DE:ADENINE DEAMINASE, (ADENASE) (ADENINE AMINASE)] |
| contig362 | 991678_f1_2 | 561 | 3966 | 846 | 281 | 232 | 9.20E-19 | [OR:Methanococcus jannaschii] [PN:adenine deaminase,] |
| contig363 | 23391442_f3_2 | 562 | 3967 | 972 | 323 | 416 | 4.00E-39 | [SP:P39584] [OR:BACILLUS SUBTILIS] [GN:YWBA] [DE:HYPOTHETICAL 47.6 KD PROTEIN IN EPR-GALK INTERGENIC REGION] |
| contig363 | 2866677_c3_4 | 563 | 3968 | 387 | 128 | 70 | 0.89 | [SP:Q01104] [OR:PSEUDOMONAS PUTIDA] [GN:PCAJ] [DE:3-OXOADIPATE COA-TRANSFERASE SUBUNIT B.] |
| contig364 | 3367202_f1_1 | 564 | 3969 | 186 | 61 | 55 | 0.52 | [AC:M19541] [OR:Human adenovirus type 41] [PN:hexon protein] |
| contig364 | 24398313_f1_2 | 565 | 3970 | 807 | 268 | 202 | 1.90E-16 | [SP:P54567] [OR:BACILLUS SUBTILIS] [GN:YQKD] [DE:HYPOTHETICAL 34.6 KD PROTEIN IN GLNQ-ANSR INTERGENIC REGION] |
| contig364 | 21928124_c1_3 | 566 | 3971 | 480 | 159 | 346 | 1.10E-31 | [AC:AB002668] [OR:Haemophilus actinomycetemcomitans] [NT:unnamed protein product] |
| contig365 | 35429692_c1_4 | 567 | 3972 | 600 | 199 | | | |
| contig365 | 14859375_c3_5 | 568 | 3973 | 936 | 311 | 900 | 2.10E-90 | [AC:U09239] [OR:Streptococcus pneumoniae] [GN:cps19fO] [NT:32.3 kDa cps19fO gene product] |
| contig366 | 80186_f3_4 | 569 | 3974 | 768 | 255 | 121 | 1.70E-07 | [SP:P27246] [OR:ESCHERICHIA COLI] [GN:MARA] [DE:MULTIPLE ANTIBIOTIC RESISTANCE PROTEIN MARA] |
| contig366 | 23712543_f1_1 | 570 | 3975 | 849 | 282 | 65 | 0.29 | [AC:U11222] [OR:Cervus elaphus] [PN:MHC class II DRB] [GN:CEEL-DRB] [NT:CEEL-DRB37 allele] |
| contig366 | 25995462_c3_11 | 571 | 3976 | 216 | 71 | 112 | 6.60E-07 | [AC:X94434] [OR:Lactobacillus plantarum] [PN:PlnM] [GN:plnM] [NT:putative] |
| contig366 | 29550659_c1_6 | 572 | 3977 | 813 | 270 | 710 | 2.80E-70 | [AC:D50453] [OR:Bacillus subtilis] [PN:homologue of Di-tripeptide transporter Dtp of L.] [GN:yclF] |
| contig367 | 11879577_c1_6 | 573 | 3978 | 609 | 202 | 108 | 0.0017 | [SP:P30314] [OR:BACTERIOPHAGE SP01] [GN:31] [DE:DNA POLYMERASE.] |
| contig367 | 25651443_c1_5 | 574 | 3979 | 735 | 244 | 93 | 0.032 | [AC:D90868] [OR:Escherichia coli] [PN:PUTATIVE PEPTIDASE IN GCVT-SPOIIIAA INTERGENIC] [GN:YQHT] [NT:similar to SwissProt Accession Number P54518] |
| contig368 | 25446000_c3_5 | 575 | 3980 | 843 | 281 | 103 | 0.009 | [OR:Streptococcus pyogenes] [PN:rofA protein] |
| contig368 | 21516012_c2_3 | 576 | 3981 | 993 | 330 | 100 | 0.0032 | [SP:P31465] [OR:ESCHERICHIA COLI] [GN:YIEF] [DE:HYPOTHETICAL 20.4 KD PROTEIN IN TNAB-BGLB INTERGENIC REGION] |
| contig369 | 4563832_f3_2 | 577 | 3982 | 1026 | 341 | 917 | 3.30E-92 | [SP:P52985] [OR:LACTOCOCCUS LACTIS] [GN:HOM] [DE:HOMOSERINE DEHYDROGENASE, (HDH)] |

TABLE 2-continued

| Contig | Orf | NT Seq Id | AA Seq ID | NT Orf Length | AA Orf Length | Score | Probability | Description |
|---|---|---|---|---|---|---|---|---|
| contig369 | 20739053_f2_1 | 578 | 3983 | 678 | 225 | 718 | 4.00E-71 | [SP:P09123] [OR:BREVIBACTERIUMBACILLUS SP] [GN:THRC] [DE:THREONINE SYNTHASE,] |
| contig37 | 201_f2_1 | 579 | 3984 | 756 | 252 | 171 | 3.70E-13 | [OR:Yersinia enterocolitica] [PN:hemin binding protein] |
| contig370 | 24657761_cl_8 | 580 | 3985 | 369 | 122 | | | |
| contig370 | 6673515_c3_11 | 581 | 3986 | 639 | 212 | 75 | 0.34 | [OR:Escherichia coli] [PN:hypothetical protein C-125] |
| contig370 | 16836591_f1_1 | 582 | 3987 | 741 | 246 | 162 | 4.50E-15 | [OR:Haemophilus influenzae] [PN:dihydrolipoamide acetyltransferase (acoC) homolog] |
| contig370 | 783156_c2_9 | 583 | 3988 | 231 | 76 | 58 | 0.29 | [OR:Lycopersicon esculentum] [PN:gamma-thionin-like protein precursor] |
| contig370 | 4867202_f3_6 | 584 | 3989 | 303 | 100 | 73 | 0.078 | [AC:K00825] [OR:Mitochondrion Neurospora crassa] [NT:cyt oxidase subunit 2 prepeptide ('taa' stop] |
| contig371 | 7214051_c2_5 | 585 | 3990 | 186 | 61 | 60 | 0.88 | [OR:Phytophthora capsici] [PN:serine/threonine kinase] |
| contig371 | 26571937_f2_1 | 586 | 3991 | 663 | 220 | 375 | 8.90E-35 | [AC:D90907] [OR:Synechocystis sp.] [PN:glutamine-binding periplasmic protein] [GN:glnH] [NT:ORF_ID] |
| contig371 | 13754838_f2_2 | 587 | 3992 | 741 | 246 | 446 | 2.70E-42 | [SP:P10346] [OR:ESCHERICHIA COLI] [GN:GLNQ] [DE:GLUTAMINE TRANSPORT ATP-BINDING PROTEIN GLNQ] |
| contig372 | 31288212_f1_1 | 588 | 3993 | 366 | 121 | 70 | 0.3 | [AC:Y13049] [OR:Sulfolobus acidocaldarius] [PN:orf1 hypothetical protein] |
| contig372 | 22694012_f3_4 | 589 | 3994 | 876 | 291 | 202 | 1.30E-14 | [SP:Q10384] [OR:MYCOBACTERIUM TUBERCULOSIS] [GN:MTCY190.02] [DE:HYPOTHETICAL 69.2 KD PROTEIN CY190.02] |
| contig372 | 26765937_f2_2 | 590 | 3995 | 387 | 128 | 51 | 0.88 | [AC:L38403] [OR:Plasmid pNB2] |
| contig372 | 36428176_f3_5 | 591 | 3996 | 279 | 92 | 67 | 0.64 | [SP:P46681] [OR:SACCHAROMYCES CEREVISIAE] [GN:AIP2] [DE:ACTIN INTERACTING PROTEIN 2] |
| contig372 | 25673905_c2_6 | 592 | 3997 | 675 | 224 | 644 | 2.80E-63 | [SP:P37550] [OR:BACILLUS SUBTILIS] [GN:YABH] [DE:HYPOTHETICAL 31.7 KD PROTEIN IN SSPF-PURR INTERGENIC REGION (ORF1)] |
| contig373 | 31272288_f3_1 | 593 | 3998 | 381 | 126 | 209 | 3.50E-17 | [SP:P54464] [OR:BACILLUS SUBTILIS] [GN:YOEY] [DE:HYPOTHETICAL 16.8 KD PROTEIN IN RPSU-PHOH INTEREGENIC REGION] |
| contig373 | 11131876_f3_2 | 594 | 3999 | 1068 | 355 | 957 | 1.90E-96 | [SP:P46343] [OR:BACILLUS SUBTILIS] [GN:PHOH] [DE:PHOH PROTEIN HOMOLOG] |
| contig374 | 14664128_f2_1 | 595 | 4000 | 675 | 224 | 635 | 2.50E-62 | [SP:P49668] [OR:PEDIOCOCCUS ACIDILACTICI] [GN:RPSB] [DE:30S RIBOSOMAL PROTEIN S2] |
| contig374 | 34650760_f2_2 | 596 | 4001 | 648 | 215 | 388 | 3.80E-36 | [SP:P19216] [OR:SPIROPLASMA CITRI] [GN:TSF] [DE:ELONGATION FACTOR TS (EF-TS)] |
| contig375 | 32131340_c2_2 | 597 | 4002 | 702 | 233 | 74 | 0.023 | [OR:Methanococcus jannaschii] [PN:hypothetical protein MJ0346] |
| contig376 | 35552181_c2_10 | 598 | 4003 | 660 | 220 | 413 | 8.40E-39 | [AC:Y14078] [OR:Bacillus subtilis] [PN:Hypothetical protein] [GN:yhaM] [NT:similarity to CMP-binding-factor-1 (cbf1) from] |
| contig376 | 26742082_c3_11 | 599 | 4004 | 2025 | 674 | 249 | 6.50E-19 | [AC:Y14078] [OR:Bacillus subtilis] [PN:Hypothetical protein] [GN:yhaN] [NT:similarity to orfX from Staphylococcus aureus] |
| contig377 | 583567_f3_2 | 600 | 4005 | 375 | 124 | 386 | 6.10E-36 | [AC:Y11463] [OR:Streptococcus pneumoniae] [NT:ORF3] |
| contig377 | 133562_cl_4 | 601 | 4006 | 552 | 183 | 61 | 0.36 | [AC:M15420] [OR:Bacillus subtilis] [NT:N-acetyl-gamma-glutamyl-phosphate reductase (EC] |
| contig377 | 4179177_c2_6 | 602 | 4007 | 501 | 166 | 82 | 0.62 | [AC:U08920] [OR:Chloroplast Lycium cestroides] [PN:NADH dehydrogenase subunit] [GN:ndhF] |
| contig377 | 26204712_cl_3 | 603 | 4008 | 423 | 140 | 68 | 0.98 | [SP:Q57741] [OR:METHANOCOCCUS JANNASCHII] [GN:MJ0293] [DE:PROBABLE THYMIDYLATE KINASE, (DTMP KINASE)] |

TABLE 2-continued

| Contig | Orf | NT Seq Id | AA Seq ID | NT Orf Length | AA Orf Length | Score | Probability | Description |
|---|---|---|---|---|---|---|---|---|
| contig378 | 35945327_c3_5 | 604 | 4009 | 657 | 218 | 158 | 3.00E-19 | [AC:U55214] [OR:*Treponema pallidum*] [PN:Pfs] [GN:pfs] [NT:similar to *E. coli* Pfs encoded by GenBank Accession] |
| contig378 | 34665913_c2_4 | 605 | 4010 | 387 | 128 | 52 | 0.93 | [AC:K03489] [OR:Human herpesvirus 4] [NT:nuclear antigen (EBNA2)] |
| contig378 | 36227187_c2_8 | 606 | 4011 | 336 | 111 | 296 | 2.10E-26 | [SP:P42904] [OR:*ESCHERICHIA COLI*] [GN:AGAV] [DE:ENZYME II, B COMPONENT 2,] |
| contig379 | 2240952_c3_9 | 607 | 4012 | 438 | 145 | 199 | 4.00E-16 | [AC:U65015] [OR:*Vibrio furnissii*] [PN:PTS permease for mannose subunit IIIMan N] [GN:manW] [NT:ManW; IIAMan] |
| contig379 | 195342_c2_7 | 608 | 4013 | 855 | 284 | 83 | 0.85 | [AC:U50300] [OR:*Caenorhabditis elegans*] [GN:R03H4.5] [NT:weak similarity to exoZ gene product from Rhizobium] |
| contig379 | 26023541_f3_1 | 609 | 4014 | 204 | 67 | 124 | 3.50E-08 | [SP:P21477] [OR:*BACILLUS SUBTILIS*] [GN:RPST] [DE:30S RIBOSOMAL PROTEIN S20 (BS20)] |
| contig38 | 6723262_c3_2 | 610 | 4015 | 327 | 108 | 196 | 8.30E-16 | [SP:P49851] [OR:*BACILLUS SUBTILIS*] [GN:YKHA] [DE:HYPOTHETICAL 20.1 KD PROTEIN IN HMP 5'REGION (ORF1)] |
| contig380 | 26828840_f3_2 | 611 | 4016 | 684 | 227 | 79 | 0.95 | [AC:AB001896] [OR:*Staphylococcus aureus*] [GN:dnaG] |
| contig380 | 7042337_f2_1 | 612 | 4017 | 864 | 287 | 664 | 2.10E-65 | [AC:D86418] [OR:*Bacillus subtilis*] [PN:YfmR] |
| contig381 | 5960778_f1_1 | 613 | 4018 | 492 | 163 | 133 | 2.90E-08 | [SP:P37189] [OR:*ESCHERICHIA COLI*] [GN:GATC] [DE:PERMEASE IIC COMPONENT) (PHOSPHOTRANSFERASE ENZYME II, C COMPONENT)] |
| contig381 | 20585887_c3_6 | 614 | 4019 | 786 | 261 | 661 | 4.40E-65 | [SP:P26422] [OR:*STREPTOCOCCUS MUTANS*] [GN:LACR] [DE:LACTOSE PHOSPHOTRANSFERASE SYSTEM REPRESSOR] |
| contig381 | 24354038_c1_4 | 615 | 4020 | 267 | 88 | 66 | 0.28 | [SP:Q05278] [OR:MYCOBACTERIOPHAGE L5] [GN:6] [DE:MINOR TAIL PROTEIN GP6] |
| contig382 | 24845937_c2_3 | 616 | 4021 | 1896 | 631 | 619 | 3.30E-87 | [AC:U93874] [OR:*Bacillus subtilis*] [PN:hypothetical protein YrhL] [GN:yrhL] [NT:similar to *Haemophilus influenzae* hypothetical |
| contig383 | 9940693_f3_5 | 617 | 4022 | 555 | 184 | 369 | 3.90E-34 | [AC:U93874] [OR:*Bacillus subtilis*] [PN:formate dehydrogenase] [GN:yrhG] [NT:similar to *Methanobacterium formicicum* formate |
| contig383 | 22832811_f1_1 | 618 | 4023 | 639 | 212 | 73 | 0.9998 | [AC:X99485] [OR:*Lupinus luteus*] [PN:G protein] [NT:alpha subunit] |
| contig383 | 192677_c2_13 | 619 | 4024 | 192 | 63 | | | |
| contig383 | 30508562_f3_6 | 620 | 4025 | 477 | 158 | 200 | 3.10E-16 | [AC:Z77663] [OR:*Caenorhabditis elegans*] [PN:F53F4.10] [NT:protein predicted using Genefinder; Similarity to] |
| contig383 | 35985342_f3_7 | 621 | 4026 | 651 | 216 | 430 | 1.30E-40 | [SP:Q56222] [OR:*THERMUS AQUATICUS*] [GN:NQO1] [DE:DEHYDROGENASE 1, CHAIN 1) (NDH-1, CHAIN 1)] |
| contig383 | 24619052_f3_8 | 622 | 4027 | 666 | 221 | 322 | 1.10E-28 | [AC:D90911] [OR:*Synechocystis sp.*] [PN:hydrogenase subunit] [GN:hoxF] [NT:ORF_ID] |
| contig383 | 2149037_f2_4 | 623 | 4028 | 336 | 112 | 162 | 3.30E-12 | [AC:D90911] [OR:*Synechocystis sp.*] [PN:hydrogenase subunit] [GN:hoxU] [NT:ORF_ID] |
| contig384 | 34250405_c3_6 | 624 | 4029 | 834 | 278 | 882 | 1.70E-88 | [OR:*Streptococcus pneumonia*] [PN:helicase recG homolog] |
| contig384 | 214818_c1_4 | 625 | 4030 | 1095 | 364 | 855 | 1.20E-85 | [OR:*Streptococcus pneumoniae*] [PN:helicase recG homolog] |
| contig384 | 7036537_c2_5 | 626 | 4031 | 216 | 71 | 63 | 0.31 | [OR:*Saccharomyces cerevisiae*] [PN:hypothetical protein YLR456w] |
| contig385 | 34651628_f3_3 | 627 | 4032 | 627 | 208 | 59 | 0.55 | [AC:D17510] [OR:Chloroplast *Pinus thunbergiana*] [PN:ORF42b] [GN:psaM] |
| contig385 | 34277265_c1_5 | 628 | 4033 | 291 | 96 | 59 | 0.57 | [SP:P44624] [OR:*HAEMOPHILUS INFLUENZAE*] [GN:AMPD] [DE:AMPD PROTEIN HOMOLOG] |
| contig385 | 4121044_c1_4 | 629 | 4034 | 1482 | 493 | 1444 | 4.70E-148 | [SP:P23920] [OR:*BACILLUS STEAROTHERMOPHILUS*] [GN:METS] [DE:(METRS)] |
| contig386 | 4565701_c1_4 | 630 | 4035 | 201 | 67 | 110 | 1.10E-05 | [SP:P14218] [OR:*PSEUDOMONAS FLUORESCENS*] [GN:LPD] [DE:DIHYDROLIPOAMIDE DEHYDROGENASE,] |

TABLE 2-continued

| Contig | Orf | NT Seq Id | AA Seq ID | NT Orf Length | AA Orf Length | Score | Probability | Description |
|---|---|---|---|---|---|---|---|---|
| contig386 | 5133558_c3_5 | 631 | 4036 | 1047 | 348 | 719 | 3.20E-71 | [SP:P54533] [OR:BACILLUS SUBTILIS] [GN:BFMBC] [DE:DEHYDROGENASE) (LPD-VAL)] |
| contig386 | 5193839_c1_2 | 632 | 4037 | 396 | 131 | 281 | 8.20E-25 | [SP:Q05619] [OR:CLOSTRIDIUM ACETOBUTYLICUM] [GN:BUK] [DE:BUTYRATE KINASE, (BK)] |
| contig387 | 35410176_f1_1 | 633 | 4038 | 699 | 232 | 476 | 1.80E-45 | [SP:P39805] [OR:BACILLUS SUBTILIS] [GN:LICT] [DE:TRANSCRIPTION ANTITERMINATOR LICT] |
| contig387 | 32620287_f2_3 | 634 | 4039 | 192 | 63 | 98 | 2.00E-05 | [AC:X00754] [OR:Bacillus subtilis] [GN:open reading frame] |
| contig387 | 5078128_f2_4 | 635 | 4040 | 726 | 241 | 550 | 2.60E-53 | [AC:L49336] [OR:Clostridium longisporum] [PN:PTS-dependent enzyme II] [GN:abgF] |
| contig387 | 23831266_f2_5 | 636 | 4041 | 249 | 82 | 162 | 4.00E-11 | [AC:L49336] [OR:Clostridium longisporum] [PN:PTS-dependent enzyme II] [GN:abgF] |
| contig388 | 32242302_c1_5 | 637 | 4042 | 360 | 119 | 424 | 5.70E-40 | [SP:P38424] [OR:BACILLUS SUBTILIS] [GN:YSXC] [DE:HYPOTHETICAL 22.0 KD PROTEIN IN LON-HEMA INTERGENIC REGION (ORFX)] |
| contig388 | 23860912_c3_7 | 638 | 4043 | 264 | 87 | 77 | 0.0034 | [AC:U66708] [OR:Vibrio parahaemolyticus] [PN:ClpX-like protein] [GN:clpX] |
| contig388 | 23626707_c2_6 | 639 | 4044 | 1008 | 335 | 1274 | 4.90E-130 | [SP:P50866] [OR:BACILLUS SUBTILIS] [GN:CLPX] [DE:ATP-DEPENDENT CLP PROTEASE ATP-BINDING SUBUNIT CLPX] |
| contig388 | 14064385_f1_1 | 640 | 4045 | 303 | 100 | 217 | 4.90E-18 | [AC:Z75208] [OR:Bacillus subtilis] [PN:hypothetical protein] [GN:ysoC] [NT:unknown function; putative] |
| contig389 | 29558587_f1_1 | 641 | 4046 | 783 | 260 | 385 | 7.80E-36 | [SP:P23878] [OR:ESCHERICHIA COLI] [GN:FEPC] [DE:FERRIC ENTEROBACTIN TRANSPORT ATP-BINDING PROTEIN FEPC] |
| contig389 | 4960842_f1_2 | 642 | 4047 | 552 | 183 | 215 | 8.10E-18 | [AC:AE000332] [OR:Escherichia coli] [NT:f159 was f126; This 126 aa orf is 33 pct identical] |
| contig389 | 24649042_f3_3 | 643 | 4048 | 573 | 191 | 210 | 2.70E-17 | [SP:P45515] [OR:CITROBACTER FREUNDII] [DE:HYPOTHETICAL 19.8 KD PROTEIN IN DHAR-DHAT INTERGENIC REGION (ORFW)] |
| contig39 | 656663_f3_1 | 644 | 4049 | 504 | 168 | 247 | 3.30E-21 | [AC:AB001488] [NT:Bacillus subtilis] [GN:ydcL] [NT:PROBABLE INTEGRASE.] |
| contig390 | 32479712_f1_1 | 645 | 4050 | 636 | 211 | 604 | 4.80E-59 | [SP:P31080] [OR:BACILLUS SUBTILIS] [GN:LEXA] [DE:SOS REGULATORY PROTEIN LEXA/DINR] |
| contig390 | 14947183_c3_7 | 646 | 4051 | 1173 | 390 | 959 | 1.20E-96 | [AC:293102] [OR:Bacillus subtilis] [PN:hypothetical 48.5 kd protein] [GN:ygaP] |
| contig390 | 29328156_c3_6 | 647 | 4052 | 189 | 62 | 77 | 0.0064 | [OR:Lactococcus lactis] [PN:dihydrofolate reductase,] |
| contig391 | 32128186_f1_1 | 648 | 4053 | 204 | 67 | 66 | 0.048 | [AC:Z33252] [OR:Mycoplasma capricolum] [PN:DNA polymerase III (alpha)] [NT:ORF identified by homology to SwissProt entry] |
| contig391 | 24883437_f2_3 | 649 | 4054 | 972 | 323 | 652 | 4.00E-64 | [AC:Z80835] [OR:Bacillus subtilis] [PN:FMN adenylyltransferase] [GN:ribC] [NT:riboflavin kinase] |
| contig391 | 4726443_f1_2 | 650 | 4055 | 570 | 189 | 118 | 1.90E-06 | [AC:P39368] [OR:ESCHERICHIA COLI] [GN:YJHQ] [DE:HYPOTHETICAL 20.0 KD PROTEIN IN FECI-FIMB INTERGENIC REGION (F181)] |
| contig391 | 10003183_f3_5 | 651 | 4056 | 276 | 91 | 51 | 0.85 | [AC:X90990] [OR:Solanum tuberosum] [PN:sucrase] [NT:potential] |
| contig392 | 30655930_f3_2 | 652 | 4057 | 1122 | 373 | 122 | 3.10E-05 | [OR:Haliotis rufescens] [PN:tropomyosin] |
| contig392 | 26443837_c2_8 | 653 | 4058 | 708 | 235 | 499 | 6.50E-48 | [AC:Y08559] [OR:Bacillus subtilis] [PN:Unknown] [GN:ywnB] |
| contig392 | 16832925_c1_5 | 654 | 4059 | 432 | 143 | 323 | 2.90E-29 | [AC:Y08559] [OR:Bacillus subtilis] [PN:Unknown] [GN:ywnA] |
| contig392 | 12144840_c3_9 | 655 | 4060 | 393 | 130 | 145 | 2.10E-10 | [AC:AE000198] [OR:Escherichia coli] [PN:hypothetical protein in helD 5' region] [GN:yccF] [NT:f148; 100 pct to fragment YCCF_ECOLI SW] |
| contig393 | 23443811_f1_1 | 656 | 4061 | 798 | 265 | 61 | 0.54 | [SP:Q53866] [OR:STREPTOMYCES COELICOLOR] |

TABLE 2-continued

| Contig | Orf | NT Seq Id | AA Seq ID | NT Orf Length | AA Orf Length | Score | Probability | Description |
|---|---|---|---|---|---|---|---|---|
| contig393 | 5111088_c3_12 | 657 | 4062 | 429 | 142 | 146 | 1.70E-10 | [DE:HYPOTHETICAL PROTEIN IN PTPA 5′REGION (ORF1) (FRAGMENT)] |
| contig393 | 32235050_c3_11 | 658 | 4063 | 588 | 195 | 104 | 5.70E-08 | [AC:U28163] [OR:Lactobacillus curvatus] [PN:EIIA-man] [GN:manA] [NT:mannose phosphotransferase system enzyme EII] |
| contig394 | 34064402_f1_1 | 659 | 4064 | 486 | 161 | 64 | 0.17 | [AC:D90872] [OR:Escherichia coli] [PN:BETA-LACTAMASE PRECURSOR (EC 3.5.2.6)] [GN:AMPC] [NT:similar to [SwissProt Accession Number P24735] |
| contig394 | 23986437_f2_3 | 660 | 4065 | 468 | 155 | 69 | 0.99 | [AC:S81098] [OR:Shigella flexneri] [PN:TEM-type beta-lactamase] [NT:This sequence comes from Table 2A. Author-given] |
| contig394 | 10400626_c2_5 | 661 | 4066 | 360 | 119 | 66 | 0.048 | [OR:infectious pancreatic necrosis virus] [PN:genome polyprotein] [SP:Q60373] [OR:METHANOCOCCUS JANNASCHII] [GN:MJ0070] [DE:HYPOTHETICAL PROTEIN MJ0070] |
| contig394 | 34276576_c3_6 | 662 | 4067 | 654 | 217 | 734 | 8.10E-73 | [SP:P43435] [OR:ENTEROCOCCUS HIRAE] [GN:NTPD] [DE:TRANSLOCATING ATPASE SUBUNIT D)] |
| contig394 | 32157531_c2_4 | 663 | 4068 | 255 | 84 | 317 | 1.30E-28 | [SP:Q08637] [OR:ENTEROCOCCUS HIRAE] [GN:NTPB] [DE:TRANSLOCATING ATPASE SUBUNIT B] |
| contig395 | 3382837_f1_1 | 664 | 4069 | 720 | 239 | 139 | 9.20E-21 | [SP:P23553] [OR:CALDOCELLUM SACCHAROLYTICUM] [GN:XYNC] [DE:ACETYL ESTERASE.] |
| contig395 | 22003187_c2_5 | 665 | 4070 | 576 | 191 | 140 | 1.10E-09 | [SP:P03038] [OR:ESCHERICHIA COLI] [GN:TETR] [DE:TETRACYCLINE REPRESSOR PROTEIN CLASS A (TRANSPOSON 1721)] |
| contig396 | 30546912_f1_1 | 666 | 4071 | 1662 | 553 | 239 | 1.10E-36 | [AC:AE000176] [OR:Escherichia coli] [GN:ybgB] [NT:o877; 100 pct identical to the first 86 residues of] |
| contig397 | 5116502_f2_1 | 667 | 4072 | 1878 | 626 | 1348 | 7.00E-138 | [AC:D86418] [OR:Bacillus subtilis] [PN:YfnI] |
| contig398 | 29407562_f3_4 | 668 | 4073 | 225 | 74 | 55 | 0.994 | [SP:Q10702] [OR:MYCOBACTERIUM TUBERCULOSIS] [GN:MTCY49.33C] [DE:HYPOTHETICAL 33.9 KD PROTEIN CY49.33C] |
| contig398 | 36129837_f1_1 | 669 | 4074 | 558 | 185 | 296 | 2.10E-26 | [SP:P41027] [OR:BACILLUS CALDOLYTICUS] [GN:SIPC] [DE:SIGNAL PEPTIDASE 1, (SPASE 1) (LEADER PEPTIDASE 1)] |
| contig399 | 31750775_f1_1 | 670 | 4075 | 399 | 132 | 460 | 8.80E-44 | [AC:Z82044] [OR:Bacillus subtilis] [PN:hypothetical 16.4 kd protein] [GN:ygaG] [NT:homology to ferric uptake regulation protein] |
| contig399 | 36207932_f1_2 | 671 | 4076 | 912 | 303 | 1257 | 3.10E-128 | [SP:P37061] [OR:ENTEROCOCCUS FAECALIS] [GN:NOX] [DE:NADH OXIDASE, (NOXASE)] |
| contig4 | 4886578_c3_2 | 672 | 4077 | 321 | 106 | 164 | 2.00E-12 | [SP:P39345] [OR:ESCHERICHIA COLI] [GN:YIGU] [DE:(EC 1.—.—.—) (F254)] |
| contig4 | 785388_c2_1 | 673 | 4078 | 363 | 120 | 301 | 6.20E-27 | [AC:X96977] [OR:Enterococcus faecalis] [GN:orf11] |
| contig40 | 7032013_f1_1 | 674 | 4079 | 615 | 205 | 505 | 1.50E-48 | [SP:P46352] [OR:BACILLUS SUBTILIS] [GN:RIPX] [DE:PROBABLE INTEGRASE/RECOMBINASE RIPX] |
| contig400 | 30474038_f3_3 | 675 | 4080 | 969 | 322 | 53 | 0.9999 | [AC:X81139] [OR:garlic latent virus] [PN:7,8K protein] [GN:coat protein] |
| contig400 | 23652182_f2_2 | 676 | 4081 | 768 | 255 | 721 | 1.90E-71 | [AC:AE000290] [OR:Escherichia coli] [NT:o238; This 238 aa orf is 40 pct identical (5 gaps)] |
| contig401 | 11218958_c2_10 | 677 | 4082 | 468 | 156 | 252 | 9.70E-22 | [SP:P54458] [OR:BACILLUS SUBTILIS] [GN:YOEM] [DE:HYPOTHETICAL 28.3 KD PROTEIN IN AROD-COMER INTERGENIC REGION] |
| contig401 | 4024213_c1_8 | 678 | 4083 | 213 | 70 | 176 | 1.10E-13 | [SP:P54457] [OR:BACILLUS SUBTILIS] [GN:YOEL] [DE:HYPOTHETICAL 13.3 KD PROTEIN IN AROD-COMER INTERGENIC REGION] |
| contig401 | 23834632_c3_12 | 679 | 4084 | 621 | 206 | 445 | 3.40E-42 | [SP:P54456] [OR:BACILLUS SUBTILIS] [GN:YOEK] |

TABLE 2-continued

| Contig | Orf | NT Seq Id | AA Seq ID | NT Orf Length | AA Orf Length | Score | Probability | Description |
|---|---|---|---|---|---|---|---|---|
| contig401 | 26462807_c2_9 | 680 | 4085 | 663 | 220 | 519 | 4.90E-50 | [DE:HYPOTHETICAL 21.3 KD PROTEIN IN AROD-COMER INTERGENIC REGION] [SP:P54455] [OR:*BACILLUS SUBTILIS*] [GN:YOEJ] |
| contig401 | 23474062_c3_11 | 681 | 4086 | 351 | 116 | 244 | 6.80E-21 | [DE:HYPOTHETICAL 22.2 KD PROTEIN IN AROD-COMER INTERGENIC REGION] [SP:P54454] [OR:*BACILLUS SUBTILIS*] [GN:YOEI] |
| contig401 | 4688164_c1_6 | 682 | 4087 | 462 | 153 | 501 | 4.00E-48 | [DE:HYPOTHETICAL 10.8 KD PROTEIN IN AROD-COMER INTERGENIC REGION] [SP:P54453] [OR:*BACILLUS SUBTILIS*] [GN:YOEH] |
| contig401 | 21689766_f3_2 | 683 | 4088 | 1752 | 583 | 229 | 1.60E-15 | [DE:HYPOTHETICAL 41.0 KD PROTEIN IN NUCB-AROD INTERGENIC REGION] [AC:Z85982] [OR:*Mycobacterium tuberculosis*] [PN:unknown] [GN:MTCY06H11.04c] [NT:MTCY06H11.04c, len] |
| contig402 | 16853836_c1_3 | 684 | 4089 | 186 | 61 | 117 | 6.50E-07 | [DE:HYPOTHETICAL 30.3 KD PROTEIN IN GLYS-DNAG/DNAE INTERGENIC REGION] [SP:P54470] [OR:*BACILLUS SUBTILIS*] [GN:YQFL] |
| contig403 | 19569007_c2_5 | 685 | 4090 | 522 | 174 | 119 | 1.20E-07 | [OR:*Haemophilus parainfluenzae*] [PN:tetracycline resistance protein] [GN:tetR] |
| contig403 | 4491000_f3_2 | 686 | 4091 | 552 | 183 | 279 | 1.30E-24 | [AC:D83026] [OR:*Bacillus subtilis*] [GN:yxkA] [NT:hypothetical] |
| contig403 | 4954693_f1_1 | 687 | 4092 | 1248 | 415 | 865 | 1.10E-86 | [SP:P25744] [OR:*ESCHERICHIA COLI*] [GN:YCEE] [DE:HYPOTHETICAL 43.9 KD PROTEIN IN MSYB-HTRB INTERGENIC REGION (ORF1)] |
| contig404 | 36535250_f2_3 | 688 | 4093 | 1821 | 606 | 1475 | 2.40E-151 | [AC:U73807] [OR:*Moorella thermoacetica*] [PN:formate dehydrogenase alpha subunit] [GN:fdhα] [NT:selenocysteine |
| contig405 | 2382628_f1_2 | 689 | 4094 | 183 | 60 | 71 | 0.015 | [AC:Y08502] [OR:*Mitochondrion Arabidopsis thaliana*] [GN:tRNA-Ser] [NT:orf107g] |
| contig406 | 15824193_c3_11 | 690 | 4095 | 468 | 155 | 194 | 1.40E-15 | [SP:P00373] [OR:ESCHERICHIA COLI] [GN:PROC] [DE:PYRROLINE-5-CARBOXYLATE REDUCTASE, (P5CR) (P5C REDUCTASE)] |
| contig406 | 15631937_c2_10 | 691 | 4096 | 1827 | 608 | 908 | 5.60E-149 | [AC:Y14079] [OR:*Bacillus subtilis*] [PN:hypothetical protein] [GN:yhxB] [NT:see EMBL M34393 and Swiss Prot P18159.; This could] |
| contig406 | 6823763_c2_9 | 692 | 4097 | 186 | 61 | 59 | 0.24 | [AC:X16625] [OR:*Mus musculus*] [PN:MALA-2 protein] [NT:N-terminal fragment (AA 1–56)] |
| contig406 | 2441309_c2_8 | 693 | 4098 | 918 | 305 | 371 | 2.40E-34 | [AC:AB001488] [OR:*Bacillus subtilis*] [GN:yydD] [NT:SIMILAR TO THE RHIZOPINE CATABOLISM (MOCR) GENE OF] |
| contig407 | 3367812_c3_9 | 694 | 4099 | 1119 | 373 | 727 | 4.50E-72 | [AC:D83026] [OR:*Bacillus subtilis*] [GN:cydD] [NT:homologous to many ATP-binding transport proteins;] |
| contig407 | 31366394_c1_7 | 695 | 4100 | 1317 | 438 | 955 | 3.10E-96 | [AC:D83026] [OR:*Bacillus subtilis*] [GN:cydC] [NT:homologous to many ATP-binding transport proteins] |
| contig408 | 7035176_f2_2 | 696 | 4101 | 807 | 268 | 336 | 1.20E-30 | [OR:*Staphylococcus aureus*] [PN:llm protein] [GN:llm] |
| contig408 | 35657558_f3_4 | 697 | 4102 | 483 | 160 | 222 | 2.20E-18 | [OR:*Staphylococcus aureus*] [PN:llm protein] [GN:llm] |
| contig408 | 34414193_f1_1 | 698 | 4103 | 795 | 264 | 350 | 4.00E-32 | [AC:X81320] [OR:*Acinetobacter calcoaceticus*] [GN:epsX] |
| contig408 | 3415936_f3_5 | 699 | 4104 | 759 | 253 | 99 | 0.009 | [SP:P37782] [OR:*SHIGELLA FLEXNERI*] [GN:RFBF] [DE:DTDP-RHAMNOSYL TRANSFERASE RFBF] |
| contig409 | 12986668_f3_3 | 700 | 4105 | 294 | 97 | 127 | 1.70E-08 | [AC:D84214] [OR:*Bacillus subtilis*] [PN:YbbG] |
| contig409 | 35942192_c1_6 | 701 | 4106 | 732 | 243 | 136 | 1.00E-12 | [OR:*Escherichia coli*] [PN:hypothetical protein o215b] |
| contig409 | 7033138_c3_9 | 702 | 4107 | 678 | 225 | 352 | 2.40E-32 | [SP:P54501] [OR:*BACILLUS SUBTILIS*] [GN:YQGX] [DE:HYPOTHETICAL 23.2 KD PROTEIN IN SODA-COMGA |

TABLE 2-continued

| Contig | Orf | NT Seq Id | AA Seq ID | NT Orf Length | AA Orf Length | Score | Probability | Description |
|---|---|---|---|---|---|---|---|---|
| contig409 | 171952_f2_1 | 703 | 4108 | 1386 | 461 | 508 | 7.20E-49 | INTERGENIC REGION] [OR:*Saccharomyces cerevisiae*] [PN:hypothetical protein YDL238c] |
| contig409 | 25665937_f2_2 | 704 | 4109 | 231 | 77 | 95 | 0.00039 | [SP:P42086] [OR:*BACILLUS SUBTILIS*] [GN:PBUX] [DE:XANTHINE PERMEASE] |
| contig41 | 21992790_c3_6 | 705 | 4110 | 453 | 151 | 310 | 6.90E-28 | [AC:Y10304] [OR:*Bacillus subtilis*] [PN:polypeptide deformylase] [GN:def] |
| contig41 | 14661542_c1_3 | 706 | 4111 | 282 | 93 | 80 | 0.023 | [AC:Y10304] [OR:*Bacillus subtilis*] [GN:priA] |
| contig41 | 14850064_c2_4 | 707 | 4112 | 279 | 93 | 214 | 8.80E-17 | [AC:Y10304] [OR:*Bacillus subtilis*] [GN:priA] |
| contig410 | 34267517_c3_6 | 708 | 4113 | 603 | 200 | 66 | 0.93 | [AC:U64502] [OR:*Homo sapiens*] [PN:immunoglobulin heavy chain variable region] |
| contig410 | 33478377_c1_4 | 709 | 4114 | 618 | 205 | 97 | 0.0086 | [AC:Z73102] [OR:*Caenorhabditis elegans*] [PN:B0035.15] [NT:cDNA EST CEESB05F comes from this gene] |
| contig410 | 29534809_c2_5 | 710 | 4115 | 276 | 91 | 118 | 8.80E-07 | [AC:AB001488] [OR:*Bacillus subtilis*] [GN:ydcR] [NT:SIMILAR TO ORF20 OF *ENTEROCOCCUS FAECALIS*] |
| contig411 | 6735937_f3_4 | 711 | 4116 | 444 | 147 | 146 | 2.90E-09 | [OR:*Pseudomonas diminuta*] [PN:isoquinoline 1-oxidoreductase 80k chain] [GN:iorB] |
| contig411 | 2244062_f1_1 | 712 | 4117 | 627 | 208 | 129 | 1.80E-07 | [AC:AF000371] [OR:*Escherichia coli*] [NT:o192; This 192 aa orf is 22 pct identical (12 gaps)] |
| contig411 | 12698400_f2_2 | 713 | 4118 | 411 | 137 | 145 | 1.40E-09 | [AC:D64004] [OR:*Synechocystis* sp.] [PN:NifS] [GN:nifS] [NT:ORF_ID] |
| contig411 | 36525062_f1_1 | 714 | 4119 | 192 | 63 | 59 | 0.65 | [OR:*Streptococcus sanguis*] [PN:hypothetical IgA1 gene 5'-region protein] |
| contig412 | 24407202_f2_4 | 715 | 4120 | 1101 | 366 | 133 | 7.20E-06 | [OR:*Staphylococcus epidermidis*] [PN:PepT protein] |
| contig412 | 34382752_f3_7 | 716 | 4121 | 501 | 166 | 289 | 1.00E-24 | [SP:P40416] [OR:*SACCHAROMYCES CEREVISIAE*] [GN:ATM1] [DE:MITOCHONDRIAL TRANSPORTER ATM1 PRECURSOR] |
| contig412 | 16296901_f3_8 | 717 | 4122 | 438 | 145 | 82 | 0.054 | [OR:*Staphylococcus aureus*] [PN:hypothetical protein] |
| contig412 | 29322032_f1_3 | 718 | 4123 | 315 | 104 | 77 | 0.054 | [AC:U51115] [OR:*Bacillus subtilis*] [PN:YebA] [GN:yebA] [NT:encodes 5 transmembrane helixes] |
| contig412 | 50076_c2_13 | 719 | 4124 | 477 | 158 | 59 | 0.38 | [AC:X00394] [OR:*Saccharomyces cerevisiae*] [NT:Ty protein] |
| contig412 | 4417817_c3_16 | 720 | 4125 | 393 | 130 | 83 | 0.0081 | [AC:AB001488] [OR:*Bacillus subtilis*] [GN:ydgF] [NT:PROBABLE AMINO ACID TRANSPORT PERMIASE.] |
| contig412 | 4885926_f3_9 | 721 | 4126 | 198 | 65 | 62 | 0.54 | [AC:Z81489] [OR:*Caenorhabditis elegans*] [PN:C55A1.d] [NT:protein predicted using Genefinder; preliminary] |
| contig413 | 24415938_f2_5 | 722 | 4127 | 270 | 89 | 54 | 0.78 | [SP:P11339] [OR:SPIROPLASMA VIRUS 4] [GN:7] [DE:GENE 7 PROTEIN] |
| contig413 | 13937768_f1_1 | 723 | 4128 | 432 | 143 | 82 | 0.035 | [SP:Q10417] [OR:*LEUCONOSTOC MESENTEROIDES*] [GN:MESC] [DE:MESC PROTEIN] |
| contig413 | 34179702_f3_6 | 724 | 4129 | 519 | 172 | 65 | 0.39 | [AC:U80453] [OR:*Caenorhabditis elegans*] [GN:C23H3.8] [NT:coded for by *C. elegans* cDNA CEESQ58F] |
| contig413 | 126576_f3_7 | 725 | 4130 | 192 | 63 | 278 | 1.70E-24 | [SP:P51833] [OR:*BACILLUS SUBTILIS*] [GN:RNC] [DE:RIBONUCLEASE III, (RNASE III)] |
| contig413 | 882927_f1_2 | 726 | 4131 | 390 | 129 | 259 | 3.60E-29 | [OR:*Saccharomyces cerevisiae*] [PN:probable membrane protein YLR034c] |
| contig414 | 24063762_c3_16 | 727 | 4132 | 825 | 275 | 267 | 2.50E-23 | [AC:JT0240] [OR:*Bacillus subtilis*] [PN:tunicamycin resistance protein] [GN:tmrB] |
| contig414 | 22445252_c1_12 | 728 | 4133 | 525 | 174 | 98 | 0.0087 | [SP:P73451] [OR:SYNECHOCYSTIS SP] [GN:NRTB] [DE:NITRATE TRANSPORT PERMEASE PROTEIN NRTB] |
| contig414 | 25399062_c1_11 | 729 | 4134 | 228 | 75 | | | |
| contig414 | 57950_f2_3 | 730 | 4135 | 861 | 286 | | | |

TABLE 2-continued

| Contig | Orf | NT Seq Id | AA Seq ID | NT Orf Length | AA Orf Length | Score | Probability | Description |
|---|---|---|---|---|---|---|---|---|
| contig414 | 5275381_c1_10 | 731 | 4136 | 249 | 82 | 61 | 0.93 | [AC:U26058] [OR:Guinea pig cytomegalovirus] [GN:UL97 homolog] [NT:similar to ganciclovir kinase, Swiss-Prot Accession] |
| contig414 | 2839150_f1_2 | 732 | 4137 | 936 | 311 | 118 | 6.40E-05 | [SP:P73451] [OR:SYNECHOCYSTIS SP] [GN:NRTB] [DE:NITRATE TRANSPORT PERMEASE PROTEIN NRTB] |
| contig414 | 2422203_f2_4 | 733 | 4138 | 375 | 124 | 237 | 3.80E-20 | [SP:Q57855] [OR:METHANOCOCCUS JANNASCHII] [GN:MJ0412] [DE:HYPOTHETICAL ABC TRANSPORTER ATP-BINDING PROTEIN MJ0412] |
| contig415 | 14642962_f3_3 | 734 | 4139 | 1152 | 383 | 432 | 8.20E-41 | [AC:Z95388] [OR:Mycobacterium tuberculosis] [PN:MurE] [GN:murE] [NT:MTCY270.10, murE. Len] |
| contig415 | 960952_c2_7 | 735 | 4140 | 573 | 190 | 92 | 0.021 | [SP:P39721] [OR:SACCHAROMYCES CEREVISIAE] [GN:YAL049C] [DE:HYPOTHETICAL 27.1 KD PROTEIN IN ACS1-GCV3 INTERGENIC REGION] |
| contig415 | 1437825_f3_4 | 736 | 4141 | 987 | 328 | 181 | 3.20E-21 | [AC:AB001488] [OR:Bacillus subtilis] [GN:ydtO] [NT:SIMILAR TO PENTACHLOROPHENOL-INDUCED PERIPLASMIC] |
| contig416 | 24399062_f1_1 | 737 | 4142 | 2139 | 712 | 1957 | 2.00E-202 | [SP:P53533] [OR:SYNECHOCOCCUS SP] [GN:CLPB] [DE:CLPB PROTEIN] |
| contig417 | 24853588_c1_7 | 738 | 4143 | 654 | 217 | 837 | 9.90E-84 | [AC:U94707] [OR:Enterococcus faecalis] [PN:cell division protein] [GN:div1B] |
| contig417 | 29425302_f2_3 | 739 | 4144 | 225 | 74 | 58 | 0.53 | [AC:AF000262] [OR:Caenorhabditis elegans] [GN:C48E7.7] |
| contig417 | 24664087_c2_9 | 740 | 4145 | 1113 | 370 | 1813 | 3.70E-187 | [AC:U94707] [OR:Enterococcus faecalis] [PN:undecaprenyl-PP-N-acetylmuramic] [GN:murG] |
| contig417 | 21680377_c1_6 | 741 | 4146 | 699 | 232 | 1037 | 6.30E-105 | [AC:U94707] [OR:Enterococcus faecalis] [PN:D-glutamic acid adding enzyme] [GN:murD] |
| contig418 | 10548918_f3_2 | 742 | 4147 | 384 | 127 | 268 | 5.80E-23 | [SP:P54596] [OR:BACILLUS SUBTILIS] [GN:YHCL] [DE:HYPOTHETICAL 49.0 KD PROTEIN IN CSPB-GLPP INTERGENIC REGION] |
| contig418 | 2867677_c3_7 | 743 | 4148 | 285 | 94 | 65 | 0.13 | [SP:P09340] [OR:CRICETULUS GRISEUS] [GN:GRO] [DE:GROWTH REGULATED PROTEIN PRECURSOR] |
| contig418 | 24299426_f3_3 | 744 | 4149 | 405 | 134 | 69 | 0.029 | [AC:Z75208] [OR:Bacillus subtilis] [PN:hypothetical protein] [GN:ysfE] [NT:unknown function; putative] |
| contig418 | 34042333_f2_1 | 745 | 4150 | 1158 | 385 | 280 | 1.00E-24 | [AC:M77275] [OR:unidentified cloning vector] [PN:alpha-amylase] [NT:fusion protein] |
| contig419 | 22072825_f3_1 | 746 | 4151 | 507 | 168 | 508 | 7.20E-49 | [AC:U58864] [OR:Bacillus subtilis] [PN:CspR] [GN:cspR] [NT:methylase homolog] |
| contig419 | 26361067_f3_2 | 747 | 4152 | 657 | 218 | 193 | 1.70E-15 | [AC:Y14084] [OR:Bacillus subtilis] [PN:hypothetical protein] [GN:yvhR] [NT:similarity to a hypothetical protein o215b from] |
| contig42 | 35160006_f1_1 | 748 | 4153 | 375 | 124 | 74 | 2.30E-05 | [AC:Z95120] [OR:Mycobacterium tuberculosis] [PN:RpoE] [GN:rpoE] [NT:MTCY07D11.03, rpoE. Len] |
| contig42 | 22736312_f3_2 | 749 | 4154 | 420 | 140 | 52 | 0.92 | [SP:Q48433] [OR:KLEBSIELLA PNEUMONIAE] [GN:ARAA] [DE:L-ARABINOSE ISOMERASE, (FRAGMENT)] |
| contig420 | 33454837_c3_15 | 750 | 4155 | 921 | 306 | 326 | 1.40E-29 | [SP:P31114] [OR:BACILLUS SUBTILIS] [GN:GERCC] [DE:SPORE GERMINATION PROTEIN C3] |
| contig420 | 33417841_f3_7 | 751 | 4156 | 918 | 305 | 171 | 2.80E-11 | [SP:P39582] [OR:BACILLUS SUBTILIS] [GN:YWAB] [DE:HYPOTHETICAL 33.8 KD PROTEIN IN DAE-TYRZ INTERGENIC REGION] |
| contig420 | 33750312_c3_14 | 752 | 4157 | 270 | 89 | 63 | 0.98 | [AC:Z72511] [OR:Caenorhabditis elegans] [PN:F55A11.2] [NT:similar to epimorphin protein] |
| contig420 | 35439378_f1_2 | 753 | 4158 | 834 | 277 | 488 | 9.50E-47 | [AC:Z93939] [OR:Bacillus subtilis] [PN:NADH dehydrogenase] [GN:yumB] [NT:putative; unknown] |

TABLE 2-continued

| Contig | Orf | NT Seq Id | AA Seq ID | NT Orf Length | AA Orf Length | Score | Probability | Description |
|---|---|---|---|---|---|---|---|---|
| contig420 | 10745300_f2_5 | 754 | 4159 | 525 | 174 | 295 | 2.70E-26 | [AC:Z93939] [OR:*Bacillus subtilis*] [PN:NADH dehydrogenase] [GN:yumB] [NT:putative; unknown] |
| contig421 | 34659550_c3_9 | 755 | 4160 | 294 | 97 | 68 | 0.98 | [AC:AF003390] [OR:*Caenorhabditis elegans*] [GN:R155.4] |
| contig421 | 24491313_c1_5 | 756 | 4161 | 189 | 62 | 55 | 0.52 | [AC:U47023] [OR:*Methanococcus maripaludis*] [PN:unknown] [NT:ORF-7] |
| contig421 | 24820301_c2_7 | 757 | 4162 | 564 | 187 | 91 | 0.013 | [SP:P44757] [OR:*HAEMOPHILUS INFLUENZAE*] [GN:HI0570] [DE:HYPOTHETICAL PROTEIN HI0570] |
| contig421 | 158467_c3_8 | 758 | 4163 | 1341 | 446 | 628 | 1.40E-61 | [OR:*Bacillus stearothermophilus*] [PN:cellobiose phosphotransferase system celB] |
| contig422 | 14102343_c2_8 | 759 | 4164 | 513 | 170 | 497 | 1.10E-47 | [AC:U09422] [OR:*Enterococcus faecalis*] [NT:ORF18] |
| contig422 | 24492215_c2_7 | 760 | 4165 | 246 | 81 | 331 | 4.10E-30 | [AC:U09422] [OR:*Enterococcus faecalis*] [NT:ORF19] |
| contig422 | 35157812_c1_4 | 761 | 4166 | 183 | 60 | 56 | 0.54 | [SP:P17792] [OR:*AGROBACTERIUM TUMEFACIENS*] [GN:VIRB2] [DE:VIRB2 PROTEIN PRECURSOR] |
| contig422 | 984536_c2_6 | 762 | 4167 | 1209 | 402 | 1080 | 1.80E-109 | [AC:U09422] [OR:*Enterococcus faecalis*] [NT:ORF20] |
| contig422 | 35197340_c3_9 | 763 | 4168 | 258 | 85 | 64 | 0.078 | [OR:*Rattus norvegicus*] [PN:merlin protein] [GN:NF2] |
| contig422 | 7135126_c2_5 | 764 | 4169 | 618 | 205 | 226 | 3.20E-18 | [SP:P09915] [OR:BACTERIOPHAGE RHO-11S] [DE:METHYLTRANSFERASE BSU P11S] |
| contig423 | 25970312_f3_2 | 765 | 4170 | 1671 | 556 | 1928 | 2.40E-199 | [AC:U51911] [OR:*Bacillus subtilis*] [PN:unknown] [GN:ykqC] [NT:similar aminopeptidase AMPS with Swiss-Prot] |
| contig423 | 29456302_c2_4 | 766 | 4171 | 267 | 88 | 300 | 7.90E-27 | [AC:X91789] [OR:*Listeria monocytogenes*] [PN:CspL protein] [GN:cspL] |
| contig423 | 1382627_c2_3 | 767 | 4172 | 609 | 202 | 516 | 1.00E-49 | [SP:Q02170] [OR:*BACILLUS SUBTILIS*] [GN:YSSXA] [DE:DNA REPAIR PROTEIN RADC HOMOLOG (ORFB)] |
| contig424 | 22392888_f3_3 | 768 | 4173 | 834 | 277 | 131 | 2.60E-05 | [AC:M69183] [OR:*Plasmodium falciparum*] [PN:mature-parasite-infected erythrocyte surface] [GN:MESA] |
| contig424 | 21679703_f2_2 | 769 | 4174 | 759 | 253 | 1050 | 2.70E-106 | [AC:Z82044] [OR:*Bacillus subtilis*] [PN:catalase] [GN:katA] |
| contig425 | 11766252_f3_6 | 770 | 4175 | 1026 | 341 | 844 | 1.80E-84 | [AC:D64005] [OR:*Synechocystis sp.*] [PN:cadmium-transporting ATPase] [GN:cadA] [NT:ORF_ID] |
| contig425 | 36225875_f1_1 | 771 | 4176 | 465 | 154 | 149 | 7.90E-11 | [AC:Z75208] [OR:*Bacillus subtilis*] [PN:hypothetical protein] [GN:yshA] [NT:unknown function; putative] |
| contig425 | 24032962_f2_5 | 772 | 4177 | 561 | 186 | 201 | 2.50E-16 | [AC:Z75208] [OR:*Bacillus subtilis*] [PN:hypothetical protein] [GN:yshB] [NT:unknown function; putative] |
| contig425 | 24479683_f1_3 | 773 | 4178 | 576 | 192 | 249 | 2.70E-20 | [AC:Z75208] [OR:*Bacillus subtilis*] [PN:hypothetical protein] [GN:yshD] [NT:shows homology to mutS of Thermus aquaticus; |
| contig426 | 24320287_f1_1 | 774 | 4179 | 1122 | 373 | 310 | 1.50E-27 | [SP:P13398] [OR:PSEUDOMONAS SP] [GN:NYLA] [DE:DEGRADING ENZYME EI] |
| contig426 | 4883518_f3_5 | 775 | 4180 | 537 | 178 | 181 | 3.20E-14 | [OR:*Escherichia coli*] [PN:hypothetical protein o215b] |
| contig426 | 21696876_f1_3 | 776 | 4181 | 1107 | 369 | 633 | 9.70E-62 | [SP:P23914] [OR:*BACILLUS SUBTILIS*] [GN:LEVR] [DE:TRANSCRIPTIONAL REGULATORY PROTEIN LEVR] |
| contig427 | 12218913_f3_3 | 777 | 4182 | 567 | 188 | 293 | 7.20E-26 | [AC:Y14080] [OR:*Bacillus subtilis*] [PN:hypothetical protein] [GN:yheL] [NT:similarity to Na(+)/H(+) antiporter from Bacillus] |
| contig427 | 21750950_f1_1 | 778 | 4183 | 480 | 159 | 198 | 5.10E-16 | [AC:AB001488] [OR:*Bacillus subtilis*] [GN:ydgI] [NT:SIMILAR TO *SALMONELLA TYPHIMURIUM* SLYY GENE] |
| contig427 | 914027_f2_2 | 779 | 4184 | 669 | 222 | 590 | 1.50E-57 | [AC:AB001488] [OR:*Bacillus subtilis*] [GN:ydgI] [NT:SIMILAR TO NITROREDUCTASE.] |
| contig427 | 31750780_c3_6 | 780 | 4185 | 741 | 246 | 264 | 5.20E-23 | [SP:P09997] [OR:*ESCHERICHIA COLI*] [GN:YIDA] [DE:HYPOTHETICAL 29.7 KD PROTEIN IN IBPA-GYRB INTERGENIC REGION] |
| contig428 | 22667562_f1_1 | 781 | 4186 | 378 | 125 | 337 | 9.50E-31 | [OR:*Streptococcus parasanguis*] [PN:hypothetical protein 5] |

TABLE 2-continued

| Contig | Orf | NT Seq Id | AA Seq ID | NT Orf Length | AA Orf Length | Score | Probability | Description |
|---|---|---|---|---|---|---|---|---|
| contig428 | 13859625_f3_6 | 782 | 4187 | 894 | 297 | 747 | 3.40E-74 | [SP:P42361] [OR:*STREPTOCOCCUS GORDONII CHALLIS*] [DE:29 KD MEMBRANE PROTEIN IN PSAA 5'REGION (ORF1)] |
| contig428 | 24494157_f1_2 | 783 | 4188 | 453 | 150 | 590 | 1.50E-57 | [AC:U03756] [OR:*Enterococcus faecalis*] [PN:endocarditis specific antigen] |
| contig428 | 21942_f3_7 | 784 | 4189 | 207 | 68 | 171 | 8.50E-13 | [AC:U03756] [OR:*Enterococcus faecalis*] [PN:endocarditis specific antigen] |
| contig428 | 21917187_f1_3 | 785 | 4190 | 456 | 151 | 693 | 1.80E-68 | [AC:U03756] [OR:*Enterococcus faecalis*] [PN:endocarditis specific antigen] |
| contig428 | 6346924_c1_11 | 786 | 4191 | 1362 | 453 | 578 | 2.80E-56 | [AC:D88802] [OR:*Bacillus subtilis*] [GN:ydiF] [NT:*H. influenzae* hypothetical ABC transporter; P44808] |
| contig428 | 34189793_c2_7 | 787 | 4192 | 408 | 136 | 249 | 1.20E-20 | [SP:P41835] [OR:*SACCHAROMYCES CEREVISIAE*] [GN:THI6] [DE:HYDROXYETHYLTHIAZOLE KINASE) (TH KINASE))] |
| contig428 | 111713_c3_9 | 788 | 4193 | 831 | 276 | 227 | 4.30E-19 | [SP:P76423] [OR:*ESCHERICHIA COLI*] [GN:THIM] [DE:HYDROXYETHYLTHIAZOLE KINASE) (TH KINASE) |
| contig428 | 31843762_c2_6 | 789 | 4194 | 636 | 211 | 60 | 0.45 | [SP:P06851] [OR:*MARCHANTIA POLYMORPHA*] [GN:PSBE] [DE:CYTOCHROME B559 ALPHA CHAIN] |
| contig429 | 9773925_f3_2 | 790 | 4195 | 978 | 325 | 1046 | 7.00E-106 | [SP:P14951] [OR:*BACILLUS SUBTILIS*] [GN:UVRC] [DE:EXCINUCLEASE ABC SUBUNIT C] |
| contig43 | 3232062_f1_1 | 791 | 4196 | 207 | 68 | 64 | 0.67 | [SP:P08158] [OR:*EMERICELLA NIDULANS*] [GN:AMDS] [DE:ACETAMIDASE.] |
| contig430 | 31735778_f1_1 | 792 | 4197 | 858 | 285 | 358 | 5.70E-33 | [AC:AB001488] [OR:*Bacillus subtilis*] [GN:ydtO] [NT:SIMILAR TO PENTACHLOROPHENOL-INDUCED PERIPLASMIC] |
| contig430 | 4001088_f1_2 | 793 | 4198 | 630 | 209 | 368 | 4.90E-34 | [SP:P29376] [OR:*Bacillus subtilis*] [GN:ywrF] |
| contig430 | 12219530_c3_7 | 794 | 4199 | 765 | 254 | 88 | 0.16 | [SP:P19385] [OR:BACTERIOPHAGE CP-7] [GN:CPL7] [DE:LYSOZYME, (ENDOLYSIN) (MURAMIDASE) (CP-7 LYSIN)] |
| contig431 | 12714652_c1_7 | 795 | 4200 | 192 | 64 | 170 | 8.20E-13 | [SP:P37550] [OR:*BACILLUS SUBTILIS*] [GN:YABH] [DE:HYPOTHETICAL 31.7 KD PROTEIN IN SSPF-PURR INTERGENIC REGION (ORF1)] |
| contig431 | 24034437_c1_6 | 796 | 4201 | 360 | 119 | 246 | 4.20E-21 | [SP:P37466] [OR:*BACILLUS SUBTILIS*] [GN:YEG] [DE:VEG PROTEIN] |
| contig431 | 20562777_c1_5 | 797 | 4202 | 603 | 200 | 142 | 4.40E-10 | [AC:X65713] [OR:*Lactococcus lactis*] [NT:ORF] |
| contig431 | 4142293_c3_8 | 798 | 4203 | 540 | 179 | 349 | 5.10E-32 | [SP:P37574] [OR:*BACILLUS SUBTILIS*] [GN:YACP] [DE:HYPOTHETICAL 19.7 KD PROTEIN IN CYSS 3'REGION] |
| contig432 | 5132826_c2_12 | 799 | 4204 | 1296 | 432 | 59 | 0.93 | [AC:X95276] [OR:*Plasmodium falciparum*] [GN:rps17] |
| contig432 | 35266887_c1_11 | 800 | 4205 | 483 | 160 | 62 | 0.22 | [OR:*Bacillus subtilis*] [PN:ribosomal protein S20] |
| contig432 | 6438877_c1_10 | 801 | 4206 | 225 | 74 | 65 | 0.084 | [SP:P53258] [OR:*SACCHAROMYCES CEREVISIAE*] [GN:YNR046W] [DE:HYPOTHETICAL 15.1 KD PROTEIN IN PET494-MSO1 INTERGENIC REGION] |
| contig432 | 36188787_c1_9 | 802 | 4207 | 831 | 276 | 98 | 0.012 | [AC:M92304] [OR:*Xenopus laevis*] [PN:smooth muscle beta-tropomyosin] [GN:beta-tropomyosin] |
| contig432 | 35187937_c1_8 | 803 | 4208 | 207 | 68 | 65 | 0.49 | [SP:Q59549] [OR:*MYCOPLASMA PNEUMONIAE*] [GN:DNAA] [DE:CHROMOSOMAL REPLICATION INITIATOR PROTEIN DNAA] |
| contig433 | 24814193_c3_13 | 804 | 4209 | 219 | 73 | 62 | 0.12 | [AC:AF000364] [OR:*Escherichia coli*] [NT:f76; This 76 aa orf is 34 pct identical (1 gaps) to] |
| contig433 | 24415937_c2_8 | 805 | 4210 | 540 | 179 | 83 | 0.059 | [SP:P40414] [OR:*SACCHAROMYCES CEREVISIAE*] [GN:TPM2] [DE:TROPOMYOSIN 2] |
| contig433 | 34010875_c3_12 | 806 | 4211 | 249 | 82 | 85 | 0.00048 | [AC:X96977] [OR:*Enterococcus faecalis*] [GN:orf6] |
| contig433 | 29569202_c2_7 | 807 | 4212 | 297 | 98 | 50 | 0.91 | [SP:P05988] [OR:*SALMONELLA TYPHIMURIUM*] [GN:ILVY] |

TABLE 2-continued

| Contig | Orf | NT Seq Id | AA Seq ID | NT Orf Length | AA Orf Length | Score | Probability | Description |
|---|---|---|---|---|---|---|---|---|
| contig433 | 21642262_c3_11 | 808 | 4213 | 1068 | 355 | 120 | 8.20E-05 | [DE:TRANSCRIPTIONAL ACTIVATOR PROTEIN ILVY (FRAGMENT)] [SP:P15132] [OR:BACTERIOPHAGE PHI-29] [GN:13] [DE:MORPHOGENESIS PROTEIN 1 (LATE PROTEIN GP13)] |
| contig433 | 587558_c3_10 | 809 | 4214 | 696 | 231 | 77 | 0.96 | [OR:Saccharomyces cerevisiae] [PN:hypothetical protein YDR299w] |
| contig433 | 11954463_c3_9 | 810 | 4215 | 207 | 68 | 60 | 0.19 | [OR:Methanococcus jannaschii] [PN:hypothetical protein MJ1617] |
| contig434 | 19620686_f2_2 | 811 | 4216 | 222 | 73 | 52 | 0.78 | [AC:JS0654] [OR:Streptomyces griseus] [PN:hypothetical 8.2K protein (kan 5' region)] |
| contig434 | 10197130_f3_6 | 812 | 4217 | 477 | 158 | 214 | 1.00E-17 | [AC:AB002668] [OR:Haemophilus actinomycetemcomitans] [NT:unnamed protein product] |
| contig434 | 5087562_f1_1 | 813 | 4218 | 363 | 120 | 81 | 0.073 | [AC:AB002668] [OR:Haemophilus actinomycetemcomitans] [NT:unnamed protein product] |
| contig434 | 33985712_f2_3 | 814 | 4219 | 825 | 274 | 1110 | 1.20E-112 | [AC:U09239] [OR:Streptococcus pneumoniae] [PN:glucose-1-phosphate thymidyl transferase] [GN:cps19fL] [NT:32.2 kDa cps19fL gene product] |
| contig434 | 2492713_f2_4 | 815 | 4220 | 552 | 183 | 455 | 3.00E-43 | [SP:P26394] [OR:SALMONELLA TYPHIMURIUM] [GN:RFBC] [DE:DEOXYGLUCOSE 3,5-EPIMERASE) (DTDP-L-RHAMNOSE SYNTHETASE] |
| contig434 | 33476563_f3_7 | 816 | 4221 | 531 | 176 | 595 | 4.40E-58 | [AC:D78182] [OR:Streptococcus mutans] [PN:dTDP-glucose-4,6-dehydratase] [GN:rmlB] |
| contig434 | 32662517_f2_5 | 817 | 4222 | 288 | 95 | 260 | 1.40E-22 | [AC:D78182] [OR:Streptococcus mutans] [PN:dTDP-glucose-4,6-dehydratase] [GN:rmlB] |
| contig435 | 7205192_f2_2 | 818 | 4223 | 381 | 126 | 227 | 4.30E-19 | [SP:P54548] [OR:BACILLUS SUBTILIS] [GN:YOJK] [DE:HYPOTHETICAL 34.0 KD PROTEIN IN GLNQ-ANSR INTERGENIC REGION] |
| contig435 | 14455827_f2_3 | 819 | 4224 | 789 | 262 | 533 | 1.60E-51 | [SP:P54554] [OR:BACILLUS SUBTILIS] [GN:YOJQ] [DE:(EC 1.-.-.-)] |
| contig435 | 23632802_f3_4 | 820 | 4225 | 495 | 164 | 61 | 0.9996 | [OR:Methanococcus vannielii] [PN:hisI protein] [GN:hisI] |
| contig435 | 24431250_f1_1 | 821 | 4226 | 1191 | 396 | 524 | 2.10E-50 | [AC:D90907] [OR:Synechocystis sp.] [PN:single-strand-DNA-specific exonuclease RecJ] [GN:recJ] [NT:ORF_ID] |
| contig436 | 22305126_f2_2 | 822 | 4227 | 195 | 64 | 274 | 4.50E-24 | [SP:P03837] [OR:ESCHERICHIA COLI] [DE:INSERTION ELEMENT IS5 HYPOTHETICAL 39.3 KD PROTEIN] |
| contig436 | 15120887_c1_10 | 823 | 4228 | 201 | 66 | 105 | 3.70E-06 | [AC:K02666] [OR:Bacillus subtilis] [NT:spo0B related protein] |
| contig436 | 2820317_f3_5 | 824 | 4229 | 1074 | 357 | 1168 | 8.30E-119 | [SP:P33898] [OR:ESCHERICHIA COLI] [GN:GAPC] [DE:GLYCERALDEHYDE 3-PHOSPHATE DEHYDROGENASE C, (GAPDH-C)] |
| contig436 | 15641938_c3_15 | 825 | 4230 | 552 | 183 | 507 | 9.20E-49 | [SP:P54574] [OR:BACILLUS SUBTILIS] [GN:YOKL] [DE:FERRIC UPTAKE REGULATION PROTEIN HOMOLOG 2] |
| contig436 | 992827_c2_12 | 826 | 4231 | 882 | 293 | 525 | 1.10E-50 | [AC:Y09476] [OR:Bacillus subtilis] [PN:YitL] [NT:putative] |
| contig436 | 24067692_c1_7 | 827 | 4232 | 654 | 217 | 75 | 0.012 | [AC:U65816] [OR:Borrelia burgdorferi] [PN:outer surface protein A] [GN:ospA] |
| contig437 | 3937561_c2_11 | 828 | 4233 | 873 | 290 | 426 | 3.50E-40 | [SP:Q57664] [OR:METHANOCOCCUS JANNASCHII] [GN:MJ0211] [DE:GALACTOSE 4-EPIMERASE] |
| contig437 | 975262_c2_10 | 829 | 4234 | 1452 | 483 | 893 | 1.10E-89 | [AC:U09239] [OR:Streptococcus pneumoniae] [GN:cps19fJ] [NT:55.1 kDa cps19fJ polysaccharide transport protein] [PN:possible gene product; RfbX homolog] |
| contig437 | 35969677_f1_3 | 830 | 4235 | 288 | 95 | 72 | 0.12 | [OR:Parthenium argentatum] [PN:rubber particle cytochrome P450] |
| contig437 | 22455215_c1_9 | 831 | 4236 | 327 | 108 | 70 | 0.18 | [OR:Rattus norvegicus] [PN:probable cytochrome P450 2C6cytochrome P450 PB-1(ps)] |

TABLE 2-continued

| Contig | Orf | NT Seq Id | AA Seq ID | NT Orf Length | AA Orf Length | Score | Probability | Description |
|---|---|---|---|---|---|---|---|---|
| contig438 | 25673781_f2_1 | 832 | 4237 | 1719 | 572 | 874 | 1.20E-87 | [AC:AB001488] [OR:*Bacillus subtilis*] [GN:ydgE] [NT:SIMILAR TO ORF16 OF *ENTEROCOCCUS FAECALIS*] |
| contig438 | 25664813_f2_2 | 833 | 4238 | 1182 | 393 | 76 | 0.98 | [OR:*Penicillium chrysogenum*] [PN:orotidine-5'-phosphate decarboxylase,] [GN:pyrG] |
| contig439 | 203200_c3_12 | 834 | 4239 | 270 | 90 | 323 | 2.90E-29 | [AC:JH0204] [OR:*Enterococcus faecalis*] [PN:hypothetical 30.5K protein] |
| contig439 | 25429640_f2_2 | 835 | 4240 | 744 | 247 | 605 | 7.00E-106 | [AC:JC5007] [OR:*Lactococcus lactis*] [PN:transposase (insertion sequence IS1297] |
| contig439 | 31646887_c1_8 | 836 | 4241 | 219 | 72 | 164 | 2.00E-12 | [AC:JC1262] [OR:*Lactococcus lactis* subsp. *lactis*] [PN:hypothetical 4.5K protein] |
| contig439 | 24648527_c2_10 | 837 | 4242 | 201 | 66 | 72 | 0.067 | [AC:X97263] [OR:*Lactococcus lactis*] [GN:aBIR] |
| contig439 | 5086088_c1_7 | 838 | 4243 | 987 | 328 | 1126 | 2.30E-114 | [SP:Q06115] [OR:*LACTOBACILLUS PLANTARUM*] [GN:CBH] [DE:HYDROLASE) (CBAH) (BILE SALT HYDROLASE)] |
| contig439 | 3947263_f2_4 | 839 | 4244 | 426 | 142 | 668 | 8.00E-66 | [AC:U17153] [OR:*Enterococcus faecalis*] [PN:transposase] |
| contig439 | 13808206_f3_6 | 840 | 4245 | 246 | 81 | 164 | 2.00E-12 | [AC:JC5008] [OR:*Lactococcus lactis*] [PN:hypothetical 6.5K protein (insertion sequence IS1297] |
| contig44 | 26211592_c3_4 | 841 | 4246 | 642 | 213 | 875 | 9.30E-88 | [SP:P36399] [OR:*STREPTOCOCCUS SALIVARIUS*] [GN:UPP] [DE:PYROPHOSPHORYLASE) (UPRTASE)] |
| contig44 | 35797061_f1_2 | 842 | 4247 | 240 | 79 | 74 | 0.007 | [AC:L31763] [OR:*Dichelobacter nodosus*] [PN:virulence-associated protein I] [GN:vapI] [NT:putative] |
| contig440 | 1171936_c3_15 | 843 | 4248 | 315 | 104 | | | |
| contig440 | 197151_f3_5 | 844 | 4249 | 312 | 103 | 118 | 1.50E-07 | [AC:U46134] [OR:*Bacillus subtilis*] [PN:putative transcriptional regulator] [GN:slr] [NT:Slr; positive regulator of competence development] |
| contig440 | 6147312_f3_6 | 845 | 4250 | 480 | 159 | 63 | 0.9999 | [SP:Q00947] [OR:*CAENORHABDITIS ELEGANS*] [GN:F12A10.6] [DE:HYPOTHETICAL 14.4 KD PROTEIN F12A10.6 IN CHROMOSOME II] |
| contig440 | 799092_f3_7 | 846 | 4251 | 597 | 198 | 78 | 0.068 | [SP:P52117] [OR:*VIBRIO CHOLERAE*] [GN:SMPA] [DE:SMALL PROTEIN A HOMOLOG] |
| contig440 | 36135252_f1_1 | 847 | 4252 | 303 | 100 | 61 | 0.97 | [SP:P39615] [OR:*BACILLUS SUBTILIS*] [GN:UNG] [DE:URACIL-DNA GLYCOSYLASE.] |
| contig440 | 16834442_f3_8 | 848 | 4253 | 1233 | 410 | 242 | 1.10E-18 | [OR:*Lactococcus lactis*] [PN:integrase] [GN:int] |
| contig440 | 24883402_c3_11 | 849 | 4254 | 477 | 158 | 572 | 1.20E-55 | [SP:P13375] [OR:*BACILLUS STEAROTHERMOPHILUS*] [GN:PGIA] [DE:ISOMERASE A)] |
| contig440 | 32678443_c1_9 | 850 | 4255 | 333 | 110 | 185 | 7.10E-14 | [SP:P13376] [OR:*BACILLUS STEAROTHERMOPHILUS*] [GN:PGIB] [DE:ISOMERASE B)] |
| contig441 | 25633317_f1_1 | 851 | 4256 | 2913 | 970 | 292 | 9.30E-25 | [OR:*Acidaminococcus fermentans*] [PN:hgdC protein] |
| contig442 | 13679637_f2_4 | 852 | 4257 | 2889 | 962 | 625 | 2.90E-61 | [AC:L20670] [OR:*Streptococcus pneumoniae*] [NT:alternative truncated translation product from] |
| contig443 | 250777_c1_3 | 853 | 4258 | 183 | 60 | 50 | 0.91 | [AC:M32362] [OR:*Clostridium cellulolyticum*] [NT:protein of unknown function] |
| contig443 | 24492330_f3_1 | 854 | 4259 | 1737 | 578 | 824 | 6.40E-118 | [AC:X65164] [OR:*Streptococcus gordonii*] [PN:fibronectin-binding protein-like protein A] [GN:fbpA] |
| contig444 | 16304530_f2_2 | 855 | 4260 | 486 | 161 | 546 | 6.80E-53 | [SP:P13522] [OR:*STREPTOCOCCUS MUTANS*] [GN:SCRB] [DE:SUCROSE-6-PHOSPHATE HYDROLASE, (SUCRASE) (INVERTASE)] |
| contig444 | 24510762_f3_4 | 856 | 4261 | 1008 | 335 | 1035 | 1.00E-104 | [AC:U46902] [OR:*Streptococcus mutans*] [PN:ScrR] [GN:scrR] [NT:regulator of scrB expression; sucrose regulator;] |
| contig444 | 24275312_c1_5 | 857 | 4262 | 366 | 121 | 134 | 3.10E-09 | [SP:P13976] [OR:*ESCHERICHIA COLI*] [GN:PEMK] [DE:PEMK |

TABLE 2-continued

| Contig | Orf | NT Seq Id | AA Seq ID | NT Orf Length | AA Orf Length | Score | Probability | Description |
|---|---|---|---|---|---|---|---|---|
| contig444 | 23634838_c2_6 | 858 | 4263 | 276 | 91 | 130 | 8.20E-09 | [SP:P18534] [OR:ESCHERICHIA COLI] [GN:CHPR] [DE:PEMI-LIKE PROTEIN 1 (MAZE PROTEIN)] |
| contig445 | 6917753_c1_9 | 859 | 4264 | 885 | 294 | 108 | 0.00083 | [AC:U29378] [OR:Caenorhabditis elegans] [GN:F08C6.4] [NT:similar to erythrocyte band 7 integral membrane] |
| contig445 | 161452_f3_4 | 860 | 4265 | 876 | 291 | 567 | 4.00E-55 | [AC:U58210] [OR:Streptococcus thermophilus] [NT:orf1091] |
| contig445 | 14484465_c1_8 | 861 | 4266 | 546 | 181 | 243 | 5.60E-20 | [OR:Enterococcus faecalis] [PN:probable pheromone binding proteinpheromone responsive gene Z protein] [GN:prgZ] |
| contig445 | 35742152_c3_12 | 862 | 4267 | 216 | 71 | 114 | 4.80E-06 | [AC:D28859] [OR:Enterococcus faecalis] [PN:TraC] [GN:traC] |
| contig445 | 16125682_c2_11 | 863 | 4268 | 189 | 62 | 96 | 0.00041 | [OR:Enterococcus faecalis] [PN:pheromone cAD1 binding protein precursor] [GN:traC] |
| contig445 | 34569416_c2_10 | 864 | 4269 | 252 | 83 | 218 | 2.60E-17 | [OR:Streptococcus "equisimilis"] [PN:hyaluronate synthase precursor] [GN:has] |
| contig445 | 24407713_c1_7 | 865 | 4270 | 657 | 218 | 210 | 2.10E-16 | [SP:P26906] [OR:BACILLUS SUBTILIS] [GN:DPPE] [DE:DIPEPTIDE-BINDING PROTEIN DPPE PRECURSOR] |
| contig446 | 24641550_f2_4 | 866 | 4271 | 801 | 266 | 68 | 0.99995 | [AC:U16732] [OR:Subterranean clover stunt virus] [GN:SCSV3] |
| contig446 | 26601642_c2_20 | 867 | 4272 | 213 | 70 | 99 | 0.0001 | [OR:Homo sapiens] [PN:transmembrane copper transporting P-type ATPase] |
| contig446 | 24725711_c2_19 | 868 | 4273 | 753 | 250 | 530 | 1.10E-50 | [AC:U42410] [OR:Proteus mirabilis] [PN:heavy-metal transporting P-type ATPase] |
| contig446 | 4820391_c1_15 | 869 | 4274 | 276 | 91 | 79 | 0.044 | [AC:U42410] [OR:Proteus mirabilis] [PN:heavy-metal transporting P-type ATPase] |
| contig446 | 29473133_c3_24 | 870 | 4275 | 1095 | 364 | 678 | 7.00E-67 | [SP:P32113] [OR:ENTEROCOCCUS FAECALIS] [GN:COPA] [DE:POTASSIUM/COPPER-TRANSPORTING ATPASE A.] |
| contig446 | 24664812_c2_17 | 871 | 4276 | 690 | 229 | 247 | 4.90E-20 | [AC:U42410] [OR:Proteus mirabilis] [PN:heavy-metal transporting P-type ATPase] |
| contig446 | 414126_c2_16 | 872 | 4277 | 483 | 160 | 297 | 1.60E-26 | [AC:U42410] [OR:Enterococcus hirae] [PN:regulatory protein copY] [GN:copY] |
| contig446 | 3297325_c1_14 | 873 | 4278 | 861 | 286 | 640 | 7.40E-63 | [SP:P26235] [OR:ENTEROCOCCUS HIRAE] [GN:NAPA] [DE:NA(+)/H(+) ANTIPORTER] |
| contig447 | 24808441_c3_23 | 874 | 4279 | 1236 | 411 | 401 | 1.60E-37 | [SP:P55340] [OR:BACILLUS SUBTILIS] [GN:ECSB] [DE:PROTEIN ECSB] |
| contig447 | 2047187_c2_20 | 875 | 4280 | 951 | 316 | 816 | 1.70E-81 | [SP:P55339] [OR:BACILLUS SUBTILIS] [GN:ECSA] [DE:ABC-TYPE TRANSPORTER ATP-BINDING PROTEIN ECSA] |
| contig447 | 26773442_f2_8 | 876 | 4281 | 444 | 147 | 412 | 1.10E-38 | [AC:Y14077] [OR:Bacillus subtilis] [PN:Hypothetical protein] [GN:yhaE] [NT:Similarity to the Hit family of proteins] |
| contig447 | 976577_f2_9 | 877 | 4282 | 213 | 70 | 61 | 0.62 | [AC:U08008] [OR:Metapenaeus ensis] [PN:tropomyosin] [NT:a stop codon immediately follows the last] |
| contig447 | 11128437_f3_13 | 878 | 4283 | 213 | 70 | 68 | 0.045 | [SP:P27183] [OR:SYNECHOCYSTIS SP] [GN:ATPG] [DE:ATP SYNTHASE B' CHAIN, (SUBUNIT II)] |
| contig447 | 391288_f1_6 | 879 | 4284 | 1107 | 368 | 376 | 7.00E-35 | [SP:Q02473] [OR:LACTOBACILLUS PARACASEI] [GN:PRTM] [DE:PROTEASE MATURATION PROTEIN PRECURSOR] |
| contig447 | 6769677_c2_17 | 880 | 4285 | 219 | 72 | 54 | 0.9999 | [SP:Q12263] [OR:SACCHAROMYCES CEREVISIAE] [GN:SBMA] [DE:SBMA PROTEIN] |
| contig447 | 5907938_c1_14 | 881 | 4286 | 231 | 76 | 237 | 3.80E-20 | [AC:Y14078] [OR:Bacillus subtilis] [PN:Hypothetical protein] [GN:yhaM] [NT:similarity to CMP-binding-factor-1 (cbf1) from] |
| contig448 | 26173161_f3_2 | 882 | 4287 | 276 | 91 | 76 | 0.13 | [SP:Q12263] [OR:ESCHERICHIA COLI] [GN:SBMA] [DE:SBMA PROTEIN] |
| contig448 | 707_f1_1 | 883 | 4288 | 2730 | 910 | 114 | 0.0054 | [OR:Bacillus sphaericus] [PN:Hypothetical 80K protein] |
| contig449 | 23718762_c1_4 | 884 | 4289 | 348 | 115 | 51 | 0.85 | [AC:L18953] [OR:Capra hircus] [GN:TCR] [NT:V region] |

TABLE 2-continued

| Contig | Orf | NT Seq Id | AA Seq ID | NT Orf Length | AA Orf Length | Score | Probability | Description |
|---|---|---|---|---|---|---|---|---|
| contig449 | 14963437_f1_1 | 885 | 4290 | 627 | 208 | 610 | 1.10E-59 | [AC:Z94043] [OR:*Bacillus subtilis*] [PN:hypothetical protein] [GN:yvfV] [NT:similar to trembl] |
| contig449 | 14571093_f1_2 | 886 | 4291 | 1485 | 494 | 1073 | 9.70E-109 | [AC:AE000137] [OR:*Escherichia coli*] [NT:o475; This 475 aa orf is 24 pct identical (9 gaps)] |
| contig449 | 12781712_f2_3 | 887 | 4292 | 438 | 145 | 83 | 0.092 | [SP:P13830] [OR:*Plasmodium falciparum*] [NT:RESA FC27 Ag46 (1 is 3rd base in codon)] |
| contig45 | 4806693_c3_5 | 888 | 4293 | 666 | 222 | 854 | 1.60E-85 | [AC:Z67739] [OR:*Streptococcus pneumoniae*] [PN:DNA topoisomerase IV] [GN:parC] [NT:ParC subunit] |
| contig45 | 24222017_c3_4 | 889 | 4294 | 432 | 143 | 379 | 1.10E-34 | [AC:Z73234] [OR:*Bacillus subtilis*] [PN:GrlB] [GN:grlB] |
| contig450 | 23631561_f2_2 | 890 | 4295 | 435 | 144 | 308 | 1.10E-27 | [SP:Q57855] [OR:*METHANOCOCCUS JANNASCHII*] [GN:MJ0412] [DE:HYPOTHETICAL ABC TRANSPORTER ATP-BINDING PROTEIN MJ0412] |
| contig450 | 25667838_f3_5 | 891 | 4296 | 276 | 91 | 51 | 0.93 | [AC:U18466] [OR:African swine fever virus] [PN:pB117L] [GN:B117L] [NT:putative transmembrane protein; contains central] |
| contig450 | 6510778_f2_3 | 892 | 4297 | 306 | 101 | 116 | 2.50E-07 | [AC:AE000170] [OR:*Escherichia coli*] [NT:o111; This 111 aa orf is 28 pct identical (4 gaps)] |
| contig450 | 21650182_c1_7 | 893 | 4298 | 249 | 82 | 66 | 0.048 | [AC:M62914] [OR:*Gallus gallus*] [PN:immunoglobulin light-chain VJ region] |
| contig451 | 16892158_f1_1 | 894 | 4299 | 597 | 198 | 312 | 1.40E-27 | [AC:D90907] [OR:*Synechocystis sp.*] [PN:glutamine-binding periplasmic protein] [GN:glnH] [NT:ORF_ID] |
| contig451 | 14876507_f2_4 | 895 | 4300 | 744 | 247 | 750 | 1.60E-74 | [SP:P27675] [OR:*BACILLUS STEAROTHERMOPHILUS*] [GN:GLNQ] [DE:GLUTAMINE TRANSPORT ATP-BINDING PROTEIN GLNQ] |
| contig451 | 4901567_c1_9 | 896 | 4301 | 405 | 134 | 76 | 0.28 | [AC:U59128] [OR:*Bacillus subtilis*] [PN:SapB] [GN:sapB] [NT:Initiates at TTG as formyl-methionine; Mutant] |
| contig451 | 34023410_c1_8 | 897 | 4302 | 360 | 119 | 163 | 2.60E-12 | [OR:*Haemophilus influenzae*] [PN:hypothetical protein HI0647] |
| contig451 | 5210312_c2_11 | 898 | 4303 | 378 | 125 | 280 | 8.20E-24 | [AC:D64005] [OR:*Synechocystis sp.*] [PN:cadmium-transporting ATPase] [GN:cadA] [NT:ORF_ID] |
| contig452 | 13797058_f2_4 | 899 | 4304 | 345 | 114 | 83 | 0.00078 | [SP:P23896] [OR:*ESCHERICHIA COLI*] [GN:YIBA] [DE:HYPOTHETICAL 15.6 KD PROTEIN IN PGI-XYLE INTERGENIC REGION (O136)] |
| contig452 | 10362501_c2_9 | 900 | 4305 | 1008 | 335 | 242 | 9.50E-20 | [SP:Q09320] [OR:*CAENORHABDITIS ELEGANS*] [GN:F40B5.2] [DE:HYPOTHETICAL 69.0 KD PROTEIN F40B5.2 IN CHROMOSOME X] |
| contig452 | 24492188_f3_5 | 901 | 4306 | 1089 | 362 | 858 | 5.90E-86 | [SP:P54518] [OR:*BACILLUS SUBTILIS*] [GN:YQHT] [DE:PUTATIVE PEPTIDASE IN GCVT-SPOIIIAA INTERGENIC REGION.] |
| contig452 | 23593805_f1_3 | 902 | 4307 | 345 | 114 | 234 | 7.80E-20 | [AC:Z94043] [OR:*Bacillus subtilis*] [PN:hypothetical protein] [GN:yvdC] |
| contig453 | 31648280_f3_3 | 903 | 4308 | 1689 | 562 | 911 | 1.40E-91 | [SP:Q07741] [OR:*LACTOCOCCUS LACTIS*] [GN:OPPA] [DE:OLIGOPEPTIDE-BINDING PROTEIN OPPA PRECURSOR] |
| contig453 | 12923577_f3_4 | 904 | 4309 | 222 | 73 | 58 | 0.62 | [AC:X62435] [OR:*Pinus strobus*] [PN:albumin 3] |
| contig453 | 821957_f2_2 | 905 | 4310 | 786 | 261 | 240 | 1.80E-20 | [AC:AB001488] [OR:*Bacillus subtilis*] [GN:ydbJ] [NT:PROBABLE TRANSPORT ATP BINDING PROTEIN.] |
| contig453 | 24495803_f3_5 | 906 | 4311 | 513 | 171 | 76 | 0.085 | [SP:P15550] [OR:*STRONGYLOCENTROTUS PURPURATUS*] [GN:ND3] [DE:NADH-UBIQUINONE OXIDOREDUCTASE CHAIN 3.] |
| contig454 | 16207963_c2_16 | 907 | 4312 | 888 | 295 | 454 | 3.80E-43 | [SP:P23496] [OR:*LACTOCOCCUS LACTIS*] [GN:LACX] [DE:LACX PROTEIN, PLASMID] |

TABLE 2-continued

| Contig | Orf | NT Seq Id | AA Seq ID | NT Orf Length | AA Orf Length | Score | Probability | Description |
|---|---|---|---|---|---|---|---|---|
| contig454 | 11125067_c2_15 | 908 | 4313 | 828 | 275 | 706 | 7.50E-70 | [SP:P39779] [OR:BACILLUS SUBTILIS] [GN:CODY] [DE:CODY PROTEIN] |
| contig454 | 13877036_c3_19 | 909 | 4314 | 183 | 60 | 212 | 9.00E-17 | [SP:P39778] [OR:BACILLUS SUBTILIS] [GN:HSLU] [DE:HEAT SHOCK PROTEIN HSLU] |
| contig454 | 14455057_c2_14 | 910 | 4315 | 759 | 252 | 657 | 1.20E-64 | [AC:X84261] [OR:Lactobacillus leichmannii] [PN:heat shock induced protein lltpO] [GN:hslV] |
| contig454 | 24511583_c1_13 | 911 | 4316 | 600 | 199 | 521 | 3.00E-50 | [AC:X84261] [OR:Lactobacillus leichmannii] [PN:heat shock induced protein lltpO] [GN:hslV] |
| contig454 | 6839061_c1_12 | 912 | 4317 | 627 | 208 | 611 | 8.80E-60 | [SP:P39070] [OR:BACILLUS SUBTILIS] [GN:HSLV] [DE:HEAT SHOCK PROTEIN HSLV PRECURSOR,] |
| contig454 | 10574317_c3_17 | 913 | 4318 | 912 | 303 | 821 | 4.90E-82 | [SP:P39776] [OR:BACILLUS SUBTILIS] [GN:CODV] [DE:PROBABLE INTEGRASE/RECOMBINASE CODV] |
| contig455 | 22539000_c2_6 | 914 | 4319 | 384 | 128 | | | |
| contig455 | 21649067_c3_7 | 915 | 4320 | 321 | 106 | | | |
| contig455 | 3906708_c1_5 | 916 | 4321 | 288 | 95 | 67 | 0.16 | [OR:Caenorhabditis elegans] [PN:hypothetical protein T07C4.10] |
| contig455 | 193812_c1_4 | 917 | 4322 | 816 | 271 | 56 | 0.96 | [OR:Zea mays] [PN:H+-transporting ATPase chain c, vacuolar (clone 16-2)] |
| contig456 | 4100393_c3_21 | 918 | 4323 | 453 | 150 | 220 | 2.40E-18 | [AC:AE000332] [OR:Escherichia coli] [NT:f233; This 233 aa orf is 23 pct identical (2 gaps)] |
| contig456 | 36369058_c1_15 | 919 | 4324 | 756 | 251 | 361 | 1.50E-46 | [SP:P76552] [OR:ESCHERICHIA COLI] [GN:EUTH] [DE:TRANSPORTER] |
| contig456 | 26430443_c3_20 | 920 | 4325 | 522 | 173 | 346 | 1.10E-31 | [SP:P54957] [OR:BACILLUS SUBTILIS] [GN:YXER] [DE:HYPOTHETICAL 38.4 KD PROTEIN IN IDH-DEOR INTERGENIC REGION] |
| contig456 | 14649193_c3_19 | 921 | 4326 | 276 | 91 | 142 | 4.40E-10 | [SP:Q03512] [OR:SYNEHOCOCCUS SP] [GN:CCML] [DE:CARBON DIOXIDE CONCENTRATING MECHANISM PROTEIN CCML] |
| contig456 | 36226553_c3_18 | 922 | 4327 | 618 | 205 | 77 | 0.91 | [AC:L32839] [OR:Drosophila melanogaster] [PN:cell division cycle 37 protein] [GN:Cdc37] |
| contig456 | 24025338_c1_14 | 923 | 4328 | 639 | 212 | 56 | 0.88 | [OR:Homo sapiens] [PN:T-cell receptor beta chain] |
| contig456 | 548253_c1_13 | 924 | 4329 | 606 | 201 | | | |
| contig456 | 31836433_c3_17 | 925 | 4330 | 264 | 87 | 206 | 7.20E-17 | [SP:P37448] [OR:SALMONELLA TYPHIMURIUM] [GN:PDUA] [DE:PDUA PROTEIN] |
| contig457 | 1057766_c1_17 | 926 | 4331 | 1614 | 538 | 1389 | 3.20E-142 | [SP:P44410] [OR:HAEMOPHILUS INFLUENZAE] [GN:UVRA] [DE:EXCINUCLEASE ABC SUBUNIT A] |
| contig457 | 32167300_c1_16 | 927 | 4332 | 1185 | 394 | 1479 | 9.20E-152 | [OR:Streptococcus pneumoniae] [PN:uvr-402 protein] |
| contig457 | 7050056_c1_15 | 928 | 4333 | 747 | 248 | 1046 | 7.00E-106 | [OR:Streptococcus pneumoniae] [PN:uvr-402 protein] |
| contig458 | 6344575_f1_1 | 929 | 4334 | 636 | 211 | 231 | 1.60E-19 | [SP:P13669] [OR:ESCHERICHIA COLI] [GN:FARR] [DE:FATTY ACYL RESPONSIVE REGULATOR (P30 PROTEIN)] |
| contig458 | 10323529_c2_3 | 930 | 4335 | 642 | 213 | 1093 | 7.40E-111 | [SP:P19775] [OR:STAPHYLOCOCCUS AUREUS] [GN:TNP] [DE:TRANSPOSASE FOR INSERTION SEQUENCE ELEMENT IS256 IN TRANSPOSON TN4001] |
| contig459 | 173393_f2_5 | 931 | 4336 | 363 | 120 | 208 | 4.40E-17 | [SP:P37738] [OR:VIBRIO ANGUILLARUM] [GN:FATD] [DE:FERRIC ANGUIBACTIN TRANSPORT SYSTEM PERMEASE PROTEIN FATD] |
| contig459 | 21722512_f1_1 | 932 | 4337 | 453 | 150 | 169 | 1.50E-12 | [AC:D50453] [OR:Bacillus subtilis] [PN:homologue of ferric anguibactin transport system] [GN:ycIO] |
| contig459 | 21679666_f1_2 | 933 | 4338 | 588 | 195 | 401 | 1.60E-37 | [AC:D50453] [OR:Bacillus subtilis] [PN:homologue of ferric anguibactin transport system] [GN:ycIO] |

TABLE 2-continued

| Contig | Orf | NT Seq Id | AA Seq ID | NT Orf Length | AA Orf Length | Score | Probability | Description |
|---|---|---|---|---|---|---|---|---|
| contig459 | 9783557_f3_8 | 934 | 4339 | 366 | 121 | 179 | 5.30E-14 | [AC:D50453] [OR:*Bacillus subtilis*] [DN:homologue of iron dicitrate transport] [GN:yclP] |
| contig459 | 5272650_f1_3 | 935 | 4340 | 186 | 61 | 115 | 9.20E-07 | [AC:D50453] [OR:*Bacillus subtilis*] [PN:homologue of iron dicitrate transport] [GN:yclP] |
| contig459 | 24817576_f2_6 | 936 | 4341 | 486 | 161 | 461 | 6.90E-44 | [AC:D50453] [OR:*Bacillus subtilis*] [PN:homologue of iron dicitrate transport] [GN:yclP] |
| contig459 | 34460391_f1_4 | 937 | 4342 | 984 | 327 | 734 | 8.10E-73 | [AC:D50453] [OR:*Bacillus subtilis*] [PN:ferric anguibactin-binding protein precursor FatB] [GN:yclQ] |
| contig459 | 24021093_f2_7 | 938 | 4343 | 834 | 278 | 392 | 1.40E-36 | [OR:*Enterococcus faecalis*] [PN:probable pheromone binding proteinpheromone responsive gene Z protein] [GN:prgZ] |
| contig46 | 292881_c3_2 | 939 | 4344 | 846 | 281 | 152 | 1.20E-08 | [AC:U36837] [OR:*Lactococcus lactis*] [PN:AbiF from pNP40] |
| contig460 | 29504167_c2_6 | 940 | 4345 | 204 | 67 | 155 | 1.80E-11 | [AC:Z74778] [OR:*Streptococcus pneumonia*] [PN:dihydrofolate reductase (DHFR)] |
| contig460 | 1067677_c3_7 | 941 | 4346 | 978 | 325 | 1280 | 1.10E-130 | [SP:P00469] [OR:*LACTOBACILLUS CASEI*] [GN:THYA] [DE:THYMIDYLATE SYNTHASE, (TS)] |
| contig460 | 25251899_c1_5 | 942 | 4347 | 792 | 263 | 473 | 3.70E-45 | [AC:D86418] [OR:*Bacillus subtilis*] [PN:YfmR] |
| contig461 | 22150025_c2_13 | 943 | 4348 | 207 | 68 | 69 | 0.024 | [AC:U01718] [OR:*Mycoplasma genitalium*] [NT:Homologous to Swiss-Prot Accession Number P13954.] |
| contig461 | 5272187_c3_15 | 944 | 4349 | 303 | 100 | 247 | | |
| contig461 | 2230250_c2_12 | 945 | 4350 | 321 | 106 | 118 | 1.50E-07 | [SP:P26835] [OR:*CLOSTRIDIUM PERFRINGENS*] [DE:HYPOTHETICAL 14.9 KD PROTEIN IN NAGH 3'REGION (ORFD)] |
| contig461 | 26772062_c3_14 | 946 | 4351 | 1791 | 596 | 93 | 0.37 | [SP:P54341] [OR:*BACILLUS SUBTILIS*] [GN:XKDV] [DE:PHAGE-LIKE ELEMENT PBSX PROTEIN XKDV] |
| contig462 | 25673905_f2_2 | 947 | 4352 | 888 | 295 | 247 | 3.40E-21 | [AC:M76991] [OR:*Acinetobacter calcoaceticus*] [PN:muconate cycloisomerase] [GN:muconate cycloisomerase] [NT:Growth with muconate or benzoate] |
| contig462 | 25557827_f3_4 | 948 | 4353 | 1323 | 440 | 98 | 0.042 | [SP:P44103] [OR:*HAEMOPHILUS INFLUENZAE*] [GN:HI1048] [DE:HYPOTHETICAL PROTEIN HI1048 PRECURSOR] |
| contig462 | 33382200_f2_3 | 949 | 4354 | 1674 | 557 | 983 | 3.30E-99 | [OR:*Enterococcus faecalis*] [PN:probable pheromone binding proteinpheromone responsive gene Z protein] [GN:prgZ] |
| contig463 | 26306550_c1_10 | 950 | 4355 | 2196 | 731 | 1538 | 5.10E-158 | [SP:P71353] [OR:*HAEMOPHILUS INFLUENZAE*] [GN:HI0568] [DE:HYPOTHETICAL PROTEIN HI0568] |
| contig463 | 786713_c3_13 | 951 | 4356 | 747 | 248 | 124 | 4.20E-06 | [AC:U51991] [OR:*Escherichia coli*] [PN:PrpA] [GN:pppA] [NT:biochemically shown as phosphatase; Allele] |
| contig463 | 259712_c3_12 | 952 | 4357 | 249 | 82 | 53 | 0.9997 | [SP:Q03974] [OR:*HAEMOPHILUS INFLUENZAE*] [GN:LEX1] [DE:LIPOOLIGOSACCHARIDE BIOSYNTHESIS PROTEIN LEX-1] |
| contig463 | 20946443_c2_11 | 953 | 4358 | 735 | 244 | 912 | 1.10E-91 | [SP:P35514] [OR:*LACTOCOCCUS LACTIS*] [GN:DNAJ] [DE:DNAJ PROTEIN] |
| contig464 | 647150_f3_4 | 954 | 4359 | 906 | 301 | 254 | 5.90E-22 | [SP:P44540] [OR:*HAEMOPHILUS INFLUENZAE*] [GN:HI0143] [DE:HYPOTHETICAL PROTEIN HI0143] |
| contig464 | 1194180_f2_2 | 955 | 4360 | 360 | 119 | 66 | 0.048 | [OR:*Neisseria gonorrhoeae*] [PN:fimbrial protein pilE1 (variant G31)] |
| contig465 | 23477317_c2_14 | 956 | 4361 | 246 | 82 | 131 | 1.20E-05 | [SP:P04993] [OR:*ESCHERICHIA COLI*] [GN:RECD] [DE:ALPHA CHAIN] |
| contig465 | 1960957_c1_12 | 957 | 4362 | 1080 | 359 | | | |
| contig465 | 14335942_c3_15 | 958 | 4363 | 1620 | 539 | 213 | 3.30E-14 | [SP:P45158] [OR:*HAEMOPHILUS INFLUENZAE*] [GN:RECD] [DE:EXODEOXYRIBONUCLEASE V ALPHA CHAIN.] |
| contig466 | 14932802_f3_3 | 959 | 4364 | 2331 | 776 | 961 | 7.20E-97 | [AC:Z95210] [OR:*Mycobacterium tuberculosis*] [PN:unknown] [GN:MTCY21C12.02] [NT:MTCY21C12.02. 797. Function] |

TABLE 2-continued

| Contig | Orf | NT Seq Id | AA Seq ID | NT Orf Length | AA Orf Length | Score | Probability | Description |
|---|---|---|---|---|---|---|---|---|
| contig466 | 15119213_f1_2 | 960 | 4365 | 1812 | 603 | 1154 | 2.50E-117 | [SP:P47762] [OR:LISTERIA MONOCYTOGENES] [GN:DNAG] [DE:DNA PRIMASE,] |
| contig467 | 22754126_f1_1 | 961 | 4366 | 1017 | 338 | 595 | 4.40E-58 | [SP:P22564] [OR:ESCHERICHIA COLI] [GN:YAAF] [DE:HYPOTHETICAL 32.6 KD PROTEIN IN LYTB-DAPB INTERGENIC REGION] |
| contig467 | 34027217_f2_3 | 962 | 4367 | 1386 | 461 | 295 | 7.30E-53 | [SP:Q47134] [OR:ESCHERICHIA COLI] [GN:DCUC] [DE:C4-DICARBOXYLATE ANAEROBIC CARRIER] |
| contig467 | 4884682_f1_2 | 963 | 4368 | 492 | 163 | 78 | 0.0046 | [AC:U92874] [OR:Sulfolobus shibatae] [PN:N-terminal acetyl transferase] |
| contig467 | 4110811_c1_8 | 964 | 4369 | 1098 | 365 | 304 | 3.00E-27 | [AC:AE000179] [OR:Escherichia coli] [GN:ybhE] [NT:o331; 92 pct identical to the 333 aa hypothetical] |
| contig468 | 24664807_c2_10 | 965 | 4370 | 468 | 155 | 369 | 3.90E-34 | [SP:P37437] [OR:BACILLUS SUBTILIS] [GN:RPLI] [DE:50S RIBOSOMAL PROTEIN L9 (BL17)] |
| contig468 | 16675902_c3_14 | 966 | 4371 | 2046 | 681 | 1097 | 2.80E-111 | [SP:P37484] [OR:BACILLUS SUBTILIS] [GN:YBT] [DE:HYPOTHETICAL 74.3 KD PROTEIN IN RPLI-COTF INTERGENIC REGION] |
| contig468 | 34102338_c3_13 | 967 | 4372 | 252 | 83 | 246 | 4.20E-21 | [SP:P10806] [OR:BACILLUS STEAROTHERMOPHILUS] [GN:RPSR] [DE:30S RIBOSOMAL PROTEIN S18 (BS21)] |
| contig468 | 23625327_c2_9 | 968 | 4373 | 567 | 188 | 434 | 5.00E-41 | [SP:P37455] [OR:BACILLUS SUBTILIS] [GN:SSB] [DE:SINGLE-STRAND BINDING PROTEIN (SSB) (HELIX-DESTABILIZING PROTEIN)] |
| contig468 | 33869437_c3_11 | 969 | 4374 | 309 | 102 | 332 | 3.20E-30 | [SP:P21468] [OR:BACILLUS SUBTILIS] [GN:RPSF] [DE:30S RIBOSOMAL PROTEIN S6 (BS9)] |
| contig469 | 15832756_f1_1 | 970 | 4375 | 1650 | 549 | 192 | 9.90E-12 | [SP:P23914] [OR:BACILLUS SUBTILIS] [GN:LEVR] [DE:TRANSCRIPTIONAL REGULATORY PROTEIN LEVR] |
| contig469 | 277186_f3_7 | 971 | 4376 | 417 | 138 | 120 | 4.50E-07 | [SP:P08186] [OR:ESCHERICHIA COLI] [GN:MANX] [DE:(EC 2.7.1.69) (EIII-MAN)] |
| contig469 | 24393812_f1_2 | 972 | 4377 | 528 | 175 | 219 | 3.00E-18 | [AC:U28163] [OR:Lactobacillus curvatus] [PN:EIIB-man] [GN:manB] [NT:mannose phosphotransferase system enzyme EII] |
| contig469 | 4772187_f3_8 | 973 | 4378 | 792 | 263 | 221 | 1.90E-18 | [SP:P42910] [OR:ESCHERICHIA COLI] [GN:AGAC] [DE:(N-ACETYLGALACTOSAMINE-PERMEASE IIC COMPONENT 1)] |
| contig469 | 4567943_f2_5 | 974 | 4379 | 684 | 228 | 351 | 3.10E-32 | [SP:P37083] [OR:KLEBSIELLA PNEUMONIAE] [GN:SORM] [DE:PERMEASE IID COMPONENT) (PHOSPHOTRANSFERASE ENZYME II, D COMPONENT)] |
| contig47 | 25586665_c2_1 | 975 | 4380 | 330 | 110 | 86 | 0.0012 | [AC:U61168] [OR:Bacillus firmus] [PN:spore germination protein C2] [GN:gerC2] |
| contig47 | 12617343_c3_2 | 976 | 4381 | 369 | 122 | 148 | 3.30E-10 | [SP:P45476] [OR:ESCHERICHIA COLI] [GN:YHCC] [DE:HYPOTHETICAL 34.6 KD PROTEIN IN ARCB-GLTB INTERGENIC REGION (F309)] |
| contig470 | 14181583_c1_8 | 977 | 4382 | 1206 | 402 | 829 | 7.00E-83 | [AC:U66480] [OR:Bacillus subtilis] [PN:YnbA] [GN:ynbA] |
| contig470 | 6839200_c1_7 | 978 | 4383 | 936 | 311 | 342 | 2.80E-31 | [SP:P16384] [OR:ESCHERICHIA COLI] [GN:MIAA] [DE:(IPP TRANSFERASE)] |
| contig470 | 22050037_c1_6 | 979 | 4384 | 642 | 213 | 246 | 4.20E-21 | [SP:P54527] [OR:BACILLUS SUBTILIS] [GN:YQIK] [DE:HYPOTHETICAL 27.0 KD PROTEIN IN SPO0A-MMGA INTERGENIC REGION] |
| contig470 | 23595785_c2_9 | 980 | 4385 | 1701 | 566 | 70 | 0.23 | [OR:Homo sapiens] [PN:calcium channel protein alpha-1 chain CACNL1A1] [GN:CACNL1A1] |
| contig471 | 24647010_c3_7 | 981 | 4386 | 1032 | 343 | 121 | 0.00044 | [AC:U08875] [OR:Haemophilus influenzae] [NT:surface-associated protein] [GN:hmw2A] [PN:adhesin] |

TABLE 2-continued

| Contig | Orf | NT Seq Id | AA Seq ID | NT Orf Length | AA Orf Length | Score | Probability | Description |
|---|---|---|---|---|---|---|---|---|
| contig471 | 31447188_c1_4 | 982 | 4387 | 690 | 229 | 82 | 0.84 | [AC:U47862] [OR:Schistosoma mansoni] [PN:gynecophoral canal protein] |
| contig472 | 5267153_c1_14 | 983 | 4388 | 1434 | 477 | 1333 | 2.70E-136 | [OR:Staphylococcus xylosus] [PN:alpha-glucosidase,] |
| contig472 | 493887_c3_19 | 984 | 4389 | 1203 | 400 | 1200 | 3.40E-122 | [SP:Q99040] [OR:STREPTOCOCCUS MUTANS] [GN:DEXB] [DE:(EXO-1,6-ALPHA-GLUCOSIDASE) (GLUCODEXTRANASE)] |
| contig472 | 24470343_c2_15 | 985 | 4390 | 204 | 67 | 207 | 4.80E-16 | [AC:Z94043] [OR:Bacillus subtilis] [PN:hypothetical protein] [GN:yvdL] [NT:similar to O16G_BACSP oligo-1,6-glucosidase] |
| contig472 | 26602192_c3_18 | 986 | 4391 | 306 | 101 | 369 | 6.60E-34 | [SP:P21332] [OR:BACILLUS CEREUS] [DE:DEXTRINASE] (ISOMALTASE) (DEXTRIN 6-ALPHA-D-GLUCANOHYDROLASE)] |
| contig472 | 657087_c3_17 | 987 | 4392 | 1461 | 486 | 1367 | 6.80E-140 | [AC:Z94043] [OR:Bacillus subtilis] [PN:hypothetical protein] [GN:yvdF] [NT:probable neopullulanase] |
| contig473 | 14646937_c1_11 | 988 | 4393 | 1155 | 385 | 841 | 3.70E-84 | [SP:P43830] [OR:HAEMOPHILUS INFLUENZAE] [GN:PROS] [DE:PROLYL-TRNA SYNTHETASE, (PROLINE--TRNA LIGASE) (PRORS)] |
| contig473 | 26386087_c2_14 | 989 | 4394 | 879 | 292 | 276 | 6.20E-24 | [SP:P37764] [OR:ESCHERICHIA COLI] [GN:YAEL] [DE:HYPOTHETICAL 49.1 KD PROTEIN IN CDSA-HLPA INTERGENIC REGION] |
| contig473 | 24663207_c1_10 | 990 | 4395 | 447 | 148 | 155 | 1.30E-10 | [SP:P37764] [OR:ESCHERICHIA COLI] [GN:YAEL] [DE:HYPOTHETICAL 49.1 KD PROTEIN IN CDSA-HLPA INTERGENIC REGION] |
| contig473 | 584657_f3_8 | 991 | 4396 | 210 | 69 | 82 | 0.0045 | [SP:P39482] [OR:BACILLUS MEGATERIUM] [DE:GLUCOSE 1-DEHYDROGENASE 1, (GLCDH-1)] |
| contig473 | 24646087_f1_2 | 992 | 4397 | 693 | 230 | 666 | 1.30E-65 | [AC:D50453] [OR:Bacillus subtilis] [PN:glucose dehydrogenase] [GN:gdh] |
| contig473 | 29741062_f1_3 | 993 | 4398 | 339 | 113 | 87 | 0.00074 | [SP:P37505] [OR:BACILLUS SUBTILIS] [GN:YAS] [DE:HYPOTHETICAL 22.0 KD PROTEIN IN COTF-TETB INTERGENIC REGION] |
| contig474 | 22692877_f2_1 | 994 | 4399 | 951 | 316 | 586 | 3.90E-57 | [SP:P35168] [OR:BACILLUS MEGATERIUM] [DE:HYPOTHETICAL 37.7 KD PROTEIN IN GAP 5'REGION (ORF1)] |
| contig474 | 976512_f2_2 | 995 | 4400 | 1041 | 346 | 1335 | 1.70E-136 | [OR:Streptococcus sp.] [PN:glyceraldehyde-3-phosphate dehydrogenase,] |
| contig474 | 32610887_f2_3 | 996 | 4401 | 1281 | 426 | 997 | 1.10E-100 | [SP:P36204] [OR:THERMOTOGA MARITIMA] [GN:PGK] [DE:PHOSPHOGLYCERATE KINASE,] |
| contig474 | 16532252_c1_10 | 997 | 4402 | 375 | 124 | 114 | 4.10E-07 | [OR:Mycobacterium leprae] [PN:B1496_F1_41 protein] |
| contig474 | 819712_f2_4 | 998 | 4403 | 795 | 264 | 1039 | 3.90E-105 | [SP:P50918] [OR:LACTOCOCCUS LACTIS] [GN:TPI] [DE:TRIOSEPHOSPHATE ISOMERASE, (TIM)] |
| contig475 | 16603592_f2_4 | 999 | 4404 | 1086 | 361 | 970 | 8.00E-98 | [SP:Q60040] [OR:THERMOTOGA NEAPOLITANA] [GN:UXUA] [DE:D-MANNONATE HYDROLASE, (MANNONATE DEHYDRATASE] |
| contig475 | 23834631_f3_7 | 1000 | 4405 | 696 | 231 | 305 | 2.30E-27 | [SP:P38448] [OR:ERWINIA CHRYSANTHEMI] [GN:EDA] [DE:(2-KETO-3-DEOXY-6-PHOSPHOGLUCONATE ALDOLASE) (KDPG-ALDOLASE)] |
| contig475 | 22867937_f2_5 | 1001 | 4406 | 486 | 161 | 125 | 2.80E-08 | [AC:Y14083] [OR:Bacillus subtilis] [PN:hypothetical protein] [GN:yhfF] [NT:Similarity to part of late embryogenesis abundant] |
| contig475 | 24664811_f1_3 | 1002 | 4407 | 234 | 77 | 71 | 0.42 | [SP:P51862] [OR:SACCHAROMYCES CEREVISIAE] [GN:ROM2] [DE:RHO1 GDP-GTP EXCHANGE PROTEIN 2] |
| contig475 | 960933_f2_6 | 1003 | 4408 | 720 | 240 | 140 | 7.90E-08 | [SP:P44726] [OR:HAEMOPHILUS INFLUENZAE] [GN:HI0467] |

TABLE 2-continued

| Contig | Orf | NT Seq Id | AA Seq ID | NT Orf Length | AA Orf Length | Score | Probability | Description |
|---|---|---|---|---|---|---|---|---|
| contig476 | 10804813_f3_5 | 1004 | 4409 | 738 | 245 | 92 | 0.26 | [DE:HYPOTHETICAL PROTEIN HI0467] [SP:P35825] [OR:*BACILLUS STEAROTHERMOPHILUS*] [GN:SBSA] [DE:S-LAYER PROTEIN PRECURSOR (SURFACE LAYER PROTEIN)] |
| contig476 | 25822162_c1_8 | 1005 | 4410 | 1206 | 401 | 509 | 5.60E-49 | [OR:*Methanococcus jannaschii*] [PN:molybdenum cofactor biosynthesis protein moeA homolog] |
| contig476 | 16977015_c2_9 | 1006 | 4411 | 342 | 113 | 212 | 1.20E-16 | [OR:*Methanococcus jannaschii*] [PN:formate dehydrogenase, alpha subunit] |
| contig477 | 26682802_c3_17 | 1007 | 4412 | 537 | 179 | 127 | 8.60E-08 | [OR:*Methanococcus jannaschii*] [PN:malic acid transport protein] |
| contig477 | 36211052_f2_3 | 1008 | 4413 | 846 | 281 | 249 | 2.00E-21 | [SP:P39647] [OR:*BACILLUS SUBTILIS*] [GN:YWFK] [DE:HYPOTHETICAL TRANSCRIPTIONAL REGULATOR IN PTA 3 REGION] |
| contig477 | 5101592_c3_16 | 1009 | 4414 | 216 | 71 | 68 | 0.17 | [AC:U39193] [OR:*Ictalurus punctatus*] [PN:T-cell antigen receptor beta] |
| contig477 | 5352188_c2_11 | 1010 | 4415 | 426 | 141 | 51 | 0.89 | [AC:M35685] [OR:*Mus musculus*] [PN:complement receptor CR2] |
| contig477 | 4880443_c2_10 | 1011 | 4416 | 372 | 123 | | | [AC:D50453] [OR:*Bacillus subtilis*] [PN:L-lactate dehydrogenase] |
| contig477 | 6837832_f2_6 | 1012 | 4417 | 957 | 318 | 817 | 1.30E-81 | [GN:lctE] |
| contig477 | 3910150_f1_2 | 1013 | 4418 | 210 | 70 | 60 | 0.38 | [SP:P36639] [OR:*HOMO SAPIENS*] [GN:MTH1] [DE:7,8-DIHYDRO-8-OXOGUANINE TRIPHOSPHATASE, (8-OXO-DGTPASE)] |
| contig477 | 10945750_c1_6 | 1014 | 4419 | 453 | 151 | 123 | 3.70E-07 | [AC:AF000204] [OR:*Escherichia coli*] [NT:f441; This 441 aa orf is 26 pct identical (25 gaps)] |
| contig478 | 4179211_c3_7 | 1015 | 4420 | 2718 | 905 | 124 | 0.00025 | [SP:P18481] [OR:*STREPTOCOCCUS PYOGENES*] [GN:TEE6] [DE:TRYPSIN-RESISTANT SURFACE T6 PROTEIN PRECURSOR] |
| contig478 | 34039188_c3_13 | 1016 | 4421 | 324 | 107 | 65 | 0.061 | [AC:X71408] [OR:*Plasmodium falciparum*] [PN:protective antigen] [NT:putative] |
| contig479 | 80075_c1_8 | 1017 | 4422 | 249 | 82 | 58 | 0.95 | [OR:*Petunia x hybrida*] [PN:dihydroflavonol-4-reductase,] |
| contig479 | 6697186_c1_7 | 1018 | 4423 | 228 | 75 | 272 | 7.40E-24 | [AC:D78257] [OR:*Enterococcus faecalis*] [PN:ORF6] [GN:orf6] |
| contig479 | 22461562_c2_10 | 1019 | 4424 | 372 | 123 | 337 | 9.50E-31 | [AC:D78257] [OR:*Enterococcus faecalis*] [PN:ORF5] [GN:orf5] |
| contig479 | 29429813_c1_6 | 1020 | 4425 | 534 | 177 | 387 | 4.80E-36 | [AC:D78257] [OR:*Enterococcus faecalis*] [PN:ORF4] [GN:orf4] |
| contig48 | 12109375_c2_2 | 1021 | 4426 | 564 | 187 | 65 | 0.099 | [AC:L40369] [OR:*Chlamydia trachomatis*] [GN:trxA] |
| contig480 | 6052215_c1_10 | 1022 | 4427 | 807 | 268 | 495 | 1.70E-47 | [SP:P73248] [OR:SYNEHOCYSTIS SP] [GN:FOLP] [DE:PYROPHOSPHORYLASE] |
| contig480 | 4900312_c3_17 | 1023 | 4428 | 597 | 198 | 265 | 4.10E-23 | [SP:P44598] [OR:*HAEMOPHILUS INFLUENZAE*] [GN:HI0260] [DE:HYPOTHETICAL PROTEIN HI0260] |
| contig480 | 26835958_c3_16 | 1024 | 4429 | 582 | 193 | 537 | 6.10E-52 | [SP:P19465] [OR:*BACILLUS SUBTILIS*] [GN:MTRA] [DE:GTP CYCLOHYDROLASE 1, (GTP-CH-1)] |
| contig480 | 20203452_c2_12 | 1025 | 4430 | 519 | 172 | 255 | 4.70E-22 | [SP:P29252] [OR:*BACILLUS SUBTILIS*] [GN:FOLK] [DE:(HPPK) (6-HYDROXYMETHYL-7,8-DIHYDROPTERIN PYROPHOSPHOKINASE) (PPPK)] |
| contig480 | 23650342_c2_11 | 1026 | 4431 | 366 | 121 | 181 | 3.20E-14 | [AC:U72662] [OR:*Methylobacterium extorquens*] [PN:dihydroneopterin aldolase] [GN:folB] |
| contig480 | 25663317_c3_15 | 1027 | 4432 | 261 | 86 | 327 | 1.10E-29 | [SP:P43783] [OR:*HAEMOPHILUS INFLUENZAE*] [GN:GOR] [DE:GLUTATHIONE REDUCTASE, (GR) (GRASE)] |
| contig480 | 13019439_c1_9 | 1028 | 4433 | 1062 | 353 | 972 | 4.90E-98 | [OR:*Streptococcus thermophilus*] [PN:glutathione reductase (NADPH),] |
| contig481 | 19532578_f3_4 | 1029 | 4434 | 468 | 155 | 51 | 0.993 | [AC:D17510] [OR:*Chloroplast Pinus thunbergiana*] [PN:ORF52] [GN:trnT] [NT:within petB intron] |

TABLE 2-continued

| Contig | Orf | NT Seq Id | AA Seq ID | NT Orf Length | AA Orf Length | Score | Probability | Description |
|---|---|---|---|---|---|---|---|---|
| contig481 | 23628575_f1_1 | 1030 | 4435 | 435 | 144 | 95 | 0.00072 | [SP:P25958] [OR:BACILLUS SUBTILIS] [GN:COMGF] [DE:COMG OPERON PROTEIN 6] |
| contig481 | 35324037_f3_6 | 1031 | 4436 | 1056 | 351 | 232 | 1.30E-19 | [SP:P37876] [OR:BACILLUS SUBTILIS] [GN:YTXK] [DE:HYPOTHETICAL PROTEIN IN ACKA 5'REGION (FRAGMENT)] |
| contig481 | 25970887_f3_7 | 1032 | 4437 | 834 | 277 | 933 | 6.60E-94 | [SP:P37877] [OR:BACILLUS SUBTILIS] [GN:ACKA] [DE:ACETATE KINASE, (ACETOKINASE)] |
| contig481 | 1285427_f1_1 | 1033 | 4438 | 774 | 257 | 651 | 5.10E-64 | [SP:Q07733] [OR:LACTOCOCCUS LACTIS] [GN:OPPD] [DE:OLIGOPEPTIDE TRANSPORT ATP-BINDING PROTEIN OPPD] |
| contig482 | 34277067_f3_6 | 1034 | 4439 | 966 | 321 | 979 | 8.90E-99 | [SP:Q07734] [OR:LACTOCOCCUSLACTOCOCCUS LACTIS] [GN:OPPF] [DE:OLIGOPEPTIDE TRANSPORT ATP-BINDING PROTEIN OPPF] |
| contig482 | 24853427_f2_4 | 1035 | 4440 | 966 | 321 | 717 | 5.10E-71 | [SP:P50989] [OR:LACTOCOCCUS LACTIS] [GN:OPPB] [DE:OLIGOPEPTIDE TRANSPORT SYSTEM PERMEASE PROTEIN OPPB] |
| contig482 | 25960937_f2_5 | 1036 | 4441 | 951 | 316 | 558 | 3.60E-54 | [SP:Q07743] [OR:LACTOCOCCUS LACTIS] [GN:OPPC] [DE:OLIGOPEPTIDE TRANSPORT SYSTEM PERMEASE PROTEIN OPPC] |
| contig483 | 10554668_f2_3 | 1037 | 4442 | 951 | 316 | 229 | 2.40E-18 | [AC:U22342] [OR:Bacteriophage T270] [PN:integrase] [GN:int] [NT:excisionase] |
| contig483 | 26773412_f1_1 | 1038 | 4443 | 690 | 229 | 82 | 0.083 | [AC:AC000375] [OR:Arabidopsis thaliana] [GN:F19K23.1] [NT:Strong similarity to Arabidopsis] |
| contig483 | 32210953_f3_6 | 1039 | 4444 | 1050 | 349 | 77 | 0.86 | [OR:Methanococcus jannaschii] [PN:hypothetical protein MJ0904] |
| contig483 | 26612900_f1_2 | 1040 | 4445 | 372 | 123 | | | |
| contig483 | 22460807_c2_10 | 1041 | 4446 | 189 | 62 | 55 | 0.6 | [AC:U92865] [OR:Chloroplast Quercus tomentella] [PN:maturase] [GN:matK] |
| contig483 | 15631655_c3_14 | 1042 | 4447 | 195 | 64 | 63 | 0.23 | [AC:X07455] [OR:Plasmodium falciparum] [NT:11-1 gene protein (172 AA)] |
| contig483 | 4964687_f3_7 | 1043 | 4448 | 582 | 194 | 73 | 0.014 | [AC:L05019] [OR:Streptococcus pyogenes] [PN:M-like protein] |
| contig484 | 23494156_f3_5 | 1044 | 4449 | 771 | 256 | 575 | 5.70E-56 | [SP:P37940] [OR:BACILLUS SUBTILIS] [GN:BFMBAA] [DE:(BCKDH E1-ALPHA)] |
| contig484 | 34651588_f3_6 | 1045 | 4450 | 1008 | 335 | 943 | 5.80E-95 | [SP:P37941] [OR:BACILLUS SUBTILIS] [GN:BFMBAB] [DE:(BCKDH E1-BETA)] |
| contig484 | 24332327_f2_3 | 1046 | 4451 | 264 | 87 | 199 | 1.80E-15 | [SP:P37942] [OR:BACILLUS SUBTILIS] [GN:BFMBB] [DE:CHAIN TRANSACYLASE] |
| contig484 | 23705090_f1_2 | 1047 | 4452 | 1137 | 378 | 732 | 1.30E-72 | [SP:P37942] [OR:BACILLUS SUBTILIS] [GN:BFMBB] [DE:CHAIN TRANSACYLASE] |
| contig484 | 6928430_f3_7 | 1048 | 4453 | 489 | 162 | 137 | 3.00E-09 | [AC:U56999] [OR:Treponema pallidum] [PN:pfoS/R] [GN:pfoS/R] [NT:potential regulatory molecule; pfoS/R-like] |
| contig485 | 24640625_c1_9 | 1049 | 4454 | 825 | 274 | 213 | 9.50E-17 | [SP:P40408] [OR:BACILLUS SUBTILIS] [GN:YBBB] [DE:HYPOTHETICAL TRANSCRIPTIONAL REGULATOR IN FEUA 5'REGION (ORF3)] |
| contig485 | 5346887_f1_1 | 1050 | 4455 | 183 | 60 | 60 | 0.28 | [AC:L76262] [OR:Mitochondrion Meloidogyne hapla] [PN:cytochrome b] [GN:cytb] |
| contig485 | 34585812_f2_2 | 1051 | 4456 | 1773 | 590 | 981 | 5.40E-99 | [AC:U50951] [OR:Thermoanacrobacterium thermosulfurigenes] [PN:AbcA] [GN:abcA] [NT:hypothetical ABC exporter component,] |
| contig485 | 7230311_f3_5 | 1052 | 4457 | 1728 | 575 | 1193 | 1.90E-121 | [AC:U50951] [OR:Thermoanacrobacterium thermosulfurigenes] [PN:AbcB] [GN:abcB] [NT:hypothetical ABC exporter component,] |

TABLE 2-continued

| Contig | Orf | NT Seq Id | AA Seq ID | NT Orf Length | AA Orf Length | Score | Probability | Description |
|---|---|---|---|---|---|---|---|---|
| contig486 | 25976012_c2_7 | 1053 | 4458 | 876 | 291 | 86 | 0.52 | [OR:*Brucella abortus*] [PN:gene htrA protein] [GN:htrA] |
| contig486 | 15625702_c3_9 | 1054 | 4459 | 912 | 303 | 999 | 6.70E-101 | [AC:Z94043] [OR:*Bacillus subtilis*] [PN:hypothetical protein] [GN:yvcL] [NT:similar to Y103_MYCGE hypothetical protein mg103] |
| contig486 | 6347155_c3_8 | 1055 | 4460 | 939 | 312 | 573 | 9.30E-56 | [AC:Z94043] [OR:*Bacillus subtilis*] [PN:hypothetical protein] [GN:yvcK] [NT:similar to hypothetical SYCSLRA] |
| contig487 | 34385961_f3_6 | 1056 | 4461 | 1005 | 334 | 370 | 7.30E-34 | [SP:Q11046] [OR:*MYCOBACTERIUM TUBERCULOSIS*] [GN:MTCY50.09] [DE:HYPOTHETICAL ABC TRANSPORTER ATP-BINDING PROTEIN CY50.09] |
| contig487 | 26037500_f1_1 | 1057 | 4462 | 846 | 281 | 487 | 1.20E-46 | [SP:P54718] [OR:*BACILLUS SUBTILIS*] [GN:YFIB] [DE:HYPOTHETICAL ABC TRANSPORTER ATP-BINDING PROTEIN 1 IN GLVBC 3'REGION] |
| contig487 | 24431677_f2_5 | 1058 | 4463 | 1863 | 620 | 1009 | 5.90E-102 | [SP:Q11047] [OR:*MYCOBACTERIUM TUBERCULOSIS*] [GN:MTCY50.10] [DE:HYPOTHETICAL ABC TRANSPORTER ATP-BINDING PROTEIN CY50.10] |
| contig487 | 24415936_c3_12 | 1059 | 4464 | 537 | 178 | 125 | 9.60E-08 | [AC:L38997] [OR:*Mycoplasma pneumoniae*] [NT:ORF9] |
| contig487 | 6910887_c2_10 | 1060 | 4465 | 186 | 62 | 55 | 0.9 | [OR:*Methanococcus jannaschii*] [PN:hypothetical protein MJ0661] |
| contig487 | 2925192_c2_9 | 1061 | 4466 | 363 | 120 | 386 | 6.10E-36 | [SP:P42980] [OR:*BACILLUS SUBTILIS*] [GN:YPIF] [DE:HYPOTHETICLA 15.1 KD PROTEIN IN DAPB-PAPS INTERGENIC REGION] |
| contig488 | 4495453_F2_3 | 1062 | 4467 | 546 | 181 | 89 | 0.018 | [AC:U30903] OR:*Klebsiella pneumoniae*] [PN:unknown] [NT:orf2c] |
| contig488 | 5353211_c1_12 | 1063 | 4468 | 849 | 282 | 296 | 2.10E-26 | [AC:U59236] [OR:*Synechococcus PCC7942*] [PN:unknown] [NT:ORF205] |
| contig488 | 11751887_c3_17 | 1064 | 4469 | 1041 | 346 | 422 | 9.40E-40 | [SP:Q28488] [OR:*MACROPUS FULIGINOSUS*] [GN:CRYM] [DE:MU-CRYSTALLIN] |
| contig488 | 4970075_f3_9 | 1065 | 4470 | 1191 | 396 | 608 | 1.80E-59 | [AC:AB001488] [OR:*Bacillus subtilis*] [GN:ydeF] [NT:SIMILAR TO HYPOTHETICAL TRANSCRIPTIONAL] |
| contig488 | 24664015_c1_5 | 1066 | 4471 | 1338 | 446 | 513 | 4.80E-49 | [SP:Q10866] [OR:*MYCOBACTERIUM TUBERCULOSIS*] [GN:MTCY39.27] [DE:PROBABLE CATION-TRANSPORTING ATPASE CY39.27.] |
| contig489 | 26192943_c2_7 | 1067 | 4472 | 840 | 279 | 883 | 1.30E-88 | [AC:D90817] [OR:*Escherichia coli*] [PN:NH(3)-dependent NAD(+) synthetase (EC 6.3.5.1)] [GN:nadE, cfg, ntrL_] [NT:ORF_ID] |
| contig489 | 30109437_c3_10 | 1068 | 4473 | 309 | 102 | 76 | 0.11 | [AC:U73200] [OR:*Mus musculus*] [PN:p116Rip] |
| contig489 | 26604062_c2_6 | 1069 | 4474 | 1275 | 424 | 489 | 7.40E-47 | [SP:Q10641] [OR:*MYCOBACTERIUM TUBERCULOSIS*] [GN:MTCY130.15C] [DE:HYPOTHETICAL 54.3 KD PROTEIN CY130.15C] |
| contig489 | 25681282_c3_8 | 1070 | 4475 | 381 | 126 | 186 | 9.50E-15 | [SP:P39602] [OR:*BACILLUS SUBTILIS*] [GN:YWCD] [DE:HYPOTHETICAL 14.3 KD PROTEIN IN EPR-GALK INTERGENIC REGION] |
| contig49 | 10753905_f3_1 | 1071 | 4476 | 759 | 252 | 188 | 2.20E-23 | [SP:P45092] [OR:*HAEMOPHILUS INFLUENZAE*] [GN:ARTP] [DE:ARGININE TRANSPORT ATP-BINDING PROTEIN ARTP] |
| contig49 | 470062_c3_2 | 1072 | 4477 | 183 | 60 | 58 | 0.68 | [OR:*Emericella Aspergillus nidulans*] [PN:chitin synthase, 2] |
| contig490 | 875312_f3_7 | 1073 | 4478 | 195 | 64 | 59 | 0.68 | [AC:Z81546] [OR:*Caenorhabditis elegans*] [PN:F53A2.k] [NT:protein predicted using Genefinder; preliminary] |
| contig490 | 4784553_f1_1 | 1074 | 4479 | 840 | 279 | 102 | 0.0036 | [SP:P16692] [OR:*ESCHERICHIA COLI*] [GN:PHNP] [DE:PHNP PROTEIN] |
| contig490 | 172076_c3_15 | 1075 | 4480 | 204 | 67 | 62 | 0.12 | [AC:U86775] [OR:Human immunodeficiency virus type 1] [PN:tat protein] [GN:tat] |
| contig490 | 26601552_c1_12 | 1076 | 4481 | 885 | 294 | 1423 | 7.90E-146 | [OR:*Enterococcus faecalis*] [PN:serine proteinase homolog] |
| contig490 | 35273587_c1_11 | 1077 | 4482 | 1560 | 519 | 2542 | 2.10E-264 | [OR:*Enterococcus faecalis*] [PN:coccolysin, gelatinase] [GN:gelE] |

TABLE 2-continued

| Contig | Orf | NT Seq Id | AA Seq ID | NT Orf Length | AA Orf Length | Score | Probability | Description |
|---|---|---|---|---|---|---|---|---|
| contig490 | 6273349_c1_10 | 1078 | 4483 | 954 | 317 | 225 | 3.10E-18 | [AC:X98110] [OR:Streptococcus gordonii] [PN:pheromone receptor] [GN:comD2] [NT:histidine kinase] |
| contig491 | 23650268_c2_9 | 1079 | 4484 | 291 | 97 | 109 | 4.50E-06 | [AC:U51911] [OR:Bacillus subtilis] [PN:unknown] [GN:ykrA] [NT:similar in C-terminus to partial sequence of orf1] |
| contig491 | 25587943_f1_1 | 1080 | 4485 | 732 | 243 | 678 | 7.00E-67 | [AC:D50453] [OR:Bacillus subtilis] [PN:homologue of alkaline phosphatase synthesis] [GN:ycIJ] |
| contig491 | 1039502_f3_3 | 1081 | 4486 | 1494 | 497 | 716 | 6.60E-71 | [AC:D50453] [OR:Bacillus subtilis] [PN:homologue of alkaline phosphatase synthesis] [GN:ycIK] |
| contig491 | 10723133_f1_2 | 1082 | 4487 | 213 | 70 | 59 | 0.3 | [OR:Rattus norvegicus] [PN:T-cell receptor beta chain C region type 1] |
| contig491 | 26834688_c3_11 | 1083 | 4488 | 573 | 190 | 88 | 0.041 | [AC:U35442] [OR:Rhodobacter sphaeroides] [PN:PepF] [GN:pepF] [NT:similar to YejF of Escherichia coli, encoded by] |
| contig491 | 6423437_c1_5 | 1084 | 4489 | 657 | 218 | 51 | 0.9992 | [OR:Squalus acanthias] [PN:Na+/K-+-exchanging ATPase,] |
| contig492 | 979640_c3_16 | 1085 | 4490 | 492 | 163 | 73 | 0.65 | [AC:Y07645] [OR:Staphylococcus aureus] [GN:rsbW] |
| contig492 | 100039682_c1_10 | 1086 | 4491 | 432 | 143 | 54 | 0.86 | [OR:Oryctolagus cuniculus] [PN:34K epidermal growth factor inhibitor, ras-like] |
| contig492 | 4307330_c2_14 | 1087 | 4492 | 1308 | 435 | 757 | 3.00E-75 | [SP:P42977] [OR:BACILLUS SUBTILIS] [GN:PAPS] [DE:POLY(A) POLYMERASE, (PAP)] |
| contig492 | 10956_c3_15 | 1088 | 4493 | 858 | 285 | 729 | 2.70E-72 | [SP:P42976] [OR:BACILLUS SUBTILIS] [GN:DAPB] [DE:DIHYDRODIPICOLINATE REDUCTASE.] |
| contig492 | 36135892_c2_12 | 1089 | 4494 | 372 | 123 | 331 | 4.10E-30 | [SP:P42979] [OR:BACILLUS SUBTILIS] [GN:YPJD] [DE:HYPOTHETICAL 13.0 KD PROTEIN IN QCRC-DAPB INTERGENIC REGION] |
| contig492 | 22476703_f3_8 | 1090 | 4495 | 885 | 294 | 392 | 1.40E-36 | [SP:P42978] [OR:BACILLUS SUBTILIS] [GN:YPJC] [DE:HYPOTHETICAL 23.6 KD PROTEIN IN QCRC-DAPB INTERGENIC REGION] |
| contig492 | 30303842_c1_9 | 1091 | 4496 | 255 | 84 | 116 | 2.50E-07 | [SP:P54390] [OR:BACILLUS SUBTILIS] [GN:YPIB] [DE:HYPOTHETICAL 21.4 KD PROTEIN IN QCRA 5'REGION] |
| contig493 | 22736042_c2_17 | 1092 | 4497 | 729 | 242 | 791 | 7.40E-79 | [SP:P37567] [OR:BACILLUS SUBTILIS] [GN:YACF] [DE:HYPOTHETICAL 37.1 KD PROTEIN IN FOLK-LYSS INTERGENIC REGION] |
| contig493 | 14600635_c3_18 | 1093 | 4498 | 945 | 314 | 844 | 1.80E-84 | [SP:P37565] [OR:BACILLUS SUBTILIS] [GN:YACC] [DE:HYPOTHETICAL 31.8 KD PROTEIN IN FTSH-CYSK INTERGENIC REGION] |
| contig493 | 24032818_c1_14 | 1094 | 4499 | 2070 | 689 | 1846 | 1.20E-190 | [SP:P46469] [OR:LACTOCOCCUS LACTIS] [GN:FTSH] [DE:CELL DIVISION PROTEIN FTSH HOMOLOG.] |
| contig494 | 35985878_f2_4 | 1095 | 4500 | 1200 | 399 | 555 | 7.50E-54 | [OR:Enterococcus faecalis] [PN:pheromone cAD1 binding protein precursor] [GN:traC] |
| contig494 | 34164201_f1_1 | 1096 | 4501 | 525 | 174 | 263 | 3.70E-22 | [AC:D78016] [OR:Enterococcus faecalis] [PN:TRAC] [GN:traC] [NT:ORF3; replication related gene] |
| contig494 | 4859378_f2_5 | 1097 | 4502 | 258 | 85 | 76 | 0.0043 | [AC:AB001488] [OR:Bacillus subtilis] [GN:ydaS] [NT:FUNCTION UNKNOWN.] |
| contig494 | 2835432_c2_11 | 1098 | 4503 | 264 | 87 | 62 | 0.81 | [OR:Trimonphomyces papilionaceus] [PN:hypothetical protein] |
| contig494 | 4710877_f1_3 | 1099 | 4504 | 1212 | 404 | 56 | 0.996 | [OR:Bos primigenius taurus] [PN:T-cell receptor eta chain] |
| contig495 | 14875927_f3_6 | 1100 | 4505 | 477 | 158 | 74 | 0.99993 | [AC:Z83217] [OR:Caenorhabditis elegans] [PN:C10C6.6] [NT:Similarity to Yeast E1-E2 ATPase YEL031W] |
| contig495 | 25586702_f2_4 | 1101 | 4506 | 882 | 293 | 62 | 0.56 | [AC:U26684] [OR:Dichelobacter nodosus] [PN:unknown] [GN:ORFE] [NT:similar to ORF1 of the B. subtilis comE operon] |
| contig495 | 22132925_f3_7 | 1102 | 4507 | 447 | 148 | 61 | 0.24 | [AC:I24929] [OR:Salmo salar] [NT:MHC class II beta 1; PCR product] |

TABLE 2-continued

| Contig | Orf | NT Seq Id | AA Seq ID | NT Orf Length | AA Orf Length | Score | Probability | Description |
|---|---|---|---|---|---|---|---|---|
| contig495 | 35977155_f2_5 | 1103 | 4508 | 363 | 120 | 75 | 0.66 | [AC:L49527] [OR:*Dictyostelium discoideum*] [PN:cortexillin 1] |
| contig495 | 254712_f1_1 | 1104 | 4509 | 684 | 227 | 56 | 0.93 | [SP:P03036] [OR:BACTERIOPHAGE 434] [GN:CRO] [DE:REGULATORY PROTEIN CRO] |
| contig495 | 34189768_f3_8 | 1105 | 4510 | 375 | 124 | 63 | 0.97 | [AC:X65264] [OR:*Mitochondrion Porphyra* sp.] [NT:orf] |
| contig495 | 12928431_f1_2 | 1106 | 4511 | 483 | 160 | 79 | 0.75 | [AC:P07602] [OR:HOMO SAPIENS] [GN:PSAP] [DE:PROTEIN 2) (SAP-2), AND SAPOSIN D (PROTEIN C) (COMPONENT C)] |
| contig495 | 25630061_f3_9 | 1107 | 4512 | 1083 | 360 | 82 | 0.97 | [OR:*Saccharomyces cerevisiae*] [PN:hypothetical protein YDL038c] |
| contig495 | 34165926_f3_10 | 1108 | 4513 | 318 | 105 | 71 | 0.98 | [SP:P22314] [OR:*HOMO SAPIENS*] [GN:UBE1] [DE:UBIQUITIN-ACTIVATING ENZYME E1 (A1S9 PROTEIN)] [OR:*Homo sapiens*] [GN:PROS1] |
| contig495 | 3914213_f1_3 | 1109 | 4514 | 369 | 123 | 55 | 0.65 | [AC:Y14080] [OR:*Bacillus subtilis*] [PN:hypothetical protein] [GN:yheI] [NT:similarity to multidrug resistance-like ATP binding] |
| contig496 | 22000192_f3_5 | 1110 | 4515 | 1554 | 517 | 1186 | 1.00E-120 | [AC:Y14080] [OR:*Bacillus subtilis*] [PN:*hypothetical protein*] [GN:yheH] [NT:similarity to multidrug resistance-like ATP binding] |
| contig496 | 26600088_f2_4 | 1111 | 4516 | 1791 | 596 | 917 | 3.30E-92 | [SP:P36923] [OR:*ENTEROCOCCUS FAECALIS*] [GN:*EBSD*] [DE:(3-DEHYDROQUINASE)] |
| contig496 | 25558187_f1_3 | 1112 | 4517 | 813 | 270 | 1275 | 3.80E-130 | [SP:P36922] [OR:*ENTEROCOCCUS FAECALIS*] [DE:EBSC PROTEIN] |
| contig496 | 33783330_f3_6 | 1113 | 4518 | 639 | 212 | 774 | 4.70E-77 | [AC:D78193] [OR:*Bacillus subtilis*] [GN:yycI] |
| contig497 | 26251702_c3_14 | 1114 | 4519 | 243 | 81 | 229 | 2.60E-19 | [AC:D78193] [OR:*Bacillus subtilis*] [GN:yycI] |
| contig497 | 7038936_c1_10 | 1115 | 4520 | 915 | 304 | 187 | 1.00E-13 | [SP:P34031] [OR:*SPIROPLASMA CITRI*] [GN:GYRB] [DE:DNA GYRASE SUBUNIT B.] |
| contig497 | 7039817_c2_12 | 1116 | 4521 | 1326 | 441 | 88 | 0.65 | [AC:D78193] [OR:*Bacillus subtilis*] [GN:yycG] [NT:homologous toPHOR_BACSU] |
| contig497 | 24628438_c3_13 | 1117 | 4522 | 1857 | 618 | 1095 | 4.50E-111 | [SP:P37478] [OR:*BACILLUS SUBTILIS*] [GN:YYCF] |
| contig497 | 1988304_c2_11 | 1118 | 4523 | 276 | 91 | 186 | 9.50E-15 | [DE:INTERGENIC REGION] |
| contig498 | 3070215_f3_2 | 1119 | 4524 | 1590 | 529 | 340 | 8.10E-31 | [SP:P05054] [OR:*ESCHERICHIA COLI*] [GN:RBSK] [DE:RIBOKINASE.] |
| contig498 | 25667801_f3_3 | 1120 | 4525 | 1515 | 504 | 60 | 0.93 | [AC:M96311] [OR:Human papillomavirus type 4] [GN:E1] |
| contig498 | 25394127_c2_4 | 1121 | 4526 | 195 | 64 | 54 | 0.6 | [SP:P29034] [OR:*HOMO SAPIENS*] [GN:S100A2] [DE:S100 CALCIUM-BINDING PROTEIN A2 (S-100L PROTEIN) (CAN19)] |
| contig498 | 22161427_c3_5 | 1122 | 4527 | 327 | 108 | 52 | 0.82 | [AC:U80301] [OR:*Oncorhynchus tschawytscha*] [PN:MHC class H beta-1] [NT:peptide binding domain] |
| contig499 | 7070212_c1_15 | 1123 | 4528 | 576 | 192 | 314 | 2.60E-28 | [SP:P54721] [OR:*BACILLUS SUBTILIS*] [GN:*YFIE*] [DE:HYPOTHETICAL 31.5 KD PROTEIN IN GLVBC 3'REGION] |
| contig499 | 24226557_c1_14 | 1124 | 4529 | 645 | 214 | 262 | 8.40E-23 | [SP:P37261] [OR:*SACCHAROMYCES CEREVISIAE*] [GN:YCLX8C] [DE:HYPOTHETICAL 21.1 KD PROTEIN IN FUSI 3'REGION] |
| contig499 | 4179768_c1_13 | 1125 | 4530 | 945 | 314 | 509 | 5.60E-49 | [SP:P37517] [OR:*BACILLUS SUBTILIS*] [GN:YYAG] [DE:HYPOTHETICAL TRANSCRIPTIONAL REGULATOR IN TETB-EXOA INTERGENIC REGION] |
| contig499 | 24088587_f1_2 | 1126 | 4531 | 252 | 83 | 62 | 0.3 | [AC:D85748] [OR:*Mus musculus*] [PN:Grb3-3] [GN:grb3-3] [NT:mouse Grb2 isoform] |
| contig499 | 120201_f2_5 | 1127 | 4532 | 195 | 64 | 61 | 0.99 | [AC:D45044] [OR:*Homo sapiens*] [PN:ceruloplasmin] |
| contig499 | 5351462_f2_6 | 1128 | 4533 | 345 | 114 | 79 | 0.43 | [AC:X94082] [OR:*Xenopus laevis*] [PN:KLP2 protein] [GN:klp21] |
| contig499 | 2501510_f1_3 | 1129 | 4534 | 552 | 183 | | | |
| contig499 | 957700_f2_7 | 1130 | 4535 | 678 | 225 | 85 | 0.27 | [AC:Z92770] [OR:*Mycobacterium tuberculosis*] [PN:unknown] [GN:MTC15.32] [MTC15.32, unknown, partial orf, contains PS00142] |

TABLE 2-continued

| Contig | Orf | NT Seq Id | AA Seq ID | NT Orf Length | AA Orf Length | Score | Probability | Description |
|---|---|---|---|---|---|---|---|---|
| contig499 | 19631324_c1_11 | 1131 | 4536 | 810 | 269 | 479 | 8.50E-46 | [AC:Y14083] [OR:Bacillus subtilis] [PN:hypothetical protein] [GN:yhfJ] [NT:Similarity to several lipoate-protein ligases] |
| contig5 | 31682253_f1_1 | 1132 | 4537 | 546 | 182 | 222 | 5.20E-33 | [AC:Z71552] [OR:Streptococcus pneumoniae] [PN:AdcA] [GN:adcA] [NT:putative lipoprotein] |
| contig50 | 20439187_c3_7 | 1133 | 4538 | 198 | 66 | 179 | 5.30E-14 | [SP:P38493] [OR:BACILLUS SUBTILIS] [GN:CMK] [DE:KINASE (CMP KINASE)] |
| contig50 | 9804808_c2_6 | 1134 | 4539 | 189 | 62 | 58 | 0.48 | [AC:U48553] [OR:Chloroplast Grayia spinosa] [PN:ORF2280 gene homolog] |
| contig50 | 24395462_c1_4 | 1135 | 4540 | 618 | 205 | 82 | 0.016 | [SP:P39046] [OR:ENTEROCOCCUS HIRAE] [DE:(MURAMIDASE 2)] |
| contig500 | 4688943_f1_1 | 1136 | 4541 | 1017 | 338 | 352 | 2.40E-32 | [SP:P27621] [OR:BACILLUS SUBTILIS] [GN:TAGB] [DE:TEICHOIC ACID BIOSYNTHESIS PROTEIN B PRECURSOR] |
| contig500 | 29382942_f2_4 | 1137 | 4542 | 768 | 255 | 407 | 3.60E-38 | [SP:P27620] [OR:BACILLUS SUBTILIS] [GN:TAGA] [DE:TEICHOIC ACID BIOSYNTHESIS PROTEIN A] |
| contig500 | 31577_f2_5 | 1138 | 4543 | 594 | 197 | 79 | 0.46 | [AC:U02970] [OR:Mitochondrion Prototheca wickerhamii] [GN:orf304 = ymf42] [NT:unique orf, function unknown] |
| contig500 | 410291_f1_2 | 1139 | 4544 | 432 | 143 | 436 | 3.10E-41 | [SP:P27623] [OR:BACILLUS SUBTILIS] [GN:TAGD] [DE:D] |
| contig500 | 14257932_c1_8 | 1140 | 4545 | 186 | 61 | 76 | 0.029 | [AC:U66480] [OR:Bacillus subtilis] [PN:YnbA] [GN:ynbA] |
| contig500 | 20970882_f1_3 | 1141 | 4546 | 1107 | 368 | 84 | 0.99 | [AC:U90522] [OR:Arabidopsis thaliana] [PN:lysine-ketoglutarate reductase/saccharopine] [GN:LKR/SDH] [NT:bifuctional enzyme; aminoadipic semialdehyde] |
| contig500 | 36335805_f2_6 | 1142 | 4547 | 312 | 103 | 59 | 0.78 | [AC:D90899] [OR:Synechocystis sp.] [PN:hypothetical protein] [GN:ctrE] [NT:ORF_ID] |
| contig501 | 976536_c1_8 | 1143 | 4548 | 309 | 103 | 194 | 1.40E-15 | [AC:X99401] [OR:Bacillus firmus] [PN:peptide release factor 2] [GN:prfB] |
| contig501 | 4507787_c2_9 | 1144 | 4549 | 1494 | 497 | 1548 | 4.50E-159 | [SP:P47847] [OR:LISTERIA MONOCYTOGENES] [GN:SECA] [DE:PREPROTEIN TRANSLOCASE SECA SUBUNIT] |
| contig501 | 14742200_c3_10 | 1145 | 4550 | 1122 | 373 | 1300 | 8.50E-133 | [SP:P47847] [OR:LISTERIA MONOCYTOGENES] [GN:SECA] [DE:PREPROTEIN TRANSLOCASE SECA SUBUNIT] |
| contig502 | 21972626_f1_1 | 1146 | 4551 | 231 | 76 | 156 | 1.10E-10 | [SP:P52410] [OR:ARABIDOPSIS THALIANA] [GN:KASI] [DE:(BETA-KETOACYL-ACP SYNTHASE 1) (KASI)] |
| contig502 | 34657287_f2_4 | 1147 | 4552 | 507 | 168 | 215 | 5.30E-24 | [AC:U59235] [OR:Synechococcus PCC7942] [PN:biotin carboxyl carrier protein)] [GN:accB] [NT:the only biotin-containing protein in Synechococcus] |
| contig502 | 978412_f2_5 | 1148 | 4553 | 429 | 142 | 331 | 4.10E-30 | [AC:Z83337] [OR:Bacillus subtilis] [GN:ywpB] [NT:similar to hydroxymyristoyl-(acyl carrier protein)] |
| contig502 | 9775312_f3_8 | 1149 | 4554 | 1374 | 457 | 1344 | 1.90E-137 | [AC:D84432] [OR:Bacillus subtilis] [PN:YqhX] |
| contig502 | 34650887_f1_2 | 1150 | 4555 | 885 | 294 | 710 | 2.80E-70 | [SP:P51198] [OR:PORPHYRA PURPUREA] [GN:ACCD] [DE:(EC 6.4.1.2)] |
| contig502 | 19766583_f2_7 | 1151 | 4556 | 831 | 276 | 572 | 1.20E-55 | [AC:D13095] [OR:Bacillus stearothermophilus] [PN:undefined open reading frame] |
| contig503 | 117208_f1_1 | 1152 | 4557 | 315 | 104 | 306 | 1.80E-27 | [SP:P45747] [OR:THERMUS AQUATICUS] [GN:GROES] [DE:10 KD CHAPERONIN (PROTEIN CPN 10) (PROTEIN GROES)] |
| contig503 | 9956880_c2_22 | 1153 | 4558 | 549 | 182 | 181 | 3.20E-14 | [AC:M15467] [OR:Mycobacterium tuberculosis] [PN:ORF F175; putative protein] [NT:ORF F175; putative] |
| contig503 | 4898518_f1_2 | 1154 | 4559 | 1638 | 545 | 1980 | 7.50E-205 | [gSP:P28598] [OR:BACILLUS SUBTILIS] [GN:GROEL] [DE:60 KD CHAPERONIN (PROTEIN CPN60) (GROEL PROTEIN)] |
| contig503 | 24698956_c2_21 | 1155 | 4560 | 399 | 132 | 241 | 1.40E-20 | [AC:M15467] [OR:Mycobacterium tuberculosis] [PN:unknown protein] [NT:ORF F175; putative] |

TABLE 2-continued

| Contig | Orf | NT Seq Id | AA Seq ID | NT Orf Length | AA Orf Length | Score | Probability | Description |
|---|---|---|---|---|---|---|---|---|
| contig503 | 29407803_f3_7 | 1156 | 4561 | 549 | 182 | 180 | 4.10E-14 | [SP:P37478] [OR:*BACILLUS SUBTILIS*] [GN:YCF] [DE:INTERGENIC REGION] |
| contig503 | 25633432_f2_4 | 1157 | 4562 | 801 | 266 | 157 | 1.40E-08 | [AC:U52064] [OR:Kaposi's sarcoma-associated herpes-like virus] [NT:*Herpesvirus saimiri* ORF73 homolog] |
| contig503 | 15820967_f3_8 | 1158 | 4563 | 1560 | 519 | 419 | 3.00E-49 | [SP:P37710] [OR:*ENTEROCOCCUS FAECALIS*] [DE:AUTOLYSIN (N-ACETYLMURAMOYL-L-ALANINE AMIDASE)] |
| contig503 | 48257813_f3_9 | 1159 | 4564 | 198 | 66 | 64 | 0.68 | [SP:P40988] [OR:*SACCHAROMYCES CEREVISIAE*] [GN:FET4] [DE:LOW-AFFINITY FE(II) TRANSPORT PROTEIN] |
| contig503 | 24430452_f3_5 | 1160 | 4565 | 480 | 159 | 263 | 6.60E-23 | [SP:P27640] [OR:*RICKETTSIA PROWAZEKII*] [GN:GREA] [DE:GREA] |
| contig504 | 36538452_f3_6 | 1161 | 4566 | 756 | 251 | 57 | 0.89 | [AC:S71594] [OR:Helenium virus S] [GN:12K] [NT:This sequence comes from FIG. 1.] |
| contig504 | 30564143_f2_3 | 1162 | 4567 | 1116 | 371 | 544 | 1.10E-52 | [AC:U81487] [OR:*Lactococcus lactis cremoris*] [PN:histidine kinase] [GN:llkinD] |
| contig504 | 2933467_f3_7 | 1163 | 4568 | 648 | 215 | 442 | 7.10E-42 | [AC:Y14079] [OR:*Bacillus subtilis*] [PN:hypothetical protein] [GN:yhcZ] [NT:similarity to the transcriptional regulator degU] |
| contig504 | 1956563_f1_1 | 1164 | 4569 | 726 | 241 | 643 | 3.60E-63 | [SP:P39760] [OR:*BACILLUS SUBTILIS*] [GN:YLXV] [DE:HYPOTHETICAL 24.3 KD PROTEIN KINC-ADEC INTERGENIC REGION (ORF4)] |
| contig504 | 9922058_f1_2 | 1165 | 4570 | 384 | 127 | 203 | 1.50E-16 | [AC:Z73234] [OR:*Bacillus subtilis*] [PN:YneR] [GN:yneR] |
| contig504 | 35401576_f2_4 | 1166 | 4571 | 768 | 256 | 494 | 2.20E-47 | [SP:Q45539] [OR:*BACILLUS SUBTILIS*] [GN:CSBB] [DE:CSBB PROTEIN] |
| contig505 | 6020062_c2_13 | 1167 | 4572 | 216 | 72 | 54 | 0.76 | [OR:*Methanococcus jannaschii*] [PN:hypothetical protein MJ1475] |
| contig505 | 24414182_c3_16 | 1168 | 4573 | 219 | 72 | 53 | 0.69 | [OR:*Saccharomyces cerevisiae*] [PN:hypothetical protein L3135 (L3133 internal orf)] |
| contig505 | 5260811_c1_10 | 1169 | 4574 | 417 | 138 | 80 | 0.58 | [AC:Z83112] [OR:*Caenorhabditis elegans*] [PN:C03C10.6] [NT:cDNA EST yk23a10.5 comes from.this gene; cDNA EST] |
| contig505 | 35365937_c3_15 | 1170 | 4575 | 855 | 284 | 85 | 0.15 | [AC:Y09454] [OR:*Lactobacillus casei* bacteriophage A2] [PN:ORF:3] |
| contig505 | 26214688_c1_9 | 1171 | 4576 | 387 | 128 | 64 | 0.9995 | [SP:P41728] [OR:*CRYPTOPHLEBIA LEUCOTRETA* GRANULOSIS VIRUS] [DE:HYPOTHETICAL 18.6 KD PROTEIN IN P143-LEF5 INTERGENIC REGION] |
| contig505 | 26735665_c2_12 | 1172 | 4577 | 420 | 139 | 57 | 0.56 | [SP:Q09310] [OR:*CAENORHABDITIS ELEGANS*] [GN:F21H12.2] [DE:VERY HYPOTHETICAL 7.0 KD PROTEIN F21H12.2 IN CHROMOSOME II] |
| contig505 | 49216_c1_8 | 1173 | 4578 | 390 | 129 | 58 | 0.41 | [OR:*Phaseolus vulgaris*] [PN:C9 protein] |
| contig505 | 7062540_c2_11 | 1174 | 4579 | 351 | 116 | 55 | 0.52 | [AC:U94718] [OR:*Ovis aries*] [PN:glyceraldehyde-3-phosphate dehydrogenase] |
| contig505 | 24886561_c1_7 | 1175 | 4580 | 201 | 66 | 68 | 0.24 | [AC:X57546] [OR:Mitochondrion *Kluyveromyces lactis*] [GN:COX1] (NT:intron orf; Author-given protein sequence is in) |
| contig505 | 36433303_c3_14 | 1176 | 4581 | 417 | 138 | 55 | 0.75 | [OR:*Homo sapiens*] [PN:APR peptide] |
| contig506 | 30701156_f3_3 | 1177 | 4582 | 1368 | 455 | 459 | 1.10E-43 | [OR:*Bacillus stearothermophilus*] [PN:regulatory gene 5' of celA] |
| contig506 | 26376718_f1_1 | 1178 | 4583 | 333 | 110 | 239 | 2.30E-20 | [OR:*Bacillus stearothermophilus*] [PN:cellobiose phosphotransferase system celA] |
| contig506 | 36048577_f1_2 | 1179 | 4584 | 1449 | 482 | 349 | 1.50E-44 | [AC:AF000268] [OR:*Escherichia coli*] [GN:celB] [NT:t452; CG Site No. 18487; residues 1-189 are 100 pct] |
| contig507 | 13175418_f1_1 | 1180 | 4585 | 408 | 135 | 255 | 4.70E-22 | [OR:*Bacillus stearothermophilus*] [PN:cellobiose phosphotransferase system celA] |
| contig507 | 34117937_c2_11 | 1181 | 4586 | 735 | 244 | 94 | 0.0004 | [AC:Z93937] [OR:*Bacillus subtilis*] [PN:unknown] [GN:yufO] |

TABLE 2-continued

| Contig | Orf | NT Seq Id | AA Seq ID | NT Orf Length | AA Orf Length | Score | Probability | Description |
|---|---|---|---|---|---|---|---|---|
| contig507 | 5860053_f1_2 | 1182 | 4587 | 255 | 84 | 63 | 0.79 | [NT:potential methylgalactoside transport ATP binding] [SP:P38009] [OR:SACCHAROMYCES CEREVISIAE] [GN:ADE17] [DE:(INOSINICASE) (IMP SYNTHETASE) (AITC)] |
| contig507 | 20829692_f1_3 | 1183 | 4588 | 1350 | 449 | 739 | 2.40E-73 | [SP:P39145] [OR:BACILLUS SUBTILIS] [GN:COMFA] [DE:COMF OPERON PROTEIN 1] |
| contig507 | 23673577_f2_4 | 1184 | 4589 | 687 | 228 | 273 | 5.80E-24 | [SP:P39147] [OR:BACILLUS SUBTILIS] [GN:COMFC] [DE:COMF OPERON PROTEIN 3] |
| contig507 | 7320327_f2_5 | 1185 | 4590 | 570 | 189 | 553 | 1.20E-53 | [SP:P28368] [OR:BACILLUS SUBTILIS] [GN:YVYD] [DE:HYPOTHETICAL 22.0 KD PROTEIN IN FLIT-SECA INTERGENIC REGION] |
| contig508 | 33883591_c3_16 | 1186 | 4591 | 876 | 292 | 554 | 9.60E-54 | [AC:D90907] [OR:Synechocystis sp.] [PN:amidase] [NT:ORF_ID] |
| contig508 | 34194077_c1_13 | 1187 | 4592 | 327 | 108 | 218 | 3.90E-18 | [AC:U92466] [OR:Bacillus subtilis] [NT:similar to Synechocystis sp. hypothetical protein.] |
| contig508 | 2845916_c1_12 | 1188 | 4593 | 198 | 65 | 145 | 1.20E-09 | [AC:D90870] [OR:Escherichia coli] [PN:DNA LIGASE (EC 6.5.1.2) (POLYDEOXYRIBONUCLEOTIDE] [GN:dnaL] [NT:similar to SwissProt Accession Number P15042] |
| contig508 | 33411062_c3_15 | 1189 | 4594 | 1914 | 637 | 1461 | 7.40E-150 | [AC:D90899] [OR:Synechocystis sp.] [PN:DNA ligase] [GN:lig] [NT:ORF_ID] |
| contig509 | 14930263_f2_3 | 1190 | 4595 | 1719 | 572 | 774 | 4.70E-77 | [AC:Z95210] [OR:Mycobacterium tuberculosis] [PN:unknown] [GN:MTCY21C12.02] [NT:MTCY21C12.02. 797. Function] |
| contig509 | 12610937_f3_8 | 1191 | 4596 | 837 | 278 | 233 | 5.90E-25 | [AC:Z95210] [OR:Mycobacterium tuberculosis] [PN:unknown] [GN:MTCY21C12.02] [NT:MTCY21C12.02. 797. Function] |
| contig509 | 24648427_f3_9 | 1192 | 4597 | 1107 | 368 | 154 | 2.50E-08 | [SP:P11000] [OR:STREPTOCOCCUS MUTANS] [GN:WAPA] [DE:WALL-ASSOCIATED PROTEIN PRECURSOR] |
| contig509 | 20492265_f2_5 | 1193 | 4598 | 489 | 162 | 108 | 1.80E-06 | [AC:A12901] [OR:Staphylococcus aureus] [PN:fibronectin binding protein] |
| contig509 | 24010263_f1_2 | 1194 | 4599 | 324 | 107 | 53 | 0.9 | [AC:Z79697] [OR:Caenorhabditis elegans] [PN:F58H10.1] |
| contig509 | 34430450_f2_6 | 1195 | 4600 | 564 | 187 | 436 | 3.10E-41 | [SP:P32726] [OR:BACILLUS SUBTILIS] [GN:YLXS] [DE:HYPOTHETICAL 17.6 KD PROTEIN IN NUSA 5'REGION (P15A) (ORF1)] |
| contig509 | 33378441_f2_7 | 1196 | 4601 | 921 | 306 | 980 | 6.90E-99 | [SP:P32727] [OR:BACILLUS SUBTILIS] [GN:NUSA] [DE:N UTILIZATION SUBSTANCE PROTEIN A HOMOLOG (NUSA PROTEIN)] |
| contig51 | 1214082_f2_1 | 1197 | 4602 | 750 | 250 | 316 | 1.60E-28 | [AC:294043] [OR:Bacillus subtilis] [PN:hypothetical protein] [GN:yvfL] [NT:similar to MALC_STRPN maltodextrin transport system] |
| contig51 | 33984635_c1_2 | 1198 | 4603 | 207 | 68 | 60 | 0.93 | [AC:Z81011] [OR:Mycobacterium tuberculosis] [PN:unknown] [GN:MTCY02B12.10] [NT:MTCY02B12.10, unknown, len] |
| contig51 | 14647040_c2_13 | 1199 | 4604 | 588 | 196 | 380 | 5.80E-49 | [AC:P42973] [OR:BACILLUS SUBTILIS] [GN:BGLA] [DE:6-PHOSPHO-BETA-GLUCOSIDASE,] |
| contig510 | 31844750_c3_18 | 1200 | 4605 | 1476 | 491 | 1655 | 2.10E-170 | [AC:AE000355] [OR:Escherichia coli] [PN:6-phospho-beta-glucosidase] [GN:ascB] [NT:o474; 98 pct identical to ASCB_ECOLI SW] |
| contig510 | 893816_c1_10 | 1201 | 4606 | 2013 | 670 | 792 | 1.20E-140 | [AC:L49336] [OR:Clostridium longisporum] [PN:PTS-dependent enzyme II] [GN:abgF] |
| contig510 | 11718766_c3_14 | 1202 | 4607 | 477 | 158 | 149 | 6.00E-16 | [SP:P26211] [OR:ERWINIA CHRYSANTHEMI] [GN:ARBG] [DE:BETA-GLUCOSIDE OPERON ANTITERMINATOR] |
| contig511 | 555203_f2_4 | 1203 | 4608 | 600 | 199 | 400 | 2.00E-37 | [OR:Bacillus stearothermophilus] [PN:cellobiose phosphotransferase system celB] |

TABLE 2-continued

| Contig | Orf | NT Seq Id | AA Seq ID | NT Orf Length | AA Orf Length | Score | Probability | Description |
|---|---|---|---|---|---|---|---|---|
| contig511 | 16594193_c1_12 | 1204 | 4609 | 234 | 77 | 62 | 0.76 | [AC:U96076] [OR:*Tetrahymena thermophila*] [PN:gamma-tubulin] [GN:GTU] [NT:GTUp] |
| contig511 | 14553953_f2_5 | 1205 | 4610 | 825 | 274 | 426 | 3.50E-40 | [AC:D88802] [OR:*Bacillus subtilis*] [GN:yodhO] [NT:*B. subtilis* cellobiose phosphotransferase system] |
| contig511 | 23631500_f1_2 | 1206 | 4611 | 543 | 180 | 137 | 1.10E-08 | [SP:P52217] [OR:*CLOSTRIDIUM LITORALE*] [GN:GRDB] [DE:GLYCINE REDUCTASE COMPLEX SELENOPROTEIN B (SELENOPROTEIN PB)] |
| contig511 | 21914192_f1_3 | 1207 | 4612 | 2484 | 827 | 183 | 5.10E-20 | [OR:*Methanococcus jannaschii*] [PN:probable ATP-dependent helicase] |
| contig511 | 34164067_f1_8 | 1208 | 4613 | 1002 | 333 | 471 | 6.00E-45 | [SP:P30363] [OR:*BACILLUS LICHENIFORMIS*[GN:ANSA] [DE:L-ASPARAGINASE, (L-ASPARAGINE AMIDOHYDROLASE)] |
| contig511 | 36226427_c3_21 | 1209 | 4614 | 609 | 202 | 137 | 1.50E-09 | [AC:AE000233] [OR:*Escherichia coli*] [NT:o87; 38 pct identical (4 gaps) to 65 residues from] |
| contig512 | 15897010_c3_20 | 1210 | 4615 | 201 | 66 | 62 | 0.8 | [AC:D38158] [OR:*Equine rotavirus*] [PN:NSP1] [GN:5] |
| contig512 | 3306562_c1_11 | 1211 | 4616 | 429 | 142 | 281 | 8.20E-25 | [AC:Z50854] [OR:*Enterococcus hirae*] [PN:ArpU] [GN:arpU] |
| contig512 | 10742327_c3_9 | 1212 | 4617 | 201 | 66 | 59 | 0.71 | [OR:*Cavia porcellus*] [PN:emopamil-binding protein] |
| contig512 | 16798767_c3_18 | 1213 | 4618 | 393 | 130 | 67 | 0.97 | [SP:Q01545] [OR:*PHARBITIS NIL*] [GN:*SHSP-2*] [DE:*18.8 KD* CLASS II HEAT SHOCK PROTEIN] |
| contig512 | 25417716_c2_14 | 1214 | 4619 | 396 | 131 | 61 | 0.89 | [SP:P08357] [OR:*ORGYIA PSEUDOTSUGATA MULTICAPSID POLYHEDROSIS VIRUS*] [GN:P10] [DE:P10 PROTEIN (FIBROUS BODY PROTEIN)] |
| contig512 | 19539077_c3_17 | 1215 | 4620 | 279 | 92 | 82 | 0.001 | [OR:phage SPP1] [PN:hypothetical 13.6K hypothetical protein 47] |
| contig512 | 32227318_c3_16 | 1216 | 4621 | 231 | 76 | 63 | 0.16 | [AC:L32967] [OR:*Moraxella bovis*] [PN:pilin] [NT:putative] |
| contig512 | 26054692_c1_10 | 1217 | 4622 | 387 | 128 | 431 | 1.00E-40 | [SP:P18007] [OR:*ENTEROCOCCUS FAECALIS*] [DE:HYPOTHETICAL 13 KD PROTEIN IN ASA1 GENE REGION (ORF1)] |
| contig512 | 25547952_c2_13 | 1218 | 4623 | 267 | 88 | 65 | 0.74 | [OR:*Pyrodictium occultum*] [PN:DNA-directed DNA polymerase, II] |
| contig512 | 3945906_c2_12 | 1219 | 4624 | 378 | 125 | 75 | 0.8 | [AC:Y07891] [OR:*Schizosaccharomyces pombe*] [PN:dynamin-related protein] [GN:MSP1] |
| contig513 | 14725937_c3_15 | 1220 | 4625 | 255 | 84 | 63 | 0.25 | [OR:*Saccharomyces cerevisiae*] [PN:partitioning protein] |
| contig513 | 33476700_c1_16 | 1221 | 4626 | 888 | 296 | 643 | 3.60E-63 | [SP:P23524] [OR:*ESCHERICHIA COLI*] [GN:YHAD] [DE:(F408)] |
| contig513 | 4116452_c1_15 | 1222 | 4627 | 1293 | 430 | 831 | 4.30E-83 | [OR:*Haemophilus influenzae*] [PN:hypothetical protein HI0092] |
| contig513 | 35678555_c3_20 | 1223 | 4628 | 654 | 217 | 156 | 1.40E-11 | [SP:P54449] [OR:*BACILLUS SUBTILIS*] [GN:YOED] [DE:HYPOTHETICAL 22.9 KD PROTEIN IN NUCB-AROD INTERGENIC REGION] |
| contig513 | 24409665_f3_9 | 1224 | 4629 | 237 | 78 | 59 | 0.81 | [AC:Z81006] [OR:*Yarrowia lipolytica*] [PN:cell wall protein] |
| contig513 | 4882887_c2_19 | 1225 | 4630 | 1080 | 359 | 627 | 1.80E-61 | [SP:P23861] [OR:*ESCHERICHIA COLI*] [GN:POTD] [DE:SPERMIDINE/PUTRESCINE-BINDING PERIPLASMIC PROTEIN PRECURSOR (SPBP)] |
| contig513 | 6463175_c1_14 | 1226 | 4631 | 693 | 230 | 336 | 1.20E-30 | [SP:P23859] [OR:*ESCHERICHIA COLI*] [GN:POTC] [DE:SPERMIDINE/PUTRESCINE TRANSPORT SYSTEM PERMEASE PROTEIN POTC] |
| contig513 | 12596885_c2_18 | 1227 | 4632 | 291 | 96 | 55 | 0.97 | [AC:U19641] [OR:*Human immunodeficiency virus type 1*] [PN:envelope glycoprotein gp120] [GN:env] [NT:V1-V2 domain] |
| contig513 | 20599732_c2_17 | 1228 | 4633 | 546 | 181 | 318 | 9.80E-29 | [SP:P23860] [OR:*ESCHERICHIA COLI*] [GN:POTB] [DE:SPERMIDINE/PUTRESCINE TRANSPORT SYSTEM PERMEASE PROTEIN POTB] |
| contig514 | 34554686_c3_17 | 1229 | 4634 | 201 | 66 | 143 | 1.40E-09 | [OR:*Enterococcus faecalis*] [PN:regulatory protein prgW] [GN:prgW] |

TABLE 2-continued

| Contig | Orf | NT Seq Id | AA Seq ID | NT Orf Length | AA Orf Length | Score | Probability | Description |
|---|---|---|---|---|---|---|---|---|
| contig514 | 23627202_c2_14 | 1230 | 4635 | 357 | 118 | 85 | 0.031 | [OR:Mesocricctus auratus] [PN:synaptonemal complex protein] [GN:syn1] |
| contig514 | 26754511_c1_11 | 1231 | 4636 | 807 | 268 | 493 | 2.80E-47 | [SP:P37522] [OR:BACILLUS SUBTILIS] [GN:SOJ] [DE:SOJ PROTEIN] |
| contig514 | 23598430_c2_13 | 1232 | 4637 | 195 | 64 | 50 | 0.91 | [SP:P13772] [OR:BACTERIOPHAGE PHI-105] [DE:IMMF CONTROL REGION 10 KD PROTEIN] |
| contig514 | 36135881_c1_10 | 1233 | 4638 | 32 | 106 | 417 | 3.20E-39 | [AC:U38590] [OR:Enterococcus faecalis] [PN:PrgN] [GN:prgN] |
| contig514 | 33452_c1_9 | 1234 | 4639 | 213 | 70 | 116 | 2.50E-07 | [AC:D78257] [OR:Enterococcus faecalis] [PN:ORF6] [GN:orf6] |
| contig514 | 13876042_c3_15 | 1235 | 4640 | 456 | 151 | | | |
| contig514 | 19737517_c1_8 | 1236 | 4641 | 320 | 439 | 663 | 5.40E-87 | [AC:U36837] [OR:Lactococcus lactis] [PN:ORFU] |
| contig515 | 35391575_f2_1 | 1237 | 4642 | 780 | 259 | 985 | 2.00E-99 | [AC:Z75208] [OR:Bacillus subtilis] [PN:phenylalanyl-tRNA synthetase beta subunit] [GN:pheS] [NT:phenylalanyl-tRNA synthetase beta subunit] |
| contig515 | 6650312_f3_3 | 1238 | 4643 | 2427 | 808 | 1854 | 1.70E-191 | [AC:Z75208] [OR:Bacillus subtilis] [PN:phenylalanyl-tRNA synthetase beta subunit] [GN:pheS] [NT:phenylalanyl-tRNA synthetase beta subunit] |
| contig515 | 36225336_c2_11 | 1239 | 4644 | 684 | 227 | 326 | 1.40E-29 | [AC:Z69371] [OR:Bacillus subtilis] [PN:integral membrane protein] [GN:glnP] [NT:putative] |
| contig515 | 34003180_c3_14 | 1240 | 4645 | 759 | 252 | 337 | 9.50E-31 | [AC:Z69371] [OR:Bacillus subtilis] [PN:integral membrane protein] [GN:glnM] [NT:putative] |
| contig515 | 24415932_c3_13 | 1241 | 4646 | 831 | 276 | 589 | 1.90E-57 | [SP:P45678] [OR:CAMPYLOBACTER JEJUNI] [GN:PEB1A] [DE:MAJOR CELL-BINDING FACTOR PRECURSOR (CBF1) (PEB1)] |
| contig515 | 25413584_c2_10 | 1242 | 4647 | 237 | 78 | 270 | 1.20E-23 | [AC:X82596] [OR:Rhizobium leguminosarum] [PN:amino acid ABC type transporter] [GN:aapP] |
| contig516 | 26367027_f1_1 | 1243 | 4648 | 294 | 97 | 195 | 1.10E-15 | [AC:Z96800] [OR:Mycobacterium tuberculosis] [PN:ribosomal protein S14] [GN:rpsN2] [NT:MTCY63.41, rpsN2. 101. Function] |
| contig516 | 12380131_f3_6 | 1244 | 4649 | 210 | 69 | 157 | 1.10E-11 | [SP:P23375] [DE:BACILLUS STEAROTHERMOPHILUS] [GN:RPMG] [DE:50S RIBOSOMAL PROTEIN 1.33] |
| contig516 | 24432961_f3_7 | 1245 | 4650 | 990 | 329 | 294 | 3.40E-26 | [AC:D90917] [OR:Synechocystis sp.] [PN:47 kD protein] [NT:ORF_ID] |
| contig516 | 12614717_f3_8 | 1246 | 4651 | 1548 | 515 | 449 | 7.40E-65 | [AC:Z71552] [OR:Streptococcus pneumoniae] [PN:AdcA] [GN:adcA] [NT:putative lipoprotein] |
| contig516 | 26573911_c1_10 | 1247 | 4652 | 927 | 308 | 249 | 2.00E-21 | [AC:D64002] [OR:Synechocystis sp.] [PN:hypothetical protein] [NT:ORF_ID] |
| contig516 | 4886330_c3_17 | 1248 | 4653 | 189 | 62 | 71 | 0.19 | [SP:P29148] [OR:BACILLUS POLYMXA1] [GN:NPR] [DE:BACILLOLYSIN PRECURSOR, (NEUTRAL PROTEASE)] |
| contig517 | 35817756_c3_25 | 1249 | 4654 | 858 | 285 | 535 | 9.90E-52 | [AC:U60901] [OR:Bacillus subtilis] [NT:orf] |
| contig517 | 3955443_c1_17 | 1250 | 4655 | 279 | 92 | 86 | 0.00038 | [AC:D90901] [OR:Synechocystis sp.] [PN:hypothetical protein] [GN:yef19] [NT:ORF_ID] |
| contig517 | 9807178_c3_24 | 1251 | 4656 | 735 | 244 | 144 | 2.70E-10 | [AC:D90905] [OR:Synechocystis sp.] [PN:hypothetical protein] [NT:ORF_ID] |
| contig517 | 22052053_c2_20 | 1252 | 4657 | 726 | 241 | 333 | 2.50E-30 | [SP:P52056] [OR:SYNECHOCYSTIS SP] [GN:SLR0556] [DE:HYPOTHETICAL 24.0 KD PROTEIN SLR0556] |
| contig517 | 33799062_c1_14 | 1253 | 4658 | 1308 | 435 | 1288 | 8.90E-138 | [AC:U94707] [OR:Enterococcus faecalis] [PN:cell division protein] [GN:ftsZ] |
| contig517 | 7209580_c2_19 | 1254 | 4659 | 198 | 65 | 222 | 4.90E-18 | [AC:U94707] [OR:Enterococcus faecalis] [PN:cell division protein] [GN:ftsZ] |
| contig517 | 993802_c2_18 | 1255 | 4660 | 1356 | 451 | 1888 | 4.20E-195 | [AC:U94707] [OR:Enterococcus faecalis] [PN:cell division protein] [GN:ftsZ] |

TABLE 2-continued

| Contig | Orf | NT Seq Id | AA Seq ID | NT Orf Length | AA Orf Length | Score | Probability | Description |
|---|---|---|---|---|---|---|---|---|
| contig517 | 30270966_c3_22 | 1256 | 4661 | 219 | 72 | 153 | 1.60E-10 | [GN:ftsA] [AC:U94707] [OR:Enterococcus faecalis] [PN:cell division protein] [GN:div1B] |
| contig518 | 24609627_c1_7 | 1257 | 4662 | 954 | 318 | 670 | 4.90E-66 | [AC:JC2266] [OR:Escherichia coli] [PN:ferrochelatase,] [GN:visA (hemH)] |
| contig518 | 16603202_c3_10 | 1258 | 4663 | 249 | 82 | 66 | 0.048 | [AC:U32739] [OR:Haemophilus influenzae] [PN:hypothetical] [GN:HI0576.1] [NT:similar toU18997_268 percent identity] |
| contig518 | 9954413_c1_6 | 1259 | 4664 | 279 | 92 | 272 | 7.40E-24 | [AC:X91789] [OR:Listeria monocytogenes] [PN:CspL protein] [GN:cspL] |
| contig518 | 10800777_c2_8 | 1260 | 4665 | 1020 | 339 | 139 | 5.80E-07 | [SP:P19385] [OR:BACTERIOPHAGE CP-7] [GN:CPL7] [DE:LYSOZYME, (ENDOLYSIN) (MURAMIDASE) (CP-7 LYSIN)] |
| contig519 | 14642886_f1_1 | 1261 | 4666 | 1122 | 373 | 1484 | 2.70E-152 | [SP:P33166] [OR:BACILLUS SUBTILIS] [GN:TUFA] [DE:ELONGATION FACTOR TU (EF-TU)] |
| contig519 | 22147187_f2_4 | 1262 | 4667 | 678 | 225 | 484 | 2.50E-46 | [SP:P39610] [OR:BACILLUS SUBTILIS] [GN:YWDB] [DE:HYPOTHETICAL 29.0 KD PROTEIN IN SACA-UNG INTERGENIC REGION] |
| contig519 | 24416076_f3_6 | 1263 | 4668 | 282 | 93 | 202 | 1.90E-16 | [SP:P39610] [OR:BACILLUS SUBTILIS] [GN:YWDB] [DE:HYPOTHETICAL 29.0 KD PROTEIN IN SACA-UNG INTERGENIC REGION] |
| contig519 | 5977137_f1_2 | 1264 | 4669 | 1326 | 441 | 630 | 8.50E-62 | [SP:P31049] [OR:PSEUDOMONAS PUTIDA] [DE:HYPOTHETICAL 44.7 KD PROTEIN IN LPD-3 5'REGION (ORF3)] |
| contig52 | 25578126_c3_2 | 1265 | 4670 | 888 | 296 | 834 | 2.10E-83 | [SP:P42973] [OR:BACILLUS SUBTILIS] [GN:BGLA] [DE:6-PHOSPHO-BETA-GLUCOSIDASE,] |
| contig520 | 31735778_f1_1 | 1266 | 4671 | 1035 | 344 | 479 | 8.50E-46 | [SP:P45246] [OR:HAEMOPHILUS INFLUENZAE] [GN:HH545] [DE:HYPOTHETICAL SYMPORTER HH545] |
| contig520 | 4790626_c2_7 | 1267 | 4672 | 288 | 95 | 63 | 0.85 | [SP:Q51910] [OR:PROTEUS MIRABILIS] [GN:FLHA] [DE:FLAGELLAR BIOSYNTHESIS PROTEIN FLHA] |
| contig520 | 25959838_f3_5 | 1268 | 4673 | 2565 | 854 | 723 | 1.40E-122 | [AC:D90910] [OR:Synechocystis sp.] [PN:H(+)-transporting ATPase] [GN:pmaI] [NT:ORF_ID] |
| contig520 | 23688175_c3_8 | 1269 | 4674 | 360 | 119 | 57 | 0.43 | [AC:Z75502] [OR:Oryza sativa] [PN:reverse transcriptase] |
| contig521 | 4692843_c1_20 | 1270 | 4675 | 543 | 181 | 342 | 2.80E-31 | [AC:AB001896] [OR:Staphytoccocus aureus] [GN:orf30] |
| contig521 | 4900965_c1_19 | 1271 | 4676 | 750 | 249 | 207 | 5.70E-17 | [AC:AB001896] [OR:Staphytoccocus aureus] [GN:of15] |
| contig521 | 117311_f2_8 | 1272 | 4677 | 2733 | 910 | 2196 | 9.60E-228 | [OR:Clostridum symbiosum] [PN:pyruvate,orthophosphate dikinase,] |
| contig521 | 22539843_c1_16 | 1273 | 4678 | 345 | 114 | 97 | 2.60E-05 | [AC:D50453] [OR:Bacillus subtilis] [GN:yonE] |
| contig521 | 2552157_f2_9 | 1274 | 4679 | 216 | 71 | 53 | 0.997 | [AC:D64004] [OR:Synechocystis sp.] [PN:hypothetical protein] [NT:ORF_ID] |
| contig521 | 32470285_c3_23 | 1275 | 4680 | 1218 | 405 | 98 | 0.043 | [AC:Z81368] [OR:Mycobacterium tuberculosis] [PN:unknown] [GN:MTCY253.04] [NT:MTCY253.04, unknown, len] |
| contig521 | 31642313_c3_22 | 1276 | 4681 | 222 | 73 | 242 | 4.50E-20 | [AC:D88802] [OR:Bacillus subtilis] [GN:ydhP] [NT:C. thermocellum beta-glucosidase; P26208 (985)] |
| contig522 | 22476087_f2_2 | 1277 | 4682 | 687 | 228 | 1141 | 6.00E-116 | [AC:U94707] [OR:Enterococcus faecalis] [PN:unknown] [GN:yHC] |
| contig522 | 33412637_f3_7 | 1278 | 4683 | 435 | 144 | 580 | 1.70E-56 | [AC:U94707] [OR:Enterococcus faecalis] [PN:cell division protein] [GN:yHD] [NT:Allele] |
| contig522 | 23712802_f2_4 | 1279 | 4684 | 2232 | 743 | 3718 | 0 | [AC:U94707] [OR:Enterococcus faecalis] [PN:penicillin-binding protein] [GN:pbpC] |
| contig522 | 34640887_f1_1 | 1280 | 4685 | 984 | 327 | 1358 | 6.10E-139 | [AC:U94707] [OR:Enterococcus faecalis] [PN:phospho N-acetylmuramic acid-pentapeptide] [GN:mraY] |
| contig522 | 26734755_f2_5 | 1281 | 4686 | 468 | 155 | 585 | 5.00E-57 | [AC:U94707] [OR:Enterococcus faecalis] [PN:D-glutamic acid adding |

TABLE 2-continued

| Contig | Orf | NT Seq Id | AA Seq ID | NT Orf Length | AA Orf Length | Score | Probability | Description |
|---|---|---|---|---|---|---|---|---|
| contig523 | 36149007_c3_14 | 1282 | 4687 | 954 | 317 | 426 | 3.50E-40 | enzyme] [GN:murI] [AC:D90910] [OR:Synechocystis sp.] [PN:hypothetical protein) [NT:ORF_ID] |
| contig523 | 29306511_c1_10 | 1283 | 4688 | 1038 | 345 | 166 | 3.10E-10 | [SP:P77728] [OR:ESCHERICHIA COLI] [GN:APBA] [DE:APBA PROTEIN] |
| contig523 | 26836062_f3_7 | 1284 | 4689 | 909 | 302 | 310 | 6.90E-28 | [SP:P39592] [OR:BACILLUS SUBTILIS] [GN:YWB1] [DE:HYPOTHETICAL TRANSCRIPTIONAL REGULATOR IN EPR-GALK INTERGENIC REGION] |
| contig523 | 10942887_c3_12 | 1285 | 4690 | 420 | 139 | 81 | 0.032 | [AC:U56999] [OR:Treponema pallidum] [PN:pfoS/R] [GN:pfoS/R] [NT:potential regulatory molecule; pfoS/R-like] |
| contig523 | 14253127_f3_8 | 1286 | 4691 | 390 | 129 | 50 | 0.91 | [SP:P51772] [OR:BACTERIOPHAGE P2] [GN:X] [DE:TAIL PROTEIN X (GPX)] |
| contig524 | 6385812_f1_1 | 1287 | 4692 | 1155 | 384 | 1196 | 9.00E-122 | [AC:U66480] [OR:Bacillus subtilis] [PN:xylose isomerase] [GN:xylA] |
| contig524 | 4689212_f2_3 | 1288 | 4693 | 1506 | 501 | 1219 | 3.30E-124 | [AC:U66480] [OR:Bacillus subtilis] [PN:xylulose kinase] [GN:xyiB] |
| contig524 | 22460816_f1_2 | 1289 | 4694 | 495 | 165 | 738 | 3.10E-73 | [SP:P19775] [OR:STAPHYLOCOCCUS AUREUS] [GN:TNP] [DE:TRANSPOSASE FOR INSERTION SEQUENCE ELEMENT IS256 IN TRANSPOSON TN4001] |
| contig525 | 1179640_f2_3 | 1290 | 4695 | 195 | 64 | 67 | 0.68 | [OR:Drosophila melanogaster] [PN:hypothetical protein 2] [GN:1-element] |
| contig525 | 36133568_f1_1 | 1291 | 4696 | 864 | 287 | 261 | 1.10E-22 | [SP:P14184] [OR:HAEMOPHILUS INFLUENZAE] [GN:LICD] [DE:LICD PROTEIN] |
| contig525 | 26751302_f1_2 | 1292 | 4697 | 2700 | 899 | 148 | 1.60E-07 | [SP:Q37976] [OR:BACTERIOPHAGE A118] [GN:PLY118] [DE:L-ALANOYL-D-GLUTAMATE PEPTIDASE,] |
| contig525 | 29531386_f3_6 | 1293 | 4698 | 258 | 85 | 68 | 0.33 | [OR:mitochondrion Ascaris suum] [PN:NADH dehydrogenase (ubiquinone), chain 5] [GN:ND5] |
| contig525 | 5995250_c1_7 | 1294 | 4699 | 363 | 120 | 310 | 6.90E-28 | [OR:Streptococcus thermophilus] [PN:transposase] |
| contig526 | 25526675_f1_1 | 1295 | 4700 | 543 | 180 | 258 | 6.80E-22 | [SP:P44788] [OR:HAEMOPHILUS INFLUENZAE] [GN:FMU] [DE:FMU PROTEIN] |
| contig526 | 26564012_f2_3 | 1296 | 4701 | 756 | 251 | 340 | 4.60E-31 | [AC:D90908] [OR:Synechocystis sp.] [PN:hypothetical protein] [NT:ORF_ID] |
| contig526 | 36147816_f1_2 | 1297 | 4702 | 2178 | 725 | 566 | 5.40E-85 | [AC:Z802331] [OR:Mycobacterium tuberculosis] [PN:unknown] [GN:MTCY10H4.14c] [NT:MTCY10H4.14c, protein kinase B, len] |
| contig526 | 7086675_f3_8 | 1298 | 4703 | 900 | 299 | 439 | 1.50E-41 | [SP:P45339] [OR:HAEMOPHILUS INFLUENZAE] [GN:HI1714] [DE:HYPOTHETICAL PROTEIN HI1714] |
| contig526 | 4335938_f2_6 | 1299 | 4704 | 690 | 229 | 610 | 1.10E-59 | [OR:Spinacia oleracea] [PN:ribulose-phosphate 3-epimerase, precursor] |
| contig527 | 2507875_f1_1 | 1300 | 4705 | 528 | 175 | 903 | 1.00E-90 | [SP:P19775] [OR:STAPHYLOCOCCUS AUREUS] [GN:TNP] [DE:TRANSPOSASE FOR INSERTION SEQUENCE ELEMENT IS256 IN TRANSPOSON TN4001] |
| contig527 | 7070428_f3_2 | 1301 | 4706 | 453 | 150 | 521 | 3.00E-50 | [OR:Staphytococcus aureus] [PN:hypothetical protein] |
| contig527 | 6673452_f3_3 | 1302 | 4707 | 1440 | 479 | 2480 | 7.70E-258 | [SP:P14507] [OR:STAPHYLOCOCCUSENTEROCOCCUS FAECALIS] [GN:AACA-APHD] [DE:AMINOGLYCOSIDE PHOSPHOTRANSFERASE, (APH(2"))] |
| contig527 | 884505_c2_6 | 1303 | 4708 | 456 | 151 | 761 | 1.10E-75 | [SP:P19775] [OR:STAPHYLOCOCCUS AUREUS] [GN:TNP] [DE:TRANSPOSASE FOR INSERTION SEQUENCE ELEMENT IS256 IN TRANSPOSON TN4001] |
| contig527 | 641887_c1_4 | 1304 | 4709 | 207 | 68 | 127 | 1.10E-07 | [SP:P19775] [OR:STAPHYLOCOCCUS AUREUS] [GN:TNP] [DE:TRANSPOSASE FOR INSERTION SEQUENCE ELEMENT IS256 IN TRANSPOSON TN4001] |

TABLE 2-continued

| Contig | Orf | NT Seq Id | AA Seq ID | NT Orf Length | AA Orf Length | Score | Probability | Description |
|---|---|---|---|---|---|---|---|---|
| contig528 | 2989063_f_3 | 1305 | 4710 | 1281 | 426 | 1244 | 7.30E-127 | [SP:P22250] [OR:BACILLUS SUBTILIS] [GN:GLTX] [DE:(GLURS)] |
| contig528 | 21539812_f1_1 | 1306 | 4711 | 555 | 184 | 527 | 7.00E-51 | [OR:Bacillus stearothermophilus] [PN:serine O-acetyltransferase,] |
| contig528 | 34195452_f2_5 | 1307 | 4712 | 1437 | 478 | 1395 | 7.30E-143 | [SP:Q06752] [OR:BACILLUS SUBTILIS] [GN:CYSS] [DE:(CYSRS)] |
| contig528 | 19742827_f1_2 | 1308 | 4713 | 399 | 132 | 177 | 8.60E-14 | [AC:D90914] [OR:Synechocystis sp.] [PN:hypothetical protein] [NT:ORF_ID] |
| contig528 | 4789078_f2_6 | 1309 | 4714 | 363 | 121 | 122 | 5.80E-08 | [AC:114580] [OR:Bacillus subtilis] [NT:ORFD1] |
| contig528 | 975092_f3_9 | 1310 | 4715 | 1581 | 526 | 916 | 4.20E-92 | [OR:Streptococcus sobrinus] [PN:phosphotransferase system enzyme II,, sucrose-specific] [GN:scrA] |
| contig529 | 4687511_f1_1 | 1311 | 4716 | 711 | 236 | 124 | 8.40E-06 | [AC:JC6007] [OR:Bacillus thuringiensis] [PN:transcriptional activator plcR] [GN:plcR] |
| contig529 | 24220463_f1_2 | 1312 | 4717 | 966 | 321 | 359 | 4.40E-33 | [SP:P05327] [OR:ANACYSTIS NIDULANS] [GN:PHR] [DE:(PHOTOREACTIVATING ENZYME)] |
| contig529 | 32475255_f2_8 | 1313 | 4718 | 609 | 202 | 563 | 1.10E-54 | [SP:Q04449] [OR:BACILLUS FIRMUS] [GN:PHR] [DE:(PHOTOREACTIVATING ENZYME) (FRAGMENT)] |
| contig529 | 35942_c1_12 | 1314 | 4719 | 618 | 205 | 548 | 4.20E-53 | [SP:P26901] [OR:BACILLUS SUBTILIS] [GN:KATA] [DE:VEGETAITVE CATALASE,] |
| contig529 | 30084542_f1_1 | 1315 | 4720 | 579 | 193 | 403 | 9.60E-38 | [OR:Streptococcus sobrinus] [PN:sucrose-6-phosphate hydrolase ScrB] [GN:scrB] |
| contig530 | 78262_f2_4 | 1316 | 4721 | 900 | 299 | 441 | 9.10E-42 | [AC:Y14027] [OR:Enterococcus faecalis] [PN:HPr kinase] [GN:hprk] |
| contig530 | 33601567_f1_2 | 1317 | 4722 | 870 | 289 | 578 | 2.80E-56 | [SP:P52282] [OR:STAPHYLOCOCCUS AUREUS] [GN:LGT] [DE:PROLIPOPROTEIN DIACYLGLYCERYL TRANSFERASE,] |
| contig530 | 10444528_f1_3 | 1318 | 4723 | 999 | 332 | 773 | 6.00E-77 | [SP:P46919] [OR:BACILLUS SUBTILIS] [GN:GPSA] [DE:DEPENDENT DIHYDROXYACETONE-PHOSPHATE REDUCTASE] |
| contig530 | 36225000_f3_7 | 1319 | 4724 | 885 | 294 | 1106 | 3.10E-112 | [SP:Q54713] [OR:STEPTOCOCCUS PYOGENES] [GN:HASC] [DE:URIDYLYLTRANSFERASE) (URIDINE DIPHOSPHOGLUCOSE PYROPHOSPHORYLASE)] |
| contig530 | 30078906_f2_5 | 1320 | 4725 | 195 | 64 | 55 | 0.52 | [AC:L09723] [OR:Autographa californica nuclear polyhedrosis virus] [PN:ecdysteroid UDP-glucosyltransferase] [GN:egt] |
| contig530 | 31742135_f3_9 | 1321 | 4726 | 753 | 250 | 540 | 2.90E-52 | [SP:P54104] [OR:LACTOBACILLUS DELBRUECKII] [GN:BRNQ] [DE:BRANCHED CHAIN AMINO ACID TRANSPORT SYSTEM CARRIER PROTEIN] |
| contig531 | 42130_c3_23 | 1322 | 4727 | 201 | 66 | 57 | 0.36 | [SP:P54058] [OR:METHANOCOCCUS JANNASCHII] [GN:MJ0707] [DE:50S RIBOSOMAL PROTEIN L40E] |
| contig531 | 4033180_f2_6 | 1323 | 4728 | 651 | 216 | 283 | 8.40E-25 | [AC:U79494] [OR:Bacillus subtilis] [PN:BrnQ] [GN:brnQ] [NT:similar to branched-chain amino acid transporters] |
| contig531 | 13726627_f2_7 | 1324 | 4729 | 348 | 115 | 350 | 4.00E-32 | [AC:D78257] [OR:Enterococcus faecalis] [PN:ORF10] [GN:orf10] |
| contig531 | 3945317_c1_14 | 1325 | 4730 | 759 | 252 | 570 | 1.90E-55 | [AC:D64126] [OR:Bacillus subtilis] [PN:unknown] [GN:orf8] |
| contig531 | 5117168_c1_13 | 1326 | 4731 | 804 | 267 | 226 | 1.70E-28 | [SP:Q50292] [OR:MYCOPLASMA PNEUMONIAE] [DE:HYPOTHETICAL PROTEIN MG181 HOMOLOG (GT9_ORF434)] |
| contig531 | 34172187_c2_19 | 1327 | 4732 | 951 | 316 | 748 | 2.70E-74 | [AC:D64126] [OR:Bacillus subtilis] [PN:unknown] [GN:orf5] |
| contig531 | 23912802_c3_20 | 1328 | 4733 | 819 | 272 | 814 | 2.70E-81 | [AC:D64126] [OR:Bacillus subtilis] [PN:unknown] [GN:orf4] |
| contig531 | 13801564_c2_17 | 1329 | 4734 | 183 | 60 | 62 | 0.76 | [SP:P43294] [OR:ARABIDOPSIS THALIANA] [GN:MHK] [DE:SERINE/THREONINE-PROTEIN KINASE MHK,] |
| contig531 | 26605194_c2_16 | 1330 | 4735 | 468 | 155 | 215 | 2.10E-17 | [SP:P54955] [OR:BACILLUS SUBTILIS] [GN:YXEP] [DE: HYPOTHETICAL 41.6 KD PROTEIN iN IDH-DEOR |

TABLE 2-continued

| Contig | Orf | NT Seq Id | AA Seq ID | NT Orf Length | AA Orf Length | Score | Probability | Description |
|---|---|---|---|---|---|---|---|---|
| contig532 | 24511256_c3_20 | 1331 | 4736 | 780 | 259 | 174 | 1.80E-13 | INTERGENIC REGION] [AC:AE000371] [OR:*Escherichia coli*] [NT: f235; This 235 aa orf is 24 pct identical (6 gaps)] |
| contig532 | 16173392_c1_15 | 1332 | 4737 | 294 | 97 | | | |
| contig532 | 13179817_c2_18 | 1333 | 4738 | 603 | 200 | 102 | 1.00E-05 | [OR:*Methanococcus jannaschii*] [PN:hypothetical protein homolog MJ0990] |
| contig532 | 26696063_c2_17 | 1334 | 4739 | 1038 | 345 | 497 | 1.10E-47 | [SP:P16456] [OR:*ESCHERICHIA COLI*] [GN:SELD] [DE:(SELENIUM DONOR PROTEIN)] |
| contig532 | 36147313_c2_16 | 1335 | 4740 | 765 | 254 | 273 | 8.10E-24 | [OR:*Mycobacterium leprae*] [PN:nitrogen fixation protein homolog nifS] |
| contig532 | 15862500_c2_19 | 1336 | 4741 | 642 | 214 | 76 | 0.99 | [SP:Q58916] [OR:METHANOCOCCUS JANNASCHII] [GN:MJ1521] [DE:HYPOTHETICAL PROTEIN MJ1521] |
| contig533 | 14492943_c1_15 | 1337 | 4742 | 2508 | 835 | 2440 | 1.30E-253 | [AC:U40604] [OR:*Listeria monocytogenes*] [PN:ClpC ATPase] |
| contig533 | 26448905_c2_18 | 1338 | 4743 | 495 | 164 | 369 | 3.90E-34 | [GN:mec] [NT:similar to the mecB gene product from Bacillus] [AC:U40604] [OR:*Listeria monocytogenes*] [NT:ORF1; putative 17 kDa protein] |
| contig533 | 12144380_f2_8 | 1339 | 4744 | 183 | 60 | 51 | 0.85 | [OR:*Saccharomyces cerevisiae*] [PN:probable membrane protein YLR444c] |
| contig533 | 3338142_c3_20 | 1340 | 4745 | 885 | 294 | 426 | 3.50E-40 | [SP:P13254] [OR:*PSEUDOMONAS PUTIDA*] [DE:METHIONE GAMMA-LYASE, (L-METHIONiNASE)] |
| contig534 | 792092_c2_9 | 1341 | 4746 | 1113 | 370 | 766 | 3.30E-76 | [AC:Y11463] [OR:*Streptococcus pneumoniae*] [NT:ORF5] |
| contig534 | 36133417_c1_7 | 1342 | 4747 | 1026 | 341 | 272 | 7.40E-24 | [AC:Y11463] [OR:*Streptococcus pneumoniae*] [GN:epoA] |
| contig534 | 5978416_c3_11 | 1343 | 4748 | 213 | 70 | 57 | 0.53 | [OR:*Saccharomyces cerevisiae*] [PN:hypothetical protein YDR445c] |
| contig534 | 1464525_c3_10 | 1344 | 4749 | 249 | 82 | 103 | 6.00E-06 | [AC:Z47547] [OR:*Miochondrion Chondrus crispus*] [GN:putative orf79.1] [NT:unique orf] |
| contig535 | 9954052_c1_16 | 1345 | 4750 | 213 | 71 | 68 | 0.24 | [OR:African swine fever virus] [NT:Description] |
| contig535 | 24120907_f1_1 | 1346 | 4751 | 249 | 82 | 71 | 0.022 | [OR:*Streptococcus equisimilis*] [PN:hypothetical protein] |
| contig535 | 23953503_f1_8 | 1347 | 4752 | 315 | 104 | 228 | 3.40E-19 | [OR:*Streptococcus equisimilis*] [PN:hypothetical protein] |
| contig535 | 24225302_f1_2 | 1348 | 4753 | 306 | 101 | 75 | 0.026 | [AC:D90910] [OR:*Synechocystis sp.*] [PN:hypothetical protein] [NT:ORF_ID] |
| contig535 | 24495462_f3_9 | 1349 | 4754 | 1317 | 438 | 1339 | 6.30E-137 | [SP:P30053] [OR:*STREPTOCOCCUS EQUISIMILIS*] [GN:HISS] [DE:(HISRS)] |
| contig535 | 24431563_f2_5 | 1350 | 4755 | 1773 | 590 | 1595 | 4.70E-164 | [SP:P21889] [OR:*ESCHERICHIA COLI*] [GN:ASPS] [DE:(ASPRS)] |
| contig535 | 36126328_f2_6 | 1351 | 4756 | 513 | 170 | 254 | 5.90E-22 | [SP:P39610] [OR:*BACILLUS SUBTILIS*] [GN:YWDB] [DE:HYPOTHETICAL 29.0 KD PROTEIN IN SACA-UNG INTERGENIC REGION] |
| contig535 | 34257750_f1_4 | 1352 | 4757 | 408 | 135 | 171 | 3.70E-13 | [OR:*Rhizobium meliloti*] [PN:Thi protein] |
| contig535 | 30526711_f2_7 | 1353 | 4758 | 525 | 174 | 201 | 2.50E-16 | [SP:P20298] [OR:*PYROCOCCUS WOESEI*] [DE:HYPOTHETICAL PROTEIN IN GAPDH 3REGION (ORF X) (FRAGMENT)] |
| contig536 | 3257705_c3_21 | 1354 | 4759 | 1686 | 561 | 459 | 1.10E-43 | [SP:Q02115] [OR:*BACILLUS SUBTILIS*] [GN:LYTR] [DE:MEMBRANE-BOUND PROTEIN LYTR] |
| contig536 | 26770312_f1_4 | 1355 | 4760 | 1317 | 438 | 224 | 8.20E-28 | [AC:U94520] [OR:*Lactococcus lactis*] [PN:abortive phage resistance protein] [GN:abiLi] [NT:AbiLi] |
| contig536 | 36017637_f3_10 | 1356 | 4761 | 672 | 223 | 75 | 0.97 | [AC:U94520] [OR:*Lactococcus lactis*] [PN:abortive phage resistance protein] [GN:abiLii] [NT:AbiLii] |
| contig536 | 14941682_c3_19 | 1357 | 4762 | 744 | 247 | 262 | 8.40E-23 | [AC:U20445] [OR:*Bacillus subtilis*] [PN:BirA protein] [GN:birA] |
| contig537 | 2738817_f3_8 | 1358 | 4763 | 822 | 273 | 771 | 9.70E-77 | [SP:P21873] [OR:*BACILLUS STEAROTHERMOPHILUS*] [GN:PDHA] [DE:PYRUVATE DEHYDROGENASE E1 COMPONENT, ALPHA SUBUNIT,] |

TABLE 2-continued

| Contig | Orf | NT Seq Id | AA Seq ID | NT Orf Length | AA Orf Length | Score | Probability | Description |
|---|---|---|---|---|---|---|---|---|
| contig537 | 6929792_f2_6 | 1359 | 4764 | 999 | 332 | 1281 | 8.80E-131 | [OR:*Bacillus subtilis*] [PN:pyruvate dehydrogenase (lipoamide), E1 beta chain precursor] |
| contig537 | 19665937_f3_10 | 1360 | 4765 | 1623 | 540 | 2292 | 6.50E-238 | [OR:*Enterococcus faecalis*] [PN:dihydrolipoamide S-acetyltransferase.] |
| contig537 | 6697186_f1_4 | 1361 | 4766 | 1185 | 394 | 1206 | 7.80E-123 | [SP:P11959] [OR:*BACILLUS STEAROTHERMOPHILUS*] [GN:PDHD] [DE:COMPLEX, (DIHYDROLIPOAMIDE DEHYDROGENASE] |
| contig537 | 24790701_f2_7 | 1362 | 4767 | 315 | 104 | 289 | 2.70E-25 | [SP:P21880] [OR:*BACILLUS SUBTILIS*] [GN:PDHD] [DE:KD SUBUNIT] |
| contig538 | 30664078_f3_4 | 1363 | 4768 | 1407 | 468 | 88 | 0.0023 | [OR:*Pseudomonas aeruginosa*] [PN:hypothetical protein] |
| contig538 | 2822263_c1_10 | 1364 | 4769 | 234 | 77 | 128 | 1.30E-08 | [SP:P50727] [OR:*BACILLUS SUBTILIS*] [GN:FER] [DE:FERREDOXIN] |
| contig538 | 13683462_f3_5 | 1365 | 4770 | 1047 | 348 | 217 | 4.60E-16 | [SP:P50728] [OR:*BACILLUS SUBTILIS*] [GN:YPBB] [DE:HYPOTHETICAL 40.7 KD PROTEIN IN FER-RECQ INTERGENIC REGION |
| contig538 | 24119737_f2_2 | 1366 | 4771 | 204 | 67 | 50 | 0.91 | [AC:U58365] [OR:*Pseudomonas aeruginosa*] [PN:Np20] [GN:np20] [NT:in vivo inducible; Eur-like protein] |
| contig538 | 14853203_f3_6 | 1367 | 4772 | 990 | 330 | 751 | 1.30E-74 | [SP:P50729] [OR:*BACILLUS SUBTILIS*] [GN:RECQ] [DE:ATP-DEPENDENT DNA HELICASE RECQ.] |
| contig539 | 4172068_c2_16 | 1368 | 4773 | 279 | 93 | 238 | 2.90E-20 | [SP:Q06756] [OR:*BACILLUS SUBTILIS*] [GN:YACN] [DE:HYPOTHETICAL 17.1 KD PROTEIN IN MECB-GLTX INTERGENIC REGION |
| contig539 | 26770302_c2_15 | 1369 | 4774 | 1167 | 388 | 881 | 2.10E-88 | [AC:U40604] [OR:*Listeria monocytogenes*] [NT:ORF:6; putative glutamyl-tRNA-transferase; similar] |
| contig539 | 2244562_c3_19 | 1370 | 4775 | 1230 | 409 | 1247 | 3.50E-127 | [SP:P37572] [OR:*BACILLUS SUBTILIS*] [GN:YACJ] [DE:HYPOTHETICAL 49.5 KD PROTEIN IN MECB-GLTX INTERGENIC REGION (ORFY)] |
| contig539 | 24649093_c3_18 | 1371 | 4776 | 492 | 163 | 165 | 1.60E-12 | [SP:P43792] [OR:*HAEMOPHILUS INFLUENZAE*] [GN:DUT] [DE:(DUTPASE) (DUTP PYROPHOSPHATASE] |
| contig539 | 194453_f1_5 | 1372 | 4777 | 852 | 283 | 720 | 2.50E-71 | [AC:X92418] [OR:*Streptococcus thermophilus*] [PN:gamma-glutamyl kinase] [GN:proB] |
| contig539 | 5273587_f2_8 | 1373 | 4778 | 480 | 160 | 326 | 1.40E-29 | [AC:X92418] [OR:*Streptococcus thermophilus*] [PN:gamma-glutamyl phosphate reductase] [GN:proA] |
| contig539 | 13692582_c1_2 | 1374 | 4779 | 198 | 65 | 58 | 0.96 | [AC:M31179] [OR:*Rattus norvegicus*] [NT:androgen-binding protein precursor] |
| contig54 | 26601682_c2_3 | 1375 | 4780 | 327 | 108 | 138 | 2.60E-09 | [AC:Y14077] [OR:*Bacillus subtilis*] [NT:C-terminal part of hypothetical protein] [GN:yhaA] [NT:Similarity to aminoacylase from] |
| contig540 | 24221876_c3_10 | 1376 | 4781 | 1089 | 362 | 1416 | 4.40E-145 | [SP:P37949] [OR:*BACILLUS SUBTILIS*] [GN:LEPA] [DE:GTP-BINDING PROTEIN LEPA |
| contig540 | 23445942_f2_4 | 1377 | 4782 | 1326 | 441 | 94 | 0.073 | [OR:*Anabaena variabilis*] [PN:hypothetical protein 2 (downstream of hydrogenase cluster)] |
| contig540 | 24234425_f1_3 | 1378 | 4783 | 513 | 170 | 65 | 0.12 | [SP:P12035] [OR:*Homo sapiens*] [NT:keratin type H (AA216-289) (2722 is 2nd base in] |
| contig541 | 33787525_c3_7 | 1379 | 4784 | 336 | 111 | 217 | 4.90E-18 | [SP:P03815] [OR:*Escherichia coli*] [NT:unknown reading frame] |
| contig541 | 1416256_c3_6 | 1380 | 4785 | 267 | 88 | 258 | 3.60E-21 | [SP:P53533] [OR:*SYNECHOCOCCUS SP*] [GN:CLPB] [DE:CLPB PROTEIN] |
| contig541 | 1042337_c2_17 | 1381 | 4786 | 309 | 103 | 344 | 1.70E-31 | [AC:Z50854] [OR:*Enterococcus hirae*] [PN:ArpU] [GN:ArpU] |
| contig541 | 6016576_c1_14 | 1382 | 4787 | 270 | 89 | 58 | 0.64 | [SP:P38175] [OR:*SACCHAROMYCES CEREVISIAE*] [GN:YBL090W] [DE:HYPOTHETICAL 20.4 KD PROTEIN IN |

TABLE 2-continued

| Contig | Orf | NT Seq Id | AA Seq ID | NT Orf Length | AA Orf Length | Score | Probability | Description |
|---|---|---|---|---|---|---|---|---|
| contig541 | 11180187_c3_20 | 1383 | 4788 | 246 | 81 | 63 | 0.45 | MAP2-TEL1 INTERGENIC REGION] [AC:Y09870] [OR:Methanosarcina barkeri] [PN:hypothetical protein] [NT:ORF3] |
| contig541 | 36523450_c1_13 | 1384 | 4789 | 276 | 91 | 113 | 5.20E-07 | [SP:P45911] [OR:BACILLUS SUBTILIS] [GN:YQAN] [DE:HYPOTHETICAL 16.1 KD PROTEIN IN SPOIIIC-CWLA INTERGENIC REGION] |
| contig541 | 34173433_c3_19 | 1385 | 4790 | 231 | 76 | 57 | 0.95 | [AC:U41549] [OR:Caenorhabditis elegans] [GN:F22F1.3] [NT:similar to mouse CREB-binding protein (PIR) |
| contig541 | 25587926_c1_12 | 1386 | 4791 | 861 | 286 | 79 | 0.81 | [OR:Bacillus subtilis] [PN:hypothetical protein 4.60] |
| contig541 | 7244427_c2_16 | 1387 | 4792 | 219 | 72 | 63 | 0.35 | [SP:Q57743] [OR:METHANOCOCCUS JANNASCHII] [GN:MJ0295] [DE:HYPOTHETICAL PROTEIN MJ0295] |
| contig541 | 30269691_c1_11 | 1388 | 4793 | 438 | 145 | 55 | 0.74 | [SP:P32221] [OR:SWINEPOX VIRUS] [GN:C12L] [DE:HYPOTHETICAL PROTEIN C12] |
| contig541 | 24500327_c2_15 | 1389 | 4794 | 219 | 72 | 68 | 0.11 | [SP:P46745] [OR:PROTOTHECA WICKERHAMII] [GN:RPS7] [DE:MITOCHONDRIAL RIBOSOMAL PROTEIN S7] |
| contig541 | 16610327_c1_10 | 1390 | 4795 | 735 | 244 | 89 | 0.25 | [SP:P39922] [OR:HYDRA ATTENUATA] [DE:MYOSIN HEAVY CHAIN, CLONE 203 (FRAGMENT)] |
| contig541 | 33454702_c3_18 | 1391 | 4796 | 318 | 105 | 61 | 0.97 | [SP:Q11048] [OR:MYCOBACTERIUM TUBERCULOSIS] [GN:MTCY50.11] [DE:HYPOTHETICAL 11.6 KD PROTEIN CY50.11 PRECURSOR] |
| contig542 | 36195332_c3_14 | 1392 | 4797 | 639 | 213 | 349 | 5.10E-32 | [AC:D88802] [OR:Bacillus subtilis] [GN:ydiC] [NT: H. influenzae hypothetical protein; P43990 (182)] |
| contig542 | 14241250_f3_7 | 1393 | 4798 | 195 | 64 | 60 | 0.65 | [AC:Z93383] [OR:Caenorhabditis elegans] [PN:F54B8.f] [NT:protein predicted using Genefinder; preliminary] |
| contig542 | 34242327_c2_12 | 1394 | 4799 | 2043 | 680 | 3219 | 0 | [OR:Enterococcus faecalis] [PN:penicillin-binding protein] |
| contig542 | 9765930_f3_8 | 1395 | 4800 | 1332 | 443 | 86 | 0.65 | [AC:X96951] [OR:Lactococcus lactis] [GN:repB] |
| contig542 | 11226567_f1_5 | 1396 | 4801 | 1101 | 367 | 70 | 0.88 | [AC:U02175] [OR:Mycoplasma genitalium] [PN:unknown] |
| contig542 | 24338828_c2_13 | 1397 | 4802 | 687 | 228 | 752 | 1.00E-74 | [SP:P42020] [OR:LACTOCOCCUS LACTIS] [GN:PEPT] [DE:PEPTIDASE T, (AMINOTRIPEPTIDASE) (TRIPEPTIDASE)] |
| contig543 | 26756317_c1_10 | 1398 | 4803 | 651 | 216 | 524 | 1.50E-50 | [SP:P42020] [OR:LACTOCOCCUS LACTIS] [GN:PEPT] [DE:PEPTIDASE T, (AMINOTRIPEPTIDASE) (TRIPEPTIDASE)] |
| contig543 | 20980325_c2_12 | 1399 | 4804 | 1137 | 378 | 811 | 5.60E-81 | [SP:P53434] [OR:LISTERIA MONOCYTOGENES] [DE:HYPOTHETICAL 41.4 KD PROTEIN IN RPOD 3'REGION (ORFA2)] |
| contig543 | 4944752_c1_9 | 1400 | 4805 | 786 | 261 | 499 | 6.50E-48 | [AC:D78182] [OR:Streptococcus mutans] [GN:ORF3] |
| contig543 | 13025003_c3_15 | 1401 | 4806 | 1020 | 339 | 677 | 8.90E-67 | [AC:D90892] [OR:Escherichia coli] [PN:ALANYL-TRNA SYNTHETASE (EC 6.1.1.7)] [GN:alaS] [NT:similar to [SwissProt Accession Number P00957] |
| contig543 | 6347040_c3_14 | 1402 | 4807 | 1530 | 509 | 967 | 1.70E-97 | [SP:P74941] [OR:THERMUS AQUATICUS] [GN:ALAS] [DE:ALANYL-TRNA SYNTHETASE, (ALANINE--TRNA LIGASE) (ALARS)] |
| contig544 | 29347252_c2_10 | 1403 | 4808 | 1479 | 492 | 745 | 5.50E-74 | [AC:U61539] [OR:Bacillus firmus] [PN:Na+/H+ antiporter] [GN:nhaC] [NT U:NahC] |
| contig544 | 29312806_c1_8 | 1404 | 4809 | 1521 | 506 | 316 | 1.90E-26 | [AC:AE000246] [OR:Escherichia coli] [PN:XasA] [GN:xasA] [NT:f511; 100 pct identical to fragment XASA_ECOLI SW] |
| contig544 | 3017176_c3_11 | 1405 | 4810 | 1827 | 608 | 120 | 1.70E-14 | [SP:Q60358] [OR:METHANOCOCCUS JANNASCHII] [GN:MJ0050] [DE:HYPOTHETICAL PROTEIN MJ0050] |
| contig545 | 33625458_f3_8 | 1406 | 4811 | 228 | 75 | 56 | 0.43 | [AC:U23293] [OR:Human immunodeficiency virus type 1] [PN:envelope glycoprotein, v3 region] [GN:env] |

TABLE 2-continued

| Contig | Orf | NT Seq Id | AA Seq ID | NT Orf Length | AA Orf Length | Score | Probability | Description |
|---|---|---|---|---|---|---|---|---|
| contig545 | 24039057_f1_1 | 1407 | 4812 | 342 | 113 | 114 | 4.10E-07 | [AC:AB001488] [OR:*Bacillus subtilis*] [GN:ydtQ] [NT:SIMILAR TO THIOREDOXIN.] |
| contig545 | 11730462_c1_13 | 1408 | 4813 | 981 | 326 | 125 | 9.40E-08 | [SP:P11470] [OR:*BACILLUS SUBTILIS*] [GN:GERE] [DE:GERMINATION PROTEIN GERE] |
| contig545 | 4476713_f3_10 | 1409 | 4814 | 264 | 87 | 155 | 7.90E-11 | [SP:P11725] [OR:*MUS MUSCULUS*] [GN:OTC] [DE:ORNITHINE CARBAMOYLTRANSFERASE PRECURSOR, (OTC)] |
| contig545 | 23884536_f1_3 | 1410 | 4815 | 801 | 266 | 482 | 4.10E-46 | [SP:Q51742] [OR:*PYROCOCCUS FURIOSUS*] [GN:ARGF] [DE:ORNITHINE CARBAMOYLTRANSFERASE, (OTCASE)] |
| contig545 | 22549027_f1_4 | 1411 | 4816 | 1413 | 470 | 188 | 5.70E-12 | [AC:AE000246] [OR:*Escherichia coli*] [PN:Xas A] [GN:xasA] [NT:f511; 100 pct identical to fragment XASA_ECOLI SW] |
| contig545 | 33992187_f2_7 | 1412 | 4817 | 783 | 261 | 53 | 0.999 | [SP:P05990] [OR:*Drosophila melanogaster*] [PN:rudimentary protein fragment] [GN:r] [NT:Description] |
| contig546 | 23689050_c2_16 | 1413 | 4818 | 1125 | 375 | 1278 | 1.80E-130 | [AC:D88802] [OR:*Bacillus subtilis*] [GN:ydhP] [NT:*C. thermocellum* beta-glucosidase; P26208 (985) |
| contig546 | 4977300_c3_18 | 1414 | 4819 | 1293 | 430 | 453 | 2.00E-60 | [SP:P46317] [OR:*BACILLUS SUBTILIS*] [GN:CELB] [DE:PERMEASE HC COMPONENT) (PHOSPHOTRANSFERASE ENZYME H, C COMPONENT)] |
| contig546 | 21657965_c1_12 | 1415 | 4820 | 360 | 119 | 264 | 5.20E-23 | [SP:P46319] [OR:*BACILLUS SUBTILIS*] [GN:CELC] [DE:(EC 2.7.1.69) (EIII-CEL)] |
| contig546 | 16835967_c3_17 | 1416 | 4821 | 333 | 110 | 239 | 2.30E-20 | [OR:*Bacillus stearothermophilus*] [PN:cellobiose phosphotransferase system celA] |
| contig546 | 7148518_c1_11 | 1417 | 4822 | 423 | 140 | 61 | 0.25 | [AC:U37447] [OR:*Homo sapiens*] [PN:endoglin] [GN:ENG] |
| contig546 | 5273380_c2_13 | 1418 | 4823 | 219 | 72 | 51 | 0.9998 | [AC:U40061] [OR:*Caenorhabditis elegans*] [GN:ZK563.4] [NT:coded for by C. elegans cDNA CEESC95F] |
| contig547 | 36017262_f2_4 | 1419 | 4824 | 1332 | 443 | 1686 | 1.10E-173 | [OR:*Bacillus subtilis*] [PN:adenylosuccinate synthase,] [GN:purA] |
| contig547 | 964842_f3_9 | 1420 | 4825 | 885 | 294 | 434 | 5.00E-41 | [AC:Z79580] [OR:*Bacillus subtilis*] [GN:putative ORF] |
| contig547 | 988441_c3_14 | 1421 | 4826 | 219 | 72 | 58 | 0.43 | [AC:U18338] [OR:Variola virus] [PN:B13L] |
| contig547 | 24508337_c2_12 | 1422 | 4827 | 1647 | 548 | 1340 | 4.90E-137 | [AC:AE000184] [OR:*Escherichia coli*] [NT:o530; This 530 aa orf is 33 pct identical (14 gaps)] |
| contig547 | 31416050_f3_10 | 1423 | 4828 | 645 | 214 | 315 | 3.10E-27 | [SP:P23914] [OR:*BACILLUS SUBTILIS*] [GN:LEVR] [DE:TRANSCRIPTIONAL REGULATORY PROTEIN LEVR] |
| contig548 | 32464192_c2_12 | 1424 | 4829 | 1950 | 650 | 131 | 0.00021 | [OR:*Methanococcus jannaschii*] [PN:hypothetical protein MJ1396] |
| contig548 | 16602217_c1_10 | 1425 | 4830 | 792 | 263 | | | |
| contig548 | 34492262_c3_14 | 1426 | 4831 | 759 | 252 | 59 | 0.998 | [AC:AE000211] [OR:*Escherichia coli*] [NT:o85; This 85 aa orf is 47 pct identical (1 gaps) to] |
| contig548 | 16803140_c1_9 | 1427 | 4832 | 390 | 129 | 75 | 0.23 | [OR:*Staphylococcus aureus*] [PN:quinolone resistance protein norA8736] |
| contig548 | 1306675_c3_13 | 1428 | 4833 | 573 | 190 | 331 | 4.10E-30 | [AC:D64000] [OR:Synechocystis sp.] [PN:hypothetical protein] [NT:ORF_ID] |
| contig549 | 3203887_f3_8 | 1429 | 4834 | 612 | 203 | 202 | 2.20E-16 | [AC:AB001488] [OR:*Bacillus subtilis*] [GN:ydtQ] [NT:SIMILAR TO PENTACHLOROPHENOL-INDUCED PERIPLASMIC] |
| contig549 | 24414818_f3_9 | 1430 | 4835 | 615 | 204 | 104 | 0.00069 | [AC:JQ0885] [OR:*Pseudomonas fluorescens*] [PN:esterase A,] [GN:estA] |
| contig549 | 22462812_c1_17 | 1431 | 4836 | 972 | 323 | 425 | 4.50E-40 | [AC:U20808] [OR:*Vigna radiata*] [PN:auxin-induced protein] |
| contig549 | 33210952_c1_16 | 1432 | 4837 | 1284 | 427 | 158 | 1.60E-11 | [AC:D90917] [OR:Synechocystis sp.] [PN:hypothetical protein] [NT:ORF_ID] |
| contig549 | 24804082_c1_15 | 1433 | 4838 | 711 | 236 | 497 | 1.10E-47 | [OR:*Methanococcus jannaschii*] [PN:ABC transporter probable ATP-binding subunit homolog] |
| contig549 | 34194056_c1_14 | 1434 | 4839 | 756 | 251 | | | |

TABLE 2-continued

| Contig | Orf | NT Seq Id | AA Seq ID | NT Orf Length | AA Orf Length | Score | Probability | Description |
|---|---|---|---|---|---|---|---|---|
| contig549 | 275291_c3_20 | 1435 | 4840 | 858 | 285 | 329 | 6.70E-30 | [SP:P54591] [OR:*BACILLUS SUBTILIS*] [GN:YHCG] [DE:INTERGENIC REGION] |
| contig549 | 32609456_c1_13 | 1436 | 4841 | 390 | 129 | 122 | 5.80E-08 | [SP:P54590] [OR:*BACILLUS SUBTILIS*] [GN:YHCF] [DE:HYPOTHETICAL TRANSCRIPTIONAL REGULATOR IN GLPD-CSPB INTERGENIC REGION] |
| contig55 | 11718766_c2_1 | 1437 | 4842 | 786 | 262 | 503 | 2.40E-48 | [AC:U56901] [OR:*Bacillus subtilis*] [PN:Ycr59c/YigZ homolog] [GN:ywhK] |
| contig550 | 22400337_c1_15 | 1438 | 4843 | 1308 | 436 | 538 | 4.80E-52 | [SP:P37555] [OR:*BACILLUS SUBTILIS*] [GN:YABM] [DE:HYPOTHETICAL 57.4 KD PROTEIN IN MFD-DIVIC INTERGENIC REGION] |
| contig550 | 4689027_c1_14 | 1439 | 4844 | 3579 | 1192 | 3077 | 0 | [SP:P37474] [OR:*BACILLUS SUBTILIS*] [GN:MFD] [DE:TRANSCRIPTION-REPAIR COUPLING FACTOR (TRCF)] |
| contig550 | 6837837_c3_17 | 1440 | 4845 | 570 | 189 | 484 | 2.50E-46 | [SP:P37470] [OR:*BACILLUS SUBTILIS*] [GN:SPOVC] [DE:SPORULATION PROTEIN C] |
| contig551 | 29426556_c3_12 | 1441 | 4846 | 1137 | 379 | 229 | 6.20E-17 | [AC:Z83360] [OR:*Bacillus subtilis*] [PN:Unknown, similar to peptidases] [GN:ywhN] |
| contig551 | 15833467_c2_10 | 1442 | 4847 | 1284 | 427 | 198 | 3.10E-13 | [SP:Q04805] [OR:*BACILLUS SUBTILIS*] [GN:YMXG] [DE:HYPOTHETICAL PROCESSING PROTEASE, (ORFP)] |
| contig551 | 33599036_f1_1 | 1443 | 4848 | 546 | 181 | 70 | 0.13 | [AC:Z83337] [OR:*Bacillus subtilis*] [GN:ywpC] [NT:highly similar to *E. coli* large conductance] |
| contig551 | 14722717_c3_11 | 1444 | 4849 | 732 | 243 | 59 | 0.61 | [SP:P43398] [OR:*TRIFOLIUM REPENS*] [GN:MT1A] [DE:METALLOTHIONEIN-LIKE PROTEIN A] |
| contig551 | 16407918_c2_8 | 1445 | 4850 | 465 | 154 | 69 | 0.59 | [SP:P36158] [OR:*SACCHAROMYCES CEREVISIAE*] [GN:YKR078W] [DE:HYPOTHETICAL 68.3 KD PROTEIN IN SIS2-MTD1 INTERGENIC REGION] |
| contig552 | 1057962_c3_14 | 1446 | 4851 | 567 | 189 | | | |
| contig552 | 24611552_c3_13 | 1447 | 4852 | 621 | 206 | 65 | 0.9992 | [SP:P24500] [OR:*BACILLUS SUBTILIS*] [GN:FLGB] [DE:PROTEIN] |
| contig552 | 11063187_f3_5 | 1448 | 4853 | 573 | 190 | 455 | 3.00E-43 | [AC:U09422] [OR:*Enterococcus faecalis*] [NT:ORF17] |
| contig552 | 26756576_c3_12 | 1449 | 4854 | 210 | 69 | 59 | 0.24 | [AC:U59592] [OR:Human immunodeficiency virus type 1] [PN:envelope glycoprotein] [GN:env] [NT:V3 region] |
| contig552 | 12275257_f1_2 | 1450 | 4855 | 1956 | 652 | 2200 | 3.60E-228 | [AC:U09422] [OR:*Enterococcus faecalis*] [NT:ORF16] |
| contig553 | 10055427_c2_24 | 1451 | 4856 | 393 | 130 | 392 | 1.40E-36 | [AC:AB001488] [OR:*Bacillus subtilis*] [GN:ydeE] [NT:FUNCTION UNKNOWN, SIMILAR PRODUCT IN MYCOBACTERIUM] |
| contig553 | 2187892_c2_23 | 1452 | 4857 | 1212 | 403 | 1049 | 3.40E-106 | [AC:Y08941] [OR:*Lactobacillus plantarum*] [PN:alanine racemase] [GN:alr] |
| contig553 | 13066312_f1_1 | 1453 | 4858 | 261 | 86 | | | |
| contig553 | 6531587_c3_25 | 1454 | 4859 | 1260 | 419 | 961 | 7.20E-97 | [AC:AB001488] [OR:*Bacillus subtilis*] [GN:ydbR] [NT:ATP-DEPENDENT RNA HELICASE DEAD HOMOLOG.] |
| contig553 | 6837686_c1_18 | 1455 | 4860 | 420 | 139 | 342 | 4.00E-31 | [AC:AB001488] [OR:*Bacillus subtilis*] [GN:ydbR] [NT:ATP-DEPENDENT RNA HELICASE DEAD HOMOLOG.] |
| contig553 | 21914187_f2_11 | 1456 | 4861 | 219 | 72 | 59 | 0.87 | [AC:Z69837] [OR:*Homo sapiens*] [PN:Huntington's Disease (HD) gene] |
| contig554 | 4882938_c2_21 | 1457 | 4862 | 1452 | 483 | 816 | 1.70E-81 | [AC:AB001488] [OR:*Bacillus subtilis*] [GN:ydbQ] [NT:PROBABLE UDP-N-ACETYLMURAMOYLALANYL-D-GLUTAMYL-2,] |
| contig554 | 5252181_f3_4 | 1458 | 4863 | 1509 | 502 | 134 | 9.20E-06 | [SP:P54309] [OR:*BACTERIOPHAGE SPP1*] [GN:6] [DE:PORTAL PROTEIN (GP6)] |
| contig554 | 5337953_f1_1 | 1459 | 4864 | 1917 | 638 | 87 | 0.72 | [AC:X99719] [OR:*Salmonella enterica*] [PN:Sty SBL1] [GN:hsdS] [NT:putative] |

TABLE 2-continued

| Contig | Orf | NT Seq Id | AA Seq ID | NT Orf Length | AA Orf Length | Score | Probability | Description |
|---|---|---|---|---|---|---|---|---|
| contig554 | 29562578_f1_2 | 1460 | 4865 | 231 | 76 | 62 | 0.13 | [AC:Z68116] [OR:*Caenorhabditis elegans*] [PN:F42F12.5] |
| contig554 | 25680377_f3_5 | 1461 | 4866 | 336 | 111 | 53 | 0.76 | [AC:U01813] [OR:*Mycoplasma genitalium*] [PN:unknown] |
| contig554 | 36454667_f2_3 | 1462 | 4867 | 672 | 223 | 76 | 0.86 | [SP:P09495] [OR:*RATTUS NORVEGICUS*] [DE:TROPOMYOSIN 4, EMBRYONIC FIBROBLAST ISOFORM (TM-4)] |
| contig554 | 19726538_f3_6 | 1463 | 4868 | 501 | 166 | 78 | 0.31 | [AC:D90826] [OR:*Escherichia coli*] [GN:YKL069W, YKL340] [NT:ORF_ID] |
| contig555 | 35407183_f3_9 | 1464 | 4869 | 567 | 188 | 239 | 2.30E-20 | [OR:*Streptococcus parasanguis*] [PN:hypothetical protein 5] |
| contig555 | 31447318_f2_7 | 1465 | 4870 | 852 | 283 | 299 | 1.00E-26 | [SP:P31606] [OR:*CYANOPHORA PARADOXA*] [DE:HYPOTHETICAL 32.8 KD PROTEIN IN YCF23-APCF INTERGENIC REGION (ORF299)] |
| contig555 | 14899187_f1_3 | 1466 | 4871 | 402 | 133 | 391 | 1.80E-36 | [SP:P37551] [OR:*BACILLUS SUBTILIS*] [GN:PURR] [DE:PUR OPERON REPRESSOR] |
| contig555 | 15828436_f1_4 | 1467 | 4872 | 435 | 144 | 419 | 1.90E-39 | [SP:P37551] [OR:*BACILLUS SUBTILIS*] [GN:PURR] [DE:PUR OPERON REPRESSOR] |
| contig555 | 16854750_f1_5 | 1468 | 4873 | 1392 | 463 | 1397 | 4.50E-143 | [OR:*Bacillus subtilis*] [PN:cell division protein tms26] [GN:tms26] |
| contig555 | 34647787_f1_6 | 1469 | 4874 | 2091 | 696 | 339 | 1.30E-50 | [SP:P44764] [OR:*HAEMOPHILUS INFLUENZAE*] [GN:CPDB] [DE:2',3'-CYCLIC-NUCLEOTIDE 2-PHOSPHODIESTERASE PRECURSOR,] |
| contig556 | 553550_c1_14 | 1470 | 4875 | 777 | 259 | 128 | 2.10E-06 | [AC:U28732] [OR:*Caenorhabditis elegans*] [GN:F45E1.3] |
| contig556 | 34182751_c1_13 | 1471 | 4876 | 261 | 86 | 68 | 0.51 | [SP:P12472] [OR:*BOVINE ROTAVIRUS*] [GN:S2] [DE:RNA-BINDING PROTEIN VP2 (MAJOR INTERNAL CORE PROTEIN)] |
| contig556 | 36539067_c1_12 | 1472 | 4877 | 669 | 222 | 120 | 8.10E-06 | [OR:*Methanococcus jannaschii*] [PN:hypothetical protein MJ0570] |
| contig556 | 21484380_f1_1 | 1473 | 4878 | 195 | 64 | | | |
| contig556 | 26040927_c2_16 | 1474 | 4879 | 816 | 271 | 591 | 1.20E-57 | [SP:P42953] [OR:*BACILLUS SUBTILIS*] [GN:TAGG] [DE:TEICHOIC ACID TRANSLOCATION PERMEASE PROTEIN TAGG] |
| contig556 | 3213962_c3_17 | 1475 | 4880 | 1407 | 468 | 762 | 8.80E-76 | [SP:P42954] [OR:*BACILLUS SUBTILIS*] [GN:TAGH] [DE:TEICHOIC ACID TRANSLOCAITON ATP-BINDING PROTEIN TAGH] |
| contig556 | 13136260_c2_15 | 1476 | 4881 | 1020 | 339 | 984 | 2.60E-99 | [SP:P37747] [OR:*ESCHERICHIA COLI*] [GN:YEFE] [DE:HYPOTHETICAL 43.0 KD PROTEIN IN RFC-RFBX INTERGENIC REGION] |
| contig557 | 783385_c2_18 | 1477 | 4882 | 837 | 278 | 100 | 0.0095 | [SP:Q50735] [OR:*MYCOBACTERIUM TUBERCULOSIS*] [GN:MTCY9C4.05C] [DE:HYPOTHETICAL 40.2 KD PROTEIN CY9C4.05C] |
| contig557 | 36069812_c1_14 | 1478 | 4883 | 615 | 204 | 139 | 1.70E-08 | [AC:295120] [OR:*Mycobacterium tuberculosis*] [PN:unknown] [GN:MTCY07D11.18c] [NT:MTCY07D11.18c. Len |
| contig557 | 24648417_c2_16 | 1479 | 4884 | 1068 | 355 | 806 | 1.90E-80 | [AC:U50951] [OR:*Thermoanaerobacterium thermosulfurigenes*] [PN:AbcB] [GN:abcB] [NT:hypothetical ABC exporter component,] |
| contig557 | 33859692_c1_13 | 1480 | 4885 | 918 | 305 | 264 | 3.80E-22 | [SP:P54719] [OR:*BACILLUS SUBTILIS*] [GN:YFIC] [DE:HYPOTHETICAL ABC TRANSPORTER ATP-BINDING PROTEIN 2 IN GLVBC 3'REGION] |
| contig557 | 287_c2_15 | 1481 | 4886 | 1503 | 500 | 872 | 1.90E-87 | [SP:P54718] [OR:*BACILLUS SUBTILIS*] [GN:YFIB] [DE:HYPOTHETICAL ABC TRANSPORTER ATP-BINDING PROTEIN 1 IN GLVBC 3'REGION] |
| contig558 | 34270312_f1_1 | 1482 | 4887 | 381 | 126 | 59 | 0.24 | [SP:P11807] [OR:*Human adenovirus* type 41] [NT:100K DNA binging protein (AA 1-33) (1 is 1st base] |
| contig558 | 3995338_f2_4 | 1483 | 4888 | 1470 | 489 | 76 | 0.99991 | [AC:M94417] [OR:*Plasmodium vivax*] [PN:merozoite surface antigen 1] [GN:MSA1] [NT:putative] |

TABLE 2-continued

| Contig | Orf | NT Seq Id | AA Seq ID | NT Orf Length | AA Orf Length | Score | Probability | Description |
|---|---|---|---|---|---|---|---|---|
| contig558 | 4066025_f2_5 | 1484 | 4889 | 540 | 179 | 244 | 6.80E-21 | [AC:U93874] [OR:*Bacillus subtilis*] [PN:RNA polymerase sigma factor SigV] [GN:sigV] [NT:similar to B. *subtilis* SigX protein] |
| contig558 | 34273462_f2_6 | 1485 | 4890 | 891 | 296 | 444 | 4.40E-42 | [AC:U93874] [OR:*Bacillus subtilis*] [PN:putative anti-Sig V factor] [GN:yrhM] |
| contig558 | 6501912_f3_8 | 1486 | 4891 | 777 | 258 | 216 | 1.60E-17 | [SP:P44514] [OR:*HAEMOPHILUS INFLUENZAE*] [GN:DAPE] [DE:*SUCCINYL-DIAMINOPIMELATE DESUCCINYLASE*, (SDAP)] |
| contig558 | 4945375_f2_7 | 1487 | 4892 | 531 | 176 | 100 | 0.0042 | [OR:*Methanococcus jannaschii*] [PN:succinyl-diaminopimelate desuccinylase,] |
| contig558 | 34085937_c2_11 | 1488 | 4893 | 765 | 254 | 52 | 0.9995 | [AC:L04520] [OR:*Bacillus subtilis*] [PN:valyl tRNA synthetase] [GN:valS] |
| contig558 | 6336567_f2_2 | 1489 | 4894 | 618 | 205 | 118 | 0.00029 | [AC:M69183] [OR:*Plasmodium falciparum*] [PN:mature-parasite-infected erythrocyte surface] [GN:MESA] |
| contig559 | 4585937_c1_15 | 1490 | 4895 | 309 | 102 | 344 | 1.70E-31 | [AC:Z93936] [OR:*Bacillus subtilis*] [PN:unknown] [GN:yugP] |
| contig559 | 5116592_f1_1 | 1491 | 4896 | 711 | 236 | 53 | 0.69 | [OR:*mitochondrion Allomyces macrogynus*] [PN:NADH dehydrogenase (ubiquinone), chain 4L] [GN:nad4L] |
| contig559 | 394638_c3_23 | 1492 | 4897 | 219 | 72 | | | |
| contig559 | 26287812_f3_5 | 1493 | 4898 | 363 | 120 | 57 | 0.68 | [OR:*Sus scrofa domestica*] [PN:apolipoprotein A-1] |
| contig559 | 6537937_c3_21 | 1494 | 4899 | 861 | 286 | 288 | 1.50E-25 | [AC:D90786] [OR:*Escherichia coli*] [GN:ydcE] [NT:ORF_ID] |
| contig559 | 3994143_c1_12 | 1495 | 4900 | 861 | 286 | 297 | 1.60E-26 | [SP:Q54087] [OR:*STREPTOCOCCUS EQUISIMILIS*] [GN:LRP] [DE:LEUCINE RICH PROTEIN] |
| contig559 | 24414825_f3_7 | 1496 | 4901 | 522 | 173 | 455 | 3.00E-43 | [SP:P21335] [OR:*BACILLUS SUBTILIS*] [GN:YAAJ] [DE:HYPOTHETICAL 17.8 KD PROTEIN IN SERS-DNAH INTERGENIC REGION] |
| contig559 | 4964387_c1_10 | 1497 | 4902 | 396 | 131 | 54 | 0.71 | [OR:*chloroplast Oryza sativa*] [PN:hypothetical 7K protein (trnH-trnV intergenic region)] |
| contig559 | 31366637_c3_19 | 1498 | 4903 | 1038 | 345 | 959 | 1.20E-96 | [AC:U51911] [OR:*Bacillus subtilis*] [PN:aminopeptidase] [GN:ampS] [NT:similar to ampS gene with GenBank Accession Number] |
| contig559 | 12527328_f1_1 | 1499 | 4904 | 351 | 116 | 70 | 0.83 | [SP:P47574] [OR:*MYCOPLASMA GENITALIUM*] [GN:MG332] [DE:HYPOTHETICAL PROTEIN MG332] |
| contig56 | 23712837_f2_3 | 1500 | 4905 | 531 | 176 | 88 | 0.0015 | [OR:*Haemophilus influenzae*] [PN:hemin permease (hemU) homolog] |
| contig56 | 5894426_c1_4 | 1501 | 4906 | 240 | 79 | 71 | 0.18 | [AC:Z48239] [OR:*Saccharomyces cerevisiae*] [GN:orf4] |
| contig560 | 24611401_f3_3 | 1502 | 4907 | 204 | 67 | 231 | 1.70E-18 | [SP:P37710] [OR:*ENTEROCOCCUS FAECALIS*] [DE:AUTOLYSIN, (N-ACETYLMURAMOYL-L-ALANINE AMIDASE)] |
| contig560 | 22683186_f1_1 | 1503 | 4908 | 2475 | 824 | 3136 | 0 | [SP:P36430] [OR:*BACILLUS SUBTILIS*] [GN:LEUS] [DE:LEUCYL-TRNA SYNTHETASE, (LEUCINE-TRNA LIGASE) (LEURS)] |
| contig560 | 23540711_c3_15 | 1504 | 4909 | 294 | 97 | 58 | 0.95 | [AC:U79526] [OR:*Homo sapiens*] [PN:orphan G-protein coupled receptor Dez isoform a] [NT:alternatively spliced] |
| contig560 | 24417337_c3_14 | 1505 | 4910 | 456 | 151 | 223 | 1.10E-18 | [SP:P37501] [OR:*BACILLUS SUBTILIS*] [GN:YBC] [DE:HYPOTHETICAL 17.6 KD PROTEIN IN COTF-TETB INTERGENIC REGION] |
| contig560 | 11753328_f3_5 | 1506 | 4911 | 330 | 109 | 238 | 2.90E-20 | [SP:P30860] [OR:*ESCHERICHIA COLI*] [GN:ARTJ] [DE:ARGININE-BINDING PERIPLASMIC PROTEIN 2 PRECURSOR] |
| contig560 | 30096075_c2_8 | 1507 | 4912 | 582 | 193 | | | |
| contig560 | 2736275_f2_2 | 1508 | 4913 | 216 | 72 | 52 | 0.78 | [AC:U15693] [OR:*Bos taurus*] [PN:nonmuscle myosin heavy chain B] [NT:near the actin binding region; is neuronal cell] |
| contig561 | 16845000_f1_1 | 1509 | 4914 | 1071 | 356 | 510 | 4.40E-49 | [OR:*Clostridium perfringens*] [PN:regulatory protein pfoR] |

TABLE 2-continued

| Contig | Orf | NT Seq Id | AA Seq ID | NT Orf Length | AA Orf Length | Score | Probability | Description |
|---|---|---|---|---|---|---|---|---|
| contig561 | 26757062_f2_4 | 1510 | 4915 | 729 | 242 | 78 | 0.29 | [SP:P42630] [OR:ESCHERICHIA COLI] [GN:YHAQ] [DE:DEAMINASE (SDH)] |
| contig561 | 2119011_f1_2 | 1511 | 4916 | 897 | 298 | 587 | 3.10E-57 | [AC:X98238] [OR:Lactobacillus sake] [NT:orf6] |
| contig561 | 4877187_f3_8 | 1512 | 4917 | 1323 | 440 | 1343 | 2.40E-137 | [SP:P37464] [OR:BACILLUS SUBTILIS] [GN:SERS] [DE:SERYL-TRNA SYNTHETASE, (SERINE-TRNA LIGASE) (SERRS)] |
| contig561 | 15628_c2_14 | 1513 | 4918 | 978 | 325 | 189 | 1.80E-13 | [AC:X94355] [OR:Cowpox virus] [GN:M5L] |
| contig561 | 9789134_c1_10 | 1514 | 4919 | 492 | 163 | 225 | 7.00E-19 | [SP:P17893] [OR:BACILLUS SUBTILIS] [GN:AHRC] [DE:ARGININE HYDROXIMATE RESISTANCE PROTEIN] |
| contig562 | 36503966_f2_4 | 1515 | 4920 | 708 | 235 | | | |
| contig562 | 34257817_f3_8 | 1516 | 4921 | 237 | 78 | | | [SP:Q60263] [OR:METHANOCOCCUS JANNASCHII] [GN:MJECL16] [DE:HYPOTHETICAL PROTEIN MJECL16] |
| contig562 | 19532203_f3_9 | 1517 | 4922 | 1065 | 354 | 55 | 0.99 | [SP:P16085] [OR:BUTYRIVIBRIO FIBRISOLVENS] [DE:(FRAGMENT)] |
| contig562 | 3230217_c2_13 | 1518 | 4923 | 1197 | 398 | 80 | 0.011 | [SP:P28805] [OR:SPINACIA OLERACEA] [GN:RPL33] [DE:CHLOROPLAST 50S RIBOSOMAL PROTEIN L33 (FRAGMENT)] |
| contig562 | 25547012_c3_16 | 1519 | 4924 | 1605 | 534 | 65 | 0.49 | [OR:Streptococcus thermophilus] [PN:hypothetical protein 1] |
| contig562 | 36601427_c3_15 | 1520 | 4925 | 594 | 197 | 78 | 0.11 | [AC:Z79580] [OR:Bacillus subtilis] [GN:putative orf] |
| contig562 | 33363827_f2_7 | 1521 | 4926 | 618 | 206 | 338 | 7.50E-31 | [SP:P29112] [OR:AGROBACTERIUM TUMEFACIENS] [DE:24.9 KD PROTEIN IN PICA LOCUS (ORF1)] |
| contig562 | 24225280_c2_18 | 1522 | 4927 | 549 | 182 | 98 | 0.0021 | [AC:U25549] [OR:Mycoplasma genitalium] [PN:PAR-E] [GN:parE] [NT:Description] |
| contig563 | 5119575_c1_16 | 1523 | 4928 | 705 | 234 | 88 | 0.071 | [SP:P39345] [OR:ESCHERICHIA COLI] [GN:YJGU] [DE:(EC 1.-.-.-) (F254)] |
| contig563 | 34195282_c3_23 | 1524 | 4929 | 810 | 269 | 601 | 1.00E-58 | [AC:AE000368] [OR:Escherichia coli] [PN:5-keto-4-deoxyuronate isomerase] [GN:kdul] [NT:t278; 74 pct identical to KDUI_ERWCH SW] |
| contig563 | 6640963_c3_22 | 1525 | 4930 | 852 | 283 | 805 | 2.40E-80 | [AC:U70664] [OR:Haloferax alicantei] [PN:2-keto-3-deoxygluconate kinase] [NT:similar to fructokinases] |
| contig563 | 22833916_c3_21 | 1526 | 4931 | 1098 | 365 | 319 | 2.10E-39 | [AC:U70664] [OR:Haloferax alicantei] [PN:2-dehydro-3-deoxyphosphogluconate aldolase] [NT:KDPG aldolase] |
| contig563 | 1189718_c2_17 | 1527 | 4932 | 657 | 218 | 319 | 7.70E-29 | [AC:D90826] [OR:Escherichia coli] [PN:Pectin degradation repressor protein KdgR.] [NT:ORF_ID] |
| contig563 | 3256251_f2_8 | 1528 | 4933 | 294 | 97 | | | [SP:P27407] [OR:FELINE CALICIVIRUS] [DE:PROTEIN)] |
| contig563 | 30109500_c1_14 | 1529 | 4934 | 780 | 259 | 300 | 7.90E-27 | [SP:P50838] [OR:BACILLUS SUBTILIS] [GN:YPSA] [DE:HYPOTHETICAL 21.1 KD PROTEIN IN COTD-KDUD INTERGENIC REGION] |
| contig563 | 25986083_c3_19 | 1530 | 4935 | 198 | 65 | 73 | 0.36 | [SP:P39792] [OR:BACILLUS SUBTILIS] [GN:YPPB] [DE:HYPOTHETICAL 24.0 KD PROTEIN IN PONA-COTI) INTERGENIC REGION (ORF1)] |
| contig564 | 4900251_c3_21 | 1531 | 4936 | 546 | 181 | 402 | 1.20E-37 | |
| contig564 | 21675333_f1_1 | 1532 | 4937 | 498 | 165 | 501 | 4.00E-48 | |
| contig564 | 25788001_c3_20 | 1533 | 4938 | 198 | 65 | 59 | 0.24 | [AC:S49803] [OR:Escherichia coli] [GN:pre] [NT:Description] |
| contig564 | 34187517_f3_7 | 1534 | 4939 | 2370 | 789 | 1655 | 2.10E-170 | [AC:Z49094] [OR:Streptococcus pneumoniae] [PN:penicillin-binding protein 1a] [GN:pbp1a] |
| contig564 | 26601558_c3_18 | 1535 | 4940 | 384 | 127 | | | |
| contig564 | 34156963_c3_17 | 1536 | 4941 | 1674 | 557 | 1918 | 2.80E-198 | [SP:P13242] [OR:BACILLUS SUBTILIS] [GN:CTRA] [DE:CTP SYNTHASE, (UTP-AMMONIA LIGASE) (CTP SYNTHETASE)] |
| contig564 | 20754837_c2_12 | 1537 | 4942 | 633 | 210 | 249 | 2.00E-21 | [SP:P12464] [OR:BACILLUS SUBTILIS] [GN:RPOE] [DE:DNA- |

TABLE 2-continued

| Contig | Orf | NT Seq Id | AA Seq ID | NT Orf Length | AA Orf Length | Score | Probability | Description |
|---|---|---|---|---|---|---|---|---|
| contig565 | 25586088_c2_14 | 1538 | 4943 | 597 | 199 | 858 | 5.90E-86 | DIRECTED RNA POLYMERASE DELTA SUBUNIT;] [AC:U35659] [OR:Streptoococcus bovis] [PN:malic enzyme] [NT:Malic enzyme ((S)-malate] |
| contig565 | 3960877_c1_12 | 1539 | 4944 | 1350 | 449 | 1961 | 7.70E-203 | [AC:U35658] [OR:Streptococcus bovis] [PN:L-malate permease] [GN:malP] [NT:probable organic acid transport protein; A deduced] |
| contig565 | 6439807_f2_8 | 1540 | 4945 | 243 | 80 | 61 | 0.19 | [AC:AF002732] [OR:Cydia pomonella granulovirus] [NT:ORF35Rb] |
| contig565 | 3457042_f1_2 | 1541 | 4946 | 1569 | 522 | 679 | 5.50E-67 | [AC:Z93937] [OR:Bacillus subtilis] [PN:unknown] [GN:yufL] |
| contig565 | 13706327_f2_9 | 1542 | 4947 | 720 | 239 | 337 | 9.50E-31 | [AC:Z93937] [OR:Bacillus subtilis] [PN:unknown] [GN:yufM] |
| contig565 | 6835927_f1_3 | 1543 | 4948 | 1509 | 502 | 2211 | 2.50E-229 | [SP:P37062] [OR:ENTEROCOCCUS FAECALIS] [GN:NPR] [DE:NADH PEROXIDASE, (NPXASE)] |
| contig565 | 36605317_c3_15 | 1544 | 4949 | 384 | 127 | 249 | 2.00E-21 | [SP:Q02115] [OR:BACILLUS SUBTILIS] [GN:LYTR] [DE:MEMBRANE-BOUND PROTEIN LYTR] |
| contig566 | 23547832_c2_15 | 1545 | 4950 | 960 | 320 | 600 | 2.20E-71 | [SP:P08188] [OR:ESCHERICHIA COLI] [GN:MANZ] [DE:(EII-M-MAN)] |
| contig566 | 23697811_c1_14 | 1546 | 4951 | 849 | 282 | 388 | 3.80E-36 | [SP:P08187] [OR:ESCHERICHIA COLI] [GN:MANY] [DE:(EII-P-MAN)] |
| contig566 | 5084757_c3_18 | 1547 | 4952 | 1158 | 385 | 618 | 1.60E-60 | [SP:P08186] [OR:ESCHERICHIA COLI] [GN:MANX] [DE:(EC 2.7.1.69) (EIII-MAN)] |
| contig566 | 97268_c3_17 | 1548 | 4953 | 594 | 197 | 498 | 8.30E-48 | [SP:P08186] [OR:ESCHERICHIA COLI] [GN:MANX] [DE:(EC 2.7.1.69) (EIII-MAN)] |
| contig566 | 6289133_c3_16 | 1549 | 4954 | 1755 | 584 | 719 | 3.20E-71 | [SP:P23914] [OR:BACILLUS SUBTILIS] [GN:LEVR] [DE:TRANSCRIPTIONAL REGULATORY PROTEIN LEVR] |
| contig567 | 12195152_f2_5 | 1550 | 4955 | 225 | 74 | 123 | 4.50E-08 | [SP:P44305] [OR:HAEMOPHILUS INFLUENZAE] [GN:RIMI] [DE:ACETYLATING ENZYME FOR N-TERMINAL OF RIBOSOMAL PROTEIN S18] |
| contig567 | 34113442_f1_1 | 1551 | 4956 | 1101 | 366 | 1028 | 5.70E-104 | [AC:D88802] [OR:Bacillus subtilis] [GN:ydiE] [NT:P. haemolytica o-sialoglycoprotein endopeptidase,] |
| contig567 | 16127267_f2_6 | 1552 | 4957 | 1797 | 598 | 928 | 2.20E-93 | [SP:Q05506] [OR:SACCHAROMYCES CEREVISIAE] [GN:YDR341C] [DE:TRNA LIGASE] (ARGRS)] |
| contig567 | 7313552_f1_2 | 1553 | 4958 | 564 | 187 | 69 | 0.52 | [AC:X85328] [OR:Pisum sativum] [PN:invertase] [GN:bfruct1] [NT:beta-fructofuranosidase] |
| contig567 | 13672262_c2_12 | 1554 | 4959 | 348 | 115 | 80 | 0.0016 | [AC:L06240] [OR:Pseudomonas aeruginosa] [NT:putative DNA binding transcription repressor;] |
| contig567 | 22829687_f1_4 | 1555 | 4960 | 372 | 123 | 52 | 0.91 | [AC:X91907] [OR:Borrelia burgdorferi] [PN:histidine kinase] [GN:cheA] |
| contig567 | 34179702_f2_8 | 1556 | 4961 | 1521 | 507 | 118 | 0.00038 | [SP:P25241] [OR:BACILLUS CEREUS] [GN:RES] [DE:(FRAGMENT)] |
| contig568 | 24397307_f1_1 | 1557 | 4962 | 264 | 87 | 64 | 0.94 | [AC:U41553] [OR:Caenorhabditis elegans] [GN:ZK1193.2] [NT:coded for by C. elegans cDNA yk8a6.3; coded for by] |
| contig568 | 25431567_f2_3 | 1558 | 4963 | 1074 | 357 | 786 | 2.50E-78 | [SP:P44785] [OR:HAEMOPHILUS INFLUENZAE] [GN:ABC] [DE:ATP-BINDING PROTEIN ABC] |
| contig568 | 25667812_f2_4 | 1559 | 4964 | 699 | 232 | 257 | 2.90E-22 | [SP:P31547] [OR:ESCHERICHIA COLI] [GN:YAEE] [DE:HYPOTHETICAL 23.3 KD PROTEIN IN RCSF-ABC INTERGENIC REGION] |
| contig568 | 24415936_f3_6 | 1560 | 4965 | 837 | 278 | 479 | 8.50E-46 | [SP:P28635] [OR:ESCHERICHIA COLI] [GN:YAEC] [DE:PRECURSOR] |
| contig568 | 26756562_f2_5 | 1561 | 4966 | 786 | 262 | 395 | 6.80E-37 | [AC:D09017] [OR:Synechocystis sp.] [PN:N-acyl-L-amino acid amidohydrolase] [GN:ama] [NT:ORF_ID] |
| contig569 | 15828390_f3_2 | 1562 | 4967 | 726 | 241 | 907 | 3.80E-91 | [SP:P19064] [OR:BACILLUS CEREUS] [GN:GLNA] |

TABLE 2-continued

| Contig | Orf | NT Seq Id | AA Seq ID | NT Orf Length | AA Orf Length | Score | Probability | Description |
|---|---|---|---|---|---|---|---|---|
| contig569 | 30117807_f2_1 | 1563 | 4968 | 3744 | 1247 | 3281 | 0 | [DE:GLUTAMINE SYNTHETASE, (GLUTAMATE-AMMONIA LIGASE)] [SP:P03833] [OR:KLEBSIELLA PNEUMONIAE] [GN:NIFJ] [DE:PYRUVATE-FLAVODOXIN OXIDOREDUCTASE,] |
| contig57 | 34253175_c2_2 | 1564 | 4969 | 480 | 159 | 301 | 6.20E-27 | [AC:D78193] [OR:Bacillus subtilis] [GN:yydJ] |
| contig570 | 3947755_f2_5 | 1565 | 4970 | 1281 | 426 | 71 | 0.997 | [SP:Q10619] [OR:MYCOBACTERIUM TUBERCULOSIS] [GN:MTCY373.23] [DE:HYPOTHETICAL 16.9 KD PROTEIN CY373.23] |
| contig570 | 33246087_f3_10 | 1566 | 4971 | 3702 | 1233 | 98 | 0.031 | [AC:X53324] [OR:group G streptococcus] [PN:Protein G'] [GN:Protein G gene] [NT:Truncated gene; Start codon TTG not ATG] |
| contig570 | 5085937_f2_7 | 1567 | 4972 | 339 | 112 | 60 | 0.91 | [AC:U58779] [OR:Human immunodeficiency virus type 1] [PN:envelope glycoprotein V3 region] [GN:env] |
| contig570 | 34093830_f1_3 | 1568 | 4973 | 729 | 242 | 79 | 0.84 | [OR:Trypanosoma cruzi] [PN:85K surface antigen] |
| contig570 | 4977250_f1_4 | 1569 | 4974 | 540 | 179 | | | |
| contig570 | 24785450_f2_8 | 1570 | 4975 | 252 | 83 | 71 | 0.044 | [OR:Bacteroides vulgatus] [PN:mobilization protein] |
| contig570 | 398577_f2_9 | 1571 | 4976 | 447 | 149 | | | |
| contig571 | 1426842_c3_26 | 1572 | 4977 | 234 | 77 | 50 | 0.997 | [AC:Z92775] [OR:Caenorhabditis elegans] [PN:C06H5.f] [NT:protein predicted using Genefinder; preliminary] |
| contig571 | 26439717_c1_19 | 1573 | 4978 | 864 | 287 | 493 | 2.80E-47 | [SP:P43909] [OR:LACTOCOCCUS LACTIS] [DE:PREPHENATE DEHYDRATASE, (PDT)] |
| contig571 | 26597816_c3_24 | 1574 | 4979 | 513 | 170 | 293 | 4.40E-26 | [SP:P43906] [OR:LACTOCOCCUS LACTIS] [GN:AROK] [DE:SHIKIMAT KINASE, (SK)] |
| contig571 | 34416088_c2_22 | 1575 | 4980 | 1293 | 430 | 1298 | 1.40E-132 | [SP:P43905] [OR:LACTOCOCCUS LACTIS] [GN:AROA] [DE:ENOLPYRUVYLSHIKIMATE-3-PHOSPHATE SYNTHASE) (EPSP SYNTHASE)] |
| contig571 | 6839090_c2_21 | 1576 | 4981 | 1128 | 375 | 806 | 1.90E-80 | [SP:P20692] [OR:BACILLUS SUBTILIS] [GN:TYRA] [DE:PREPHENATE DEHYDROGENASE, (PDH)] |
| contig571 | 26761057_c2_20 | 1577 | 4982 | 1188 | 395 | 944 | 4.50E-95 | [SP:P31104] [OR:BACILLUS SUBTILIS] [GN:AROF] [DE:PHOSPHOLYASE] |
| contig571 | 23703462_c1_18 | 1578 | 4983 | 1107 | 368 | 566 | 5.10E-55 | [AC:D90911] [OR:Synechocystis sp.] [PN:3-dehydroquinate synthase] [GN:aroB] [NT:ORF_ID] |
| contig571 | 25673902_c3_23 | 1579 | 4984 | 531 | 176 | 468 | 1.20E-44 | [AC:D90901] [OR:Synechocystis sp.] [PN:carboxysome formation protein] [GN:ccmA] [NT:ORF_ID] |
| contig572 | 6929707_c3_19 | 1580 | 4985 | 1092 | 364 | 826 | 1.40E-82 | [AC:D90905] [OR:Synechocystis sp.] [PN:beta ketoacyl-acyl carrier protein synthase] [GN:fabF] [NT:ORF_ID] |
| contig572 | 994062_c3_18 | 1581 | 4986 | 741 | 246 | 610 | 1.10E-59 | [AC:U59433] [OR:Bacillus subtilis] [PN:3-ketoacyl-acyl carrier protein reductase] [GN:fabG] [NT:also called 3-oxoacyl-acyl carrier protein] |
| contig572 | 34414061_c3_17 | 1582 | 4987 | 948 | 315 | 605 | 3.80E-59 | [SP:P25715] [OR:ESCHERICHIA COLI] [GN:FABD] [DE:MALONYL COA-ACYL CARRIER PROTEIN TRANSACYLASE, (MCT)] |
| contig572 | 13917202_c1_14 | 1583 | 4988 | 999 | 332 | 354 | 7.00E-39 | [AC:Z82098] [OR:Mycobacterium tuberculosis] [PN:unknown] [GN:MTCY03C7.02c] [NT:MTCY03C7.02c, 355 aa, unknown, some similarity] |
| contig572 | 5353562_c2_16 | 1584 | 4989 | 981 | 326 | 538 | 4.80E-52 | [SP:P43711] [OR:HAEMOPHILUS INFLUENZAE] [GN:FABH] [DE:KETOACYL-ACP SYNTHASE III] (KAS III) |
| contig572 | 4007952_c2_15 | 1585 | 4990 | 441 | 146 | 87 | 0.0003 | [SP:P54182] [OR:BACILLUS SUBTILIS] [GN:YPOP] [DE:HYPOTHETICAL TRANSCRIPTIONAL REGULATOR IN ILVA 3'REGION] |
| contig573 | 35834377_f3_6 | 1586 | 4991 | 474 | 157 | 161 | 6.50E-12 | [AC:U28163] [OR:Lactobacillus curvatus] [PN:EIIC-man] [GN:manC] |

TABLE 2-continued

| Contig | Orf | NT Seq Id | AA Seq ID | NT Orf Length | AA Orf Length | Score | Probability | Description |
|---|---|---|---|---|---|---|---|---|
| contig573 | 24334652_f1_1 | 1587 | 4992 | 891 | 296 | 426 | 3.50E-40 | [NT:mannose phosphotransferase system enzyme EII] [SP:P08188] [OR:ESCHERICHIA COLI] [GN:MANZ] [DE:(EII-M-MAN)] |
| contig573 | 3914713_f1_2 | 1588 | 4993 | 489 | 162 | 275 | 3.50E-24 | [SP:P37081] [OR:KLEBSIELLA PNEUMONIAE] [GN:SORB] [DE:(EC 2.7.1.69) (EII-B-SOR)] |
| contig573 | 35352137_f2_5 | 1589 | 4994 | 873 | 290 | 291 | 7.10E-26 | [AC:AB002150] [OR:Bacillus subtilis] [PN:YbbH] |
| contig573 | 14542287_f1_3 | 1590 | 4995 | 942 | 313 | 722 | 1.50E-71 | [SP:P76535] [OR:ESCHERICHIA COLI] [GN:YFEU] [DE:HYPOTHETICAL 31.2 KD PROTEIN IN CYSP-AMIA INTERGENIC REGION] |
| contig573 | 21681557_f1_4 | 1591 | 4996 | 432 | 143 | 111 | 5.80E-06 | [SP:Q06317] [OR:NOCARDIA LACTAMDURANS] [GN:PBP] [DE:PENILLIN-BINDING PROTEIN 4 (PBP-4)] |
| contig574 | 6257628_f1_1 | 1592 | 4997 | 2394 | 797 | 68 | 0.35 | [SP:P17820] [OR:Bacillus subtilis] [NT:partiat dnaK gene (AA 572)] |
| contig574 | 4335207_c2_20 | 1593 | 4998 | 216 | 71 | 68 | 0.35 | [AC:AE000181] [OR:Escherichia coli] [NT:f318; This 318 aa orf is 28 pct identical (12 gaps)] |
| contig574 | 10407557_c1_14 | 1594 | 4999 | 2481 | 826 | 119 | 0.00034 | |
| contig574 | 16610881_f2_7 | 1595 | 5000 | 273 | 90 | 68 | 0.076 | [AC:D86440] [OR:Gluconobacter suboxydans] [PN:the smallest subunit precursor of membrane-bound] |
| contig574 | 16448438_c2_18 | 1596 | 5001 | 480 | 159 | 297 | 1.60E-26 | [SP:P37552] [OR:BACILLUS SUBTILIS] [GN:YABJ] [DE:HYPOTHETICAL 13.7 KD PROTEIN IN PURR-SPOVG INTERGENIC REGION (ORF2)] |
| contig574 | 26437805_c2_17 | 1597 | 5002 | 1254 | 417 | 924 | 6.00E-93 | [AC:U65013] [OR:Vibrio furnissii] [PN:beta-cystathionase] [GN:malY] |
| contig574 | 6775313_c3_21 | 1598 | 5003 | 1572 | 523 | 1383 | 1.40E-141 | [AC:U65013] [OR:Vibrio furnissii] [PN:PTS permease for glucose] [GN:malX] |
| contig574 | 4334838_f1_1 | 1599 | 5004 | 732 | 243 | 415 | 5.20E-39 | [SP:P44785] [OR:HAEMOPHILUS INFLUENZAE] [GN:ABC] [DE:ATP-BINDING PROTEIN ABC] |
| contig574 | 16133443_f3_8 | 1600 | 5005 | 720 | 239 | 216 | 6.30E-18 | [SP:P31547] [OR:ESCHERICHIA COLI] [GN:YAEE] [DE:HYPOTHETICAL 23.3 KD PROTEIN IN RCSF-ABC INTERGENIC REGION] |
| contig575 | 34176713_f3_9 | 1601 | 5006 | 837 | 278 | 342 | 2.80E-31 | [SP:P28635] [OR:ESCHERICHIA COLI] [GN:YAEC] [DE:PRECURSOR] |
| contig575 | 15914813_f1_2 | 1602 | 5007 | 1785 | 594 | 1470 | 8.30E-151 | [AC:142945] [OR:Staphylococcus aureus] [GN:lytS] |
| contig575 | 832702_f2_5 | 1603 | 5008 | 729 | 242 | 477 | 1.40E-45 | [AC:Z75208] [OR:Bacillus subtilis] [DN:autolysin response regulator] [GN:lytT] [NT:homology to lytR of Staphytococcus aureus;] |
| contig575 | 24038437_f3_10 | 1604 | 5009 | 447 | 148 | 321 | 4.70E-29 | [AC:Z75208] [OR:Bacillus subtilis] [PN:hypothetical protein] [GN:ysbA] [NT:homology to ywbH of Bacillus subtilis; putative] |
| contig576 | 651055_c3_22 | 1605 | 5010 | 1035 | 345 | 571 | 1.50E-55 | [AC:D64005] [OR:Synechocystis sp.] [PN:ABC transporter] [NT:ORF_ID] |
| contig576 | 6832753_c1_15 | 1606 | 5011 | 693 | 230 | 361 | 2.50E-37 | [AC:D64005] [OR:Synechocystis sp.] [PN:ABC transporter] [NT:ORF_ID] |
| contig576 | 36210962_c2_21 | 1607 | 5012 | 819 | 272 | 422 | 9.40E-40 | [AC:D64005] [OR:Synechocystis sp.] [PN:molybdate-binding periplasmic protein] [GN:modA] [NT:ORF_ID] |
| contig576 | 14650282_c2_20 | 1608 | 5013 | 975 | 324 | 172 | 3.10E-10 | [OR:Methanococcus jannaschii] [PN:molybdenum cofactor biosynthesis protein moeA homolog] |
| contig576 | 23446957_c2_19 | 1609 | 5014 | 486 | 161 | 342 | 2.30E-30 | [SP:Q03555] [OR:RATTUS NORVEGICUS] [DE:GEPHYRIN (PUTAITVE GLYCINE RECEPTOR-TUBULIN LINKER PROTEIN)] |
| contig576 | 85312_c1_14 | 1610 | 5015 | 498 | 165 | 96 | 0.0031 | [SP:P43976] [OR:HAEMOPHILUS INFLUENZAE] [GN:HI0278] [DE:HYPOTHETICAL PROTEIN HI0278] |

TABLE 2-continued

| Contig | Orf | NT Seq Id | AA Seq ID | NT Orf Length | AA Orf Length | Score | Probability | Description |
|---|---|---|---|---|---|---|---|---|
| contig576 | 3400401_c2_18 | 1611 | 5016 | 666 | 221 | 285 | 3.10E-25 | [AC:X99625] [OR:Synechococcus sp.] [GN:moaA] |
| contig576 | 4567203_c1_13 | 1612 | 5017 | 357 | 118 | 205 | 2.60E-16 | [OR:Arthrobacter nicotinovorans] [PN:molybdopterin cofactor synthesis protein] |
| contig576 | 4899143_c2_17 | 1613 | 5018 | 519 | 172 | 383 | 1.30E-35 | [AC:D88802] [OR:Bacillus subtilis] [GN:ydiG] [NT:E. coli moaC protein; P30747 (368)] |
| contig577 | 6754541_c1_16 | 1614 | 5019 | 324 | 108 | 133 | 3.90E-09 | [AC:D84214] [OR:Bacillus subtilis] [PN:YbbG] |
| contig577 | 24886263_c2_19 | 1615 | 5020 | 393 | 130 | 140 | 2.00E-09 | [SP:P37767] [OR:ESCHERICHIA COLI] [GN:YFHH] [DE:HYPOTHETICAL 30.7 KD PROTEIN IN PURL-DPJ INTERGENIC REGION (O306)] |
| contig577 | 890705_f1_1 | 1616 | 5021 | 963 | 320 | 662 | 3.50E-65 | [SP:P54448] [OR:BACILLUS SUBTILIS] [GN:YQEC] [DE:HYPOTHETICAL 32.8 KD PROTEIN IN NUCB-AROD INTERGENIC REGION] |
| contig577 | 6642842_f1_2 | 1617 | 5022 | 1014 | 337 | 435 | 3.90E-41 | [OR:Methanococcus jannaschii] [PN:phosphoglycerate dehydrogenase.] |
| contig577 | 34649050_f3_9 | 1618 | 5023 | 1125 | 374 | 448 | 1.60E-42 | [AC:AE000165] [OR:Escherichia coli] [PN:hypothetical protein in cstA 3'region] [GN:ybdH] [NT:f362; 100 pct identical to 81 aa fragment] |
| contig577 | 14742938_f3_10 | 1619 | 5024 | 813 | 270 | 83 | 0.3 | [SP:P37082] [OR:KLEBSIELLA PNEUMONIAE] [GN:SORA] [DE:PERMEASE IIC COMPONENT) (PHOSPHOTRANSFERASE ENZYME II, C COMPONENT] |
| contig577 | 5116660_f3_11 | 1620 | 5025 | 720 | 239 | 289 | 1.20E-25 | [SP:P08188] [OR:ESCHERICHIA COLI] [GN:MANZ] [DE:(EII-M-MAN)] |
| contig577 | 26757937_f3_12 | 1621 | 5026 | 528 | 175 | 184 | 1.60E-14 | [SP:P37081] [OR:KLEBSIELLA PNEUMONIAE] [GN:SORB] [DE:(EC 2.7.1.69) (EIII-B-SOR)] |
| contig578 | 23086077_c2_19 | 1622 | 5027 | 921 | 307 | 1014 | 1.70E-102 | [SP:P39148] [OR:BACILLUS SUBTILIS] [GN:GLYA][DE:(SHMT)] |
| contig578 | 1042337_c2_18 | 1623 | 5028 | 1038 | 345 | 729 | 2.70E-72 | [SP:P39153] [OR:BACILLUS SUBTILIS] [GN:YWLC] [DE:HYPOTHETICAL 37.0 KD PROTEIN IN SPOIIR-GLYC INTERGENIC REGION] |
| contig578 | 24070962_c1_16 | 1624 | 5029 | 846 | 281 | 422 | 9.40E-40 | [SP:P45873] [OR:BACILLUS SUBTILIS] [GN:YWKE] [DE:POSSIBLE PROTOPORPHYRINOGEN OXIDASE,] |
| contig578 | 34038442_c3_20 | 1625 | 5030 | 1095 | 364 | 1150 | 6.70E-117 | [SP:P45872] [OR:BACILLUS SUBTILIS] [GN:PREA] [DE:PEPTIDE CHAIN RELEASE FACTOR 1 (RF-1)] |
| contig578 | 6148466_c1_15 | 1626 | 5031 | 603 | 200 | 716 | 6.60E-71 | [SP:P47848] [OR:STREPTOCOCCUS GORDONII CHALLIS] [GN:TDK] [DE:THYMIDINE KINASE.] |
| contig578 | 20812650_f2_8 | 1627 | 5032 | 264 | 87 | 70 | 0.24 | [AC:U39996] [OR:Caenorhabditis elegans] [GN:C56E6.5] [NT:coded for by C. elegans cDNA cm12b5; similar in |
| contig578 | 16221002_c2_17 | 1628 | 5033 | 597 | 198 | 433 | 6.40E-41 | [SP:Q02469] [OR:SHEWANELLA PUTREFACIENS] [DE:(FLAVOCYTOCHROME C)] |
| contig578 | 7319561_c1_14 | 1629 | 5034 | 201 | 66 | 75 | 0.059 | [SP:P32614] [OR:SACCHAROMYCES CEREVISIAE] [GN:YEL047C] [DE:HYPOTHETICAL 50.8 KD PROTEIN IN PAU2-GLY1 INTERGENIC REGION] |
| contig579 | 162787_c3_20 | 1630 | 5035 | 1920 | 640 | 2122 | 6.70E-220 | [SP:P05653] [OR:BACILLUS SUBTILIS] [GN:GYRA] [DE:DNA GYRASE SUBUNIT A.] |
| contig579 | 164657_c2_15 | 1631 | 5036 | 2001 | 666 | 2442 | 8.20E-254 | [AC:Z67740] [OR:Streptococcus pneumoniae] [PN:DNA gyrase] [GN:gyrB] [NT:GyrB subunit] |
| contig579 | 14666562_c3_18 | 1632 | 5037 | 1149 | 382 | 1081 | 1.40E-109 | [SP:P05651] [OR:BACILLUS SUBTILIS] [GN:RECF] [DE:RECF PROTEIN] |
| contig579 | 36539062_c2_14 | 1633 | 5038 | 264 | 87 | 178 | 6.70E-14 | [SP:P05650] [OR:BACILLUS SUBTILIS] [GN:YAAA] [DE:HYPOTHETICAL 7.9 KD PROTEIN IN DNAN-RECF INTERGENIC REGION] |

TABLE 2-continued

| Contig | Orf | NT Seq Id | AA Seq ID | NT Orf Length | AA Orf Length | Score | Probability | Description |
|---|---|---|---|---|---|---|---|---|
| contig579 | 4484413_c3_17 | 1634 | 5039 | 546 | 181 | 477 | 1.40E-45 | [AC:AF000658] [OR:*Streptococcus pneumoniae*] [PN:beta subunit of DNA polymerase III] [GN:spdnaN] [NT:SPDnaN] |
| contig579 | 16605338_c3_16 | 1635 | 5040 | 426 | 141 | 95 | 6.90E-09 | [SP:P05649] [OR:*BACILLUS SUBTILIS*] [GN:DNAN] [DE:DNA POLYMERASE III, BETA CHAIN,] |
| contig58 | 24094094_c1_4 | 1636 | 5041 | 1134 | 378 | 239 | 2.50E-18 | [AC:D14399] [OR:*Bacillus subtilis*] [PN:hypothetical protein] [GN:B65G] |
| contig580 | 130326_c2_27 | 1637 | 5042 | 435 | 145 | 57 | 0.9999 | [SP:P17310] [OR:*BACTERIOPHAGE T4*] [GN:Y13A) [DE:HYPOTHETICAL 11.1 KD PROTEIN IN GP30-RIII INTERGENIC REGION (ORF D)] |
| contig580 | 24415943_c1_23 | 1638 | 5043 | 1470 | 489 | 123 | 0.00013 | [SP:P37966] [OR:*BACILLUS SUBTILIS*] [GN:LPLA] [DE:LIPOPROTEIN LPLA PRECURSOR] |
| contig580 | 6756718_c2_26 | 1639 | 5044 | 672 | 223 | 505 | 1.50E-48 | [AC:Z77855] [OR:*Anaerocellum thermophilum*] [PN:sugar-binding transport protein] [NT:putative] |
| contig580 | 16148406_f1_1 | 1640 | 5045 | 240 | 79 | 61 | 0.65 | [SP:Q10280] [OR:*SCHIZOSACCHAROMYCES POMBE*] [GN:GAF1] [DE:GAF1 PROTEIN (GAF-1)] |
| contig580 | 33602157_c1_22 | 1641 | 5046 | 384 | 127 | 113 | 2.30E-06 | [AC:Z77855] [OR:*Anaerocellum thermophilum*] [PN:sugar-binding transport protein] [NT:putative] |
| contig580 | 24332887_c2_25 | 1642 | 5047 | 1038 | 345 | 638 | 1.20E-62 | [AC:Z77855] [OR:*Anaerocellum thermophilum*] [PN:sugar-binding transport protein] [NT:putative] |
| contig580 | 25890687_f3_17 | 1643 | 5048 | 183 | 60 | 50 | 0.999 | [AC:U40799] [OR:*Caenorhabditis elegans*] [GN:F42C5.1] |
| contig580 | 20093801_f2_9 | 1644 | 5049 | 195 | 64 | 71 | 0.71 | [SP:P00792] [OR:*BOS TAURUS*] [DE:PEPSINOGEN A, (FRAGMENT)] |
| contig580 | 24102191_c1_20 | 1645 | 5050 | 1113 | 370 | | | |
| contig580 | 23345166_c2_24 | 1646 | 5051 | 300 | 99 | 57 | 0.36 | [OR:*Homo sapiens*] [PN:hypothetical protein B, 6.8K] |
| contig580 | 13675751_c3_28 | 1647 | 5052 | 2610 | 869 | 100 | 0.11 | [OR:*Campylobacter jejuni*] [PN:flagellin protein] [GN:fla] |
| contig581 | 86038_f2_3 | 1648 | 5053 | 759 | 252 | 706 | 7.50E-70 | [SP:P25813] [OR:*BACILLUS SUBTILIS*] [GN:GIDB] [DE:GLUCOSE INHIBITED DIVISION PROTEIN B] |
| contig581 | 14352263_f2_4 | 1649 | 5054 | 777 | 258 | 868 | 5.10E-87 | [SP:P37522] [OR:*BACILLUS SUBTILIS*] [GN:SOJ] [DE:SOJ PROTEIN] |
| contig581 | 30667811_f3_8 | 1650 | 5055 | 909 | 302 | 687 | 7.80E-68 | [SP:P26497] [OR:*BACILLUS SUBTILIS*] [GN:SPO0J] [DE:STAGE 0 SPORULATION PROTEIN J] |
| contig581 | 167555_f1_9 | 1651 | 5056 | 231 | 76 | 206 | 7.20E-17 | [AC:AF000658] [OR:*Streptococcus pneumoniae*] [NT:ORFX] |
| contig581 | 24495382_f2_6 | 1652 | 5057 | 1140 | 379 | 1330 | 5.70E-136 | [SP:P37518] [OR:*BACILLUS SUBTILIS*] [GN:YYAF] [DE:REGION] |
| contig582 | 817033_f2_7 | 1653 | 5058 | 762 | 253 | | | |
| contig582 | 23636377_f2_3 | 1654 | 5059 | 855 | 284 | 712 | 1.70E-70 | [AC:D78016] [OR:*Enterococcus faecalis*] [PN:REPA] [GN:repA] [NT:ORF2; pheromone related transfer gene] |
| contig582 | 162551_c1_11 | 1655 | 5060 | 189 | 62 | 60 | 0.19 | [SP:P42544] [OR:*BACTERIOPHAGE L2*] [DE:HYPOTHETICAL 9.3 KD PROTEIN (ORF9)] |
| contig582 | 24094175_f1_1 | 1656 | 5061 | 1674 | 557 | 2644 | 3.20E-275 | [OR:*Enterococcus faecalis*] [PN:probable pheromone binding proteinpheromone responsive gene Z protein] [GN:prgZ] |
| contig582 | 35345942_f2_4 | 1657 | 5062 | 1173 | 390 | 1669 | 6.70E-172 | [OR:*Enterococcus faecalis*] [PN:prgY protein] [GN:prgY] |
| contig582 | 4969677_c1_8 | 1658 | 5063 | 888 | 295 | 1425 | 4.80E-146 | [OR:*Enterococcus faecalis*] [PN:probable pheromone-responsive regulatory protein X] |
| contig583 | 14885936_f1_1 | 1659 | 5064 | 861 | 286 | 184 | 4.70E-13 | [AC:D50453] [OR:*Bacillus subtilis*] [PN:homologue of als operon regulatory protein AlsR] [GN:yclA] |
| contig583 | 34193950_f1_2 | 1660 | 5065 | 1410 | 469 | 510 | 4.40E-49 | [OR:*Streptomyces pristinaespiralis*] [PN:integral membrane protein] |
| contig583 | 4882827_f3_5 | 1661 | 5066 | 2061 | 686 | 1310 | 7.40E-134 | [AC:D86418] [OR:*Bacillus subtilis*] [PN:YfnI] |
| contig583 | 6304572_c1_6 | 1662 | 5067 | 636 | 211 | 1004 | 2.00E-101 | [SP:P19775] [OR:*STAPHYLOCOCCUS AUREUS*] [GN:TNP] |

TABLE 2-continued

| Contig | Orf | NT Seq Id | AA Seq ID | NT Orf Length | AA Orf Length | Score | Probability | Description |
|---|---|---|---|---|---|---|---|---|
| contig584 | 6347033_f3_10 | 1663 | 5068 | 1005 | 334 | 1015 | 1.40E-102 | [DE:TRANSPOSASE FOR INSERTION SEQUENCE ELEMENT IS256 IN TRANSPOSON TN4001] |
| contig584 | 35962937_f1_1 | 1664 | 5069 | 984 | 327 | 352 | 2.40E-32 | [AC:Z93939] [OR:*Bacillus subtilis*] [PN:thioredoxine reductase] [GN:yumC] [NT:putative] SP:P45637] [OR:*CORYNEBACTERIUM GLUTAMICUM*] [DE:HYPOTHETICAL 33.0 KD PROTEIN IN PROB-PROA INTERGENIC REGION] |
| contig584 | 10003756_c3_22 | 1665 | 5070 | 1593 | 530 | 333 | 1.80E-42 | [SP:P44764] [OR:*HALMOPHILUS INFLUENZAE*] [GN:CPDB] [DE:2',3'-CYCLIC-NUCLEOTIDE 2'-PHOSPHODIESTERASE PRECURSOR,] |
| contig584 | 15657837_c2_19 | 1666 | 5071 | 1344 | 447 | 212 | 1.20E-14 | [AC:U43526] [OR:*Streptococcus pneumoniae*] [NT:ORF-2] |
| contig584 | 36573442_c3_21 | 1667 | 5072 | 2112 | 703 | 434 | 1.60E-40 | [OR:*Clostridium perfringens*] [PN:probable membrane transport protein] |
| contig584 | 33208176_c2_17 | 1668 | 5073 | 468 | 155 | 177 | 1.90E-13 | [AC:X89810] [OR:*Bacillus subtilis*] [PN:putative integral membrane protein] [GN:araP] |
| contig585 | 22836077_c2_28 | 1669 | 5074 | 453 | 150 | 53 | 0.69 | [OR:*Rattus norvegicus*] [PN:fetal troponin T 3] |
| contig585 | 26386092_c1_23 | 1670 | 5075 | 795 | 264 | 54 | 0.69 | |
| contig585 | 7164812_c1_22 | 1671 | 5076 | 372 | 123 | 64 | 0.998 | [AC:Z46792] [OR:*Caenorhabditis elegans*] [PN:C52A11.2] [NT:weak similarity with globin V] |
| contig585 | 960932_c1_21 | 1672 | 5077 | 384 | 127 | 54 | 0.69 | [OR:*Streptococcus pyogenes*] [PN:M-like protein precursor] |
| contig585 | 34160912_c2_27 | 1673 | 5078 | 357 | 118 | 88 | 0.0011 | [AC:L76202] [OR:*Schistosoma haematobium*] [PN:tropomyosin] [NT:*Schistosoma haematobium* tropomyosin'] |
| contig585 | 14880436_c1_20 | 1674 | 5079 | 1926 | 641 | 356 | 6.50E-30 | [SP:P46321] [OR:*BACILLUS SUBTILIS*] [GN:CELR] [DE:PUTAITVE CEL OPERON REGULATOR] |
| contig585 | 13709691_c2_26 | 1675 | 5080 | 252 | 83 | 51 | 0.85 | [OR:*Mus musculus*] [PN:T-cell receptor alpha chain (AK8)] |
| contig585 | 251567_c3_29 | 1676 | 5081 | 1056 | 351 | 263 | 6.60E-23 | [SP:P49305] [OR:*RHIZOBIUM MELILOTI*] [DE:HYPOTHETICAL 36.4 KD PROTEIN IN MOCC-MOCA INTERGENIC REGION (ORF:334)] |
| contig585 | 34178452_c1_19 | 1677 | 5082 | 342 | 113 | 300 | 7.90E-27 | [AC:AB001488] [OR:*Bacillus subtilis*] [GN:ydcE] [NT:FUNCTION UNKNOWN, SIMILAR PRODUCT IN MYCOBACTERIUM] |
| contig585 | 22923568_c1_18 | 1678 | 5083 | 627 | 208 | 397 | 4.20E-37 | [SP:P31218] [OR:*ESCHERICHIA COLI*] [GN:UDK] [DE:*RIBONUCLEOSIDE KINASE*] |
| contig586 | 10053418_f2_1 | 1679 | 5084 | 705 | 234 | 467 | 1.60E-44 | [SP:P42953] [OR:*BACILLUS SUBTILIS*] [GN:TAGG] [DE:TEICHOIC ACID TRANSLOCATION PERMEASE PROTEIN TAGG] |
| contig586 | 25979818_f2_2 | 1680 | 5085 | 1230 | 409 | 598 | 2.10E-58 | [SP:Q07698] [OR:*AEROMONAS SALMONICIDA*] [GN:ABCA] [DE:ABCA PROEIN] |
| contig586 | 35350277_f3_4 | 1681 | 5086 | 3171 | 1056 | 579 | 1.50E-67 | [SP:P55465] [OR:*RHIZOBIUM SP*] [GN:Y4GI] [DE:HYPOTHETICAL 102.8 KD PROTEIN Y4GI] |
| contig586 | 24709530_f2_3 | 1682 | 5087 | 1602 | 534 | 755 | 4.80E-75 | [SP:P55465] [OR:*RHIZOBIUM SP*] [GN:Y4GI] [DE:HYPOTHETICAL 102.8 KD PROTEIN Y4GI] |
| contig587 | 16603135_c1_19 | 1683 | 5088 | 219 | 72 | 63 | 0.55 | [AC:U04954] [OR:*Actinobacillus pleuropneumoniae*] [GN:afuA] |
| contig587 | 10975702_f3_10 | 1684 | 5089 | 561 | 186 | 79 | 0.95 | [SP:P54888] [OR:*ARABIDOPSIS THALIANA*] [GN:P5CSB] [DE:DEHYDROGENASE)] |
| contig587 | 4964693_f1_1 | 1685 | 5090 | 246 | 81 | 70 | 0.078 | [SP:P44207] [OR:*HAEMOPHILUS INFLUENZAE*] [GN:HI1476] DE:HYPOTHETICAL PROTEIN HI1476] |
| contig587 | 19554712_f3_11 | 1686 | 5091 | 195 | 64 | 76 | 0.019 | [AC:U72279] [OR:*Mitochondrion Apis mellifera*] [PN:NADH dehydrogenase subunit 2] [GN:ND2] |
| contig587 | 34182827_f3_12 | 1687 | 5092 | 216 | 71 | 55 | 0.997 | [SP:P45468] [OR:*ESCHERICHIA COLI*] [GN:YRAQ] |

TABLE 2-continued

| Contig | Orf | NT Seq Id | AA Seq ID | NT Orf Length | AA Orf Length | Score | Probability | Description |
|---|---|---|---|---|---|---|---|---|
| contig587 | 24397751_f1_2 | 1688 | 5093 | 387 | 128 | 55 | 0.69 | [DE:HYPOTHETICAL 37.3 KD PROTEIN IN AGA1-MTR INTERGENIC REGION (F346)] |
| contig587 | 10585337_f2_6 | 1689 | 5094 | 2148 | 715 | 187 | 1.90E-10 | [SP:P32099] [OR:Escherichia coli] [GN:smp] [NT:URF] [SP:P08799] [OR:DICTYOSTELIUM DISCOIDEUM] [GN:MHCA] [DE:MYOSIN H HEAVY CHAIN, NON MUSCLE] |
| contig587 | 25569702_f2_7 | 1690 | 5095 | 600 | 199 | 80 | 0.991 | [OR:Saccharomyces cerevisiae] [PN:probable membrane protein YPR049c] |
| contig587 | 7273450_f3_13 | 1691 | 5096 | 183 | 60 | 62 | 0.79 | [SP:P43784] [OR:HAEMOPHILUS INFLUENZAE] [GN:LPDA] [DE:AND 2-OXOGLUTARATE DEHYDROGENASES COMPLEXES] |
| contig587 | 1182925_f3_14 | 1692 | 5097 | 657 | 218 | 94 | 0.021 | [AC:U01302] [OR:Onchocerca volvulus] [PN:repetitive antigen] |
| contig587 | 15086536_f2_8 | 1693 | 5098 | 723 | 240 | 212 | 1.70E-17 | [AC:D78193] [OR:Bacillus subtilis] [GN:yycI] |
| contig587 | 19720312_f1_3 | 1694 | 5099 | 795 | 264 | 198 | 5.10E-16 | [SP:P39787] [OR:BACILLUS SUBTILIS] [GN:DNAD] [DE:DNA REPLICATION PROTEIN DNAD] |
| contig587 | 15914688_f1_4 | 1695 | 5100 | 435 | 144 | 126 | 2.20E-08 | [SP:Q49422] [OR:MYCOPLASMA GENITALIUM] [GN:MG352] [DE:HYPOTHETICAL PROTEIN MG352] |
| contig587 | 2246816_f2_9 | 1696 | 5101 | 285 | 94 | 356 | 9.20E-33 | [SP:P19775] [OR:STAPHYLOCOCCUS AUREUS] [GN:TNP] [DE:TRANSPOSASE FOR INSERTION SEQUENCE ELEMENT IS256 IN TRANSPOSON TN4001] |
| contig587 | 13851375_f3_12 | 1697 | 5102 | 375 | 124 | 312 | 4.20E-28 | [SP:P37543] [OR:BACILLUS SUBTILIS] [GN:YABB] [DE:HYPOTHETICAL 28.3 KD PROTEIN IN XPAC-ABRB INTERGENIC REGION] |
| contig588 | 29928342_f1_1 | 1698 | 5103 | 279 | 92 | 222 | 1.50E-18 | IAC:X70925] [OR:Pediococcus acidilactici] [GNy98] |
| contig588 | 4977187_c1_23 | 1699 | 5104 | 711 | 236 | 486 | 1.50E-46 | [SP:P45113] [OR:HAEMOPHILUS INFLUENZAE] [GN:PFS] [DE:PFS PROTEIN HOMOLOG] |
| contig588 | 16196068_c1_22 | 1700 | 5105 | 309 | 102 | 67 | 0.06 | [AC:M23650] [OR:artificial sequence] [PN:parathyroid hormone] [NT:parathyroid hormone-like protein-(1-141)] |
| contig588 | 2932837_c2_27 | 1701 | 5106 | 291 | 96 | 161 | 4.30E-12 | [SP:P54570] [OR:BACILLUS SUBTILIS] [GN:YOKG] [DE:HYPOTHETICAL 21.0 KD PROTEIN IN GLNQ-ANSR INTERGENIC REGION] |
| contig588 | 390627_c1_21 | 1702 | 5107 | 462 | 153 | 322 | 3.70E-29 | [SP:P54570] [OR:BACILLUS SUBTILIS] [GN:YOKG] [DE:HYPOTHETICAL 21.0 KD PROTEIN IN GLNQ-ANSR INTERGENIC REGION] |
| contig588 | 973452_f2_9 | 1703 | 5108 | 681 | 226 | 173 | 2.30E-13 | [SP:P37467] [OR:BACILLUS SUBTILIS] [GN:XPAC] [DE:XPAC PROTEIN] |
| contig588 | 14649193_f3_13 | 1704 | 5109 | 1200 | 399 | 1061 | 1.80E-107 | [SP:P37535] [OR:BACILLUS SUBTILIS] [GN:YAAN] [DE:HYPOTHETICAL 43.8 KD PROTEIN IN XPAC-ABRB INTERGENIC REGION] |
| contig588 | 34173410_f3_14 | 1705 | 5110 | 867 | 288 | 244 | 6.80E-21 | [OR:Methanococcus jannaschii] [PN:mutator protein mutT] |
| contig588 | 22445187_f1_2 | 1706 | 5111 | 561 | 186 | 83 | 0.071 | [OR:Salmonella typhimurium] [PN:hypothetical protein 5] |
| contig588 | 23929635_c2_26 | 1707 | 5112 | 510 | 169 | 56 | 0.74 | [AC:L48688] [OR:Rattus norvegicus] [PN:voltage-dependent Na+ channel beta-1 subunit] [GN:beta 1] [NT:Xxx] |
| contig588 | 4789751_c3_28 | 1708 | 5113 | 342 | 113 | 61 | 0.27 | [SP:P00108] [OR:PETALONIA FASCIA] [DE:CYTOCHROME C6 (SOLUBLE CYTOCHROME F) (CYTOCHROME C553)] |
| contig588 | 2855090_c2_25 | 1709 | 5114 | 897 | 298 | 316 | 2.50E-28 | [AC:X85787] [OR:Streptococcus pneumoniae] [PN:capsular polysaccharide synthesis protein] [GN:cps14A] |
| contig588 | 24728412_c2_24 | 1710 | 5115 | 1188 | 395 | 520 | 2.80E-61 | [AC:U63329] [OR:Homo sapiens] [PN:mutY homolog] [GN:hMYH] |
| contig588 | 897828_c1_16 | 1711 | 5116 | 801 | 266 | 113 | 1.80E-06 | [SP:Q56647] [OR:VIBRIO CHOLERAE] [GN:RECX] [DE:REGULATORY PROTEIN RECX] |

TABLE 2-continued

| Contig | Orf | NT Seq Id | AA Seq ID | NT Orf Length | AA Orf Length | Score | Probability | Description |
|---|---|---|---|---|---|---|---|---|
| contig589 | 26745712_f2_3 | 1712 | 5117 | 210 | 69 | 122 | 5.80E-08 | [AC:U81957] [OR:Streptococcus gordonii] [PN:putative DNA binding protein] [NT:orfE] |
| contig589 | 36210450_f1_1 | 1713 | 5118 | 309 | 102 | 147 | 1.30E-10 | [AC:U81957] [OR:Streptococcus gordonii] [PN:putative DNA binding protein] [NT:orfE] |
| contig589 | 4331562_f2_4 | 1714 | 5119 | 2310 | 769 | 1096 | 3.50E-111 | [AC:AB001488] [OR:Bacillus subtilis] [PN:PROBABLE DNA TOPOISOMERASE III] [GN:topB] |
| contig589 | 11128427_f2_5 | 1715 | 5120 | 924 | 307 | 596 | 3.40E-58 | [AC:AB001488] [OR:Bacillus subtilis] [GN:ydcE] [NT:PROBABLE HTH_ARAC_FAMILY OF TRANSCRIPTIONAL] |
| contig589 | 4947203_f2_6 | 1716 | 5121 | 363 | 120 | 61 | 0.94 | [SP:P44026] [OR:HAEMOPHILUS INFLUENZAE] [GN:H10633] [DE:HYPOTHETICAL PROTEIN H10633] |
| contig589 | 7203432_f1_2 | 1717 | 5122 | 1473 | 490 | 1227 | 4.60E-125 | [AC:D83026] [OR:Bacillus subtilis] [GN:cydA] [NT:homologous to cytochrome d ubiquinol oxidase] |
| contig589 | 29330468_f1_11 | 1718 | 5123 | 1029 | 342 | 685 | 1.30E-67 | [AC:D83026] [OR:Bacillus subtilis] [GN:cydB] [NT:homologous to cytochrome d ubiquinol oxidase] |
| contig59 | 11991562_f2_1 | 1719 | 5124 | 789 | 263 | 197 | 5.60E-15 | [SP:P47609] [OR:MYCOPLASMA GENITALIUM] [GN:MG369] [DE:HYPOTHETICAL PROTIN MG369] |
| contig590 | 24429768_c3_22 | 1720 | 5125 | 630 | 209 | 499 | 6.50E-48 | [SP:P18156] [OR:BACILLUS SUBTILIS] [GN:GLPF] [DE:GLYCEROL UPTAKE FACILITATOR PROTEIN] |
| contig590 | 24501553_c2_19 | 1721 | 5126 | 1854 | 617 | 746 | 4.20E-108 | [SP:P18158] [OR:BACILLUS SUBTILIS] [GN:GLPD] [DE:AEROBIC GLYCEROL-3-PHOSPHATE DEHYDROGENASE,] |
| contig590 | 1039067_c3_21 | 1722 | 5127 | 1542 | 513 | 1641 | 6.30E-169 | [SP:P18157] [OR:BACILLUS SUBTILIS] [GN:GLPK] [DE:(GLYCEROKINASE) (GK)] |
| contig590 | 31275465_c3_20 | 1723 | 5128 | 1497 | 498 | 140 | 2.00E-06 | [OR:Streptococcus pyogenes] [PN:rofA protein] |
| contig590 | 22712550_c2_18 | 1724 | 5129 | 1323 | 440 | 488 | 9.50E-47 | [SP:P37061] [OR:ENTEROCOCCUS FAECALIS] [GN:NOX] [DE:NADH OXIDASE, (NOXASE)] |
| contig591 | 4394591_f1_1 | 1725 | 5130 | 3651 | 1216 | 187 | 1.20E-10 | [AC:AE000237] [OR:Escherichia coli] [PN:hypothetical protein near replication terminus] [GN:ydbA_1] [NT:o852; 99 pct identical to 376 aa of fragment] |
| contig591 | 15015941_f2_5 | 1726 | 5131 | 621 | 206 | 75 | 0.84 | [SP:P06350] [OR:ONCORHYNCHUS MYKISS] [DE:HISTONE H1] |
| contig591 | 22058180_f3_9 | 1727 | 5132 | 423 | 140 | 73 | 0.94 | [OR:Streptococcus pyogenes] [PN:fibronectin-binding protein II precursor] [GN:sfbII] |
| contig591 | 157558_f1_3 | 1728 | 5133 | 267 | 88 | 49 | 0.998 | [SP:P54520] [OR:BACILLUS SUBTILIS] [GN:YOHZ] [DE:N UTILIZATION SUBSTANCE PROTEIN B HOMOLOG (NUSB PROTEIN)] |
| contig592 | 7082001_f2_3 | 1729 | 5134 | 285 | 94 | 429 | 1.70E-40 | [SP:P07515] [OR:ENTEROCOCCUS FAECALIS] [GN:PTSH] [DP:PHOSPHOCARRIER PROTEIN HPR (HISTIDINE-CONTAINING PROTEIN)] |
| contig592 | 25478427_f1_1 | 1730 | 5135 | 1731 | 576 | 2237 | 4.40E-232 | [SP:P30299] [OR:STREPTOCOCCUS SALIVARIUS] [GN:PTS1] [DE:(PHOSPHOTRANSFERASE SYSTEM, ENZYME 1)] |
| contig592 | 4301537_c2_10 | 1731 | 5136 | 1089 | 362 | 82 | 0.96 | [SP:P34219] [OR:SACCHAROMYCES CEREVISIAE] [GN:YBL054W] [DE:HYPOTHETICAL 59.2 KD PROTEIN IN SHP1-SEC17 INTERGENIC REGION] |
| contig592 | 24415937_c3_16 | 1732 | 5137 | 741 | 246 | 55 | 0.93 | [AC:PQ0704] [OR:Oryza sativa] [PN:Acyl-CoA oxidase,] |
| contig592 | 16072933_f3_5 | 1733 | 5138 | 282 | 93 | 68 | 0.18 | [AC:X96953] [OR:Escherichia coli] [PN:EspB] [GN:cspB] |
| contig592 | 4400776_c3_15 | 1734 | 5139 | 933 | 310 | 87 | 0.88 | [SP:P08640] [OR:SACCHAROMYCES CEREVISIAE] [GN:STA1] [DE:GLUCOSIDASE) (1,4-ALPHA-D-GLUCAN GLUCOHYDROLASE] |
| contig592 | 22003884_c2_9 | 1735 | 5140 | 207 | 68 | 58 | 0.48 | [SP:P50718] [OR:TRICHOPLUSIA NI] [DE:LYSOZYME PRECURSOR, (1,4-BETA-N-ACETYLMURAMIDASE)] |

TABLE 2-continued

| Contig | Orf | NT Seq Id | AA Seq ID | NT Orf Length | AA Orf Length | Score | Probability | Description |
|---|---|---|---|---|---|---|---|---|
| contig593 | 1188760_f2_2 | 1736 | 5141 | 1533 | 510 | 1844 | 1.90E-190 | [SP:P50099] [OR:STREPTOCOCCUS PYOGENES] [GN:GUAB] [DE:DEHYDROGENASE) (IMPDH) (IMPD)] |
| contig593 | 24414818_c2_10 | 1737 | 5142 | 1284 | 427 | 1418 | 2.70E-145 | [SP:P37464] [OR:BACILLUS SUBTILIS] [GN:SERS] [DE:SERYL-TRNA SYNTHETASE, (SERINE-TRNA LIGASE) (SERRS)] |
| contig593 | 26617180_c3_13 | 1738 | 5143 | 183 | 60 | 51 | 0.85 | [AC:L29324] [OR:Streptococcus pneumoniae] [PN:ORF8] |
| contig593 | 1053463_c1_7 | 1739 | 5144 | 1254 | 417 | 429 | 1.70E-40 | [SP:Q06240] [OR:ENTEROCOCCUS FAECIUM] [GN:VANS] [DE:(VANCOMYCIN HISTIDINE PROTEIN KINASE)] |
| contig593 | 24640832_c3_12 | 1740 | 5145 | 696 | 231 | 436 | 3.10E-41 | [SP:Q06239] [OR:ENTEROCOCCUS FAECIUM] [GN:VANR] [DE:REGULATORY PROTEIN VANR] |
| contig594 | 14648458_f3_11 | 1741 | 5146 | 417 | 138 | 66 | 0.32 | [OR:Streptococcus pyogenes] [PN:M protein precursor] [GN:emm19] |
| contig594 | 24667090_f1_1 | 1742 | 5147 | 492 | 163 | 84 | 0.093 | [OR:Methanococcus jannaschii] [PN:DNA-(apurinic or apyrimidinic site) lyase,] |
| contig594 | 35330262_c2_22 | 1743 | 5148 | 252 | 83 | 54 | 0.9999 | [AC:X54687] [OR:Escherichia coli] [NT:ORF401] |
| contig594 | 26386075_c1_19 | 1744 | 5149 | 366 | 121 | 288 | 1.50E-25 | [SP:P32731] [OR:BACILLUS SUBTILIS] [GN:RBFA] [DE:RIBOSOME-BINDING FACTOR A (P15B PROTEIN)] |
| contig594 | 29502313_c1_18 | 1745 | 5150 | 2409 | 802 | 2611 | 9.90E-288 | [SP:P18311] [OR:ENTEROCOCCUS FAECIUM] [GN:INFB] [DE:INITIATION FACTOR IF-2] |
| contig594 | 24409661_c1_17 | 1746 | 5151 | 339 | 112 | 351 | 3.10E-32 | [SP:P55768] [OR:ENTEROCOCCUS FAECIUM] [DE:PROBABLE RIBOSOMAL PROTEIN IN INFB 5'REGION] |
| contig594 | 14492807_c3_23 | 1747 | 5152 | 330 | 109 | 232 | 1.30E-19 | [SP:P32728] [OR:BACILLUS SUBTILIS] [GN:YLXR] [DE:HYPOTHETICAL 10.4 KD PROTEIN IN NUSA-INFB INTERGENIC REGION (ORF3)] |
| contig595 | 6335778_f1_1 | 1748 | 5153 | 621 | 206 | 551 | 2.00E-53 | [SP:Q06795] [OR:BACILLUS SUBTILIS] [GN:NUSG] [DE:TRANSCRIPTION ANTITERMINATION PROTEIN NUSG] |
| contig595 | 957075_c3_22 | 1749 | 5154 | 186 | 61 | 60 | 0.94 | [AC:D83659] [OR:Schizosaccharomyces pombe] [NT:homology to Saccharomyces cerevisiae hypothetical] |
| contig595 | 22462812_f2_2 | 1750 | 5155 | 711 | 236 | 73 | 0.034 | [AC:D86999] [OR:Homo sapiens] [GN:V3-3] |
| contig595 | 1181550_f2_4 | 1751 | 5156 | 243 | 80 | 72 | 0.089 | [AC:U05681] [OR:Homo sapiens] [GN:BCL3] [NT:homologous to members of the 1-kappa B family;] |
| contig595 | 36126630_c1_15 | 1752 | 5157 | 744 | 247 | 126 | 3.30E-06 | [SP:P54717] [OR:BACILLUS SUBTILIS] [GN:YFIA] [DE:HYPOTHETICAL 29.3 KD PROTEIN IN GLVG-GLVBC INTERGENIC REGION] |
| contig595 | 3906643_f3_6 | 1753 | 5158 | 1638 | 545 | 1011 | 3.60E-102 | [OR:Enterococcus faecalis] [PN:pheromone cAD1 binding protein precursor] [GN:traC] |
| contig595 | 4042003_f1_3 | 1754 | 5159 | 1158 | 385 | 544 | 1.10E-52 | [AC:Z75208] [OR:Bacillus subtilis] [PN:hypothetical protein] [GN:ysdC] [NT:homology to celA of Clostridium thermocellum and] |
| contig595 | 34064061_f3_8 | 1755 | 5160 | 891 | 296 | 209 | 3.50E-17 | [OR:Bacillus subtilis] [PN:dciAA protein] [GN:dciAA] |
| contig595 | 13861592_c3_18 | 1756 | 5161 | 885 | 294 | 534 | 1.30E-51 | [AC:X98238] [OR:Lactobacillus sake] [NT:orf6] |
| contig595 | 2630379_c2_16 | 1757 | 5162 | 465 | 154 | 180 | 2.20E-13 | [OR:Bacillus subtilis] [PN:phosphoglycerate dehydrogenase,] |
| contig596 | 34375952_c3_28 | 1758 | 5163 | 225 | 74 | 82 | 0.001 | [AC:X96977] [OR:Enterococcus faecalis] [GN:orf6] |
| contig596 | 36205015_c3_27 | 1759 | 5164 | 1086 | 361 | 119 | 0.00012 | [SP:P15132] [OR:BACTERIOPHAGE PHI-29] [GN:13] [DE:MORPHOGENESIS PROTEIN 1 (LATE PROTEIN GP13)] |
| contig596 | 26386287_f3_12 | 1760 | 5165 | 234 | 77 | 63 | 0.25 | [SP:P46764] [OR:ACANTHAMOEBA CASTELLANII] [GN:RPL5] [DE:MITOCHONDRIAL 60S RIBOSOMAL PROTEIN L5] |
| contig596 | 25664813_c1_22 | 1761 | 5166 | 2061 | 686 | 98 | 0.18 | [AC:Z81451] [OR:Mycobacterium tuberculosis] [PN:unknown] [GN:MTCY428.02] [NT:MTCY428.02, len] |
| contig596 | 35198461_c1_21 | 1762 | 5167 | 2040 | 679 | 922 | 9.70E-93 | [AC:AB001488] [OR:Bacillus subtilis] [GN:ydE] [NT:SIMILAR TO ORF16 OF ENTEROCOCCUS FAECALIS] |
| contig596 | 23867137_c3_26 | 1763 | 5168 | 555 | 184 | 152 | 7.20E-10 | [AC:AB001488] [OR:Bacillus subtilis] [GN:ydE] [NT:SIMILAR TO |

TABLE 2-continued

| Contig | Orf | NT Seq Id | AA Seq ID | NT Orf Length | AA Orf Length | Score | Probability | Description |
|---|---|---|---|---|---|---|---|---|
| contig596 | 23631251_f1_2 | 1764 | 5169 | 252 | 83 | 66 | 0.13 | ORF16 OF *ENTEROCOCCUS FAECALIS* [AC:PN0109] [OR:*Rattus norvegicus*] [PN:keratin-like protein] [GN:K51] |
| contig596 | 7032811_f3_18 | 1765 | 5170 | 327 | 108 | 57 | 0.45 | [AC:L38705] [OR:Bovine viral diarrhea virus] [PN:surface glycoprotein gp53] [GN:E2] |
| contig596 | 25678513_c2_23 | 1766 | 5171 | 405 | 134 | | | |
| contig596 | 13869051_c3_24 | 1767 | 5172 | 228 | 75 | 67 | 0.25 | [SP:P40707] [OR:*SHIGELLA FLEXNERI*] [GN:*SPAS*] [DE:SURFACE PRESENTATION OF ANTIGENS PROTEIN SPAS (SPA40 PROTEIN)] |
| contig597 | 33322837_f3_5 | 1768 | 5173 | 1116 | 371 | 1054 | 1.00E-106 | [SP:Q04797] [OR:*BACILLUS SUBTILIS*] [GN:ASD] [DE:DEHYDROGENASE] |
| contig597 | 4141087_f3_6 | 1769 | 5174 | 906 | 301 | 758 | 2.30E-75 | [SP:Q04796] [OR:*BACILLUS SUBTILIS*] [GN:DAPA] [DE:DIHYDRODIPICOLINATE SYNTHASE, (DHDPS)] |
| contig597 | 23682192_f3_7 | 1770 | 5175 | 1719 | 572 | 1094 | 5.80E-111 | [AC:U51911] [OR:*Bacillus subtilis*] [PN:unknown] [GN:ykqC] [NT:similar aminopeptidase AMPS with Swiss-Prot] |
| contig597 | 17010927_f1_2 | 1771 | 5176 | 1398 | 466 | 157 | 3.10E-08 | [SP:P21589] [OR:*HOMO SAPIENS*] [GN:NT5] [DE:(CD73)] |
| contig598 | 23472141_c2_21 | 1772 | 5177 | 1950 | 650 | 345 | 3.40E-31 | [AC:U17696] [OR:Lactococcus lactis] [PN:N-acetylmuramidase] [GN:acmA] [NT:similar to muramidase-2 encoded by Enterococcus] |
| contig598 | 6430442_c2_20 | 1773 | 5178 | 5400 | 1799 | 309 | 7.10E-24 | [AC:D42041] [OR:*Homo sapiens*] [GN:KIAA0088] [NT:The ha1225 gene product is related to human] |
| contig599 | 24509503_f2_2 | 1774 | 5179 | 624 | 207 | 79 | 0.87 | [AC:U72505] [OR:*Arabidopsis thaliana*] [PN:G6p] [GN:AtG6] |
| contig599 | 19532010_c1_15 | 1775 | 5180 | 1128 | 375 | 72 | 0.077 | [SP:Q60259] [OR:*METHANOCOCCUS JANNASCHII*] [GN:MJECL22] [DE:HYPOTHETICAL PROTEIN MJECL22] |
| contig599 | 13719037_c3_18 | 1776 | 5181 | 744 | 247 | 502 | 3.10E-48 | [AC:X82620] [OR:*Lactococcus lactis*] [PN:alpha-acetolactate decarboxylase] [GN:aldB] |
| contig599 | 5256675_c1_13 | 1777 | 5182 | 1683 | 560 | 1772 | 8.20E-183 | [AC:L16975] [OR:Lactococcus lactis] [PN:alpha-acetolactate synthase] [GN:als] |
| contig599 | 24490881_f2_8 | 1778 | 5183 | 480 | 159 | 269 | 1.50E-23 | [SP:Q02115] [OR:*BACILLUS SUBTILIS*] [GN:LYTR] [DE:MEMBRANE-BOUND PROTEIN LYTR] |
| contig6 | 29485338_f3_1 | 1779 | 5184 | 534 | 178 | 285 | 2.40E-38 | [AC:U36837] [OR:*Lactococcus lactis*] [PN:ORFU] |
| contig60 | 5960790_f2_2 | 1780 | 5185 | 324 | 107 | 230 | 1.10E-18 | [SP:P54547] [OR:*BACILLUS SUBTILIS*] [GN:ZWF] [DE:GLUCOSE-6-PHOSPHATE 1-DEHYDROGENASE, (G6PD)] |
| contig60 | 2345958_c3_4 | 1781 | 5186 | 462 | 153 | 268 | 2.00E-23 | [SP:Q45477] [OR:*BACILLUS SUBTILIS*] [GN:iLES] [DE:(ILERS) (FRAGMENTS)] |
| contig600 | 24487507_f3_20 | 1782 | 5187 | 381 | 126 | 55 | 0.55 | [OR:*Homo sapiens*] [PN:guanylyl cyclase C] |
| contig600 | 24609380_f1_1 | 1783 | 5188 | 417 | 138 | | | |
| contig600 | 29977300_c1_36 | 1784 | 5189 | 576 | 191 | 52 | 0.98 | [AC:S75113] [OR:*Azotobacter vinelandii*] [PN:GDP-mannose dehydrogenase] [NT:Description] |
| contig600 | 994078_f3_22 | 1785 | 5190 | 252 | 83 | 57 | 0.36 | [AC:M30553] [OR:*Mus musculus*] [NT:Ig mu-chain V-D-J region] |
| contig600 | 6021962_f2_23 | 1786 | 5191 | 366 | 121 | 51 | 0.9 | [SP:P13636] [OR:*URSUS TIBETANUS*] [DE:PEPSINOGEN A, (FRAGMENT)] |
| contig600 | 4101718_f3_24 | 1787 | 5192 | 393 | 130 | 199 | 4.00E-16 | [AC:D88802] [OR:*Bacillus subtilis*] [GN:ydhQ] [NT:*K. aerogenes*, histidine utilization repressor;] |
| contig600 | 5078530_f1_4 | 1788 | 5193 | 228 | 75 | 56 | 0.46 | [AC:M83757] [OR:*Mitochondrion Mytilus edulis*] [GN:COII] [NT:Codons as in Cyt b. Nucleotides 386-649 not] |
| contig600 | 24484377_f3_26 | 1789 | 5194 | 1035 | 344 | 399 | 2.60E-37 | [SP:P42602] [OR:*ESCHERICHIA COLI*] [GN:YGJU] [DE:HYPOTHETICAL 43.5 KD PROTEIN IN EBGC-UXAA INTERGENIC REGION (O414)] |

TABLE 2-continued

| Contig | Orf | NT Seq Id | AA Seq ID | NT Orf Length | AA Orf Length | Score | Probability | Description |
|---|---|---|---|---|---|---|---|---|
| contig600 | 11917811_f1_5 | 1790 | 5195 | 414 | 137 | 146 | 1.10E-09 | [SP:P45246] [OR:HAEMOPHILUS INFLUENZAE] [GN:HI1545] [DE:HYPOTHETICAL SYMPORTER HI1545] |
| contig600 | 547050_c1_35 | 1791 | 5196 | 183 | 60 | 62 | 0.33 | [AC:JC1065] [OR:beet necrotic yellow vein mosaic virus] [PN:coat protein] |
| contig600 | 23709453_f3_27 | 1792 | 5197 | 465 | 154 | 196 | 8.30E-16 | [SP:P39303] [OR:ESCHERICHIA COLI] [GN:YIFU] [DE:INTERGENIC REGION, (O158)] |
| contig600 | 24303137_f1_6 | 1793 | 5198 | 369 | 122 | 81 | 0.0013 | [SP:P39021] [OR:ESCHERICHIA COLI] [GN:YIFT] [DE:HYPOTHETICAL 10.9 KD PROTEIN IN AIDB-RPSF INTERGENIC REGION (O101)] |
| contig600 | 3399187_f2_15 | 1794 | 5199 | 264 | 87 | 123 | 6.70E-07 | [SP:P75291] [OR:MYCOPLASMA PNEUMONIAE] [GN:SGAT] [DE:SGAT PROTEIN HOMOLOG (P02hd —ORF:660)] |
| contig600 | 22902165_f1_7 | 1795 | 5200 | 483 | 160 | 67 | 0.998 | [SP:Q00844] [OR:RICE STRIPE VIRUS] [DE:(STRIPE DISEASE-SPECIFIC PROTEIN)] |
| contig600 | 4328568_c2_42 | 1796 | 5201 | 915 | 304 | 321 | 4.70E-29 | [SP:P54181] [OR:BACILLUS SUBTILIS] [GN:YPNP] [DE:HYPOTHETICAL 48.5 KD PROTEIN IN ILVA 3'REGION] |
| contig600 | 24845662_f1_9 | 1797 | 5202 | 183 | 60 | 64 | 0.68 | [SP:P33471] [OR:BLUETONGUE VIRUS] [GN:S6] [DE:NONSTRUCTURAL PROTEIN NS1] |
| contig600 | 36214092_f2_17 | 1798 | 5203 | 690 | 229 | 562 | 1.40E-54 | [SP:P44865] [OR:HAEMOPHILUS INFLUENZAE] [GN:GPMA] [DE:(BPG-DEPENDENT PGAM)] |
| contig600 | 23610662_f2_18 | 1799 | 5204 | 318 | 105 | 158 | 8.80E-12 | [OR:Methanococcus jannaschii] [PN:hypothetical protein MJ1558] |
| contig600 | 31287757_f1_11 | 1800 | 5205 | 939 | 312 | 791 | 7.40E-79 | [OR:Methanococcus jannaschii] [PN:hypothetical protein MJ1665] |
| contig601 | 29312781_f1_1 | 1801 | 5206 | 531 | 176 | 155 | 1.40E-10 | [AC:D90872] [OR:Escherichia coli] [GN:AMPC] [NT:similar to [SwissProt Accession Number P24735] PRECURSOR (EC 3.5.2.6)] [PN:BETA-LACTAMASE |
| contig601 | 21523963_f3_6 | 1802 | 5207 | 1002 | 333 | 914 | 6.80E-92 | [AC:D16594] [OR:Streptococcus mutans] [PN:Mannosephosphate Isomerase] [GN:pmi] |
| contig601 | 34570763_c3_15 | 1803 | 5208 | 585 | 194 | 70 | 0.997 | [SP:Q00260] [OR:CUCUMBER MOSAIC VIRUS] [DE:COAT PROTEIN] |
| contig601 | 10557936_c1_7 | 1804 | 5209 | 1020 | 339 | 452 | 6.20E-43 | [AC:AE000169] [OR:Escherichia coli] [GN:ybcK] [NT:f311; 100 pct identical to fragment YBEK_ECOLI SW] |
| contig601 | 30084787_c2_11 | 1805 | 5210 | 270 | 89 | 114 | 1.20E-06 | [AC:D90909] [OR:Synechocystis sp.] [PN:hypothetical protein] [GN:phr] [NT:ORF_ID] |
| contig601 | 23525452_c3_14 | 1806 | 5211 | 480 | 159 | 186 | 9.50E-15 | [AC:D90909] [OR:Synechocystis sp.] [PN:hypothetical protein] [GN:phr] [NT:ORF_ID] |
| contig601 | 24473137_c2_10 | 1807 | 5212 | 1398 | 465 | 501 | 4.00E-48 | [AC:D90914] [OR:Synechocystis sp.] [PN:hypothetical protein] [NT:ORF_ID] |
| contig602 | 10272012_f1_1 | 1808 | 5213 | 183 | 60 | 54 | 0.998 | [SP:P40699] [OR:SALMONELLA TYPHIMURIUM] [GN:SPAO] [DE:SUREACE PRESENTATION OF ANTIGENS PROTEIN SPAO] |
| contig602 | 12692842_f3_10 | 1809 | 5214 | 810 | 269 | 348 | 6.50E-32 | [SP:PO5054] [OR:ESCHERICHIA COLI] [GN:RBSK] [DE:RIBOKINASE,] |
| contig602 | 34508562_f3_11 | 1810 | 5215 | 411 | 136 | 304 | 3.00E-27 | [SP:P44734] [OR:HAEMOPHILUS INFLUENZAE] [GN:RBSD] [DE:HIGH AFFINITY RIBOSE TRANSPORT PROTEIN RBSD] |
| contig602 | 36214082_f3_12 | 1811 | 5216 | 909 | 302 | 320 | 6.00E-29 | [SP:P40419] [OR:BACILLUS MEGATERIUM] [DE:HYPOTHETICAL 30.5 KD PROTEIN IN GDHI 5'REGION (ORF 2)] |
| contig602 | 51928_c1_19 | 1812 | 5217 | 915 | 304 | 237 | 3.80E-20 | [SP:P39592] [OR:BACILLUS SUBTILIS] [GN:YWB1] [DE:HYPOTHETICAL TRANSCRIPTIONAL REGULATOR IN EPR-GALK INTERGENIC REGION] |
| contig602 | 33803178_f3_14 | 1813 | 5218 | 642 | 213 | 278 | 1.70E-24 | [SP:P40892] [OR:SACCHAROMYCES CEREVISIAE] |

TABLE 2-continued

| Contig | Orf | NT Seq Id | AA Seq ID | NT Orf Length | AA Orf Length | Score | Probability | Description |
|---|---|---|---|---|---|---|---|---|
| contig602 | 4102318_f2_8 | 1814 | 5219 | 750 | 249 | 563 | 1.10E-54 | [GN:YIL218W] [DE:(EC 2.3.1.—)] [SP:P25145] [OR:LISTERIA MONOCYTOGENES] [DE:HYPOTHETICAL OXIDOREDUCTASE IN INLA 5'REGION, (ORFA)] |
| contig602 | 13850136_c3_23 | 1815 | 5220 | 1188 | 395 | 411 | 1.40E-38 | [AC:U22342] [OR:Bacteriophage T270] [PN:integrase] [GN:int] [NT:excisionase] |
| contig603 | 5182663_f3_7 | 1816 | 5221 | 261 | 86 | 85 | 0.0047 | [AC:X94434] [OR:Lactobacillus plantarum] [PN:histidine protein kinase PlnB] [GN:plnB] [NT:putative; ttg start codon] |
| contig603 | 3939712_c2_20 | 1817 | 5222 | 744 | 247 | 97 | 0.022 | [OR:mitochondrion Sauroleishmania tarentolae] [PN:NADH dehydrogenase (ubiquinone, chain 4] |
| contig603 | 33438760_c1_16 | 1818 | 5223 | 795 | 264 | 301 | 6.20E-27 | [AC:AB001488] [OR:Bacillus subtilis] [GN:ydbJ] [NT:PROBABLE TRANSPORT ATP BINDING PROTEIN.] |
| contig603 | 5117202_c2_19 | 1819 | 5224 | 759 | 252 | 90 | 0.00014 | [SP:Q09723] [OR:SCHIZOSACCHAROMYCES POMBE] [GN:SPAC31A2.02] [DE:HYPOTHETICAL 14.1 KD PROTEIN C31A2.02 IN CHROMOSOME 1] |
| contig603 | 34197152_c1_14 | 1820 | 5225 | 315 | 104 | | | |
| contig603 | 35314750_c3_23 | 1821 | 5226 | 714 | 237 | 281 | 4.70E-23 | [AC:AF000149] [OR:Mus musculus] [PN:ATP-binding cassette transporter] [GN:ABCR] [NT:nm protein; RmP] |
| contig603 | 2195967_c2_18 | 1822 | 5227 | 816 | 271 | 70 | 0.99 | [AC:U4OI78] [OR:Mitochondrion Melospiza melodia] [DN:cytochrome b] |
| contig603 | 26219187_f1_3 | 1823 | 5228 | 210 | 69 | 80 | 0.027 | [AC:PC4002] [OR:Schizosaccharomyces pombe] [PN:phosphatidylinositol-3 kinase,] [GN:pi-3] |
| contig603 | 24416068_c3_22 | 1824 | 5229 | 1146 | 381 | 196 | 1.50E-13 | [AC:X57583] [OR:Escherichia coli] [GN:mccB] |
| contig603 | 22460816_c1_6 | 1825 | 5230 | 519 | 172 | 815 | 2.10E-81 | [SP:P19775] [OR:STAPHYLOCOCCUS AUREUS] [GN:TNP] [DE:TRANSPOSASE FOR INSERTION SEQUENCE ELEMENT IS256 IN TRANSPOSON TN4001] |
| contig604 | 2774218_c2_20 | 1826 | 5231 | 204 | 68 | 125 | 2.30E-07 | [SP:P46317] [OR:BACILLUS SUBTILIS] [GN:CELB] [DE:PERMEASE HC COMPONENT) (PHOSPHOTRANSFERASE ENZYME II, C COMPONENT)] |
| contig604 | 23595088_c2_19 | 1827 | 5232 | 630 | 209 | 101 | 0.0065 | [SP:P45262] [OR:HAEMOPHILUS INFLUENZAE] [GN:HI1590] [DE:HYPOTHETICAL PROTEIN HI1590] |
| contig604 | 32500407_f3_10 | 1828 | 5233 | 789 | 262 | 122 | 2.10E-09 | [SP:P54717] [OR:BACILLUS SUBTILIS] [GN:YFIA] [DE:HYPOTHETICAL 29.3 KD PROTEIN IN GLVG-GLVBC INTERGENIC REGION] |
| contig604 | 35820425_f2_5 | 1829 | 5234 | 579 | 192 | 60 | 0.48 | [OR:Mus musculus] [PN:serum albumin] |
| contig604 | 23710942_c2_18 | 1830 | 5235 | 822 | 273 | 78 | 0.56 | [SP:P52093] [OR:HELICOBACTER PYLORI] [GN:PFR] [DE:NONHEME IRON-CONTAINING FERRITIN |
| contig604 | 14478461_c1_15 | 1831 | 5236 | 231 | 76 | 148 | 1.60E-10 | [SP:P39345] [OR:ESCHERICHIA COLI] [GN:YIGU] [DE:EC 1,—,—,—) (F254)] |
| contig604 | 23439202_c1_14 | 1832 | 5237 | 504 | 167 | 345 | 1.40E-31 | [SP:P50199] [OR:GLUCONOBACTER OXYDANS] [GN:GNO] [DE:REDUCTASE)] |
| contig604 | 4902212_c2_17 | 1833 | 5238 | 855 | 284 | 811 | 5.60E-81 | [AC:AF000368] [OR:Escherichia coli] [PN:5-keto-4-deoxyuronate isomerase] [GN:kduI] [NT:f278; 74 pct identical to KDU1_ERWCH SW] |
| contig604 | 13703313_c3_21 | 1834 | 5239 | 744 | 247 | 239 | 2.30E-20 | [AC:U70664] [OR:Haloferax alicantei] [PN:2-keto-3-deoxygluconate kinase] [NT:similar to fructokinases] |
| contig605 | 16441577_c1_23 | 1835 | 5240 | 360 | 120 | 384 | 1.00E-35 | [AC:Z75208] [OR:Bacillus subtilis] [PN:translation initiation factor IF3] [GN:infC] [NT:homology to infC of Bacillus stearothermophilus;] |
| contig605 | 25549143_c1_22 | 1836 | 5241 | 1083 | 360 | 541 | 2.30E-52 | [AC:JC4292] [OR:thermophilic bacterium PS-3] [PN:insertion |

TABLE 2-continued

| Contig | Orf | NT Seq Id | AA Seq ID | NT Orf Length | AA Orf Length | Score | Probability | Description |
|---|---|---|---|---|---|---|---|---|
| contig605 | 26306550_c3_27 | 1837 | 5242 | 960 | 319 | 1019 | 5.10E-103 | sequence element 1341] [GN:acp] [OR:Bacillus subtilis] [DN:sporulation initiation protein spoOKE] [GN:spoOKE] |
| contig605 | 26594702_c1_20 | 1838 | 5243 | 1059 | 352 | 1097 | 2.80E-111 | [AC:M57689] [OR:Bacillus subtilis] [PN:sporulation protein] [GN:spoOKD] |
| contig605 | 9964030_c1_19 | 1839 | 5244 | 1089 | 362 | 713 | 1.40E-70 | [AC:U78885] [OR:Listeria monocytogenes] [PN:transport system permease homolog] [NT:similar to bacterial transport system permease] |
| contig605 | 16053215_c2_26 | 1840 | 5245 | 885 | 294 | 655 | 1.90E-64 | [SP:P24138] [OR:BACILLUS SUBTILIS] [GN:OPPB] [DE:OLIGOPEPTIDE TRANSPORT SYSTEM PERMEASE PROTEIN OPPB] |
| contig605 | 24417178_c2_25 | 1841 | 5246 | 210 | 69 | 56 | 0.43 | [OR:Chlamydia trachomatis] [PN:hypothetical protein N-5] |
| contig605 | 4476643_f3_16 | 1842 | 5247 | 360 | 119 | 86 | 0.0026 | [SP:P54142] [OR:CAENORHABDITIS ELEGANS] [GN:SRB-7] [DE:SRB-7 PROTEIN] |
| contig605 | 5860431_c2_24 | 1843 | 5248 | 705 | 234 | 437 | 2.40E-41 | [OR:Enterococcus faecalis] [PN:probable pheromone binding protein;pheromone responsive gene Z protein] [GN:prgZ] |
| contig606 | 34646067_c2_17 | 1844 | 5249 | 345 | 114 | 75 | 0.12 | [AC:AB003080] [OR:Xenopus laevis] [PN:cardiac troponin C] |
| contig606 | 32423135_c2_16 | 1845 | 5250 | 474 | 157 | 239 | 2.30E-20 | [SP:P54604] [OR:BACILLUS SUBTILIS] [GN:YHCT] [DE:HYPOTHETICAL 33.7 KD PROTEIN IN CSPB-GLPP INTERGENIC REGION] |
| contig606 | 994082_c3_20 | 1846 | 5251 | 228 | 75 | 74 | 0.046 | [SP:P44433] [OR:HAEMOPHILUS INFLUENZAE] [GN:HI0412] [DE:HYPOTHETICAL PROTEIN HI0412] |
| contig606 | 3142842_c2_15 | 1847 | 5252 | 810 | 269 | 234 | 7.80E-20 | [SP:P47374] [OR:MYCOPLASMA GENITALIUM] [GN:MG128] [DE:HYPOTHETICAL PROTEIN MG128] |
| contig606 | 23835952_c2_14 | 1848 | 5253 | 705 | 234 | 398 | 3.30E-37 | [SP:P39583] [OR:BACILLUS SUBTILIS] [GN:YWAC] [DE:HYPOTHETICAL 24.6 KD PROTEIN IN DAE-TYRZ INTERGENIC REGION] |
| contig606 | 9767187_f1_4 | 1849 | 5254 | 669 | 222 | 91 | 0.061 | [SP:P45267] [OR:HAEMOPHILUS INFLUENZAE] [GN:HI1598] [DE:HYPOTHETICAL PROTEIN HI1598] |
| contig606 | 4891077_f1_5 | 1850 | 5255 | 660 | 219 | 80 | 0.66 | [SP:P16169] [OR:RUMINOCOCCUS FLAVEFACIENS] [GN:CELA] [DE:CELLODEXTRINASE A,] |
| contig606 | 26056507_c3_18 | 1851 | 5256 | 1815 | 604 | 1573 | 1.00E-161 | [AC:D88209] [OR:Bacillus licheniformis] [PN:Pz-peptidase] |
| contig606 | 4105213_c1_13 | 1852 | 5257 | 198 | 65 | 71 | 0.13 | [AC:U76757] [OR:Pinus radiata] [PN:FLORICAULA/LEAFY-like protein] [GN:NEEDLY] [NT:floral meristem identity gene] |
| contig607 | 3907882_c3_42 | 1853 | 5258 | 1722 | 573 | 124 | 0.00031 | [SP:P32380] [OR:SACCHAROMYCES CEREVISIAE] [GN:NUF1] [DE:NUF1 PROTEIN (SPINDLE POLY BODY SPACER PROTEIN SPC110)] |
| contig607 | 24230002_c1_32 | 1854 | 5259 | 702 | 233 | 337 | 9.50E-31 | [OR:Methanococcus jannaschii] [PN:phosphate transport system regulatory protein homolog] |
| contig607 | 30194036_c2_37 | 1855 | 5260 | 918 | 305 | 841 | 3.70E-84 | [OR:Methanococcus jannaschii] [PN:phosphate transport system ATP-binding protein] |
| contig607 | 4397202_c1_31 | 1856 | 5261 | 792 | 263 | 811 | 5.60E-81 | [OR:Methanococcus jannaschii] [DN:phosphate transport system ATP-binding protein] |
| contig607 | 2620963_c2_36 | 1857 | 5262 | 903 | 300 | 560 | 2.20E-54 | [SP:P46340] [OR:BACILLUS SUBTILIS] [GN:YOG1] [DE:REGION (ORF73)] |
| contig607 | 36132765_c3_41 | 1858 | 5263 | 981 | 326 | 582 | 1.00E-56 | [SP:P46339] [OR:BACILLUS SUBTILIS] [GN:YOGH] |
| contig607 | 11991250_c1_30 | 1859 | 5264 | 921 | 306 | 728 | 3.50E-72 | [SP:P46338] [OR:BACILLUS SUBTILIS] [GN:YOGG] [DE:REGION PRECURSOR (ORF108)] |

TABLE 2-continued

| Contig | Orf | NT Seq Id | AA Seq ID | NT Orf Length | AA Orf Length | Score | Probability | Description |
|---|---|---|---|---|---|---|---|---|
| contig607 | 24302012_c3_40 | 1860 | 5265 | 402 | 133 | 114 | 1.80E-06 | [AC:U76418] [OR:*Neisseria gonorrhoeae*] [NT:putative integral membrane protein] |
| contig607 | 6258302_c1_29 | 1861 | 5266 | 630 | 209 | 73 | 0.023 | [SP:P43047] [OR:*MYCOPLASMA CAPRICOLUM*] [DE:HYPOTHEICAL PROTEIN IN LICA 3REGION (ORF R8) (FRAGMENT)] |
| contig607 | 4719136_c3_39 | 1862 | 5267 | 735 | 244 | 598 | 2.10E-58 | [AC:Z95150] [OR:*Mycobacterium tuberculosis*] [PN:FtsE] [GN:ftsE] [NT:MTCY164.13c, ftsE. len] |
| contig607 | 4082892_c3_38 | 1863 | 5268 | 750 | 249 | 809 | 9.20E-81 | [SP:P28367] [OR:*BACILLUS SUBTILIS*] [GN:PREB] [DE:PROBABLE PEPTIDE CHAIN RELEASE FACTOR 2 (RF-2) (FRAGMENT)] |
| contig608 | 1204703_c2_29 | 1864 | 5269 | 279 | 93 | 59 | 0.35 | [OR:*Methanococcus jannaschii*] [DN:hypothetical protein MJ1503] |
| contig608 | 6680437_c2_28 | 1865 | 5270 | 534 | 177 | 61 | 0.9995 | [AC:U78866] [OR:*Arabidopsis thaliana*] [GN:gene400] |
| contig608 | 23445452_c2_27 | 1866 | 5271 | 297 | 98 | 74 | 0.097 | [AC:JS0673] [OR:*Bacillus* sp.] [PN:neopullulanase,] |
| contig608 | 1058443_c2_26 | 1867 | 5272 | 282 | 93 | 69 | 0.41 | [AC:Z70314] [OR:*Arabidopsis thaliana*] [PN:heat-shock protein] |
| contig608 | 24406327_c2_25 | 1868 | 5273 | 1509 | 502 | 634 | 3.20E-62 | [AC:AB001488] [OR:*Bacillus subtilis*] [GN:ydcQ] [NT:SIMILAR TO ORI:21 OF *ENTEROCOCCUS FAECALIS*] |
| contig608 | 1367842_c2_24 | 1869 | 5274 | 387 | 128 | 92 | 8.70E-05 | [SP:Q57589] [OR:*METHANOCOCCUS JANNASCHII*] [GN:MJ0125] [DE:HYPOTHETICAL PROTEIN MJ0125] |
| contig608 | 26381332_c1_17 | 1870 | 5275 | 354 | 117 | 120 | 9.40E-08 | [SP:Q57877] [OR:*METHANOCOCCUS JANNASCHII*] [GN:MJ0435] [DE:HYPOTHETICAL PROTEIN MJ0435] |
| contig608 | 10996088_c2_23 | 1871 | 5276 | 345 | 114 | 60 | 0.82 | [AC:U29627] [OR:*Mus musculus*] [PN:Ig kappa chain] [NT:V-J region] |
| contig608 | 8462_c2_22 | 1872 | 5277 | 267 | 88 | 75 | 0.066 | [SP:P47267] [OR:*MYCOPLASMA GENITALIUM*] [GN:METS] [DE:(METRS)] |
| contig608 | 26367003_c1_16 | 1873 | 5278 | 198 | 65 | 73 | 0.19 | [AC:L29389] [OR:*Saccharomyces cerevisiae*] [PN:Fun12p] [GN:FUN12] |
| contig608 | 31447212_c2_21 | 1874 | 5279 | 228 | 75 | 65 | 0.57 | [SP:P39883] [OR:*BACTEROIDES NODOSUS*] [GN:PREC] [DE:PEPTIDE CHAIN RELEASE FACTOR 3 (RF-3)] |
| contig608 | 1072177_c1_15 | 1875 | 5280 | 408 | 135 | 71 | 0.41 | [AC:U09422] [OR:*Enterococcus faecalis*] [NT:ORF22] |
| contig608 | 4901587_c2_20 | 1876 | 5281 | 342 | 113 | 76 | 0.5 | [OR:*Methanococcus vannielii*] [PN:hypothetical protein] |
| contig608 | 34647187_c2_19 | 1877 | 5282 | 270 | 89 | 66 | 0.26 | [AC:U46570] [OR:*Homo sapiens*] [PN:tetratricopeptide repeat protein] [GN:tpr1] |
| contig608 | 7245312_c3_30 | 1878 | 5283 | 201 | 66 | 68 | 0.11 | [OR:*Cylindrotheca fusiformis*] [PN:hypothetical protein 217] |
| contig608 | 5131261_f1_6 | 1879 | 5284 | 390 | 129 | 252 | 9.70E-22 | [AC:AB001488] [OR:*Bacillus subtilis*] [GN:ydcN] [NT:PROBABLE REPRESSOR PROTEIN.] |
| contig608 | 11994193_f1_7 | 1880 | 5285 | 276 | 92 | 132 | 5.00E-09 | [AC:AB001488] [OR:*Bacillus subtilis*] [GN:ydcM] [NT:SIMILAR TO IMMUNITY REGION PROTEIN IN BACTERIOPHAGE] |
| contig608 | 24490755_f1_1 | 1881 | 5286 | 1491 | 496 | 82 | 0.59 | [AC:D64000] [OR:*Synechocystis* sp.] [PN:hypothetical protein] [NT:ORF_ID] |
| contig609 | 14746002_f3_7 | 1882 | 5287 | 195 | 64 | 149 | 7.90E-11 | [AC:Z80360] [OR:*Bacillus subtilis*] [PN:Unknown, highly similar to *Pseudomonas putida*] [GN:ywhB] |
| contig609 | 1171913_f3_8 | 1883 | 5288 | 2049 | 682 | 2321 | 5.50E-241 | [SP:P18255] [OR:*BACILLUS SUBTILIS*] [GN:THRS] [DE:(THRRS)] |
| contig609 | 960017_f2_3 | 1884 | 5289 | 2007 | 668 | 1240 | 1.90E-126 | [SP:P10524] [OR:*STREPTOCOCCUS PNEUMONIAE*] [GN:PENA] [DE:PENICILLIN-BINDING PROTEIN 2B] |
| contig609 | 31345627_c1_15 | 1885 | 5290 | 186 | 61 | 56 | 0.43 | [AC:Z92613] [OR:Human Immunodeficiency virus type 1] [PN:gp120, c2/v3 region] [GN:env] |
| contig609 | 21484388_f2_4 | 1886 | 5291 | 306 | 101 | 181 | 4.40E-13 | [AC:U582101 [OR:*Streptococcus thermophilus*] [PN:penicillin-binding protein 2b] [GN:pbp2b] [NT:pbp2b gene disruption causes cessation of |

TABLE 2-continued

| Contig | Orf | NT Seq Id | AA Seq ID | NT Orf Length | AA Orf Length | Score | Probability | Description |
|---|---|---|---|---|---|---|---|---|
| contig609 | 29378438_f1_2 | 1887 | 5292 | 192 | 63 | 225 | 7.00E-19 | [SP:P23375] [OR:*BACILLUS STEAROTHERMOPHILUS*] [GN:RPMG] [DE:50S RIBOSOMAL PROTEIN 1,33] |
| contig609 | 24428187_c1_12 | 1888 | 5293 | 681 | 226 | 287 | 1.90E-25 | [AC:U22342] [OR:*Bacteriophage* T270] [PN:integrase] [GN:int] [NT:excisionase] |
| contig609 | 14587808_c1_11 | 1889 | 5294 | 504 | 167 | 169 | 2.40E-12 | [AC:U22342] [OR:*Bacteriophage* T270] [PN:integrase] [GN:int] [NT:excisionase] |
| contig609 | 30564687_c3_28 | 1890 | 5295 | 786 | 261 | 139 | 2.70E-12 | [SP:P22459] [OR:*HOMO SAPIENS*] [GN:KCNA4] [DE:POTASSIUM CHANNEL PROTEIN KV 1.4 (HKI) (HPCN2) (HUKII)] |
| contig609 | 29585903_c3_27 | 1891 | 5296 | 363 | 120 | 60 | 0.22 | OR:*Bacillus subtilis* phage PBSX] [PN:hypothetical 6.5K protein (xre 3'region)] |
| contig61 | 10724937_c3_1 | 1892 | 5297 | 750 | 250 | 92 | 0.046 | [SP:P32677] [OR:*ESCHERICHIA COLI*] [GN:YIJO] [DE:(F283)] |
| contig610 | 2777188_f3_9 | 1893 | 5298 | 1200 | 399 | 60 | 0.84 | [AC:U37066] [OR:*Human endogenous retrovirus*] [PN:pol polyprotein] [GN:pol] |
| contig610 | 10562550_f2_5 | 1894 | 5299 | 576 | 191 | 262 | 8.40E-23 | [AC:U65015] [OR:*Vibrio furnissii*] [PN:PTS permease for mannose subunit IIIMan C] [GN:manx] [NT:ManX: IIAMan] |
| contig610 | 26761087_f1_2 | 1895 | 5300 | 840 | 279 | 309 | 8.80E-28 | [SP:P42910] [OR:*ESCHERICHIA COLI*] [GN:AGAC] [DE:(N-ACETYLGALACTOSAMINE-PERMEASE IIC COMPONENT 1)] |
| contig610 | 34651590_f2_6 | 1896 | 5301 | 837 | 278 | 260 | 1.40E-22 | [AC:U18997] [OR:*Escherichia coli*][[NT:ORF_o290; Geneplot suggests frameshift linking to] |
| contig610 | 34187562_f2_7 | 1897 | 5302 | 1950 | 649 | 127 | 0.00011 | [AC:U27586] [OR:*Cytophaga heparina*] [PN:heparinase III protein] [GN:HepC] |
| contig610 | 4687578_c2_16 | 1898 | 5303 | 225 | 74 | 55 | 0.52 | [AC:U82399] [OR:*Arabidopsis thaliana*] [PN:putative protein kinase PK 1] [GN:PK 1] [NT:similar to Arabidopsis thaliana receptor protein] |
| contig610 | 25583467_f2_8 | 1899 | 5304 | 429 | 142 | 175 | 1.40E-13 | [AC:U28163] [OR:*Lactobacillus curvatus*] [PN:EHA-man] [GN:mantA] [NT:mannose phosphotransferase system enzyme EII] |
| contig610 | 33464688_f1_4 | 1900 | 5305 | 663 | 220 | 336 | 1.20E-30 | [AC:U70664] [OR:*Haloferax alicantei*] [PN:2-dehydro-3-deoxyphosphogluconate aldolase] [NT:KDPG aldolase] |
| contig610 | 15757192_f2_4 | 1901 | 5306 | 1023 | 340 | 297 | 1.80E-26 | [AC:D64002] [OR:*Synechocystis* sp.] [PN:dGTP triphosphohydrolase] [GN:dgt] [NT:ORF_ID] |
| contig611 | 25680333_f2_5 | 1902 | 5307 | 2787 | 928 | 868 | 5.10E-87 | [SP:P23914] [OR:*BACILLUS SUBTILIS*] [GN:LEVR] [DE:TRANSCRIPTIONAL REGULATORY PROTEIN LEVR] |
| contig611 | 34664812_f1_1 | 1903 | 5308 | 486 | 161 | 127 | 1.70E-08 | [SP:P26379] [OR:*BACILLUS SUBTILIS*] [GN:LEVD] [DE:(EC 2.7.1.69) (P16)] |
| contig611 | 33204692_f3_10 | 1904 | 5309 | 507 | 168 | 225 | 7.00E-19 | [SP:P37081] [OR:*KLEBSIELLA PNEUMONIAE*] [GN:SORB] [DE:(EC 2.7.1.69) (EIII-B-SOR)] |
| contig611 | 4899187_f3_11 | 1905 | 5310 | 807 | 268 | 328 | 8.60E-30 | [AC:U65015] [OR:*Vibrio furnissii*] [PN:PTS permease for mannose subunit IIPMan] [GN:manY] [NT:ManY: Pel: IIDMan] |
| contig611 | 14884700_f1_2 | 1906 | 5311 | 837 | 278 | 439 | 1.50E-41 | [SP:P08188] [OR:*ESCHERICHIA COLI*] [GN:MANZ] [DE:(EII-M-MAN)] |
| contig611 | 159825_f2_6 | 1907 | 5312 | 405 | 134 | 135 | 3.20E-08 | [SP:P40831] [OR:*MYCOBACTERIUM LEPRAE*] [GN:GLMS] [DE:FRUCTOSE-6-PHOSPHATE AMIDOTRANSFERASE] |
| contig611 | 10978561_f3_12 | 1908 | 5313 | 255 | 84 | 55 | 0.89 | [AC:U84971] [OR:*Homo sapiens*] [PN:unknown] |
| contig611 | 26367207_f3_13 | 1909 | 5314 | 483 | 160 | 104 | 0.00068 | [SP:P72720] [OR:SYNECHOCYSTIS SP] [GN:GLMS] [DE:AMIDOTRANSFERASE] (GLUCOSAMINE-6-PHOSPHATE SYNTHASE)] |
| contig611 | 26364637_f2_7 | 1910 | 5315 | 771 | 257 | 215 | 1.20E-17 | [AC:U19620] [OR:*Agrobacterium tumefaciens*] [GN:MocD] [GN:mocD] |
| contig612 | 31301443_c3_45 | 1911 | 5316 | 435 | 145 | 70 | 0.028 | [AC:L14772] [OR:*Human herpesvirus* 6] [GN:CB5R] |

TABLE 2-continued

| Contig | Orf | NT Seq Id | AA Seq ID | NT Orf Length | AA Orf Length | Score | Probability | Description |
|---|---|---|---|---|---|---|---|---|
| contig612 | 24402187_c3_44 | 1912 | 5317 | 210 | 69 | 68 | 0.24 | [AC:AC001229] [OR:*Arabidopsis thaliana*] [GN:F5I14.7] [NT:Similar to Saccharomyces hypothetical protein] |
| contig612 | 4876327_c2_37 | 1913 | 5318 | 1554 | 517 | 360 | 2.50E-31 | [SP:Q01262] [OR:*PSEUDOMONAS SP*] [GN:HYUA] [DE:HYDANTOIN UTILIZATION PROTEIN A (ORF2)] |
| contig612 | 25589437_c2_36 | 1914 | 5319 | 1125 | 374 | 77 | 0.25 | [SP:P25525] [OR:*ESCHERICHIA COLI*] [GN:CODB] [DE:CYTOSINE PERMEASE] |
| contig612 | 87800_c1_28 | 1915 | 5320 | 408 | 135 | | | |
| contig612 | 34414818_c3_43 | 1916 | 5321 | 1053 | 350 | 186 | 2.50E-12 | [SP:P25525] [OR:*ESCHERICHIA COLI*] [GN:CODB] [DE:CYTOSINE PERMEASE] |
| contig612 | 24257813_c1_26 | 1917 | 5322 | 1596 | 531 | 122 | 0.00012 | [SP:P44509] [OR:*HAEMOPHILUS INFLUENZAE*] [GN:H10093] [DE:HYPOTHETICAL PROTEIN H10093] |
| contig612 | 861002_c2_33 | 1918 | 5323 | 1275 | 424 | 476 | 2.80E-63 | [AC:D90846] [OR:*Escherichia coli*] [PN:Collagenase precursor (EC 3.4.—.—.)] [NT:ORF_ID] |
| contig612 | 24253582_c2_32 | 1919 | 5324 | 948 | 315 | 207 | 1.00E-18 | [AC:D90846] [OR:*Escherichia coli*] [PN:Collagenase precursor(EC 3.4.—.—.)] [NT:ORF_ID] |
| contig612 | 5204505_f3_6 | 1920 | 5325 | 2136 | 711 | 58 | 0.999 | [AC:X07718] [OR:*Homo sapiens*] [NT:fibronectin (63 AA) (2998 is 2nd base in codon)] |
| contig613 | 34257967_c1_9 | 1921 | 5326 | 1542 | 513 | 189 | 3.30E-14 | [SP:P43461] [OR:*ALTEROMONAS CARRAGEENOVORA*] [DE:HYPOTHETICAL TRANSCRIPTIONAL REGULATOR IN CGKA 5'REGION (FRAGMENT)] |
| contig613 | 6151890_c2_12 | 1922 | 5327 | 1776 | 591 | 274 | 5.00E-21 | [AC:I42945] [OR:*Staphylococcus aureus*] [GN:lytS] |
| contig613 | 11725127_c1_8 | 1923 | 5328 | 312 | 103 | 65 | 0.16 | [OR:*mitochondrion Paracentrotus lividus*] [PN:NADH dehydrogenase, chain ND4L] |
| contig614 | 23831508_c1_21 | 1924 | 5329 | 414 | 138 | 65 | 0.9 | [AC:U34331] [OR:*Drosophila melanogaster*] [PN:cytochrome P450] [GN:Cyp4e4] [NT:Description] |
| contig614 | 23516080_c3_25 | 1925 | 5330 | 345 | 114 | 240 | 1.40E-19 | [SP:P34038] [OR:*LACTOBACILLUS DELBRUECKII*] [GN:PYK] [DE:PYRUVATE KINASE,] |
| contig614 | 784676_c2_23 | 1926 | 5331 | 1476 | 491 | 1479 | 9.20E-152 | [SP:Q02499] [OR:*BACILLUS STEAROTHERMOPHILUS*] [GN:PYK] [DE:PYRUVATE KINASE, (PK)] |
| contig614 | 32228441_c1_20 | 1927 | 5332 | 966 | 321 | 1046 | 7.00E-106 | [SP:P00512] [OR:*BACILLUS STEAROTHERMOPHILUS*] [DE:(PHOSPHOHEXOKINASE)] |
| contig614 | 34642188_c3_24 | 1928 | 5333 | 3381 | 1126 | 1341 | 3.90E-137 | [SP:P14567] [OR:*SALMONELLA TYPHIMURIUM*] [GN:DNAE] [DE:DNA POLYMERASE III, ALPHA CHAIN,] |
| contig614 | 15914687_f1_8 | 1929 | 5334 | 201 | 66 | 64 | 0.55 | [AC:U40075] [OR:*Oxalobacter formigenes*] [PN:oxalate] [GN:oxlT] [NT:OxlT; OxlT is a hydrophobic membrane antiport] |
| contig615 | 29880442_f3_8 | 1930 | 5335 | 1209 | 402 | 930 | 1.40E-93 | [AC:U78036] [OR:*Lactococcus lactis*] [PN:dipeptidase] |
| contig615 | 24433427_f3_9 | 1931 | 5336 | 249 | 82 | 64 | 0.32 | [AC:Y12655] [OR:*Pseudomonas putida*] [PN:putative regulatory protein] [GN:oxoS] |
| contig615 | 12695151_f3_10 | 1932 | 5337 | 192 | 63 | 62 | 0.29 | [SP:P10068] [OR:*RATTUS NORVEGICUS*] [DE:GAMMA CRYSTALLIN F (4-1)] |
| contig615 | 24664057_c3_26 | 1933 | 5338 | 1059 | 352 | 115 | 0.00035 | [SP:P55431] [OR:*RHIZOBIUM SP*] [GN:NOLL] [DE:NODULATION PROTEIN NOLL] |
| contig615 | 4881577_f1_2 | 1934 | 5339 | 954 | 317 | 648 | 1.10E-63 | [SP:Q45460] [OR:*BACILLUS SUBTILIS*] [GN:PROV] [DE:GLYCINE BETAINE/L-PROLINE TRANSPORT ATP-BINDING PROTEIN PROV] |
| contig615 | 2867077_f1_3 | 1935 | 5340 | 1518 | 505 | 373 | 1.50E-34 | [SP:Q45462] [OR:*BACILLUS SUBTILIS*] [GN:PROX] [DE:GLYCINE BETAINE-BINDING PROTEIN PROX PRECURSOR] |
| contig615 | 5959812_f1_4 | 1936 | 5341 | 222 | 73 | 121 | 7.40E-08 | [SP:P17893] [OR:*BACILLUS SUBTILIS*] [GN:AHRC] |

TABLE 2-continued

| Contig | Orf | NT Seq Id | AA Seq ID | NT Orf Length | AA Orf Length | Score | Probability | Description |
|---|---|---|---|---|---|---|---|---|
| contig615 | 24228178_f3_11 | 1937 | 5342 | 312 | 103 | 132 | 5.00E-09 | [DE:ARGININE HYDROXIMATE RESISTANCE PROTEIN] [SP:P17893] [OR:BACILLUS SUBTILIS] [GN:AHRC] |
| contig615 | 55462_f3_12 | 1938 | 5343 | 1563 | 520 | 820 | 6.30E-82 | [DE:ARGININE HYDROXYMATE RESISTANCE PROTEIN] [AC:X75898] [OR:Spinacia oleracea] [PN:phosphoglucomutase] [GN:pgm] |
| contig615 | 33397930_f2_7 | 1939 | 5344 | 597 | 198 | 149 | 7.90E-11 | [SP:P37354] [OR:ESCHERICHIA COLI] [GN:SPEG] [DE:ACETYLTRANSFERASE] (SAT) |
| contig615 | 1274192_c2_17 | 1940 | 5345 | 606 | 201 | 375 | 8.90E-35 | [SP:P54604] [OR:BACILLUS SUBTILIS] [GN:YHCT] [DE:HYPOTHETICAL 33.7 KD PROTEIN IN CSPB-GLPP INTERGENIC REGION] |
| contig616 | 4504382_c1_21 | 1941 | 5346 | 2346 | 782 | 2439 | 1.70E-253 | [SP:P49022] [OR:LACTOCOCCUS LACTIS] [GN:PIP] [DE:PHAGE INFECTION PROTEIN] |
| contig616 | 26369068_c1_20 | 1942 | 5347 | 234 | 77 | 74 | 0.13 | [AC:U41081] [OR:Danio rerio] [PN:b-catenin] [NT:cadherin-associated protein] |
| contig616 | 33790912_c2_25 | 1943 | 5348 | 735 | 244 | 175 | 1.40E-13 | [AC:Z92770] [OR:Mycobacterium tuberculosis] [PN:unknown] [GN:MTC15.27c] [NT:MTC15.27c, unknown, len] |
| contig616 | 3166553_f2_10 | 1944 | 5349 | 1485 | 494 | 76 | 0.97 | [OR:Vibrio cholerae] [PN:hypothetical protein] |
| contig616 | 11719813_c2_23 | 1945 | 5350 | 594 | 197 | 127 | 1.70E-08 | [SP:P41027] [OR:BACILLUS CALDOLYTICUS] [GN:SIPC] [DE:SIGNAL PEPTIDASE 1, (SPASE 1) (LEADER PEPTIDASE 1)] |
| contig616 | 24612911_c2_22 | 1946 | 5351 | 333 | 110 | 82 | 0.016 | [SP:P39046] [OR:ENTEROCOCCUS HIRAE] [DE:(MURAMIDASE 2)] |
| contig616 | 34179077_c1_17 | 1947 | 5352 | 1296 | 431 | 122 | 1.60E-05 | [AC:M63109] [OR:Leishmania major] [PN:glycoprotein 96-92] [GN:GP 96-92] |
| contig617 | 207068_f1_1 | 1948 | 5353 | 243 | 80 | 180 | 7.70E-13 | [SP:Q24803] [OR:ENTAMOEBA HISTOLYTICA] [GN:ADH2] [DE:ALCOHOL DEHYDROGENASE 2.] |
| contig617 | 24347552_f2_7 | 1949 | 5354 | 855 | 284 | 755 | 4.80E-75 | [SP:Q24803] [OR:ENTAMOEBA HISTOLYTICA] [GN:ADH2] [DE:ALCOHOL DEHYDROGENASE 2.] |
| contig617 | 24890826_c1_15 | 1950 | 5355 | 1122 | 373 | 478 | 1.10E-45 | [AC:D90913] [OR:Synechocystis sp] [PN:hypothetical protein] [NT:ORF_ID] |
| contig617 | 5114677_c3_21 | 1951 | 5356 | 1113 | 370 | 162 | 1.20E-09 | [SP:Q58487] [OR:METHANOCOCCUS JANNASCHII] [GN:MJ1087] [DE:MEVALONATE KINASE, (MK)] |
| contig617 | 14317312_c1_14 | 1952 | 5357 | 1080 | 359 | 330 | 5.30E-30 | [SP:P32377] [OR:SACCHAROMYCES CEREVISIAE] [GN:ERG19] [DE:PYROPHOSPHATE DECARBOXYLASE] |
| contig617 | 11916394_c2_17 | 1953 | 5358 | 561 | 186 | 135 | 1.40E-08 | [SP:P46086] [OR:ARABIDOPSIS THALIANA] [DE:MEVALONATE KINASE, (MK)] |
| contig617 | 21504717_f1_1 | 1954 | 5359 | 1197 | 398 | 570 | 1.90E-55 | [AC:D90905] [OR:Synechocystis sp.] [PN:hypothetical protein] [NT:ORF_ID] |
| contig618 | 21617177_c2_15 | 1955 | 5360 | 429 | 142 | 65 | 0.68 | [AC:X95276] [OR:Plasmodium falciparum] [GN:rp14] |
| contig618 | 30078825_c2_14 | 1956 | 5361 | 3162 | 1053 | 1902 | 1.40E-196 | [AC:AE000389] [OR:Escherichia coli] [PN:phospho-beta-D-gatactosidase; alpha-subunit] [GN:ebgA][NT:o1042; This 1042 aa orf is 99 pct identical (1] |
| contig618 | 23475178_c1_13 | 1957 | 5362 | 1536 | 511 | 1442 | 7.70E-148 | [AC:D49537] [OR:Clostridium perfringens] [PN:membrane-spanning transporter protein] [GN:ORF54] |
| contig618 | 33408567_f2_9 | 1958 | 5363 | 843 | 280 | 236 | 4.80E-20 | [SP:Q00753] [OR:STREPTOCOCCUS MUTANS] [GN:MSMR] [DE:MSM OPERON REGULATORY PROTEIN] |
| contig618 | 36135303_f3_12 | 1959 | 5364 | 447 | 148 | 50 | 0.98 | [AC:U42599] [OR:Borrelia burgdorferi] [PN:OspE] [GN:ospE] |
| contig619 | 24422252_f3_7 | 1960 | 5365 | 981 | 326 | 183 | 6.30E-20 | [AC:U70214] [OR:Escherichia coli] [GN:yaeG] [NT:hypothetical] |
| contig619 | 12556693_f2_3 | 1961 | 5366 | 915 | 304 | 392 | 1.40E-36 | [SP:P39074] [OR:BACILLUS SUBTILIS] [GN:BMRU] [DE:BMRU PROTEIN] |

TABLE 2-continued

| Contig | Orf | NT Seq Id | AA Seq ID | NT Orf Length | AA Orf Length | Score | Probability | Description |
|---|---|---|---|---|---|---|---|---|
| contig619 | 23647812_f2_4 | 1962 | 5367 | 813 | 270 | 93 | 0.083 | [AC:D90900] [OR:Synechocystis sp.] [PN:hypothetical protein] [NT:ORF_ID] |
| contig619 | 24645332_c2_15 | 1963 | 5368 | 1716 | 571 | 573 | 9.30E-56 | [SP:P46921] [OR:BACILLUS SUBTILIS] [GN:OPUAB] [DE:GLYCINE BETAINE TRANSPORT SYSTEM PERMEASE PROTEIN OPUAB] |
| contig619 | 22051018_c1_10 | 1964 | 5369 | 1122 | 373 | 1093 | 7.40E-111 | [SP:P46920] [OR:BACILLUS SUBTILIS] [GN:OPUAA] [DE:GLYCINE BETAINE TRANSPORT ATP-BINDING PROTEIN OPUAA] |
| contig619 | 161081_f2_2 | 1965 | 5370 | 798 | 265 | 822 | 3.80E-82 | [SP:Q54089] [OR:STREPTOCOCCUS EQUISIMILIS] [GN:RELA] [DE:PROTEIN] |
| contig620 | 156251_c1_13 | 1966 | 5371 | 252 | 84 | 65 | 0.78 | [AC:Y09632] [OR:Mus musculus] [PN:Kinesin-like protein 174] |
| contig620 | 25442152_c3_21 | 1967 | 5372 | 789 | 262 | 872 | 1.90E-87 | [OR:Mycobacterium leprae] [PN:pps1 protein] |
| contig620 | 25682817_c2_16 | 1968 | 5373 | 528 | 175 | 390 | 2.30E-35 | [OR:Mycobacterium leprae] [PN:pps1 protein] |
| contig620 | 1042200_c2_15 | 1969 | 5374 | 504 | 167 | 289 | 1.20E-25 | [OR:Mycobacterium leprae] [PN:nitrogen fixation gene homolog nifU7] |
| contig620 | 23492342_c1_11 | 1970 | 5375 | 1251 | 416 | 1009 | 5.90E-102 | [AC:D64004] [OR:Synechocystis s.] [PN:NifS] [GN:nifS] [NT:ORF_ID] |
| contig620 | 6835952_c2_14 | 1971 | 5376 | 1287 | 428 | 329 | 1.10E-40 | [OR:Mycobacterium leprae] [PN:pps1 protein] |
| contig620 | 34414008_c3_19 | 1972 | 5377 | 825 | 274 | 714 | 1.10E-70 | [SP:P48255] [OR:CYANOPHORA PARADOXA] [GN:YCF16] [DE:PROBABLE ATP-DEPENDENT TRANSPORTER YCF16] |
| contig620 | 22285030_f3_9 | 1973 | 5378 | 264 | 87 | 64 | 0.078 | [SP:34851] [OR:APIS MELLIFERA] [GN:ND3] [DE:NADH-UBIQUINONE OXIDOREDUCTASE CHAIN 3,] |
| contig620 | 23525317_c3_18 | 1974 | 5379 | 561 | 186 | 516 | 1.00E-49 | [AC:D90915] [OR:Synechocystis sp.] [PN:ribosome releasing factor] [GN:frr] [NT:ORF_ID] |
| contig620 | 26565942_c3_17 | 1975 | 5380 | 744 | 247 | 719 | 3.20E-71 | [AC:D90915] [OR:Synechocystis sp.] [PN:uridine monophosphate kinase] [GN:pyrH] [NT:ORF_ID] |
| contig621 | 634687_c2_24 | 1976 | 5381 | 654 | 217 | 159 | 6.90E-12 | [SP:Q10516] [OR:MYCOBACTERIUM TUBERCULOSIS] [GN:MTCY427.14] [DE:HYPOTHETICAL 14.3 KD PROTEIN CY427.14] |
| contig621 | 33247761_c3_26 | 1977 | 5382 | 1170 | 389 | 1120 | 1.00E-113 | [SP:P39131] [OR:BACILLUS SUBTILIS] [GN:YVYH] [DE:GLCNAC-2-EPIMERASE] |
| contig621 | 7291075_c2_22 | 1978 | 5383 | 186 | 61 | 113 | 5.20E-07 | [SP:Q57752] [OR:METHANOCOCCUS JANNASCHII] [GN:MJ0304] [DE:HYPOTHETICAL PROTEIN MJ0304] |
| contig621 | 24611586_c1_17 | 1979 | 5384 | 426 | 141 | 293 | 4.40E-26 | [OR:Coxiella burnetii] [PN:hypothetical protein 206] |
| contig621 | 676885_c2_20 | 1980 | 5385 | 1806 | 601 | 1098 | 2.20E-111 | [SP:Q11047] [OR:MYCOBACTERIUM TUBERCULOSIS] [GN:MTCY50.10] [DE:HYPOTHETICAL ABC TRANSPORTER ATP-BINDING PROTEIN CY50.10] |
| contig621 | 4698450_c3_25 | 1981 | 5386 | 1728 | 575 | 1000 | 5.30E-101 | [SP:Q11046] [OR:MYCOBACTERIUM TUBERCULOSIS] [GN:MTCY50.09] [DE:HYPOTHETICAL ABC TRANSPORTER ATP-BINDING PROTEIN CY50.09] |
| contig621 | 976577_f2_9 | 1982 | 5387 | 387 | 128 | 143 | 3.40E-10 | [SP:P45808] [OR:ESCHERICHIA COLI] [GN:YBAN] [DE:HYPOTHETICAL 14.8 KD PROTEIN IN PRIC-APT INTERGENIC REGION] |
| contig621 | 25586592_f3_14 | 1983 | 5388 | 213 | 71 | 62 | 0.26 | [SP:P01283] [OR:Rattus norvegicus] [NT:VIP precursor (1 is 2nd base in codon)] |
| contig622 | 34187712_f3_12 | 1984 | 5389 | 228 | 75 | 176 | 1.10E-13 | [OR:Methanococcus jannaschii] [PN:hypothetical protein MJ0272] |
| contig622 | 26225187_c1_22 | 1985 | 5390 | 1056 | 351 | 797 | 1.70E-79 | [SP:P21516] [OR:ESCHERICHIA COLI] [GN:QUEA] [DE:(QUEUOSINE BIOSYNTHESIS PROTEIN QUEA] |
| contig622 | 22299053_f1_1 | 1986 | 5391 | 207 | 68 | 131 | 6.40E-09 | [AC:L43135] [OR:Methylobacterium extorquens] [PN:dioxygenase] |

TABLE 2-continued

| Contig | Orf | NT Seq Id | AA Seq ID | NT Orf Length | AA Orf Length | Score | Probability | Description |
|---|---|---|---|---|---|---|---|---|
| contig622 | 976567_f1_2 | 1987 | 5392 | 681 | 226 | 230 | 2.10E-19 | [NT:ORF88; putative] [AC:AB001488] [OR:*Bacillus subtilis*] [GN:ydtO] [NT:SIMILAR TO PENTACHLOROPHENOL-INDUCED PERIPLASMIC] |
| contig622 | 9772763_f3_15 | 1988 | 5393 | 387 | 128 | 298 | 1.30E-26 | [SP:Q45460] [OR:*BACILLUS SUBTILIS*] [GN:PROV] [DE:GLYCINE BETAINE/L-PROLINE TRANSPORT ATP-BINDING PROTEIN PROV] |
| contig622 | 12704715_f3_16 | 1989 | 5394 | 711 | 236 | 666 | 1.30E-65 | [SP:Q45460] [OR:*BACILLUS SUBTILIS*] [GN:PROV] [DE:GLYCINE BETAINE/L-PROLINE TRANSPORT ATP-BINDING PROTEIN PROV] |
| contig622 | 33478433_f3_17 | 1990 | 5395 | 639 | 212 | 488 | 9.50E-47 | [SP:Q45461] [OR:*BACILLUS SUBTILIS*] [GN:PROW] [DE:GLYCINE BETAINE/L-PROLINE TRANSPORT SYSTEM PERMEASE PROTEIN PROW] |
| contig622 | 33725676_f2_8 | 1991 | 5396 | 1047 | 348 | 734 | 8.10E-73 | [SP:Q45462] [OR:*BACILLUS SUBTILIS*] [GN:PROX] [DE:GLYCINE BETAINE-BINDING PROTEIN PROX PRECURSOR] |
| contig622 | 23634711_f2_9 | 1992 | 5397 | 666 | 221 | 407 | 3.60E-38 | [AC:U38418] [OR:*Bacillus subtilis*] [PN:ProZ] [GN:proZ] [NT:Method] |
| contig622 | 21882186_f1_5 | 1993 | 5398 | 552 | 183 | 73 | 0.79 | [SP:Q08021] [OR:*SALMONELLA TYPHIMURIUM*] [GN:YIGM] [DE:HYPOTHETICAL 18.3 KD PROTEIN IN MIAE 3'REGION (ORF 18.3)] |
| contig622 | 25673899_c1_18 | 1994 | 5399 | 1776 | 591 | 1285 | 3.30E-131 | [AC:AB001488] [OR:*Bacillus subtilis*] [GN:ydaO] NT:FUNCTION UNKNOWN, WEAK SIMILARITY TO YEEF_ECOL1.] |
| contig622 | 35679675_f3_10 | 1995 | 5400 | 543 | 180 | 468 | 1.20E-44 | [SP:P49778] [OR:*BACILLUS SUBTILIS*] [GN:YOHU] [DE:PUTATIVE ELONGATION FACTOR P (EF-P)] |
| contig623 | 4875918_f1_1 | 1996 | 5401 | 840 | 279 | 712 | 1.70E-70 | [AC:U93874] [OR:*Bacillus subtilis*] [PN:cysteine synthase] [GN:yrhA] [NT:similar to cysteine synthase from Spinacia] |
| contig623 | 504838_f1_2 | 1997 | 5402 | 1149 | 382 | 1141 | 6.00E-116 | [AC:U93874] [OR:*Bacillus subtilis*] [PN:cystathionine gamma-lyase] [GN:yrhB] [NT:similar to Rattus norvegicus cystathionine] |
| contig623 | 26802318_c1_15 | 1998 | 5403 | 1371 | 456 | 1555 | 8.10E-160 | [SP:P42973] [OR:*BACILLUS SUBTILIS*] [GN:BGLA][DE:6-PHOSPHO-BETA-GLUCOSIDASE,] |
| contig623 | 892332_c2_18 | 1999 | 5404 | 1380 | 459 | 451 | 1.20E-54 | [AC:D88802] [OR:*Bacillus subtilis*] [GN:ydhO] [NT:*B. subtilis* cellobiose phosphotransferase system] |
| contig623 | 15754667_f1_5 | 2000 | 5405 | 258 | 85 | 63 | 0.66 | [AC:AB001721] [OR:*Leptospira interrogans*] [NT:ORF5] |
| contig623 | 13714717_c3_20 | 2001 | 5406 | 774 | 257 | 188 | 5.90E-15 | [SP:P54717] [OR:*BACILLUS SUBTILIS*] [GN:YFIA] [DE:HYPOTHETICAL 29.3 KD PROTEIN IN GLVG-GLVBC INTERGENIC REGION] |
| contig623 | 34375017_f2_9 | 2002 | 5407 | 597 | 198 | 324 | 2.30E-29 | [SP:P45862] [OR:*BACILLUS SUBTILIS*] [GN:YWJB] [DE:HYPOTHETICAL 19.6 KD PROTEIN IN ACDA 5'REGION] |
| contig623 | 1218831_f1_8 | 2003 | 5408 | 567 | 189 | 345 | 1.40E-31 | [SP:P43440] [OR:*ENTEROCOCCUS HIRAE*] [GN:NTPJ] [DE:TRANSLOCATING ATPASE SUBUNIT J] |
| contig624 | 15634811_f3_8 | 2004 | 5409 | 390 | 129 | 150 | 6.20E-11 | [SP:P44994] [OR:*HAEMOPHILUS INFLUENZAE*] [GN:HI1030] [DE:HYPOTHETICAL PROTEIN HI1030] |
| contig624 | 24804712_f2_5 | 2005 | 5410 | 1320 | 439 | 713 | 1.40E-70 | [SP:P40800] [OR:*SALMONELLA TYPHIMURIUM*] [GN:YGIK] [DE:HYPOTHETICAL 46.1 KD PROTEIN IN PLSC 3'REGION] |
| contig624 | 3922338_c3_25 | 2006 | 5411 | 882 | 293 | 134 | 2.00E-12 | [SP:P28809] [OR:*PSEUDOMONAS AERUGINOSA*] [GN:MMSR] [DE:MMSAB OPERON REGULATORY PROTEIN] |
| contig624 | 1252302_c1_13 | 2007 | 5412 | 240 | 79 | 65 | 0.085 | [SP:P23896] [OR:*ESCHERICHIA COLI*] [GN:YBA] [DE:HYPOTHETICAL 15.6 KD PROTEIN IN PGI-XYLE INTERGENIC REGION (O136)] |

TABLE 2-continued

| Contig | Orf | NT Seq Id | AA Seq ID | NT Orf Length | AA Orf Length | Score | Probability | Description |
|---|---|---|---|---|---|---|---|---|
| contig624 | 223171730_f1_3 | 2008 | 5413 | 1536 | 511 | 1247 | 3.50E-127 | [AC:Z93938] [OR:*Bacillus subtilis*] [PN:rhamnulose kinase] [GN:yulC] NT:putative] |
| contig624 | 23629650_f3_9 | 2009 | 5414 | 1335 | 444 | 1346 | 1.10E-137 | [AC:Z93938] [OR:*Bacillus subtilis*] [PN:L-rhamnose isomerase] [GN:yulE] [NT:putative] |
| contig624 | 36213436_f3_10 | 2010 | 5415 | 870 | 289 | 715 | 8.40E-71 | [SP:P32169] [OR:*ESCHERICHIA COLI*] [GN:RHAD] [DE:RHAMNULOSE-1-PHOSPHATE ALDOLASE,] |
| contig624 | 569142_f2_7 | 2011 | 5416 | 375 | 124 | 226 | 5.50E-19 | [SP:P32156] [OR:*ESCHERICHIA COLI*] [GN:YIJL] [DE:HYPOTHETICAL 12.3 KD PROTEIN IN RHAD 3'REGION (F104)] |
| contig624 | 4507943_c1_17 | 2012 | 5417 | 357 | 119 | 137 | 3.30E-09 | [SP:P39398] [OR:*ESCHERICHIA COLI*] [GN:YIJL] [DE:HYPOTHETICAL. 28.5 KD PROTEIN IN TSR-MDOB INTERGENIC REGION (F261B)] |
| contig625 | 1428183_c1_16 | 2013 | 5418 | 843 | 280 | 1280 | 1.10E-130 | [SP:P77129] [OR:*ESCHERICHIA COLI*] [GN:YLBE] [DE:HYPOTHETICAL 45.0 KD PROTEIN IN FDRA-PURK INTERGENIC REGION (ORF2)] |
| contig625 | 22275307_c3_23 | 2014 | 5419 | 3015 | 1004 | | | |
| contig625 | 4381250_f1_5 | 2015 | 5420 | 1626 | 541 | 115 | 0.00079 | [AC:U07214] [OR:*Escherichia coli*] [GN:yaeG] [NT:hypothetical] |
| contig625 | 22707943_f2_8 | 2016 | 5421 | 273 | 90 | 77 | 0.0099 | [AC:JU0313] [OR:*Escherichia coli*] [PN:hypothetical 22.7K protein (visA 3'region)] |
| contig625 | 24390877_f2_9 | 2017 | 5422 | 552 | 183 | 91 | 0.0008 | [SP:Q58049] [OR:*METHANOCOCCUS JANNASCHII*] [GN:MJ0632] [DE:HYPOTHETICAL ATP-BINDING PROTEIN MJ0632] |
| contig625 | 20360260_f3_14 | 2018 | 5423 | 279 | 92 | | | |
| contig626 | 4179702_f2_10 | 2019 | 5424 | 342 | 113 | 93 | 6.80E-05 | [AC:X98141] [OR:*Escherichia coli*] [GN:doc] |
| contig626 | 2397837_c2_16 | 2020 | 5425 | 345 | 115 | 232 | 1.50E-19 | [SP:P45213] [OR:*HAEMOPHILUS INFLUENZAE*] [GN:HI1455] [DE:HYPOTHETICAL PROTEIN HI1455] |
| contig626 | 3449312_c2_15 | 2021 | 5426 | 579 | 192 | 384 | 1.00E-35 | [SP:Q02169] [OR:*BACILLUS SUBTILIS*] [GN:MAF] [DE:MAF PROTEIN] |
| contig626 | 31838313_c2_14 | 2022 | 5427 | 2160 | 719 | 1054 | 7.80E-178 | [SP:P14160] [OR:*STREPTOCOCCUS PNEUMONIAE*] [GN:HEXB] [DE:DNA MISMATCH REPAIR PROTEIN HEXB] |
| contig626 | 24397702_c1_12 | 2023 | 5428 | 2577 | 858 | 2281 | 9.50E-237 | [SP:P49849] [OR:*BACILLUS SUBTILIS*] [GN:MUTS] [DE:DNA MISMATCH REPAIR PROTEIN MUTS] |
| contig626 | 7228462_c1_11 | 2024 | 5429 | 390 | 129 | 104 | 0.00016 | [OR:*Homo sapiens*] [PN:CG1 protein] |
| contig627 | 30251308_f2_3 | 2025 | 5430 | 840 | 279 | 168 | 9.00E-11 | [SP:P77728] [OR:*ESCHERICHIA COLI*] [GN:APBA] [DE:APBA PROTEIN] |
| contig627 | 25604812_f3_6 | 2026 | 5431 | 1029 | 342 | 271 | 9.40E-24 | [AC:U56999] [OR:*Treponema pallidum*] [PN:pfoS/R] [GN:pfoS/R] [NT:potential regulatory molecule; pfoS/R-like] |
| contig627 | 11039717_c3_18 | 2027 | 5432 | 810 | 269 | 615 | 3.30E-60 | [OR:*Streptococcus thermophilus*] [PN:transposase] |
| contig627 | 3947263_f3_7 | 2028 | 5433 | 648 | 215 | 1128 | 1.40E-114 | [OR:*Enterococcus faecium*] [PN:transposase] |
| contig627 | 13808206_f1_1 | 2029 | 5434 | 246 | 81 | 164 | 2.00E-12 | [AC:JC5008] [OR:*Lactococcus lactis*] [PN:hypothetical 6.5K protein (insertion sequence IS1297] |
| contig627 | 14578162_f1_2 | 2030 | 5435 | 450 | 149 | 77 | 0.77 | [SP:Q08430] [OR:*BACILLUS SUBTILIS*] [GN:KINB] [DE:SPORULATION KINASE B,] |
| contig627 | 23865952_c3_17 | 2031 | 5436 | 201 | 66 | 143 | 3.40E-10 | [OR:*Methanococcus jannaschii*] [PN:hypothetical protein MJ0272] |
| contig627 | 36226561_c3_16 | 2032 | 5437 | 303 | 100 | | | |
| contig627 | 34042840_f3_9 | 2033 | 5438 | 222 | 73 | 171 | 3.70E-13 | [OR:*Enterococcus faecalis*] [PN:cyIL-L protein] |
| contig627 | 3179042_f1_10 | 2034 | 5439 | 198 | 65 | 320 | 6.00E-29 | [OR:*Enterococcus faecalis*] [PN:cyIL-S protein] |
| contig627 | 15901287_f3_11 | 2035 | 5440 | 1422 | 473 | 2160 | 6.30E-224 | [OR:*Enterococcus faecalis*] [PN:cyIM protein] |
| contig628 | 6332831_f3_7 | 2036 | 5441 | 1188 | 395 | 306 | 1.80E-27 | [AC:U77778] [OR:*Staphylococcus epidermidis*] [PN:putative |

TABLE 2-continued

| Contig | Orf | NT Seq Id | AA Seq ID | NT Orf Length | AA Orf Length | Score | Probability | Description |
|---|---|---|---|---|---|---|---|---|
| contig628 | 23706300_f1_1 | 2037 | 5442 | 1080 | 359 | 629 | 1.10E-61 | membrane protein] [GN:epiH] [NT:EpiH] [AC:AB001488] [OR:Bacillus subtilis] [GN:ydb] [NT:FUNCTION UNKNOWN, SIMILAR PRODUCTS IN SYNECHOCYSTIS] |
| contig628 | 6757825_c3_22 | 2038 | 5443 | 2412 | 803 | 934 | 5.20E-94 | [AC:Z82038] [OR:Thermoanaerobacterium thermosaccharolyticum] [PN:acetyl coenzyme A acetyltransferase (thiolase)] [GN:thlA] |
| contig628 | 9775176_f1_2 | 2039 | 5444 | 1350 | 449 | 310 | 9.20E-35 | [OR:Caenorhabditis elegans] [PN:hydroxymethylglutaryl-CoA synthase homolog] |
| contig628 | 24413428_c1_16 | 2040 | 5445 | 810 | 269 | 100 | 0.073 | [AC:Z49130] [OR:Caenorhabditis elegans] [PN:T06D8.1] [NT:cDNA EST yk19H2.3 comes from this gene; cDNA EST |
| contig628 | 994087_c1_15 | 2041 | 5446 | 606 | 201 | 352 | 2.40E-32 | [AC:AE000218] [OR:Escherichia coli] [NT:f210; 30 pct identical (16 gaps) to 181 residues] |
| contig628 | 4882827_c1_14 | 2042 | 5447 | 984 | 327 | 599 | 8.30E-68 | [AC:AE000218] [OR:Escherichia coli] [NT:f366; 35 pct identical (32 gaps) to 355 residues] |
| contig629 | 19629155_f3_13 | 2043 | 5448 | 246 | 81 | 230 | 2.10E-19 | [SP:P12044] [OR:BACILLUS SUBTILIS] [GN:PURE] [DE:(EC 4.1.1.21) (AIR CARBOXYLASE) (AIRC)] |
| contig629 | 10757836_f1_1 | 2044 | 5449 | 1188 | 395 | 867 | 6.50E-87 | [SP:P12045] [OR:BACILLUS SUBTILIS] [GN:PURE] [DE:(AIR CARBOXYLASE) (AIRC)] |
| contig629 | 24805253_f2_8 | 2045 | 5450 | 657 | 218 | 550 | 2.60E-53 | [SP:P12046] [OR:BACILLUS SUBTILIS] [GN:PURC] [DE:(SAICAR SYNTHETASE)] |
| contig629 | 25428336_f2_9 | 2046 | 5451 | 276 | 91 | 208 | 4.40E-17 | [SP:P12049] [OR:BACILLUS SUBTILIS] [GN:YEXA] [DE:HYPOTHETICAL 9.7 KD PROTEIN IN PUR OPERON] |
| contig629 | 16804702_f2_10 | 2047 | 5452 | 675 | 224 | 727 | 4.50E-72 | [SP:P12041] [OR:BACILLUS SUBTILIS] [GN:PURQ] [DE:SYNTHASE I] |
| contig629 | 24843937_f1_2 | 2048 | 5453 | 1419 | 472 | 1637 | 1.70E-168 | [SP:P12042] [OR:BACILLUS SUBTILIS] [GN:PURL] [DE:SYNTHASE II] |
| contig629 | 14962831_f2_11 | 2049 | 5454 | 846 | 281 | 751 | 1.30E-74 | [SP:P12042] [OR:BACILLUS SUBTILIS] [GN:PURL] [DE:SYNTHASE II] |
| contig629 | 954765_f1_3 | 2050 | 5455 | 1494 | 497 | 1513 | 2.30E-155 | [SP:P00497] [OR:BACILLUS SUBTILIS] [GN:PURF] [DE:PHOSPHORIBOSYLPYROPHOSPHATE AMIDOTRANSFERASE) (ATASE)] |
| contig629 | 2932812_f2_12 | 2051 | 5456 | 1056 | 351 | 919 | 2.00E-92 | [SP:P12043] [OR:BACILLUS SUBTILIS] [GN:PURM] [DE:(PHOSPHORIBOSYL-AMINOIMIDAZOLE SYNTHETASE) (AIR SYNTHASE)] |
| contig629 | 3927193_f1_5 | 2052 | 5457 | 582 | 193 | 532 | 2.10E-51 | [SP:P12040] [OR:BACILLUS SUBTILIS] [GN:PURN] [DE:TRANSFORMYLASE] (5-PHOSPHORIBOSYLGLYCINAMIDE TRANSFORMYLASE) |
| contig629 | 7070808_f3_15 | 2053 | 5458 | 1614 | 538 | 1619 | 1.30E-166 | [SP:P12048] [OR:BACILLUS SUBTILIS] [GN:PURH] [DE:(INOSINICASE) (IMP SYNTHETASE) (AITC)] |
| contig63 | 36132250_c3_6 | 2054 | 5459 | 252 | 83 | 66 | 0.048 | [OR:Oryctolagus cuniculus] [PN:beta-myosin] |
| contig63 | 16600832_c2_5 | 2055 | 5460 | 744 | 247 | 438 | 1.90E-41 | [AC:AE000157] [NT:o292; This 292 aa orf is 44 pct identical (1 gaps)] |
| contig630 | 13789052_f3_7 | 2056 | 5461 | 501 | 166 | 59 | 0.47 | [SP:P48274] [OR:CYANOPHORA PARADOXA] [GN:YCF34] [DE:HYPOTHETICAL 8.9 KD PROTEIN YCF34 |
| contig630 | 26228381_f2_4 | 2057 | 5462 | 249 | 82 | 117 | 2.00E-07 | [AC:U09422] [OR:Enterococcus faecalis] [NT:ORF8] |
| contig630 | 4085762_c2_16 | 2058 | 5463 | 198 | 65 | 61 | 0.18 | [SP:P12079] [OR:HOMO SAPIENS] [DE:GLUTATHIONE PEROXIDASE-RELATED PROTEIN 1, (GPRP)] |
| contig630 | 3953160_f2_5 | 2059 | 5464 | 300 | 99 | 88 | 0.00023 | [SP:P22876] [OR:SACCHAROPOLYSPORA ERYTHRAEA] [GN:XIS] [DE:POSSIBLE EXCISIONASE] |
| contig630 | 24392762_f3_8 | 2060 | 5465 | 1218 | 405 | 233 | 9.00E-18 | [AC:AB00148] [OR:Bacillus subtilis] [GN:ydcL] [NT:PROBABLE |

TABLE 2-continued

| Contig | Orf | NT Seq Id | AA Seq ID | NT Orf Length | AA Orf Length | Score | Probability | Description |
|---|---|---|---|---|---|---|---|---|
| contig630 | 24508562_c2_15 | 2061 | 5466 | 2166 | 721 | 1171 | 4.00E-119 | INTEGRASE.] [OR:*Methanococcus jannaschii*] [PN:ferrous iron transport protein B] |
| contig630 | 1281577_c3_18 | 2062 | 5467 | 474 | 157 | 98 | 2.00E-05 | [SP:P33649] [OR:*ESCHERICHIA COLI*] [GN:FEOA] [DE:FERROUS IRON TRANSPORT PROTEIN A] |
| contig631 | 34490800_c2_22 | 2063 | 5468 | 1413 | 471 | 1085 | 5.20E-110 | [SP:P43752] [OR:*HAEMOPHILUS INFLUENZAE*] [GN:NRDD] [DE:ANAEROBIC RIBONUCLEOSIDE-TRIPHOSPHATE REDUCTASE.] |
| contig631 | 35207811_f3_11 | 2064 | 5469 | 789 | 262 | 600 | 1.30E-58 | [SP:P42423] [OR:*BACILLUS SUBTILIS*] [GN:YXDL] [DE:HYPOTHETICAL ABC TRANSPORTER ATP-BINDING PROTEIN IN IDH 3'REGION] |
| contig631 | 24069087_f1_3 | 2065 | 5470 | 2136 | 711 | 134 | 3.90E-14 | [AC:Z94043] [OR:*Bacillus subtilis*] [PN:hypothetical protein] [GN:yvcS] [NT:probable permease] |
| contig631 | 33984816_f2_7 | 2066 | 5471 | 1545 | 514 | 1352 | 2.60E-138 | [SP:P35854] [OR:*LACTOBACILLUS CASEI*] [GN:DLTA] [DE:CARRIER PROTEIN LIGASE) (DCL] |
| contig631 | 22117268_f1_4 | 2067 | 5472 | 1218 | 405 | 1123 | 4.90E-114 | [SP:P35855] [OR:*LACTOBACILLUS CASEI*] [GN:DLTB] [DE:DLTB PROTEIN (BASIC MEMBRANE PROTEIN) (BMP)] |
| contig631 | 392535_c2_20 | 2068 | 5473 | 231 | 76 | 62 | 0.72 | [SP:P22015] [OR:*USTILAGO MAYDIS*] [DE:MATING-TYPE LOCUS ALLELE B1 PROTEIN] |
| contig631 | 24407802_f3_13 | 2069 | 5474 | 273 | 90 | 223 | 1.10E-18 | [SP:P55153] [OR:*LACTOBACILLUS CASEI*] [GN:DLTC] [DE:D-ALANYL CARRIER PROTEIN (DCP)] |
| contig631 | 24900267_f2_9 | 2070 | 5475 | 1326 | 441 | 549 | 3.30E-53 | [SP:P39578] [OR:*BACILLUS SUBTILIS*] [GN:DLTD] [DE:PROTEIN DLTD PRECURSOR] |
| contig631 | 26250035_c1_14 | 2071 | 5476 | 297 | 98 | 53 | 0.69 | [OR:*Mycoplasma capricolum*] [PN:hypothetical protein] |
| contig631 | 10598431_c1_14 | 2072 | 5477 | 1779 | 592 | 1128 | 5.60E-119 | [SP:Q11047] [OR:*MYCOBACTERIUM TUBERCULOSIS*] [GN:MTCY50.10] [DE:HYPOTHETICAL ABC TRANSPORTER ATP-BINDING PROTEIN CY50.10] |
| contig632 | 2922200_c2_17 | 2073 | 5478 | 1728 | 575 | 1041 | 2.40E-105 | [SP:Q11046] [OR:*MYCOBACTERIUM TUBERCULOSIS*] [GN:MTCY50.09] [DE:HYPOTHETICAL ABC TRANSPORTER ATP-BINDING PROTEIN CY50.09] |
| contig632 | 4345686_c3_20 | 2074 | 5479 | 708 | 235 | 126 | 2.50E-06 | [AC:Z92669] [OR:*Mycobacterium tuberculosis*] [PN:unknown] [GN:MTCY08D5.28] [NT:MTCY08D5.28, probable regulatory protein, len] |
| contig632 | 34398312_c3_19 | 2075 | 5480 | 594 | 197 | 187 | 7.50E-15 | [SP:P47353] [OR:*MYCOPLASMA GENITALIUM*] [GN:GMK] [DE:GUANYLATE KINASE. (GMP KINASE)] |
| contig632 | 35194712_c2_16 | 2076 | 5481 | 1470 | 489 | 1448 | 1.80E-148 | [AC:D31856] [OR:*Bacillus subtilis*] [PN:hypothetical protein] [GN:N17D] [NT:homologous to 6-phospho-beta-glucosidase] |
| contig632 | 193825_c2_15 | 2077 | 5482 | 951 | 316 | 572 | 1.20E-55 | [AC:L49336] [OR:*Clostridium longisporum*] [PN:PTS-dependent enzyme II] [GN:abgF] |
| contig632 | 79181_f1_6 | 2078 | 5483 | 315 | 104 | 103 | 6.00E-06 | [OR:*Pinus taeda*] [PN:arabinogalactan-like protein] |
| contig633 | 1407037_f3_8 | 2079 | 5484 | 555 | 184 | 194 | 5.60E-15 | [SP:P44941] [OR:*HAEMOPHILUS INFLUENZAE*] [GN:HI0933] [DE:HYPOTHETICAL PROTEIN HI0933] |
| contig633 | 29975066_c1_16 | 2080 | 5485 | 1515 | 504 | 804 | 3.10E-80 | [SP:P23212] [OR:*STAPHYLOCOCCUS EPIDERMIDIS*] [GN:MSRA] [DE:ERYTHROMYCIN RESISTANCE ATP-BINDING PROTEIN MSRA] |
| contig633 | 23834388_f3_12 | 2081 | 5486 | 636 | 211 | 51 | 0.999 | [AC:X77084] [OR:Aleutian mink disease parvovirus] [GN:NS-3] |
| contig633 | 21671936_c1_15 | 2082 | 5487 | 1422 | 473 | 1239 | 2.50E-126 | [SP:P46320] [OR:*BACILLUS SUBTILIS*] [GN:CELF] [DE:PROBABLE 6-PHOSPHO-BETA-GLUCOSIDASE.] |
| contig633 | 11056562_f1_3 | 2083 | 5488 | 1002 | 333 | 444 | 4.40E-42 | [AC:Y14081] [OR:*Bacillus subtilis*] [PN:hypothetical protein] [GN:yhjM] [NT:Similarity to repressors of the lacI family; like |

TABLE 2-continued

| Contig | Orf | NT Seq Id | AA Seq ID | NT Orf Length | AA Orf Length | Score | Probability | Description |
|---|---|---|---|---|---|---|---|---|
| contig633 | 31834452_c2_17 | 2084 | 5489 | 888 | 295 | 229 | 8.20E-19 | [AC:Z54312] [OR:Lactobacillus sake] [PN:unknown] [GN:orf414] |
| contig634 | 34163952_c3_30 | 2085 | 5490 | 417 | 138 | 64 | 0.998 | [AC:JQ0472] [OR:Bos primigenius taurus] [PN:T-cell receptor beta chain (BTB4)] [GN:BTB4] |
| contig634 | 25820187_c2_28 | 2086 | 5491 | 300 | 99 | 60 | 0.44 | [AC:D89228] [OR:Schizosaccharomyces pombe] [NT:unnamed protein product] |
| contig634 | 2932682_c2_27 | 2087 | 5492 | 546 | 181 | 131 | 5.20E-08 | [SP:P07905] [OR:ESCHERICHIA COLI] [GN:DNAC] [DE:DNA REPLICATION PROTEIN DNAC] |
| contig634 | 42505_c1_20 | 2088 | 5493 | 381 | 126 | 77 | 0.22 | [AC:U20184] [OR:Arabidopsis thaliana] [PN:MADS-box protein AGL14] [GN:AGL14] [NT:putative transcription factor] |
| contig634 | 34511087_c2_25 | 2089 | 5494 | 804 | 267 | 226 | 5.50E-19 | [OR:phage SPP1] [PN:gene 38 protein] |
| contig634 | 3962715_c2_24 | 2090 | 5495 | 855 | 284 | 58 | 0.86 | [OR:phage T4] [PN:dexA.1 protein] [GN:dexA.1] |
| contig634 | 35535792_c1_19 | 2091 | 5496 | 1056 | 351 | 154 | 2.40E-09 | [AC:D90774] [OR:Escherichia coli] [PN:RecT protein (P33).] [GN:recT] [NT:ORF_ID] |
| contig634 | 5116632_c1_18 | 2092 | 5497 | 231 | 76 | 66 | 0.048 | [AC:S78737] [OR:Homo sapiens] [PN:ATP-regulated potassium channel] [NT:This sequence comes from FIG. 1.] |
| contig634 | 9878942_c2_22 | 2093 | 5498 | 366 | 121 | 71 | 0.96 | [SP:Q10907] [OR:CAENORHABDITIS ELEGANS] [GN:AH9.4] [DE:HYPOTHETICAL 45.0 KD PROT EIN AH9.4 IN CHROMOSOME X] |
| contig634 | 36520303_c1_17 | 2094 | 5499 | 354 | 117 | | | |
| contig634 | 6855307_c2_21 | 2095 | 5500 | 276 | 91 | | | |
| contig634 | 16447338_c3_29 | 2096 | 5501 | 282 | 93 | 70 | 0.019 | [OR:Coxiella burnetii] [PN:hypothetical protein] |
| contig634 | 24640887_f2_11 | 2097 | 5502 | 321 | 106 | 71 | 0.9 | [AC:AC000108] [OR:Helicobacter pylori] [PN:ORF14] [NT:ORF14-similar to axoneme-associated protein] |
| contig634 | 2345260_f2_12 | 2098 | 5503 | 441 | 146 | 65 | 0.96 | [SP:P18415] [OR:STAPHYLOCOCCUS AUREUS] [GN:BLA1] [DE:REPRESSOR PROTEIN] |
| contig634 | 656250_c1_15 | 2099 | 5504 | 249 | 82 | 60 | 0.68 | [AC:Z33071] [OR:Mycoplasma capricolum] [PN:DNA gyrase (alpha)] [NT:ORF identified by homology to SwissProt entry] |
| contig634 | 25396878_f1_7 | 2100 | 5505 | 258 | 86 | 62 | 0.12 | [AC:X02297] [OR:Paramecium primaurelia] [NT:51A immobilization antigen fragment (1 is 3rd base) |
| contig634 | 34648462_c3_19 | 2101 | 5506 | 336 | 111 | 156 | 7.60E-11 | [SP:Q084321] [OR:BACILLUS SUBTILIS] [GN:PATB] [DE:PUTAITVE AMINOTRANSFERASE B.] |
| contig635 | 26679803_f2_3 | 2102 | 5507 | 414 | 137 | 252 | 9.70E-22 | [AC:293934] [OR:Bacillus subtilis] [PN:unknown] [GN:yug1] |
| contig635 | 25428187_f3_4 | 2103 | 5508 | 384 | 127 | 67 | 0.6 | [SP:P32090] [OR:PROTEUS VULGARIS] [GN:MUTT] [DE:(8-OXO-DGTPASE), DGTP PYROPHOSPHOHYDROLASE)] |
| contig635 | 13172588_c3_16 | 2104 | 5509 | 219 | 72 | 119 | 1.20E-07 | [OR:Homo sapiens] [PN:pG1 protein] |
| contig636 | 19798212_c3_24 | 2105 | 5510 | 966 | 322 | 100 | 0.011 | [OR:Clostridium perfringens] [PN:virS protein] [GN:virS] |
| contig636 | 13710942_f3_7 | 2106 | 5511 | 267 | 88 | 54 | 0.6 | [OR:Lepidoglyphus destructor] [PN:lepdI allergen] |
| contig636 | 24414137_c1_14 | 2107 | 5512 | 729 | 242 | 299 | 1.00E-26 | [AC:D14877] [OR:Clostridium perfringens] [PN:positive regulator for virulence factors] |
| contig636 | 15729837_f1_2 | 2108 | 5513 | 444 | 147 | 53 | 0.93 | [SP:P39243] [OR:BACTERIOPHAGE T4] [GN:Y16K] [DE:HYPOTHETICAL 8.1 KD PROTEIN IN NDD-DENB INTERGENIC REGION] |
| contig636 | 36609387_f1_3 | 2109 | 5514 | 933 | 310 | 892 | 1.50E-89 | [AC:Z94043] [OR:Bacillus subtilis] [PN:hypothetical protein] [GN:yvcH] [NT:probable thioredoxin reductase] |
| contig636 | 30351587_c1_9 | 2110 | 5515 | 486 | 161 | 77 | 0.85 | [SP:P19935] [OR:ESCHERICHIA COLI] [GN:TOLB] [DE:TOLB PROTEIN PRECURSOR] |
| contig636 | 23625202_c3_22 | 2111 | 5516 | 531 | 176 | 71 | 0.97 | [AC:M77730] [OR:Plasmodium falciparum] [PN:major merozoite surface antigen] [GN:p190] |
| contig636 | 16538127_f3_8 | 2112 | 5517 | 213 | 70 | 72 | 0.039 | [SP:P25198] [OR:RHIZOBIUM MELILOTI] [GN:NOlH] |

TABLE 2-continued

| Contig | Orf | NT Seq Id | AA Seq ID | NT Orf Length | AA Orf Length | Score | Probability | Description |
|---|---|---|---|---|---|---|---|---|
| contig636 | 5917126_c2_18 | 2113 | 5518 | 2385 | 794 | 427 | 6.10E-47 | [DE:NODULATION PROTEIN NOLH PRECURSOR] [AC:AE000189] [OR:Escherichia coli] [NT:o648 was o669; This 669 aa orf is 40 pct identical] |
| contig636 | 25977328_f1_6 | 2114 | 5519 | 510 | 169 | 93 | 0.00078 | [SP:P55740] [OR:ESCHERICHIA COLI] [GN:SLYA] [DE:TRANSCRIPTIONAL REGULATOR SLYA] |
| contig636 | 23572126_c3_21 | 2115 | 5520 | 867 | 288 | 487 | 1.20E-46 | [OR:Klebsiella oxytoca] [PN:malG protein homolog cymG] [GN:cymG] |
| contig636 | 957275_c3_20 | 2116 | 5521 | 510 | 169 | 365 | 1.00E-33 | [OR:Klebsiella oxytoca] [PN:malF protein homolog cymF] [GN:cymF] |
| contig637 | 19665937_c1_18 | 2117 | 5522 | 354 | 117 | 448 | 1.60E-42 | [SP:P09122] [OR:BACILLUS SUBTILIS] [GN:DNAX] [DE:DNA POLYMERASE III SUBUNITS GAMMA AND TAU.] |
| contig637 | 34074076_c2_24 | 2118 | 5523 | 1305 | 434 | 461 | 6.90E-44 | [AC:U21942] [OR:Streptococcus mutans] [PN:galactose-1-P-uridyl transferase] |
| contig637 | 979687_c1_17 | 2119 | 5524 | 1026 | 341 | 1095 | 4.50E-111 | [AC:U21942] [OR:Streptococcus mutans] [PN:UDP-galactose 4-epimerase] |
| contig637 | 6907812_c1_15 | 2120 | 5525 | 1860 | 619 | 63 | 0.79 | [OR:Trichosporon beigelii] [PN:phenol hydroxylase] |
| contig637 | 5120217_c3_26 | 2121 | 5526 | 357 | 118 | 266 | 3.20E-23 | [AC:AE000274] [OR:Escherichia coli] [NT:o122; This 122 aa orf is 34 pct identical (5 gaps)] |
| contig637 | 27317_c2_22 | 2122 | 5527 | 414 | 137 | 296 | 2.10E-26 | [SP:P54510] [OR:BACILLUS SUBTILIS] [GN:YQHL] [DE:HYPOTHETICAL 14.6 KD PROTEIN IN GCVT-SPOIIIAA INTERGENIC REGION] |
| contig637 | 24798577_c2_21 | 2123 | 5528 | 972 | 323 | 544 | 1.10E-52 | [SP:P54495] [OR:BACILLUS SUBTILIS] [GN:YQGR] [DE:HYPOTHETICAL 33.5 KD PROTEIN IN SODA-COMGA INTERGENIC REGION] |
| contig637 | 1428437_c2_20 | 2124 | 5529 | 258 | 85 | 138 | 1.20E-09 | [SP:P54494] [OR:BACILLUS SUBTILIS] [GN:YQGQ] [DE:HYPOTHETICAL 8.6 KD PROTEIN IN SODA-COMGA INTERGENIC REGION] |
| contig637 | 24662500_c3_25 | 2125 | 5530 | 798 | 265 | 287 | 6.60E-25 | [SP:P54493] [OR:BACILLUS SUBTILIS] [GN:YQGP] [DE:HYPOTHETICAL 56.4 KD PROTEIN IN SODA-COMGA INTERGENIC REGION] |
| contig637 | 9767342_c2_19 | 2126 | 5531 | 630 | 209 | 145 | 2.10E-10 | [SP:P54491] [OR:BACILLUS SUBTILIS] [GN:YQGN] [DE:HYPOTHETICAL 21.4 KD PROTEIN IN SODA-COMGA INTERGENIC REGION] |
| contig637 | 19968768_f2_11 | 2127 | 5532 | 828 | 275 | 287 | 1.90E-25 | [SP:P54544] [OR:BACILLUS SUBTILIS] [GN:YQJG] [DE:PRECURSOR] |
| contig638 | 25899193_c3_37 | 2128 | 5533 | 207 | 68 | 67 | 0.05 | [AC:D90906] [OR:Synechocystis sp.] [PN:DNA binding protein HU] [NT:ORF_ID] |
| contig638 | 23948427_c3_36 | 2129 | 5534 | 2121 | 706 | 1633 | 4.40E-168 | [SP:P54381] [OR:BACILLUS SUBTILIS] [GN:GLYS] [DE:BETA CHAIN) (GLYRS)] |
| contig638 | 11754377_c2_32 | 2130 | 5535 | 972 | 323 | 1234 | 8.40E-126 | [SP:P54380] [OR:BACILLUS SUBTILIS] [GN:GLYQ] [DE:ALPHA CHAIN) (GLYRS)] |
| contig638 | 35944827_c1_27 | 2131 | 5536 | 789 | 262 | 441 | 9.10E-42 | [SP:P42095] [OR:BACILLUS SUBTILIS] [GN:YQXN] [DE:(ORF3)] |
| contig638 | 20704400_c3_34 | 2132 | 5537 | 963 | 320 | 1053 | 1.30E-106 | [SP:P37214] [OR:STREPTOCOCCUS MUTANS] [GN:SPG] [DE:GTP-BINDING PROTEIN ERA HOMOLOG] |
| contig638 | 16830202_c2_31 | 2133 | 5538 | 408 | 135 | 256 | 3.60E-22 | [OR:Streptococcus mutans] [PN:diacylglycerol kinase homolog] |
| contig638 | 4119051_c1_26 | 2134 | 5539 | 483 | 160 | 460 | 8.80E-44 | [SP:P46347] [OR:BACILLUS SUBTILIS] [GN:YOFG] [DE:HYPOTHETICAL 17.8 KD PROTEIN IN PHOH-DGKA INTERGENIC REGION] |
| contig638 | 16425759_c2_30 | 2135 | 5540 | 2109 | 702 | 891 | 1.90E-89 | [SP:P46344] [OR:BACILLUS SUBTILIS] [GN:YOFF] [DE:HYPOTHETICAL 79.2 KD PROTEIN IN PHOH-DGKA |

TABLE 2-continued

| Contig | Orf | NT Seq Id | AA Seq ID | NT Orf Length | AA Orf Length | Score | Probability | Description |
|---|---|---|---|---|---|---|---|---|
| contig639 | 1429217_f2_4 | 2136 | 5541 | 1419 | 472 | 352 | 1.50E-60 | INTERGENIC REGION] [SP:P43440] [OR:ENTEROCOCCUS HIRAE] [GN:NTPJ] [DE:TRANSLOCATING ATPASE SUBUNIT J] |
| contig639 | 21725430_c3_12 | 2137 | 5542 | 3600 | 1199 | 3480 | 0 | [SP:P19543] [OR:ENTEROBACTER AGGLOMERANS] [GN:NIFJ] [DE:PYRUVATE-FLAVODOXIN OXIDOREDUCTASE,] |
| contig639 | 30739712_c1_8 | 2138 | 5543 | 1437 | 478 | 1090 | 1.50E-110 | [AC:D86223] [OR:Pyrococcus sp.] [PN:glutamate synthase] |
| contig64 | 30125205_f1_1 | 2139 | 5544 | 297 | 98 | 66 | 0.048 | [AC:U34772] [OR:Dichelobacter nodosus] [PN:virulence-associated protein 1] [GN:vapI] |
| contig64 | 23962762_f2_3 | 2140 | 5545 | 498 | 165 | 52 | 0.98 | [OR:Lactobacillus curvatus] [PN:hypothetical protein] |
| contig64 | 9803925_f1_2 | 2141 | 5546 | 204 | 68 | 54 | 0.6 | [SP:P10720] [OR:HOMO SAPIENS] [GN:PF4V1] [DE:PLATELET FACTOR 4 VARIANT PRECURSOR (PF4VAR1)] |
| contig640 | 26617692_c3_30 | 2142 | 5547 | 1482 | 493 | 782 | 6.60E-78 | [SP:P17547] [OR:ESCHERICHIA COLI] [GN:ADHE] [DE:(PFL DEACTIVASE)] |
| contig640 | 914077_c1_24 | 2143 | 5548 | 519 | 172 | 135 | 2.40E-09 | [SP:P45690] [OR:THIOBACILLUS NEAPOLITANUS] [GN:CSOS1B] [DE:MAJOR CARBOXYSOME SHELL PROTEIN 1B] |
| contig640 | 24635962_c3_29 | 2144 | 5549 | 681 | 226 | 577 | 3.50E-56 | [AC:AE000331] [OR:Escherichia coli] [NT:f219; This 219 aa orf is 30 pct identical (17 gaps)] |
| contig640 | 7239052_c2_26 | 2145 | 5550 | 933 | 310 | 479 | 8.50E-46 | [AC:D90873] [OR:Escherichia coli] [PN:ETHANOLAMINE AMMONIA-LYASE LIGHT CHAIN (EC] [GN:eutC] [NT:similar to SwissProt Accession Number P19636] |
| contig640 | 34648425_c3_28 | 2146 | 5551 | 1386 | 461 | 1493 | 3.00E-153 | [AC:D90873] [OR:Escherichia coli] [PN:ETHANOLAMINE AMMONIA-LYASE HEAVY CHAIN (EC] [GN:eutB] [NT:similar to SwissProt Accession Number P19635] |
| contig640 | 29297703_c1_23 | 2147 | 5552 | 1461 | 486 | 735 | 6.40E-73 | [AC:AE000332] [OR:Escherichia coli] [NT:f467; This 467 aa orf is 31 pct identical (2 gaps)] |
| contig640 | 1039077_c1_22 | 2148 | 5553 | 1434 | 477 | 330 | 1.10E-28 | [AC:Z95120] [OR:Mycobacterium tuberculosis] [GN:MYCY07D11.06] [NT:MTCY07D11.06. 501. Function] |
| contig640 | 36520462_c1_21 | 2149 | 5554 | 594 | 197 | 376 | 7.00E-35 | [AC:Z95554] [OR:Mycobacterium tuberculosis] [GN:MTCY01B2.18] [NT:MTCY01B2.18. 205. Function] |
| contig640 | 16678137_c1_20 | 2150 | 5555 | 447 | 148 | 280 | 1.00E-24 | [AC:AE000332] [OR:Escherichia coli] [NT:f135] |
| contig641 | 6345280_f3_11 | 2151 | 5556 | 423 | 140 | 269 | 1.50E-23 | [AC:D64004] [OR:Synechocystis sp.] [PN:hypothetical protein] [NT:ORF_ID] |
| contig641 | 24409376_f2_6 | 2152 | 5557 | 189 | 62 | 50 | 0.96 | [SP:P13556] [OR:RHODOBACTER CAPSULATUS] [GN:GLNB] [DE:NITROGEN REGULATORY PROTEIN P-II] |
| contig641 | 7057325_f3_12 | 2153 | 5558 | 1260 | 419 | 303 | 3.90E-27 | [SP:P45539] [OR:ESCHERICHIA COLI] [GN:YHFM] [DE:HYPOTHETICAL 47.5 KD PROTEIN IN CYSG-TRPS INTERGENIC REGION] |
| contig641 | 7067183_c3_35 | 2154 | 5559 | 261 | 86 | 55 | 0.57 | [AC:M76419] [OR:Mus musculus] [PN:mu-immunoglobulin] [GN:IgM] |
| contig641 | 22150325_c2_29 | 2155 | 5560 | 192 | 63 | 51 | 0.9999 | [SP:P45089] [OR:HAEMOPHILUS INFLUENZAE] [GN:ARTM] [DE:ARGININE TRANSPORT SYSTEM PERMEASE PROTEIN ARTM] |
| contig641 | 24422827_f3_13 | 2156 | 5561 | 969 | 322 | 649 | 8.20E-64 | [AC:U81957] [OR:Streptococcus gordonii] [PN:putative ABC transporter subunit ComYA] [GN:comYA] |
| contig641 | 35417813_f1_1 | 2157 | 5562 | 1062 | 353 | 390 | 2.30E-36 | [AC:U81957] [OR:Streptococcus gordonii] [PN:putative ABC transporter subunit ComYB] [GN:comYB] |
| contig641 | 172000_f3_14 | 2158 | 5563 | 228 | 75 | 63 | 0.54 | [SP:P12311] [OR:BACILLUS STEAROTHERMOPHILUS] [GN:ADHT] [DE:ALCOHOL DEHYDROGENASE, (ADH-T)] |

TABLE 2-continued

| Contig | Orf | NT Seq Id | AA Seq ID | NT Orf Length | AA Orf Length | Score | Probability | Description |
|---|---|---|---|---|---|---|---|---|
| contig641 | 19705332_f3_15 | 2159 | 5564 | 390 | 129 | 133 | 3.90E-09 | [AC:U81957] [OR:Streptococcus gordonii] [PN:ComYC] [GN:comYC] |
| contig641 | 33863802_f2_7 | 2160 | 5565 | 519 | 172 | 73 | 0.25 | [SP:P25956] [OR:BACILLUS SUBTILIS] [GN:COMGD] [DE:COMG OPERON PROTEIN 4 PRECURSOR] |
| contig641 | 5860633_c2_27 | 2161 | 5566 | 1197 | 398 | 327 | 1.10E-29 | [AC:AB001488] [OR:Bacillus subtilis] [GN:ydcL] [NT:PROBABLE INTEGRASE.] |
| contig641 | 7307956_f1_2 | 2162 | 5567 | 267 | 88 | 104 | 4.70E-06 | [AC:JN0536] [OR:Lactobacillus gasseri] [PN:hypothetical 8.3K protein] |
| contig641 | 5087517_c2_26 | 2163 | 5568 | 657 | 218 | 124 | 3.50E-08 | [AC:PN0468] [OR:Lactobacillus gasseri] [PN:hypothetical protein 106] |
| contig641 | 601387_c3_33 | 2164 | 5569 | 678 | 225 | 61 | 0.51 | [AC:V00667] [OR:Neurospora crassa] [NT:unidentified reading frame] |
| contig641 | 20314203_c2_25 | 2165 | 5570 | 342 | 113 | 110 | 1.10E-06 | [AC:U93364] [OR:Lactococcus lactis cremoris] [PN:EpsR] [GN:epsR] |
| contig641 | 970000_f1_4 | 2166 | 5571 | 249 | 82 | 71 | 0.079 | [AC:AB004635] [OR:Chlamys nipponensis] [PN:tropomyosin] |
| contig641 | 1227302_f3_17 | 2167 | 5572 | 327 | 108 | 52 | 0.82 | [AC:Y13856] [OR:Escherichia coli] [PN:RmoA] [GN:rmoA] |
| contig641 | 5359652_f1_5 | 2168 | 5573 | 759 | 252 | 152 | 5.30E-11 | [OR:phage phi-80] [PN:rha protein] |
| contig641 | 6152087_c3_31 | 2169 | 5574 | 204 | 67 | 50 | 0.995 | [OR:Methanococcus jannaschii] [PN:hypothetical protein MJ1624] |
| contig641 | 548540_f2_9 | 2170 | 5575 | 342 | 113 | | | |
| contig641 | 13839193_f2_10 | 2171 | 5576 | 354 | 117 | 58 | 0.91 | [SP:P77883] [OR:LACTOBACILLUS PLANTARUM] [GN:PYRB] [DE:TRANSCARBAMYLASE) (ATCASE) |
| contig642 | 14626378_c1_15 | 2172 | 5577 | 654 | 217 | 138 | 4.70E-08 | [AC:Y09476] [OR:Bacillus subtilis] [PN:AdaA] |
| contig642 | 34417182_c1_14 | 2173 | 5578 | 2835 | 944 | 1790 | 1.00E-184 | [SP:P23478] [OR:BACILLUS SUBTILIS] [GN:ADDA] [DE:ATP-DEPENDENT NUCLEASE SUBUNIT A] |
| contig642 | 24073342_c3_18 | 2174 | 5579 | 3621 | 1206 | 1248 | 2.80E-127 | [SP:P23477] [OR:BACILLUS SUBTILIS] [GN:ADDB] [DE:ATP-DEPENDENT NUCLEASE SUBUNIT B] |
| contig642 | 7220263_c1_13 | 2175 | 5580 | 570 | 189 | 366 | 8.00E-34 | [SP:P41027] [OR:BACILLUS CALDOLYTICUS] [GN:SIPC] [DE:SIGNAL PEPTIDASE I, (SPASE 1) (LEADER PEPTIDASE I] |
| contig642 | 24354567_c3_17 | 2176 | 5581 | 324 | 107 | 218 | 3.90E-18 | [AC:AE000137] [OR:Escherichia coli] [NT:o282; This 282 aa orf is 26 pct identical (2 gaps)] |
| contig643 | 1304837_f1_1 | 2177 | 5582 | 576 | 191 | 115 | 0.00023 | [SP:Q05233] [OR:MYCOBACTERIOPHAGE 1.5] [GN:26] [DE:MINOR TAIL PROTEIN GP26] |
| contig643 | 3365965_f2_5 | 2178 | 5583 | 813 | 270 | 61 | 0.61 | [AC:250863] [OR:Caenorhabditis elegans] [PN:F44A6.5] |
| contig643 | 25913143_f1_2 | 2179 | 5584 | 2820 | 939 | 128 | 5.60E-05 | [SP:P15132] [OR:BACTERIOPHAGE PHI-29] [GN:13] [DE:MORPHOGENESIS PROTEIN 1 (LATE PROTEIN GP13)] |
| contig643 | 24734836_f2_6 | 2180 | 5585 | 747 | 248 | 74 | 0.999 | [OR:Bombyx mori] [PN:DNA supercoiling factor] |
| contig643 | 16694203_f3_11 | 2181 | 5586 | 597 | 198 | 83 | 0.76 | [SP:P41513] [OR:ERWINIA CAROTOVORA] [GN:GYRA] [DE:DNA GYRASE SUBUNIT A,] |
| contig643 | 4116577_f2_7 | 2182 | 5587 | 288 | 95 | 59 | 0.34 | [SP:P30763] [OR:MYCOBACTERIUM LEPRAE] [GN:RPLL] [DE:50S RIBOSOMAL PROTEIN L7/L12] |
| contig643 | 36596062_f1_3 | 2183 | 5588 | 510 | 169 | 129 | 1.00E-08 | [AC:PC1127] [OR:Lactococcus lactis phage US3] [PN:hypothetical 110 protein (lytA 5' region)] |
| contig643 | 3914578_f2_8 | 2184 | 5589 | 354 | 117 | 53 | 0.69 | [AC:U70990] [OR:Stigmatella aurantiaca] [PN:cold shock-like protein] [GN:cspA] |
| contig643 | 321037_f3_12 | 2185 | 5590 | 192 | 63 | 57 | 0.36 | [SP:P54343] [OR:BACILLUS SUBTILIS] [GN:XKDX] [DE:PHAGE-LIKE ELEMENT PBSX PROTEIN XKDX] |
| contig643 | 33476678_f1_4 | 2186 | 5591 | 240 | 79 | 76 | 0.051 | [SP:Q04746] [OR:SACCHAROMYCES CEREVISIAE] [GN:YMR065W] [DE:HYPOTHETICAL 58.4 KD PROTEIN IN NCA1-HMS1 INTERGENIC REGION] |
| contig643 | 24644677_f2_9 | 2187 | 5592 | 312 | 103 | 78 | 0.016 | [AC:U15180] [OR:Mycobacterium leprae] [PN:malf] |
| contig644 | 35423311_f1_1 | 2188 | 5593 | 1137 | 378 | 120 | 0.00016 | [AC:AE000451] [OR:Escherichia coli] [GN:kup] [NT:o519; 100 pct identical (0 gaps) to 505 residues of] |

TABLE 2-continued

| Contig | Orf | NT Seq Id | AA Seq ID | NT Orf Length | AA Orf Length | Score | Probability | Description |
|---|---|---|---|---|---|---|---|---|
| contig644 | 34570312_c1_16 | 2189 | 5594 | 777 | 258 | 109 | 4.60E-06 | [SP:P06966] [OR:*ESCHERICHIA COLI*] [GN:DICA] [DE:REPRESSOR PROTEIN OF DIVISION INHIBITION GENE DICB] |
| contig644 | 10625061_f2_5 | 2190 | 5595 | 699 | 232 | 654 | 2.40E-64 | [SP:P05425] [OR:*ENTEROCOCCUS FAECALIS*] [GN:COPB] [DE:POTASSIUM/COPPER-TRANSPORTING ATPASE B,] |
| contig644 | 642268_f2_6 | 2191 | 5596 | 1464 | 487 | 1726 | 6.20E-178 | [SP:P05425] [OR:*ENTEROCOCCUS FAECALIS*] [GN:COPB] [DE:POTASSIUM/COPPER-TRANSPORTING ATPASE B,] |
| contig644 | 25667936_f2_7 | 2192 | 5597 | 1449 | 482 | 304 | 1.30E-35 | [AC:AF000260] [OR:*Escherichia coli*] [NT:f298; This 298 aa orf is 51 pct identical (5 gaps)] |
| contig644 | 6851637_f1_4 | 2193 | 5598 | 951 | 316 | | | |
| contig644 | 26360375_f2_8 | 2194 | 5599 | 2457 | 818 | 2334 | 2.30E-242 | [SP:P13252] [OR:*STREPTOCOCCUS PNEUMONIAE*] [GN:POLA] [DE:DNA POLYMERASE I, (POL.I)] |
| contig644 | 30277177_c2_13 | 2195 | 5600 | 3177 | 1059 | 4268 | 0 | [AC:X89229] [OR:*Listeria innocua*] [PN:DNA-directed RNA polymerase] [GN:rpoC] [NT:B' subunit] |
| contig645 | 583403_f1_4 | 2196 | 5601 | 195 | 64 | 57 | 0.59 | [AC:295972] [OR:*Mycobacterium tuberculosis*] [PN:unknown] [GN:MTI376.15] [NT:MTI376.15, unknown, len] |
| contig645 | 22350089_c1_12 | 2197 | 5602 | 2205 | 734 | 2938 | 0 | [SP:P37870] [OR:*BACILLUS SUBTILIS*] [GN:RPOB] [DE:BETA CHAIN) (RNA POLYMERASE:BETA SUBUNIT] |
| contig645 | 24710962_f3_10 | 2198 | 5603 | 705 | 234 | 101 | 0.0055 | [AC:D90906] [OR:*Synechocystis sp.*] [PN:hypothetical protein] [NT:ORF_ID] |
| contig645 | 4976587_f3_11 | 2199 | 5604 | 663 | 220 | 305 | 2.30E-27 | [SP:P75256] [OR:*MYCOPLASMA PNEUMONIAE*] [DE:HYPOTHETICAL PROTEIN MG347 HOMOLOG] |
| contig645 | 51462_f1_1 | 2200 | 5605 | 192 | 63 | 64 | 0.13 | [AC:S67983] [OR:*Homo sapiens*] [PN:anti-HIV gp41 antibody heavy chain variable] [GN:Ig VHI JH4] [NT:This sequence comes from FIG. 1C.] |
| contig646 | 36148462_c3_44 | 2201 | 5606 | 768 | 255 | 162 | 1.60E-10 | [AC:U32700] [OR:*Haemophilus influenzae*] [PN:hypothetical] [GN:H10143] [NT:similar to GB] |
| contig646 | 22266437_f3_13 | 2202 | 5607 | 981 | 326 | 333 | 2.50E-30 | [SP:P23539] [OR:*ESCHERICHIA COLI*] [GN:FRUK] [DE:1-PHOSPHOFRUCTOKINASE, (FRUCTOSE 1-PHOSPHATE KINASE)] |
| contig646 | 34565692_f1_2 | 2203 | 5608 | 747 | 248 | 479 | 8.50E-46 | [SP:P23387] [OR:*RHODOBACTER CAPSULATUS*] [GN:FRUA] [DE:(EC 2.7.1.69) (EII-FRU)] |
| contig646 | 6913925_f1_3 | 2204 | 5609 | 696 | 231 | 413 | 8.40E-39 | [AC:U64312] [OR:*Bacillus firmus*] [PN:phosphotransferase enzyme II] [GN:FruA] [NT:BC complex; fructose permease HBC component; PTS] |
| contig646 | 35945461_f3_15 | 2205 | 5610 | 483 | 160 | 180 | 5.10E-13 | [SP:P54745] [OR:*ESCHERICHIA COLI*] [GN:HRSA] [DE:HRSA PROTEIN,] |
| contig646 | 34640930_f2_8 | 2206 | 5611 | 999 | 332 | 997 | 1.10E-100 | [SP:P26593] [OR:*LACTOCOCCUS LACTIS*] [GN:LACD] [DE:TAGATOSE 1,6-DIPHOSPHATE ALDOLASE,] |
| contig646 | 13676886_f1_4 | 2207 | 5612 | 570 | 189 | 298 | 1.30E-26 | [AC:Z82044] [OR:*Bacillus subtilis*] [PN:hypothetical 12.2 kd protein] [GN:ygaC] |
| contig646 | 13164066_f3_16 | 2208 | 5613 | 207 | 68 | 60 | 0.51 | [OR:*Escherichia coli*] [PN:espA protein] [GN:espA] |
| contig646 | 33209880_c1_20 | 2209 | 5614 | 402 | 133 | 259 | 1.80E-22 | [SP:P52080] [OR:*STAPHYLOCOCCUS AUREUS*] [DE:HYPOTHETICAL 16.6 KD PROTEIN IN ATL 5' REGION (ORF3)] |
| contig646 | 4301313_c2_28 | 2210 | 5615 | 240 | 79 | 55 | 0.52 | [AC:U40424] [OR:*Caenorhabditis elegans*] [GN:C24A3.8] |
| contig646 | 36620951_f1_5 | 2211 | 5616 | 456 | 151 | 68 | 0.64 | [AC:X99400] [OR:*Streptococcus pneumoniae*] [PN:membrane protein] |
| contig646 | 29328250_f3_17 | 2212 | 5617 | 198 | 65 | 55 | 0.81 | [AC:S47695] [OR:*Saccharomyces cerevisiae*] [GN:YBL03-19] |
| contig646 | 23830251_f3_18 | 2213 | 5618 | 669 | 222 | 264 | 5.20E-23 | [AC:X99400] [OR:*Streptococcus pneumoniae*] [PN:membrane protein] |

TABLE 2-continued

| Contig | Orf | NT Seq Id | AA Seq ID | NT Orf Length | AA Orf Length | Score | Probability | Description |
|---|---|---|---|---|---|---|---|---|
| contig646 | 1189450_f3_19 | 2214 | 5619 | 1086 | 361 | 365 | 1.00E-33 | [AC:D90914] [OR:Synechocystis sp.] [PN:hemolysin] [NT:ORF_ID] |
| contig646 | 31679937_f1_6 | 2215 | 5620 | 252 | 83 | 95 | 0.00011 | [SP:P54428] [OR:BACILLUS SUBTILIS] [GN:YRKA] [DE:HYPOTHETICAL PROTEIN IN BLTD 5' REGION (FRAGMENT)] |
| contig647 | 22308213_c2_24 | 2216 | 5621 | 549 | 182 | 385 | 7.80E-36 | [AC:U23376] [OR:Lactococcus lactis] [NT:putative 20-kDa protein] |
| contig647 | 23473217_c1_19 | 2217 | 5622 | 714 | 237 | 72 | 0.53 | [OR:mitochondrion Saccharomyces cerevisiae] [PN:probable membrane protein Q0270] |
| contig647 | 23720312_c2_23 | 2218 | 5623 | 312 | 103 | 63 | 0.51 | [SP:P23648] [OR:LACTOCOCCUS LACTIS] [GN:NSR] [DE:NISIN-RESISTANCE PROTEIN] |
| contig647 | 6687762_c1_18 | 2219 | 5624 | 621 | 206 | 138 | 8.60E-08 | [AC:U25181] [OR:Lactococcus lactis] [PN:nisin-resistance protein] |
| contig647 | 24412580_c2_22 | 2220 | 5625 | 492 | 163 | 71 | 0.17 | [SP:P30397] [OR:EUGLENA GRACILIS] [DE:HYPOTHETICAL 64.3 KD PROTEIN IN RPS3 3'REGION (ORF516)] |
| contig647 | 2504182_c2_21 | 2221 | 5626 | 228 | 75 | | | |
| contig647 | 4885875_c1_17 | 2222 | 5627 | 573 | 190 | 78 | 0.92 | [AC:U11491] [OR:Human rotavirus] [PN:Non-structural protein NSP1] [NT:NS53] |
| contig647 | 3914077_c3_26 | 2223 | 5628 | 984 | 327 | 90 | 0.14 | [AC:U28972] [OR:Spiroplasma citri] [NT:SpV1 ORF1] |
| contig647 | 4767187_f3_13 | 2224 | 5629 | 240 | 79 | 56 | 0.82 | [SP:P23161] [OR:CLOSTRIDIUM PASTEURIANUM] [DE:20 KD PROTEIN IN RUBREDOXIN OPERON (ORF C)] |
| contig647 | 10578566_c3_25 | 2225 | 5630 | 1290 | 429 | 1971 | 6.70E-204 | [OR:Enterococcus faecalis] [PN:cytolysin activator, precursor] [GN:cylA] |
| contig647 | 36209628_c1_16 | 2226 | 5631 | 2163 | 720 | 2966 | 0 | [OR:Enterococcus faecalis] [PN:hemolysin secretion protein CylB] [GN:cylB] |
| contig647 | 23945463_f2_8 | 2227 | 5632 | 204 | 67 | | | [OR:Enterococcus faecalis] [PN:cylM protein] |
| contig647 | 21933038_c2_20 | 2228 | 5633 | 468 | 155 | 757 | 3.00E-75 | [AC:AB002366] [OR:Homo sapiens] [GN:K1AA0368] |
| contig648 | 32301927_f3_8 | 2229 | 5634 | 183 | 60 | 62 | 0.995 | [SP:P37537] [OR:BACILLUS SUBTILIS] [GN:TMK] [DE:THYMIDYLATE KINASE, (DTMP KINASE)] |
| contig648 | 9776700_f2_7 | 2230 | 5635 | 654 | 217 | 536 | 7.80E-52 | |
| contig648 | 5275282_f3_9 | 2231 | 5636 | 333 | 110 | 325 | 1.80E-29 | [SP:P37538] [OR:BACILLUS SUBTILIS] [GN:YAAQ] [DE:HYPOTHETICAL 12.0 KD PROTEIN IN XPAC-ABRB INTERGENIC REGION] |
| contig648 | 2760458_f1_1 | 2232 | 5637 | 1002 | 333 | 538 | 4.80E-52 | [SP:P37540] [OR:BACILLUS SUBTILIS] [GN:YAAS] [DE:HYPOTHETICAL 37.6 KD PROTEIN IN XPAC-ABRB INTERGENIC REGION] |
| contig648 | 24886502_f3_10 | 2233 | 5638 | 855 | 284 | 816 | 1.70E-81 | [SP:P37541] [OR:BACILLUS SUBTILIS] [GN:YAAT] [DE:HYPOTHETICAL 31.2 KD PROTEIN IN XPAC-ABRB INTERGENIC REGION] |
| contig648 | 10946028_f1_2 | 2234 | 5639 | 456 | 151 | 210 | 2.70E-17 | [SP:P37542] [OR:BACILLUS SUBTILIS] [GN:YABA] [DE:HYPOTHETICAL 14.1 KD PROTEIN IN XPAC-ABRB INTERGENIC REGION] |
| contig648 | 25819461_f1_3 | 2235 | 5640 | 942 | 313 | 675 | 1.40E-66 | [SP:P37544] [OR:BACILLUS SUBTILIS] [GN:YABC] [DE:HYPOTHETICAL 33.0 KD PROTEIN IN XPAC-ABRB INTERGENIC REGION] |
| contig648 | 865942_f3_11 | 2236 | 5641 | 696 | 231 | 449 | 1.30E-42 | [AC:AF000155] [OR:Escherichia coli] [NT:o225; This 225 aa orf is 32 pct identical (7 gaps)] |
| contig648 | 30742336_f1_5 | 2237 | 5642 | 780 | 259 | 606 | 3.00E-59 | [AC:AF000155] [OR:Escherichia coli] [NT:o268; This 268 aa orf is 27 pct identical (9 gaps)] |
| contig648 | 14647805_f3_13 | 2238 | 5643 | 1269 | 422 | 625 | 2.90E-61 | [SP:Q47155] [OR:ESCHERICHIA COLI] [GN:DINP] [DE:DNA-DAMAGE-INDUCIBLE PROTEIN P] |
| contig648 | 54812_c3_29 | 2239 | 5644 | 612 | 203 | 248 | 2.60E-21 | [SP:P39329] [OR:ESCHERICHIA COLI] [GN:NRDG] [DE:(EC |

TABLE 2-continued

| Contig | Orf | NT Seq Id | AA Seq ID | NT Orf Length | AA Orf Length | Score | Probability | Description |
|---|---|---|---|---|---|---|---|---|
| contig648 | 25510192_c1_16 | 2240 | 5645 | 888 | 295 | 840 | 4.70E-84 | 1.97.1.—)] [SP:P28903] [OR:*ESCHERICHIA COLI*] [GN:NRDD] [DE:ANAEROBIC RIBONUCLEOSIDE-TRIPHOSPHATE REDUCTASE,] |
| contig649 | 29307168_f3_7 | 2241 | 5646 | 378 | 125 | 75 | 0.15 | [OR:*Bacillus subtilis*] [PN:hypothetical protein 5 (xre region)] |
| contig649 | 26369200_f3_8 | 2242 | 5647 | 396 | 131 | 77 | 0.0034 | [AC:D78016] [OR:*Enterococcus faecalis*] [GN:orfY] [NT:ORF9] |
| contig649 | 13931556_f1_1 | 2243 | 5648 | 411 | 136 | 97 | 3.10E-05 | [SP:Q03182] [OR:BACTERIOPHAGE PHI-11] [GN:RNA] [DE:TRANSCRIPTIONAL ACTIVATOR RINA] |
| contig649 | 24628431_f3_9 | 2244 | 5649 | 432 | 143 | 50 | 0.991 | [SP:P41669] [OR:*AUTOGRAPHA CALIFORNICA* NUCLEAR POLYHEDROSIS VIRUS] [DE:HYPOTHETICAL 6.4 KD PROTEIN IN HE65-PK2 INTERGENIC REGION] |
| contig649 | 10554838_f3_10 | 2245 | 5650 | 525 | 174 | 76 | 0.97 | [SP:P71528] [OR:*METHANOCOCCUS MARIPALUDIS*] [GN:NIFE] [DE:NITROGENASE IRON-MOLYBDENUM COFACTOR BIOSYNTHESIS PROTEIN NIFE] |
| contig649 | 197187_f2_5 | 2246 | 5651 | 363 | 120 | 52 | 0.9 | [AC:AB001768] [OR:*Asparagus officinalis*] [PN:histidine containing protein] [GN:ptsH] [NT:HPr] |
| contig649 | 24892192_f1_2 | 2247 | 5652 | 474 | 157 | 73 | 0.8 | [SP:P20163] [OR:*CAENORHABDITIS ELEGANS*] [GN:HSP-4] [DE:HEAT SHOCK 70 KD PROTEIN D (FRAGMENT)] |
| contig649 | 25589202_f2_6 | 2248 | 5653 | 2934 | 977 | 60 | 0.95 | [SP:P01095] [OR:*SACCHAROMYCES CEREVISIAE*] [GN:PBI2] [DE:PROTEASE B INHIBITORS 2 AND 1 (PROTEINASE INHIBITOR (B)2)] |
| contig649 | 26774188_f3_11 | 2249 | 5654 | 942 | 313 | 81 | 0.89 | [SP:P22236] [OR:*HAEMOPHILUS INFLUENZAE*] [GN:BEXD] [DE:CAPSULE POLYSACCHARIDE EXPORT PROTIN BEXD PRECURSOR] |
| contig649 | 16834452_f3_12 | 2250 | 5655 | 1038 | 345 | 87 | 0.45 | [SP:P55802] [OR:*MYCOPLASMA MYCOIDES*] [DE:HYPOTHETICAL PROTEIN IN P72 5′ REGION (ORF1) (FRAGMENT)] |
| contig649 | 33798285_f3_13 | 2251 | 5656 | 195 | 64 | 72 | 0.36 | [OR:*Homo sapiens*] [PN:microtubule-vesicle linker CLIP-170] |
| contig649 | 24251887_f2_2 | 2252 | 5657 | 303 | 100 | 69 | 0.22 | [AC:X97563] [OR:*Lactobacillus casei* bacteriophage A2] [PN:terminase enzyme Gp3, small subunit] [GN:gp3] |
| contig65 | 34267012_f1_1 | 2253 | 5658 | 477 | 158 | 235 | 6.10E-20 | [AC:U46071] [OR:*Rhodobacter capsulatus*] [PN:unknown] [NT:ORF3; similar to hypothetical protein from *E. coli*.] |
| contig65 | 14180252_c3_28 | 2254 | 5659 | 660 | 220 | 173 | 2.30E-13 | [AC:AE000139] [OR:*Escherichia coli*] [NT:o201; This 201 aa orf is 28 pct identical (6 gaps)] |
| contig650 | 24640705_c1_18 | 2255 | 5660 | 1050 | 349 | 73 | 0.31 | [OR:*Mus musculus*] [PN:Ig heavy chain V region N10] |
| contig650 | 3917763_c2_23 | 2256 | 5661 | 999 | 332 | 82 | 0.89 | [AC:U59862] [OR:*Plasmodium vinckei*] [PN:SERA-3] |
| contig650 | 24391927_c1_17 | 2257 | 5662 | 1011 | 336 | 80 | 0.84 | [OR:*Methanococcus jannaschii*] [PN:formylmethanofuran dehydrogenase (tungsten), subunit C related protein] |
| contig650 | 35960187_f1_4 | 2258 | 5663 | 1503 | 500 | 411 | 2.20E-38 | [AC:D78193] [OR:*Bacillus subtilis*] [GN:yycG] [NT:homologous toPHOR_BACSU] |
| contig650 | 12697187_f3_15 | 2259 | 5664 | 696 | 231 | 436 | 3.10E-41 | [SP:P35163] [OR:*BACILLUS SUBTILIS*] [GN:RESD] [DE:RESD PROTEIN] |
| contig650 | 19572186_c2_20 | 2260 | 5665 | 1149 | 382 | 1027 | 7.30E-104 | [SP:P31672] [OR:*LACTOBACILLUS DELBRUECKII*] [DE:NIFS PROTEIN HOMOLOG (FRAGMENT)] |
| contig651 | 34651687_c1_23 | 2261 | 5666 | 1542 | 514 | 187 | 5.70E-13 | [SP:P54341] [OR:*BACILLUS SUBTILIS*] [GN:XKDV] [DE:PHAGE-LIKE ELEMENT PBSX PROTEIN XKDV] |
| contig651 | 14897050_c1_22 | 2262 | 5667 | 636 | 211 | 63 | 0.27 | [OR:*Homo sapiens*] [GN:Ig VH] [NT:Description] |
| contig651 | 24257937_c3_33 | 2263 | 5668 | 234 | 77 | 58 | 0.29 | [AC:U66186] [OR:*Listeria monocytogenes*] [PN:LemB] [GN:lemB] [NT:putative cytoplasmic membrane protein] |

TABLE 2-continued

| Contig | Orf | NT Seq Id | AA Seq ID | NT Orf Length | AA Orf Length | Score | Probability | Description |
|---|---|---|---|---|---|---|---|---|
| contig651 | 25416035_c2_27 | 2264 | 5669 | 954 | 317 | 71 | 0.66 | [OR:*Saccharomyces cerevisiae*] [PN:hypothetical protein YLR053c] |
| contig651 | 19689416_c1_21 | 2265 | 5670 | 375 | 124 | 58 | 0.97 | [OR:*Homo sapiens*] [PN:myosin] |
| contig651 | 2533518_c2_26 | 2266 | 5671 | 345 | 114 | 64 | 0.37 | [AC:D84146] [OR:*Pseudomonas aeruginosa*] [GN:orfl2] |
| contig651 | 13867952_c3_31 | 2267 | 5672 | 831 | 276 | 59 | 0.8 | [SP:P25921] [OR:*STAPHYLOCOCCUS AUREUS*] [DE:COP-6 PROTEIN] |
| contig651 | 33985077_c3_30 | 2268 | 5673 | 219 | 72 | 67 | 0.68 | [SP:P40021] [OR:*SACCHAROMYCES CEREVISIAE*] [GN:YER033C] [DE:HYPOTHETICAL 119.3 KD PROTEIN IN YPT8-GLN3 INTERGENIC REGION] |
| contig651 | 24875635_c3_29 | 2269 | 5674 | 585 | 194 | 97 | 0.019 | [SP:Q01839] [OR:*LISTERIA WELSHIMERI*] [GN:IAP] [DE:PROTEIN P60 PRECURSOR (INVASION-ASSOCIATED PROTEIN)] |
| contig651 | 34651525_c1_20 | 2270 | 5675 | 5190 | 1729 | 217 | 7.90E-14 | [AC:D90915] [OR:*Synechocystis* sp.] [PN:lipoprotein NlpD] [GN:nlpD] [NT:ORF_ID] |
| contig651 | 23438813_f1_1 | 2271 | 5676 | 201 | 66 | 70 | 0.25 | [AC:X86091] [OR:*Ascaris lumbricoides*] [PN:cytoplasmic intermediate filament protein] [GN:IF D1] |
| contig652 | 2734502_f2_8 | 2272 | 5677 | 204 | 67 | 70 | 0.11 | [AC:Z79701] [OR:*Mycobacterium tuberculosis*] [PN:unknown] [GN:MTCY277.31] [NT:MTCY277.31, unknown, len] |
| contig652 | 33411713_c3_30 | 2273 | 5678 | 261 | 86 | 65 | 0.36 | [AC:U41007] [OR:*Caenorhabditis elegans*] [GN:C33H5.15] |
| contig652 | 3414067_c1_17 | 2274 | 5679 | 186 | 61 | 67 | 0.52 | [SP:P15623] [OR:*BACTEROIDES FRAGILIS*] [GN:GLNA] [DE:GLUTAMINE SYNTHETASE, (GLUTAMATE–AMMONIA LIGASE) (GS)] |
| contig652 | 26563752_c3_28 | 2275 | 5680 | 465 | 154 | 186 | 9.50E-15 | [SP:Q48709] [OR:*LACTOCOCCUS LACTIS*] [GN:NRDI] [DE:NRDI PROTEIN] |
| contig652 | 390655_f1_2 | 2276 | 5681 | 372 | 123 | 87 | 0.011 | [AC:X07453] [OR:*Plasmodium falciparum*] [PN:11-1 polypeptide] [GN:11-1] |
| contig652 | 3916587_f2_9 | 2277 | 5682 | 1989 | 662 | 1315 | 2.20E-134 | [OR:*Enterococcus hirae*] [PN:ntpM protein] [GN:ntpM] |
| contig652 | 19562812_f2_10 | 2278 | 5683 | 501 | 166 | 681 | 3.40E-67 | [SP:P43457] [OR:*ENTEROCOCCUS HIRAE*] [GN:NTPK] [DE:TRANSLOCATING ATPASE SUBUNIT K) (SODIUM ATPASE PROTEOLIPID COMPONENT] |
| contig652 | 30349193_f3_14 | 2279 | 5684 | 594 | 197 | 264 | 5.20E-23 | [OR:*Enterococcus hirae*] [PN:ntpE protein] |
| contig652 | 585961_f1_6 | 2280 | 5685 | 1038 | 345 | 877 | 5.70E-88 | [SP:P43456] [OR:*ENTEROCOCCUS HIRAE*] [GN:NTPC] [DE:TRANSLOCATING ATPASE SUBUNIT C] |
| contig652 | 26651875_f2_11 | 2281 | 5686 | 375 | 124 | 365 | 1.00E-33 | [SP:P43455] [OR:*ENTEROCOCCUS HIRAE*] [GN:NTPG] [DE:TRANSLOCATING ATPASE SUBUNIT G] |
| contig652 | 29489687_f1_7 | 2282 | 5687 | 1827 | 608 | 2369 | 4.50E-246 | [SP:Q08636] [OR:*ENTEROCOCCUS HIRAE*] [GN:NTPA] [DE:TRANSLOCATING ATPASE SUBUNIT A] |
| contig652 | 23478441_f2_13 | 2283 | 5688 | 900 | 300 | 1225 | 7.60E-125 | [SP:Q08637] [OR:*ENTEROCOCCUS HIRAE*] [GN:NTPB] [DE:TRANSLOCATING ATPASE SUBUNIT B] |
| contig653 | 33212875_f2_5 | 2284 | 5689 | 516 | 171 | 92 | 0.065 | [AC:Y09579] [OR:*Pisum sativum*] [PN:Cop1 protein] [GN:cop1] |
| contig653 | 679692_c1_15 | 2285 | 5690 | 435 | 144 | 129 | 1.00E-08 | [AC:D90901] [OR:*Synechocystis* sp.] [PN:hypothetical protein] [NT:ORF_ID] |
| contig653 | 4885941_f3_8 | 2286 | 5691 | 2913 | 970 | 119 | 0.003 | [SP:P17953] [OR:*ENTEROCOCCUS FAECALIS*] [GN:ASA1] [DE:AGGREGATION SUBSTANCE PRECURSOR] |
| contig653 | 24492937_f3_9 | 2287 | 5692 | 399 | 132 | 84 | 0.0066 | [SP:P37249] [OR:*PEDIOCOCCUS ACIDILACTICI*] [GN:PEDC] [DE:PEDIOCIN PA-1 BIOSYNTHESIS PROTEIN PEDC] |
| contig653 | 21486252_f2_6 | 2288 | 5693 | 543 | 180 | 184 | 1.30E-13 | [AC:Y14082] [OR:*Bacillus subtilis*] [PN:hypothetical protein] [GN:yhdW] [NT:Similarity to glycerol diester phosphodiesterase] |
| contig653 | 6930387_f1_2 | 2289 | 5694 | 1803 | 600 | | | |
| contig653 | 1461567_f2_7 | 2290 | 5695 | 426 | 141 | 97 | 2.60E-05 | [AC:AB001488] [OR:*Bacillus subtilis*] [GN:mutT] [NT:FUNCTION |

TABLE 2-continued

| Contig | Orf | NT Seq Id | AA Seq ID | NT Orf Length | AA Orf Length | Score | Probability | Description |
|---|---|---|---|---|---|---|---|---|
| contig653 | 20351713_f1_3 | 2291 | 5696 | 213 | 70 | 286 | 2.40E-25 | UNKNOWN, CONTAINS MUTT MOTIF, SIMILAR [AC:Y08940] [OR:Lactobacillus plantarum] [PN:cold shock protein] [GN:cspl] |
| contig653 | 14850326_f1_4 | 2292 | 5697 | 1371 | 456 | 907 | 3.80E-91 | [AC:X93169] [OR:Listeria monocytogenes] [PN:sigma-54 protein] [GN:rpoN] |
| contig654 | 32239437_f3_10 | 2293 | 5698 | 327 | 108 | 77 | 0.039 | [AC:U77612] [OR:Heloderma suspectum] [PN:proglucagon] [GN:LPII] [NT:pancreatic proglucagon] |
| contig654 | 23947182_f3_11 | 2294 | 5699 | 1956 | 651 | 90 | 0.87 | [AC:Z97208] [OR:Schizosaccharomyces pombe] [PN:hypothetical protein] [GN:SPAC15A10.15] [NT:SPAC15A10.15, partial; unknown, len] |
| contig654 | 9820327_c3_22 | 2295 | 5700 | 498 | 165 | 657 | 1.20E-64 | [AC:U40997] [OR:Listeria monocytogenes] [PN:dihydrofolate reductase] [NT:DHFR L1 protein] |
| contig654 | 36113801_c2_18 | 2296 | 5701 | 1029 | 342 | 1077 | 3.60E-109 | [AC:Y14083] [OR:Bacillus subtilis] [PN:hypothetical protein] [GN:yhfI] [NT:Similarity to several lipoate-protein ligases] |
| contig654 | 19781402_c3_21 | 2297 | 5702 | 873 | 290 | 474 | 2.90E-45 | [AC:Y14083] [OR:Bacillus subtilis] [PN:hypothetical protein] [GN:yhfI] [NT:Similarity to arylsulphatase precursor 'ats' from] [OR:Bacillus megaterium] [PN:hypothetical protein 1] |
| contig654 | 276577_c2_17 | 2298 | 5703 | 792 | 263 | 156 | 8.50E-11 | [AC:Z75208] [OR:Bacillus subtilis] [PN:hypothetical protein] [GN:ysdC] [NT:homology to celA of Clostridium thermocellum and |
| contig654 | 2838437_f1_5 | 2299 | 5704 | 210 | 69 | | | |
| contig654 | 11262_c3_20 | 2300 | 5705 | 1110 | 369 | 1166 | 1.40E-118 | [AC:Z93397] [OR:Caenorhabditis elegans] [PN:ZC482.f] [NT:protein predicted using Genefinder; preliminary] |
| contig655 | 23632837_c2_15 | 2301 | 5706 | 765 | 254 | 68 | 0.45 | [AC:D83706] [OR:Bacillus stearothermophilus] [PN:pyruvate carboxylase] |
| contig655 | 3912678_c1_11 | 2302 | 5707 | 3492 | 1163 | 3802 | 0 | [AC:U58049] [OR:Enterococcus hirae] [PN:putative cell division protein ftsW] |
| contig655 | 24321883_c2_14 | 2303 | 5708 | 1212 | 403 | 495 | 1.70E-47 | [AC:Z97025] [OR:Bacillus subtilis] [GN:ylaN] |
| contig655 | 5939818_c2_13 | 2304 | 5709 | 321 | 106 | 184 | 1.60E-14 | [SP:P15043] [OR:ESCHERICHIA COLI] [GN:RECQ] [DE:ATP-DEPENDENT DNA HELICASE RECQ.] |
| contig655 | 908452_f1_12 | 2305 | 5710 | 1770 | 589 | 1139 | 9.80E-116 | |
| contig655 | 10058593_c1_10 | 2306 | 5711 | 816 | 271 | 979 | 8.90E-99 | [AC:Z97025] [OR:Bacillus subtilis] [GN:ylaG] [NT:product highly similar to elongation factor EF-G] |
| contig656 | 22870316_f3_16 | 2307 | 5712 | 1200 | 399 | 256 | 3.60E-22 | [AC:X99400] [OR:Streptococcus pneumoniae] [PN:membrane protein] |
| contig656 | 34430313_c2_28 | 2308 | 5713 | 1143 | 380 | 728 | 3.50E-72 | [AC:D83026] [OR:Bacillus subtilis] [GN:yxjH] [NT:hypothetical] |
| contig656 | 24806686_c3_32 | 2309 | 5714 | 1353 | 450 | 266 | 1.50E-22 | [SP:P13692] [OR:ENTEROCOCCUS FAECIUM] [DE:P54 PROTEIN PRECURSOR] |
| contig656 | 9843750_f3_18 | 2310 | 5715 | 306 | 101 | 69 | 0.072 | [OR:Saccharomyces cerevisiae] [PN:probable membrane protein YLR217w] |
| contig656 | 12504678_f1_4 | 2311 | 5716 | 216 | 71 | 55 | 0.75 | [SP:P75555] [OR:MYCOPLASMA PNEUMONIAE] DE:HYPOTHETICAL PROTEIN MG076 HOMOLOG] |
| contig656 | 26571938_c3_31 | 2312 | 5717 | 2331 | 776 | 75 | 0.48 | [AC:U51459] [OR:Mus musculus] [PN:IgG anti-nucleosome kappa light chain variable] [NT:Vk 4/5 family] |
| contig656 | 24431693_c2_27 | 2313 | 5718 | 1236 | 411 | 536 | 7.80E-52 | [SP:P25524] [OR:ESCHERICHIA COLI] [GN:CODA] [DE:CYTOSINE DEAMINASE.] |
| contig656 | 1348165_c2_26 | 2314 | 5719 | 219 | 72 | 56 | 0.94 | [SP:P25354] [OR:SACCHAROMYCES CEREVISIAE] [GN:YCR7C] [DE:HYPOTHETICAL 27.6 KD PROTEIN IN SUF2 5' REGION] |
| contig656 | 17058177_c1_21 | 2315 | 5720 | 1329 | 442 | 84 | 0.78 | [SP:P45546] [OR:ESCHERICHIA COLI] [GN:YHFT] [DE:HYPOTHETICAL 45.3 KD PROTEIN IN CYSG-TRPS INTERGENIC REGION (F423) |
| contig656 | 29343811_c2_25 | 2316 | 5721 | 792 | 263 | 791 | 7.40E-79 | [AC:AF000157] [OR:Escherichia coli] [NT:f349; This 349 aa orf is |

TABLE 2-continued

| Contig | Orf | NT Seq Id | AA Seq ID | NT Orf Length | AA Orf Length | Score | Probability | Description |
|---|---|---|---|---|---|---|---|---|
| contig657 | 13832950_f2_5 | 2317 | 5722 | 741 | 246 | 330 | 5.30E-30 | 35 pct identical (11 gaps) [SP:P09375] [OR:ESCHERICHIA COLI] [GN:NAGB] [DE:PHOSPHATE DEAMINASE] |
| contig657 | 6287752_f1_1 | 2318 | 5723 | 804 | 267 | 256 | 3.60E-22 | [SP:P26606] [OR:ESCHERICHIA COLI] [GN:YHID] [DE:(F215)] |
| contig657 | 25938825_f3_10 | 2319 | 5724 | 606 | 201 | 247 | 3.30E-21 | [OR:Methanococcus jannaschii] [PN:hypothetical protein M11576] |
| contig657 | 26574068_f2_6 | 2320 | 5725 | 1293 | 430 | 170 | 1.90E-10 | [SP:P55140] [OR:ESCHERICHIA COLI] [GN:YGCG] [DE:HYPOTHETICAL 34.9 KD PROTEIN IN CYSJ-ENO INTERGENIC REGION (O313)] |
| contig657 | 3004680_c3_20 | 2321 | 5726 | 1005 | 334 | 716 | 6.60E-71 | [AC:U41100] [OR:Mycobacterium tuberculosis] [PN:ribonucleotide reductase R2-2 small subunit] |
| contig657 | 979715_c1_13 | 2322 | 5727 | 2169 | 722 | 1865 | 1.10E-192 | [SP:P50640] [OR:MYCOBACTERIUM TUBERCULOSIS] [GN:NRDE] [DE:(RIBONUCLEOTIDE REDUCTASE) (R1 SUBUNIT) (FRAGMENT)] |
| contig657 | 3360912_c3_19 | 2323 | 5728 | 396 | 131 | 292 | 5.60E-26 | [SP:Q48709] [OR:LACTOCOCCUS LACTIS] [GN:NRDI] [DE:NRDI PROTEIN] |
| contig657 | 33313752_c2_17 | 2324 | 5729 | 267 | 88 | 208 | 4.40E-17 | [SP:Q48708] [OR:LACTOCOCCUS LACTIS] [GN:NRDH] [DE:GLUTAREDOXIN-LIKE PROTEIN NRDH] |
| contig657 | 14269013_f2_6 | 2325 | 5730 | 333 | 110 | 212 | 1.70E-17 | [SP:P42366] [OR:STREPTOCOCCUS GORDONII CHALLIS] [DE:18 KD PROTEIN IN SCAA 3' REGION (ORF 4)] |
| contig658 | 21900800_f3_10 | 2326 | 5731 | 2685 | 894 | 3433 | 0 | [OR:Bacillus stearothermophilus] [PN:valine–tRNA ligase,] |
| contig658 | 16878375_c2_16 | 2327 | 5732 | 696 | 231 | 91 | 0.017 | [AC:D64005] [OR:Synechocystis sp.] [PN:hypothetical protein] [NT:ORF_ID] |
| contig658 | 23593750_c1_12 | 2328 | 5733 | 2592 | 863 | 58 | 0.999 | [SP:P25877] [OR:HORDEUM VULGARE] [GN:PSBK] [DE:PHOTOSYSTEM II 4 KD REACTION CENTRE PROTEIN PRECURSOR] |
| contig658 | 33251005_c3_19 | 2329 | 5734 | 216 | 71 | 72 | 0.064 | [SP:P16400] [OR:LACTOCOCCUS LACTIS] [GN:MLER] [DE:MALOLACTIC FERMENTATION SYSTEM TRANSCRIPTIONAL ACTIVATOR] |
| contig658 | 23595876_f3_11 | 2330 | 5735 | 1362 | 453 | 840 | 4.70E-84 | [SP:Q05865] [OR:BACILLUS SUBTILIS] [GN:FOLC] [DE:SYNTHETASE] (FPGS)] |
| contig658 | 5117338_f1_5 | 2331 | 5736 | 666 | 221 | 224 | 9.00E-19 | [SP:P35924] [OR:LACTOBACILLUS CASEI] [DE:HYPOTHETICAL 22.8 KD PROTEIN IN FGS 3' REGION] |
| contig658 | 24407762_f2_9 | 2332 | 5737 | 192 | 64 | 75 | 0.023 | [SP:P52601] [OR:SYNECHOCYSTIS SP] [GN:SLL0766] [DE:DNA REPAIR PROTEIN RADC HOMOLOG] |
| contig659 | 10970142_f1_1 | 2333 | 5738 | 453 | 150 | 61 | 0.29 | [AC:M27947] [OR:Human immunodeficiency virus type 1] [PN:envelope protein] [NT:putative] |
| contig659 | 22854686_f1_2 | 2334 | 5739 | 1113 | 370 | 242 | 1.10E-20 | [SP:Q04729] [OR:BACILLUS STEAROTHERMOPHILUS] [DE:(ORF2)] |
| contig659 | 19932800_f3_6 | 2335 | 5740 | 237 | 78 | 173 | 5.30E-13 | [AC:Z71552] [OR:Streptococcus pneumoniae] [PN:AdcA] [GN:adcA] [NT:putative lipoprotein] |
| contig659 | 6914002_f2_4 | 2336 | 5741 | 462 | 153 | 217 | 4.90E-18 | [AC:U93875] [OR:Bacillus subtilis] [PN:YrpE] [GN:yrpE] |
| contig659 | 11720888_f1_3 | 2337 | 5742 | 489 | 162 | 55 | 0.78 | [OR:Ovis orientalis aries] [PN:14-3-3 protein isoform epsilon] |
| contig659 | 23988452_f2_5 | 2338 | 5743 | 960 | 319 | 1680 | 4.60E-173 | [AC:L28754] [OR:Insertion sequence IS6770] [PN:transposase] [NT:putative] |
| contig659 | 32519551_c3_11 | 2339 | 5744 | 420 | 139 | 637 | 1.50E-62 | [SP:P19775] [OR:STAPHYLOCOCCUS AUREUS] [GN:TNP] [DE:TRANSPOSASE FOR INSERTION SEQUENCE ELEMENT IS256 IN TRANSPOSON TN4001] |
| contig66 | 4791251_f1_1 | 2340 | 5745 | 684 | 227 | 453 | 2.30E-42 | [AC:D84432] [OR:Bacillus subtilis] [PN:ComEC] |
| contig660 | 36598427_c1_17 | 2341 | 5746 | 420 | 139 | 77 | 0.47 | [OR:Trypanosoma cruzi] [PN:85K surface antigen] |

TABLE 2-continued

| Contig | Orf | NT Seq Id | AA Seq ID | NT Orf Length | AA Orf Length | Score | Probability | Description |
|---|---|---|---|---|---|---|---|---|
| contig660 | 33783425_c2_20 | 2342 | 5747 | 2484 | 827 | 429 | 1.00E-39 | [SP:P18579] [OR:*BACILLUS SUBTILIS*] [GN:MURB] [DE:ACETYLMURAMATE DEHYDROGENASE] |
| contig660 | 24227217_c3_22 | 2343 | 5748 | 864 | 287 | 57 | 0.93 | [AC:U41515] [OR:*Homo sapiens*] [GN:DSS1] [NT:Method] |
| contig660 | 4902203_c1_16 | 2344 | 5749 | 2529 | 842 | 349 | 4.90E-31 | [AC:Z71928] [OR:*Bacillus subtilis*] [PN:hypothetical protein] [GN:yveT] [NT:similar to Ggab of *B. subtilis*] |
| contig660 | 36222937_c1_15 | 2345 | 5750 | 1485 | 494 | 167 | 7.10E-12 | [SP:P22639] [OR:*ANABAENA SP*] [DE:HYPOTHETICAL PROTEIN IN HETA 3' REGION (FRAGMENT)] |
| contig660 | 9953467_c1_14 | 2346 | 5751 | 1182 | 393 | 914 | 6.80E-92 | [SP:P13485] [OR:*BACILLUS SUBTILIS*] [GN:TAGF] [DE:TEICHOIC ACID BIOSYNTHESIS PROTEIN F] |
| contig660 | 25906252_c3_21 | 2347 | 5752 | 579 | 192 | 281 | 8.20E-25 | [SP:U51683] [OR:*Brucella abortus*] [PN:CdsA] [GN:cdsA] [NT:phosphatidate cytidyltransferase; similar to] |
| contig661 | 36142187_c1_20 | 2348 | 5753 | 267 | 88 | 161 | 4.30E-12 | [AC:D90901] [OR:*Synechocystis sp.*] [PN:hypothetical protein] [NT:ORF_ID] |
| contig661 | 32664681_c1_19 | 2349 | 5754 | 1395 | 464 | 918 | 2.60E-92 | [SP:P51835] [OR:*BACILLUS SUBTILIS*] [GN:FTSY] [DE:CELL DIVISION PROTEIN FTSY HOMOLOG] |
| contig661 | 34117306_c2_22 | 2350 | 5755 | 852 | 283 | 510 | 4.40E-49 | [AC:AE0000446] [OR:*Escherichia coli*] [PN:hypothetical 29.7 kD protein in ibpA-gyrB] [GN:yidA] [NT:f270; 99 pct identical amino acid sequence and] |
| contig661 | 25505458_c2_21 | 2351 | 5756 | 3627 | 1208 | 2093 | 7.90E-217 | [SP:P51834] [OR:*BACILLUS SUBTILIS*] [GN:YLQA] [DE:HYPOTHETICAL 135.4 KD PROTEIN IN RNC-SRB INTERGENIC REGION (ORF4)] |
| contig661 | 792827_c3_47 | 2352 | 5757 | 219 | 73 | 238 | 2.90E-20 | [AC:L29323] [OR:*Streptococcus pneumoniae*] [PN:methyl transferase] [NT:member of the mtr gene cluster; putative] |
| contig662 | 16995687_c1_31 | 2353 | 5758 | 864 | 287 | 92 | 0.16 | [AC:U09180] [OR:*Meloidogyne incognita*] [PN:SEC-1] [GN:sec-1] |
| contig662 | 24315678_c3_46 | 2354 | 5759 | 483 | 160 | 79 | 0.29 | [AC:U29378] [OR:*Caenorhabditis elegans*] [GN:F08C6.7] [NT:similar to zinc finger proteins] |
| contig662 | 5176887_c3_45 | 2355 | 5760 | 1401 | 466 | 1294 | 3.70E-132 | [AC:U09422] [OR:*Enterococcus faecalis*] [NT:ORF21] |
| contig662 | 4182828_c2_40 | 2356 | 5761 | 354 | 117 | 61 | 0.93 | [OR:*Haemophilus influenzae*] [PN:negative regulator of translation (relB) homolog] |
| contig662 | 24407963_c2_39 | 2357 | 5762 | 384 | 127 | 385 | 7.80E-36 | [AC:U09422] [OR:*Enterococcus faecalis*] [NT:ORF22] |
| contig662 | 24433937_c2_38 | 2358 | 5763 | 330 | 109 | 246 | 4.20E-21 | [AC:U09422] [OR:*Enterococcus faecalis*] [NT:ORF23] |
| contig662 | 15046932_c1_30 | 2359 | 5764 | 3291 | 1096 | 68 | 0.59 | [OR:phage 82] [PN:hypothetical protein 56] |
| contig662 | 5187502_c3_44 | 2360 | 5765 | 186 | 61 | 67 | 0.14 | [SP:P35528] [OR:*BACILLUS SUBTILIS*] [GN:FLIP] [DE:FLAGELLAR BIOSYNTHETIC PROTEIN FLIP] |
| contig662 | 24728452_c1_29 | 2361 | 5766 | 1833 | 610 | 185 | 4.90E-17 | [SP:Q58960] [OR:*METHANOCOCCUS JANNASCHII*] [GN:MJ1565] [DE:HYPOTHETICAL PROTEIN MJ1565] |
| contig662 | 38252_c3_43 | 2362 | 5767 | 1404 | 467 | 72 | 0.97 | [SP:Q60386] [OR:*METHANOCOCCUS JANNASCHII*] [GN:MJ0080] [DE:HYPOTHETICAL PROTEIN MJ0080] |
| contig662 | 127318_c2_33 | 2363 | 5768 | 945 | 314 | 78 | 0.017 | [SP:P45903] [OR:*BACILLUS SUBTILIS*] [GN:YQAF] [DE:HYPOTHETICAL 8.8 KD PROTEIN IN SPOIIIC-CWLA INTERGENIC REGION (ORF8)] |
| contig662 | 14964437_c3_42 | 2364 | 5769 | 237 | 78 | 58 | 0.29 | [OR:*Saccharomyces cerevisiae*] [PN:probable membrane protein YDR102c] |
| contig662 | 281344_c2_32 | 2365 | 5770 | 804 | 267 | 1099 | 1.70E-111 | [SP:P37949] [OR:*BACILLUS SUBTILIS*] [GN:LEPA] [DE:GTP-BINDING PROTEIN LEPA] |
| contig663 | 6834701_c1_19 | 2366 | 5771 | 279 | 92 | 62 | 0.78 | [SP:P43451] [OR:*ENTEROCOCCUS FAECALIS*] [GN:ATPD] [DE:ATP SYNTHASE BETA CHAIN.] |
| contig663 | 4876652_f1_2 | 2367 | 5772 | 1143 | 380 | 1143 | 3.70E-116 | [SP:P41972] [OR:*STAPHYLOCOCCUS AUREUS*] [GN:ILES] [DE:(ILERS)] |

TABLE 2-continued

| Contig | Orf | NT Seq Id | AA Seq ID | NT Orf Length | AA Orf Length | Score | Probability | Description |
|---|---|---|---|---|---|---|---|---|
| contig663 | 19923467_f3_11 | 2368 | 5773 | 1698 | 565 | 1733 | 1.10E-178 | [SP:P41972] [OR:*STAPHYLOCOCCUS AUREUS*] [GN:ILES] [DE:(ILERS)] |
| contig663 | 4710943_c2_23 | 2369 | 5774 | 1533 | 510 | 1365 | 1.10E-139 | [SP:P54547] [OR:*BACILLUS SUBTILIS*] [GN:ZWF] [DE:GLUCOSE-6-PHOSPHATE 1-DEHYDROGENASE, (G6PD)] |
| contig663 | 14875158_c3_28 | 2370 | 5775 | 675 | 224 | 381 | 2.10E-35 | [AC:X99128] [OR:*Staphylococcus epidermidis*] [PN:putative iron dependant repressor] [GN:sirR] |
| contig663 | 36225092_c2_22 | 2371 | 5776 | 387 | 128 | 78 | 0.49 | [AC:X90564] [OR:*Saccharomyces cerevisiae*] [GN:orfX] |
| contig663 | 6823387_c1_17 | 2372 | 5777 | 201 | 66 | 60 | 0.19 | [SP:P15811] [OR:*CYANOPHORA PARADOXA*] [DE:HYPOTHETICAL 12.3 KD PROTEIN IN RPL3-RPL33 INTERGENIC REGION (ORF102)] |
| contig663 | 26350950_f3_12 | 2373 | 5778 | 819 | 272 | 254 | 5.90E-22 | [SP:P18273] [OR:*ESCHERICHIA COLI*] [GN:SFSA] [DE:SUGAR FERMENTATION STIMULATION PROTEIN] |
| contig663 | 24410927_f3_13 | 2374 | 5779 | 1026 | 341 | 418 | 2.50E-39 | [SP:P42599] [OR:*ESCHERICHIA COLI*] [GN:YGJR] [DE:HYPOTHETICAL 24.8 KD PROTEIN IN EBGC-UXAA INTERGENIC REGION (O221)] |
| contig663 | 24027188_f2_10 | 2375 | 5780 | 1314 | 437 | 523 | 1.90E-50 | [AC:JC2118] [OR:*Homo sapiens*] [PN:DEAD-box RNA helicase homolog] |
| contig663 | 4898542_f1_6 | 2376 | 5781 | 1470 | 490 | 699 | 1.70E-75 | [SP:P23914] [OR:*BACILLUS SUBTILIS*] [GN:LEVR] [DE:TRANSCRIPTIONAL REGULATORY PROTEIN LEVR] |
| contig664 | 6328431_f1_1 | 2377 | 5782 | 1698 | 565 | 809 | 9.20E-81 | [SP:Q11046] [OR:*MYCOBACTERIUM TUBERCULOSIS*] [GN:MTCY50.09] [DE:HYPOTHETICAL ABC TRANSPORTER ATP-BINDING PROTEIN CY50.09] |
| contig664 | 54712_f2_4 | 2378 | 5783 | 1806 | 601 | 954 | 3.90E-96 | [SP:Q11047] [OR:*MYCOBACTERIUM TUBERCULOSIS*] [GN:MTCY50.10] [DE:HYPOTHETICAL ABC TRANSPORTER ATP-BINDING PROTEIN CY50.10] |
| contig664 | 13869057_c1_17 | 2379 | 5784 | 1008 | 335 | 1141 | 6.00E-116 | [SP:Q46127] [OR:*CLOSTRIDIUM LONGISPORUM*] [GN:TRPS] [DE:(TRPRS)] |
| contig664 | 34611257_c2_18 | 2380 | 5785 | 3849 | 1282 | 129 | 0.00012 | [AC:Y12758] [OR:*Rhizobium leguminosarum*] [PN:polysaccharidase] [GN:plyA] |
| contig665 | 14667875_f2_10 | 2381 | 5786 | 1083 | 360 | 272 | 2.40E-29 | [SP:P54965] [OR:*CLOSTRIDIUM PERFRINGENS*] [DE:HYDROLASE] (CBAH) (BILE SALT HYDROLASE)] |
| contig665 | 24240962_c3_44 | 2382 | 5787 | 681 | 226 | 267 | 2.50E-23 | [SP:P44013] [OR:*HAEMOPHILUS INFLUENZAE*] [GN:HI0552] [DE:HYPOTHETICAL PROTEIN HI0552] |
| contig665 | 2914087_c3_43 | 2383 | 5788 | 1236 | 411 | 127 | 3.00E-05 | [AC:AE000327] [OR:*Escherichia Coli*] [NT:o418 was o397; This 397 aa orf is 26 pct identical] |
| contig665 | 10019677_f1_3 | 2384 | 5789 | 189 | 62 | 55 | 0.87 | [OR:*Gallus gallus*] [PN:B-G antigen] |
| contig665 | 24228452_c1_30 | 2385 | 5790 | 1659 | 552 | 175 | 2.40E-10 | [AC:Z82015] [OR:*Bacillus subtilis*] [GN:yukF] |
| contig665 | 34189517_f2_12 | 2386 | 5791 | 903 | 300 | 105 | 0.0021 | [AC:AE000139] [OR:*Escherichia coli*] [NT:o287; This 287 aa orf is 28 pct identical (6 gaps)] |
| contig665 | 5860662_f3_22 | 2387 | 5792 | 318 | 105 | 216 | 4.20E-17 | [AC:AE000139] [OR:*Escherichia coli*] [NT:o515; This 515 aa orf is 29 pct identical (8 gaps)] |
| contig665 | 14884402_f1_5 | 2388 | 5793 | 408 | 135 | 322 | 8.70E-29 | [AC:AE000139] [OR:*Escherichia coli*] [NT:o515; This 515 aa orf is 29 pct identical (8 gaps)] |
| contig665 | 11944515_f1_6 | 2389 | 5794 | 942 | 313 | 598 | 2.10E-58 | [AC:AE000139] [OR:*Escherichia coli*] [NT:o515; This 515 aa orf is 29 pct identical (8 gaps)] |
| contig665 | 14714212_f2_13 | 2390 | 5795 | 825 | 274 | 909 | 2.30E-91 | [AC:AE000139] [OR:*Escherichia coli*] [NT:o472; This 472 aa orf is 32 pct identical (7 gaps)] |
| contig665 | 30187661_f3_23 | 2391 | 5796 | 651 | 216 | 740 | 1.90E-73 | [AC:AE000139] [OR:*Escherichia coli*] [NT:o472; This 472 aa orf is 32 pct identical (7 gaps)] |

TABLE 2-continued

| Contig | Orf | NT Seq Id | AA Seq ID | NT Orf Length | AA Orf Length | Score | Probability | Description |
|---|---|---|---|---|---|---|---|---|
| contig665 | 2929500_f3_24 | 2392 | 5797 | 1224 | 407 | 57 | 0.9996 | [AC:M22530] [OR:*Rana temporaria*] [NT:gamma-6-crystallin] |
| contig665 | 21884561_c3_41 | 2393 | 5798 | 282 | 93 | 68 | 0.49 | [SP:Q03714] [OR:*SACCHAROMYCES CEREVISIAE*] [GN:YML029W] [DE:HYPOTHETICAL 96.7 KD PROTEIN IN NDC1-TSA1 INTERGENIC REGION] |
| contig665 | 10739581_f3_25 | 2394 | 5799 | 186 | 61 | 52 | 0.78 | [OR:*Homo sapiens*] [PN:inter-alpha-trypsin inhibitor heavy chain H1] |
| contig665 | 20083462_f3_26 | 2395 | 5800 | 666 | 221 | 83 | 0.97 | [AC:Z83116] [OR:*Caenorhabditis elegans*] [PN:M01B2.b] [NT:protein predicted using Genefinder; preliminary] |
| contig666 | 9805325_c1_34 | 2396 | 5801 | 300 | 99 | 334 | 2.00E-30 | [AC:M26414] [OR:*Bacillus subtilis*] [PN:initiation factor1] [GN:infA] |
| contig666 | 10265643_c1_33 | 2397 | 5802 | 723 | 240 | 783 | 5.20E-78 | [SP:P27143] [OR:*LACTOCOCCUS LACTIS*] [GN:ADK] [DE:ADENYLATE KINASE, (ATP-AMP TRANSPHOSPHORYLASE)] |
| contig666 | 3315700_c2_43 | 2398 | 5803 | 1299 | 432 | 1338 | 8.00E-137 | [SP:P27148] [OR:*LACTOCOCCUS LACTIS*] [GN:SECY] [DE:PREPROTEIN TRANSLOCASE SECY SUBUNIT] |
| contig666 | 23955443_c2_42 | 2399 | 5804 | 456 | 151 | 597 | 2.70E-58 | [AC:U96620] [OR:*Staphylococcus aureus*] [PN:ribosomal protein L15] [GN:L15] |
| contig666 | 34251902_c3_47 | 2400 | 5805 | 219 | 72 | 187 | 7.50E-15 | [OR:*Bacillus subtilis*] [PN:ribosomal protein L30] |
| contig666 | 3332812_c1_31 | 2401 | 5806 | 540 | 179 | 689 | 4.80E-68 | [SP:P21467] [OR:*BACILLUS SUBTILIS*] [GN:RPSE] [DE:30S RIBOSOMAL PROTEIN S5 (BS5)] |
| contig666 | 7242152_c2_41 | 2402 | 5807 | 375 | 124 | 412 | 1.10E-38 | [SP:P46899] [OR:*BACILLUS SUBTILIS*] [GN:RPLR] [DE:50S RIBOSOMAL PROTEIN L18] |
| contig666 | 4161578_c1_30 | 2403 | 5808 | 537 | 178 | 599 | 1.60E-58 | [SP:P02391] [OR:*BACILLUS STEAROTHERMOPHILUS*] [GN:RPLF] [DE:50S RIBOSOMAL PROTEIN 1.6 (B1.10)] |
| contig666 | 24255132_c3_46 | 2404 | 5809 | 426 | 141 | 574 | 7.30E-56 | [AC:L47971] [OR:*Bacillus subtilis*] [PN:ribosomal protein S8] [GN:rpsH] |
| contig666 | 17010885_c1_29 | 2405 | 5810 | 204 | 67 | 279 | 1.30E-24 | [OR:*Bacillus stearothermophilus*] [PN:ribosomal protein S14] [GN:rps14] |
| contig666 | 2598452_c1_28 | 2406 | 5811 | 540 | 179 | 785 | 3.20E-78 | [SP:P08895] [OR:*BACILLUS STEAROTHERMOPHILUS*] [GN:RPLE] [DE:50S RIBOSOMAL PROTEIN L5] |
| contig666 | 26027217_c3_45 | 2407 | 5812 | 330 | 109 | 393 | 1.10E-36 | [SP:P04455] [OR:*BACILLUS STEAROTHERMOPHILUS*] [GN:RPLX] [DE:50S RIBOSOMAL PROTEIN L24] |
| contig666 | 10741542_c1_27 | 2408 | 5813 | 399 | 132 | 482 | 4.10E-46 | [SP:P12875] [OR:*BACILLUS SUBTILIS*] [GN:RPLN] [DE:50S RIBOSOMAL PROTEIN L14] |
| contig666 | 26615926_c1_26 | 2409 | 5814 | 294 | 97 | 389 | 2.90E-36 | [AC:L47971] [OR:*Bacillus subtilis*] [PN:ribosomal protein L17] [GN:rpsQ] |
| contig666 | 24884787_c2_39 | 2410 | 5815 | 216 | 71 | 227 | 4.30E-19 | [SP:P04457] [OR:*BACILLUS STEAROTHERMOPHILUS*] [GN:RPMC] [DE:50S RIBOSOMAL PROTEIN L29] |
| contig666 | 26839688_c1_25 | 2411 | 5816 | 453 | 150 | 604 | 4.80E-59 | [SP:P14577] [OR:*BACILLUS SUBTILIS*] [GN:RPLP] [DE:50S RIBOSOMAL PROTEIN L16] |
| contig666 | 22557963_c2_38 | 2412 | 5817 | 672 | 223 | 918 | 2.60E-92 | [AC:U43929] [OR:*Bacillus subtilis*] [PN:S3] [GN:rpsC] [NT:ribosomal protein] |
| contig666 | 23436687_c2_37 | 2413 | 5818 | 192 | 63 | 194 | 1.40E-15 | [SP:P23311] [OR:*BACILLUS STEAROTHERMOPHILUS*] [GN:RPLV] [DE:50S RIBOSOMAL PROTEIN L22] |
| contig666 | 6298806_c2_36 | 2414 | 5819 | 312 | 103 | 395 | 6.80E-37 | [AC:D50302] [OR:*Bacillus subtilis*] [PN:Ribosomal Protein S19] [GN:rpsS] |
| contig666 | 5203543_c2_35 | 2415 | 5820 | 834 | 277 | 1170 | 5.10E-119 | [AC:U43929] [OR:*Bacillus subtilis*] [PN:L2] [GN:rplB] [NT:ribosomal protein] |
| contig666 | 14594455_f1_10 | 2416 | 5821 | 402 | 133 | 185 | 1.20E-14 | [OR:chloroplast *Zea mays*] [PN:hypothetical protein 137] |
| contig667 | 33986643_f2_7 | 2417 | 5822 | 1491 | 496 | 1323 | 4.20E-153 | [SP:P12655] [OR:*STREPTOCOCCUS MUTANS*] [GN:SCRA] [DE:COMPONENT], (EII-SCR) |

TABLE 2-continued

| Contig | Orf | NT Seq Id | AA Seq ID | NT Orf Length | AA Orf Length | Score | Probability | Description |
|---|---|---|---|---|---|---|---|---|
| contig667 | 4350817_c1_21 | 2418 | 5823 | 213 | 70 | 59 | 0.24 | [SP:Q59686] [OR:*PASTEURELLA MULTOCIDA*] [GN:GROES] [DE:10 KD CHAPERONIN (PROTEIN CPN10) (PROTEIN GROES)] |
| contig667 | 26214837_c1_20 | 2419 | 5824 | 270 | 89 | 58 | 0.71 | [AC:L07952] [OR:*Saccharomyces cerevisiae*] [NT:orf3] |
| contig667 | 23601577_c2_25 | 2420 | 5825 | 270 | 89 | 76 | 0.0043 | [OR:*Bacillus thuringiensis*] [PN:hypothetical protein 2 (Tn5401)] |
| contig667 | 19540900_c1_18 | 2421 | 5826 | 348 | 115 | 66 | 0.97 | [AC:U05989] [OR:*Rattus norvegicus*] [NT:induced in androgen-independent prostate cells by] |
| contig667 | 22460816_f3_13 | 2422 | 5827 | 1203 | 400 | 2003 | 2.70E-207 | [SP:P19775] [OR:*STAPHYLOCOCCUS AUREUS*] [GN:TNP] [DE:TRANSPOSASE FOR INSERTION SEQUENCE ELEMENT IS256 IN TRANSPOSON TN4001] |
| contig667 | 7070428_f2_8 | 2423 | 5828 | 1815 | 604 | 137 | 8.80E-06 | [AC:AE000198] [OR:*Escherichia coli*] [NT:f720; This 720 aa orf is 38 pct identical (20 gaps)] |
| contig667 | 9769625_f1_3 | 2424 | 5829 | 243 | 80 | 68 | 0.18 | [OR:*Xanthomonas campestris*] [PN:copD homolog] |
| contig667 | 22553437_c2_23 | 2425 | 5830 | 924 | 307 | 473 | 3.70E-45 | [AC:U09422] [OR:*Enterococcus faecalis*] [NT:ORF13] |
| contig667 | 21490686_c3_27 | 2426 | 5831 | 795 | 264 | 962 | 5.60E-97 | [AC:U09422] [OR:*Enterococcus faecalis*] [NT:ORF14] |
| contig667 | 14880385_c2_22 | 2427 | 5832 | 291 | 96 | 94 | 0.00033 | [AC:U09422] [OR:*Enterococcus faecalis*] [NT:ORF14] |
| contig667 | 14166285_c3_26 | 2428 | 5833 | 2154 | 717 | 1587 | 3.30E-163 | [AC:U09422] [OR:*Enterococcus faecalis*] [NT:ORF15] |
| contig667 | 16510317_f3_16 | 2429 | 5834 | 336 | 111 | 54 | 0.9998 | [AC:U78639] [OR:*Mycobacterium tuberculosis*] [NT:ORFc] |
| contig667 | 10581692_c1_17 | 2430 | 5835 | 249 | 82 | 341 | 3.80E-30 | [AC:U09422] [OR:*Enterococcus faecalis*] [NT:ORF16] |
| contig667 | 24609568_f1_1 | 2431 | 5836 | 1275 | 424 | 807 | 1.50E-80 | [OR:*Bacillus stearothermophilus*] [PN:cellobiose phosphotransferase system celB] |
| contig667 | 3424091_f1_2 | 2432 | 5837 | 1107 | 368 | 57 | 0.98 | [AC:M37606] [OR:*Drosophila melanogaster*] [PN:polytene protein] |
| contig668 | 24485627_f3_9 | 2433 | 5838 | 1065 | 354 | 66 | 0.997 | [AC:U88315] [OR:*Caenorhabditis elegans*] [GN:C37115.11] |
| contig668 | 24104681_f1_3 | 2434 | 5839 | 1155 | 384 | 136 | 2.10E-06 | [SP:P13254] [OR:*PSEUDOMONAS PUTIDA*] [DE:METHIONINE GAMMA-LYASE, (L-METHIONINASE)] |
| contig668 | 869028_f1_4 | 2435 | 5840 | 747 | 248 | 54 | 0.992 | [SP:P14422] [OR:*ORYCTOLAGUS CUNICULUS*] [GN:PLA2G2A] [DE:(PHOSPHATIDYLCHOLINE 2-ACYLHYDROLASE) (FRAGMENTS)] |
| contig668 | 5272953_f1_5 | 2436 | 5841 | 1020 | 339 | 185 | 2.20E-12 | [AC:U70664] [OR:*Haloferax alicantei*] [PN:2-keto-3-deoxygluconate kinase] [NT:similar to fructokinases] |
| contig668 | 173252_c3_21 | 2437 | 5842 | 189 | 62 | 200 | 1.20E-16 | [AC:U35453] [OR:*Clostridium acetobutylicum*] [PN:DNA gyrase subunit B] [GN:gyrB] |
| contig668 | 14664050_f1_6 | 2438 | 5843 | 1062 | 353 | 294 | 3.40E-26 | [SP:P52309] [OR:*LISTERIA MONOCYTOGENES*] [DE:HYPOTHETICAL 17.1 KD PROTEIN IN DNAG/DNAE 5' REGION (P17)] |
| contig668 | 39077_f3_10 | 2439 | 5844 | 447 | 148 | 294 | 3.40E-26 | [AC:U00457] [OR:*Enterococcus faecalis*] [PN:D-alanine] [GN:ddl] [NT:TTG start codon translated as Leu by the author] |
| contig668 | 22845588_f2_8 | 2440 | 5845 | 894 | 298 | 1283 | 5.40E-131 | [AC:U65015] [OR:*Vibrio furnissii*] [PN:GlcNAc 6-P deacetylase] [GN:manD] [NT:ManD] |
| contig669 | 6851692_f1_1 | 2441 | 5846 | 1170 | 389 | 439 | 1.50E-41 | [AC:U65015] [OR:*Vibrio furnissii*] [PN:PTS permease for mannose subunit IIPMan] [GN:manY] [NT:ManY; Pel; IIDMan] |
| contig669 | 23526582_f1_2 | 2442 | 5847 | 798 | 265 | 500 | 5.10E-48 | [AC:U65015] [OR:*Vibrio furnissii*] [PN:PTS permease for mannose subunit IIBMan] [GN:manZ] [NT:ManZ] |
| contig669 | 963201_f2_11 | 2443 | 5848 | 903 | 300 | 636 | 2.00E-62 | [AC:AF005240] [OR:Mitochondrion *Fusarium oxysporum*] [PN:putative reverse transcriptase] [GN:RT] |
| contig669 | 789087_c1_31 | 2444 | 5849 | 285 | 94 | 65 | 0.28 | [OR:*Enterococcus faecalis*] [PN:probable pheromone binding proteinpheromone responsive gene Z protein] [GN:prgZ] |
| contig669 | 30602312_c3_44 | 2445 | 5850 | 1671 | 556 | 1192 | 2.40E-121 | [SP:P27646] [OR:SYNECHOCOCCUS SP] [GN:MPEA] [DE:C-PHYCOERYTHRIN CLASS II ALPHA CHAIN |
| contig669 | 937_c3_43 | 2446 | 5851 | 444 | 147 | 64 | 0.9999 | |

TABLE 2-continued

| Contig | Orf | NT Seq Id | AA Seq ID | NT Orf Length | AA Orf Length | Score | Probability | Description |
|---|---|---|---|---|---|---|---|---|
| contig669 | 35212541_f2_f2 | 2447 | 5852 | 1128 | 375 | 1008 | 7.50E-102 | [AC:X81089] [OR:Lactococcus lactis] [PN:glutanyl-aminopeptidase] [GN:pepA] |
| contig669 | 11875327_f1_5 | 2448 | 5853 | 315 | 104 | 231 | 1.60E-19 | [AC:X81089] [OR:Lactococcus lactis] [NT:ORF3] |
| contig669 | 13089055_f1_6 | 2449 | 5854 | 501 | 166 | 182 | 2.50E-14 | [AC:Z95554] [OR:Mycobacterium tuberculosis] [PN:unknown] [GN:MYCY01B2.28] [NT: MTCY01B2.28, 146, Function] |
| contig669 | 5086438_12_14 | 2450 | 5855 | 618 | 205 | 138 | 1.90E-09 | [SP:P16684] [OR:ESCHERICHIA COLI] [GN:PHNF] [DE:PHNF PROTEIN] |
| contig669 | 7245302_f1_7 | 2451 | 5856 | 429 | 142 | 68 | 0.77 | [SP:P37080] [OR:KLEBSIELLA PNEUMONIAE] [GN:SORF] [DE:(EC 2.7.1.69) (EIII-F-SOR)] |
| contig669 | 36225125_f3_23 | 2452 | 5857 | 552 | 183 | 91 | 0.026 | [AC:D90902] [OR:Synechocystis sp.] [PN:hypothetical protein] [GN:pleD] [NT:ORF_ID] |
| contig669 | 1359712_f3_24 | 2453 | 5858 | 210 | 69 | 83 | 0.0043 | [AC:Z69383] [OR:Caenorhabditis elegans] [PN:F13E9.3] [NT:protein predicted using Genefinder] |
| contig669 | 5120927_f2_15 | 2454 | 5859 | 480 | 159 | 254 | 5.90E-22 | [SP:P42904] [OR:ESCHERICHIA COLI] [GN:AGAV] [DE:ENZYME II, B COMPONENT 2).] |
| contig669 | 14898577_f2_16 | 2455 | 5860 | 771 | 256 | 301 | 6.20E-27 | [SP:P08187] [OR:ESCHERICHIA COLI] [GN:MANY] [DE:(EII-P-MAN)] |
| contig669 | 23884703_f3_25 | 2456 | 5861 | 855 | 284 | 456 | 2.30E-43 | [SP:P08188] [OR:ESCHERICHIA COLI] [GN:MANZ] [DE:(EII-M-MAN)] |
| contig669 | 194376_f1_9 | 2457 | 5862 | 261 | 86 | 69 | 0.45 | [AC:AB002348] [OR:Homo sapiens] [GN:KIAA0350] |
| contig67 | 22439777_c2_2 | 2458 | 5863 | 561 | 186 | 165 | 5.20E-12 | [SP:P46828] [OR:BACILLUS MEGATERIUM] [GN:CCPA] [DE:GLUCOSE-RESISTANCE AMYLASE REGULATOR (CATABOLITE CONTROL PROTEIN)] |
| contig670 | 21972660_f3_8 | 2459 | 5864 | 1356 | 451 | 1391 | 1.90E-142 | [SP:P25811] [OR:BACILLUS SUBTILIS] [GN:THDF] [DE:POSSIBLE THIOPHENE AND FURAN OXIDATION PROTEIN THDF] |
| contig670 | 15032813_f1_1 | 2460 | 5865 | 1926 | 641 | 2246 | 4.90E-233 | [SP:P25812] [OR:BACILLUS SUBTILIS] [GN:GIDA] [DE:GLUCOSE INHIBITED DIVISION PROTEIN A] |
| contig670 | 22458337_f1_2 | 2461 | 5866 | 831 | 276 | 731 | 1.70E-72 | [SP:P37079] [OR:KLEBSIELLA PNEUMONIAE] [GN:SORD] [DE:PHOSPHATE DEHYDROGENASE) (KETOSEPHOSPHATE REDUCTASE)] |
| contig670 | 6666577_f1_3 | 2462 | 5867 | 1863 | 620 | 203 | 1.10E-26 | [SP:P46321] [OR:BACILLUS SUBTILIS] [GN:CELR] [DE:PUTATIVE CEL OPERON REGULATOR] |
| contig670 | 15837942_f3_10 | 2463 | 5868 | 516 | 171 | 130 | 8.20E-09 | [SP:P15081] [OR:ESCHERICHIA COLI] [GN:GUTM] [DE:GLUCITOL OPERON ACTIVATOR PROTEIN] |
| contig670 | 24022767_f2_6 | 2464 | 5869 | 588 | 195 | 499 | 6.50E-48 | [AC:D90892] [OR:Escherichia coli] [PN:PTS SYSTEM, GLUCITOL/SORBITOL-SPECIFIC IIBC] [GN:gutA] [NT:similar to SwissProt Accession Number P05705] |
| contig670 | 30493817_f3_11 | 2465 | 5870 | 1029 | 342 | 721 | 1.90E-71 | [SP:P05705] [OR:ESCHERICHIA COLI] [GN:SRLA] [DE:II, BC COMPONENT). (EII-GUT)] |
| contig670 | 312_f3_12 | 2466 | 5871 | 381 | 126 | 158 | 8.80E-12 | [AC:M93585] [OR:Escherichia coli] [PN:PTS enzyme III glucitol] [GN:guiB] [NT:putative] |
| contig670 | 994087_f3_13 | 2467 | 5872 | 681 | 226 | 346 | 1.10E-31 | [SP:P32669] [OR:ESCHERICHIA COLI] [GN:TALC] [DE:TRANSALDOLASE-LIKE PROTEIN.] |
| contig670 | 26429812_f3_14 | 2468 | 5873 | 204 | 67 | 53 | 0.69 | [AC:U30754] [OR:Human immunodeficiency virus type 1] [PN:envelope glycoprotein gp41] [GN:env] |
| contig670 | 4866513_f3_15 | 2469 | 5874 | 873 | 290 | 902 | 1.30E-90 | [AC:U09352] [OR:Streptococcus pyogenes] [PN:67 kDa Myosin-crossreactive streptococcal] [NT:ORF2] |
| contig671 | 5289005_f3_9 | 2470 | 5875 | 252 | 83 | 152 | 3.80E-11 | [SP:P54510] [OR:BACILLUS SUBTILIS] [GN:YQHL] |

TABLE 2-continued

| Contig | Orf | NT Seq Id | AA Seq ID | NT Orf Length | AA Orf Length | Score | Probability | Description |
|---|---|---|---|---|---|---|---|---|
| contig671 | 58898452_f3_10 | 2471 | 5876 | 1650 | 549 | 646 | 1.70E-63 | [DE:HYPOTHETICAL 14.6 KD PROTEIN IN GCVT-SPOIIAA INTERGENIC REGION] |
| contig671 | 23603437_f1_1 | 2472 | 5877 | 303 | 100 | 166 | 1.30E-12 | [OR:*Methanococcus jannaschii*] [PN:NADH oxidase] [SP:P54433] [OR:*BACILLUS SUBTILIS*] [GN:YRKF] [DE:HYPOTHETICAL 20.7 KD PROTEIN IN BLTR-SPOIIC INTERGENIC REGION] |
| contig671 | 11132827_f1_2 | 2473 | 5878 | 1167 | 388 | 99 | 0.032 | [AC:D90845] [OR:*Escherichia coli*] [PN:Membrane fusion protein MtrC precursor.] [NT:ORF_ID] |
| contig671 | 5116451_f2_8 | 2474 | 5879 | 681 | 226 | 521 | 3.00E-50 | [OR:*Methanococcus jannaschii*] [PN:glutamine transport ATP-binding protein Q homolog] [SP:Q58902] [OR:*METHANOCOCCUS JANNASCHII*] [GN:MJ1507] [DE:HYPOTHETICAL PROTEIN MJ1507] |
| contig671 | 210965_f1_3 | 2475 | 5880 | 1236 | 411 | 174 | 1.00E-10 | [AC:M88587] [OR:Fowlpox virus] [PN:envelope protein] [GN:p74K] [NT:disruption of the gene results in a small plaque] |
| contig671 | 31287502_f3_11 | 2476 | 5881 | 765 | 254 | 90 | 0.24 | [AC:S80442] [OR:Mus sp.] [NT:Description] |
| contig671 | 30745885_f3_12 | 2477 | 5882 | 315 | 105 | 57 | 0.36 | [SP:P42369] [OR:*LACTOCOCCUS LACTIS*] [GN:GRPE] [DE:GRPE PROTEIN] |
| contig672 | 5879683_c1_25 | 2478 | 5883 | 585 | 194 | 354 | 1.50E-32 | |
| contig672 | 4744217_c1_24 | 2479 | 5884 | 1059 | 352 | 675 | 1.40E-66 | [AC:Y09446] [OR:*Bacillus stearothermophilus*] [PN:repressor protein of class I heat shock genes] [GN:hrcA] |
| contig672 | 4714162_c3_34 | 2480 | 5885 | 1194 | 397 | 937 | 2.50E-94 | [AC:D84432] [OR:*Bacillus subtilis*] [PN:YqcR] |
| contig672 | 26601587_c3_33 | 2481 | 5886 | 2667 | 888 | 1975 | 2.50E-204 | [SP:P39168] [OR:*ESCHERICHIA COLI*] [GN:MGTA] [DE:MG(2+) TRANSPORT ATPASE, P-TYPE 1.] |
| contig672 | 22085880_f1_6 | 2482 | 5887 | 957 | 318 | 233 | 1.00E-19 | [AC:D90801] [OR:*Escherichia coli*] [PN:als operon regulatory protein.] [NT:ORF_ID] |
| contig672 | 1272792_f3_21 | 2483 | 5888 | 954 | 317 | 228 | 3.40E-19 | [SP:P27111] [OR:*ESCHERICHIA COLI*] [GN:CYNR] [DE:CYN OPERON TRANSCRIPTIONAL ACTIVATOR] |
| contig672 | 13862952_c1_23 | 2484 | 5889 | 1149 | 382 | 399 | 2.60E-37 | [SP:P39604] [OR:*BACILLUS SUBTILIS*] [GN:YWCF] [DE:HYPOTHETICAL 43.3 KD PROTEIN IN QOXD-VPR INTERGENIC REGION] |
| contig672 | 26367300_c3_30 | 2485 | 5890 | 1200 | 399 | 714 | 1.10E-70 | [AC:U58049] [OR:*Enterococcus hirae*] [PN:putative cell division protein ftsW] |
| contig672 | 190902_c1_22 | 2486 | 5891 | 309 | 102 | 64 | 0.21 | [SP:P15281] [OR:*BACILLUS SUBTILIS*] [GN:SPOIIID] [DE:STAGE III SPORULATION PROTEIN D (14 KD TRANSCRIPTION FACTOR)] |
| contig672 | 243065542_c3_29 | 2487 | 5892 | 345 | 114 | 58 | 0.29 | [AC:U24868] [OR:Human immunodeficiency virus type 1] [PN:envelope glycoprotein, V3 region] [GN:env] |
| contig672 | 10563511_f2_14 | 2488 | 5893 | 195 | 65 | | | |
| contig673 | 13830318_f1_1 | 2489 | 5894 | 639 | 212 | 289 | 1.20E-25 | [SP:Q06174] [OR:*BACILLUS STEAROTHERMOPHILUS*] [GN:EST] [DE:CARBOXYLESTERASE PRECURSOR.] |
| contig673 | 4726693_f3_14 | 2490 | 5895 | 2379 | 792 | 1178 | 7.20E-120 | [SP:P21499] [OR:*ESCHERICHIA COLI*] [GN:VACB] [DE:VACB PROTEIN] |
| contig673 | 3214717_f3_15 | 2491 | 5896 | 477 | 158 | 700 | 3.30E-69 | [SP:P43659] [OR:*ENTEROCOCCUS FAECALIS*] [GN:SMPB] [DE:SMALL PROTEIN B HOMOLOG] |
| contig673 | 26564127_f2_7 | 2492 | 5897 | 726 | 241 | 850 | 4.10E-85 | [SP:P43454] [OR:*ENTEROCOCCUS FAECALIS*] [GN:ATPB] [DE:ATP SYNTHASE A CHAIN, (PROTEIN 6)] |
| contig673 | 13867805_f2_8 | 2493 | 5898 | 270 | 89 | 205 | 9.30E-17 | [SP:P26682] [OR:*ENTEROCOCCUS FAECALIS*] [GN:ATPE] [DE:[DICYCLOHEXYLCARBODIIMIDE-BINDING PROTEIN]] |
| contig673 | 3159413_f1_5 | 2494 | 5899 | 537 | 178 | 494 | 2.20E-47 | [SP:P26681] [OR:*ENTEROCOCCUS FAECALIS*] [GN:ATPF] [DE:ATP SYNTHASE B CHAIN,] |

TABLE 2-continued

| Contig | Orf | NT Seq Id | AA Seq ID | NT Orf Length | AA Orf Length | Score | Probability | Description |
|---|---|---|---|---|---|---|---|---|
| contig673 | 4870303_f2_9 | 2495 | 5900 | 552 | 183 | 581 | 1.30E-56 | [SP:P26680] [OR:ENTEROCOCCUS FAECALIS] [GN:ATPH] [DE:ATP SYNTHASE DELTA CHAIN,] |
| contig673 | 23860452_f3_16 | 2496 | 5901 | 1557 | 518 | 2306 | 2.10E-239 | [SP:P26679] [OR:ENTEROCOCCUS FAECALIS] [GN:ATPA] [DE:ATP SYNTHASE ALPHA CHAIN,] |
| contig673 | 36335333_f3_17 | 2497 | 5902 | 915 | 304 | 1182 | 2.70E-120 | [SP:P43452] [OR:ENTEROCOCCUS FAECALIS] [GN:ATPG] [DE:ATP SYNTHASE GAMMA CHAIN,] |
| contig673 | 26376251_f1_6 | 2498 | 5903 | 1434 | 477 | 1884 | 1.10E-194 | [SP:P43451] [OR:ENTEROCOCCUS FAECALIS] [GN:ATPD] [DE:ATP SYNTHASE BETA CHAIN,] |
| contig673 | 24485257_f2_11 | 2499 | 5904 | 195 | 64 | 126 | 2.20E-08 | [SP:P43453] [OR:ENTEROCOCCUS FAECALIS] [GN:ATPC] [DE:ATP SYNTHASE EPSILON CHAIN,] |
| contig673 | 6678588_f2_6 | 2500 | 5905 | 330 | 109 | 62 | 0.12 | [AC:U01723] [OR:Mycoplasma genitalium] [NT:Homologous to Swiss-Prot Accession Number P32333.] |
| contig674 | 35395677_f1_1 | 2501 | 5906 | 273 | 90 | 66 | 0.31 | [AC:U07678] [OR:Felis pardalis] [PN:MHC class I antigen] [GN:FLA-I] [NT:membrane glycoprotein] |
| contig674 | 36220300_f2_7 | 2502 | 5907 | 1086 | 361 | 419 | 1.90E-39 | [SP:Q07429] [OR:BACILLUS SUBTILIS] [GN:NRGA] [DE:PROBABLE AMMONIUM TRANSPORTER (MEMBRANE PROTEIN NRGA)] |
| contig674 | 9845452_c1_23 | 2503 | 5908 | 198 | 65 | 62 | 0.48 | [SP:Q47677] [OR:ESCHERICHIA COLI] [GN:GLOB] [DE:II] |
| contig674 | 24431552_f2_8 | 2504 | 5909 | 1137 | 378 | 131 | 1.30E-07 | [SP:P50736] [OR:BACILLUS SUBTILIS] [GN:YPDA] [DE:HYPOTHETICAL 36.3 KD PROTEIN IN RECQ-CMK INTERGENIC REGION] |
| contig674 | 19703777_c2_27 | 2505 | 5910 | 189 | 62 | 77 | 0.055 | [SP:P12655] [OR:STREPTOCOCCUS MUTANS] [GN:SCRA] [DE:COMPONENT], (EII-SCR) |
| contig674 | 26250625_c3_30 | 2506 | 5911 | 339 | 112 | 324 | 2.30E-29 | [AC:U30714] [OR:Bacillus anthracis] [NT:ORFB; similar to B. anthracis SterneL element ORFB.] |
| contig674 | 24407268_c3_29 | 2507 | 5912 | 309 | 102 | 187 | 7.50E-15 | [AC:U30712] [OR:Bacillus anthracis] [NT:truncated ORFB due to a basepair deletion; similar] |
| contig674 | 23836016_f2_10 | 2508 | 5913 | 240 | 79 | 74 | 0.17 | [AC:Z77133] [OR:Caenorhabditis elegans] [PN:K03A11.1] [NT:Weak homology with Worm proteins (zinc] |
| contig674 | 34589000_c2_26 | 2509 | 5914 | 1182 | 393 | 505 | 1.50E-48 | [AC:Z71474] [OR:Bacillus megaterium] [PN:xyl repressor] [GN:xylR] |
| contig674 | 4774006_f1_3 | 2510 | 5915 | 213 | 70 | 62 | 0.78 | [OR:Drosophila teissieri] [PN:reverse transcriptase] [GN:Dtei/R2-element] |
| contig674 | 25429813_f2_11 | 2511 | 5916 | 2094 | 697 | 1313 | 3.60E-134 | [SP:Q01336] [OR:ERWINIA HERBICOLA] [DE:HYPOTHETICAL PROTEIN IN CRTE 3' REGION (ORF2) (FRAGMENT)] |
| contig674 | 977318_f1_4 | 2512 | 5917 | 798 | 265 | 260 | 1.40E-22 | [SP:P08187] [OR:ESCHERICHIA COLI] [GN:MANY] [DE:(EII-P-MAN)] |
| contig674 | 9929676_c2_25 | 2513 | 5918 | 225 | 74 | 64 | 0.6 | [AC:L76740] [OR:Epichloe typhina] [PN:protease] |
| contig674 | 30371086_f2_12 | 2514 | 5919 | 831 | 276 | 355 | 1.20E-32 | [SP:P08188] [OR:ESCHERICHIA COLI] [GN:MANZ] [DE:(EII-M-MAN)] |
| contig674 | 30079637_f2_13 | 2515 | 5920 | 507 | 168 | 243 | 8.70E-21 | [SP:P08186] [OR:ESCHERICHIA COLI] [GN:MANX] [DE:(EC 2.7.1.69) (EIII-MAN)] |
| contig674 | 4812_f1_5 | 2516 | 5921 | 447 | 148 | 177 | 2.10E-13 | [OR:Escherichia coli] [PN:phosphotransferase system enzyme II, mannose-specific, factor III] [GN:manX] |
| contig674 | 192137_f3_16 | 2517 | 5922 | 225 | 75 | 209 | 1.60E-16 | [SP:P29441] [OR:CLOSTRIDIUM THERMOSACCHAROLYTICUM] [GN:XYLA] [DE:XYLOSE ISOMERASE,] |
| contig675 | 5189077_c2_28 | 2518 | 5923 | 405 | 135 | 168 | 2.50E-12 | [AC:D90848] [OR:Escherichia coli] [PN:PTS system, Galactitol-specific IIC component] [GN:gatC] [NT:ORF_ID] |
| contig675 | 21970443_f1_1 | 2519 | 5924 | 327 | 108 | 62 | 0.12 | [AC:L41654] [OR:Trypanosoma brucei] [PN:microtubule-associated |

TABLE 2-continued

| Contig | Orf | NT Seq Id | AA Seq ID | NT Orf Length | AA Orf Length | Score | Probability | Description |
|---|---|---|---|---|---|---|---|---|
| contig675 | 30162691_c1_21 | 2520 | 5925 | 423 | 140 | 64 | 0.68 | protein) [GN:MAPP15] [SP:P39302] [OR:ESCHERICHIA COLI] [GN:YIFT] [DE:HYPOTHETICAL 10.9 KD PROTEIN IN AIDB-RPSF INTERGENIC REGION (O101)] |
| contig675 | 26359635_c3_37 | 2521 | 5926 | 519 | 172 | 90 | 0.0061 | [AC:AF000298] [OR:Escherichia coli] [PN:pts system, galactitol-specific IIA component] [GN:gatA] [NT:f150; 99 pct identical to PTKA_ECOLI SW] |
| contig675 | 3908135_f2_6 | 2522 | 5927 | 522 | 173 | 459 | 1.10E-43 | [SP:P23494] [OR:LACTOCOCCUS LACTIS] [GN:LACA] [DE:GALACTOSE-6-PHOSPHATE ISOMERASE LACA SUBUNIT,] |
| contig675 | 34273385_f3_10 | 2523 | 5928 | 534 | 177 | 637 | 1.50E-62 | [SP:P26592] [OR:STAPHYLOCOCCUS AUREUS] [GN:LACB] [DE:GALACTOSE-6-PHOSPHATE ISOMERASE LACB SUBUNIT,] |
| contig675 | 6074017_c3_35 | 2524 | 5929 | 303 | 100 | | | |
| contig675 | 26449063_f3_11 | 2525 | 5930 | 447 | 148 | 141 | 5.60E-10 | [SP:P26379] [OR:BACILLUS SUBTILIS] [GN:LEVD] [DE:(EC 2.7.1.69) (P16)] |
| contig675 | 2117942_f2_7 | 2526 | 5931 | 525 | 174 | 120 | 9.40E-08 | [AC:U28163] [OR:Lactobacillus curvatus] [PN:EIIB-man] [GN:manB] [NT:mannose phosphotransferase system enzyme EII] |
| contig675 | 34589187_f2_8 | 2527 | 5932 | 870 | 289 | 75 | 0.24 | [AC:U61059] [OR:Saguinus oedipus] [PN:T-cell receptor beta] [GN:TCRB] [NT:V beta; J rearrangement] |
| contig675 | 14648282_f2_9 | 2528 | 5933 | 816 | 271 | 301 | 6.20E-27 | [SP:P08188] [OR:ESCHERICHIA COLI] [GN:MANZ] [DE:(EII-M-MAN)] |
| contig675 | 3339050_c1_15 | 2529 | 5934 | 729 | 242 | 411 | 1.40E-38 | [SP:P18156] [OR:BACILLUS SUBTILIS] [GN:GLPF] [DE:GLYCEROL UPTAKE FACILITATOR PROTEIN] |
| contig675 | 5261512_c2_25 | 2530 | 5935 | 1035 | 344 | 429 | 1.70E-40 | [AC:D90900] [OR:Synechocystis sp.] [PN:hypothetical protein] [NT:ORF_ID] |
| contig675 | 24022818_f3_12 | 2531 | 5936 | 330 | 109 | 54 | 0.63 | [AC:D10865] [OR:Saccharomyces cerevisiae] [PN:pyruvate dehydrogenase alpha] |
| contig675 | 972252_f1_5 | 2532 | 5937 | 1128 | 375 | 996 | 1.40E-100 | [SP:P20368] [OR:ZYMOMONAS MOBILIS] [GN:ADHA] [DE:ALCOHOL DEHYDROGENASE I, (ADH I)] |
| contig675 | 22070380_f3_14 | 2533 | 5938 | 414 | 137 | 74 | 0.72 | [AC:U51115] [OR:Bacillus subtilis] [PN:unknown protein] [NT:transmembrane protein; similar to hypothetical] |
| contig675 | 23594650_c2_23 | 2534 | 5939 | 219 | 72 | 63 | 0.97 | [SP:P53935] [OR:SACCHAROMYCES CEREVISIAE] [GN:YNL091W] [DE:HYPOTHETICAL 141.5 KD PROTEIN IN YPT53-RHO2 INTERGENIC REGION] |
| contig675 | 29541405_f3_9 | 2535 | 5940 | 1122 | 373 | 331 | 4.10E-30 | [AC:Z69371] [OR:Bacillus subtilis] [PN:integral membrane protein] [GN:glnM] [NT:putative] |
| contig676 | 35289127_f1_1 | 2536 | 5941 | 654 | 217 | 724 | 9.30E-72 | [SP:P54537] [OR:BACILLUS SUBTILIS] [GN:YQIZ] [DE:INTERGENIC REGION] |
| contig676 | 12263562_f1_2 | 2537 | 5942 | 1170 | 389 | 626 | 2.30E-61 | [SP:P23034] [OR:BACILLUS SP] [DE:ASPARTATE AMINOTRANSFERASE, (TRANSAMINASE A) (ASPAT)] |
| contig676 | 24117937_c2_24 | 2538 | 5943 | 327 | 108 | 67 | 0.998 | [SP:P41884] [OR:CAENORHABDITIS ELEGANS] [GN:F37A4.6] [DE:HYPOTHETICAL 43.5 KD PROTEIN F37A4.6 IN CHROMSOME III] |
| contig676 | 24900462_c2_23 | 2539 | 5944 | 864 | 287 | 81 | 0.26 | [AC:AB001488] [OR:Bacillus subtilis] [GN:ydjI] [NT:FUNCTION UNKNOWN] |
| contig676 | 29895062_c1_18 | 2540 | 5945 | 1758 | 585 | | | |
| contig676 | 24886552_c2_22 | 2541 | 5946 | 381 | 126 | 53 | 0.78 | [AC:U32205] [OR:Human immunodeficiency virus type 1] [PN:envelope glycoprotein V1/V2 region] [GN:env] |
| contig676 | 22539818_c3_31 | 2542 | 5947 | 1275 | 424 | 928 | 2.20E-93 | [AC:AB001488] [OR:Bacillus subtilis] [GN:ydaM] [NT:FUNCTION UNKNOWN, SIMILAR PRODUCT IN MANY] |

TABLE 2-continued

| Contig | Orf | NT Seq Id | AA Seq ID | NT Orf Length | AA Orf Length | Score | Probability | Description |
|---|---|---|---|---|---|---|---|---|
| contig676 | 24617342_c1_16 | 2543 | 5948 | 1590 | 529 | 68 | 0.31 | [OR:*Homo sapiens*] [PN:retinoblastoma 1] [GN:RB1] |
| contig676 | 4570393_c3_30 | 2544 | 5949 | 1530 | 509 | 81 | 0.67 | [SP:P15577] [OR:*PARAMECIUM TETRAURELIA*] [GN:ND2] [DE:NADH-UBIQUINONE OXIDOREDUCTASE CHAIN 2.] |
| contig676 | 22070132_c2_19 | 2545 | 5950 | 558 | 185 | 135 | 3.90E-08 | [AC:AB001488] [OR:*Bacillus subtilis*] [GN:ydaJ] [NT:FUNCTION UNKNOWN.] |
| contig677 | 22691312_c1_24 | 2546 | 5951 | 1092 | 363 | 385 | 7.80E-36 | [SP:Q58341] [OR:*METHANOCOCCUS JANNASCHII*] [GN:MJ0931] [DE:HYPOTHETICAL PROTEIN MJ0931 |
| contig677 | 24851502_c3_42 | 2547 | 5952 | 213 | 70 | 220 | 1.00E-17 | [AC:U51115] [OR:*Bacillus subtilis*] [PN:unknown protein] [NT:transmembrane protein; similar to hypothetical] |
| contig677 | 36225002_c3_41 | 2548 | 5953 | 1041 | 346 | 830 | 5.40E-83 | [AC:U51115] [OR:*Bacillus subtilis*] [PN:unknown protein] [NT:transmembrane protein; similar to hypothetical] |
| contig677 | 24728212_c1_23 | 2549 | 5954 | 198 | 65 | 59 | 0.38 | [SP:P36813] [OR:HUMAN PAPILLOMAVIRUS TYPE 49] [GN:E6] [DE:E6 PROTEIN] |
| contig677 | 19652265_c3_40 | 2550 | 5955 | 294 | 97 | 57 | 0.89 | [SP:Q03671] [OR:*CANDIDA PARAPSILOSIS*] [GN:ATP6] [DE:ATP SYNTHASE A CHAIN PRECURSOR, (PROTEIN 6) |
| contig677 | 29494001_c3_39 | 2551 | 5956 | 342 | 113 | 54 | 0.6 | [OR:*Cricetinae gen. sp.*] [PN:potassium channel protein HaK-7] |
| contig677 | 20345042_c3_38 | 2552 | 5957 | 243 | 80 | 63 | 0.66 | [SP:Q10917] [OR:CAENORHABDITIS ELEGANS] [GN:B0252.3] [DE:HYPOTHETICAL 48.6 KD PROTEIN B0252.3 IN CHROMOSOME II] |
| contig677 | 10000286_c1_22 | 2553 | 5958 | 354 | 117 | 65 | 0.82 | [AC:U35440] [OR:Rhodobacter sphaeroides] [PN:PepE] [GN:pepE] [NT:similar to YejE of *Escherichia coli*, Swiss-Prot] |
| contig677 | 30658418_c3_37 | 2554 | 5959 | 291 | 96 | 52 | 0.91 | [AC:U09422] [OR:*Enterococcus faecalis*] [NT:ORF19] |
| contig677 | 35273453_c2_29 | 2555 | 5960 | 204 | 67 | 174 | 1.80E-13 | [SP:P27484] [OR:*NICOTIANA SYLVESTRIS*] [GN:GRP-2] [DE:GLYCINE-RICH CELL WALL STRUCTURAL PROTEIN 2 PRECURSOR] |
| contig677 | 15917802_c1_21 | 2556 | 5961 | 591 | 196 | 71 | 0.037 | [AC:U86650] [OR:*Tragulus napu*] [PN:gamma fibrinogen] [NT:blood clotting protein] |
| contig677 | 24640937_c2_28 | 2557 | 5962 | 219 | 72 | 59 | 0.24 | [AC:D09022] [OR:Synechocystis sp.] [PN:hypothetical protein] [GN:patA] [NT:ORF_ID] |
| contig677 | 490668_c2_26 | 2558 | 5963 | 246 | 81 | 65 | 0.37 | [SP:Q09272] [*CAENORHABDITIS ELEGANS*] GN:C41C4.1] [DE:HYPOTHETICAL 39.0 KD PROTEIN C41C4.1 IN CHROMOSOME II] |
| contig677 | 6102317_c1_19 | 2559 | 5964 | 543 | 180 | 81 | 0.0027 | [OR:*Macaca mulatta*] [PN:gene MHC DQ-beta 1 protein] |
| contig677 | 24337637_c3_35 | 2560 | 5965 | 564 | 187 | 72 | 0.95 | [SP:P47838] [OR:*GALLUS GALLUS*] [GN:RPS6] [DE:40S RIBOSOMAL PROTEIN S6] |
| contig677 | 34589038_c3_34 | 2561 | 5966 | 201 | 66 | 76 | 0.027 | [AC:AC000103] [OR:*Arabidopsis thaliana*] [PN:F2119.15] [NT:dehydrogenase isolog] |
| contig677 | 32222803_c3_33 | 2562 | 5967 | 459 | 152 | 59 | 0.39 | [AC:J01685] [OR:*Escherichia coli*] [GN:rpsD] [NT:ribosomal protein S4] |
| contig677 | 4181312_c2_25 | 2563 | 5968 | 2388 | 795 | 747 | 3.40E-74 | [OR:*Streptococcus thermophilus*] [PN:hypothetical protein 2] |
| contig677 | 32477217_c1_18 | 2564 | 5969 | 258 | 85 | 64 | 0.46 | [OR:*Xenopus laevis*] [PN:annexin II type 2] [GN:Anx II-2] |
| contig678 | 24423558_f2_10 | 2565 | 5970 | 258 | 85 | 160 | 5.40E-12 | [AC:295398] [OR:*Mycobacterium leprae*] [PN:unknown] [GN:MLCL622.07] [NT:MLCL622.07, unknown, len] |
| contig678 | 26775450_c3_33 | 2566 | 5971 | 1278 | 425 | 261 | 1.20E-20 | [SP:P37489] [OR:*BACILLUS SUBTILIS*] [GN:YYBO] [DE:HYPOTHETICAL 48.2 KD PROTEIN IN COTF-TETB INTERGENIC REGION] |
| contig678 | 2921928_c2_28 | 2567 | 5972 | 249 | 82 | 64 | 0.81 | [SP:P49007] [OR:ALTEROMONAS SP] [GN:NAG096] [DE:(BETA-NAHASE)] |
| contig678 | 4015968_c3_32 | 2568 | 5973 | 1218 | 405 | 513 | 2.10E-49 | [SP:P09139] [OR:*RATTUS NORVEGICUS*] [DE:(EC 2.6.1.44) |

TABLE 2-continued

| Contig | Orf | NT Seq Id | AA Seq ID | NT Orf Length | AA Orf Length | Score | Probability | Description |
|---|---|---|---|---|---|---|---|---|
| contig678 | 7245312_f2_12 | 2569 | 5974 | 1644 | 547 | 157 | 2.20E-08 | (AGT) [AC:D50453] [OR:Bacillus subtilis] [PN:homologue of hypothetical protein HI0093 of H.] [gn:ycgP] |
| contig678 | 36133388_c3_31 | 2570 | 5975 | 807 | 268 | 764 | 5.40E-76 | [SP:P75713] [OR:ESCHERICHIA COLI] [GN:YLBA] [DE:HYPOTHETICAL 28.7 KD PROTEIN IN GCL-FDRA INTERGENIC REGION] |
| contig678 | 35964442_c3_30 | 2571 | 5976 | 1278 | 425 | 1257 | 3.10E-128 | [SP:P77425] [OR:ESCHERICHIA COLI] [GN:YLBB] [DE:HYPOTHETICAL 45.7 KD PROTEIN IN GCL-FDRA INTERGENIC REGION] |
| contig678 | 26304577_c2_26 | 2572 | 5977 | 1365 | 454 | 1321 | 5.10E-135 | [AC:AE000157] [OR:Escherichia coli] NTo453; This 453 aa orf is 33 pct identical (19 gaps)] |
| contig678 | 1383562_c2_25 | 2573 | 5978 | 1512 | 503 | 1225 | 7.60E-125 | [AC:U82664] [OR:Escherichia coli] [NT:similar to Pseudomonas sp. ORF5] |
| contig678 | 26462825_c2_24 | 2574 | 5979 | 516 | 171 | 445 | 3.40E-42 | [SP:P21340] [OR:BACILLUS SUBTILIS] [GN:PAIA] [DE:PROTEASE SYNTHASE AND SPORULATION NEGATIVE REGULATORY PROTEIN PAI 1] |
| contig678 | 32934_c2_23 | 2575 | 5980 | 447 | 148 | 529 | 4.30E-51 | [SP:P37503] [OR:BACILLUS SUBTILIS] [GN:YYBA] [DE:HYPOTHETICAL TRANSCRIPTIONAL REGULATOR IN COTF-TTEIB INTERGENIC REGION] |
| contig679 | 29336088_c3_38 | 2576 | 5981 | 261 | 87 | 109 | 1.40E-06 | [OR:Streptococcus sobrinus] [PN:hypothetical protein (par 3' region)] |
| contig679 | 30193760_f1_1 | 2577 | 5982 | 198 | 65 | 50 | 0.91 | [SP:P13994] [OR:HOMO SAPIENS] [DE:9 KD PROTEIN] |
| contig679 | 20894063_c3_37 | 2578 | 5983 | 672 | 223 | 68 | 0.095 | [OR:Ovis orientalis Ovis ammon aries] [PN:14-3-3 protein isoform tau] |
| contig679 | 35367967_c2_34 | 2579 | 5984 | 801 | 266 | 78 | 0.76 | [OR:U50210] [OR:Mycoplasma hyopneumoniae] [PN:24 kDa protein] [GN:p24] |
| contig679 | 34172160_f2_11 | 2580 | 5985 | 756 | 251 | 553 | 1.20E-53 | [AC:M77279] [OR:unidentified cloning vector] [PN:fusion protein] [NT:fusion protein] |
| contig679 | 32208317_f1_4 | 2581 | 5986 | 183 | 60 | 55 | 0.73 | [AC:U80455] [OR:Caenorhabditis elegans] [GN:T01D1.1] [NT:weak similarity to part of human heme oxygenase 2] |
| contig679 | 1187535_c1_28 | 2582 | 5987 | 303 | 100 | | | |
| contig679 | 7078537_c3_36 | 2583 | 5988 | 477 | 158 | 293 | 4.40E-26 | [SP:P41893] [OR:SCHIZOSACCHAROMYCES POMBE] [GN:STP1] [DE:(PTPASE) (SMALL TYROSINE PHOSPHATASE)] |
| contig679 | 22298217_c2_33 | 2584 | 5989 | 603 | 200 | 116 | 7.10E-05 | [SP:P46330] [OR:BACILLUS SUBTILIS] [GN:YXAT] [DE:HYPOTHETICAL 44.3 KD PROTEIN IN GNTR-HTPG INTERGENIC REGION] |
| contig679 | 24412802_c2_32 | 2585 | 5990 | 1494 | 497 | 357 | 7.20E-33 | [SP:P13692] [OR:ENTEROCOCCUS FAECIUM] [DE:P54 PROTEIN PRECURSOR] |
| contig679 | 35782882_c3_35 | 2586 | 5991 | 198 | 65 | 70 | 0.037 | [SP:P07380] [OR:EQUUS CABALLUS] [DE:BETA-LACTOGLOBULIN II, MINOR MONOMERIC] |
| contig679 | 25631642_c1_26 | 2587 | 5992 | 588 | 195 | 111 | 1.90E-05 | [SP:Q01467] [OR:BACILLUS SUBTILIS] [GN:MRED] [DE:ROD SHAPE-DETERMINING PROTEIN MRED] |
| contig679 | 35422180_c2_31 | 2588 | 5993 | 915 | 304 | 351 | 3.10E-32 | [SP:Q01466] [OR:BACILLUS SUBTILIS] [GN:MREC] [DE:ROD SHAPE-DETERMINING PROTEIN MREC] |
| contig679 | 4961592_c1_25 | 2589 | 5994 | 2127 | 708 | 2255 | 5.40E-234 | [SP:P50849] [OR:BACILLUS SUBTILIS] [GN:PNPA] [DE:PHOSPHORYLASE) (PNPASE)] |
| contig679 | 35400018_c1_24 | 2590 | 5995 | 366 | 121 | 329 | 6.70E-30 | [AC:Z80835] [OR:Bacillus subtilis] [PN:ribosomal protein S15] [GN:rpsO] |
| contig68 | 12219530_f3_2 | 2591 | 5996 | 813 | 271 | 436 | 3.10E-41 | [SP:P12623] [OR:ANABAENA SP] [GN:NIFS] [DE:NIFS PROTEIN] |
| contig680 | 30564025_f2_3 | 2592 | 5997 | 768 | 255 | 318 | 9.80E-29 | [SP:P44458] [OR:HAEMOPHILUS INFLUENZAE] [GN:CITG] [DE:CITG PROTEIN HOMOLOG] |

TABLE 2-continued

| Contig | Orf | NT Seq Id | AA Seq ID | NT Orf Length | AA Orf Length | Score | Probability | Description |
|---|---|---|---|---|---|---|---|---|
| contig680 | 4892132_f3_4 | 2593 | 5998 | 189 | 62 | 60 | 0.19 | [SP:Q01049] [OR:*HERPESVIRUS SAIMIRI*] [GN:53] [DE:PUTATIVE MEMBRANE PROTEIN 53] |
| contig680 | 4714093_f3_5 | 2594 | 5999 | 5244 | 1747 | 160 | 2.50E-17 | [AC:Z72496] [OR:*Homo sapiens*] [PN:mucin MUC5B] [GN:MUC5B] |
| contig681 | 25673905_f3_17 | 2595 | 6000 | 1098 | 365 | 392 | 1.40E-36 | [SP:P44329] [OR:*HAEMOPHILUS INFLUENZAE*] [GN:RBSR] [DE:RIBOSE OPERON REPRESSOR] |
| contig681 | 24010937_f2_9 | 2596 | 6001 | 1464 | 487 | 1427 | 3.00E-146 | [AC:JT0875] [OR:*Bacillus stearothermophilus*] [PN:Pyridine nucleoside phosphorylase, III] |
| contig681 | 24804662_f2_10 | 2597 | 6002 | 690 | 229 | 667 | 1.00E-65 | [SP:P39121] [OR:*BACILLUS SUBTILIS*] [GN:DRA] [DE:(DEOXY)RIBOALDOLASE] |
| contig681 | 1962561_f3_18 | 2598 | 6003 | 468 | 155 | 344 | 1.70E-31 | [SP:P19079] [OR:*BACILLUS SUBTILIS*] [GN:CDD] [DE:CYTIDINE DEAMINASE, (CYTIDINE AMINOHYDROLASE) (CDA)] |
| contig681 | 31251093_f2_11 | 2599 | 6004 | 1089 | 362 | 738 | 3.10E-73 | [AC:Z93937] [OR:*Bacillus subtilis*] [PN:unknown] [GN:yufN] [NT:potential membrane protein] |
| contig681 | 20500075_f1_4 | 2600 | 6005 | 1128 | 375 | 699 | 4.10E-69 | [AC:Z93937] [OR:*Bacillus subtilis*] [PN:unknown] [GN:yufN] [NT:potential membrane protein] |
| contig681 | 21571907_f2_13 | 2601 | 6006 | 1572 | 523 | 1671 | 4.10E-172 | [AC:Z93937] [OR:*Bacillus subtilis*] [PN:unknown] [GN:yufO] [NT:potential methylgalactoside transport ATP binding] |
| contig681 | 24667092_f3_20 | 2602 | 6007 | 1149 | 382 | 483 | 3.20E-46 | [AC:Z93937] [OR:*Bacillus subtilis*] [PN:unknown] [GN:yufP] |
| contig681 | 33724167_f2_14 | 2603 | 6008 | 996 | 331 | 898 | 3.40E-90 | [AC:Z93937] [OR:*Bacillus subtilis*] [PN:unknown] [GN:yufQ] |
| contig681 | 7033157_c2_39 | 2604 | 6009 | 207 | 68 | 58 | 0.29 | [OR:Trametes versicolor] [PN:manganese(II) peroxidase, 2] |
| contig681 | 211_f1_6 | 2605 | 6010 | 672 | 223 | 71 | 0.8 | [AC:K03089] [OR:Plasmid NR1] [NT:15.0 kd merTC protein] |
| contig681 | 4726516_f2_15 | 2606 | 6011 | 1221 | 406 | 1270 | 1.30E-129 | [AC:D84432] [OR:*Bacillus subtilis*] [PN:YqkN] |
| contig681 | 23985902_f3_21 | 2607 | 6012 | 849 | 282 | 833 | 2.60E-83 | [SP:P77834] [OR:*BACILLUS STEAROTHERMOPHILUS*] [GN:DEOD] [DE:(PNP)] |
| contig681 | 34414657_f2_16 | 2608 | 6013 | 714 | 237 | 732 | 1.30E-72 | [SP:Q56037] [OR:*STREPTOCOCCUS THERMOPHILUS*] [GN:DEOD] [DE:(PNP) (FRAGMENT)] |
| contig681 | 35407183_c3_46 | 2609 | 6014 | 906 | 301 | 271 | 9.40E-24 | [SP:P37580] [OR:*BACILLUS SUBTILIS*] [GN:FHUD] [DE:FERRICHROME-BINDING PROTEIN PRECURSOR] |
| contig682 | 24259713_c1_28 | 2610 | 6015 | 1005 | 334 | 191 | 8.10E-14 | [AC:D90848] [OR:*Escherichia coli*] [PN:Lysozyme M1 precursor (EC 3.2.1.17)] [NT:ORF_ID] |
| contig682 | 13870316_c2_30 | 2611 | 6016 | 240 | 79 | 52 | 0.78 | [OR:Eubacterium sp.] [PN:baiG] |
| contig682 | 24814753_c3_36 | 2612 | 6017 | 267 | 88 | 85 | 0.0046 | [OR:*Schistosoma mansoni*] [PN:paramyosin] |
| contig682 | 29352140_c3_35 | 2613 | 6018 | 444 | 147 | 77 | 0.76 | [SP:P09806] [OR:*KLUYVEROMYCES LACTIS*] [GN:RF4] [DE:RF4 PROTEIN] |
| contig682 | 808587_c1_27 | 2614 | 6019 | 1200 | 399 | 57 | 0.7 | [OR:*Streptococcus pyogenes*] [PN:M protein precursor] |
| contig682 | 4037968_c3_34 | 2615 | 6020 | 501 | 166 | | | |
| contig682 | 24650332_c3_33 | 2616 | 6021 | 696 | 231 | | | |
| contig682 | 33306556_c1_26 | 2617 | 6022 | 2580 | 859 | 122 | 0.00024 | [SP:P15132] [OR:BACTERIOPHAGE PHI-29] [GN:13] [DE:MORPHOGENESIS PROTEIN 1 (LATE PROTEIN GP13)] |
| contig682 | 2785637_c3_32 | 2618 | 6023 | 792 | 263 | 53 | 0.999 | [SP:P28503] [OR:*HIRUDO MEDICINALIS*] [DE:HIRUDIN IIA] |
| contig682 | 23682963_c1_25 | 2619 | 6024 | 1131 | 376 | 79 | 0.017 | [AC:X87201] [OR:*Carcinus maenas*] [PN:metallothionein] |
| contig682 | 2049068_c3_31 | 2620 | 6025 | 2595 | 864 | 93 | 0.071 | [AC:X87201] [OR:*Borrelia burgdorferi*] [GN:orfE] |
| contig682 | 4788941_f1_8 | 2621 | 6026 | 606 | 202 | 554 | 9.60E-54 | [SP:P35880] [OR:*LACTOBACILLUS HELVETICUS*] [DE:TRANSPOSASE FOR INSERTION SEQUENCE ELEMENT IS1201] |
| contig683 | 31741033_f1_1 | 2622 | 6027 | 1140 | 379 | 1286 | 2.60E-131 | [SP:P16962] [OR:*STREPTOCOCCUS PYOGENES*] [GN:SAGP] [DE:STREPTOCOCCAL ACID GLYCOPROTEIN] |
| contig683 | 24219442_f3_5 | 2623 | 6028 | 1059 | 352 | 1039 | 3.90E-105 | [AC:X99978] [OR:*Lactobacillus plantarum*] [PN:anabolic ornithine |

TABLE 2-continued

| Contig | Orf | NT Seq Id | AA Seq ID | NT Orf Length | AA Orf Length | Score | Probability | Description |
|---|---|---|---|---|---|---|---|---|
| contig683 | 12359450_f3_6 | 2624 | 6029 | 1005 | 334 | 748 | 2.70E-74 | carbamoyltransferase] [GN:argF] [SP:Q46807] [OR:ESCHERICHIA COLI] [GN:YQEA] [DE:CARBAMATE KINASE-LIKE PROTEIN 1] |
| contig683 | 834642_f3_7 | 2625 | 6030 | 717 | 238 | 297 | 1.60E-26 | [AC:JH0364] [OR:Streptococcus pyogenes] [PN:hypothetical protein 176 (SAGP 5' region)] |
| contig683 | 16829837_f2_3 | 2626 | 6031 | 1458 | 485 | 293 | 2.10E-47 | [SP:P44023] [OR:HAEMOPHILUS INFLUENZAE] [GN:HI0594] [DE:HYPOTHETICAL PROTEIN HI0594] |
| contig683 | 14547808_c3_18 | 2627 | 6032 | 738 | 245 | 259 | 1.80E-22 | [OR:Saccharomyces cerevisiae] [PN:hypothetical protein YDR533c] [SP:P30340] [OR:SYNECHOCOCCUS SP] [GN:SMTB] |
| contig683 | 12707562_c1_12 | 2628 | 6033 | 363 | 120 | 121 | 7.40E-08 | [DE:TRANSCRIPTIONAL REPRESSOR SMTB] |
| contig683 | 24886062_f3_8 | 2629 | 6034 | 1041 | 346 | 437 | 7.40E-51 | [AC:U20808] [OR:Vigna radiata] [PN:auxin-induced protein] |
| contig683 | 24806693_f2_4 | 2630 | 6035 | 816 | 271 | 81 | 0.0062 | [AC:AE000233] [OR:Escherichia coli] [NT:o87; 38 pct identical (4 gaps) to 65 residues from] |
| contig683 | 33415937_f3_9 | 2631 | 6036 | 705 | 234 | 86 | 0.083 | [AC:Y08257] [OR:Sulfolobus solfataricus] [GN:orf c04007] |
| contig683 | 34172677_c3_16 | 2632 | 6037 | 525 | 174 | 838 | 7.70E-84 | [SP:P19775] [OR:STAPHYLOCOCCUS AUREUS] [GN:TNP] [DE:TRANSPOSASE FOR INSERTION SEQUENCE ELEMENT IS256 IN TRANSPOSON TN4001] |
| contig684 | 36423427_c1_30 | 2633 | 6038 | 1161 | 386 | 100 | 0.0081 | [SP:P03224] [OR:EPSTEIN-BARR VIRUS] [GN:BDLF3] [DE:PROBABLE MEMBRANE ANTIGEN GP85] |
| contig684 | 15909377_f2_9 | 2634 | 6039 | 213 | 70 | 68 | 0.56 | [SP:P72689] [OR:SYNECHOCYSTIS SP] [GN:INFB] [DE:TRANSLATION INITIATION FACTOR IF-2] |
| contig684 | 23828128_c2_35 | 2635 | 6040 | 2742 | 913 | 88 | 0.76 | [SP:P20599] [OR:TRITICUM AESTIVUM] [DE:ATP SYNTHASE A CHAIN, (PROTEIN 6)] |
| contig684 | 25582175_c1_29 | 2636 | 6041 | 2247 | 748 | 83 | 0.97 | [SP:P22929] [OR:SACCHAROMYCOPSIS FIBULIGERA] [GN:PEP1] [DE:ACID PROTEASE PRECURSOR,] |
| contig684 | 2869687_c1_28 | 2637 | 6042 | 828 | 275 | 57 | 0.91 | [AC:S71401] [OR:Human herpesvirus 4] [PN:U2 protein] [GN:U2] [NT:This sequence comes from FIG. 3.] |
| contig684 | 32656705_c3_38 | 2638 | 6043 | 3837 | 1278 | 113 | 0.016 | [SP:P47179] [OR:SACCHAROMYCES CEREVISIAE] [GN:YIR151C] [DE:PRECURSOR] |
| contig684 | 5917186_c2_32 | 2639 | 6044 | 432 | 143 | 51 | 0.97 | [SP:P01559] [OR:ESCHERICHIA COLI] [GN:STA1] [DE:HEAT-STABLE ENTEROTOXIN ST-IA/ST-P PRECURSOR] |
| contig684 | 4971041_c2_31 | 2640 | 6045 | 852 | 283 | 164 | 3.90E-17 | [SP:P39582] [OR:BACILLUS SUBTILIS] [GN:YWAB] [DE:HYPOTHETICAL 33.8 KD PROTEIN IN DAE-TYRZ INTERGENIC REGION] |
| contig685 | 35941386_f2_8 | 2641 | 6046 | 195 | 64 | 56 | 0.43 | [SP:P41460] [OR:AUTOGRAPHA CALIFORNICA NUCLEAR POLYHEDROSIS VIRUS] [DE:HYPOTHETICAL 9.9 KD PROTEIN IN LEF8-FP INTERGENIC REGION] |
| contig685 | 24804700_f3_26 | 2642 | 6047 | 975 | 324 | 212 | 2.80E-16 | [AC:L38252] [OR:Acinetobacter lwoffii] [PN:esterase] [GN:est] |
| contig685 | 29480061_c1_37 | 2643 | 6048 | 1404 | 467 | 343 | 2.20E-31 | [SP:P39301] [OR:ESCHERICHIA COLI] [GN:YJFS] [DE:HYPOTHETICAL 53.6 KD PROTEIN IN AIDB-RPSF INTERGENIC REGION (O488)] |
| contig685 | 24636465_c2_43 | 2644 | 6049 | 357 | 118 | 62 | 0.88 | [SP:[P29302] [OR:ESCHERICHIA COLI] [GN:YJFT] [DE:HYPOTHETICAL 10.9 KD PROTEIN IN AIDB-RPSF INTERGENIC REGION (O101)] |
| contig685 | 17010800_c1_36 | 2645 | 6050 | 2031 | 676 | 228 | 5.10E-20 | [AC:U18943] [OR:Bacillus stearothermophilus] [GN:MtlR] [NT:putative transcriptional regulator] |
| contig685 | 24037812_c2_42 | 2646 | 6051 | 438 | 145 | 67 | 0.27 | [AC:U79944] [OR:Human immunodeficiency virus type 1] [PN:envelope glycoprotein] [GN:env] [NT:gp120; V1/V2 hypervariable |
| contig685 | 4867338_c1_34 | 2647 | 6052 | 1146 | 381 | | | |

TABLE 2-continued

| Contig | Orf | NT Seq Id | AA Seq ID | NT Orf Length | AA Orf Length | Score | Probability | Description |
|---|---|---|---|---|---|---|---|---|
| contig685 | 23602181_c1_33 | 2648 | 6053 | 714 | 237 | 98 | 0.02 | [AC:D90793] [OR:*Escherichia coli*] [GN:ydeK#orfT] [NT:ORF_ID region] |
| contig685 | 4726393_c2_41 | 2649 | 6054 | 981 | 326 | 128 | 1.10E-05 | [SP:P08078] [OR:*STREPTOMYCES GRISEUS*] [GN:STRB] [DE:AMIDINOTRANSFERASE) (ADT] |
| contig685 | 20495336_c2_40 | 2650 | 6055 | 1524 | 507 | 1377 | 5.90E-141 | [AC:D88802] [OR:*Bacillus subtilis*] [GN:phoB] [NT:*B. subtilis* alkaline phosphatase IIIA; P19405] |
| contig685 | 25660302_c2_39 | 2651 | 6056 | 2136 | 711 | 704 | 1.20E-69 | [AC:Z75208] [OR:*Bacillus subtilis*] [PN:hypothetical protein] [GN:yshD] [NT:shows homology to mutS of *Thermus aquaticus*;] |
| contig685 | 26344125_c1_32 | 2652 | 6057 | 432 | 143 | 54 | 0.86 | [SP:P14422] [OR:*ORYCTOLAGUS CUNICULUS*] [GN:PLA2G2A] [DE:(PHOSPHATIDYLCHOLINE 2-ACYLHYDROLASE) (FRAGMENTS)] |
| contig686 | 6035151_f1_1 | 2653 | 6058 | 342 | 113 | 131 | 1.50E-08 | [AC:D90767] [OR:*Escherichia coli*] [NT:ORF_ID] |
| contig686 | 25640700_c2_47 | 2654 | 6059 | 897 | 298 | 827 | 1.10E-82 | [OR:*Leishmania major*] [PN:probable reductase protein] |
| contig686 | 4095302_c1_41 | 2655 | 6060 | 408 | 135 | 51 | 0.98 | [AC:L19863] [OR:*Mitochondrion Unerus colonus*] [PN:NADH dehydrogenase] [NT:This codes for the last 43 amino acids of NADH |
| contig686 | 34172760_f3_26 | 2656 | 6061 | 960 | 319 | 207 | 5.70E-17 | [AC:Z95150] [OR:*Mycobacterium tuberculosis*] [PN:unknown] [GN:MTCY164.14c] [NT:MTCY164.14c, unknown, len |
| contig686 | 395317_c3_54 | 2657 | 6062 | 1182 | 393 | 531 | 2.60E-51 | [AC:Y14083] [OR:*Bacillus subtilis*] [PN:N-terminal part of hypothetical protein] [GN:yhaA] [NT:Similarity to aminoacylase from Bacillus |
| contig686 | 20442325_c3_53 | 2658 | 6063 | 702 | 233 | 151 | 1.70E-14 | [AC:M88485] [OR:*Pseudomonas syringae*] [GN:tabB] [NT:ORF 3; homology with *E. coli* dapD; belongs to the |
| contig686 | 24484692_c1_40 | 2659 | 6064 | 516 | 171 | 127 | 6.50E-08 | [AC:Y08257] [OR:*Sulfolobus solfataricus*] [GN:orf c04012] |
| contig686 | 7277211_c3_52 | 2660 | 6065 | 726 | 241 | 636 | 2.00E-62 | [SP:P39306] [OR:*ESCHERICHIA COLI*] [GN:YIFX] [DE:HYPOTHETICAL 25.3 KD PROTEIN IN AIDB-RPSF INTERGENIC REGION (O228A)] |
| contig686 | 32228826_c2_46 | 2661 | 6066 | 999 | 332 | 742 | 1.20E-73 | [SP:P37679] [OR:*ESCHERICHIA COLI*] [GN:YIAR] [DE:HYPOTHETICAL 33.7 KD PROTEIN IN AVTA-SELB INTERGENIC REGION (O297)] |
| contig686 | 24400140_c1_39 | 2662 | 6067 | 714 | 237 | 543 | 1.40E-52 | [SP:P37678] [OR:*ESCHERICHIA COLI*] [GN:YIAQ] [DE:HYPOTHETICAL 23.4 KD PROTEIN IN AVTA-SELB INTERGENIC REGION (O220)] |
| contig686 | 34062812_c3_51 | 2663 | 6068 | 333 | 110 | 105 | 3.70E-06 | [SP:P39302] [OR:*ESCHERICHIA COLI*] [GN:YIFT] [DE:HYPOTHETICAL 10.9 KD PROTEIN IN AIDB-RPSF INTERGENIC REGION (O101)] |
| contig686 | 10742343_c1_38 | 2664 | 6069 | 1500 | 499 | 358 | 1.60E-55 | [SP:P75291] [OR:*MYCOPLASMA PNEUMONIAE*] [GN:SGAT] [DE:SGAT PROTEIN HOMOLOG (P02_ORF660)] |
| contig686 | 9800910_c1_37 | 2665 | 6070 | 501 | 166 | 171 | 3.70E-13 | [SP:P32058] [OR:*ESCHERICHIA COLI*] [GN:CMTB] [DE:ENZYME II, A COMPONENT).] |
| contig686 | 22381542_c2_45 | 2666 | 6071 | 1104 | 367 | 1260 | 1.50E-128 | [SP:P39300] [OR:*ESCHERICHIA COLI*] [GN:YIFR] [DE:HYPOTHETICAL 40.3 KD PROTEIN IN AIDB-RPSF INTERGENIC REGION (F356)] |
| contig686 | 20714717_f1_7 | 2667 | 6072 | 780 | 259 | 290 | 9.10E-26 | [AC:Z83337] [OR:*Bacillus subtilis*] [GN:ywpI] [NT:highly similar to phosphotransferase system] |
| contig686 | 32228213_c1_36 | 2668 | 6073 | 525 | 174 | 320 | 6.00E-29 | [AC:Z75208] [OR:*Bacillus subtilis*] [PN:hypothetical protein] [GN:ysnB] [NT:homology to H10260 of *Haemophilus influenzae*;] |
| contig686 | 24726713_c1_35 | 2669 | 6074 | 1368 | 455 | 802 | 5.10E-80 | [SP:P28619] [OR:*BACILLUS SUBTILIS*] [GN:RPH] [DE:NUCLEOTIDYLTRANSFERASE)] |
| contig686 | 16594063_c3_49 | 2670 | 6075 | 573 | 190 | 398 | 3.30E-37 | [AC:Z75208] [OR:*Bacillus subtilis*] [PN:glutamate racemase] |

TABLE 2-continued

| Contig | Orf | NT Seq Id | AA Seq ID | NT Orf Length | AA Orf Length | Score | Probability | Description |
|---|---|---|---|---|---|---|---|---|
| contig686 | 22938_f3_34 | 2671 | 6076 | 222 | 73 | 54 | 0.8 | [GN:racE] [AC:D63341] [OR:*Pseudomonas putida*] [GN:xylU] |
| contig686 | 24117177_c3_48 | 2672 | 6077 | 273 | 90 | 299 | 1.00E-26 | [AC:Z75208] [OR:*Bacillus subtilis*] [PN:glutamate racemase] [GN:racE] |
| contig686 | 34648325_f2_25 | 2673 | 6078 | 372 | 124 | 337 | 9.50E-31 | [SP:P27675] [OR:*BACILLUS STEAROTHERMOPHILUS*] [GN:GLNQ] [DE:GLUTAMINE TRANSPORT ATP-BINDING PROTEIN GLNQ] |
| contig687 | 9808593_f3_15 | 2674 | 6079 | 684 | 227 | 61 | 0.49 | [OR:*Saguinus oedipus*] [PN:MHC protein] |
| contig687 | 4976562_f2_8 | 2675 | 6080 | 186 | 61 | 116 | 2.50E-07 | [SP:Q45479] [OR:*BACILLUS SUBTILIS*] [GN:LSPA] [DE:PEPTIDASE) (SIGNAL PEPTIDASE II) (SPASE II)] |
| contig687 | 5120318_f2_9 | 2676 | 6081 | 309 | 102 | 165 | 1.60E-12 | [SP:P31024] [OR:*STAPHYLOCOCCUS AUREUS*] [GN:LSP] [DE:PEPTIDASE) (SIGNAL PEPTIDASE II) (SPASE II)] |
| contig687 | 22851577_f3_16 | 2677 | 6082 | 933 | 310 | 988 | 9.80E-100 | [SP:Q45480] [OR:*BACILLUS SUBTILIS*] [GN:YLYB] [DE:HYPOTHETICAL 33.7 KD PROTEIN IN LSP-PYRR INTERGENIC REGION (ORF-X)] |
| contig687 | 21578875_c2_42 | 2678 | 6083 | 213 | 70 | 55 | 0.52 | [SP:P51418] [OR:*ARABIDOPSIS THALIANA*] [GN:RPL18A] [DE:60S RIBOSOMAL PROTEIN L18A (FRAGMENT)] |
| contig687 | 19727318_f1_3 | 2679 | 6084 | 549 | 182 | 603 | 6.20E-59 | [AC:Z54240] [OR:*Lactobacillus plantarum*] [GN:pyrR] |
| contig687 | 10947807_f2_10 | 2680 | 6085 | 1287 | 428 | 491 | 6.40E-74 | [SP:P41006] [OR:*BACILLUS CALDOLYTICUS*] [GN:PYRP] [DE:URACIL PERMEASE (URACIL TRANSPORTER)] |
| contig687 | 24863750_f3_17 | 2681 | 6086 | 975 | 324 | 871 | 2.50E-87 | [SP:P77883] [OR:*LACTOBACILLUS PLANTARUM*] [GN:PYRB] [DE:TRANSCARBAMYLASE) (ATCASE)] |
| contig687 | 19549091_f2_11 | 2682 | 6087 | 1347 | 448 | 1189 | 4.90E-121 | [SP:P46538] [OR:*BACILLUS CALDOLYTICUS*] [GN:PYRC] [DE:DIHYDROOROTASE, (DHOASE)] |
| contig687 | 9813332_c1_27 | 2683 | 6088 | 267 | 88 | 295 | 2.70E-26 | [AC:U25093] [OR:*Enterococcus faecalis*] [PN:pyrimidine biosynthesis protein C] [GN:pyrC] |
| contig687 | 33239716_f1_4 | 2684 | 6089 | 1116 | 371 | 1200 | 3.40E-122 | [AC:Z54240] [OR:*Lactobacillus plantarum*] [PN:glutaminase of carbamoyl-phosphate synthase] [GN:pyrAA] |
| contig687 | 35312816_f3_18 | 2685 | 6090 | 3225 | 1074 | 3955 | 0 | [AC:Z54240] [OR:*Lactobacillus plantarum*] [PN:carbamoyl-phosphate synthase] [GN:pyrAB] |
| contig687 | 5100342_f2_12 | 2686 | 6091 | 801 | 266 | 729 | 2.70E-72 | [SP:P46536] [OR:*BACILLUS CALDOLYTICUS*] [DE:HYPOTHETICAL 27.6 KD PROTEIN IN PYRAB-PYRD INTERGENIC REGION (ORF2)] |
| contig687 | 3923143_f1_7 | 2687 | 6092 | 948 | 315 | 1586 | 4.20E-163 | [AC:U24692] [OR:*Enterococcus faecalis*] [PN:pyrimidine biosynthesis D] [GN:pyrD] |
| contig687 | 33886588_f2_13 | 2688 | 6093 | 555 | 184 | 526 | 8.90E-51 | [SP:P50924] [OR:*LACTOCOCCUS LACTIS*] [GN:PYRF] [DE:DECARBOXYLASE)] |
| contig687 | 24019703_f3_20 | 2689 | 6094 | 774 | 257 | 631 | 6.70E-62 | [SP:P25972] [OR:*BACILLUS SUBTILIS*] [GN:PYRE] [DE:OROTATE PHOSPHORIBOSYLTRANSFERASE, (OPRT)] |
| contig687 | 25490628_f2_14 | 2690 | 6095 | 381 | 126 | 84 | 0.0028 | [AC:U72708] [OR:Anabaena PCC7120] [PN:carbonic anhydrase] [GN:cesA] |
| contig687 | 4381581_f3_21 | 2691 | 6096 | 369 | 123 | 120 | 1.10E-07 | [AC:U11547] [OR:*Neisseria gonorrhoeae*] [PN:unknown] [NT:ORF2] |
| contig688 | 20504378_c2_42 | 2692 | 6097 | 438 | 146 | 171 | 3.70E-13 | [SP:P45911] [OR:*BACILLUS SUBTILIS*] [GN:YQAN] [DE:HYPOTHETICAL 16.1 KD PROTEIN IN SPOIIIC-CWLA INTERGENIC REGION] |
| contig688 | 24650301_c3_52 | 2693 | 6098 | 873 | 290 | 105 | 0.0013 | [SP:Q51762] [OR:*PSEUDOMONAS FLUORESCENS*] [DE:INSERTION SEQUENCE IS1162 PUTATIVE ATP-BINDING PROTEIN] |
| contig688 | 33359702_c2_41 | 2694 | 6099 | 876 | 291 | 64 | 0.34 | [AC:M95073] [GR:*Zea mays*] [NT:putative, similar to carbonic |

TABLE 2-continued

| Contig | Orf | NT Seq Id | AA Seq ID | NT Orf Length | AA Orf Length | Score | Probability | Description |
|---|---|---|---|---|---|---|---|---|
| contig688 | 1214202_c1_37 | 2695 | 6100 | 819 | 272 | 90 | 0.08 | anhydrases] [AC:U47023] [OR:*Methanococcus maripaludis*] [PN:unknown] [NT:ORF-3] |
| contig688 | 26775062_c3_51 | 2696 | 6101 | 942 | 313 | 141 | 8.80E-08 | [AC:D90774] [OR:*Escherichia coli*] [PN:RecT protein (P33).] [GN:recT] [NT:ORF_ID] |
| contig688 | 819712_c2_40 | 2697 | 6102 | 381 | 126 | 88 | 0.0092 | [SP:P28666] [OR:*MUS MUSCULUS*] [GN:MUG2] |
| contig688 | 24413952_c1_36 | 2698 | 6103 | 297 | 98 | | | DE:MURINOGLOBULIN 2 PRECURSOR (MUG2)] |
| contig688 | 24485950_c1_35 | 2699 | 6104 | 327 | 108 | 57 | 0.87 | [OR:*Drosophila melanogaster*] [PN:TAF-II-60 protein] |
| contig688 | 24882887_c1_34 | 2700 | 6105 | 228 | 75 | 59 | 0.24 | [SP:P48117] [OR:*CYANOPHORA PARADOXA*] [GN:PSAJ] [DE:PHOTOSYSTEM I REACTION CENTRE SUBUNIT IX (PSI-J)] |
| contig688 | 36542177_c3_50 | 2701 | 6106 | 270 | 89 | 68 | 0.2 | [AC:U32836] [OR:*Haemophilus influenzae*] [PN:purine nucleotide synthesis repressor protein] [GN:HI1635] [NT:similar to GB] |
| contig688 | 32062811_c1_33 | 2702 | 6107 | 552 | 183 | 60 | 0.42 | [AC:X56058] [OR:*Homo sapiens*] [PN:retinoic acid receptor-alpha] |
| contig688 | 22555425_c1_32 | 2703 | 6108 | 189 | 62 | 62 | 0.45 | [OR:phage SPO1] [PN:E22 protein] |
| contig688 | 36147285_c1_31 | 2704 | 6109 | 222 | 73 | 137 | 1.50E-09 | [SP:P45903] [OR:*BACILLUS SUBTILIS*] [GN:YQAF] [DE:HYPOTHETICAL 8.8 KD PROTEIN IN SPOIIIC-CWLA INTERGENIC REGION (ORF8)] |
| contig688 | 11773436_f3_24 | 2705 | 6110 | 450 | 149 | 198 | 5.10E-16 | [SP:P45902] [OR:*BACILLUS SUBTILIS*] [GN:YQAE] [DE:REGION (ORF7)] |
| contig688 | 6855067_f2_11 | 2706 | 6111 | 468 | 155 | 84 | 0.033 | [SP:P10426] [OR:BACTERIOPHAGE PHI-105] DE:HYPOTHETICAL IMMUNITY REGION PROTEIN 2] |
| contig688 | 22273377_f3_25 | 2707 | 6112 | 927 | 308 | 94 | 0.084 | [SP:P29019] [OR:*BACILLUS SP*] [DE:(CELLULASE) (ENDO-K)] |
| contig688 | 25865687_f3_26 | 2708 | 6113 | 1167 | 388 | 236 | 3.90E-18 | [AC:AB001488] [OR:*Bacillus subtilis*] [GN:ydcL] [NT:PROBABLE INTEGRASE,] |
| contig688 | 30681300_f3_27 | 2709 | 6114 | 1509 | 502 | 62 | 0.75 | [SP:P03917] [OR:GORILLA GORILLA GORILLA] [GN:ND5] [DE:NADH-UBIQUINONE OXIDOREDUCTASE CHAIN 5, (FRAGMENT)] |
| contig688 | 26183467_c3_44 | 2710 | 6115 | 978 | 325 | 63 | 0.999 | [SP:P25767] [OR:*METHANOCOCCUS THERMOLITHOTROPHICUS*] [GN:NIF111] [DE:(NITROGENASE REDUCTASE)] |
| contig688 | 21679827_c2_38 | 2711 | 6116 | 291 | 96 | | | |
| contig688 | 4712937_c3_43 | 2712 | 6117 | 1284 | 427 | 548 | 4.20E-53 | [AC:U23713] [OR:*Staphylococcus epidermidis*] [PN:FEMA] [GN:femA] [NT:factor essential for methicillin resistance] |
| contig688 | 114627_f3_30 | 2713 | 6118 | 195 | 64 | 83 | 0.0015 | [SP:P06544] [OR:*ANABAENA SP*] [GN:TRXA] |
| contig688 | 29926443_f1_1 | 2714 | 6119 | 531 | 176 | | | DE:THIOREDOXIN 1 (TRX-1) (THIOREDOXIN M)] |
| contig689 | 25683540_f2_5 | 2715 | 6120 | 411 | 136 | 137 | 1.50E-09 | [SP:P42621] [OR:*ESCHERICHIA COLI*] [GN:YHAH] [DE:HYPOTHETICAL 15.4 KD PROTEIN IN EXUR-TDCC INTERGENIC REGION (O130)] |
| contig689 | 19720380_c1_17 | 2716 | 6121 | 1554 | 517 | 100 | 0.044 | [OR:*Bacillus anthracis*] [PN:toxin synthesis trans-activator atxA] |
| contig689 | 21521951_f1_2 | 2717 | 6122 | 3465 | 1154 | 107 | 0.02 | [SP:P22865] [OR:*LACTOCOCCUS LACITS*] [GN:USP45] [DE:SECRETED 45 KD PROTEIN PRECURSOR] |
| contig689 | 24415930_f1_3 | 2718 | 6123 | 1434 | 477 | 273 | 1.60E-21 | [OR:*Lactobacillus leichmannii*] [PN:hypothetical protein 2] |
| contig689 | 19932192_f3_10 | 2719 | 6124 | 1980 | 659 | 279 | 1.20E-21 | [OR:*Lactobacillus leichmannii*] [PN:hypothetical protein 2] |
| contig689 | 10678250_f3_11 | 2720 | 6125 | 948 | 315 | 200 | 3.10E-16 | [AC:U85709] [OR:*Actinomyces naeslundii*] [PN:putative fimbrial-associated protein] [NT:orf4] |
| contig689 | 24037942_c1_13 | 2721 | 6126 | 345 | 114 | 54 | 0.98 | [AC:Z70681] [OR:*Caenorhabditis elegans*] [PN:C30F2.2] |
| contig689 | 23635927_f1_4 | 2722 | 6127 | 258 | 85 | | | |

TABLE 2-continued

| Contig | Orf | NT Seq Id | AA Seq ID | NT Orf Length | AA Orf Length | Score | Probability | Description |
|---|---|---|---|---|---|---|---|---|
| contig689 | 16492188_f3_12 | 2723 | 6128 | 630 | 209 | 71 | 0.048 | [AC:D50803] [OR:Borrelia tanukii] [PN:outer surface protein C] |
| contig69 | 19925182_c3_3 | 2724 | 6129 | 771 | 257 | 305 | 2.30E-27 | [SP:P33023] [OR:ESCHERICHIA COLI] [GN:YEIL] [DE:HYPOTHETICAL 25.3 KD PROTEIN IN NFO-FRUA INTERGENIC REGION] |
| contig69 | 12117337_c2_2 | 2725 | 6130 | 192 | 63 | 60 | 0.79 | [AC:X88849] [OR:Campylobacter coli] [GN:ceuE] |
| contig690 | 489033_f1_1 | 2726 | 6131 | 489 | 162 | 175 | 1.40E-13 | [SP:P05332] [OR:BACILLUS LICHENIFORMIS] [GN:P20] [DE:HYPOTHETICAL P20 PROTEIN] |
| contig690 | 522900_f2_5 | 2727 | 6132 | 588 | 195 | 305 | 2.30E-27 | [AC:U51911] [OR:Bacillus subtilis] [PN:unknown] [GN:yktB] |
| contig690 | 10941075_f3_10 | 2728 | 6133 | 4320 | 1439 | 149 | 2.00E-07 | [OR:Homo sapiens] [PN:mucin 5AC (clone JER58)] [GN:MUC5AC] |
| contig690 | 26306657_c3_36 | 2729 | 6134 | 294 | 97 | 69 | 0.64 | [OR:Streptomyces hygroscopicus] [PN:orf3 3' of bah] |
| contig690 | 23694503_c2_23 | 2730 | 6135 | 219 | 72 | 55 | 0.99 | [AC:U50357] [OR:Streptococcus zooepidemicus] [PN:bacteriocin-like inhibitory substance] [GN:zooA] |
| contig690 | 16881881_f2_9 | 2731 | 6136 | 3318 | 1106 | 118 | 0.0048 | [SP:P32334] [OR:SACCHAROMYCES CEREVISIAE] [GN:MSB2] [DE:MSB2 PROTEIN (MULITCOPY SUPPRESSION OF A BUDDING DEFECT 2)] |
| contig690 | 33633952_f1_1 | 2732 | 6137 | 390 | 129 | 68 | 0.9 | [AC:Z83760] [OR:Ciona intestinalis] [PN:COS41.2] [NT:Ras-related protein] |
| contig691 | 24433937_f2_9 | 2733 | 6138 | 330 | 109 | 260 | 1.40E-22 | [AC:U09422] [OR:Enterococcus faecalis] [NT:ORF23] |
| contig691 | 24804838_f2_10 | 2734 | 6139 | 387 | 128 | 381 | 2.10E-35 | [AC:U09422] [OR:Enterococcus faecalis] [NT:ORF22] |
| contig691 | 3948453_f2_11 | 2735 | 6140 | 354 | 117 | 62 | 0.12 | [SP:Q57755] [OR:METHANOCOCCUS JANNASCHII] [GN:MJ0307] [DE:HYPOTHETICAL THIOREDOXIN-LIKE PROTEIN MJ0307] |
| contig691 | 26620455_f2_12 | 2736 | 6141 | 1038 | 345 | 765 | 4.20E-76 | [AC:U09422] [OR:Enterococcus faecalis] [NT:ORF21] |
| contig691 | 4892533_c1_27 | 2737 | 6142 | 246 | 81 | 65 | 0.061 | [SP:P28255] [OR:GALDIERIA SULPHURARIA] [GN:YCF19] [DE:HYPOTHETICAL 1.6 KD PROTEIN IN PSBC-RPS16 INTERGENIC REGION] |
| contig691 | 468778_f1_2 | 2738 | 6143 | 1230 | 409 | 900 | 2.10E-90 | [AC:X98606] [OR:Clostridium difficile] [NT:potential coding region] |
| contig691 | 35585832_f3_17 | 2739 | 6144 | 837 | 278 | 311 | 3.00E-27 | [AC:X98606] [OR:Clostridium difficile] [NT:potential coding region] |
| contig691 | 85130_c2_35 | 2740 | 6145 | 264 | 87 | 66 | 0.2 | [OR:Methanococcus jannaschii] [PN:hypothetical protein MJ0902] |
| contig691 | 14959452_f2_13 | 2741 | 6146 | 357 | 118 | 502 | 3.10E-48 | [AC:U09422] [OR:Enterococcus faecalis] [NT:ORF21] |
| contig691 | 36501967_f1_3 | 2742 | 6147 | 465 | 154 | 93 | 0.00033 | [OR:Streptococcus pyogenes] [PN:hypothetical protein zeta] |
| contig691 | 10723761_f3_18 | 2743 | 6148 | 213 | 70 | 77 | 0.056 | [AC:U68542] [OR:Mus musculus] [PN:mCASP] [GN:cux] [NT:lacks homeodomain and cut repeats of cux/CDP;] |
| contig691 | 984536_f3_19 | 2744 | 6149 | 1209 | 402 | 1113 | 5.60E-113 | [AC:U09422] [OR:Enterococcus faecalis] [NT:ORF20] |
| contig691 | 4120650_c1_25 | 2745 | 6150 | 1314 | 437 | 94 | 2.70E-07 | [SP:P19257] [OR:MORAXELLA LACUNATA] [GN:PIV] [DE:PILIN GENE INVERTING PROTEIN (PIVML)] |
| contig691 | 26610750_f1_4 | 2746 | 6151 | 255 | 84 | 53 | 0.69 | [OR:Escherichia coli] [PN:hypothetical 8K protein (insertion sequence IS1)] |
| contig691 | 21500087_f1_5 | 2747 | 6152 | 261 | 86 | 331 | 4.10E-30 | [AC:U09422] [OR:Enterococcus faecalis] [NT:ORF19] |
| contig691 | 14117943_f1_6 | 2748 | 6153 | 516 | 171 | 553 | 1.20E-53 | [AC:U09422] [OR:Enterococcus faecalis] [NT:ORF18] |
| contig691 | 36128135_f2_14 | 2749 | 6154 | 849 | 282 | 162 | 3.20E-10 | [AC:U41294] [OR:Lactococcus lactis] [PN:abortive phage resistance protein] [GN:abi-859] |
| contig691 | 26593750_c3_43 | 2750 | 6155 | 747 | 248 | 70 | 0.083 | [SP:P20563] [OR:VACCINIA VIRUS] [GN:F ORF E] [DE:HYPOTHETICAL 7.8 KD PROTEIN] |
| contig691 | 31916062_f2_15 | 2751 | 6156 | 408 | 135 | 448 | 1.60E-42 | [AC:U09422] [OR:Enterococcus faecalis] [NT:ORF17] |
| contig691 | 12275257_f3_20 | 2752 | 6157 | 2451 | 816 | 3127 | 0 | [AC:U09422] [OR:Enterococcus faecalis] [NT:ORF16] |
| contig691 | 33605083_f1_8 | 2753 | 6158 | 585 | 195 | 525 | 1.40E-50 | [AC:U09422] [OR:Enterococcus faecalis] [NT:ORF15] |
| contig692 | 6648582_f2_6 | 2754 | 6159 | 2001 | 666 | 577 | 3.50E-56 | [AC:AB001488] [OR:Bacillus subtilis] [GN:ydaA] [NT:PROBABLE HTH_LYSR_FAMILY TRANSCRIPTIONAL] |

TABLE 2-continued

| Contig | Orf | NT Seq Id | AA Seq ID | NT Orf Length | AA Orf Length | Score | Probability | Description |
|---|---|---|---|---|---|---|---|---|
| contig692 | 25400338_f3_11 | 2755 | 6160 | 438 | 145 | 288 | 1.50E-25 | SP:Q02420] [OR:STREPTOCOCCUS MUTANS] [GN:MTLF] [DE:(EC 2.7.1.69) (EIII-MTL)] |
| contig692 | 13922561_f1_2 | 2756 | 6161 | 2031 | 676 | 1213 | 1.40E-123 | SP:P50852] [OR:BACILLUS STEAROTHERMOPHILUS] [GN:MTLA] [DE:(EC 2.7.1.69) (EII-MTL)] |
| contig692 | 283412_f3_14 | 2757 | 6162 | 486 | 161 | 708 | 4.60E-70 | SP:P27547] [OR:ENTEROCOCCUS FAECALIS] [GN:MTLF] [DE:(EC 2.7.1.69) (EIII-MTL)] |
| contig692 | 23633442_f2_8 | 2758 | 6163 | 1203 | 400 | 1644 | 3.00E-169 | OR:Enterococcus faecalis] [PN:mannitol-1-phosphate 5-dehydrogenase, mtlD] |
| contig692 | 10187936_c3_42 | 2759 | 6164 | 1194 | 397 | 125 | 3.20E-05 | [AC:L48934] [OR:Pseudomonas aeruginosa] [GN:dada*] [NT:homologus to D-amino acid dehydrogenase enzyme] |
| contig692 | 4422093_c3_41 | 2760 | 6165 | 648 | 215 | 164 | 3.30E-12 | OR:Saccharomyces cerevisiae] [PN:hypothetical protein YLR290c] |
| contig692 | 14657943_f1_3 | 2761 | 6166 | 1197 | 398 | 126 | 2.70E-05 | SP:P37636] [OR:ESCHERICHIA COLI] [GN:YHIU] [DE:PRECURSOR (O385)] |
| contig692 | 5083588_f1_4 | 2762 | 6167 | 720 | 239 | 549 | 3.30E-53 | OR:Methanococcus jannaschii] [PN:glutamine transport ATP-binding protein Q homolog] |
| contig692 | 23562827_f3_15 | 2763 | 6168 | 1230 | 409 | 284 | 3.90E-25 | [AC:D90917] [OR:Synechocystis sp.] [PN:hypothetical protein] [NT:ORF_ID] |
| contig692 | 30736568_c2_26 | 2764 | 6169 | 726 | 241 | 66 | 0.19 | [AC:U93078] [OR:Thermococcus sp. AN1] [PN:histone-like protein HAN1 A subunit] [GN:hanlA] |
| contig692 | 962800_c3_37 | 2765 | 6170 | 1521 | 506 | 1100 | 1.30E-111 | [AC:D50453] [OR:Bacillus subtilis] [PN:homologue of multidrug resistance protein B,] [GN:ycnB] |
| contig692 | 19558192_f3_8 | 2766 | 6171 | 1521 | 506 | 176 | 2.40E-10 | [OR:Arthrobacter sp.] [PN:4-chlorobenzoate-CoA ligase, 4-CBA-CoA-ligase] |
| contig693 | 24642808_f2_3 | 2767 | 6172 | 705 | 234 | 543 | 1.40E-52 | SP:P31470] [OR:ESCHERICHIA COLI] [GN:YIEK] [DE:HYPOTHETICAL 23.3 KD PROTEIN IN TNAB-BGLB INTERGENIC REGION] |
| contig693 | 21520327_c1_20 | 2768 | 6173 | 1104 | 367 | 615 | 3.30E-60 | OR:Amycolatopsis sp.] [PN:N-Acylamino acid racemase] |
| contig693 | 24486582_c1_19 | 2769 | 6174 | 849 | 282 | 232 | 1.30E-19 | SP:P44611] [OR:HAEMOPHILUS INFLUENZAE] [GN:HI0282] [DE:HYPOTHETICAL PROTEIN HI0282] |
| contig693 | 31305215_c2_24 | 2770 | 6175 | 1896 | 631 | 880 | 2.70E-88 | SP:P23970] [OR:BACILLUS SUBTILIS] [GN:MEND] [DE:KETOGLUTARATE DICARBOXYLASE) (KDC)] |
| contig693 | 14660332_c3_27 | 2771 | 6176 | 1473 | 490 | 718 | 4.00E-71 | SP:P23973] [OR:BACILLUS SUBTILIS] [GN:MENF] [DE:MENAQUINONE-SPECIFIC ISOCHORISMATE SYNTHASE,] |
| contig693 | 32462951_c1_15 | 2772 | 6177 | 1572 | 523 | 529 | 2.20E-59 | [AC:Y14083] [OR:Bacillus subtilis] [PN:hypothetical protein] [GN:yhfL] [NT:Similarity to LefA, Long-chain fatty acid-CoA] |
| contig693 | 23728375_c3_26 | 2773 | 6178 | 306 | 101 | 390 | 2.30E-36 | SP:P23963] [OR:BACILLUS SUBTILIS] [GN:MENB] [DE:(DHNA SYNTHETASE)] |
| contig693 | 25678513_c1_38 | 2774 | 6179 | 192 | 64 | 60 | 0.2 | SP:P27196] [OR:SYNECHOCYSTIS SP] [DE:HYPOTHETICAL 13.0 KD PROTEIN IN ATP1 5' REGION] |
| contig694 | 13869051_c2_48 | 2775 | 6180 | 228 | 75 | 60 | 0.94 | SP:P18812] [OR:ENTEROBACTER AEROGENES] [GN:MALF] [DE:MALTOSE TRANSPORT SYSTEM PERMEASE PROTEIN MALF] |
| contig694 | 4105463_c3_51 | 2776 | 6181 | 996 | 331 | 164 | 7.00E-10 | [AC:AB001488] [OR:Bacillus subtilis] [GN:yddB] [NT:SIMILAR TO ORF13 OF ENTEROCOCCUS FAECALIS] |
| contig694 | 24787552_c2_47 | 2777 | 6182 | 501 | 166 | 72 | 0.9996 | SP:P12926] [OR:VACCINIA VIRUS] [GN:17L] [DE:PROTEIN 17] |
| contig694 | 36227125_c3_50 | 2778 | 6183 | 570 | 189 | 74 | 0.99 | [AC:Z73102] [OR:Caenorhabditis elegans] [PN:B0035.2] [NT:protein predicted using Genefinder; Similarity to] |
| contig694 | 24415925_c2_46 | 2779 | 6184 | 732 | 243 | 171 | 3.70E-13 | [AC:Z83337] [OR:Bacillus subtilis] [GN:ywpE] |
| contig694 | 24410662_c2_45 | 2780 | 6185 | 2010 | 669 | 108 | 0.01 | [OR:Mus musculus] [PN:oncofetal antigen] |

TABLE 2-continued

| Contig | Orf | NT Seq Id | AA Seq ID | NT Orf Length | AA Orf Length | Score | Probability | Description |
|---|---|---|---|---|---|---|---|---|
| contig694 | 34267517_c3_49 | 2781 | 6186 | 603 | 200 | 78 | 0.83 | [AC:Z69383] [OR:Caenorhabditis elegans] [PN:F13F9.5] |
| contig694 | 33478377_c1_36 | 2782 | 6187 | 618 | 205 | 453 | 4.90E-43 | [AC:U09422] [OR:Enterococcus faecalis] [NT:ORF20] |
| contig694 | 4470642_c2_44 | 2783 | 6188 | 1320 | 439 | 74 | 0.0078 | [SP:P23370] [OR:THERMUS AQUATICUS] [GN:RPSF] [DE:30S RIBOSOMAL PROTEIN S6 (TS9)] |
| contig694 | 4886328_c1_35 | 2784 | 6189 | 414 | 137 | | | |
| contig694 | 3989817_c1_34 | 2785 | 6190 | 348 | 115 | 77 | 0.015 | [SP:P15913] [OR:FOWLPOX VIRUS] [GN:FP5] [DE:(FP5 PROTEIN)] |
| contig694 | 24845877_c2_43 | 2786 | 6191 | 558 | 185 | 70 | 0.04 | [AC:Z73234] [OR:Bacillus subtilis] [PN:YnfE] [GN:ynfE] |
| contig694 | 34181686_c2_42 | 2787 | 6192 | 1173 | 390 | 596 | 3.40E-58 | [AC:AB001488] [OR:Bacillus subtilis] [GN:ydcQ] [NT:SIMILAR TO ORF21 OF ENTEROCOCCUS FAECALIS] |
| contig694 | 24412577_c2_41 | 2788 | 6193 | 339 | 112 | 60 | 0.19 | [AC:U92672] [OR:Mitochondrion Dahlella caldariensis] [PN:cytochrome oxidase I] [GN:COI] |
| contig694 | 24610712_c2_40 | 2789 | 6194 | 390 | 129 | 82 | 0.058 | [SP:Q57876] [OR:METHANOCOCCUS JANNASCHII] [GN:MJ0434] [DE:HYPOTHETICAL PROTEIN MJ0434] |
| contig694 | 5117677_c1_33 | 2790 | 6195 | 339 | 112 | 140 | 7.10E-10 | [SP:Q57877] [OR:METHANOCOCCUS JANNASCHII] [GN:MJ0435] [DE:HYPOTHETICAL PROTEIN MJ0435] |
| contig694 | 24507875_c1_32 | 2791 | 6196 | 447 | 148 | 52 | 0.97 | [SP:P18926] [OR:CENTRUROIDES LIMPIDUS TECOMANUS] [DE:NEUROTOXIN 1] |
| contig694 | 2429078_c2_39 | 2792 | 6197 | 243 | 80 | 66 | 0.048 | [AC:JQ2192] [OR:porcine epidemic diarrhea virus] [PN:1 protein] [GN:I] |
| contig694 | 31447212_c1_31 | 2793 | 6198 | 228 | 75 | 59 | 0.83 | [AC:U75930] [OR:Orgyia pseudotsugata nuclear polyhedrosis virus] [PN:occlusion-derived virus envelope protein E27] [NT:ORF141; odv-e27, AcMNPV ORF144 homolog] |
| contig694 | 12363508_f1_1 | 2794 | 6199 | 624 | 207 | 89 | 0.043 | [SP:P54421] [OR:BACILLUS SUBTILIS] [GN:PAPQ] [DE:PHOSPHATASE-ASSOCIATED PROTEIN PAPQ PRECURSOR] |
| contig695 | 34570375_c3_54 | 2795 | 6200 | 705 | 234 | 603 | 6.20E-59 | [AC:D86418] [OR:Bacillus subtilis] [PN:YfmB] |
| contig695 | 1040932_c1_37 | 2796 | 6201 | 786 | 261 | 308 | 1.10E-27 | [AC:D63999] [OR:Synechocystis sp.] [PN:hypothetical protein] [NT:ORF_ID] |
| contig695 | 6728378_f1_3 | 2797 | 6202 | 612 | 203 | 327 | 1.10E-29 | [SP:P14194] [OR:BACILLUS SUBTILIS] [GN:CTC] [DE:GENERAL STRESS PROTEIN CTC] |
| contig695 | 24410928_f3_25 | 2798 | 6203 | 348 | 115 | | | |
| contig695 | 25937583_c3_51 | 2799 | 6204 | 3048 | 1015 | 907 | 3.80E-91 | [AC:L20670] [OR:Streptococcus pneumoniae] [PN:hyaluronidase] [NT:putative] |
| contig695 | 633336_c3_50 | 2800 | 6205 | 891 | 296 | 311 | 5.40E-28 | [AC:U18997] [OR:Escherichia coli] [NT:ORF_o290; Geneplot suggests frameshift linking to] |
| contig695 | 9804838_c2_41 | 2801 | 6206 | 804 | 267 | 90 | 0.0013 | [SP:P42905] [OR:ESCHERICHIA COLI] [GN:AGAW] [DE:(N-ACETYLGALACTOSAMINE-PERMEASE IIC COMPONENT 2)] |
| contig695 | 980443_c2_40 | 2802 | 6207 | 939 | 312 | 379 | 3.40E-35 | [SP:P08186] [OR:ESCHERICHIA COLI] [GN:MANX] [DE:(EC 2.7.1.69) (EIII-MAN)] |
| contig695 | 24117887_f2_17 | 2803 | 6208 | 723 | 240 | 186 | 9.50E-15 | [SP:P13669] [OR:ESCHERICHIA COLI] [GN:FARR] [DE:FATTY ACYL RESPONSIVE REGULATOR (P30 PROTEIN)] |
| contig695 | 4883592_c3_49 | 2804 | 6209 | 1791 | 596 | 904 | 7.80E-91 | [SP:P48982] [OR:XANTHOMONAS MANIHOTIS] [GN:BGA] [DE:BETA-GALACTOSIDASE PRECURSOR, (LACTASE)] |
| contig695 | 26603568_c3_48 | 2805 | 6210 | 1176 | 391 | 72 | 0.94 | [SP:Q09947] [OR:CAENORHABDITIS ELEGANS] [GN:F12A10.6] [DE:HYPOTHETICAL 14.4 KD PROTEIN F12A10.6 IN CHROMOSOME II] |
| contig695 | 578386_f2_20 | 2806 | 6211 | 234 | 77 | 66 | 0.27 | [AC:D90916] [OR:Synechocystis sp.] [PN:sensory transduction histidine kinase] [NT:ORF_ID] |

TABLE 2-continued

| Contig | Orf | NT Seq Id | AA Seq ID | NT Orf Length | AA Orf Length | Score | Probability | Description |
|---|---|---|---|---|---|---|---|---|
| contig695 | 24259687_c2_39 | 2807 | 6212 | 831 | 276 | 66 | 0.98 | [SP:Q50786] [OR:METHANOBACTERIUM THERMOAUTOTROPHICUM] [GN:GLNBA] [DE:NITROGEN FIXATION NIFHD REGION GLNB-LIKE PROTEIN 1] |
| contig695 | 34105302_c2_38 | 2808 | 6213 | 696 | 231 | | | |
| contig696 | 24806678_f3_15 | 2809 | 6214 | 831 | 276 | 463 | 4.20E-44 | [SP:Q01625] [OR:BACILLUS SUBTILIS] [GN:SPOIIIJ] [DE:STAGE III SPORULATION PROTEIN J PRECURSOR] |
| contig696 | 26835938_f2_7 | 2810 | 6215 | 813 | 270 | 245 | 3.50E-28 | [SP:Q01629] [OR:BACILLUS SUBTILIS] [GN:JAG] [DE:JAG PROTEIN (SPOIIIJ ASSOCIATED PROTEIN)] |
| contig696 | 12539677_c1_29 | 2811 | 6216 | 270 | 89 | 55 | 0.6 | [AC:Z27398] [OR:Ovis aries] [PN:MHC class II] [NT:Author-given protein sequence is in conflict with] |
| contig696 | 35989192_f2_8 | 2812 | 6217 | 747 | 248 | 309 | 8.80E-28 | [AC:U67196] [OR:Thermotoga maritima] [PN:DNA-binding response regulator] [GN:drrA] [NT:DrrA; OmpR/PhoB subfamily response regulator] |
| contig696 | 34642662_c1_28 | 2813 | 6218 | 756 | 251 | 101 | 1.10E-05 | [AC:D88802] [OR:Bacillus subtilis] [GN:ydhC] [[NT:B. subtilis gluconate operon repressor; P10585] |
| contig696 | 24396916_c3_55 | 2814 | 6219 | 1437 | 478 | 504 | 3.00E-86 | [SP:P42308] [OR:BACILLUS SUBTILIS] [GN:YXIQ] [DE:HYPOTHETICAL 45.5 KD PROTEIN IN BGLS-KATB INTERGENIC REGION] |
| contig696 | 49008_f3_20 | 2815 | 6220 | 441 | 146 | 73 | 0.51 | [OR:Drosophila melanogaster] [PN:gdl protein] |
| contig696 | 26366325_f1_2 | 2816 | 6221 | 444 | 147 | 238 | 1.50E-29 | [SP:P29337] [OR:STREPTOCOCCUS MUTANS] [DE:BIOTIN CARBOXYL CARRIER PROTEIN (BCCP)] |
| contig696 | 6854813_f3_21 | 2817 | 6222 | 1134 | 377 | 661 | 5.70E-71 | [SP:Q03031] [OR:SALMONELLA TYPHIMURIUM] [GN:OADB] [DE:OXALOACETATE DECARBOXYLASE BETA CHAIN,] |
| contig696 | 26756562_f2_12 | 2818 | 6223 | 1032 | 343 | 483 | 3.20E-46 | [SP:P44462] [OR:HAEMOPHILUS INFLUENZAE] [GN:CITC] [DE:SYNTHETASE) (ACETATE] |
| contig696 | 34164592_f1_3 | 2819 | 6224 | 396 | 131 | 136 | 1.90E-09 | [SP:P77618] [OR:ESCHERICHIA COLI] [GN:CITD] [DE:CITRATE LYASE ACYL CARRIER PROTEIN (CITRATE LYASE GAMMA CHAIN)] |
| contig696 | 6929825_f3_22 | 2820 | 6225 | 906 | 301 | 785 | 3.20E-78 | [SP:P44460] [OR:HAEMOPHILUS INFLUENZAE] [GN:CITE] [DE:CITRATE LYASE BETA CHAIN, (ACYL LYASE SUBUNIT) (CITRASE)] |
| contig696 | 31798377_f2_14 | 2821 | 6226 | 1560 | 519 | 1304 | 3.20E-133 | [SP:P44459] [OR:HAEMOPHILUS INFLUENZAE] [GN:CITF] [DE:CITRATE LYASE ALPHA CHAIN, (CITRASE)] |
| contig696 | 20947200_f3_23 | 2822 | 6227 | 552 | 183 | 217 | 4.90E-18 | [AC:AE000166] [OR:Escherichia coli] [NT:f183; This 183 aa orf is 33 pct identical (0 gaps)] |
| contig696 | 34648536_f1_4 | 2823 | 6228 | 1416 | 471 | 1415 | 5.60E-145 | [OR:Methanococcus jannaschii] [PN:oxaloacetate decarboxylase, alpha subunit] |
| contig696 | 23837591_f1_5 | 2824 | 6229 | 1203 | 400 | 820 | 6.30E-82 | [SP:P16468] [OR:BACILLUS STEAROTHERMOPHILUS] [DE:MALATE OXIDOREDUCTASE (NAD), (MALIC ENZYME)] |
| contig696 | 16837715_c3_58 | 2825 | 6230 | 570 | 190 | 359 | 4.40E-33 | [SP:P39843] [OR:BACILLUS SUBTILIS] [GN:BLT] [DE:MULTIDRUG RESISTANCE PROTEIN 2 (MULTIDRUG-EFFLUX TRANSPORTER 2)] |
| contig697 | 1230342_c2_47 | 2826 | 6231 | 456 | 151 | 113 | 5.20E-07 | [AC:Y09323] [OR:Bacillus cereus] [PN:hypothetical protein] [GN:332b] |
| contig697 | 4775061_c3_57 | 2827 | 6232 | 789 | 262 | 157 | 6.00E-10 | [SP:P04827] [OR:STAPHYLOCOCCUS AUREUS] [GN:SPC] [DE:STREPTOMYCIN 3''-ADENYLYLTRANSFERASE, (AAD(9))] |
| contig697 | 16211012_c3_56 | 2828 | 6233 | 537 | 178 | 57 | 0.74 | [OR:Nautilus pompitius] [PN:engrailed protein A homolog] |
| contig697 | 650203_c1_39 | 2829 | 6234 | 333 | 110 | 55 | 0.96 | [AC:U41536] [OR:Caenorhabditis elegans] [GN:F56E3.1] |
| contig697 | 585836_c1_38 | 2830 | 6235 | 576 | 191 | 169 | 1.50E-12 | [OR:Streptomyces lincolnensis] [PN:hypothetical protein 1] |

TABLE 2-continued

| Contig | Orf | NT Seq Id | AA Seq ID | NT Orf Length | AA Orf Length | Score | Probability | Description |
|---|---|---|---|---|---|---|---|---|
| contig697 | 34433875_c1_37 | 2831 | 6236 | 1011 | 336 | 458 | 1.40E-43 | [AC:Z94043] [OR:*Bacillus subtilis*] [PN:hypothetical protein] [GN:yvfJ] [NT:probable transcriptional regulator (LacI family)] |
| contig697 | 22477302_c1_36 | 2832 | 6237 | 1509 | 502 | 1434 | 5.40E-147 | [AC:U21942] [OR:*Streptococcus mutans*] [PN:galactose-1-P-uridyl transferase] |
| contig697 | 31952_c2_44 | 2833 | 6238 | 990 | 329 | 1100 | 1.30E-111 | [AC:U21942] [OR:*Streptococcus mutans*] [PN:UDP-galactose 4-epimerase] |
| contig697 | 1042337_c2_43 | 2834 | 6239 | 1179 | 392 | 1227 | 4.60E-125 | [AC:U21942] [OR:*Streptococcus mutans*] [PN:galactokinase] |
| contig697 | 24492180_c1_35 | 2835 | 6240 | 195 | 64 | 60 | 0.57 | [SP:P53028] [OR:*TRYPANOSOMA BRUCEI RHODESIENSE*] [GN:RPL10A] [DE:60S RIBOSOMAL PROTEIN L10A] |
| contig697 | 1366557_f3_26 | 2836 | 6241 | 1089 | 362 | 526 | 8.90E-51 | [SP:P05149] [OR:*ACINETOBACTER CALCOACETICUS*] [GN:MRO] [DE:ALDOSE 1-EPIMERASE PRECURSOR, (MUTAROTASE)] |
| contig697 | 19926463_f1_5 | 2837 | 6242 | 219 | 72 | 68 | 0.33 | [AC:Z93380] [OR:*Caenorhabditis elegans*] [PN:F28C12.d] [NT:protein predicted using Genefinder; preliminary] |
| contig697 | 19661592_f1_6 | 2838 | 6243 | 651 | 216 | 441 | 9.10E-42 | [SP:P40892] [OR:*SACCHAROMYCES CEREVISIAE*] [GN:YIL218W] [DE:(EC 2.3.1.—)] |
| contig697 | 34433837_c3_53 | 2839 | 6244 | 387 | 128 | 78 | 0.045 | [SP:P16681] [OR:*ESCHERICHIA COLI*] [GN:PHNB] [DE:PHNB PROTEIN] |
| contig697 | 6484411_c3_52 | 2840 | 6245 | 534 | 177 | 266 | 3.20E-23 | [AC:D90826] [OR:*Escherichia coli*] [GN:YKL069W, YKL340] [NT:ORF_ID] |
| contig697 | 21907902_c3_51 | 2841 | 6246 | 555 | 184 | 256 | 1.20E-21 | [AC:AE000139] [OR:*Escherichia coli*] [NT:o460: This 460 aa orf is 23 pct identical (24 gaps)] |
| contig697 | 24298917_c3_50 | 2842 | 6247 | 687 | 228 | 348 | 6.50E-32 | [AC:AE000139] [OR:*Escherichia coli*] [NT:o460: This 460 aa orf is 23 pct identical (24 gaps)] |
| contig697 | 36142200_c1_33 | 2843 | 6248 | 1251 | 416 | 744 | 7.10E-74 | [AC:AE000139] [OR:*Escherichia coli*] [NT:o460: This 460 aa orf is 23 pct identical (24 gaps)] |
| contig697 | 5367887_c1_32 | 2844 | 6249 | 1677 | 558 | 855 | 1.20E-85 | [OR:*Enterococcus faecalis*] [PN:probable pheromone binding protein pheromone responsive gene Z protein] [GN:prgZ] |
| contig697 | 24397150_f3_29 | 2845 | 6250 | 1095 | 364 | 82 | 0.96 | [OR:*Bacillus stearothermophilus*] [PN:alpha-amylase,] |
| contig697 | 15720313_f1_11 | 2846 | 6251 | 543 | 180 | 142 | 3.20E-09 | [AC:Z82015] [OR:*Bacillus subtilis*] [GN:yukF] |
| contig697 | 661556_c3_48 | 2847 | 6252 | 222 | 73 | 56 | 0.86 | [OR:*Bos primigenius taurus*] [PN:charybdotoxin receptor beta chain] |
| contig697 | 978427_c1_31 | 2848 | 6253 | 429 | 142 | 112 | 6.60E-07 | [SP:P42297] [OR:*BACILLUS SUBTILIS*] [GN:YXIE] [DE:HYPOTHETICAL PROTEIN 15.9 KD IN BGLH-WAPA INTERGENIC REGION PRECURSOR] |
| contig698 | 19628761_c2_40 | 2849 | 6254 | 882 | 293 | 241 | 8.10E-20 | [OR:*Oryza sativa*] [PN:Nramp1 protein] |
| contig698 | 36140907_c3_79 | 2850 | 6255 | 267 | 88 | 174 | 1.90E-12 | [SP:P31458] [OR:*ESCHERICHIA COLI*] [GN:YIDU] [DE:HYPOTHETICAL 64.0 KD PROTEIN IN IBPA-GYRB INTERGENIC REGION] |
| contig698 | 2110751_c1_54 | 2851 | 6256 | 573 | 190 | 159 | 4.40E-11 | [SP:P37189] [OR:*ESCHERICHIA COLI*] [GN:GATC] [DE:PERMEASE IIC COMPONENT) (PHOSPHOTRANSFERASE ENZYME II, C COMPONENT] |
| contig698 | 14554051_f1_27 | 2852 | 6257 | 186 | 61 | 56 | 0.7 | [AC:M31647] [OR:*Mus musculus*] [NT:T-cell receptor alpha-chain precursor V-J-C region] |
| contig698 | 36128451_c3_78 | 2853 | 6258 | 768 | 255 | 326 | 1.40E-29 | [AC:D90847] [OR:*Escherichia coli*] [PN:PTS system, Galactitol-specific IIC component] [GN:gatC] [NT:ORF_ID] |
| contig698 | 26776510_c3_77 | 2854 | 6259 | 297 | 98 | 180 | 4.10E-14 | [AC:D90847] [OR:*Escherichia coli*] [PN:PTS system, Galactitol-specific IIB component] [GN:gatB] [NT:ORF_ID] |
| contig698 | 34430427_c3_76 | 2855 | 6260 | 474 | 157 | 153 | 3.00E-11 | [SP:P37187] [OR:*ESCHERICHIA COLI*] [GN:GATA] [DE:(EC 2.7.1.69)] |

TABLE 2-continued

| Contig | Orf | NT Seq Id | AA Seq ID | NT Orf Length | AA Orf Length | Score | Probability | Description |
|---|---|---|---|---|---|---|---|---|
| contig698 | 2164038_c1_53 | 2856 | 6261 | 645 | 214 | 250 | 1.60E-21 | [AC:U70664] [OR:*Haloferax alicantei*] [PN:2-dehydro-3-deoxyphosphogluconate aldolase] [NT:KDPG aldolase] |
| contig698 | 35625212_c3_75 | 2857 | 6262 | 2103 | 700 | 181 | 1.80E-16 | [AC:U18943] [OR:*Bacillus stearothermophilus*] [GN:MtlR] [NT:putative transcriptional regulator] |
| contig698 | 208562_c2_63 | 2858 | 6263 | 1245 | 414 | 999 | 6.70E-101 | [SP:P35881] [OR:*LACTOCOCCUS LACTIS*] [DE:TRANSPOSASE FOR INSERTION SEQUENCE ELEMENT IS905] |
| contig698 | 14540887_c3_72 | 2859 | 6264 | 588 | 195 | 73 | 0.98 | [SP:Q39757] [OR:*FUCUS VESICULOSUS*] [DE:14-3-3-LIKE PROTEIN] |
| contig698 | 21525463_c3_71 | 2860 | 6265 | 3045 | 1014 | 1395 | 7.30E-143 | [AC:M63891] [OR:Plasmid pTB19] [NT:ORF] |
| contig698 | 23988452_f3_37 | 2861 | 6266 | 585 | 194 | 852 | 2.50E-85 | [AC:L28754] [OR:Insertion sequence IS6770] [PN:transposase] [NT:putative] |
| contig698 | 34183201_f1_4 | 2862 | 6267 | 291 | 96 | 474 | 2.90E-45 | [AC:L28754] [OR:Insertion sequence IS6770] [PN:transposase] [NT:putative] |
| contig698 | 32073575_c3_70 | 2863 | 6268 | 393 | 130 | 77 | 0.0064 | [AC:U09422] [OR:*Enterococcus faecalis*] [NT:ORF17] |
| contig698 | 34069068_c2_62 | 2864 | 6269 | 309 | 102 | 70 | 0.019 | [AC:U09422] [OR:*Enterococcus faecalis*] [NT:ORF19] |
| contig698 | 7035717_c2_61 | 2865 | 6270 | 240 | 79 | 61 | 0.15 | [AC:X99694] [OR:*Enterobacter agglomerans*] [GN:mfW] |
| contig698 | 21526068_c3_69 | 2866 | 6271 | 993 | 330 | 387 | 4.80E-36 | [SP:P55665] [OR:RHIZOBIUM SP] [GN:Y4TK] [DE:HYPOTHETICAL CYCLODEAMINASE Y4TK_] |
| contig698 | 39213_c3_68 | 2867 | 6272 | 891 | 296 | 88 | 0.12 | [SP:P54437] [OR:*BACILLUS SUBTILIS*] [GN:YRKJ] [DE:HYPOTHETICAL 27.6 KD PROTEIN IN BLTR-SPOIIIC INTERGENIC REGION] |
| contig698 | 14665930_c3_67 | 2868 | 6273 | 804 | 267 | 274 | 4.50E-24 | [AC:U93874] [OR:*Bacillus subtilis*] [PN:YrhO] [GN:yrhO] [NT:similar to CymJ protein from *Klebsiella oxytoca*] |
| contig698 | 10937_c2_57 | 2869 | 6274 | 216 | 71 | 50 | 0.98 | [SP:Q03548] [OR:BACTERIOPHAGE P22] [GN:EAF] [DE:EAF PROTEIN] |
| contig698 | 24315762_f3_43 | 2870 | 6275 | 348 | 115 | 162 | 4.30E-12 | [SP:P42911] [OR:*ESCHERICHIA COLI*] [GN:AGAD] [DE:ENZYME II, D COMPONENT] |
| contig698 | 4781325_f2_23 | 2871 | 6276 | 282 | 93 | | | |
| contig698 | 15667875_f2_24 | 2872 | 6277 | 591 | 196 | 100 | 0.0011 | [SP:P08188] [OR:*ESCHERICHIA COLI*] [GN:MANZ] [DE:(EII-M-MAN)] |
| contig698 | 4587828_f3_45 | 2873 | 6278 | 684 | 227 | 87 | 0.41 | [AC:U27586] [OR:*DICTYOSTELIUM DISCOIDEUM*] [GN:PORN] [GN:HepC] |
| contig698 | 16292063_f1_12 | 2874 | 6279 | 495 | 164 | 89 | 0.036 | [SP:Q01501] [OR:*DICTYOSTELIUM DISCOIDEUM* [GN:PORN] [DE:SELECTIVE CHANNEL PROTEIN] (VDAC)] |
| contig698 | 4882188_c3_66 | 2875 | 6280 | 207 | 68 | 56 | 0.43 | [AC:M19656] [OR:*Bos taurus*] [NT:adrenodoxin] |
| contig698 | 22460816_f3_46 | 2876 | 6281 | 450 | 149 | 647 | 1.30E-63 | [SP:P19775] [OR:*STAPHYLOCOCCUS AUREUS*] [GN:TNP] [DE:TRANSPOSASE FOR INSERTION SEQUENCE ELEMENT IS256 IN TRANSPOSON TN4001] |
| contig698 | 24409642_f2_25 | 2877 | 6282 | 249 | 82 | 172 | 1.40E-12 | [SP:P19775] [OR:*STAPHYLOCOCCUS AUREUS*] [GN:TNP] [DE:TRANSPOSASE FOR INSERTION SEQUENCE ELEMENT IS256 IN TRANSPOSON TN4001] |
| contig698 | 24221913_c3_65 | 2878 | 6283 | 327 | 108 | 51 | 0.85 | [AC:U42580] [OR:*Paramecium bursaria* Chlorella virus 1] [GN:a272R] |
| contig698 | 11910468_f3_16 | 2879 | 6284 | 780 | 259 | 376 | 7.00E-35 | [SP:P39128] [OR:*BACILLUS SUBTILIS*] [GN:LPLB] [DE:LPLB PROTEIN] |
| contig699 | 26851457_f1_1 | 2880 | 6285 | 1026 | 341 | 502 | 3.10E-48 | [SP:P39129] [OR:*BACILLUS SUBTILIS*] [GN:LPLC] [DE:LPLC PROTEIN] |
| contig699 | 10001262_f3_17 | 2881 | 6286 | 1803 | 600 | 196 | 1.90E-12 | [SP:P37966] [OR:*BACILLUS SUBTILIS*] [GN:LPLA] [DE:LIPOPROTEIN LPLA PRECURSOR] |

TABLE 2-continued

| Contig | Orf | NT Seq Id | AA Seq ID | NT Orf Length | AA Orf Length | Score | Probability | Description |
|---|---|---|---|---|---|---|---|---|
| contig699 | 26774053_f2_8 | 2882 | 6287 | 654 | 217 | 54 | 0.95 | [SP:P34836] [OR:ANOPHELES GAMBIAE] [DE:ATP SYNTHASE PROTEIN 8, (A6L)] |
| contig699 | 4464453_f3_18 | 2883 | 6288 | 927 | 308 | 322 | 3.70E-29 | [AC:D50453] [OR:Bacillus subtilis] [PN:cephalosporin C deacetylase] [GN:cah] |
| contig699 | 24429592_f1_2 | 2884 | 6289 | 876 | 291 | 98 | 0.02 | [AC:Y09797] [OR:Hydra vulgaris] [PN:Hyp1 protein] [GN:hyp1] |
| contig699 | 20901462_f2_9 | 2885 | 6290 | 2184 | 727 | 805 | 9.00E-136 | [SP:P33363] [OR:ESCHERICHIA COLI] [GN:BGLX] [DE:(CELLOBIOSE) (BETA-D-GLUCOSIDE GLUCOHYDROLASE)] |
| contig699 | 5259628_f1_4 | 2886 | 6291 | 3279 | 1092 | 109 | 0.099 | [SP:P20471] [OR:RHIZOBIUM MELILOTI] [GN:NDVB] [DE:319 KD PROTEIN] |
| contig699 | 35994030_f1_5 | 2887 | 6292 | 969 | 322 | 390 | 2.30E-36 | [SP:P46828] [OR:BACILLUS MEGATERIUM] [GN:CCPA] [DE:GLUCOSE-RESISTANCE AMYLASE REGULATOR (CATABOLITE CONTROL PROTEIN)] |
| contig699 | 4062693_c2_34 | 2888 | 6293 | 561 | 186 | 61 | 0.33 | [OR:Homo sapiens] [PN:guanylyl cyclase C] |
| contig699 | 2074092_c2_33 | 2889 | 6294 | 726 | 241 | 308 | 1.10E-27 | [AC:D88802] [OR:Bacillus subtilis] [GN:ydhQ] [NT:K. aerogenes, histidine utilization repressor;] |
| contig699 | 26367786_f2_13 | 2890 | 6295 | 1458 | 485 | 1601 | 1.10E-164 | [SP:P42403] [OR:BACILLUS SUBTILIS] [GN:YCKE] [DE:(BETA-D-GLUCOSIDE GLUCOHYDROLASE) (AMYGDALASE)] |
| contig699 | 6135938_f2_14 | 2891 | 6296 | 1068 | 355 | 888 | 3.90E-89 | [SP:P46853] [OR:ESCHERICHIA COLI] [GN:YHHX] [DE:HYPOTHETICAL 38.8 KD PROTEIN IN GNTR-GGT INTERGENIC REGION (F345)] |
| contig699 | 4186_c3_43 | 2892 | 6297 | 222 | 73 | 57 | 0.77 | [AC:D85547] [OR:Bacillus sp.] [PN:cytochrome c oxidase subunit III] [NT:Author-given protein sequence is in conflict with] |
| contig699 | 26370887_f2_15 | 2893 | 6298 | 519 | 172 | 171 | 3.70E-13 | [AC:D90822] [OR:Escherichia coli] [NT:ORF_ID] |
| contig699 | 103825_c1_21 | 2894 | 6299 | 471 | 156 | 74 | 0.73 | [SP:P54657] [OR:DICTYOSTELIUM DISCOIDEUM] [GN:CADA] [DE:CALCIUM-DEPENDENT CELL ADHESION MOLECULE-1 (DDCAD-1)] |
| contig699 | 5362937_c3_42 | 2895 | 6300 | 246 | 81 | 63 | 0.69 | [AC:D90803] [OR:Escherichia coli] [PN:Arginine/ornithine antiporter.] [NT:ORF_ID] |
| contig7 | 28384812_c1_3 | 2896 | 6301 | 792 | 264 | 563 | 1.10E-54 | [AC:AF000129] [OR:Escherichia coli] [GN:abc] [NT:f343; 98 pct identical to fragment (231 aa)] |
| contig70 | 12118765_f3_1 | 2897 | 6302 | 786 | 261 | 720 | 1.60E-70 | [SP:P37870] [OR:BACILLUS SUBTILIS] [GN:RPOB] [DE:BETA CHAIN) (RNA POLYMERASE BETA SUBUNIT)] |
| contig700 | 23546952_c3_53 | 2898 | 6303 | 672 | 223 | 54 | 0.96 | [SP:P45999] [OR:ESCHERICHIA COLI] [GN:FASC] [DE:FASC PROTEIN (FRAGMENT)] |
| contig700 | 14539202_c3_52 | 2899 | 6304 | 918 | 305 | 474 | 2.90E-45 | [OR:Clostridium perfringens] [PN:probable membrane transport protein] |
| contig700 | 4798461_c1_39 | 2900 | 6305 | 915 | 304 | 516 | 1.00E-49 | [AC:D90905] [OR:Synechocystis sp.] [PN:lactose transport system permease protein LacF] [GN:lacF] [NT:ORF_ID] |
| contig700 | 7031527_f2_8 | 2901 | 6306 | 222 | 73 | 50 | 0.91 | [OR:Methanococcus jannaschii] [PN:hypothetical protein MJ0975] |
| contig700 | 7244802_c1_38 | 2902 | 6307 | 1296 | 431 | 160 | 5.80E-09 | [SP:Q00749] [OR:STREPTOCOCCUS MUTANS] [GN:MSME] [DE:MULTIPLE SUGAR-BINDING PROTEIN PRECURSOR] |
| contig700 | 20511093_c3_51 | 2903 | 6308 | 1158 | 385 | 61 | 0.78 | [AC:L76684] [OR:Macaca nemestrina] [PN:major histocompatibility complex] [GN:Mane-DRB5*01a] |
| contig700 | 34429700_c3_50 | 2904 | 6309 | 1818 | 605 | 56 | 0.9999 | [AC:PT0204] [OR:Rattus norvegicus] [PN:protein kinase, SK2] |
| contig700 | 26454775_c2_43 | 2905 | 6310 | 408 | 135 | 55 | 0.74 | [AC:M32809] [OR:Cauliflower mosaic virus] [NT:aphid acquisition factor] |
| contig700 | 24273437_f1_4 | 2906 | 6311 | 1026 | 341 | 254 | 2.40E-29 | [AC:Z94043] [OR:Bacillus subtilis] [PN:hypothetical protein] [GN:yvfI] [NT:probable transcriptional regulator (LacI family)] |

TABLE 2-continued

| Contig | Orf | NT Seq Id | AA Seq ID | NT Orf Length | AA Orf Length | Score | Probability | Description |
|---|---|---|---|---|---|---|---|---|
| contig700 | 24628217_f2_13 | 2907 | 6312 | 222 | 73 | 86 | 0.0025 | [OR:*Streptomyces lividans*] [PN:hypothetical protein] |
| contig700 | 24256510_c2_42 | 2908 | 6313 | 867 | 288 | 77 | 0.66 | [SP:P00307] [OR:*MASTIGOCLADUS LAMINOSUS*] [GN:CPCA] [DE:C-PHYCOCYANIN ALPHA CHAIN] |
| contig700 | 13689692_c3_48 | 2909 | 6314 | 1185 | 394 | 414 | 6.60E-39 | [AC:AB001488] [OR:*Bacillus subtilis*] [GN:ydcL] [NT:PROBABLE INTEGRASE.] |
| contig700 | 16525213_c1_35 | 2910 | 6315 | 216 | 71 | 69 | 0.026 | [AC:D90915] [OR:*Synechocystis sp.*] [PN:hypothetical protein] [NT:ORF_ID] |
| contig700 | 5132812_c1_33 | 2911 | 6316 | 225 | 74 | 74 | 0.017 | [SP:P23672] [OR:*CLOSTRIDIUM ACETOBUTYLICUM*] [DE:HYPOTHETICAL 21.6 KD PROTEIN IN ADC 5' REGION (ORF2)] |
| contig700 | 23683432_c3_47 | 2912 | 6317 | 186 | 61 | 60 | 0.55 | [SP:P21341] [OR:*BACILLUS SUBTILIS*] [GN:PAIB] [DE:PROTEASE SYNTHASE AND SPORULATION NEGATIVE REGULATORY PROTEIN PAI 2] |
| contig700 | 35189213_c1_32 | 2913 | 6318 | 492 | 163 | 92 | 0.0034 | [AC:X92982] [OR:*Clostridium difficile*] [GN:tcdD] |
| contig700 | 195258_c3_46 | 2914 | 6319 | 558 | 185 | 78 | 0.72 | [OR:*Haemophilus influenzae*] [PN:isg locus hypothetical protein HI1699] |
| contig700 | 2109385_c1_31 | 2915 | 6320 | 768 | 255 | 95 | 0.015 | [SP:Q06239] [OR:*ENTEROCOCCUS FAECIUM*] [GN:VANR] [DE:REGULATORY PROTEIN VANR] |
| contig700 | 35972785_c3_45 | 2916 | 6321 | 237 | 78 | 60 | 0.82 | [SP:P35350] [OR:*BOS TAURUS*] [DE:POSSIBLE GUSTATORY RECEPTOR TYPE B (PPR1 PROTEIN)] |
| contig700 | 24415925_c1_30 | 2917 | 6322 | 3018 | 1005 | 128 | 9.40E-05 | [SP:P34284] [OR:*CAENORHABDITIS ELEGANS*] [GN:C02F5.7] [DE:HYPOTHETICAL 54.9 KD PROTEIN C02F5.7 IN CHROMOSOME III] |
| contig700 | 35737937_c1_29 | 2918 | 6323 | 243 | 80 | 52 | 0.84 | [OR:*Rattus norvegicus*] [PN:ribosomal protein L37] |
| contig700 | 13675828_c1_28 | 2919 | 6324 | 1509 | 502 | 96 | 0.062 | [OR:*Plasmodium falciparum*] [PN:hypothetical protein 10] |
| contig701 | 4023910_f2_15 | 2920 | 6325 | 231 | 76 | 67 | 0.07 | [AC:U96915] [OR:*Homo sapiens*] [PN:sin3 associated polypeptide p18] [GN:SAP18] [NT:SAP18p] |
| contig701 | 26062768_f1_1 | 2921 | 6326 | 516 | 171 | 61 | 0.36 | [SP:P28538] [OR:*CHLAMYDIA TRACHOMATIS*] [GN:RPMC] [DE:50S RIBOSOMAL PROTEIN L29] |
| contig701 | 32611312_c3_67 | 2922 | 6327 | 1320 | 439 | 217 | 2.00E-17 | [OR:*Azotobacter vinelandii*] [PN:hypothetical protein 1 (vnfA 5' region)] |
| contig701 | 87937_c1_48 | 2923 | 6328 | 1035 | 344 | 842 | 1.50E-83 | [SP:P49610] [OR:*STREPTOCOCCUS PNEUMONIAE*] [GN:STRH] [DE:BETA-N-ACETYLHEXOSAMINIDASE PRECURSOR,] |
| contig701 | 26367958_c3_66 | 2924 | 6329 | 1671 | 556 | 293 | 1.70E-25 | [SP:P36912] [OR:*FLAVOBACTERIUM MENINGOSEPTICUM*] [GN:ENDOF2] [DE:(ENDOGLYCOSIDASE F2)] |
| contig701 | 13907687_c2_60 | 2925 | 6330 | 213 | 70 | 74 | 0.034 | [SP:P21060] [OR:*VACCINIA VIRUS*] [GN:A37R] [DE:PROTEIN A37] |
| contig701 | 22460816_f1_6 | 2926 | 6331 | 1203 | 400 | 2003 | 2.70E-207 | [SP:P19775] [OR:*STAPHYLOCOCCUS AUREUS*] [GN:TNP] [DE:TRANSPOSASE FOR INSERTION SEQUENCE ELEMENT IS256 IN TRANSPOSON TN4001] |
| contig701 | 16525643_f2_20 | 2927 | 6332 | 399 | 132 | 71 | 0.77 | [SP:P05738] [OR:*SACCHAROMYCES CEREVISIAE*] [GN:RPL9A] [DE:60S RIBOSOMAL PROTEIN L9 A (YL11) (RP25)] |
| contig701 | 1376262_f1_7 | 2928 | 6333 | 774 | 257 | 132 | 1.20E-08 | [SP:Q01894] [OR:*ENTEROCOCCUS FAECALIS*] [DE:HYPOTHETICAL 12.4 KD PROTEIN IN SEAI 5' REGION (ORFY)] |
| contig701 | 36532877_f1_8 | 2929 | 6334 | 213 | 70 | 58 | 0.29 | [SP:P50779] [OR:*HUMAN PAPILLOMAVIRUS TYPE 21*] [GN:E7] [DE:E7 PROTEIN] |
| contig701 | 24789212_f1_9 | 2930 | 6335 | 240 | 79 | 67 | 0.37 | [OR:*Saccharomyces cerevisiae*] [PN:hypothetical protein YDR346c] |
| contig701 | 35820425_f3_34 | 2931 | 6336 | 366 | 121 | 75 | 0.25 | [OR:*Methanococcus jannaschii*] [PN:hypothetical protein MJ1356] |

TABLE 2-continued

| Contig | Orf | NT Seq Id | AA Seq ID | NT Orf Length | AA Orf Length | Score | Probability | Description |
|---|---|---|---|---|---|---|---|---|
| contig701 | 6843752_f2_21 | 2932 | 6337 | 342 | 113 | 53 | 0.77 | [AC:D37778] [OR:*Rana nigromaculata*] [PN:tyrosinase] [GN:TYR] [NT:partial cds on an exon similar to exon4 of the] |
| contig701 | 34274178_f2_22 | 2933 | 6338 | 354 | 117 | 62 | 0.996 | [SP:Q57728] [OR:*METHANOCOCCUS JANNASCHII*] [GN:MJ0280] [DE:HYPOTHETICAL PROTEIN MJ0280] |
| contig701 | 4695318_f1_10 | 2934 | 6339 | 441 | 146 | 176 | 1.10E-13 | [SP:P21318] [OR:*ESCHERICHIA COLI*] [DE:HYPOTHETICAL 11.0 KD PROTEIN (ORFD) (RETRON EC67)] |
| contig701 | 3945327_f2_23 | 2935 | 6340 | 318 | 105 | 81 | 0.036 | [AC:U57047] [OR:Spinach latent virus] [PN:replicase] [NT:putative] |
| contig701 | 14570967_f1_11 | 2936 | 6341 | 219 | 72 | 55 | 0.77 | [OR:*Oncorhynchus tschawytscha*] [PN:transcription factor pit-1, pituitary-specific] |
| contig701 | 26620430_f3_35 | 2937 | 6342 | 195 | 64 | 66 | 0.048 | [SP:P02399] [OR:*ARTEMIA SALINA*] [DE:60S ACIDIC RIBOSOMAL PROTEIN P2 (EL12)] |
| contig701 | 29297578_f1_12 | 2938 | 6343 | 624 | 207 | 105 | 0.00019 | [SP:P39784] [OR:*BACILLUS SUBTILIS*] [GN:XPF] [DE:POSITIVE CONTROL FACTOR] |
| contig701 | 14237583_f3_36 | 2939 | 6344 | 276 | 91 | 57 | 0.43 | [SP:P42541] [OR:BACTERIOPHAGE L2] [DE:HYPOTHETICAL 9.8 KD PROTEIN (ORF6)] |
| contig701 | 24412786_f1_13 | 2940 | 6345 | 744 | 247 | 170 | 4.70E-13 | [SP:P44193] [OR:*HAEMOPHILUS INFLUENZAE*] [GN:HI1422] [DE:HYPOTHETICAL PROTEIN HI1422] |
| contig701 | 9960013_c1_41 | 2941 | 6346 | 705 | 234 | 64 | 0.3 | [SP:Q34940] [OR:*LEISHMANIA TARENTOLAE*] [GN:RPS12] [DE:MITOCHONDRIAL RIBOSOMAL PROTEIN S12] |
| contig701 | 4881461_f2_26 | 2942 | 6347 | 726 | 241 | 91 | 0.1 | [AC:AB001488] [OR:*Bacillus subtilis*] [GN:yddI] [NT:PROBABLE PROTEIN ASP-PHOSPHATASE.] |
| contig701 | 7246062_f2_27 | 2943 | 6348 | 744 | 247 | 122 | 5.30E-06 | [OR:*Bacillus subtilis*] [PN:hypothetical protein 8 (xre region)] |
| contig701 | 22087811_f3_37 | 2944 | 6349 | 1440 | 479 | 82 | 0.98 | [SP:P40504] [OR:*SACCHAROMYCES CEREVISIAE*] [GN:YIL085C] [DE:HYPOTHETICAL 61.4 KD PROTEIN IN SGA1-THS1 INTERGENIC REGION] |
| contig701 | 4105452_f1_14 | 2945 | 6350 | 1395 | 464 | 288 | 1.50E-23 | [SP:P44183] [OR:*HAEMOPHILUS INFLUENZAE*] [GN:HI1409] [DE:HYPOTHETICAL PROTEIN HI1409] |
| contig701 | 4884625_f2_29 | 2946 | 6351 | 1188 | 396 | 236 | 1.10E-17 | [OR:*Haemophilus influenzae*] [PN:traN protein (traN) homolog] |
| contig701 | 24855530_f3_16 | 2947 | 6352 | 909 | 302 | 149 | 4.70E-08 | [SP:P13457] [OR:*ESCHERICHIA COLI*] [GN:SBCD] [DE:EXONUCLEASE SBCD] |
| contig702 | 26641562_f2_5 | 2948 | 6353 | 270 | 89 | 85 | 0.015 | [AC:Z78416] [OR:*Caenorhabditis elegans*] [PN:C23H4.6] [NT:protein predicted using Genefinder; Similarity to] |
| contig702 | 24406251_f2_6 | 2949 | 6354 | 312 | 103 | 104 | 2.10E-05 | [AC:Y09476] [OR:*Bacillus subtilis*] [PN:YirY] [NT:putative] |
| contig702 | 24609411_f3_17 | 2950 | 6355 | 2457 | 818 | 258 | 6.30E-19 | [AC:M64787] [OR:*Escherichia coli*] [GN:sbcC] |
| contig702 | 34252126_f1_1 | 2951 | 6356 | 3222 | 1073 | 1568 | 3.40E-161 | [AC:X98455] [OR:*Bacillus cereus*] [GN:SNF] |
| contig702 | 19615825_f2_8 | 2952 | 6357 | 960 | 319 | 82 | 0.0062 | [OR:*Lactococcus lactis* subsp. *lactis*] [PN:hypothetical protein 3 (pip 3' region)] |
| contig702 | 21542562_c2_46 | 2953 | 6358 | 234 | 77 | 56 | 0.95 | [AC:*Saccharomyces cerevisiae*] [PN:hypothetical protein YOR060c] |
| contig702 | 20508425_f2_9 | 2954 | 6359 | 2199 | 732 | 425 | 2.30E-37 | [OR:*Listeria monocytogenes*] [PN:internalin A precursor] [GN:inlA] |
| contig702 | 2228593_f2_10 | 2955 | 6360 | 372 | 123 | 89 | 0.0096 | [SP:P16271] [OR:*LACTOCOCCUS LACTIS*] [GN:PRTP] [DE:PROTEINASE] |
| contig702 | 3419532_f3_19 | 2956 | 6361 | 807 | 268 | 82 | 0.027 | [AC:L28677] [OR:*Mitochondrion Tetrahymena pyriformis*] [PN:ribosomal protein L14] |
| contig702 | 34649087_f3_20 | 2957 | 6362 | 795 | 264 | 85 | 0.95 | [AC:L22982] [OR:*Plasmodium chabaudi*] [PN:merozoite surface protein-1] [NT:precursor] |
| contig702 | 24648542_f2_11 | 2958 | 6363 | 1032 | 343 | 82 | 0.88 | [AC:D90901] [OR:*Synechocystis* sp.] [PN:hypothetical protein] [NT:ORF_ID] |
| contig702 | 4414702_c2_41 | 2959 | 6364 | 714 | 237 | 201 | 2.50E-16 | [AC:U61539] [OR:*Bacillus firmus*] [NT:OrfB] |
| contig702 | 6038427_f2_12 | 2960 | 6365 | 216 | 71 | 58 | 0.57 | [AC:U60315] [OR:*Molluscum contagiosum* virus subtype 1] |

TABLE 2-continued

| Contig | Orf | NT Seq Id | AA Seq ID | NT Orf Length | AA Orf Length | Score | Probability | Description |
|---|---|---|---|---|---|---|---|---|
| contig702 | 1203568_f3_22 | 2961 | 6366 | 1722 | 573 | 1715 | 9.00E-177 | [PN:MC143R] [GN:MC143R] [NT:putative extracellular virion glycoprotein; |
| contig702 | 191590_c2_40 | 2962 | 6367 | 699 | 232 | 682 | 2.60E-67 | [SP:P45861] [OR:*BACILLUS SUBTILIS*] [GN:YWIA] [DE:HYPOTHETICAL ABC TRANSPORTER ATP-BINDING PROTEIN IN ACDA 5′ REGION] |
| contig703 | 10820468_f3_23 | 2963 | 6368 | 297 | 98 | 86 | 0.0024 | [SP:P00953] [OR:BACILLUS STEAROTHERMOPHILUS] [GN:TRPS] [DE:(TRPRS)] |
| contig703 | 10827_c1_43 | 2964 | 6369 | 645 | 214 | 73 | 0.997 | [SP:Q07234] [OR:*BUCHNERA APHIDICOLA*] [GN:GAPA] [DE:GLYCERALDEHYDE 3-PHOSPHATE DEHYDROGENASE, (GAPDH)] |
| contig703 | 6814062_f3_24 | 2965 | 6370 | 195 | 64 | 55 | 0.76 | [AC:U58493] [OR:*Mitochondrion Flexamia canyonensis* canyonensis] [PN:NADH dehydrogenase 1] |
| contig703 | 23439217_c1_42 | 2966 | 6371 | 747 | 248 | 131 | 2.60E-07 | [SP:P01947] [OR:CAVIA PORCELLUS] [DE:HEMOGLOBIN ALPHA CHAIN] |
| contig703 | 20510950_c2_52 | 2967 | 6372 | 444 | 147 | 55 | 0.7 | [AC:X99400] [OR:*Streptococcus pneumoniae*] [PN:membrane protein] [AC:X85250] [OR:*Pyrococcus furiosus*] [PN:putative transmembrane protein] [GN:frxB] |
| contig703 | 3167950_c3_58 | 2968 | 6373 | 216 | 71 | 57 | 0.36 | [OR:*Borrelia burgdorferi*] [PN:hypothetical protein 8] |
| contig703 | 35367750_c2_51 | 2969 | 6374 | 4080 | 1359 | 84 | 0.86 | [OR:*Saccharomyces cerevisiae*] [PN:probable membrane protein YOR383c] |
| contig703 | 24495913_c3_56 | 2970 | 6375 | 423 | 140 | 147 | 4.80E-10 | [OR:*Escherichia coli*] [PN:phosphotransferase system enzyme II, mannose-specific, factor III] [GN:manX] |
| contig703 | 22750680_f1_4 | 2971 | 6376 | 192 | 63 | 52 | 0.78 | [SP:P75459] [OR:*MYCOPLASMA PNEUMONIAE*] [DE:HYPOTHETICAL PROTEIN MG233 HOMOLOG] |
| contig703 | 36383275_c2_50 | 2972 | 6377 | 876 | 291 | 295 | 2.70E-26 | [SP:P08188] [OR:*ESCHERICHIA COLI*] [GN:MANZ] [DE:(EII-M-MAN)] |
| contig703 | 34642186_c1_40 | 2973 | 6378 | 921 | 306 | 214 | 1.00E-17 | [AC:U65015] [OR:*Vibrio furnissii*] [PN:PTS permease for mannose subunit HPMan] [GN:manY] [NT:ManY; Pel; HDMan] |
| contig703 | 34189067_c3_54 | 2974 | 6379 | 501 | 166 | 303 | 3.80E-27 | [SP:P26380] [OR:*BACILLUS SUBTILIS*] [GN:LEVE] [DE:(EC 2.7.1.69) (P18)] |
| contig703 | 667177_c1_39 | 2975 | 6380 | 1851 | 616 | 930 | 1.40E-93 | [SP:P48982] [OR:*XANTHOMONAS MANIHOTIS*] [GN:BGA] [DE:BETA-GALACTOSIDASE PRECURSOR, (LACTASE) |
| contig703 | 4586700_c2_49 | 2976 | 6381 | 957 | 318 | 823 | 3.00E-82 | [SP:P23391] [OR:*LACTOCOCCUS LACTIS*] [GN:LACC] [DE:TAGATOSE-6-PHOSPHATE KINASE, (PHOSPHOTAGATOKINASE)] |
| contig703 | 14875066_c2_48 | 2977 | 6382 | 1038 | 345 | 1053 | 1.30E-106 | [SP:P11100] [OR:*STAPHYLOCOCCUS AUREUS*] [GN:LACD] [DE:TAGATOSE 1,6-DIPHOSPHATE ALDOLASE,] |
| contig703 | 1383550_c1_38 | 2978 | 6383 | 1188 | 395 | 714 | 1.10E-70 | [SP:P42907] [OR:*ESCHERICHIA COLI*] [GN:AGAS] [DE:AGAS PROTEIN] |
| contig703 | 7297306_c2_47 | 2979 | 6384 | 756 | 251 | 285 | 3.10E-25 | [SP:P13669] [OR:*ESCHERICHIA COLI*] [GN:FARR] [DE:FATTY ACYL RESPONSIVE REGULATOR (P30 PROTEIN)] |
| contig703 | 4898328_c1_37 | 2980 | 6385 | 912 | 303 | 623 | 4.70E-61 | [SP:P25148] [OR:*BACILLUS SUBTILIS*] [GN:GSPA] [DE:GENERAL STRESS PROTEIN A] |
| contig703 | 6917837_c3_53 | 2981 | 6386 | 864 | 287 | 582 | 1.00E-56 | [SP:P25148] [OR:*BACILLUS SUBTILIS*] [GN:GSPA] [DE:GENERAL STRESS PROTEIN A] |
| contig703 | 22460816_f3_36 | 2982 | 6387 | 495 | 165 | 719 | 3.20E-71 | [SP:P19775] [OR:*STAPHYLOCOCCUS AUREUS*] [GN:TNP] [DE:TRANSPOSASE FOR INSERTION SEQUENCE ELEMENT IS256 IN TRANSPOSON TN4001] |
| contig704 | 22839077_c2_41 | 2983 | 6388 | 477 | 159 | 136 | 5.90E-09 | [SP:P37783] [OR:*SHIGELLA FLEXNERI*] [GN:RFBG] [DE:DTDP- |

TABLE 2-continued

| Contig | Orf | NT Seq Id | AA Seq ID | NT Orf Length | AA Orf Length | Score | Probability | Description |
|---|---|---|---|---|---|---|---|---|
| contig704 | 4095963_c2_40 | 2984 | 6389 | 837 | 278 | 311 | 5.40E-28 | RHAMNOSYL TRANSFERASE RFBG,] [OR:*Haemophilus influenzae*] [PN:lic-1 operon protein (licD) homolog] |
| contig704 | 20156875_c2_39 | 2985 | 6390 | 240 | 79 | 50 | 0.99 | [SP:P47629] [OR:*MYCOPLASMA GENITALIUM*] [GN:MG389] [DE:HYPOTHETICAL PROTEIN MG389] |
| contig704 | 4120450_c1_33 | 2986 | 6391 | 1248 | 415 | 88 | 0.44 | [SP:P44067] [OR:*HAEMOPHILUS INFLUENZAE*] [GN:HI0874] [DE:HYPOTHETICAL PROTEIN HI0874] |
| contig704 | 26694212_c3_53 | 2987 | 6392 | 993 | 330 | 449 | 1.30E-42 | [AC:X85787] [OR:*Streptococcus pneumoniae*] [PN:ss-1,4-galactosyltransferase] [GN:cps14J] |
| contig704 | 5878135_f1_2 | 2988 | 6393 | 270 | 89 | 110 | 4.10E-06 | [OR:*Vigna unguiculata*] [PN:extensin-like protein] |
| contig704 | 13886590_c2_38 | 2989 | 6394 | 1071 | 356 | 333 | 2.50E-30 | [AC:D90911] [OR:*Synechocystis sp.*] [PN:dTDP-glucose 4-6-dehydratase] [GN:rfbB] [NT:ORF_ID] |
| contig704 | 26437926_c3_51 | 2990 | 6395 | 651 | 216 | 227 | 2.10E-18 | [OR:*Haemophilus influenzae*] [PN:hypothetical protein 1] |
| contig704 | 2734702_f3_19 | 2991 | 6396 | 606 | 201 | 546 | 6.80E-53 | [SP:P35880] [OR:*LACTOBACILLUS HELVETICUS*] [DE:TRANSPOSASE FOR INSERTION SEQUENCE ELEMENT IS1201] |
| contig704 | 12691037_f1_4 | 2992 | 6397 | 672 | 223 | 513 | 2.10E-49 | [OR:*Streptococcus thermophilus*] [PN:transposase] |
| contig704 | 788377_c1_32 | 2993 | 6398 | 378 | 125 | 291 | 7.10E-26 | [SP:Q02170] [OR:*BACILLUS SUBTILIS*] [GN:YSXA] [DE:DNA REPAIR PROTEIN RADC HOMOLOG (ORFB)] |
| contig704 | 12681625_c1_31 | 2994 | 6399 | 333 | 110 | 85 | 0.01 | [SP:P33541] [OR:*NEUROSPORA INTERMEDIA*] [DE:PROBABLE DNA-DIRECTED RNA POLYMERASE,] |
| contig704 | 26353427_c2_37 | 2995 | 6400 | 216 | 71 | 51 | 0.85 | [AC:AB001684] [OR:*Chloroplast Chlorella vulgaris C-27*] [GN:trnG] [NT:ORF46c] |
| contig704 | 20742090_c3_49 | 2996 | 6401 | 630 | 209 | 351 | 3.10E-32 | [SP:P20384] [OR:*STAPHYLOCOCCUS AUREUS*] [GN:BIN3] [DE:POTENTIAL DNA-INVERTASE BIN3 (TRANSPOSON TN552)] |
| contig704 | 24226577_c3_48 | 2997 | 6402 | 513 | 170 | 98 | 0.007 | [OR:*Schistosoma mansoni*] [PN:paramyosin] |
| contig704 | 4195137_c3_47 | 2998 | 6403 | 360 | 119 | 104 | 7.60E-06 | [SP:Q60310] [OR:*METHANOCOCCUS JANNASCHII*] [GN:MJECS11] [DE:HYPOTHETICAL PROTEIN MJECS11] |
| contig704 | 16448437_c1_30 | 2999 | 6404 | 705 | 234 | 1160 | 5.80E-118 | [AC:L40841] [OR:*Enterococcus faecium*] [PN:transposase] [NT:ISS1 homolog; putative] |
| contig704 | 13808206_c2_36 | 3000 | 6405 | 246 | 81 | 162 | 3.30E-12 | [AC:JC5008] [OR:*Lactococcus lactis*] [PN:hypothetical 6.5K protein (insertion sequence IS1297)] |
| contig704 | 33441890_f2_14 | 3001 | 6406 | 231 | 76 | 1160 | 5.80E-118 | [AC:L40841] [OR:*Enterococcus faecium*] [PN:transposase] [NT:ISS1 homolog; putative] |
| contig704 | 16448437_f1_5 | 3002 | 6407 | 705 | 234 | | | |
| contig704 | 13808206_f2_15 | 3003 | 6408 | 246 | 81 | 162 | 3.30E-12 | [AC:JC5008] [OR:*Lactococcus lactis*] [PN:hypothetical 6.5K protein (insertion sequence IS1297)] |
| contig704 | 34015677_f3_22 | 3004 | 6409 | 705 | 234 | 379 | 3.40E-35 | [AC:D78257] [OR:*Enterococcus faecalis*] [PN:ORF4] [GN:orf4] |
| contig704 | 14632840_f1_7 | 3005 | 6410 | 411 | 136 | 331 | 4.10E-30 | [AC:D78257] [OR:*Enterococcus faecalis*] [PN:ORF5] [GN:orf5] |
| contig704 | 16447186_f3_23 | 3006 | 6411 | 213 | 70 | 174 | 1.80E-13 | [AC:D78257] [OR:*Enterococcus faecalis*] [PN:ORF6] [GN:orf6] |
| contig704 | 24805312_f3_24 | 3007 | 6412 | 246 | 81 | 66 | 0.048 | [AC:U09422] [OR:*Enterococcus faecalis*] [NT:ORF9] |
| contig704 | 36141037_c1_27 | 3008 | 6413 | 204 | 67 | 50 | 0.992 | [SP:P14969] [OR:CASSAVA LATENT VIRUS] [GN:AC3] [DE:AL3 PROTEIN (15.9 KD PROTEIN)] |
| contig704 | 24417263_f3_25 | 3009 | 6414 | 276 | 91 | 65 | 0.11 | [SP:P17146] [OR:*HUMAN CYTOMEGALOVIRUS*] [GN:UL4] [DE:EARLY GLYCOPROTEIN GP48 PRECURSOR] |
| contig704 | 15117276_f1_8 | 3010 | 6415 | 618 | 205 | 255 | 3.80E-44 | [AC:U36837] [OR:*Lactococcus lactis*] [PN:ORFU] |
| contig704 | 13130311_f2_17 | 3011 | 6416 | 828 | 275 | 398 | 3.30E-37 | [AC:U36837] [OR:*Lactococcus lactis*] [PN:ORFU] |
| contig704 | 24806561_f2_18 | 3012 | 6417 | 222 | 73 | 69 | 0.17 | [AC:AF00314] [OR:*Caenorhabditis elegans*] [GN:F57C9.1] |

TABLE 2-continued

| Contig | Orf | NT Seq Id | AA Seq ID | NT Orf Length | AA Orf Length | Score | Probability | Description |
|---|---|---|---|---|---|---|---|---|
| contig705 | 33400927_c2_34 | 3013 | 6418 | 243 | 80 | 60 | 0.87 | [NT:similar to several sugar kinases; coded for by C.] [SP:P07775] [OR:*ACINETOBACTER CALCOACETICUS*] [GN:BENE] [DE:BENZOATE MEMBRANE TRANSPORT PROTEIN] |
| contig705 | 30274012_c3_45 | 3014 | 6419 | 543 | 180 | 87 | 0.31 | [SP:P36776] [OR:*HOMO SAPIENS*] [DE:MITOCHONDRIAL LON PROTEASE HOMOLOG PRECURSOR.] |
| contig705 | 15818_f3_16 | 3015 | 6420 | 969 | 322 | 336 | 1.20E-30 | [SP:P49305] [OR:*RHIZOBIUM MELILOTI*] [DE:HYPOTHETICAL 36.4 KD PROTEIN IN MOCC-MOCA INTERGENIC REGION (ORF334)] |
| contig705 | 35744063_c3_42 | 3016 | 6421 | 1356 | 451 | 1497 | 1.10E-153 | [SP:P39972] [OR:*BACILLUS SUBTILIS*] [GN:ASNS] [DE:(ASNRS)] |
| contig705 | 10598452_c2_33 | 3017 | 6422 | 1200 | 399 | 1120 | 1.00E-113 | [SP:P23034] [OR:*BACILLUS SUBTILIS*] [DE:ASPARTATE AMINOTRANSFERASE, (TRANSAMINASE A) (ASPAT)] |
| contig705 | 34038288_c3_40 | 3018 | 6423 | 540 | 179 | 100 | 0.00012 | [SP:P54396] [OR:*BACILLUS SUBTILIS*] [GN:YPMB] [DE:HYPOTHETICAL 17.9 KD PROTEIN IN DING-ASPB INTERGENIC REGION] |
| contig705 | 6539077_c3_39 | 3019 | 6424 | 2790 | 929 | 1047 | 5.50E-106 | [SP:P54394] [OR:*BACILLUS SUBTILIS*] [GN:DING] [DE:PROBABLE ATP-DEPENDENT HELICASE DING HOMOLOG] |
| contig705 | 24782813_c3_38 | 3020 | 6425 | 1398 | 465 | 112 | 0.01 | [SP:P24733] [OR:*AEQUIPECTEN IRRADIANS*] [DE:MYOSIN HEAVY CHAIN, STRIATED MUSCLE] |
| contig705 | 667202_c1_27 | 3021 | 6426 | 1500 | 499 | 1428 | 2.30E-146 | [AC:AE000192] [OR:*Escherichia coli*] [NT:o540; This 540 aa orf is 22 pct identical (10 gaps)] |
| contig705 | 21542337_c3_36 | 3022 | 6427 | 4371 | 1456 | 4375 | 0 | [SP:P13267] [OR:*BACILLUS SUBTILIS*] [GN:POLC] [DE:DNA POLYMERASE III, ALPHA CHAIN.] |
| contig705 | 4694063_c2_50 | 3023 | 6428 | 414 | 137 | 71 | 0.94 | [SP:Q01540] [OR:*BRASSICA NAPUS*] [GN:AGI] [DE:AGAMOUS PROTEIN] |
| contig706 | 2942202_c1_40 | 3024 | 6429 | 273 | 90 | 71 | 0.2 | [AC:Z34802] [OR:*Caenorhabditis elegans*] [PN:M88.6] [NT:contains 16 leucine-rich repeats; cDNA EST yk43h2.3] |
| contig706 | 3133325_c2_49 | 3025 | 6430 | 840 | 279 | 313 | 3.30E-28 | [AC:D43692] [OR:*Brevibacillus borstelensis*] [PN:rep protein] |
| contig706 | 33317042_c3_64 | 3026 | 6431 | 525 | 174 | 51 | 0.991 | [AC:D43699] [OR:*Cyprinus carpio*] [PN:light meromyosin] |
| contig706 | 4891943_c1_39 | 3027 | 6432 | 339 | 112 | 53 | 0.77 | [AC:X00615] [OR:*Escherichia coli*] [NT:gp37 (aa 770–832 of phage T4)] |
| contig706 | 2928415_f1_3 | 3028 | 6433 | 894 | 297 | 92 | 0.004 | [SP:P06966] [OR:*ESCHERICHIA COLI*] [GN:DICA] [DE:REPRESSOR PROTEIN OF DIVISION INHIBITION GENE DICB] |
| contig706 | 33370682_c2_47 | 3029 | 6434 | 384 | 127 | 87 | 0.0012 | [AC:U47023] [OR:*Methanococcus maripaludis*] [PN:unknown] [NT:ORF-3] |
| contig706 | 24426577_f3_22 | 3030 | 6435 | 231 | 76 | 85 | 0.00048 | [OR:*plasmid RK2*] [PN:trbA protein] [GN:trbA] |
| contig706 | 4788941_c2_46 | 3031 | 6436 | 1212 | 403 | 1059 | 2.90E-107 | [OR:*Streptococcus thermophilus*] [PN:transposase] |
| contig706 | 25589077_f2_11 | 3032 | 6437 | 2463 | 820 | 87 | 0.69 | [SP:P12053] [OR:*STAPHYLOCOCCUS AUREUS*] [GN:REPE] [DE:REPLICATION INITIATION PROTEIN] |
| contig706 | 22312502_f3_23 | 3033 | 6438 | 1071 | 356 | 102 | 0.092 | [SP:P09975] [OR:*MARCHANTIA POLYMORPHA*] [GN:YCF2] [DE:HYPOTHETICAL 259 KD PROTEIN (ORF 2136)] |
| contig706 | 1461502_f1_5 | 3034 | 6439 | 435 | 144 | 138 | 1.20E-09 | [AC:Z95584] [OR:*Mycobacterium tuberculosis*] [PN:MutT] [GN:mutT] [NT:MTC165.27, mutT, len] |
| contig706 | 30526562_f2_13 | 3035 | 6440 | 546 | 181 | 90 | 0.092 | [SP:P45860] [OR:*BACILLUS SUBTILIS*] [GN:YWIE] [DE:HYPOTHETICAL 58.2 PROTEIN IN NARL-ACDA INTERGENIC REGION] |

TABLE 2-continued

| Contig | Orf | NT Seq Id | AA Seq ID | NT Orf Length | AA Orf Length | Score | Probability | Description |
|---|---|---|---|---|---|---|---|---|
| contig706 | 34585751_f3_24 | 3036 | 6441 | 2223 | 740 | 231 | 7.60E-16 | [OR:*Saccharomyces cerevisiae*] [PN:hypothetical protein YDR332w] [AC:JT0289] [OR:*Plasmodium falciparum*] [PN:phosphoprotein PP300] |
| contig706 | 21520332_f2_14 | 3037 | 6442 | 297 | 98 | 60 | 0.19 | |
| contig706 | 22447281_c1_33 | 3038 | 6443 | 2337 | 778 | 551 | 2.30E-75 | [SP:P23914] [OR:*BACILLUS SUBTILIS*] [GN:LEVR] [DE:TRANSCRIPTIONAL REGULATORY PROTEIN LEVR] |
| contig706 | 650277_c3_58 | 3039 | 6444 | 237 | 78 | 72 | 0.011 | [SP:P10022] [OR:*BACILLUS THURINGIENSIS*] [DE:HYPOTHETICAL 13 KD PROTEIN (ORF 1)] |
| contig706 | 26042092_c3_57 | 3040 | 6445 | 867 | 288 | 347 | 8.30E-32 | [SP:P08188] [OR:*ESCHERICHIA COLI*] [GN:MANZ] [DE:(EII-M-MAN)] |
| contig706 | 3931557_c1_31 | 3041 | 6446 | 819 | 272 | 217 | 4.90E-18 | [SP:P42910] [OR:*ESCHERICHIA COLI*] [GN:AGAC] [DE:(N-ACETYLGALACTOSAMINE-PERMEASE IIC COMPONENT 1)] |
| contig706 | 23476713_c3_54 | 3042 | 6447 | 504 | 167 | 199 | 4.00E-16 | [SP:P37081] [OR:*KLEBSIELLA PNEUMONIAE*] [GN:SORB] [DE:(EC 2.7.1.69) (EIII-B-SOR)] |
| contig706 | 34062932_c3_53 | 3043 | 6448 | 516 | 171 | 66 | 0.1 | [AC:U02109] [OR:*Mycoplasma genitalium*] [NT:homology to triosephosphate isomerase L01654] |
| contig706 | 32042318_f1_8 | 3044 | 6449 | 948 | 315 | 1183 | 2.10E-120 | [SP:P36879] [OR:*ESCHERICHIA COLI*] [GN:YADG] [DE:INTERGENIC REGION] |
| contig706 | 34475067_f2_21 | 3045 | 6450 | 822 | 274 | 825 | 1.80E-82 | [AC:AE000122] [OR:*Escherichia coli*] [GN:yadH] [NT:o256; 100 pct identical to YADH_ECOLI SW] |
| contig706 | 26256507_c2_69 | 3046 | 6451 | 2130 | 710 | 404 | 1.90E-66 | [AC:Z83318] [OR:*Caenorhabditis elegans*] [PN:F55B11.e] [NT:protein predicted using Genefinder; preliminary] |
| contig706 | 30366567_c2_68 | 3047 | 6452 | 1038 | 345 | 203 | 1.90E-22 | [AC:AE000371] [OR:*Escherichia coli*] [NT:f541; This 541 aa orf is 28 pct identical (7 gaps)] |
| contig706 | 32235937_c3_81 | 3048 | 6453 | 387 | 128 | 151 | 7.30E-11 | [AC:M94855] [OR:*Haemophilus influenzae*] [NT:ORF 7] |
| contig706 | 36148562_c3_80 | 3049 | 6454 | 1341 | 446 | 582 | 1.00E-56 | [SP:P42086] [OR:*BACILLUS SUBTILIS*] [GN:PBUX] [DE:XANTHINE PERMEASE] |
| contig706 | 26206567_c3_79 | 3050 | 6455 | 405 | 134 | 375 | 8.90E-35 | [SP:Q10121] [OR:*CAENORHABDITIS ELEGANS*] [GN:C23G10.2] [DE:HYPOTHETICAL 19.6 KD PROTEIN C23G10.2 IN CHROMOSOME III PRECURSOR] |
| contig707 | 4820393_c1_54 | 3051 | 6456 | 954 | 317 | 822 | 3.80E-82 | [SP:Q46807] [OR:*ESCHERICHIA COLI*] [GN:YQEA] [DE:CARBAMATE KINASE-LIKE PROTEIN 1] |
| contig707 | 1252250_c1_53 | 3052 | 6457 | 1287 | 428 | 1292 | 6.00E-132 | [AC:AE000370] [OR:*Escherichia coli*] [NT:o363; This 363 aa orf is 27 pct identical (43 gaps)] |
| contig707 | 35714457_c2_65 | 3053 | 6458 | 549 | 182 | 495 | 1.70E-47 | [AC:AE000370] [OR:*Escherichia coli*] [NT:o403; This 403 aa orf is 30 pct identical (44 gaps)] |
| contig707 | 3907812_c1_52 | 3054 | 6459 | 798 | 265 | 794 | 3.60E-79 | [AC:AE000370] [OR:*Escherichia coli*] [NT:o403; This 403 aa orf is 30 pct identical (44 gaps)] |
| contig707 | 24223417_c2_63 | 3055 | 6460 | 1227 | 408 | 907 | 3.80E-91 | [AC:AE000370] [OR:*Escherichia coli*] [NT:o398; This 398 aa orf is 27 pct identical (19 gaps)] |
| contig707 | 1985077_c3_76 | 3056 | 6461 | 1374 | 457 | 941 | 9.40E-95 | [AC:JC2310] [OR:*Bacillus stearothermophilus*] [PN:dihydropyrimidinase,] |
| contig707 | 6929677_c1_50 | 3057 | 6462 | 3024 | 1007 | 2013 | 2.40E-208 | [AC:AE000371] [OR:*Escherichia coli*] NT:o1032; This 1032 aa orf is 35 pct identical [36] |
| contig707 | 4980082_c1_49 | 3058 | 6463 | 1371 | 456 | 654 | 2.40E-64 | [AC:AE000371] [OR:*Escherichia coli*] [NT:o464; This 464 aa orf is 25 pct identical (12 gaps)] |
| contig707 | 397261_f1_11 | 3059 | 6464 | 234 | 77 | 56 | 0.43 | (AC:Z81119] [OR:*Caenorhabditis elegans*] [PN:T10H4.d] [NT:protein predicted using Genefinder; preliminary] |
| contig707 | 5868937_f2_29 | 3060 | 6465 | 678 | 225 | 185 | 1.20E-14 | [SP:P44761] [OR:*HAEMOPHILUS INFLUENZAE*] [GN:HI0575] [DE:HYPOTHETICAL PROTEIN HI0575] |

TABLE 2-continued

| Contig | Orf | NT Seq Id | AA Seq ID | NT Orf Length | AA Orf Length | Score | Probability | Description |
|---|---|---|---|---|---|---|---|---|
| contig707 | 6663937_c3_74 | 3061 | 6466 | 534 | 177 | 128 | 1.30E-08 | [AC:AB001488] [OR:Bacillus subtilis] [GN:yddQ] [NT:FUNCTION UNKNOWN.] |
| contig707 | 5257838_f1_12 | 3062 | 6467 | 2307 | 768 | 321 | 5.20E-39 | [AC:D90892] [OR:Escherichia coli] [PN:glutamate--cysteine ligase (EC 6.3.2.2)] [GN:gshA] [NT:similar to [PIR Accession Number A24136] |
| contig707 | 25556337_f1_13 | 3063 | 6468 | 186 | 61 | 62 | 0.13 | [OR:phage phi-C31] [PN:hypothetical protein 7] |
| contig707 | 25588577_c1_47 | 3064 | 6469 | 453 | 150 | 83 | 0.31 | [SP:P17967] [OR:Saccharomyces cerevisiae] [PN:precursor TRG1 protein] [GN:PDI1] |
| contig707 | 277062_f2_31 | 3065 | 6470 | 297 | 99 | 155 | 5.80E-11 | [AC:D50453] [OR:Bacillus subtilis] [PN:homologue of ferric anguibactin transport system] [GN:yclN] |
| contig708 | 4876563_f3_27 | 3066 | 6471 | 612 | 203 | 89 | 0.11 | [AC:D31764] [OR:Homo sapiens] [GN:KIAA0064] |
| contig708 | 34453_f3_28 | 3067 | 6472 | 207 | 68 | 72 | 0.039 | [AC:D12540] [OR:Pisum sativum] [PN:GTP-binding protein] |
| contig708 | 472176_c1_57 | 3068 | 6473 | 762 | 253 | 85 | 0.22 | [AC:D90907] [OR:Synechocystis sp.] [PN:hypothetical protein] [GN:glgP] [NT:ORF_ID] |
| contig708 | 961077_f2_16 | 3069 | 6474 | 183 | 60 | 60 | 0.8 | [SP:Q57819] [OR:METHANOCOCCUS JANNASCHII] [GN:MJ0374] [DE:HYPOTHETICAL PROTEIN MJ0374] |
| contig708 | 783131_f1_2 | 3070 | 6475 | 300 | 99 | | | |
| contig708 | 16604678_f1_3 | 3071 | 6476 | 585 | 194 | | | |
| contig708 | 34027337_f3_30 | 3072 | 6477 | 426 | 141 | 51 | 0.92 | [OR:Candida albicans] [PN:IgE-binding antigen, 37K] |
| contig708 | 20181552_f2_18 | 3073 | 6478 | 378 | 125 | 82 | 0.0038 | [AC:D90915] [OR:Synechocystis sp.] [PN:hypothetical protein] [NT:ORF_ID] |
| contig708 | 14181562_f1_4 | 3074 | 6479 | 456 | 151 | 69 | 0.96 | [AC:X76231] [OR:Drosophila melanogaster] [PN:fc proteins] [GN:dec-1] [NT:Description] |
| contig708 | 25431537_f3_32 | 3075 | 6480 | 1731 | 576 | 328 | 2.60E-28 | [AC:AF000214] [OR:Escherichia coli] NT:o455; This 455 aa orf is 36 pct identical (4 gaps)] |
| contig708 | 25677317_f3_33 | 3076 | 6481 | 1242 | 413 | 82 | 0.92 | [OR:Homo sapiens] [PN:gamma enolase] [GN:ENO2] |
| contig708 | 7089217_f1_6 | 3077 | 6482 | 588 | 195 | 116 | 3.40E-06 | [OR:Mycobacterium tuberculosis] [PN:unknown] [GN:MTCY336.27] [NT:MTCY336.27. Len] |
| contig708 | 3914213_f1_7 | 3078 | 6483 | 1377 | 458 | 58 | 0.96 | [AC:M72718] [OR:Bacillus subtilis] [NT:ORF 11] |
| contig708 | 6047328_f2_19 | 3079 | 6484 | 291 | 96 | 74 | 0.22 | [SP:P75271] [OR:MYCOPLASMA PNEUMONIAE] [GN:RPOC] [DE:BETA' CHAIN) (RNA POLYMERASE BETA' SUBUNIT)] |
| contig708 | 12926525_f3_34 | 3080 | 6485 | 333 | 110 | 72 | 0.48 | [SP:Q47189] [OR:ERWINIA CAROTOVORA] [GN:EXPR] [DE:EXPR REGULATORY PROTEIN] |
| contig708 | 3933128_f1_8 | 3081 | 6486 | 348 | 115 | 51 | 0.93 | [AC:Z75525] [OR:Caenorhabditis elegans] [PN:C03D6.6] |
| contig708 | 24616018_f2_20 | 3082 | 6487 | 375 | 124 | 79 | 0.31 | [AC:D88532] [OR:Homo sapiens] [PN:p55pik] |
| contig708 | 25548437_f1_9 | 3083 | 6488 | 684 | 227 | 56 | 0.93 | [AC:J02582] [OR:Rattus norvegicus] [NT:ORF1] |
| contig708 | 24353427_f3_35 | 3084 | 6489 | 459 | 152 | | | |
| contig708 | 24406442_f2_21 | 3085 | 6490 | 261 | 86 | 59 | 0.8 | [AC:U32936] [OR:Synechocystis PCC6803] [NT:orf277] |
| contig708 | 16292813_f2_22 | 3086 | 6491 | 2319 | 772 | 109 | 0.013 | [AC:U53445] [OR:Homo sapiens] [PN:DOC1] [GN:Doc1] [NT:myosin heavy chain homolog] |
| contig708 | 30745876_f1_10 | 3087 | 6492 | 732 | 243 | 127 | 7.20E-05 | [SP:P15132] [OR:BACTERIOPHAGE PHI-29] [GN:13] [DE:MORPHOGENESIS PROTEIN 1 (LATE PROTEIN GP13)] |
| contig708 | 833338_f3_37 | 3088 | 6493 | 2808 | 935 | | | |
| contig708 | 26776691_f3_38 | 3089 | 6494 | 927 | 308 | 81 | 0.7 | [AC:M13518] [OR:Rattus norvegicus] [NT:proteoglycan] |
| contig708 | 25447182_f1_11 | 3090 | 6495 | 321 | 106 | 58 | 0.29 | [SP:P45360] [OR:CLOSTRIDIUM ACETOBUTYLICUM] [DE:HYPOTHETICAL PROTEIN IN THL 5' REGION (FRAGMENT)] |
| contig708 | 203952_f2_24 | 3091 | 6496 | 318 | 105 | 68 | 0.64 | [SP:P38016] [OR:CHLAMYDIA TRACHOMATIS] [GN:RPSA] [DE:30S RIBOSOMAL PROTEIN S1 (70 KD ANTIGEN) |

TABLE 2-continued

| Contig | Orf | NT Seq Id | AA Seq ID | NT Orf Length | AA Orf Length | Score | Probability | Description |
|---|---|---|---|---|---|---|---|---|
| contig708 | 16834792_f1_12 | 3092 | 6497 | 558 | 185 | 87 | 0.43 | (FRAGMENT)] [AC:U83447] [OR:*Rickettsia montana*] [PN:ompA] [GN:ompA] |
| contig708 | 26617927_f3_39 | 3093 | 6498 | 393 | 130 | 67 | 0.038 | [SP:Q09005] [OR:*XENOPUS LAEVIS*] [DE:STATHMIN (CLONE XO20) (FRAGMENT)] |
| contig708 | 26455842_f3_40 | 3094 | 6499 | 252 | 83 | 66 | 0.27 | [SP:P39800] [OR:*BACILLUS SUBTILIS*] [GN:XLYA] [DE:(CELL WALL HYDROLASE) (AUTOLYSIN)] |
| contig708 | 29461467_f2_25 | 3095 | 6500 | 321 | 106 | 263 | 1.40E-22 | [SP:P19385] [OR:BACTERIOPHAGE CP-7] [GN:CPL7] [DE:LYSOZYME, (ENDOLYSIN) (MURAMIDASE) (CP-7 LYSIN)] |
| contig708 | 22539000_f1_13 | 3096 | 6501 | 1326 | 441 | | | |
| contig708 | 22460816_f3_41 | 3097 | 6502 | 465 | 154 | 720 | 2.50E-71 | [SP:P19775] [OR:*STAPHYLOCOCCUS AUREUS*] [GN:TNP] [DE:TRANSPOSASE FOR INSERTION SEQUENCE ELEMENT IS256 IN TRANSPOSON TN4001] |
| contig708 | 16839056_f1_15 | 3098 | 6503 | 606 | 201 | 947 | 2.20E-95 | [SP:P19775] [OR:*STAPHYLOCOCCUS AUREUS*] [GN:TNP] [DE:TRANSPOSASE FOR INSERTION SEQUENCE ELEMENT IS256 IN TRANSPOSON TN4001] |
| contig709 | 1222561_f3_32 | 3099 | 6504 | 1581 | 526 | 973 | 3.80E-98 | [AC:U09422] [OR:*Enterococcus faecalis*] [NT:ORF15] |
| contig709 | 197187_f2_13 | 3100 | 6505 | 1008 | 335 | 1150 | 6.70–117 | [AC:U09422] [OR:*Enterococcus faecalis*] [NT:ORF14] |
| contig709 | 36210963_f2_14 | 3101 | 6506 | 930 | 309 | 566 | 5.10E-55 | [AC:U09422] [OR:*Enterococcus faecalis*] [NT:ORF13] |
| contig709 | 34195312_c1_68 | 3102 | 6507 | 1257 | 418 | 1041 | 2.40E-105 | [SP:P35881] [OR:*LACTOCOCCUS LACTIS*] [DE:TRANSPOSASE FOR INSERTION SEQUENCE ELEMENT IS905] |
| contig709 | 21885313_f1_2 | 3103 | 6508 | 240 | 79 | 55 | 0.68 | [OR:Drosophila] [PN:fork head domain 5, FD5=putative transcription factor] |
| contig709 | 24103385_c3_111 | 3104 | 6509 | 291 | 96 | 77 | 0.027 | [SP:P15104] [OR:*Homo sapiens*] [NT:glutamine synthetase (AA 1–373)] |
| contig709 | 33447337_f2_15 | 3105 | 6510 | 183 | 60 | | | |
| contig709 | 36638958_f3_36 | 3106 | 6511 | 417 | 138 | 73 | 0.24 | [SP:P39910] [OR:*BACILLUS SUBTILIS*] [GN:SLP] [DE:PAL-RELATED LIPOPROTEIN PRECURSOR] |
| contig709 | 4460937_f2_16 | 3107 | 6512 | 678 | 225 | 121 | 1.40E-06 | [SP:P52237] [OR:*PSEUDOMONAS FLUORESCENS*] [GN:TIPB] [DE:BIOGENESIS PROTEIN TIPB] |
| contig709 | 30125063_f3_37 | 3108 | 6513 | 306 | 101 | 67 | 0.73 | [OR:*Methanococcus jannaschii*] [PN:heterodisulfide reductase, subunit C] |
| contig709 | 20707510_f3_38 | 3109 | 6514 | 456 | 151 | 193 | 1.70E-15 | [OR:*Methanococcus jannaschii*] [PN:hypothetical protein MJ0749] |
| contig709 | 24225925_c3_107 | 3110 | 6515 | 240 | 79 | 59 | 0.77 | [AC:Z75953] [OR:*Caenorhabditis elegans*] [PN:F57F5.3] |
| contig709 | 6699067_f3_39 | 3111 | 6516 | 1296 | 431 | 142 | 5.30E-07 | [AC:D50453] [OR:*Bacillus subtilis*] [PN:homologue of hypothetical protein in a rapamycin] [GN:ycII] |
| contig709 | 4726588_f3_40 | 3112 | 6517 | 666 | 221 | 379 | 3.40E-35 | [AC:D50453] [OR:*Bacillus subtilis*] [PN:homologue of hypothetical protein in a rapamycin] [GN:ycII] |
| contig709 | 24259677_f2_18 | 3113 | 6518 | 1218 | 405 | 236 | 8.80E-18 | [AC:D50453] [OR:*Bacillus subtilis*] [PN:homologue of hypothetical protein in a rapamycin] [GN:ycII] |
| contig709 | 22947328_f3_41 | 3114 | 6519 | 183 | 60 | | | |
| contig709 | 15703562_c3_102 | 3115 | 6520 | 225 | 74 | 64 | 0.5 | [SP:P35237] [OR:*HOMO SAPIENS*] [GN:P16] [DE:(PROTEASE INHIBITOR 6)] |
| contig709 | 35585752_c1_63 | 3116 | 6521 | 789 | 262 | 820 | 6.30E-82 | [AC:L34675] [OR:Insertion sequence IS1251] [PN:transposase] [NT:putative] |
| contig709 | 20352187_c2_84 | 3117 | 6522 | 423 | 140 | 580 | 1.70E-56 | [AC:L34675] [OR:Insertion sequence IS1251] [PN:transposase] [NT:putative] |
| contig709 | 20370453_f1_4 | 3118 | 6523 | 666 | 221 | 353 | 1.90E-32 | [SP:Q47744] [OR:*ENTEROCOCCUS FAECALIS*] [GN:VANRB] [DE:REGULATORY PROTEIN VANRB] |
| contig709 | 24821002_f3_43 | 3119 | 6524 | 576 | 191 | 81 | 0.88 | [AC:U23178] [OR:*Caenorhabditis elegans*] [GN:F08B1.2] [NT:similar |

TABLE 2-continued

| Contig | Orf | NT Seq Id | AA Seq ID | NT Orf Length | AA Orf Length | Score | Probability | Description |
|---|---|---|---|---|---|---|---|---|
| contig709 | 11077_f2_19 | 3120 | 6525 | 765 | 254 | 210 | 1.30E-16 | to atrial natriuretic peptides (guanylate) [SP:Q47745] [OR:*ENTEROCOCCUS FAECALIS*] [GN:VANSB] [DE:PROTEIN VANSB) (VANCOMYCIN HISTIDINE PROTEIN KINASE)] |
| contig709 | 4148450_c3_100 | 3121 | 6526 | 1023 | 340 | 837 | 9.90E-84 | [SP:P35881] [OR:*LACTOCOCCUS LACTIS*] [DE:TRANSPOSASE FOR INSERTION SEQUENCE ELEMENT IS905] |
| contig709 | 395130_f1_5 | 3122 | 6527 | 873 | 290 | 136 | 7.10E-07 | [AC:Z95557] [OR:*Mycobacterium tuberculosis*] [PN:unknown] [GN:MTCY07H7B.19] [NT:MTCY07H7B.19, unknown, len] |
| contig709 | 13867202_f3_44 | 3123 | 6528 | 828 | 275 | 622 | 6.00E-61 | [SP:P52996] [OR:*BACILLUS SUBTILIS*] [GN:PANB] [DE:(KETO)PANTOATE HYDROXYMETHYLTRANSFERASE)] |
| contig709 | 24484390_f2_21 | 3124 | 6529 | 885 | 294 | 608 | 1.80E-59 | [SP:P52998] [OR:*BACILLUS SUBTILIS*] [GN:PANC] [DE:(PANTOATE ACTIVATING ENZYME)] |
| contig709 | 4719843_f2_22 | 3125 | 6530 | 408 | 135 | 345 | 1.40E-31 | [SP:P52999] [OR:*BACILLUS SUBTILIS*] [GN:PAND] [DE:DECARBOXYLASE)] |
| contig709 | 24860913_c1_57 | 3126 | 6531 | 222 | 73 | 163 | 1.30E-11 | [AC:U23813] [OR:*Lactococcus lactis*] [PN:transposase] |
| contig709 | 16593760_c2_80 | 3127 | 6532 | 918 | 305 | 355 | 1.20E-32 | [AC:D10543] [OR:*Bacillus stearothermophilus*] [PN:ORF1] [GN:IS-T1] [NT:Author-given protein sequence is in conflict with] |
| contig709 | 24489176_c3_97 | 3128 | 6533 | 348 | 115 | 148 | 1.00E-10 | [AC:U03772] [OR:*Acinetobacter calcoaceticus*] [PN:ORF1 gene product] [NT:ORF1] |
| contig709 | 2343876_f3_46 | 3129 | 6534 | 309 | 102 | 77 | 0.0034 | [AC:D78257] [OR:*Enterococcus faecalis*] [PN:ORF7] [GN:orf7] |
| contig709 | 2381306_f3_47 | 3130 | 6535 | 1365 | 454 | 661 | 4.40E-65 | [AC:U44828] [OR:*Burkholderia cepacia*] [PN:transposase] |
| contig709 | 9791677_f2_24 | 3131 | 6536 | 1302 | 433 | 360 | 4.00E-46 | [SP:P39584] [OR:*BACILLUS SUBTILIS*] [GN:YWBA] [DE:HYPOTHETICAL 47.6 KD PROTEIN EPR-GALK INTERGENIC REGION] |
| contig709 | 33984711_f3_48 | 3132 | 6537 | 183 | 60 | 113 | 4.60E-06 | [AC:D90816] [OR:*Escherichia coli*] [PN:PTS system, cellobiose-specific IIC component] [GN:celB] [NT:ORF_ID] |
| contig709 | 26750260_f2_25 | 3133 | 6538 | 1857 | 618 | 930 | 1.40E-93 | [SP:P23780] [OR:*MUS MUSCULUS*] [GN:GLB1] [DE:GALACTOSIDASE)] |
| contig709 | 817842_f2_27 | 3134 | 6539 | 417 | 138 | 103 | 6.00E-06 | [AC:U09422] [OR:*Enterococcus faecalis*] [NT:ORF7] |
| contig709 | 24422182_f1_8 | 3135 | 6540 | 270 | 89 | 131 | 6.40E-09 | [AC:U09422] [OR:*Enterococcus faecalis*] [NT:ORF8] |
| contig709 | 6019387_f1_9 | 3136 | 6541 | 381 | 126 | 52 | 0.88 | [SP:P14570] [OR:*LOCUSTA MIGRATORIA*] [GN:ATP8] [DE:ATP SYNTHASE PROTEIN 8, (A6L)] |
| contig709 | 4101702_f1_10 | 3137 | 6542 | 1179 | 392 | 212 | 2.40E-15 | [SP:P20709] [OR:BACTERIOPHAGE L54A] [GN:INT] [DE:INTEGRASE] |
| contig709 | 4727262_f3_49 | 3138 | 6543 | 183 | 60 | 51 | 0.9992 | [OR:*Homo sapiens*] [PN:ALL-1 protein] [GN:ALL-1] |
| contig709 | 25469025_f2_29 | 3139 | 6544 | 258 | 85 | 71 | 0.16 | [AC:AB003186] [OR:*Comamonas acidovorans*] [PN:polyhydroxybutyrate depolymerase] [GN:phaZCac] |
| contig709 | 4742963_f3_50 | 3140 | 6545 | 429 | 142 | 86 | 0.083 | [AC:U66004] [OR:*Sulfolobus shibatae*] [PN:tRNA nucleotidyltransferase] [GN:cca] |
| contig709 | 4721883_c3_90 | 3141 | 6546 | 447 | 148 | 97 | 0.002 | [AC:Y14082] [OR:*Bacillus subtilis*] [PN:hypothetical protein] [GN:yheN] [NT:Similarity to hypothetical protein Yfu2 from] |
| contig709 | 34651556_c2_74 | 3142 | 6547 | 411 | 136 | 108 | 6.20E-06 | [SP:Q04729] [OR:*BACILLUS STEAROTHERMOPHILUS*] [DE:(ORF2)] |
| contig709 | 5995938_f1_11 | 3143 | 6548 | 594 | 197 | 418 | 2.50E-39 | [SP:Q04731] [OR:*LACTOCOCCUS LACTIS*] [DE:HYPOTHETICAL PROTEIN IN PEPC 5' REGION (ORF 2) (FRAGMENT)] |
| contig709 | 33785837_f2_31 | 3144 | 6549 | 477 | 159 | 67 | 0.99 | [AC:Z83864] [OR:*Mycobacterium tuberculosis*] [PN:unknown] [GN:MTCY01A6.28c] [NT:MTCY01A6.28c, 181 aa, similar to ferritin eg] |

TABLE 2-continued

| Contig | Orf | NT Seq Id | AA Seq ID | NT Orf Length | AA Orf Length | Score | Probability | Description |
|---|---|---|---|---|---|---|---|---|
| contig71 | 25507180_f2_2 | 3145 | 6550 | 441 | 146 | 92 | 0.0021 | [SP:P40414] [OR:SACCHAROMYCES CEREVISIAE] [GN:TPM2] [DE:TROPOMYOSIN 2] |
| contig71 | 23679176_f1_1 | 3146 | 6551 | 225 | 75 | 56 | 0.85 | [AC:JC1065] [OR:beet necrotic yellow vein mosaic virus] [PN:coat protein] |
| contig71 | 31535081_c1_16 | 3147 | 6552 | 183 | 60 | 58 | 0.89 | [OR:Drosophila melanogaster] [PN:hypothetical protein (pcx region) [GN:pcx] |
| contig710 | 10346942_c3_21 | 3148 | 6553 | 249 | 82 | 63 | 0.18 | [AC:U28078] [OR:Paracoccus denitrificans] [PN:nitric oxide reductase, small subunit] [GN:norC] [NT:contains one heme c binding site] |
| contig710 | 627181_f3_14 | 3149 | 6554 | 204 | 67 | | | |
| contig710 | 26678587_c3_20 | 3150 | 6555 | 372 | 123 | 145 | 2.10E-10 | [AC:Z47547] [OR:Mitochondrion Chondrus crispus] [GN:putative orf79.1] [NT:unique orf] |
| contig710 | 23723842_c3_19 | 3151 | 6556 | 252 | 83 | 64 | 0.72 | [AC:Z49912] [OR:Caenorhabditis elegans] [PN:T24F1.3] [NT:similar to DAG binding domain; cDNA EST yk31g9.3] |
| contig710 | 6464751_c1_35 | 3152 | 6557 | 1317 | 439 | 1540 | 3.20E-158 | [SP:P37710] [OR:ENTEROCOCCUS FAECALIS] [DE:AUTOLYSIN, (N-ACETYLMURAMOYL-L-ALANINE AMIDASE)] |
| contig711 | 22460816_c1_34 | 3153 | 6558 | 1203 | 400 | 2003 | 2.70E-207 | [SP:P19775] [OR:STAPHYLOCOCCUS AUREUS] [GN:TNP] [DE:TRANSPOSASE FOR INSERTION SEQUENCE ELEMENT IS256 IN TRANSPOSON TN4001] |
| contig711 | 26376277_c1_33 | 3154 | 6559 | 717 | 238 | 571 | 1.50E-55 | [AC:L35176] [OR:Lactococcus lactis] [PN:iso-ISS1 transposase] [NT:Tnase] |
| contig711 | 20707312_f2_10 | 3155 | 6560 | 249 | 82 | 52 | 0.9999 | [SP:P43869] [OR:HAEMOPHILUS INFLUENZAE] [GN:PROC] [DE:PYRROLINE-5-CARBOXYLATE REDUCTASE, (P5CR) (P5C REDUCTASE)] |
| contig711 | 23594677_f2_11 | 3156 | 6561 | 192 | 63 | 51 | 0.85 | [AC:U42580] [OR:Paramecium bursaria Chlorella virus 1] [GN:a221L] |
| contig711 | 24487812_c1_32 | 3157 | 6562 | 501 | 166 | 242 | 1.10E-20 | [AC:Z83337] [OR:Bacillus subtilis] [GN:ywpH] [NT:similar to single strand binding protein] |
| contig711 | 24319687_c3_42 | 3158 | 6563 | 1326 | 441 | 80 | 0.6 | [AC:D90911] [OR:Synechocystis sp.] [PN:transposase] [NT:ORF_ID] |
| contig711 | 3957818_c2_37 | 3159 | 6564 | 765 | 254 | 89 | 0.14 | [AC:X96801] [OR:Yersinia enterocolitica] [PN:V antigen] |
| contig711 | 34407587_c3_41 | 3160 | 6565 | 273 | 90 | 59 | 0.24 | [AC:Y09636] [OR:Zea mays] [PN:40S ribosomal subunit protein S21] |
| contig711 | 21532266_c3_40 | 3161 | 6566 | 462 | 153 | 56 | 0.93 | [OR:Apis mellifera] [PN:homeotic protein H17] |
| contig711 | 25470661_f1_5 | 3162 | 6567 | 195 | 64 | 61 | 0.9 | [SP:Q09653] [OR:CAENORHABDITIS ELEGANS] [GN:ZK1320.4] [DE:PUTATIVE CYTOCHROME P450 ZK1320.4 IN CHROMOSOME II.] |
| contig711 | 34430450_c3_39 | 3163 | 6568 | 504 | 167 | 75 | 0.093 | [OR:Methanococcus jannaschii] [PN:hypothetical protein MJ0925] [AC:D64005] [OR:Synechocystis sp.] [PN:phosphoenolpyruvate synthase] [GN:ppsA] [NT:ORF_ID] |
| contig711 | 11915936_c1_27 | 3164 | 6569 | 789 | 262 | 70 | 0.33 | |
| contig711 | 24422127_c1_26 | 3165 | 6570 | 351 | 116 | | | |
| contig711 | 6270288_c3_36 | 3166 | 6571 | 2223 | 740 | 118 | 2.70E-08 | [OR:Leuconostoc oenos] [PN:hypothetical protein 2] |
| contig711 | 12503879_c1_24 | 3167 | 6572 | 909 | 302 | 154 | 1.30E-08 | [AC:L04159] [OR:Plasmodium falciparum] |
| contig712 | 7228468_c3_59 | 3168 | 6573 | 252 | 84 | 62 | 0.59 | [OR:Methanococcus jannaschii] [PN:hypothetical protein MJ1290] |
| contig712 | 20093062_c2_51 | 3169 | 6574 | 471 | 156 | 499 | 6.50E-48 | [AC:X96977] [OR:Enterococcus faecalis] [GN:orf16] |
| contig712 | 23682952_c3_58 | 3170 | 6575 | 276 | 91 | 281 | 8.20E-25 | [AC:X96977] [OR:Enterococcus faecalis] [GN:orf15] |
| contig712 | 23712837_c3_50 | 3171 | 6576 | 1038 | 345 | 1263 | 7.10E-129 | [AC:X96977] [OR:Enterococcus faecalis] [GN:orf14] |
| contig712 | 22693817_c1_41 | 3172 | 6577 | 321 | 106 | 470 | 7.70E-45 | [AC:X96977] [OR:Enterococcus faecalis] [GN:orf13] |
| contig712 | 4886578_c2_49 | 3173 | 6578 | 417 | 138 | 563 | 1.10E-54 | [AC:X96977] [OR:Enterococcus faecalis] [GN:orf12] |
| contig712 | 34063750_c1_39 | 3174 | 6579 | 645 | 214 | 362 | 2.10E-33 | [AC:X96977] [OR:Enterococcus faecalis] [GN:orf11] |
| contig712 | 4408338_c2_48 | 3175 | 6580 | 1281 | 426 | 1113 | 5.60E-113 | [AC:X96977] [OR:Enterococcus faecalis] [GN:orf9] |

TABLE 2-continued

| Contig | Orf | NT Seq Id | AA Seq ID | NT Orf Length | AA Orf Length | Score | Probability | Description |
|---|---|---|---|---|---|---|---|---|
| contig712 | 270308_c3_57 | 3176 | 6581 | 195 | 64 | 221 | 1.90E-18 | [AC:X96977] [OR:*Enterococcus faecalis*] [GN:orf9] |
| contig712 | 24414678_f2_13 | 3177 | 6582 | 240 | 79 | 66 | 0.79 | [AC:U56100] [OR:*Emericella nidulans*] [PN:DNA binding regulatory protein AmdX] [GN:amdX] [NT:Description] |
| contig712 | 31848465_c1_38 | 3178 | 6583 | 921 | 306 | 692 | 2.30E-68 | [AC:X96977] [OR:*Enterococcus faecalis*] [GN:orf8] [NT:cell wall anchoring signal] |
| contig712 | 23678287_c3_56 | 3179 | 6584 | 900 | 299 | 1262 | 9.10E-129 | [AC:X96977] [OR:*Enterococcus faecalis*] [GN:orf7] |
| contig712 | 22384540_c2_47 | 3180 | 6585 | 291 | 96 | 360 | 3.50E-33 | [AC:X96977] [OR:*Enterococcus faecalis*] [GN:orf6] |
| contig712 | 15057803_c1_37 | 3181 | 6586 | 408 | 135 | 650 | 6.50E-64 | [AC:X96977] [OR:*Enterococcus faecalis*] [GN:orf5] |
| contig712 | 26367692_c1_36 | 3182 | 6587 | 414 | 137 | 542 | 1.80E-52 | [OR:*Enterococcus faecalis*] [PN:hypothetical protein 3] |
| contig712 | 21681535_c3_54 | 3183 | 6588 | 3927 | 1308 | 5528 | 0 | [OR:*Enterococcus faecalis*] [PN:aggregation protein asp1] |
| contig712 | 84687_c2_44 | 3184 | 6589 | 219 | 72 | 53 | 0.69 | [OR:*Methanococcus jannaschii*] [PN:hypothetical protein homolog MJ0990] |
| contig712 | 32600186_c1_35 | 3185 | 6590 | 2787 | 928 | 2908 | 0 | [OR:*Enterococcus faecalis*] [PN:surface exclusion protein seal precursor] [GN:scal] |
| contig712 | 14876563_c3_53 | 3186 | 6591 | 312 | 103 | 519 | 4.90E-50 | [SP:Q01894] [OR:*ENTEROCOCCUS FAECALIS*] [DE:HYPOTHETICAL 12.4 KD PROTEIN IN SEA1 5' REGION (ORFY)] |
| contig712 | 197303_c3_52 | 3187 | 6592 | 276 | 91 | 469 | 9.80E-45 | [OR:*Enterococcus faecalis*] [PN:probable pheromone-responsive regulatory protein S] |
| contig712 | 24406568_c1_53 | 3188 | 6593 | 1116 | 372 | 527 | 7.00E-51 | [SP:P39606] [OR:*BACILLUS SUBTILIS*] [GN:YWCH] [DE:HYPOTHETICAL 36.6 KD PROTEIN IN QOXD-VPR INTERGENIC REGION] |
| contig713 | 31656562_f3_19 | 3189 | 6594 | 696 | 231 | 258 | 2.20E-22 | [AC:X93081] [OR:*Bacillus subtilis*] [GN:orf4] |
| contig713 | 14492943_f3_20 | 3190 | 6595 | 1029 | 342 | 1004 | 2.00E-101 | [SP:P08577] [OR:*ESCHERICHIA COLI*] [GN:RUVB] [DE:HOLLIDAY JUNCTION DNA HELICASE RUVB] |
| contig713 | 25563800_c2_72 | 3191 | 6596 | 477 | 158 | 346 | 1.10E-31 | [SP:P45426] [OR:*ESCHERICHIA COLI*] [GN:YHCJ] [DE:HYPOTHETICAL 24.1 KD PROTEIN IN GLTF-NANT INTERGENIC REGION (F229)] |
| contig713 | 3164143_f2_10 | 3192 | 6597 | 852 | 283 | | | |
| contig713 | 569055_f2_11 | 3193 | 6598 | 2481 | 826 | 762 | 5.90E-128 | [SP:P42592] [OR:*ESCHERICHIA COLI*] [GN:YGJK] [DE:(O783)] |
| contig713 | 4121087_f2_12 | 3194 | 6599 | 930 | 309 | 125 | 1.50E-05 | [OR:*Enterococcus faecalis*] [PN:traA protein] |
| contig713 | 24805302_c1_45 | 3195 | 6600 | 717 | 238 | 206 | 7.20E-17 | [SP:P46908] [OR:*BACILLUS SUBTILIS*] [GN:FNR] [DE:ANAEROBIC REGULATORY PROTEIN] |
| contig713 | 33470268_f3_25 | 3196 | 6601 | 921 | 306 | 824 | 2.40E-82 | [AC:Y14081] [OR:*Bacillus subtilis*] [PN:hypothetical protein] [GN:yhxD] [NT:bp 1–501 overlaps with bp 1525–1947 (cnd) from EMBL] |
| contig713 | 10008588_f1_26 | 3197 | 6602 | 585 | 194 | 83 | 0.2 | [AC:X53155] [OR:*Drosophila melanogaster*] [GN:Mhc] [NT:Description] |
| contig713 | 13914838_f3_27 | 3198 | 6603 | 204 | 67 | 75 | 0.0055 | [AC:U23376] [OR:*Lactococcus lactis*] [NT:putative 6-kDa protein] |
| contig713 | 16797338_f3_28 | 3199 | 6604 | 525 | 174 | 397 | 4.20E-37 | [AC:U23376] [OR:*Lactococcus lactis*] [NT:putative 20-kDa protein] |
| contig713 | 23712782_f1_2 | 3200 | 6605 | 564 | 187 | 453 | 4.90E-43 | [AC:U23376] [OR:*Lactococcus lactis*] [NT:putative 20-kDa protein] |
| contig713 | 14667342_f3_29 | 3201 | 6606 | 258 | 85 | 101 | 9.70E-06 | [AC:AB001488] [OR:*Bacillus subtilis*] [GN:ydaS] [NT:FUNCTON UNKNOWN.] |
| contig713 | 4879561_f3_30 | 3202 | 6607 | 1281 | 426 | 453 | 4.90E-43 | [AC:Z82987] [OR:*Bacillus subtilis*] [PN:unknown similar to quinolon resistance protein] [GN:ywoG] |
| contig713 | 33620807_f2_16 | 3203 | 6608 | 219 | 72 | 62 | 0.12 | [SP:P41714] [OR:*CHORISTONEURA FUMIFERANA* NUCLEAR POLYHEDROSIS VIRUS] [GN:P10] [DE:P10 PROTEIN (FIBROUS BODY PROTEIN)] |
| contig713 | 21718913_c1_40 | 3204 | 6609 | 468 | 155 | 75 | 0.997 | [SP:P22258] [OR:*ACETOGENIUM KIVUI*] [DE:CELL SURFACE |

TABLE 2-continued

| Contig | Orf | NT Seq Id | AA Seq ID | NT Orf Length | AA Orf Length | Score | Probability | Description |
|---|---|---|---|---|---|---|---|---|
| contig713 | 36572877_c2_65 | 3205 | 6610 | 1137 | 378 | 119 | 0.00022 | PROTEIN PRECURSOR (S-LAYER PROTEIN)] [OR:*Bacillus anthracis*] [PN:toxin synthesis trans-activator atxA] |
| contig713 | 24484681_c3_83 | 3206 | 6611 | 1509 | 502 | 110 | 0.0038 | [OR:*Streptococcus pyogenes*] [PN:virR protein] |
| contig713 | 976512_f3_32 | 3207 | 6612 | 6165 | 2054 | 154 | 9.50E-15 | [AC:U31980] [OR:*Streptococcus pyogenes*] [PN:protein F2] [GN:PRTF2] |
| contig713 | 26766942_f1_5 | 3208 | 6613 | 930 | 309 | 225 | 7.00E-19 | [SP:P39074] [OR:*BACILLUS SUBTILIS*] [GN:BMRU] [DE:BMRU PROTEIN] |
| contig713 | 30275432_f1_6 | 3209 | 6614 | 1509 | 502 | 190 | 5.80E-12 | [OR:*Bacillus anthracis*] [PN:toxin synthesis trans-activator atxA] |
| contig713 | 22346893_f3_33 | 3210 | 6615 | 300 | 99 | 55 | 0.66 | [AC:Y11759] [OR:*Desulfovibrio fructosovorans*] [PN:cytochrome-c3 hydrogenase] [GN:hydB] |
| contig713 | 34266033_f2_18 | 3211 | 6616 | 1962 | 654 | 81 | 0.98 | [OR:*Streptococcus*] [PN:C protein alpha antigen] |
| contig714 | 30290910_c3_143 | 3212 | 6617 | 741 | 247 | 75 | 0.56 | [OR:*Methanococcus jannaschii*] [PN:hypothetical protein MJ1540] |
| contig714 | 6385126_c2_117 | 3213 | 6618 | 1113 | 370 | 66 | 0.31 | [AC:D90902] [OR:*Synechocystis sp.*] [PN:hypothetical protein] [GN:patA] [NT:ORF_ID] |
| contig714 | 29584838_c3_142 | 3214 | 6619 | 888 | 295 | 83 | 0.69 | [AC:D90917] [OR:*Synechocystis sp.*] [PN:47 kD protein] [NT:ORF_ID] |
| contig714 | 4691018_c3_141 | 3215 | 6620 | 3159 | 1052 | 118 | 0.00025 | [AC:U28154] [OR:*Haemophilus somnus*] [NT:orf13; not preceded by a good RBS site] |
| contig714 | 4974043_f1_54 | 3216 | 6621 | 738 | 245 | 135 | 4.60E-07 | [AC:M74170] [OR:*Schistosoma mansoni*] [NT:ORF 3] |
| contig714 | 406250_c1_98 | 3217 | 6622 | 348 | 115 | 78 | 0.21 | [AC:U57510] [OR:*Sus scrofa*] [PN:type I cytochrome p450 aromatase] |
| contig714 | 19666567_c2_116 | 3218 | 6623 | 486 | 161 | 52 | 0.96 | [AC:AC000133] [OR:*Emericella nidulans*] [PN:ORF] [NT:F5P12 homology to klc, kinesin light chain] |
| contig714 | 35197591_c2_115 | 3219 | 6624 | 651 | 216 | 55 | 0.95 | [OR:*Pseudomonas putida*] [PN:4-oxalocrotonate tautomerase] [GN:xylH] |
| contig714 | 26384703_c1_97 | 3220 | 6625 | 387 | 128 | 61 | 0.9999 | [AC:U55369] [OR:*Caenorhabditis elegans*] [GN:C18C4.8] |
| contig714 | 24807328_c1_96 | 3221 | 6626 | 432 | 143 | 70 | 0.96 | [OR:*Methanococcus jannaschii*] [PN:adenine deaminase,] |
| contig714 | 7235937_c3_138 | 3222 | 6627 | 357 | 118 |  |  |  |
| contig714 | 23572338_c1_95 | 3223 | 6628 | 546 | 181 |  |  |  |
| contig714 | 161517_c1_94 | 3224 | 6629 | 324 | 107 | 60 | 0.9 | [SP:P30052] [OR:*DROSOPHILA MELANOGASTER*] [GN:SD] [DE:SCALLOPED PROTEIN] |
| contig714 | 995450_c2_113 | 3225 | 6630 | 879 | 292 | 108 | 0.00012 | [OR:phage SPP1] [PN:scaffold protein] |
| contig714 | 26604062_c2_112 | 3226 | 6631 | 579 | 192 | 64 | 0.23 | [SP:P16011] [OR:BACTERIOPHAGE T4] [GN:53] [DE:BASEPLATE STRUCTURAL PROTEIN GP53] |
| contig714 | 4397536_c1_93 | 3227 | 6632 | 264 | 87 |  |  |  |
| contig714 | 36331311_c1_92 | 3228 | 6633 | 210 | 69 | 61 | 0.78 | [AC:U23449] [OR:*Caenorhabditis elegans*] [GN:K06A1.1] [NT:similar to transcription factor AP-2] |
| contig714 | 10976406_c3_136 | 3229 | 6634 | 1470 | 489 | 311 | 1.10E-27 | [OR:phage SPP1] [PN:gene 7 protein] |
| contig714 | 132952_c2_111 | 3230 | 6635 | 1533 | 510 | 412 | 1.10E-38 | [SP:P54309] [OR:BACTERIOPHAGE SPP1] [GN:6] [DE:PORTAL PROTEIN (GP6)] |
| contig714 | 34410650_c3_135 | 3231 | 6636 | 1263 | 420 | 66 | 0.39 | [AC:JQ1284] [OR:*Culex pipiens quinquefasciatus*] [PN:hypothetical 9.3K protein] |
| contig714 | 3954010_c1_88 | 3232 | 6637 | 540 | 179 | 85 | 0.029 | [SP:Q57637] [OR:*METHANOCOCCUS JANNASCHII*] [GN:MJ0173] [DE:HYPOTHETICAL PROTEIN MJ0173] |
| contig714 | 24251900_c1_87 | 3233 | 6638 | 483 | 160 | 60 | 0.4 | [AC:K02837] [OR:*Mus musculus*] [NT:Ig H-chain (V-region VHD6.96)] |
| contig714 | 24611575_c2_110 | 3234 | 6639 | 1380 | 459 | 248 | 5.90E-18 | [AC:X98455] [OR:*Bacillus cereus*] [GN:SNF] |
| contig714 | 33536_c2_109 | 3235 | 6640 | 405 | 134 | 71 | 0.88 | [SP:P33048] [OR:*CAPRA HIRCUS*] [GN:CSN2] [DE:BETA CASEIN PRECURSOR] |
| contig714 | 3010911_c1_84 | 3236 | 6641 | 2244 | 747 | 537 | 6.10E-52 | [AC:L31763] [OR:*Dichelobacter nodosus*] [PN:virulence-associated |

TABLE 2-continued

| Contig | Orf | NT Seq Id | AA Seq ID | NT Orf Length | AA Orf Length | Score | Probability | Description |
|---|---|---|---|---|---|---|---|---|
| contig714 | 34273462_c3_133 | 3237 | 6642 | 222 | 73 | 60 | 0.49 | protein E] [GN:vapE] [NT:putative] [AC:Z46381] [OR:Caenorhabditis elegans] [PN:M01F1.7] |
| contig714 | 2931562_c3_132 | 3238 | 6643 | 306 | 101 | 63 | 0.69 | [SP:P11546] [OR:LACTOCOCCUS LACTIS] [GN:LACG] [DE:GALACTOHYDROLASE) (PGALASE) (P-BETA-GAL) (PBG) |
| contig714 | 5250463_c3_131 | 3239 | 6644 | 252 | 83 | 67 | 0.26 | [SP:P30033] [OR:RATTUS NORVEGICUS] [GN:GNA0] [DE:GUANINE NUCLEOTIDE-BINDING PROTEIN G(O), ALPHA SUBUNIT 2] |
| contig714 | 14650311_c3_130 | 3240 | 6645 | 1965 | 654 | 1699 | 4.50E-175 | [SP:P06225] [OR:BACTERIOPHAGE SP02] [GN:L] [DE:DNA POLYMERASE.] |
| contig714 | 24648438_c1_83 | 3241 | 6646 | 555 | 184 | 82 | 0.18 | [AC:K02263] [OR:Gallus gallus] [NT:troponin T] |
| contig714 | 97887_c3_129 | 3242 | 6647 | 255 | 84 | 65 | 0.93 | [AC:U28735] [OR:Caenorhabditis elegans] [GN:F48E3.3] [NT:coded for by C. elegans cDNA cm06e4; coded for by] |
| contig714 | 4875063_c2_106 | 3243 | 6648 | 585 | 194 | 83 | 0.82 | [SP:P18493] [OR:BOS TAURUS] [GN:ADPRT] [DE:POLYMERASE) (PARP) (ADPRT) |
| contig714 | 26853587_c3_128 | 3244 | 6649 | 345 | 114 | 64 | 0.62 | [AC:U60434] [OR:Xenopus laevis] [PN:TCR VDJ BV6 B17] [NT:the constant region is the same as BV18] |
| contig714 | 6924217_c3_127 | 3245 | 6650 | 261 | 86 | 66 | 0.13 | [AC:U80452] [OR:Caenorhabditis elegans] [GN:C16C8.5] [NT:weak similarity to Arabidopisis thaliana] |
| contig714 | 12927177_c1_82 | 3246 | 6651 | 1179 | 392 | 83 | 0.68 | [OR:Saccharomyces cerevisiae] [PN:hypothetical protein YOR281c] |
| contig714 | 24353437_c2_105 | 3247 | 6652 | 483 | 160 | 55 | 0.71 | [SP:P11519] [OR:ESCHERICHIA COLI] [GN:FLMC] [DE:FLMC PROTEIN] |
| contig714 | 1206436_c2_104 | 3248 | 6653 | 198 | 65 | 66 | 0.048 | [OR:Methanococcus jannaschii] [PN:hypothetical protein MJ0272] |
| contig714 | 3415712_c1_81 | 3249 | 6654 | 255 | 84 | 72 | 0.082 | [SP:Q12765] [OR:HOMO SAPIENS] [GN:KIAA0193] [DE:HYPOTHETICAL PROTEIN KIAA0193] |
| contig714 | 36132911_c3_126 | 3250 | 6655 | 711 | 236 | 70 | 0.84 | [SP:Q02842] [OR:SIMIAN IMMUNODEFICIENCY VIRUS] [GN:VPX] [DE:VPX PROTEIN (X ORF PROTEIN)] |
| contig714 | 16521952_c3_80 | 3251 | 6656 | 195 | 64 | 55 | 0.52 | [OR:Picea abies] [PN:dal2 protein] |
| contig714 | 33828462_c1_79 | 3252 | 6657 | 213 | 70 | 54 | 0.998 | [AC:Z75531] [OR:Caenorhabditis elegans] [PN:C54D10.6] |
| contig714 | 25628216_c2_103 | 3253 | 6658 | 252 | 83 | 62 | 0.98 | [SP:Q02099] [OR:SCHIZOSACCHAROMYCES POMBE] [GN:RAD3] [DE:DNA REPAIR PROTEIN RAD3] |
| contig714 | 15807063_c3_123 | 3254 | 6659 | 243 | 80 | 63 | 0.2 | [AC:X98508] [OR:Agaricus bisporus] [PN:heat shock protein 70] [GN:hspA] |
| contig714 | 34042963_c2_102 | 3255 | 6660 | 288 | 95 | 122 | 5.80E-08 | [AC:L29324] [OR:Streptococcus pneumoniae] [PN:excisionase] [NT:ORF5] |
| contig714 | 20119062_c3_122 | 3256 | 6661 | 357 | 118 | 83 | 0.00078 | [AC:Z50854] [OR:Enterococcus hirae] [GN:orf1] |
| contig714 | 26461577_c1_121 | 3257 | 6662 | 231 | 76 | 103 | 6.00E-06 | [OR:Methanococcus jannaschii] [PN:hypothetical protein MJ0272] |
| contig714 | 23442842_f1_21 | 3258 | 6663 | 375 | 124 | 144 | 2.70E-10 | [AC:AB001488] [OR:Bacillus subtilis] [GN:ydeN] [NT:PROBABLE REPRESSOR PROTEIN.] |
| contig714 | 19720328_f2_49 | 3259 | 6664 | 705 | 234 | 92 | 0.053 | [AC:Z95556] [OR:Mycobacterium tuberculosis] [NT:unknown] [GN:MTCY07A7.21c] [NT:MTCY07A7.21c, unknown, len] |
| contig714 | 34257902_f1_22 | 3260 | 6665 | 552 | 183 | 52 | 0.84 | [AC:U40423] [OR:Caenorhabditis elegans] [GN:C24H10.4] |
| contig714 | 2425378_f3_75 | 3261 | 6666 | 1239 | 412 | 309 | 8.80E-28 | [SP:P20709] [OR:BACTERIOPHAGE L54A] [GN:INT] [DE:INTEGRASE] |
| contig714 | 25598587_c3_118 | 3262 | 6667 | 1401 | 466 | 1410 | 1.90E-144 | [OR:Streptococcus thermophilus] [PN:cysteine aminopeptidase C] [GN:pepC] |
| contig715 | 884505_f2_13 | 3263 | 6668 | 459 | 152 | 777 | 2.30E-77 | [SP:P19775] [OR:STAPHYLOCOCCUS AUREUS] [GN:TNP] [DE:TRANSPOSASE FOR INSERTION SEQUENCE ELEMENT IS256 IN TRANSPOSON TN4001] |
| contig715 | 5113757_c1_58 | 3264 | 6669 | 225 | 74 | | | |

TABLE 2-continued

| Contig | Orf | NT Seq Id | AA Seq ID | NT Orf Length | AA Orf Length | Score | Probability | Description |
|---|---|---|---|---|---|---|---|---|
| contig715 | 228853150_f3_27 | 3265 | 6670 | 3921 | 1306 | 5811 | 0 | [OR:*Enterococcus faecalis*] [PN:150K mating aggregate formation protein Asc10 precursor] |
| contig715 | 26367692_f1_1 | 3266 | 6671 | 414 | 137 | 542 | 1.80E-52 | [OR:*Enterococcus faecalis*] [PN:hypothetical protein 3] |
| contig715 | 1218750_c3_91 | 3267 | 6672 | 186 | 61 | 59 | 0.78 | [SP:P21248] [OR:*BACILLUS SUBTILIS*] [GN:HEMD] [DE:III COSYNTHETASE) (HYDROXYMETHYLBILANE HYDROLYASE (CYCLIZING))] |
| contig715 | 24823428_f1_2 | 3268 | 6673 | 408 | 135 | 659 | 7.20E-65 | [AC:X96977] [OR:*Enterococcus faecalis*] [GN:orf5] |
| contig715 | 22384540_f2_15 | 3269 | 6674 | 291 | 96 | 360 | 3.50E-33 | [AC:X96977] [OR:*Enterococcus faecalis*] [GN:orf6] |
| contig715 | 23678287_f3_29 | 3270 | 6675 | 900 | 299 | 1116 | 2.70E-113 | [AC:X96977] [OR:*Enterococcus faecalis*] [GN:orf7]] |
| contig715 | 31848465_f1_3 | 3271 | 6676 | 876 | 291 | 767 | 2.60E-76 | [AC:X96977] [OR:*Enterococcus faecalis*] [GN:orf8] [NT:cell wall anchoring signal] |
| contig715 | 24414683_c2_72 | 3272 | 6677 | 240 | 79 | 66 | 0.79 | [AC:U56100] [OR:*Emericella nidulans*] [PN:DNA binding regulatory protein AmdX] [GN:amdX] [NT:Description] |
| contig715 | 4408338_f2_16 | 3273 | 6678 | 1281 | 426 | 1123 | 4.90E-114 | [AC:X96977] [OR:*Enterococcus faecalis*] [GN:orf9] |
| contig715 | 34063750_f1_4 | 3274 | 6679 | 645 | 214 | 358 | 5.70E-33 | [AC:X96977] [OR:*Enterococcus faecalis*] [GN:orf11] |
| contig715 | 4886578_f2_17 | 3275 | 6680 | 417 | 138 | 567 | 4.00E-55 | [AC:X96977] [OR:*Enterococcus faecalis*] [GN:orf12] |
| contig715 | 2269317_f1_5 | 3276 | 6681 | 321 | 106 | 470 | 7.70E-45 | [AC:X96977] [OR:*Enterococcus faecalis*] [GN:orf13] |
| contig715 | 6836062_f2_18 | 3277 | 6682 | 984 | 327 | 1264 | 5.60E-129 | [AC:X96977] [OR:*Enterococcus faecalis*] [GN:orf14] |
| contig715 | 23682952_f3_30 | 3278 | 6683 | 276 | 91 | 281 | 8.20E-25 | [AC:X96977] [OR:*Enterococcus faecalis*] [GN:orf15] |
| contig715 | 20093062_f2_19 | 3279 | 6684 | 471 | 156 | 499 | 6.50E-48 | [AC:X96977] [OR:*Enterococcus faecalis*] [GN:orf16] |
| contig715 | 4726713_f2_20 | 3280 | 6685 | 498 | 165 | 433 | 6.40E-41 | [SP:P37455] [OR:*BACILLUS SUBTILIS*] [GN:SSB] [DE:SINGLE-STRAND BINDING PROTEIN (SSB) (HELIX-DESTABILIZING PROTEIN)] |
| contig715 | 24492077_f1_7 | 3281 | 6686 | 570 | 189 | | | |
| contig715 | 24410927_f2_21 | 3282 | 6687 | 300 | 99 | | | |
| contig715 | 4882827_f3_32 | 3283 | 6688 | 2532 | 843 | 569 | 1.80E-53 | [AC:AB001488] [OR:*Bacillus subtilis*] [GN:ydeE] [NT:SIMILAR TO ORF16 OF *ENTEROCOCCUS FAECALIS*] |
| contig715 | 31260215_f1_8 | 3284 | 6689 | 426 | 141 | 69 | 0.67 | [AC:D13576] [OR:Influenza A virus] [PN:hemagglutinin] [GN:HA] |
| contig715 | 13877317_f1_9 | 3285 | 6690 | 2358 | 785 | 116 | 0.00086 | [AC:Z70204] [OR:*Caenorhabditis elegans*] [PN:C11G6.3] [NT:cDNA EST CEESG55F comes from this gene] |
| contig715 | 6270288_f2_23 | 3286 | 6691 | 2268 | 755 | 96 | 8.40E-06 | [OR:*Leuconostoc oenos*] [PN:hypothetical protein 2] |
| contig715 | 25676937_f2_24 | 3287 | 6692 | 801 | 266 | 75 | 0.8 | [SP:P47667] [OR:*MYCOPLASMA GENITALIUM*] [GN:MG428] [DE:HYPOTHETICAL PROTEIN MG428] |
| contig715 | 34430450_f1_10 | 3288 | 6693 | 504 | 167 | 70 | 0.97 | [SP:Q57729] [OR:*METHANOCOCCUS JANNASCHII*] [GN:MJ0281] [DE:HYPOTHETICAL PROTEIN MJ0281] |
| contig715 | 34198462_f1_11 | 3289 | 6694 | 282 | 93 | 67 | 0.46 | [SP:P47658] [OR:*MUS MUSCULUS*] [DE:SIGNAL RECOGNITION PARTICLE RECEPTOR BETA SUBUNIT (SR-BETA)] |
| contig715 | 14734687_f3_35 | 3290 | 6695 | 558 | 185 | 115 | 3.20E-07 | [OR:*Nicotiana tabacum*] [PN:GUT 7-2a protein] |
| contig715 | 13946068_f3_36 | 3291 | 6696 | 261 | 86 | 138 | 1.20E-09 | [SP:Q06426] [OR:BACTERIOPHAGE P2] [GN:ORF91] [DE:HYPOTHETICAL 12.9 KD PROTEIN IN GPA 3' REGION (ORF5)] |
| contig715 | 1047187_f3_37 | 3292 | 6697 | 489 | 162 | 234 | 7.80E-20 | [OR:Eubacterium sp.] [PN:single-stranded DNA-binding protein] |
| contig715 | 2824092_f2_25 | 3293 | 6698 | 597 | 198 | 397 | 4.20E-37 | [AC:U66480] [OR:*Bacillus subtilis*] [PN:YncB] [GN:yncB] |
| contig715 | 34187752_f1_12 | 3294 | 6699 | 360 | 119 | 75 | 0.0055 | [SP:Q47150] [OR:*ESCHERICHIA COLI*] [GN:DINJ] [DE:DNA-DAMAGE-INDUCIBLE PROTEIN J] |
| contig715 | 4890827_f2_26 | 3295 | 6700 | 276 | 91 | 144 | 2.70E-10 | [SP:Q47149] [OR:*ESCHERICHIA COLI*] [GN:YAFQ] [DE:HYPOTHETICAL 10.8 KD PROTEIN IN GMHA-DINJ INTERGENIC REGION] |

TABLE 2-continued

| Contig | Orf | NT Seq Id | AA Seq ID | NT Orf Length | AA Orf Length | Score | Probability | Description |
|---|---|---|---|---|---|---|---|---|
| contig716 | 24814793_f2_31 | 3296 | 6701 | 1167 | 388 | 864 | 1.40E-86 | [AC:JH0206] [OR:Enterococcus faecalis] [PN:hypothetical 57.4K protein] |
| contig716 | 34379002_f3_60 | 3297 | 6702 | 378 | 125 | 108 | 1.80E-05 | [SP:P14752] [OR:STREPTOCOCCUS PYOGENES] [GN:REPS] [DE:REPS PROTEIN] |
| contig716 | 7308311_f1_1 | 3298 | 6703 | 1326 | 441 | 2009 | 6.30E-208 | [OR:Enterococcus faecalis] [PN:probable pheromone binding protein pheromone responsive gene Z protein] [GN:prgZ] |
| contig716 | 16448437_f1_2 | 3299 | 6704 | 705 | 234 | 1150 | 6.70E-117 | [AC:L40841] [OR:Enterococcus faecium] [PN:transposase] [NT:ISS1 homolog; putative] |
| contig716 | 13808206_f2_32 | 3300 | 6705 | 246 | 81 | 162 | 3.30E-12 | [AC:JC5008] [OR:Lactococcus lactis] [PN:hypothetical 6.5K protein (insertion sequence IS1297)] |
| contig716 | 20969002_c3_159 | 3301 | 6706 | 222 | 73 | 57 | 0.37 | [AC:M58451] [OR:Mus musculus] [PN:immunoglobulin light chain] [NT:Hed 10] |
| contig716 | 2744553_c1_109 | 3302 | 6707 | 204 | 67 | 219 | 3.00E-18 | [OR:Enterococcus faecalis] [PN:erythromycin resistance protein, ORF3] |
| contig716 | 165751_c3_158 | 3303 | 6708 | 783 | 260 | 1268 | 2.10E-129 | [OR:Streptococcus pyogenes] [PN:erm2 protein] |
| contig716 | 4876077_c3_157 | 3304 | 6709 | 795 | 264 | 1411 | 1.50E-144 | [SP:P00554] [OR:ENTEROCOCCUS STAPHYLOCOCCUS AUREUS] [GN:APHA] [DE:(APH(3' )III)] |
| contig716 | 19534635_c1_108 | 3305 | 6710 | 261 | 86 | 454 | 3.80E-43 | [AC:U01945] [OR:Campylobacter coli] [PN:streptothricine-acetyl-transferase] [GN:sat4] |
| contig716 | 26445885_c3_156 | 3306 | 6711 | 276 | 91 | 335 | 1.60E-30 | [AC:U51474] [OR:Staphylococcus aureus] [PN:truncated streptothricin acetyl transferase] [GN:sat] [NT:full-length protein function] |
| contig716 | 26258452_c1_107 | 3307 | 6712 | 909 | 302 | 900 | 2.10E-90 | [SP:P17585] [OR:BACILLUS SUBTILIS] [GN:AADK] [DE:AMINOGLYCOSIDE 6-ADENYLYLTRANSFERASE, (AAD(6)] |
| contig716 | 6917832_c2_135 | 3308 | 6713 | 750 | 249 | 334 | 2.00E-30 | [SP:P44074] [OR:HAEMOPHILUS INFLUENZAE] [GN:HI0912] [DE:HYPOTHETICAL PROTEIN HI0912] |
| contig716 | 26756566_c1_106 | 3309 | 6714 | 891 | 296 | 74 | 0.02 | [OR:Streptomyces wednorensis] [PN:epoxidase FOM4] |
| contig716 | 30745632_c2_134 | 3310 | 6715 | 240 | 79 | 175 | 2.30E-22 | [AC:U15027] [OR:Clostridium perfringens] [PN:TnpX] [GN:tnpX] |
| contig716 | 24885437_c1_105 | 3311 | 6716 | 1578 | 525 | 60 | 0.25 | [AC:M73765] [OR:Mus musculus] [PN:T cell receptor] [GN:Tcra-V2] |
| contig716 | 4069827_c3_155 | 3312 | 6717 | 417 | 138 | 56 | 0.44 | [AC:M19879] [OR:Homo sapiens] [PN:calbindin 27] |
| contig716 | 26384426_c3_154 | 3313 | 6718 | 330 | 109 | 64 | 0.078 | [SP:P12320] [OR:ERWINIA CAROTOVORA] [GN:TRPD] [DE:ANTHRANILATE PHOSPHORIBOSYLTRANSFERASE, (FRAGMENT)] |
| contig716 | 25814638_c3_153 | 3314 | 6719 | 198 | 65 | | | |
| contig716 | 139471175_c2_133 | 3315 | 6720 | 696 | 231 | 1148 | 1.10E-116 | [OR:Streptococcus pyogenes] [PN:hypothetical protein gamma] [GN:gamma' ] |
| contig716 | 19812826_c2_132 | 3316 | 6721 | 648 | 215 | 673 | 2.40E-66 | [AC:JQ1326] [OR:Enterococcus faecalis] [PN:hypothetical 23.9K protein] |
| contig716 | 23621003_c1_103 | 3317 | 6722 | 195 | 64 | 275 | 3.50E-24 | [OR:Streptococcus pyogenes] [PN:hypothetical protein alpha] |
| contig716 | 4540637_c3_151 | 3318 | 6723 | 624 | 207 | 58 | 0.71 | [SP:Q57643] [OR:METHANOCOCCUS JANNASCHII] [GN:MJ0184] [DE:HYPOTHETICAL PROTEIN MJ0184] |
| contig716 | 4902217_c2_131 | 3319 | 6724 | 555 | 184 | 73 | 0.15 | [AC:U02109] [OR:Mycoplasma genitalium] [NT:homology to triosephosphate isomerase 1.01654] |
| contig716 | 25603436_c3_150 | 3320 | 6725 | 2184 | 727 | | | |
| contig716 | 26367812_c1_102 | 3321 | 6726 | 555 | 184 | 53 | 0.97 | [OR:Neisseria meningitidis] [PN:transferrin-binding protein 2] |
| contig716 | 29929702_c2_129 | 3322 | 6727 | 480 | 159 | 73 | 0.14 | [SP:P11188] [OR:BACTERIOPHAGE PHI-29] [GN:14] [DE:LYSIS PROTEIN (LATE PROTEIN GP14)] |
| contig716 | 6015675_c1_100 | 3323 | 6728 | 702 | 233 | 88 | 0.47 | [SP:P54275] [OR:RATTUS NORVEGICUS] [GN:MSH2] [DE:DNA MISMATSCH REPAIR PROTEIN MSH2] |

TABLE 2-continued

| Contig | Orf | NT Seq Id | AA Seq ID | NT Orf Length | AA Orf Length | Score | Probability | Description |
|---|---|---|---|---|---|---|---|---|
| contig716 | 3907893_c2_128 | 3324 | 6729 | 1776 | 591 | 215 | 6.90E-17 | [SP:P07540] [OR:BACTERIOPHAGE PZA] [GN:15] [DE:GP15] |
| contig716 | 23848262_f2_46 | 3325 | 6730 | 843 | 280 | 93 | 0.2 | [SP:P20676] [OR:SACCHAROMYCES CEREVISIAE] [GN:NUP1] [DE:NUCLEOPORIN NUP1 (NUCLEAR PORE PROTEIN NUP1)] |
| contig716 | 11740677_c1_98 | 3326 | 6731 | 282 | 93 | 70 | 0.086 | [OR:Staphylococcus aureus] [PN:hypothetical membrane spanning protein] |
| contig716 | 5321062_c1_97 | 3327 | 6732 | 204 | 67 | 60 | 0.27 | [AC:D13576] [OR:Influenza A virus] [PN:hemagglutinin] [GN:HA] |
| contig716 | 34037817_c3_148 | 3328 | 6733 | 687 | 228 | 71 | 0.84 | [OR:bacteriophage A511] [PN:hypothetical protein 1] |
| contig716 | 26808438_c2_127 | 3329 | 6734 | 351 | 116 | 71 | 0.068 | [SP:P14363] [OR:FOWLPOX VIRUS] [DE:HYPOTHETICAL BAMH1-ORF5 PROTEIN] |
| contig716 | 24406566_c1_96 | 3330 | 6735 | 471 | 156 | 50 | 0.996 | [OR:Macaca fascicularis] [PN:MHC class II DQB2 protein] [GN:MHC DQB2] |
| contig716 | 24415628_c1_95 | 3331 | 6736 | 768 | 255 | 53 | 0.99 | [OR:Wolinella recta] [PN:45K outer membrane protein] |
| contig716 | 16448437_c3_147 | 3332 | 6737 | 705 | 234 | 1160 | 5.80E-118 | [AC:L40841] [OR:Enterococcus faecium] [PN:transposase] [NT:ISS1 homolog; putative] |
| contig716 | 13808206_c1_93 | 3333 | 6738 | 246 | 81 | 162 | 3.30E-12 | [AC:JC5008] [OR:Lactococcus lactis] [PN:hypothetical 6.5K protein (insertion sequence IS1297)] |
| contig716 | 7320437_c2_125 | 3334 | 6739 | 1065 | 354 | 614 | 1.10E-80 | [AC:U36837] [OR:Lactococcus lactis] [PN:ORFU] |
| contig716 | 3915955_c1_92 | 3335 | 6740 | 4404 | 1467 | 279 | 1.30E-20 | [OR:Mycoplasma pneumoniae] [PN:hypothetical protein C09_orf718] |
| contig716 | 4876652_c3_146 | 3336 | 6741 | 834 | 277 | 141 | 8.50E-08 | [OR:Mycoplasma pneumoniae] [PN:hypothetical protein C09_orf251] |
| contig716 | 4788941_f2_56 | 3337 | 6742 | 1212 | 403 | 1064 | 8.70E-108 | [OR:Streptococcus thermophilus] [PN:transposase] |
| contig716 | 25444825_c3_145 | 3338 | 6743 | 2709 | 902 | 126 | 9.10E-05 | [OR:Gallus gallus] [PN:Ig V-region-like B-G antigen 3 precursor] |
| contig716 | 29843787_c3_144 | 3339 | 6744 | 375 | 124 | 52 | 0.84 | [OR:Saccharomyces cerevisiae] [GN:ODPI] |
| contig716 | 5370313_c1_90 | 3340 | 6745 | 603 | 200 | 84 | 0.47 | [AC:X99140] [OR:Homo sapiens] [PN:type II intermediate filament of hair keratin] [GN:hHb5] |
| contig716 | 26180463_c2_121 | 3341 | 6746 | 1347 | 448 | 73 | 0.97 | [AC:U91527] [OR:Enterococcus faecium] [PN:aggregation substance] [GN:ash701] [NT:putative adhesin protein] |
| contig716 | 21647338_c2_120 | 3342 | 6747 | 453 | 150 | 85 | 0.076 | [AC:U93711] [OR:Borrelia garinii] [PN:outer surface protein A] [GN:ospA] |
| contig716 | 24241702_c2_119 | 3343 | 6748 | 390 | 129 | 70 | 0.35 | [AC:X87771] [OR:Torpedo marmorata] [GN:MVP100] |
| contig716 | 6837767_c2_118 | 3344 | 6749 | 219 | 72 | 59 | 0.999 | [SP:Q34940] [OR:LEISHMANIA TARENTOLAE] [GN:RPS12] [DE:MITOCHONDRIAL RIBOSOMAL PROTEIN S12] |
| contig716 | 2501018_c3_142 | 3345 | 6750 | 720 | 239 | 59 | 0.36 | [AC:U22863] [OR:Rabies virus] [PN:nucleoprotein] |
| contig716 | 837836_c2_117 | 3346 | 6751 | 1182 | 393 | 79 | 0.14 | [AC:U27312] [OR:Caenorhabditis elegans] [GN:F26A1.5] |
| contig716 | 10819003_c2_116 | 3347 | 6752 | 1071 | 356 | 69 | 0.88 | [OR:Streptococcus pyogenes] [PN:M-like protein precursor] |
| contig716 | 26074188_c1_89 | 3348 | 6753 | 324 | 107 | 55 | 0.74 | [OR:Gallus gallus] [PN:homeotic protein Hox 7] [GN:hox7] |
| contig716 | 24511530_c2_115 | 3349 | 6754 | 243 | 80 | 54 | 0.12 | [SP:P12839] [OR:RATTUS NORVEGICUS] [GN:NEFM] [DE:NEUROFILAMENT TRIPLET M PROTEIN (160 KD NEUROFILAMENT PROTEIN) (NF-M)] |
| contig716 | 24744007_c3_140 | 3350 | 6755 | 333 | 110 | 75 | | |
| contig716 | 24652183_c2_114 | 3351 | 6756 | 588 | 195 | 71 | 0.56 | [AC:U41007] [OR:Caenorhabditis elegans] [GN:C33H5.3] [NT:weak similarity to myosin] |
| contig716 | 9961693_c1_88 | 3352 | 6757 | 546 | 181 | 54 | 0.92 | [AC:X90432] [OR:Canine herpesvirus] [PN:membrane glycoprotein B] |
| contig716 | 14656952_c2_112 | 3353 | 6758 | 1281 | 426 | 81 | 0.94 | [AC:U97040] [OR:Methanococcus voltae] [PN:putative flagella-related protein D] [GN:flaD] |
| contig716 | 13870336_c3_139 | 3354 | 6759 | 1590 | 529 | 59 | 0.97 | [SP:P10512] [OR:ESCHERICHIA COLI] [GN:TRAY] [DE:TRAY PROTEIN] |
| contig716 | 7204442_c2_111 | 3355 | 6760 | 450 | 149 | 66 | 0.085 | [SP:P10713] [OR:NEUROSPORA CRASSA] [GN:CON-10] [DE:CONIDIATION-SPECIFIC PROTEIN 10] |
| contig716 | 34271887_c1_86 | 3356 | 6761 | 522 | 173 | 151 | 1.40E-10 | [SP:P14243] [OR:CITROBACTER FREUNDII] [GN:CFR9IM] |

TABLE 2-continued

| Contig | Orf | NT Seq Id | AA Seq ID | NT Orf Length | AA Orf Length | Score | Probability | Description |
|---|---|---|---|---|---|---|---|---|
| contig72 | 426099_c1_5 | 3357 | 6762 | 729 | 243 | 546 | 3.80E-52 | [DE:METHYLTRANSFERASE CFR9I] (M.CFR9I) [SP:P37278] [OR:SYNECHOCOCCUS SP] [GN:PACL] |
| contig72 | 7032011_f2_1 | 3358 | 6763 | 420 | 139 | 195 | 1.10E-15 | [DE:CATION-TRANSPORTING ATPASE PACL] [AC:X85757] [OR:Saccharomyces cerevisiae] [PN:unknown] [GN:internal of G1669] |
| contig73 | 25192_f2_1 | 3359 | 6764 | 705 | 234 | 276 | 1.00E-33 | [AC:D38552] [OR:Homo sapiens] [GN:KIAA0073] [NT:The hal539 protein is related to cyclophilin.] |
| contig74 | 4883438_c2_5 | 3360 | 6765 | 249 | 82 | 62 | 0.77 | [AC:Z81492] [OR:Caenorhabditis elegans] [PN:E03H4.5] [NT:protein predicted using Genefinder] |
| contig74 | 15787525_c2_4 | 3361 | 6766 | 546 | 181 | 143 | 1.30E-09 | [SP:P54538] [OR:BACILLUS SUBTILIS] [GN:YQJA] [DE:HYPOTHETICAL 37.1 KD PROTEIN IN BMRU-ANSR INTERGENIC REGION] |
| contig75 | 26067717_f3_1 | 3362 | 6767 | 540 | 179 | 204 | 1.20E-16 | [SP:P26832] [OR:CLOSTRIDIUM PERFRINGENS] [DE:HYPOTHETICAL PROTEIN IN NAGH 5' REGION (ORFA) (FRAGMENT)] |
| contig76 | 34273407_f3_3 | 3363 | 6768 | 657 | 218 | 384 | 1.00E-35 | [SP:P54564] [OR:BACILLUS SUBTILIS] [GN:YOKA] [DE:HYPOTHETICAL 39.0 KD PROTEIN IN GLNQ-ANSR INTERGENIC REGION] |
| contig76 | 5406_c2_5 | 3364 | 6769 | 381 | 126 | 193 | 8.90E-15 | [SP:P55189] [OR:BACILLUS SUBTILIS] [GN:YBAR] [DE:HYPOTHETICAL 46.4 KD PROTEIN IN RRNG-FEUC INTERGENIC REGION] |
| contig76 | 12612832_f1_2 | 3365 | 6770 | 285 | 95 | 54 | 0.6 | [SP:P47419] [OR:MYCOPLASMA GENITALIUM] [GN:INFA] [DE:INITIATION FACTOR IF-1] |
| contig77 | 31750785_f2_1 | 3366 | 6771 | 768 | 256 | 641 | 5.80E-63 | [AC:D50453] [OR:Bacillus subtilis] [PN:homologue of aspartokinase 2 alpha and beta] [GN:yclM] |
| contig78 | 1269680_f3_1 | 3367 | 6772 | 612 | 203 | 112 | 1.00E-06 | [SP:P37348] [OR:ESCHERICHIA COLI] [GN:YECE] [DE:HYPOTHETICAL PROTEIN IN ASPS 5' REGION (FRAGMENT)] |
| contig79 | 26744086_c2_3 | 3368 | 6773 | 777 | 259 | 146 | 4.50E-08 | [AC:D90912] [OR:Synechocystis sp.] [PN:hypothetical protein] [NT:ORF_ID] |
| contig8 | 4898461_f2_1 | 3369 | 6774 | 432 | 143 | 230 | 2.10E-19 | [SP:P32058] [OR:ESCHERICHIA COLI] [GN:CMTB] [DE:ENZYME II, A COMPONENT], |
| contig80 | 23445462_f3_1 | 3370 | 6775 | 555 | 184 | 82 | 0.63 | [SP:P53166] [OR:SACCHAROMYCES CEREVISIAE] [DE:PUTATIVE ATP-DEPENDENT RNA HELICASE YGL064C] |
| contig81 | 31726407_c3_2 | 3371 | 6776 | 528 | 175 | 95 | 0.003 | [AC:U01945] [OR:Campylobacter coli] [PN:streptothricine-acetyl-transferase] [GN:sat4] |
| contig82 | 14894567_f2_1 | 3372 | 6777 | 714 | 237 | 770 | 1.20E-76 | [SP:P19670] [OR:BACILLUS SUBTILIS] [GN:MURA] [DE:ENOLPYRUVYL TRANSFERASE) (EPT] |
| contig83 | 24511017_c3_4 | 3373 | 6778 | 663 | 220 | 122 | 3.70E-06 | [AC:AB001488] [OR:Bacillus subtilis] [GN:ydtS] [NT:SIMILAR TO YDFR GENE PRODUCT OF THIS ENTRY] |
| contig83 | 29411250_f3_2 | 3374 | 6779 | 192 | 63 | 53 | 0.98 | [OR:Thermus aquaticus] [PN:fms protein homolog] |
| contig83 | 4711593_c3_3 | 3375 | 6780 | 246 | 81 | 64 | 0.1 | [AC:M97678] [OR:Manduca sexta] [PN:cytochrome P450 (CYP4M3)] |
| contig84 | 20714557_c3_3 | 3376 | 6781 | 747 | 249 | 981 | 5.40E-99 | [AC:M97678] [OR:Bacillus subtilis] [PN:Rho Factor] [GN:rho] |
| contig85 | 11179530_f3_2 | 3377 | 6782 | 441 | 146 | 218 | 3.90E-18 | [AC:U92563] [OR:Streptomyces lavendulae] [PN:mitomycin-binding protein] [GN:mrd] [NT:MRD] |
| contig85 | 5292176_f2_1 | 3378 | 6783 | 189 | 62 | 494 | 2.20E-47 | [OR:Enterococcus faecalis] [PN:copy control protein repB] [GN:repB] |
| contig86 | 34190928_f2_1 | 3379 | 6784 | 816 | 271 | 102 | 7.60E-06 | [AC:D49537] [OR:Clostridium perfringens] [PN:unknown] |
| contig87 | 12144541_f1_1 | 3380 | 6785 | 408 | 135 | | | |

TABLE 2-continued

| Contig | Orf | NT Seq Id | AA Seq ID | NT Orf Length | AA Orf Length | Score | Probability | Description |
|---|---|---|---|---|---|---|---|---|
| contig87 | 24085942_c3_4 | 3381 | 6786 | 201 | 66 | 65 | 0.34 | [GN:ORF18] [SP:P50177] [OR:LACTOCOCCUS LACTIS] [GN:LLAIIC] [DE:(R.LLAII)] |
| contig87 | 4070275_c1_2 | 3382 | 6787 | 504 | 167 | 91 | 0.0028 | [OR:Streptococcus pneumoniae] [PN:gyrb protein] [GN:gyrb] |
| contig88 | 781528_f3_4 | 3383 | 6788 | 771 | 256 | 697 | 6.80E-69 | [AC:D50453] [OR:Bacillus subtilis] [PN:homologue of Di-tripeptide transporter Dtp of L.] [GN:yelF] |
| contig89 | 23322788_f2_1 | 3384 | 6789 | 621 | 206 | 185 | 1.20E-14 | [AC:Y11043] [OR:Bacillus subtilis] [GN:azlC] [NT:product similar to Haemophilus influenzae] |
| contig9 | 30724631_f1_1 | 3385 | 6790 | 687 | 229 | 468 | 1.20E-44 | [AC:D28859] [OR:Enterococcus faecalis] [PN:TraC] [GN:traC] |
| contig90 | 22011551_f2_2 | 3386 | 6791 | 660 | 219 | 644 | 2.80E-63 | [SP:P19672] [OR:BACILLUS SUBTILIS] [GN:YQXC] [DE:HYPOTHETICAL 29.7 KD PROTEIN IN FOLD-AHRC INTERGENIC REGION] |
| contig91 | 36443953_c1_4 | 3387 | 6792 | 771 | 257 | 713 | 1.40E-70 | [SP:P36640] [OR:SALMONELLA TYPHIMURIUM] [GN:MGTA] [DE:MG(2+) TRANSPORT ATPASE, P-TYPE 1,] |
| contig91 | 12531281_c3_5 | 3388 | 6793 | 243 | 80 | 58 | 0.29 | [SP:P01054] [OR:HORDEUM VULGARE] [DE:SUBTILISIN-CHYMOTRYPSIN INHIBITOR C1-1C] |
| contig92 | 6273282_f2_1 | 3389 | 6794 | 732 | 243 | 671 | 3.80E-66 | [SP:P22045] [OR:LEISHMANIA MAJOR] [GN:P100/11E] [DE:PROBABLE REDUCTASE] |
| contig92 | 26461676_f3_2 | 3390 | 6795 | 288 | 95 | 72 | 0.014 | [OR:Staphylococcus sp.] [PN:fofB protein] |
| contig93 | 30059687_f2_1 | 3391 | 6796 | 216 | 71 | 118 | 9.60E-07 | [SP:P46545] [OR:LACTOBACILLUS DELBRUECKII] [GN:PEPQ] [DE:DIPEPTIDASE) (PROLIDASE) (AMIDODIPEPTIDASE)] |
| contig93 | 10548751_f3_2 | 3392 | 6797 | 630 | 210 | 489 | 7.40E-47 | [SP:P46545] [OR:LACTOBACILLUS DEBRUECKII] [GN:PEPQ] [DE:DIPEPTIDASE) (PROLIDASE) (IMIDODIPEPTIDASE)] |
| contig94 | 2931568_c1_1 | 3393 | 6798 | 657 | 218 | 61 | 0.998 | [SP:P02726] [OR:EQUUS CABALLUS] [DE:GLYCOPHORIN HA] |
| contig95 | 11885082_f3_1 | 3394 | 6799 | 435 | 144 | 83 | 0.003 | [AC:Z69371] [OR:Bacillus subtilis] [PN:ATP-binding subunit] [GN:glnQ] [NT:putative] |
| contig95 | 3418042_f3_2 | 3395 | 6800 | 207 | 68 | | | |
| contig96 | 6930437_c1_2 | 3396 | 6801 | 600 | 199 | 407 | 3.60E-38 | [AC:X98341] [OR:Bacillus subtilis] [GN:orfRM1] |
| contig97 | 30713280_f3_4 | 3397 | 6802 | 258 | 85 | 166 | 1.30E-12 | [SP:P21878] [OR:BACILLUS STEAROTHERMOPHILUS] [DE:HYPOTHETICAL PROTEIN IN PDHA 5' REGION (ORF1) (FRAGMENT)] |
| contig97 | 20007188_c3_6 | 3398 | 6803 | 252 | 83 | 56 | 0.86 | [AC:L41543] [OR:Bos taurus] [PN:epithelial mucin] [GN:MUC1] [NT:<l.283 membrane-proximal domain; 283..375] |
| contig97 | 34172785_f2_3 | 3399 | 6804 | 780 | 259 | 81 | 0.76 | [SP:P42946] [OR:SACCHAROMYCES CEREVISIAE] [GN:YIL108C] [DE:HYPOTHETICAL 41.5 KD PROTEIN IN GZF3-SMEI INTERGENIC REGION] |
| contig97 | 10031665_f1_2 | 3400 | 6805 | 213 | 70 | 53 | 0.9992 | [SP:P23629] [OR:RASPBERRY BUSHY DWARF VIRUS] [DE:COAT PROTEIN] |
| contig98 | 976626_f2_2 | 3401 | 6806 | 567 | 188 | 191 | 2.80E-15 | [AC:X99908] [OR:Escherichia coli] [PN:belongs to alcohol dehydrogenase/rybitol] [GN:ucpA] |
| contig99 | 21759558_f1_1 | 3402 | 6807 | 327 | 108 | 69 | 0.24 | [AC:U15286] [OR:Homo sapiens] [PN:Na,K-ATPase alpha subunit] |
| contig99 | 22460893_c2_4 | 3403 | 6808 | 429 | 142 | | | |
| contig1 | 24020301_c2_3.aa | 3404 | 6809 | 531 | 177 | 128 | 7.90E-07 | [AC:AB001488] [GN:yddE] [OR:Bacillus subtilis] [SR:Bacillus subtilis (strain:168) DNA] [NT: SIMILAR TO ORF16 OF ENTEROCOCCUS FAECALIS] [LE:71970] [RE:74465] [DI:direct] |
| contig10 | 25948474_c1_1.aa | 3405 | 6810 | 456 | 151 | 767 | 2.60E-76 | [PN:cylM protein] [OR:Enterococcus faecalis] |

TABLE 3

| E. faccalis ORF Name | ntSeqID | aaSeqID | Length | E. faccium ORF Name | Length | Overlap | Precent ID |
|---|---|---|---|---|---|---|---|
| contig100_35409705_f3_1.aa | 1 | 3406 | 305 | contig313_22656280_f2_1.aa | 335 | 208 | 85.58% |
| contig101_31647702_f1_1.aa | 2 | 3407 | 246 | contig495_24105313_f3_29.aa | 301 | 246 | 76.42% |
| contig102_32602186_c2_2.aa | 3 | 3408 | 208 | contig392_1210966_f2_8.aa | 345 | 129 | 46.51% |
| contig104_781525_c1_3.aa | 5 | 3410 | 216 | contig350_25548211_f1_3.aa | 286 | 198 | 55.05% |
| contig105_22321062_c2_3.aa | 7 | 3412 | 184 | contig307_1461636_c3_24.aa | 225 | 183 | 24.04% |
| contig106_5132942_f2_2.aa | 8 | 3413 | 62 | contig10_23628432_c2_4.aa | 62 | 62 | 100.00% |
| contig107_16302276_f1_1.aa | 9 | 3414 | 202 | contig100_15117217_f1_2.aa | 202 | 202 | 100.00% |
| contig107_19726707_f1_2.aa | 10 | 3415 | 121 | contig238_16824135_c1_6.aa | 377 | 95 | 76.84% |
| contig108_33690625_c3_11.aa | 11 | 3416 | 197 | contig330_6645051_c3_18.aa | 304 | 141 | 25.53% |
| contig109_17162_f3_2.aa | 14 | 3419 | 107 | contig500_34179817_c2_72.aa | 491 | 109 | 40.37% |
| contig11_35677382_f1_1.aa | 16 | 3421 | 202 | contig114_375_c2_2.aa | 202 | 202 | 100.00% |
| contig110_33400061_c2_6.aa | 17 | 3422 | 321 | contig200_33600253_f2_5.aa | 533 | 317 | 68.45% |
| contig110_19817885_c2_5.aa | 18 | 3423 | 134 | contig200_33208266_f2_4.aa | 104 | 100 | 81.00% |
| contig111_3994212_f3_3.aa | 19 | 3424 | 63 | contig205_24645311_f2_2.aa | 243 | 36 | 66.67% |
| contig111_22151437_f1_1.aa | 20 | 3425 | 220 | contig105_4345442_f1_1.aa | 220 | 220 | 100.00% |
| contig112_25485887_c2_4.aa | 22 | 3427 | 122 | contig334_16532202_f3_8.aa | 307 | 98 | 80.61% |
| contig113_594567_f1_1.aa | 23 | 3428 | 90 | contig266_9805463_f2_3.aa | 134 | 88 | 95.46% |
| contig113_14501449_c1_5.aa | 24 | 3429 | 195 | contig266_12890943_c1_5.aa | 408 | 187 | 55.08% |
| contig114_5910137_f3_2.aa | 25 | 3430 | 251 | contig489_6923462_c3_45.aa | 447 | 246 | 52.44% |
| contig114_4486088_f1_1.aa | 26 | 3431 | 167 | contig108_24901712_c3_4.aa | 197 | 102 | 100.00% |
| contig115_22382306_c3_3.aa | 27 | 3432 | 281 | contig120_35281312_c2_7.aa | 397 | 279 | 87.81% |
| contig116_253181_f1_1.aa | 28 | 3433 | 238 | contig468_33336053_c3_51.aa | 336 | 232 | 92.24% |
| contig118_7082011_f2_1.aa | 30 | 3435 | 167 | contig348_6821058_f1_1.aa | 157 | 157 | 70.06% |
| contig118_14625627_c3_4.aa | 31 | 3436 | 93 | contig372_34617207_c1_14.aa | 240 | 94 | 38.30% |
| contig119_23861675_c2_3.aa | 32 | 3437 | 240 | contig160_34636627_f2_1.aa | 417 | 236 | 41.10% |
| contig12_25551286_c1_1.aa | 33 | 3438 | 189 | contig435_24480062_c1_33.aa | 291 | 189 | 99.47% |
| contig120_34648427_f2_1.aa | 35 | 3440 | 185 | contig326_24619150_f1_1.aa | 203 | 138 | 81.88% |
| contig121_24069450_c3_4.aa | 36 | 3441 | 273 | contig301_22478183_c1_10.aa | 439 | 132 | 34.85% |
| contig122_6148577_f1_3.aa | 38 | 3443 | 179 | contig429_3026702_f3_20.aa | 228 | 142 | 54.23% |
| contig123_22460816_c2_3.aa | 39 | 3444 | 105 | contig454_22460816_f2_6.aa | 199 | 105 | 99.05% |
| contig124_976590_f1_1.aa | 41 | 3446 | 410 | contig417_24414202_c1_22.aa | 519 | 409 | 66.75% |
| contig125_3945468_f3_2.aa | 43 | 3448 | 141 | contig242_26599213_c2_10.aa | 423 | 134 | 67.91% |
| contig126_36142138_f2_2.aa | 45 | 3450 | 232 | contig121_255442_f3_1.aa | 232 | 232 | 100.00% |
| contig127_4100463_c1_2.aa | 46 | 3451 | 156 | contig190_14726530_c1_9.aa | 177 | 173 | 60.69% |
| contig128_35162513_c2_6.aa | 48 | 3453 | 262 | contig123_30277138_f2_3.aa | 262 | 262 | 100.00% |
| contig128_4328591_c2_5.aa | 49 | 3454 | 62 | contig123_5119068_c1_4.aa | 62 | 62 | 100.00% |
| contig129_36207812_c1_6.aa | 50 | 3455 | 264 | contig124_33673317_f1_1.aa | 264 | 264 | 100.00% |
| contig129_24645438_c1_5.aa | 51 | 3456 | 266 | contig505_546887_f1_11.aa | 174 | 133 | 79.70% |
| contig13_21973437_c2_4.aa | 53 | 3458 | 80 | contig125_30347635_f1_1.aa | 80 | 80 | 100.00% |
| contig13_4688465_c3_5.aa | 54 | 3459 | 235 | contig126_35601061_c3_2.aa | 235 | 235 | 100.00% |
| contig130_35316275_f2_2.aa | 56 | 3461 | 62 | contig486_30359425_f2_20.aa | 268 | 32 | 65.63% |
| contig130_35194512_c3_3.aa | 57 | 3462 | 162 | contig433_10664787_c1_40.aa | 270 | 161 | 86.34% |
| contig131_782751_f2_2.aa | 58 | 3463 | 168 | contig234_12765875_c2_19.aa | 124 | 118 | 77.97% |
| contig132_26209843_f2_2.aa | 59 | 3464 | 265 | contig216_161000_f3_3.aa | 536 | 265 | 72.45% |
| contig133_4801442_c3_5.aa | 60 | 3465 | 246 | contig478_19706301_f3_18.aa | 230 | 214 | 47.66% |
| contig133_10573524_c1_3.aa | 61 | 3466 | 288 | contig129_7079160_f3_2.aa | 288 | 288 | 100.00% |
| contig134_19823425_f3_2.aa | 62 | 3467 | 238 | contig332_15792212_c2_13.aa | 238 | 91 | 52.75% |
| contig134_35183438_f2_1.aa | 63 | 3468 | 115 | contig371_11720053_c2_14.aa | 408 | 93 | 61.29% |
| contig135_5910176_f3_2.aa | 64 | 3469 | 61 | contig435_24781312_f3_19.aa | 242 | 53 | 66.04% |
| contig135_34177192_f2_1.aa | 65 | 3470 | 194 | contig435_24781312_f3_19.aa | 242 | 193 | 91.71% |
| contig135_11931254_c1_4.aa | 66 | 3471 | 239 | contig131_6142713_f3_3.aa | 161 | 161 | 100.00% |
| contig136_34179767_c2_3.aa | 67 | 3472 | 239 | contig131_5197263_f1_1.aa | 239 | 239 | 100.00% |
| contig137_35406287_f1_1.aa | 68 | 3473 | 369 | contig455_24428387_c3_50.aa | 686 | 362 | 43.92% |
| contig137_2923202_c3_2.aa | 69 | 3474 | 197 | contig132_6524143_f1_2.aa | 197 | 197 | 100.00% |
| contig138_24823512_c3_3.aa | 70 | 3475 | 151 | contig133_26595441_f1_1.aa | 151 | 150 | 100.00% |
| contig138_24328187_f1_1.aa | 71 | 3476 | 205 | contig134_23726062_c1_6.aa | 205 | 205 | 100.00% |
| contig139_14101442_f3_1.aa | 72 | 3477 | 344 | contig296_13714202_f3_12.aa | 458 | 341 | 85.34% |
| contig14_11931555_c3_3.aa | 74 | 3479 | 92 | contig191_23881274_c1_5.aa | 237 | 89 | 60.67% |
| contig140_1073426_c1_1.aa | 76 | 3481 | 269 | contig87_13703181_c2_3.aa | 247 | 221 | 57.47% |
| contig140_12579377_c2_5.aa | 77 | 3482 | 131 | contig468_25546881_c2_45.aa | 581 | 123 | 26.02% |
| contig141_4961528_c2_5.aa | 78 | 3483 | 111 | contig441_21563137_c3_29.aa | 340 | 92 | 63.04% |
| contig141_16611010_f3_3.aa | 80 | 3485 | 68 | contig138_5270942_f1_1.aa | 68 | 68 | 100.00% |
| contig142_289688_c1_4.aa | 81 | 3486 | 137 | contig397_34258337_f3_13.aa | 348 | 135 | 33.33% |
| contig143_23377_f2_3.aa | 85 | 3490 | 313 | contig379_24740936_c1_19.aa | 512 | 298 | 26.17% |
| contig144_34617817_f1_1.aa | 86 | 3491 | 257 | contig141_24648452_f1_1.aa | 257 | 257 | 100.00% |
| contig144_6281316_f2_2.aa | 87 | 3492 | 92 | contig345_24899062_f1_4.aa | 168 | 88 | 64.77% |
| contig145_36133462_f3_1.aa | 88 | 3493 | 153 | contig415_34062502_f1_4.aa | 171 | 148 | 56.08% |
| contig147_26596327_c1_4.aa | 92 | 3497 | 64 | contig483_24105467_c2_34.aa | 174 | 46 | 82.61% |
| contig148_25423317_f2_2.aa | 93 | 3498 | 432 | contig387_24415953_c1_21.aa | 700 | 383 | 27.42% |
| contig149_16406308_f3_4.aa | 94 | 3499 | 116 | contig511_4026518_c1_55.aa | 102 | 57 | 31.58% |
| contig149_2742882_f2_3.aa | 95 | 3500 | 157 | contig287_788182_c1_9.aa | 519 | 141 | 42.55% |
| contig15_3360312_f1_1.aa | 96 | 3501 | 152 | contig435_14714842_c1_32.aa | 323 | 150 | 98.67% |
| contig150_10010957_c1_4.aa | 97 | 3502 | 136 | contig451_4494812_c1_29.aa | 775 | 119 | 77.31% |
| contig150_444662_c3_6.aa | 98 | 3503 | 86 | contig451_20963952_c3_39.aa | 254 | 86 | 61.63% |
| contig150_24042813_c3_5.aa | 99 | 3504 | 63 | contig451_20963952_c3_39.aa | 254 | 36 | 61.11% |
| contig152_5334552_f1_1.aa | 102 | 3507 | 96 | contig423_20320463_c1_22.aa | 123 | 88 | 88.64% |
| contig152_12923552_c1_4.aa | 103 | 3508 | 128 | contig484_4773542_c2_50.aa | 130 | 127 | 39.37% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig153__24636010__f2__2.aa | 105 | 3510 | 102 | contig151__35406555__f1__1.aa | 102 | 102 | 100.00% |
| contig153__5370716__c3__3.aa | 106 | 3511 | 191 | contig151__7081311__f2__2.aa | 191 | 191 | 100.00% |
| contig154__24015950__c3__5.aa | 107 | 3512 | 204 | contig152__3335827__c3__6.aa | 204 | 204 | 100.00% |
| contig155__6095133__f1__1.aa | 109 | 3514 | 170 | contig425__4103427__f1__2.aa | 199 | 166 | 76.51% |
| contig155__19687530__f2__3.aa | 110 | 3515 | 103 | contig425__23937825__f1__3.aa | 325 | 60 | 61.67% |
| contig155__21724200__f1__2.aa | 111 | 3516 | 151 | contig425__23937825__f1__3.aa | 325 | 144 | 43.06% |
| contig156__259825__c3__5.aa | 112 | 3517 | 220 | contig154__31454811__f1__1.aa | 220 | 220 | 100.00% |
| contig156__23953562__c3__4.aa | 113 | 3518 | 181 | contig232__21925337__f2__1.aa | 387 | 88 | 40.91% |
| contig157__14665802__f3__1.aa | 114 | 3519 | 268 | contig417__1054050__f2__12.aa | 755 | 267 | 82.40% |
| contig158__207340__f3__2.aa | 115 | 3520 | 352 | contig305__36540712__f2__8.aa | 390 | 335 | 75.22% |
| contig159__16611577__f3__3.aa | 117 | 3522 | 166 | contig97__16504580__c2__6.aa | 78 | 72 | 72.22% |
| contig16__7082035__f2__1.aa | 118 | 3523 | 322 | contig150__34640906__f1__1.aa | 449 | 249 | 84.34% |
| contig160__2601444__c1__1.aa | 119 | 3524 | 108 | contig443__5891652__c3__21.aa | 175 | 108 | 97.22% |
| contig161__19729692__f3__2.aa | 120 | 3525 | 137 | contig328__129817__c2__18.aa | 308 | 118 | 76.27% |
| contig161__23469005__f2__1.aa | 121 | 3526 | 196 | contig328__129817__c2__18.aa | 308 | 174 | 65.52% |
| contig162__14582001__f1__1.aa | 122 | 3527 | 292 | contig478__35235667__f2__7.aa | 717 | 228 | 17.98% |
| contig163__24331561__c2__5.aa | 123 | 3528 | 341 | contig509__23625427__f1__20.aa | 382 | 338 | 87.87% |
| contig164__35957051__f1__1.aa | 124 | 3529 | 417 | contig160__34636627__f2__1.aa | 417 | 417 | 100.00% |
| contig164__2242937__f1__2.aa | 125 | 3530 | 102 | contig366__24064712__f3__13.aa | 487 | 102 | 44.12% |
| contig165__6542687__f1__2.aa | 127 | 3532 | 107 | contig486__3167677__f2__28.aa | 385 | 85 | 34.12% |
| contig166__34197182__c3__3.aa | 128 | 3533 | 239 | contig236__4727217__f3__6.aa | 221 | 208 | 76.44% |
| contig167__26220638__c1__4.aa | 129 | 3534 | 102 | contig509__4884637__c1__86.aa | 227 | 87 | 51.72% |
| contig167__12535400__c1__3.aa | 130 | 3535 | 166 | contig465__26569505__f3__26.aa | 223 | 156 | 65.39% |
| contig168__24628186__c2__4.aa | 131 | 3536 | 221 | contig443__979713__c2__16.aa | 594 | 207 | 32.37% |
| contig169__14114030__f3__1.aa | 133 | 3538 | 291 | contig463__16210375__f3__17.aa | 336 | 287 | 48.78% |
| contig169__24401533__c3__5.aa | 134 | 3539 | 200 | contig165__21640791__c1__7.aa | 200 | 200 | 100.00% |
| contig17__5117318__f2__1.aa | 135 | 3540 | 360 | contig166__20878791__c1__5.aa | 360 | 360 | 100.00% |
| contig170__24425150__f3__1.aa | 136 | 3541 | 202 | contig468__36120887__c2__48.aa | 822 | 196 | 53.06% |
| contig170__13148452__f3__2.aa | 137 | 3542 | 80 | contig468__36120887__c2__48.aa | 822 | 74 | 35.14% |
| contig171__5098212__f1__1.aa | 138 | 3543 | 189 | contig77__24392882__f1__1.aa | 97 | 81 | 40.74% |
| contig172__16800967__f1__1.aa | 140 | 3545 | 545 | contig415__22849092__f3__14.aa | 623 | 528 | 63.64% |
| contig173__7071877__f1__1.aa | 141 | 3546 | 283 | contig245__12113530__f2__3.aa | 354 | 272 | 29.04% |
| contig174__1300800__c2__3.aa | 142 | 3547 | 113 | contig17__1203327__c3__3.aa | 113 | 113 | 100.00% |
| contig175__6330408__f2__2.aa | 143 | 3548 | 124 | contig35__1453128__f1__1.aa | 254 | 106 | 27.36% |
| contig175__35360936__f3__3.aa | 144 | 3549 | 229 | contig503__24640875__c1__78.aa | 228 | 221 | 28.05% |
| contig176__26306587__c2__6.aa | 146 | 3551 | 241 | contig171__26176375__c1__9.aa | 241 | 241 | 100.00% |
| contig177__13861532__c2__4.aa | 148 | 3553 | 270 | contig340__40932__c1__11.aa | 669 | 304 | 36.84% |
| contig177__26839662__c3__5.aa | 149 | 3554 | 204 | contig498__6773287__c1__34.aa | 79 | 78 | 34.62% |
| contig179__6523282__f1__1.aa | 152 | 3557 | 149 | contig493__34179712__c2__31.aa | 414 | 125 | 33.60% |
| contig179__20078317__f3__3.aa | 153 | 3558 | 175 | contig493__36024193__c1__26.aa | 910 | 175 | 48.00% |
| contig18__25414063__f3__1.aa | 154 | 3559 | 267 | contig149__34292569__c2__9.aa | 382 | 232 | 53.02% |
| contig180__3907966__f1__1.aa | 155 | 3560 | 192 | contig335__32229561__f1__7.aa | 218 | 186 | 32.80% |
| contig181__20507325__f1__1.aa | 156 | 3561 | 181 | contig391__22382927__c3__26.aa | 267 | 177 | 72.32% |
| contig181__34275682__f2__3.aa | 157 | 3562 | 259 | contig391__24807092__c1__18.aa | 333 | 265 | 29.43% |
| contig181__4875063__c2__4.aa | 158 | 3563 | 105 | contig391__6929702__f2__11.aa | 186 | 97 | 70.10% |
| contig182__24808067__c3__7.aa | 160 | 3565 | 127 | contig496__36370187__c1__32.aa | 156 | 125 | 26.40% |
| contig182__31853510__c3__6.aa | 161 | 3566 | 228 | contig395__15836693__c2__15.aa | 391 | 219 | 27.40% |
| contig183__35290627__f2__1.aa | 162 | 3567 | 169 | contig451__24493750__c2__33.aa | 219 | 164 | 55.49% |
| contig183__25680250__f2__2.aa | 163 | 3568 | 315 | contig451__14585967__c3__38.aa | 210 | 197 | 76.14% |
| contig184__34632787__f3__3.aa | 164 | 3569 | 123 | contig211__261593__c2__8.aa | 127 | 109 | 22.94% |
| contig184__34586007__f1__4.aa | 165 | 3570 | 128 | contig137__16828451__c3__18.aa | 118 | 116 | 62.93% |
| contig184__401683__c3__5.aa | 166 | 3571 | 101 | contig509__4900463__c3__113.aa | 338 | 101 | 86.14% |
| contig185__11832325__f2__2.aa | 167 | 3572 | 282 | contig358__26776700__c1__17.aa | 434 | 279 | 74.19% |
| contig185__14272500__c2__4.aa | 168 | 3573 | 121 | contig358__24350652__f2__5.aa | 211 | 117 | 78.63% |
| contig186__36026883__f1__1.aa | 169 | 3574 | 123 | contig179__6260927__c1__8.aa | 123 | 123 | 100.00% |
| contig186__14501578__f2__3.aa | 170 | 3575 | 86 | contig179__33207930__f3__5.aa | 86 | 86 | 100.00% |
| contig187__24742937__c1__5.aa | 171 | 3576 | 64 | contig179__5078155__c1__7.aa | 64 | 64 | 100.00% |
| contig187__35253525__c2__6.aa | 172 | 3577 | 144 | contig179__24415942__c3__11.aa | 144 | 144 | 100.00% |
| contig188__6350281__f1__1.aa | 173 | 3578 | 216 | contig18__9853200__f2__2.aa | 216 | 216 | 100.00% |
| contig189__34252285__c2__3.aa | 174 | 3579 | 319 | contig398__14101593__f3__10.aa | 339 | 251 | 45.02% |
| contig19__32657757__c2__1.aa | 176 | 3581 | 181 | contig297__1057838__c3__14.aa | 79 | 51 | 70.59% |
| contig190__29392275__f2__2.aa | 178 | 3583 | 285 | contig181__282253__f1__1.aa | 285 | 284 | 100.00% |
| contig190__26570830__c1__6.aa | 179 | 3584 | 229 | contig375__25392340__f1__13.aa | 260 | 222 | 59.91% |
| contig190__14631452__c3__7.aa | 180 | 3585 | 72 | contig375__25412811__f1__1.aa | 282 | 70 | 47.14% |
| contig191__24728386__c3__4.aa | 181 | 3586 | 244 | contig503__4876643__c2__102.aa | 789 | 243 | 75.72% |
| contig191__20523312__c2__3.aa | 182 | 3587 | 180 | contig503__4876643__c2__102.aa | 789 | 171 | 79.53% |
| contig192__24656655__f2__3.aa | 183 | 3588 | 96 | contig97__4901707__c1__4.aa | 127 | 89 | 89.89% |
| contig193__7032562__f1__1.aa | 186 | 3591 | 314 | contig390__31678183__c2__15.aa | 256 | 250 | 86.40% |
| contig194__1953142__f1__1.aa | 188 | 3593 | 173 | contig476__46386719__c1__7.aa | 257 | 121 | 58.68% |
| contig194__32226087__f2__2.aa | 189 | 3594 | 284 | contig476__46386719__c1__7.aa | 257 | 168 | 62.50% |
| contig195__4884708__c3__3.aa | 190 | 3595 | 415 | contig350__14587505__c3__12.aa | 386 | 316 | 53.80% |
| contig196__22270327__f3__4.aa | 191 | 3596 | 60 | contig429__3026702__f3__20.aa | 228 | 59 | 54.24% |
| contig196__30578406__c3__6.aa | 192 | 3597 | 71 | contig417__26689067__f2__10.aa | 355 | 65 | 64.62% |
| contig196__23906264__c1__5.aa | 193 | 3598 | 463 | contig417__26689067__f2__10.aa | 355 | 297 | 82.16% |
| contig197__21680187__f2__2.aa | 194 | 3599 | 82 | contig188__11182836__f3__2.aa | 82 | 82 | 100.00% |
| contig2__23646932__f2__1.aa | 197 | 3602 | 95 | contig339__6150437__f1__2.aa | 128 | 70 | 37.14% |
| contig20__23632010__f3__1.aa | 198 | 3603 | 153 | contig502__5272126__c3__53.aa | 721 | 154 | 61.04% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig20_32429577_f3_2.aa | 199 | 3604 | 128 | contig256_22868762_c3_19.aa | 73 | 69 | 39.13% |
| contig200_16142807_f3_2.aa | 200 | 3605 | 66 | contig293_16609642_f2_3.aa | 649 | 43 | 76.74% |
| contig200_2460378_c3_7.aa | 202 | 3607 | 168 | contig373_11223286_c2_13.aa | 62 | 55 | 56.36% |
| contig201_10664542_f1_3.aa | 203 | 3608 | 332 | contig225_2210312_f2_2.aa | 431 | 230 | 25.65% |
| contig202_34084415_f3_3.aa | 204 | 3609 | 63 | contig509_4884671_c1_86.aa | 227 | 64 | 53.13% |
| contig202_3945463_f3_4.aa | 205 | 3610 | 442 | contig509_24860083_c2_106.aa | 454 | 443 | 79.23% |
| contig202_32242840_f1_1.aa | 206 | 3611 | 77 | contig509_31426437_c1_88.aa | 172 | 59 | 71.19% |
| contig203_22868761_f1_1.aa | 207 | 3612 | 138 | contig396_16422552_f2_6.aa | 188 | 93 | 22.58% |
| contig203_25676592_f3_2.aa | 208 | 3613 | 575 | contig190_21516680_c3_13.aa | 575 | 575 | 100.00% |
| contig204_3946941_c1_3.aa | 209 | 3614 | 132 | contig402_24495467_f2_10.aa | 119 | 119 | 36.98% |
| contig204_7244062_c3_4.aa | 210 | 3615 | 82 | contig402_3907135_f3_18.aa | 85 | 78 | 38.46% |
| contig205_5132817_f2_1.aa | 211 | 3616 | 297 | contig247_4901711_f3_8.aa | 325 | 297 | 51.85% |
| contig206_19728452_c2_8.aa | 212 | 3617 | 274 | contig469_19728426_f1_17.aa | 153 | 150 | 54.00% |
| contig206_25445312_c1_6.aa | 215 | 3620 | 185 | contig469_4023593_f3_16.aa | 415 | 173 | 57.80% |
| contig207_36375811_f1_1.aa | 216 | 3621 | 266 | contig245_12113530_f2_3.aa | 354 | 257 | 78.60% |
| contig207_23957837_c2_3.aa | 217 | 3622 | 206 | contig245_15628125_c3_15.aa | 847 | 200 | 48.00% |
| contig208_969452_c3_3.aa | 218 | 3623 | 241 | contig511_34175252_c2_67.aa | 291 | 232 | 28.02% |
| contig209_35406412_f2_1.aa | 219 | 3624 | 178 | contig107_2151058_f3_3.aa | 115 | 111 | 60.36% |
| contig209_22526950_f3_2.aa | 220 | 3625 | 127 | contig107_32212575_f1_2.aa | 109 | 101 | 73.27% |
| contig209_24414127_f3_3.aa | 221 | 3626 | 295 | contig193_3401928_c1_11.aa | 295 | 295 | 100.00% |
| contig209_3907127_f3_4.aa | 222 | 3627 | 72 | contig509_23625427_f1_20.aa | 382 | 50 | 52.00% |
| contig21_4328382_c3_1.aa | 223 | 3628 | 152 | contig490_1407563_c1_53.aa | 254 | 143 | 49.65% |
| contig210_32221951_c3_1.aa | 224 | 3629 | 235 | contig366_4882937_f1_3.aa | 281 | 226 | 69.03% |
| contig211_14648452_c2_6.aa | 225 | 3630 | 229 | contig469_2985905_f1_4.aa | 258 | 219 | 39.27% |
| contig212_19579212_c3_1.aa | 226 | 3631 | 138 | contig195_2526555_f3_4.aa | 138 | 138 | 100.00% |
| contig214_5164025_f1_1.aa | 230 | 3635 | 300 | contig474_34182687_c2_35.aa | 208 | 135 | 26.67% |
| contig215_22535885_c3_2.aa | 231 | 3636 | 161 | contig196_26459687_c2_10.aa | 161 | 161 | 100.00% |
| contig215_25667192_f1_1.aa | 232 | 3637 | 123 | contig86_1175293_c1_5.aa | 210 | 123 | 77.24% |
| contig216_24025151_c2_3.aa | 233 | 3638 | 305 | contig272_6664000_c3_20.aa | 333 | 233 | 31.33% |
| contig216_20488149_c1_2.aa | 234 | 3639 | 144 | contig445_9959767_c1_43.aa | 549 | 104 | 26.92% |
| contig217_10743932_c3_6.aa | 237 | 3642 | 132 | contig488_2759566_c2_43.aa | 347 | 128 | 91.41% |
| contig218_34570202_f3_1.aa | 238 | 3643 | 308 | contig441_2242936_f3_15.aa | 648 | 226 | 28.32% |
| contig219_16853152_f2_2.aa | 239 | 3644 | 205 | contig199_26015691_f2_2.aa | 205 | 205 | 100.00% |
| contig22_23457281_f3_1.aa | 240 | 3645 | 288 | contig447_14223437_c2_31.aa | 426 | 268 | 54.10% |
| contig220_17002213_c1_3.aa | 241 | 3646 | 138 | contig205_14657875_f1_3.aa | 190 | 140 | 57.14% |
| contig220_25679500_c3_4.aa | 242 | 3647 | 214 | contig205_3948338_f3_4.aa | 283 | 207 | 62.80% |
| contig221_4039802_f2_1.aa | 243 | 3648 | 280 | contig87_13703181_c2_3.aa | 247 | 118 | 29.66% |
| contig221_34195262_f3_2.aa | 244 | 3649 | 169 | contig279_24423588_f3_9.aa | 430 | 117 | 23.93% |
| contig222_12218900_f2_2.aa | 245 | 3650 | 104 | contig200_33208266_f2_4.aa | 104 | 104 | 100.00% |
| contig222_16822026_f3_3.aa | 246 | 3651 | 273 | contig397_34258337_f1_13.aa | 348 | 198 | 35.35% |
| contig222_30078177_f3_4.aa | 247 | 3652 | 188 | contig461_4307062_c2_45.aa | 337 | 186 | 70.43% |
| contig223__33400316_c2_5.aa | 248 | 3653 | 132 | contig395_15836093_c2_15.aa | 391 | 125 | 32.00% |
| contig223_864187_c2_4.aa | 249 | 3654 | 220 | contig440_1369013_f3_7.aa | 493 | 220 | 28.64% |
| contig224_23523557_c1_5.aa | 250 | 3655 | 84 | contig412_25596051_f2_11.aa | 214 | 79 | 39.24% |
| contig224_6739062_c3_7.aa | 252 | 3657 | 315 | contig363_9267066_c2_20.aa | 353 | 318 | 38.68% |
| contig225_35394531_f2_1.aa | 253 | 3658 | 227 | contig330_31250463_c2_16.aa | 318 | 206 | 66.02% |
| contig225_33396937_f1_2.aa | 254 | 3659 | 663 | contig202_13070292_c1_8.aa | 696 | 585 | 83.76% |
| contig226_7146942_c1_5.aa | 255 | 3660 | 202 | contig158_4074027_f2_1.aa | 252 | 140 | 28.57% |
| contig228_33672192_f2_1.aa | 259 | 3664 | 409 | contig350_14587505_c3_12.aa | 386 | 376 | 70.48% |
| contig229_158568_f1_1.aa | 260 | 3665 | 281 | contig353_15720716_f3_7.aa | 297 | 269 | 53.16% |
| contig23_26179687_c3_5.aa | 261 | 3666 | 129 | contig472_29306501_c1_27.aa | 129 | 113 | 72.57% |
| contig23_494557_c3_4.aa | 262 | 3667 | 128 | contig472_24664692_c2_31.aa | 1242 | 116 | 46.55% |
| contig230_33401717_c1_3.aa | 263 | 3668 | 283 | contig205_3948338_f3_4.aa | 283 | 283 | 100.00% |
| contig232_14652268_c2_2.aa | 266 | 3671 | 285 | contig181_282253_f1_1.aa | 285 | 275 | 64.00% |
| contig233_11116326_f2_1.aa | 267 | 3672 | 294 | contig206_30270437_c3_10.aa | 294 | 294 | 100.00% |
| contig234_22474077_c1_3.aa | 268 | 3673 | 274 | contig490_24431587_f1_5.aa | 673 | 280 | 46.43% |
| contig234_22464077_f1_1.aa | 269 | 3674 | 116 | contig123_30277138_f2_3.aa | 262 | 118 | 65.25% |
| contig235_30642252_f3_3.aa | 270 | 3675 | 567 | contig421_34651562_f2_11.aa | 717 | 564 | 45.39% |
| contig236_99932836_c1_3.aa | 271 | 3676 | 164 | contig193_3401928_c1_11.aa | 295 | 64 | 87.50% |
| contig236_14567268_c1_2.aa | 272 | 3677 | 101 | contig207_13751251_f2_3.aa | 101 | 101 | 100.00% |
| contig237_25439437_c3_7.aa | 273 | 3678 | 250 | contig499_34240836_c3_83.aa | 277 | 232 | 27.59% |
| contig238_26423437_f1_1.aa | 275 | 3680 | 252 | contig355_23995942_f2_3.aa | 314 | 234 | 57.27% |
| contig238_33261461_f2_3.aa | 276 | 3681 | 122 | contig209_867813_c2_8.aa | 122 | 122 | 100.00% |
| contig239_7082001_f1_1.aa | 278 | 3683 | 66 | contig326_24619150_11_1.aa | 203 | 58 | 77.59% |
| contig239_35979692_f3_2.aa | 279 | 3684 | 263 | contig209_5289812_c3_1_1.aa | 263 | 263 | 100.00% |
| contig24_15026400_c1_3.aa | 280 | 3685 | 226 | contig256_23707580_c2_17.aa | 445 | 218 | 32.11% |
| contig240_20000332_c3_6.aa | 281 | 3686 | 433 | contig447_14223437_c2_31.aa | 426 | 422 | 82.23% |
| contig241_16532892_f2_3.aa | 282 | 3687 | 91 | contig285_976550_f3_7.aa | 247 | 35 | 54.29% |
| contig241_23992175_f1_2.aa | 283 | 3688 | 282 | contig36_24892763_c3_4.aa | 167 | 158 | 82.28% |
| contig242_4431426_f1_1.aa | 285 | 3690 | 347 | contig339_24641250_f1_3.aa | 144 | 66 | 36.36% |
| contig243_1370311_f2_1.aa | 287 | 3692 | 362 | contig499_34065626_c1_60.aa | 410 | 372 | 32.53% |
| contig244_1222061_f2_2.aa | 288 | 3693 | 101 | contig263_292944_c2_12.aa | 709 | 82 | 45.12% |
| contig244_14629663_f1_1.aa | 289 | 3694 | 492 | contig401_24007952_c2_26.aa | 478 | 472 | 42.59% |
| contig246_35391578_f2_2.aa | 293 | 3698 | 259 | contig212_12288180_c3_22.aa | 290 | 151 | 45.03% |
| contig247_30565805_f3_2.aa | 294 | 3699 | 431 | contig212_23650256_c2_19.aa | 149 | 149 | 100.00% |
| contig249_4804703_c3_8.aa | 297 | 3702 | 151 | contig477_21676577_f2_10.aa | 165 | 112 | 28.57% |
| contig249_30272056_c2_6.aa | 299 | 3704 | 171 | contig212_25673799_c1_15.aa | 105 | 105 | 100.00% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig250_13923401_c3_5.aa | 301 | 3706 | 389 | contig486_24650302_f1_4.aa | 390 | 381 | 59.84% |
| contig250_129032_c2_4.aa | 302 | 3707 | 357 | contig214_24492338_c2_5.aa | 385 | 278 | 99.64% |
| contig251_34414724_c1_4.aa | 304 | 3709 | 478 | contig500_34179817_c2_72.aa | 491 | 363 | 43.80% |
| contig252_26260912_f2_1.aa | 306 | 3711 | 78 | contig215_26775936_c1_6.aa | 78 | 78 | 100.00% |
| contig252_6064443_f3_3.aa | 307 | 3712 | 275 | contig215_4064078_c1_5.aa | 275 | 275 | 100.00% |
| contig253_34179786_c2_2.aa | 308 | 3713 | 234 | contig215_45562718_c2_8.aa | 234 | 234 | 100.00% |
| contig254_33243877_f3_6.aa | 310 | 3715 | 124 | contig469_31797875_f2_7.aa | 122 | 113 | 30.97% |
| contig254_14667842_f2_5.aa | 311 | 3716 | 291 | contig355_15125405_f2_5.aa | 284 | 263 | 40.68% |
| contig255_22470386_f2_2.aa | 313 | 3718 | 173 | contig217_31908561_f1_1.aa | 64 | 64 | 100.00% |
| contig256_38557_f2_2.aa | 314 | 3719 | 82 | contig218_32085953_c2_12.aa | 82 | 82 | 100.00% |
| contig256_33802182_f1_1.aa | 315 | 3720 | 266 | contig301_33710307_c3_13.aa | 487 | 254 | 92.52% |
| contig257_7070428_c3_3.aa | 316 | 3721 | 155 | contig166_20878791_c1_5.aa | 360 | 54 | 79.63% |
| contig257_24300674_c1_2.aa | 318 | 3723 | 211 | contig501_22460816_c2_51.aa | 400 | 210 | 98.57% |
| contig258_12219781_f3_3.aa | 319 | 3724 | 278 | contig351_14878802_c2_23.aa | 544 | 272 | 31.25% |
| contig258_23604838_f2_2.aa | 321 | 3726 | 91 | contig510_12698577_c3_117.aa | 631 | 78 | 38.46% |
| contig259_1172752_f2_3.aa | 322 | 3727 | 291 | contig219_583285_c2_8.aa | 291 | 291 | 100.00% |
| contig259_423125_f1_1.aa | 323 | 3728 | 255 | contig359_25580342_c3_12.aa | 246 | 240 | 26.67% |
| contig259_4814625_f2_4.aa | 324 | 3729 | 252 | contig192_19636050_c3_5.aa | 190 | 144 | 28.47% |
| contig26_23647555_c1_3.aa | 325 | 3730 | 239 | contig189_2399192_c3_9.aa | 212 | 211 | 64.93% |
| contig260_14220443_f1_1.aa | 326 | 3731 | 69 | contig220_4789068_f1_1.aa | 69 | 69 | 100.00% |
| contig260_25651702_c3_6.aa | 327 | 3732 | 394 | contig183_36225926_c2_4.aa | 393 | 387 | 72.35% |
| contig261_781432_f3_1.aa | 328 | 3733 | 257 | contig221_14881900_c2_13.aa | 257 | 257 | 100.00% |
| contig261_33292342_c3_2.aa | 329 | 3734 | 68 | contig443_33292342_f1_1.aa | 68 | 68 | 95.59% |
| contig262_15710913_f3_2.aa | 330 | 3735 | 418 | contig502_157717_c2_47.aa | 473 | 417 | 69.07% |
| contig263_4688263_f1_1.aa | 331 | 3736 | 208 | contig313_14725287_c3_16.aa | 483 | 186 | 76.34% |
| contig264_7082026_f1_1.aa | 332 | 3737 | 295 | contig481_5879557_f1_3.aa | 339 | 229 | 30.57% |
| contig265_29392933_f1_1.aa | 333 | 3738 | 382 | contig66_26375453_f1_1.aa | 237 | 229 | 69.00% |
| contig266_26023917_f1_1.aa | 334 | 3739 | 175 | contig483_4869017_f2_13.aa | 193 | 155 | 83.87% |
| contig266_21679664_c2_5.aa | 336 | 3741 | 60 | contig223_23922806_f3_11.aa | 60 | 60 | 100.00% |
| contig267_2757327_c1_3.aa | 337 | 3742 | 70 | contig223_13017917_f2_8.aa | 70 | 70 | 100.00% |
| contig268_14875000_f1_1.aa | 340 | 3745 | 540 | contig476_6253_f1_2.aa | 731 | 337 | 27.30% |
| contig269_3917842_c3_9.aa | 341 | 3746 | 171 | contig345_26181537_f3_17.aa | 184 | 150 | 72.67% |
| contig269_23697187_c1_5.aa | 342 | 3747 | 226 | contig345_36062917_f3_15.aa | 121 | 120 | 48.33% |
| contig269_29785134_c2_6.aa | 343 | 3748 | 364 | contig345_6523576_f2_11.aa | 353 | 350 | 59.71% |
| contig27_36366450_f2_1.aa | 344 | 3749 | 181 | contig351_3907968_c2_22.aa | 906 | 178 | 30.90% |
| contig270_35407675_f2_2.aa | 345 | 3750 | 471 | contig492_33398450_f1_1.aa | 662 | 461 | 80.48% |
| contig271_34661566_c2_4.aa | 346 | 3751 | 111 | contig331_26776461_c1_13.aa | 300 | 104 | 32.69% |
| contig271_26250012_c3_5.aa | 347 | 3752 | 406 | contig509_23625427_f1_20.aa | 382 | 369 | 36.31% |
| contig272_209811_f1_1.aa | 348 | 3753 | 243 | contig164_34589052_f2_1.aa | 319 | 243 | 76.13% |
| contig272_21978881_c1_2.aa | 349 | 3754 | 359 | contig210_6837500_c3_13.aa | 155 | 145 | 50.35% |
| contig273_26760250_c1_2.aa | 351 | 3756 | 91 | contig368_6929687_f2_8.aa | 215 | 82 | 62.20% |
| contig274_969092_f2_1.aa | 352 | 3757 | 255 | contig498_3944212_c3_49.aa | 333 | 119 | 27.73% |
| contig275_4042878_c2_2.aa | 356 | 3761 | 289 | contig228_1188577_c2_13.aa | 289 | 289 | 100.00% |
| contig276_14954143_c2_8.aa | 357 | 3762 | 144 | contig274_30115936_f1_3.aa | 202 | 128 | 67.19% |
| contig276_23445432_c1_5.aa | 358 | 3763 | 158 | contig222_35163169_c2_8.aa | 176 | 148 | 57.43% |
| contig277_6736631_f3_2.aa | 359 | 3764 | 170 | contig228_5939790_c3_15.aa | 170 | 170 | 100.00% |
| contig277_5116543_f3_3.aa | 360 | 3765 | 130 | contig433_24414717_c3_50.aa | 203 | 121 | 81.82% |
| contig278_31461062_c3_2.aa | 361 | 3766 | 71 | contig229_5361561_f1_1.aa | 71 | 71 | 100.00% |
| contig279_26282885_f3_5.aa | 362 | 3767 | 108 | contig229_16682836_f2_3.aa | 108 | 108 | 100.00% |
| contig28_53886_f1_1.aa | 364 | 3769 | 145 | contig242_26599213_c2_10.aa | 423 | 142 | 64.79% |
| contig28_5197813_f1_2.aa | 365 | 3770 | 151 | contig242_26442131_c1_9.aa | 200 | 147 | 46.94% |
| contig280_12188261_f1_1.aa | 366 | 3771 | 129 | contig230_4788941_c3_6.aa | 129 | 129 | 100.00% |
| contig280_24406282_f3_4.aa | 367 | 3772 | 74 | contig230_24805312_f1_3.aa | 74 | 74 | 100.00% |
| contig281_29882092_c3_7.aa | 369 | 3774 | 66 | contig306_6648337_c3_28.aa | 191 | 29 | 34.48% |
| contig281_56552_f3_1.aa | 370 | 3775 | 159 | contig230_16807806_c3_5.aa | 159 | 159 | 100.00% |
| contig282_245962_c3_4.aa | 371 | 3776 | 339 | contig231_26365925_c3_4.aa | 339 | 339 | 100.00% |
| contig282_19688909_c2_3.aa | 372 | 3777 | 73 | contig413_5114455_f1_3.aa | 280 | 51 | 52.94% |
| contig283_25820313_f1_1.aa | 373 | 3778 | 215 | contig410_36125000_c3_23.aa | 283 | 209 | 33.49% |
| contig284_902187_c3_7.aa | 375 | 3780 | 258 | contig416_24662501_f3_19.aa | 230 | 207 | 22.71% |
| contig284_24643812_f2_2.aa | 376 | 3781 | 254 | contig243_29578175_f1_1.aa | 214 | 188 | 39.36% |
| contig285_9881557_f2_3.aa | 380 | 3785 | 145 | contig234_34180380_c1_17.aa | 145 | 145 | 100.00% |
| contig286_963342_c1_3.aa | 381 | 3786 | 364 | contig234_16056341_c1_16.aa | 364 | 364 | 100.00% |
| contig287_20745436_f3_2.aa | 382 | 3787 | 291 | contig294_34117967_f1_3.aa | 235 | 212 | 35.38% |
| contig287_93757_f3_3.aa | 383 | 3788 | 159 | contig502_23446063_f1_2.aa | 390 | 138 | 21.74% |
| contig288_25673900_f3_1.aa | 384 | 3789 | 227 | contig356_26808437_f2_2.aa | 250 | 223 | 48.43% |
| contig288_24242056_c3_5.aa | 385 | 3790 | 158 | contig463_15089663_c3_49.aa | 496 | 127 | 36.22% |
| contig289_7082027_f1_1.aa | 386 | 3791 | 87 | contig235_22656701_f3_6.aa | 87 | 87 | 100.00% |
| contig29_13006930_f2_1.aa | 387 | 3792 | 215 | contig235_11901667_c3_13.aa | 215 | 215 | 100.00% |
| contig29_13711592_f2_2.aa | 388 | 3793 | 168 | contig199_26015691_f2_2.aa | 205 | 163 | 55.83% |
| contig290_26808211_f3_3.aa | 389 | 3794 | 448 | contig307_22057333_f1_1.aa | 413 | 408 | 69.85% |
| contig290_24875093_f1_1.aa | 390 | 3795 | 80 | contig459_34574092_f1_5.aa | 674 | 64 | 85.94% |
| contig291_12508578_f2_1.aa | 391 | 3796 | 483 | contig408_35314168_c2_42.aa | 514 | 415 | 64.58% |
| contig291_26282182_f2_2.aa | 392 | 3797 | 168 | contig236_26803192_f3_5.aa | 168 | 168 | 100.00% |
| contig292_3928318_f1_1.aa | 393 | 3798 | 200 | contig389_34070332_c2_23.aa | 205 | 198 | 89.90% |
| contig292_34187592_c2_3.aa | 394 | 3799 | 180 | contig453_516027_13_31.aa | 192 | 179 | 59.78% |
| contig293_24431562_c2_4.aa | 395 | 3800 | 194 | contig429_26460925_c2_37.aa | 416 | 193 | 55.44% |
| contig293_24413142_c2_3.aa | 396 | 3801 | 181 | contig65_1054667_c2_5.aa | 178 | 161 | 32.30% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig294_22400450_f3_2.aa | 397 | 3802 | 585 | contig401_35579687_c3_29.aa | 368 | 359 | 92.20% |
| contig296_14142542_f3_3.aa | 401 | 3806 | 107 | contig417_3131500_f3_16.aa | 269 | 103 | 53.40% |
| contig296_34063527_f2_1.aa | 402 | 3807 | 321 | contig417_13864818_f2_8.aa | 236 | 231 | 76.62% |
| contig297_5161663_f1_1.aa | 403 | 3808 | 596 | contig478_35235667_f2_7.aa | 717 | 554 | 79.42% |
| contig299_4798587_f3_1.aa | 406 | 3811 | 578 | contig275_4489213_f1_2.aa | 855 | 751 | 30.49% |
| contig3_24410169_c1_1.aa | 407 | 3812 | 142 | contig179_24415942_c3_11.aa | 144 | 117 | 37.61% |
| contig30_33861563_c1_4.aa | 408 | 3813 | 345 | contig301_26745337_c1_11.aa | 323 | 296 | 76.69% |
| contig300_10353950_f2_2.aa | 409 | 3814 | 335 | contig321_7229093_f1_1.aa | 435 | 326 | 78.22% |
| contig300_35432011_f1_1.aa | 410 | 3815 | 129 | contig321_24804702_f1_2.aa | 900 | 116 | 79.31% |
| contig300_10007652_f3_3.aa | 411 | 3816 | 68 | contig321_24804702_f1_2.aa | 900 | 39 | 53.85% |
| contig301_26375006_f2_1.aa | 412 | 3817 | 429 | contig245_15628125_c3_15.aa | 847 | 402 | 62.94% |
| contig301_2625187_f2_2.aa | 413 | 3818 | 62 | contig245_15628125_c3_15.aa | 847 | 27 | 55.56% |
| contig302_36223418_f3_2.aa | 414 | 3819 | 74 | contig240_29505312_c3_8.aa | 74 | 74 | 100.00% |
| contig302_15117317_f1_1.aa | 415 | 3820 | 304 | contig240_14667801_c2_6.aa | 304 | 304 | 100.00% |
| contig303_21875903_f3_3.aa | 416 | 3821 | 161 | contig479_112882_f2_6.aa | 159 | 161 | 42.86% |
| contig303_4884838_f2_2.aa | 417 | 3822 | 281 | contig479_16187501_f2_7.aa | 354 | 215 | 34.88% |
| contig304_6285250_c3_3.aa | 419 | 3824 | 249 | contig478_33362800_c3_41.aa | 299 | 243 | 69.55% |
| contig305_31533516_c3_6.aa | 420 | 3825 | 408 | contig433_35952_c1_43.aa | 424 | 407 | 57.99% |
| contig306_26383507_c3_9.aa | 421 | 3826 | 283 | contig449_1250141_c1_40.aa | 314 | 278 | 50.00% |
| contig306_4343752_f3_6.aa | 422 | 3827 | 65 | contig242_29531562_c3_12.aa | 65 | 65 | 100.00% |
| contig307_14537691_f2_2.aa | 423 | 3828 | 128 | contig242_25585008_c1_8.aa | 92 | 92 | 100.00% |
| contig307_35937841_c1_4.aa | 424 | 3829 | 382 | contig425_3906313_f2_11.aa | 318 | 313 | 59.11% |
| contig309_13183591_f3_4.aa | 426 | 3831 | 95 | contig485_15115642_f3_22.aa | 439 | 65 | 38.46% |
| contig309_34100687_f2_3.aa | 427 | 3832 | 220 | contig288_24645157_f3_3.aa | 212 | 212 | 49.06% |
| contig31_24687678_c3_4.aa | 429 | 3834 | 211 | contig244_4736627_c3_12.aa | 211 | 211 | 100.00% |
| contig310_15120887_f2_1.aa | 430 | 3835 | 444 | contig148_4384652_f1_1.aa | 383 | 229 | 96.07% |
| contig311_36329057_f1_1.aa | 431 | 3836 | 60 | contig244_35937592_c2_9.aa | 60 | 60 | 100.00% |
| contig311_5271078_f2_2.aa | 432 | 3837 | 82 | contig455_24667087_c3_49.aa | 426 | 82 | 51.22% |
| contig312_1283452_f2_2.aa | 433 | 3838 | 552 | contig256_22464375_c1_14.aa | 606 | 552 | 40.22% |
| contig314_4720463_c1_3.aa | 437 | 3842 | 123 | contig271_6417137_f2_2.aa | 345 | 112 | 33.04% |
| contig315_5196062_f1_3.aa | 439 | 3844 | 145 | contig436_15039038_f3_11.aa | 270 | 145 | 31.03% |
| contig315_16979712_f1_1.aa | 440 | 3845 | 382 | contig246_34071008_f2_2.aa | 382 | 382 | 100.00% |
| contig316_34157952_c1_3.aa | 441 | 3846 | 325 | contig247_4901711_f3_8.aa | 325 | 325 | 100.00% |
| contig316_207811_c2_4.aa | 442 | 3847 | 266 | contig469_34626877_f2_10.aa | 270 | 224 | 28.13% |
| contig317_1220462_f2_1.aa | 443 | 3848 | 556 | contig367_29322150_f1_1.aa | 745 | 553 | 86.08% |
| contig318_11754215_f2_1.aa | 444 | 3849 | 451 | contig282_6057318_f3_1.aa | 564 | 447 | 62.86% |
| contig319_4876643_c2_3.aa | 446 | 3851 | 252 | contig249_4882877_f1_1.aa | 252 | 252 | 100.00% |
| contig319_2932937_c3_4.aa | 447 | 3852 | 351 | contig249_24884838_f3_5.aa | 351 | 351 | 100.00% |
| contig320_13001076_c1_13.aa | 450 | 3855 | 244 | contig25_24899175_c1_4.aa | 244 | 244 | 100.00% |
| contig320_33835942_f3_8.aa | 451 | 3856 | 61 | contig25_35817062_c2_5.aa | 61 | 61 | 100.00% |
| contig320_4695187_f2_7.aa | 452 | 3857 | 79 | contig250_24417177_f3_2.aa | 79 | 79 | 100.00% |
| contig321_25430443_c3_4.aa | 453 | 3858 | 333 | contig267_14890705_c2_16.aa | 376 | 239 | 47.28% |
| contig322_35839066_c2_3.aa | 455 | 3860 | 102 | contig250_26767800_f3_3.aa | 102 | 102 | 100.00% |
| contig322_24394206_c1_2.aa | 456 | 3861 | 425 | contig273_21541281_c2_12.aa | 449 | 433 | 29.33% |
| contig324_33395317_c3_11.aa | 460 | 3865 | 280 | contig309_991702_f1_2.aa | 284 | 264 | 80.68% |
| contig324_9923452_c2_10.aa | 461 | 3866 | 162 | contig309_22442162_f1_1.aa | 164 | 152 | 68.42% |
| contig324_10724144_c1_8.aa | 462 | 3867 | 159 | contig102_864818_f1_1.aa | 124 | 118 | 31.36% |
| contig325_25977343_c3_10.aa | 463 | 3868 | 259 | contig174_24648265_c3_13.aa | 250 | 245 | 54.29% |
| contig325_24803800_c1_7.aa | 464 | 3869 | 179 | contig252_12696068_c1_8.aa | 179 | 179 | 100.00% |
| contig326_30562806_f3_2.aa | 465 | 3870 | 604 | contig506_23572187_c1_69.aa | 1057 | 631 | 20.92% |
| contig327_198302_f2_2.aa | 466 | 3871 | 640 | contig453_19742312_f1_1.aa | 655 | 485 | 63.09% |
| contig327_34652213_c1_6.aa | 467 | 3872 | 94 | contig365_34501568_c3_35.aa | 148 | 95 | 26.32% |
| contig328_6445250_f1_1.aa | 469 | 3874 | 437 | contig420_26369063_c3_33.aa | 431 | 406 | 33.01% |
| contig328_4098527_f2_2.aa | 471 | 3876 | 570 | contig253_34265693_c2_11.aa | 570 | 570 | 100.00% |
| contig328_4882827_f3_6.aa | 472 | 3877 | 80 | contig214_24492338_c2_5.aa | 385 | 52 | 46.15% |
| contig329_1050900_c1_2.aa | 474 | 3879 | 125 | contig254_400716_f3_6.aa | 125 | 125 | 100.00% |
| contig33_33237700_c2_2.aa | 475 | 3880 | 60 | contig254_14455387_f2_5.aa | 60 | 60 | 100.00% |
| contig330_4414768_f1_1.aa | 476 | 3881 | 85 | contig254_23829635_f1_3.aa | 85 | 85 | 100.00% |
| contig330_25673512_f1_2.aa | 477 | 3882 | 172 | contig255_12504386_f2_4.aa | 172 | 172 | 100.00% |
| contig331_19582805_f2_5.aa | 480 | 3885 | 267 | contig131_6142713_f3_3.aa | 161 | 124 | 72.58% |
| contig332_94063_c3_7.aa | 482 | 3887 | 445 | contig256_23707580_c2_17.aa | 445 | 445 | 100.00% |
| contig333_35401562_c2_4.aa | 483 | 3888 | 125 | contig318_35429712_c1_13.aa | 293 | 111 | 63.06% |
| contig333_10801250_c1_3.aa | 484 | 3889 | 231 | contig478_19706301_f3_18.aa | 230 | 226 | 75.22% |
| contig333_985383_c3_5.aa | 485 | 3890 | 128 | contig478_35235667_f2_7.aa | 717 | 128 | 76.56% |
| contig334_26384567_f1_1.aa | 486 | 3891 | 179 | contig366_24064712_f3_13.aa | 487 | 157 | 42.68% |
| contig334_26603431_f3_4.aa | 487 | 3892 | 311 | contig366_26615760_f2_9.aa | 310 | 310 | 67.74% |
| contig335_9766068_f1_1.aa | 488 | 3893 | 472 | contig424_26382202_f1_3.aa | 648 | 470 | 54.04% |
| contig336_26572687_f2_2.aa | 489 | 3894 | 446 | contig265_5370937_c2_15.aa | 586 | 450 | 56.44% |
| contig336_36189717_f1_1.aa | 490 | 3895 | 109 | contig265_5109677_c3_17.aa | 106 | 100 | 71.00% |
| contig337_4118938_f3_1.aa | 491 | 3896 | 152 | contig257_29337535_c1_4.aa | 152 | 152 | 100.00% |
| contig337_24430287_f3_2.aa | 492 | 3897 | 329 | contig371_11897656_c3_17.aa | 469 | 314 | 32.48% |
| contig338_6929713_f2_3.aa | 495 | 3900 | 163 | contig258_16511067_c1_9.aa | 163 | 163 | 100.00% |
| contig339_33361378_f3_6.aa | 496 | 3901 | 683 | contig258_10651003_c1_8.aa | 683 | 683 | 100.00% |
| contig339_19723451_c2_7.aa | 497 | 3902 | 496 | contig367_23634628_c2_15.aa | 527 | 480 | 84.79% |
| contig34_4867943_c2_3.aa | 498 | 3903 | 175 | contig202_34641436_c2_9.aa | 177 | 171 | 92.40% |
| contig340_79806_f2_1.aa | 499 | 3904 | 145 | contig368_3392837_f1_1.aa | 347 | 143 | 48.25% |
| contig340_52318_f2_2.aa | 500 | 3905 | 262 | contig368_1995327_f3_11.aa | 245 | 251 | 43.03% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig341__31773887__c1__3.aa | 501 | 3906 | 555 | contig495__14741253__c3__66.aa | 585 | 529 | 48.39% |
| contig341__11896090__c2__4.aa | 502 | 3907 | 194 | contig260__34641818__c3__28.aa | 194 | 194 | 100.00% |
| contig342__31742010__f3__1.aa | 503 | 3908 | 446 | contig441__2242936__f3__15.aa | 648 | 451 | 44.35% |
| contig343__1208443__f3__3.aa | 505 | 3910 | 255 | contig417__3131500__f3__16.aa | 269 | 236 | 29.24% |
| contig344__23494127__c1__3.aa | 507 | 3912 | 100 | contig260__11961635__c2__19.aa | 100 | 100 | 100.00% |
| contig344__36070188__c2__4.aa | 508 | 3913 | 226 | contig260__10664213__c3__26.aa | 226 | 226 | 100.00% |
| contig344__23849218__c3__5.aa | 509 | 3914 | 220 | contig440__1369013__f3__7.aa | 493 | 196 | 27.55% |
| contig345__4571905__c2__1.aa | 511 | 3916 | 84 | contig419__421937__f2__13.aa | 592 | 70 | 28.57% |
| contig347__26766903__f2__2.aa | 517 | 3922 | 240 | contig262__6054077__c2__18.aa | 161 | 161 | 100.00% |
| contig347__24398507__c1__5.aa | 518 | 3923 | 133 | contig328__6695327__c2__19.aa | 450 | 130 | 89.23% |
| contig348__12303138__f1__1.aa | 519 | 3924 | 742 | contig262__24273437__c1__16.aa | 742 | 742 | 100.00% |
| contig348__4961578__c3__6.aa | 520 | 3925 | 257 | contig448__24897342__c2__44.aa | 255 | 255 | 51.77% |
| contig348__9772555__c3__5.aa | 521 | 3926 | 251 | contig88__5277192__f1__1.aa | 125 | 123 | 45.53% |
| contig349__5088212__c1__3.aa | 523 | 3928 | 97 | contig252__34390905__f3__5.aa | 153 | 75 | 78.67% |
| contig349__29735006__c3__5.aa | 524 | 3929 | 216 | contig264__2929503__f2__3.aa | 216 | 216 | 100.00% |
| contig350__4111032__f2__2.aa | 526 | 3931 | 115 | contig119__26595012__c3__4.aa | 93 | 76 | 59.21% |
| contig351__33252217__c1__5.aa | 530 | 3935 | 228 | contig418__6069005__c2__33.aa | 242 | 212 | 41.04% |
| contig351__16932962__c1__4.aa | 531 | 3936 | 174 | contig427__798812__f1__2.aa | 217 | 165 | 44.85% |
| contig352__24727050__c2__9.aa | 532 | 3937 | 134 | contig266__9805463__f2__3.aa | 134 | 134 | 100.00% |
| contig352__672081__f3__4.aa | 535 | 3940 | 137 | contig319__4726713__f1__1.aa | 107 | 108 | 29.63% |
| contig352__26384687__f1__5.aa | 536 | 3941 | 224 | contig506__24319002__c3__88.aa | 241 | 136 | 24.27% |
| contig353__26567068__f1__1.aa | 537 | 3942 | 120 | contig237__4901662__f2__3.aa | 288 | 114 | 29.83% |
| contig353__14898587__f2__3.aa | 538 | 3943 | 304 | contig413__24695162__f3__9.aa | 307 | 300 | 57.67% |
| contig353__24782806__f3__4.aa | 539 | 3944 | 204 | contig413__4490930__f2__5.aa | 240 | 183 | 59.56% |
| contig354__31735783__f3__2.aa | 540 | 3945 | 193 | contig428__33314637__c1__38.aa | 257 | 183 | 69.95% |
| contig355__15079207__f1__1.aa | 542 | 3947 | 279 | contig490__24648438__f3__38.aa | 255 | 252 | 44.05% |
| contig355__16595327__f1__3.aa | 544 | 3949 | 348 | contig268__23441667__f2__4.aa | 348 | 348 | 100.00% |
| contig356__25673900__f2__2.aa | 545 | 3950 | 436 | contig169__24666031__f1__1.aa | 533 | 427 | 63.23% |
| contig357__11002__c3__6.aa | 546 | 3951 | 425 | contig475__2148910__c1__30.aa | 631 | 434 | 42.63% |
| contig358__30566880__f1__3.aa | 547 | 3952 | 213 | contig480__19781552__f3__10.aa | 240 | 211 | 54.98% |
| contig358__26053762__f2__2.aa | 549 | 3954 | 243 | contig269__14664077__f1__10.aa | 243 | 243 | 100.00% |
| contig359__23439707__c1__4.aa | 551 | 3956 | 150 | contig269__26774187__f1__3.aa | 150 | 150 | 100.00% |
| contig359__35344432__c1__3.aa | 552 | 3957 | 67 | contig269__22682662__c2__15.aa | 67 | 67 | 100.00% |
| contig36__14648432__c1__1.aa | 553 | 3958 | 118 | contig269__11907628__f2__9.aa | 118 | 118 | 100.00% |
| contig36__33242125__c2__2.aa | 554 | 3959 | 81 | contig269__36224037__f1__4.aa | 81 | 80 | 100.00% |
| contig360__5910087__f1__1.aa | 555 | 3960 | 229 | contig27__29807343__c1__2.aa | 229 | 229 | 100.00% |
| contig360__35995177__f1__2.aa | 556 | 3961 | 89 | contig270__32224026__c2__6.aa | 89 | 89 | 100.00% |
| contig361__22459375__c2__2.aa | 557 | 3962 | 461 | contig270__16695192__c3__8.aa | 461 | 461 | 100.00% |
| contig361__234812__c1__4.aa | 558 | 3963 | 82 | contig504__36581891__f1__9.aa | 521 | 76 | 35.53% |
| contig362__6347031__f2__3.aa | 559 | 3964 | 178 | contig499__11039067__c2__69.aa | 378 | 142 | 25.35% |
| contig362__10759680__f1__1.aa | 560 | 3965 | 189 | contig271__35410056__f2__1.aa | 67 | 67 | 100.00% |
| contig362__991678__f1__2.aa | 561 | 3966 | 281 | contig419__421937__f2__13.aa | 592 | 203 | 27.59% |
| contig363__23991442__f3__2.aa | 562 | 3967 | 323 | contig410__6542894__c2__14.aa | 412 | 339 | 32.74% |
| contig364__3367202__f1__1.aa | 564 | 3969 | 61 | contig324__33361050__f3__6.aa | 182 | 58 | 25.86% |
| contig364__24398313__f1__2.aa | 565 | 3970 | 268 | contig504__2931500__f1__7.aa | 312 | 263 | 41.07% |
| contig365__35429692__c1__4.aa | 567 | 3972 | 199 | contig273__22478437__f1__2.aa | 316 | 180 | 32.78% |
| contig365__14859375__c3__5.aa | 568 | 3973 | 68 | contig272__21698340__f2__5.aa | 68 | 68 | 100.00% |
| contig366__80186__f3__4.aa | 569 | 3974 | 83 | contig272__16989701__f3__11.aa | 83 | 83 | 100.00% |
| contig366__23712543__f1__1.aa | 570 | 3975 | 63 | contig272__6047881__f2__6.aa | 63 | 63 | 100.00% |
| contig366__29550659__c1__6.aa | 572 | 3977 | 270 | contig386__34572876__c3__11.aa | 346 | 256 | 74.61% |
| contig367__11879577__c1__6.aa | 573 | 3978 | 64 | contig273__33859377__f3__5.aa | 64 | 64 | 100.00% |
| contig367__25651443__c1__5.aa | 574 | 3979 | 283 | contig273__22478437__f1__2.aa | 316 | 41 | 97.56% |
| contig368__25446000__c3__5.aa | 575 | 3980 | 281 | contig440__1369013__f3__7.aa | 493 | 275 | 26.91% |
| contig368__21516012__c2__3.aa | 576 | 3981 | 286 | contig274__26462953__f1__1.aa | 286 | 286 | 100.00% |
| contig369__20739053__f2__1.aa | 578 | 3983 | 256 | contig274__35352137__f2__4.aa | 173 | 173 | 100.00% |
| contig37__201__f2__1.aa | 579 | 3984 | 323 | contig274__35172062__c3__11.aa | 323 | 323 | 100.00% |
| contig370__6673515__c3__11.aa | 581 | 3986 | 202 | contig274__30115936__f1__3.aa | 202 | 202 | 100.00% |
| contig370__16836591__f1__1.aa | 582 | 3987 | 246 | contig412__9455__c1__20.aa | 263 | 236 | 42.80% |
| contig370__4867202__f3__6.aa | 584 | 3989 | 100 | contig412__19572337__c2__30.aa | 867 | 94 | 51.06% |
| contig371__26571937__f2__1.aa | 586 | 3991 | 220 | contig401__26620432__c2__24.aa | 239 | 219 | 68.95% |
| contig371__13754838__f2__2.aa | 587 | 3992 | 246 | contig401__36225326__c2__25.aa | 217 | 211 | 64.46% |
| contig372__31288212__f1__1.aa | 588 | 3993 | 92 | contig276__24042961__c1__12.aa | 92 | 92 | 100.00% |
| contig372__22694012__f3__4.aa | 589 | 3994 | 750 | contig276__31648428__c2__14.aa | 750 | 750 | 100.00% |
| contig372__36428176__f1__5.aa | 591 | 3996 | 113 | contig277__970028__f2__4.aa | 113 | 113 | 100.00% |
| contig372__25673905__c2__6.aa | 592 | 3997 | 219 | contig277__1190931__c3__16.aa | 219 | 219 | 100.00% |
| contig373__31272288__f3__1.aa | 593 | 3998 | 126 | contig286__35211627__f2__7.aa | 153 | 123 | 79.68% |
| contig373__11131876__f3__2.aa | 594 | 3999 | 355 | contig286__16558__f2__8.aa | 355 | 319 | 79.00% |
| contig374__14664128__f2__1.aa | 595 | 4000 | 379 | contig277__5323390__c3__15.aa | 379 | 379 | 100.00% |
| contig375__32131340__c2__2.aa | 597 | 4002 | 233 | contig494__11125132__f1__3.aa | 329 | 234 | 26.92% |
| contig376__35352181__c2__10.aa | 598 | 4003 | 117 | contig277__24510787__c1__10.aa | 117 | 117 | 100.00% |
| contig376__26742082__c3__11.aa | 599 | 4004 | 674 | contig493__36024193__c1__26.aa | 910 | 681 | 35.24% |
| contig377__133562__c1__4.aa | 601 | 4006 | 76 | contig278__4954760__f2__2.aa | 76 | 76 | 100.00% |
| contig377__4179177__c2__6.aa | 602 | 4007 | 292 | contig278__10720380__f2__3.aa | 292 | 292 | 100.00% |
| contig378__35945327__c3__5.aa | 604 | 4009 | 218 | contig307__4976687__f1__9.aa | 212 | 206 | 25.73% |
| contig379__36227187__c2__8.aa | 606 | 4011 | 312 | contig279__4492943__f3__8.aa | 312 | 312 | 100.00% |
| contig379__2240952__c3__9.aa | 607 | 4012 | 145 | contig370__4196052__c2__17.aa | 334 | 143 | 36.36% |
| contig379__195342__c2__7.aa | 608 | 4013 | 284 | contig484__34160877__c3__61.aa | 373 | 261 | 36.40% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig380__26828840__f3__2.aa | 611 | 4016 | 227 | contig405__235008__c3__21.aa | 691 | 215 | 40.00% |
| contig380__7042337__f2__1.aa | 612 | 4017 | 287 | contig405__4496068__c3__22.aa | 631 | 281 | 76.87% |
| contig381__5960778__f1__1.aa | 613 | 4018 | 163 | contig474__1408437__f2__14.aa | 471 | 154 | 34.42% |
| contig381__20585887__c3__6.aa | 614 | 4019 | 108 | contig280__34192183__c3__14.aa | 108 | 108 | 100.00% |
| contig381__24354038__c1__4.aa | 615 | 4020 | 89 | contig280__25601562__c1__8.aa | 89 | 89 | 100.00% |
| contig382__24845937__c2__3.aa | 616 | 4021 | 120 | contig280__6836077__f1__2.aa | 120 | 120 | 100.00% |
| contig383__9940693__f3__5.aa | 617 | 4022 | 213 | contig280__265762__f2__5.aa | 213 | 213 | 100.00% |
| contig383__22832811__f1__1.aa | 618 | 4023 | 87 | contig281__12908567__c1__8.aa | 87 | 87 | 100.00% |
| contig383__192677__c2__13.aa | 619 | 4024 | 161 | contig281__4979680__f1__2.aa | 161 | 161 | 100.00% |
| contig383__30508562__f3__6.aa | 620 | 4025 | 830 | contig281__2945452__f3__3.aa | 830 | 830 | 100.00% |
| contig383__2149037__f2__4.aa | 623 | 4028 | 110 | contig282__198790__c3__8.aa | 110 | 110 | 100.00% |
| contig384__34250405__c3__6.aa | 624 | 4029 | 289 | contig283__34260792__c1__17.aa | 289 | 289 | 100.00% |
| contig384__214818__c1__4.aa | 625 | 4030 | 364 | contig289__26777217__c1__11.aa | 676 | 350 | 75.71% |
| contig384__7036537__c2__5.aa | 626 | 4031 | 71 | contig289__6697091__c2__12.aa | 428 | 67 | 41.79% |
| contig385__4121044__c1__4.aa | 629 | 4034 | 493 | contig459__34574092__f1__5.aa | 674 | 471 | 84.29% |
| contig386__4565701__c1__4.aa | 630 | 4035 | 67 | contig253__25604715__c3__13.aa | 406 | 55 | 36.36% |
| contig386__5133558__c3__5.aa | 631 | 4036 | 348 | contig253__25604715__c3__13.aa | 406 | 340 | 34.71% |
| contig387__35410176__f1__1.aa | 633 | 4038 | 232 | contig91__15647706__f1__1.aa | 235 | 184 | 63.04% |
| contig387__32620287__f2__3.aa | 634 | 4039 | 63 | contig156__36023462__f1__2.aa | 267 | 39 | 30.77% |
| contig387__5078128__f2__4.aa | 635 | 4040 | 174 | contig284__22738187__c1__14.aa | 174 | 174 | 100.00% |
| contig387__23831266__f2__5.aa | 636 | 4041 | 119 | contig284__963942__c2__19.aa | 119 | 119 | 100.00% |
| contig388__32242302__c1__5.aa | 637 | 4042 | 119 | contig417__29303837__f1__1.aa | 216 | 110 | 86.36% |
| contig388__23860912__c3__7.aa | 638 | 4043 | 87 | contig417__35175786__f3__13.aa | 264 | 78 | 76.92% |
| contig388__23626707__c2__6.aa | 639 | 4044 | 335 | contig417__35175786__f313.aa | 264 | 185 | 90.81% |
| contig388__14064385__f1__1.aa | 640 | 4045 | 100 | contig417__14845635__c3__49.aa | 96 | 96 | 72.92% |
| contig389__29558587__f1__1.aa | 641 | 4046 | 260 | contig469__34626877__f2__10.aa | 270 | 241 | 34.03% |
| contig39__656663__f3__1.aa | 644 | 4049 | 168 | contig319__10238507__c3__23.aa | 399 | 165 | 27.88% |
| contig390__14947183__c3__7.aa | 646 | 4051 | 390 | contig480__34507711__f1__3.aa | 389 | 380 | 73.16% |
| contig390__29328156__c3__6.aa | 647 | 4052 | 62 | contig405__14876712__c3__23.aa | 197 | 26 | 46.15% |
| contig391__32128186__f1__1.aa | 648 | 4053 | 67 | contig461__4307062__c2__45.aa | 337 | 66 | 53.03% |
| contig391__24883437__f2__3.aa | 649 | 4054 | 465 | contig286__26775050__c3__27.aa | 465 | 465 | 100.00% |
| contig392__30565930__f3__2.aa | 652 | 4057 | 373 | contig387__24415953__c1__21.aa | 700 | 231 | 29.87% |
| contig392__26443837__c2__8.aa | 653 | 4058 | 235 | contig420__1449062__f3__15.aa | 214 | 211 | 44.55% |
| contig392__16832925__c1__5.aa | 654 | 4059 | 143 | contig457__24650186__c1__18.aa | 157 | 138 | 44.20% |
| contig393__23443811__f1__1.aa | 656 | 4061 | 265 | contig290__35409431__c1__6.aa | 264 | 247 | 42.51% |
| contig393__5111088__c3__12.aa | 657 | 4062 | 142 | contig416__23633250__c3__37.aa | 141 | 139 | 30.94% |
| contig393__32235050__c3__11.aa | 658 | 4063 | 195 | contig502__23446063__f1__2.aa | 390 | 172 | 25.00% |
| contig394__34064402__f1__1.aa | 659 | 4064 | 156 | contig287__5173219__c1__8.aa | 156 | 156 | 100.00% |
| contig394__34276576__c3__6.aa | 662 | 4067 | 217 | contig455__16837628__c3__56.aa | 65 | 63 | 73.02% |
| contig394__32157531__c2__4.aa | 663 | 4068 | 84 | contig455__282903__c3__55.aa | 369 | 83 | 79.52% |
| contig395__3382837__f1__1.aa | 664 | 4069 | 239 | contig200__23547001__f3__6.aa | 203 | 155 | 76.77% |
| contig395__22003187__c2__5.aa | 665 | 4070 | 191 | contig22__26563932__f2__3.aa | 63 | 57 | 42.11% |
| contig396__30546912__f1__1.aa | 666 | 4071 | 553 | contig321__24804702__f1__2.aa | 900 | 542 | 60.33% |
| contig397__5116502__f2__1.aa | 667 | 4072 | 626 | contig444__15899050__f2__10.aa | 715 | 621 | 77.62% |
| contig398__36129837__f1__1.aa | 669 | 4074 | 264 | contig290__35409431__c1__6.aa | 264 | 264 | 100.00% |
| contig399__31750775__f1__1.aa | 670 | 4075 | 132 | contig328__15032885__c3__20.aa | 160 | 123 | 83.74% |
| contig399__36207932__f1__2.aa | 671 | 4076 | 303 | contig328__6695327__c2__19.aa | 450 | 280 | 80.36% |
| contig4__4886578__c3__2.aa | 672 | 4077 | 106 | contig361__23620262__c1__17.aa | 275 | 80 | 91.25% |
| contig40__7032013__f1__1.aa | 674 | 4079 | 205 | contig236__2401702__f2__3.aa | 159 | 106 | 73.59% |
| contig400__30474038__f3__3.aa | 675 | 4080 | 322 | contig403__32464717__c1__20.aa | 387 | 315 | 48.57% |
| contig400__23652182__f2__2.aa | 676 | 4081 | 255 | contig403__4860662__c2__24.aa | 249 | 245 | 82.45% |
| contig401__11218958__c2__10.aa | 677 | 4082 | 156 | contig403__19665886__c1__19.aa | 247 | 150 | 72.00% |
| contig401__4024213__c1__8.aa | 678 | 4083 | 70 | contig403__4336088__c1__18.aa | 121 | 70 | 67.14% |
| contig401__26462807__c2__9.aa | 680 | 4085 | 220 | contig238__4416068__c1__8.aa | 122 | 101 | 69.31% |
| contig401__23474062__c3__11.aa | 681 | 4086 | 116 | contig238__24883443__c1__7.aa | 10g | 103 | 71.85% |
| contig401__4688164__c1__6.aa | 682 | 4087 | 153 | contig238__16824135__c1__6.aa | 377 | 152 | 83.55% |
| contig402__21689766__f3__2.aa | 683 | 4088 | 183 | contig293__30586068__c3__10.aa | 183 | 183 | 100.00% |
| contig403__19569007__c2__5.aa | 685 | 4090 | 575 | contig294__4881452__f1__2.aa | 575 | 575 | 100.00% |
| contig403__4954693__f1__1.aa | 687 | 4092 | 415 | contig58__3126033__f2__3.aa | 192 | 191 | 80.11% |
| contig406__15824193__c3__11.aa | 690 | 4095 | 155 | contig390__80032__f1__2.aa | 289 | 136 | 33.82% |
| contig406__15631937__c2__10.aa | 691 | 4096 | 72 | contig294__9792562__c2__14.aa | 72 | 72 | 100.00% |
| contig406__6823763__c2__9.aa | 692 | 4097 | 71 | contig294__3914033__f3__10.aa | 71 | 71 | 100.00% |
| contig406__2441309__c2__8.aa | 693 | 4098 | 305 | contig287__788182__c1__9.aa | 519 | 292 | 43.49% |
| contig407__3367812__c3__9.aa | 694 | 4099 | 373 | contig389__645635__f2__6.aa | 598 | 380 | 20.79% |
| contig407__31366394__c1__7.aa | 695 | 4100 | 438 | contig509__29406567__f1__19.aa | 608 | 436 | 27.75% |
| contig408__7035176__f2__2.aa | 696 | 4101 | 268 | contig364__23475026__f1__1__1.aa | 386 | 203 | 64.04% |
| contig408__35657558__f3__4.aa | 697 | 4102 | 160 | contig364__23475026__f3__11.aa | 386 | 156 | 55.13% |
| contig408__34414193__f1__1.aa | 698 | 4103 | 264 | contig364__34572215__f3__12.aa | 167 | 148 | 64.87% |
| contig408__3415936__f3__5.aa | 699 | 4104 | 253 | contig364__16855453__f2__7.aa | 282 | 250 | 39.60% |
| contig409__12986668__f3__3.aa | 700 | 4105 | 97 | contig479__23472132__c1__24.aa | 291 | 83 | 34.94% |
| contig409__35942192__c1__6.aa | 701 | 4106 | 243 | contig441__23636088__f1__14.aa | 238 | 227 | 64.32% |
| contig409__7033138__c3__9.aa | 702 | 4107 | 225 | contig441__24495303__f2__6.aa | 239 | 226 | 69.91% |
| contig41__21992790__c3__6.aa | 705 | 4110 | 87 | contig296__26852187__c1__15.aa | 87 | 87 | 100.00% |
| contig41__14661542__c1__3.aa | 706 | 4111 | 93 | contig468__36120887__c2__48.aa | 822 | 62 | 58.07% |
| contig41__14850064__c2__4.aa | 707 | 4112 | 93 | contig468__36120887__c2__48.aa | 822 | 86 | 75.58% |
| contig410__29534809__c2__5.aa | 710 | 4115 | 91 | contig427__25587817__f1__8.aa | 405 | 54 | 33.33% |
| contig411__6735937__f3__4.aa | 711 | 4116 | 110 | contig297__9774057__c1__10.aa | 110 | 110 | 100.00% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig411__2444062__f1__1.aa | 712 | 4117 | 208 | contig502__24489717__c2__49.aa | 238 | 194 | 24.23% |
| contig411__12698400__f2__2.aa | 713 | 4118 | 137 | contig239__33867817__f2__5.aa | 344 | 115 | 29.57% |
| contig412__24407202__f2__4.aa | 715 | 4120 | 366 | contig443__979713__c2__16.aa | 594 | 386 | 21.50% |
| contig412__34382752__f3__7.aa | 716 | 4121 | 166 | contig460__33829037__f2__10.aa | 598 | 167 | 34.73% |
| contig412__16296901__f3__8.aa | 717 | 4122 | 145 | contig437__33242186__c3__24.aa | 257 | 120 | 45.00% |
| contig412__29322032__f1__3.aa | 718 | 4123 | 104 | contig437__33242186__c3__24.aa | 257 | 100 | 25.00% |
| contig412__50076__c2__13.aa | 719 | 4124 | 96 | contig298__34181661__c2__20.aa | 96 | 96 | 100.00% |
| contig412__4417817__c3__16.aa | 720 | 4125 | 212 | contig298__9804628__f3__13.aa | 212 | 212 | 100.00% |
| contig413__882927__f1__2.aa | 726 | 4131 | 129 | contig426__25814693__c2__38.aa | 241 | 109 | 84.40% |
| contig414__24063762__c3__16.aa | 727 | 4132 | 275 | contig297__9949218__f3__5.aa | 532 | 241 | 78.01% |
| contig414__57950__f2__3.aa | 730 | 4135 | 286 | contig456__5117091__c2__31.aa | 286 | 295 | 23.05% |
| contig414__2839150__f1__2.aa | 732 | 4137 | 311 | contig312__5864155__c1__7.aa | 563 | 200 | 24.00% |
| contig414__2422203__f2__4.aa | 733 | 4138 | 124 | contig509__23625427__f1__20.aa | 382 | 107 | 42.06% |
| contig415__14642962__f3__3.aa | 734 | 4139 | 383 | contig404__979657__c2__24.aa | 512 | 383 | 61.88% |
| contig415__960952__c2__7.aa | 735 | 4140 | 190 | contig474__34182687__c2__35.aa | 208 | 197 | 28.43% |
| contig415__1437825__f3__4.aa | 736 | 4141 | 328 | contig474__14647180__c1__26.aa | 291 | 276 | 32.97% |
| contig416__24399062__f1__1.aa | 737 | 4142 | 145 | contig302__23884838__c3__15.aa | 145 | 145 | 100.00% |
| contig417__24853588__c1__7.aa | 738 | 4143 | 260 | contig302__2245337__f2__2.aa | 260 | 260 | 100.00% |
| contig417__24664087__c2__9.aa | 740 | 4145 | 370 | contig446__4884687__c2__43.aa | 363 | 364 | 63.74% |
| contig417__21680377__c1__6.aa | 741 | 4146 | 232 | contig446__24648591__c1__34.aa | 455 | 227 | 64.32% |
| contig418__10548918__f3__2.aa | 742 | 4147 | 115 | contig303__21531288__f1__1.aa | 115 | 115 | 100.00% |
| contig418__24298426__f3__3.aa | 744 | 4149 | 134 | contig186__4501582__f2__2.aa | 120 | 121 | 55.37% |
| contig418__34042333__f2__1.aa | 745 | 4150 | 385 | contig502__23446063__f1__2.aa | 390 | 371 | 32.88% |
| contig419__22072825__f3__1.aa | 746 | 4151 | 168 | contig381__10191067__c1__20.aa | 92 | 91 | 84.62% |
| contig419__26361067__f3__2.aa | 747 | 4152 | 218 | contig381__2353387__c2__25.aa | 176 | 152 | 62.50% |
| contig42__35160006__f1__1.aa | 748 | 4153 | 124 | contig322__26758418__c2__21.aa | 174 | 103 | 27.18% |
| contig420__33454837__c3__15.aa | 750 | 4155 | 306 | contig340__24315782__f3__8.aa | 330 | 287 | 43.55% |
| contig420__33417841__f1__7.aa | 751 | 4156 | 305 | contig305__14709818__f2__9.aa | 321 | 309 | 40.13% |
| contig420__35439378__f1__2.aa | 753 | 4158 | 73 | contig304__24429838__c1__16.aa | 73 | 73 | 100.00% |
| contig421__10745300__f2__5.aa | 754 | 4159 | 174 | contig234__16056341__c1__16.aa | 364 | 112 | 29.46% |
| contig421__34659550__c3__9.aa | 755 | 4160 | 97 | contig338__33492936__f2__10.aa | 101 | 90 | 51.11% |
| contig421__24820301__c2__7.aa | 757 | 4162 | 187 | contig397__10583125__f2__12.aa | 216 | 176 | 34.66% |
| contig421__158467__c3__8.aa | 758 | 4163 | 446 | contig410__6542894__c2__14.aa | 412 | 403 | 47.40% |
| contig422__14102343__c2__8.aa | 759 | 4164 | 170 | contig465__14336718__c3__43.aa | 171 | 170 | 82.94% |
| contig422__24492215__c2__7.aa | 760 | 4165 | 81 | contig465__16197587__c3__42.aa | 90 | 68 | 95.59% |
| contig422__984536__c2__6.aa | 762 | 4167 | 457 | contig305__9847200__c2__17.aa | 457 | 457 | 100.00% |
| contig422__35197340__c3__9.aa | 763 | 4168 | 85 | contig471__5314712__f1__5.aa | 101 | 84 | 73.81% |
| contig422__7135126__c2__5.aa | 764 | 4169 | 205 | contig471__10343953__f3__20.aa | 235 | 198 | 84.34% |
| contig423__25970312__f3__2.aa | 765 | 4170 | 556 | contig509__24667313__c2__104.aa | 564 | 551 | 40.47% |
| contig423__29456302__c2__4.aa | 766 | 4171 | 88 | contig458__20573500__c1__30.aa | 99 | 70 | 77.14% |
| contig423__1382627__c2__3.aa | 767 | 4172 | 146 | contig306__34251712__c2__26.aa | 146 | 146 | 100.00% |
| contig424__22392888__f3__3.aa | 768 | 4173 | 65 | contig306__4183192__c3__31.aa | 65 | 65 | 100.00% |
| contig424__21679703__f2__2.aa | 769 | 4174 | 119 | contig306__4195137__c2__25.aa | 119 | 119 | 100.00% |
| contig425__11766252__f3__6.aa | 770 | 4175 | 341 | contig278__24738763__f1__1.aa | 513 | 333 | 40.24% |
| contig425__36225875__f1__1.aa | 771 | 4176 | 81 | contig467__13808206__f2__6.aa | 81 | 81 | 100.00% |
| contig425__21479683__f1__3.aa | 773 | 4178 | 192 | contig503__4876643__c2__102.aa | 789 | 165 | 70.30% |
| contig426__24320287__f1__1.aa | 774 | 4179 | 64 | contig306__25630342__c1__16.aa | 64 | 64 | 100.00% |
| contig426__4883518__f3__5.aa | 775 | 4180 | 178 | contig100__15117217__f3__2.aa | 202 | 88 | 36.36% |
| contig427__12218913__f1__3.aa | 777 | 4182 | 188 | contig313__14725287__c3__16.aa | 483 | 175 | 80.57% |
| contig427__21750950__f1__1.aa | 778 | 4183 | 416 | contig307__4508392__c3__25.aa | 416 | 416 | 100.00% |
| contig427__914027__f2__2.aa | 779 | 4184 | 222 | contig335__32229561__f3__7.aa | 218 | 218 | 77.52% |
| contig427__31750780__c3__6.aa | 780 | 4185 | 246 | contig251__26761575__f2__4.aa | 276 | 251 | 31.08% |
| contig428__22667562__f1__1.aa | 781 | 4186 | 125 | contig480__32245388__f3__8.aa | 249 | 125 | 64.80% |
| contig428__13859625__f3__6.aa | 782 | 4187 | 297 | contig480__15017013__f2__5.aa | 291 | 275 | 75.27% |
| contig428__24494157__f1__2.aa | 783 | 4188 | 212 | contig307__4976687__f1__9.aa | 212 | 211 | 100.00% |
| contig428__21942__f3__7.aa | 784 | 4189 | 68 | contig443__2141250__c1__11.aa | 333 | 55 | 43.64% |
| contig428__21917187__f1__3.aa | 785 | 4190 | 151 | contig480__24335952__f2__6.aa | 316 | 138 | 66.67% |
| contig428__6346924__c1__11.aa | 786 | 4191 | 453 | contig373__33865965__f2__3.aa | 507 | 440 | 59.55% |
| contig43__9773925__f3__2.aa | 790 | 4195 | 325 | contig503__35448508__c2__103.aa | 646 | 307 | 84.69% |
| contig430__31735778__f1__1.aa | 792 | 4197 | 285 | contig474__14647180__c1__26.aa | 291 | 276 | 71.01% |
| contig430__4001088__f1__2.aa | 793 | 4198 | 209 | contig395__26070437__c2__13.aa | 209 | 205 | 39.51% |
| contig430__12219530__c3__7.aa | 794 | 4199 | 144 | contig31__25673900__f3__2.aa | 144 | 144 | 100.00% |
| contig431__24034437__c1__6.aa | 796 | 4201 | 119 | contig449__26225325__c3__54.aa | 83 | 59 | 86.44% |
| contig431__20562777__c1__5.aa | 797 | 4202 | 200 | contig449__3.0079707__c3__.53.aa | 200 | 188 | 31.38% |
| contig431__4142293__c3__8.aa | 798 | 4203 | 179 | contig449__24415907__c2__44.aa | 177 | 174 | 79.89% |
| contig432__6438877__c1__10.aa | 801 | 4206 | 100 | contig311__24492817__f2__5.aa | 100 | 100 | 100.00% |
| contig432__35187937__c1__8.aa | 803 | 4208 | 68 | contig491__29876292__c3__90.aa | 105 | 54 | 61.11% |
| contig433__24814193__c3__13.aa | 804 | 4209 | 73 | contig285__976550__f3__7.aa | 247 | 79 | 35.44% |
| contig433__587558__c3__10.aa | 809 | 4214 | 231 | contig377__2039178__c1__13.aa | 448 | 195 | 22.56% |
| contig434__10197130__f1__6.aa | 812 | 4217 | 158 | contig364__21614376__f3__13.aa | 248 | 136 | 61.03% |
| contig434__5087562__f1__1.aa | 813 | 4218 | 120 | contig364__21614376__f3__13.aa | 248 | 101 | 56.44% |
| contig434__33985712__f2__3.aa | 814 | 4219 | 274 | contig364__36132637__f3__14.aa | 296 | 267 | 92.51% |
| contig434__24492713__f2__4.aa | 815 | 4220 | 183 | contig364__3230002__f1__1.aa | 200 | 181 | 82.32% |
| contig434__33476563__f3__7.aa | 816 | 4221 | 176 | contig364__34646938__f1__2.aa | 349 | 145 | 87.59% |
| contig434__32662517__f2__5.aa | 817 | 4222 | 95 | contig364__34646938__f1__2.aa | 349 | 79 | 78.48% |
| contig435__7205192__f2__2.aa | 818 | 4223 | 192 | contig314__13877202__f1__3.aa | 192 | 192 | 100.00% |
| contig435__14454827__f2__3.aa | 819 | 4224 | 262 | contig50__22468765__c2__4.aa | 144 | 117 | 73.50% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig435_23632802_f3_4.aa | 820 | 4225 | 164 | contig50_995328_c2_5.aa | 141 | 131 | 48.09% |
| contig435_24431250_f1_1.aa | 821 | 4226 | 396 | contig202_13070292_c1_8.aa | 696 | 292 | 64.38% |
| contig436_22305126_f1_1.aa | 822 | 4227 | 153 | contig314_4788941_f1_9.aa | 153 | 153 | 100.00% |
| contig436_15120887_c1_10.aa | 823 | 4228 | 97 | contig315_12398268_c1_51.aa | 97 | 97 | 100.00% |
| contig436_2820317_f3_5.aa | 824 | 4229 | 357 | contig80_7078912_f1_1.aa | 274 | 256 | 89.84% |
| contig436_15641938_c3_15.aa | 825 | 4230 | 655 | contig315_33682842_c1_47.aa | 655 | 655 | 100.00% |
| contig436_992827_c2_12.aa | 826 | 4231 | 293 | contig26_24345378_c1_2.aa | 165 | 161 | 67.08% |
| contig436_24067692_c1_7.aa | 827 | 4232 | 217 | contig387_24415953_c1_21.aa | 700 | 210 | 50.00% |
| contig437_3937561_c2_11.aa | 828 | 4233 | 290 | contig502_6640676_c1_44.aa | 329 | 283 | 68.55% |
| contig437_22455215_c1_9.aa | 831 | 4236 | 139 | contig316_26604558_f3_7.aa | 102 | 102 | 100.00% |
| contig438_25673781_f2_1.aa | 832 | 4237 | 572 | contig465_12275257_c3_44.aa | 816 | 534 | 23.60% |
| contig439_203200_c3_12.aa | 834 | 4239 | 75 | contig316_12850962_f1_3.aa | 75 | 75 | 100.00% |
| contig439_25429640_f2_2.aa | 835 | 4240 | 247 | contig507_25429640_c1_73.aa | 238 | 232 | 92.24% |
| contig439_31646887_c1_8.aa | 836 | 4241 | 72 | contig507_31256262_f2_27.aa | 65 | 62 | 88.71% |
| contig439_5086088_c1_7.aa | 838 | 4243 | 328 | contig425_13915882_c1_24.aa | 325 | 324 | 82.41% |
| contig439_3947263_f2_4.aa | 839 | 4244 | 526 | contig317_30085937_c1_16.aa | 526 | 526 | 100.00% |
| contig439_13808206_f3_6.aa | 840 | 4245 | 81 | contig489_13808206_f1_6.aa | 81 | 81 | 98.77% |
| contig44_26211592_c3_4.aa | 841 | 4246 | 213 | contig203_24119062_c1_5.aa | 104 | 103 | 88.35% |
| contig440_197151_f3_5.aa | 844 | 4249 | 103 | contig224_12925307_f2_3.aa | 123 | 101 | 22.77% |
| contig440_6147312_f3_6.aa | 845 | 4250 | 190 | contig319_5371066_f3_9.aa | 102 | 102 | 100.00% |
| contig440_36135252_f1_1.aa | 847 | 4252 | 79 | contig319_25507827_f3_10.aa | 79 | 79 | 100.00% |
| contig440_16834442_c1_8.aa | 848 | 4253 | 410 | contig339_36135262_f3_10.aa | 414 | 415 | 55.18% |
| contig440_24883402_c3_11.aa | 849 | 4254 | 158 | contig339_22477318_c1_11.aa | 452 | 155 | 80.00% |
| contig440_32678443_c1_9.aa | 850 | 4255 | 288 | contig319_34652187_f3_13.aa | 288 | 288 | 100.00% |
| contig443_250777_c1_3.aa | 853 | 4258 | 165 | contig32_24666001_f1_1.aa | 165 | 165 | 100.00% |
| contig443_24492330_f3_1.aa | 854 | 4259 | 95 | contig32_6048427_c2_3.aa | 95 | 95 | 100.00% |
| contig444_24510762_f3_4.aa | 856 | 4261 | 335 | contig245_12113530_f2_3.aa | 354 | 326 | 28.53% |
| contig444_24275312_c1_5.aa | 857 | 4262 | 121 | contig402_24495467_f2_10.aa | 119 | 87 | 28.74% |
| contig444_23634838_c2_6.aa | 858 | 4263 | 324 | contig320_23472002_c2_20.aa | 324 | 324 | 100.00% |
| contig445_6917753_c1_9.aa | 859 | 4264 | 288 | contig320_33617192_c2_18.aa | 288 | 288 | 100.00% |
| contig445_161452_f3_4.aa | 860 | 4265 | 291 | contig423_10426582_f1_8.aa | 278 | 267 | 54.68% |
| contig445_14484465_c1_8.aa | 861 | 4266 | 181 | contig65_1054667_c2_5.aa | 178 | 159 | 33.96% |
| contig445_16125682_c2_11.aa | 863 | 4268 | 62 | contig66_26375453_f1_1.aa | 237 | 48 | 54.17% |
| contig445_34569416_c2_10.aa | 864 | 4269 | 83 | contig66_26375453_f1_1.aa | 237 | 82 | 48.78% |
| contig445_24407713_c1_7.aa | 865 | 4270 | 218 | contig66_26375453_f1_1.aa | 237 | 121 | 38.84% |
| contig446_26601642_c2_20.aa | 867 | 4272 | 252 | contig321_32064597_c3_20.aa | 252 | 252 | 100.00% |
| contig446_24725711_c2_19.aa | 868 | 4273 | 453 | contig322_34094062_c3_26.aa | 453 | 453 | 100.00% |
| contig446_4820391_c1_15.aa | 869 | 4274 | 67 | contig322_20161377_f1_2.aa | 67 | 67 | 100.00% |
| contig446_29473133_c3_24.aa | 870 | 4275 | 364 | contig304_25674042_c3_22.aa | 733 | 354 | 52.54% |
| contig446_24664812_c2_17.aa | 871 | 4276 | 174 | contig322_26758418_c2_21.aa | 174 | 174 | 100.00% |
| contig446_414126_c2_16.aa | 872 | 4277 | 108 | contig322_5134756_c3_23.aa | 108 | 108 | 100.00% |
| contig446_3297325_c1_14.aa | 873 | 4278 | 286 | contig371_11720053_c2_14.aa | 408 | 273 | 60.07% |
| contig447_24808441_c3_23.aa | 874 | 4279 | 411 | contig493_33870936_c1_30.aa | 401 | 463 | 45.91% |
| contig447_2047187_c2_20.aa | 875 | 4280 | 316 | contig493_24257802_c3_42.aa | 254 | 244 | 77.05% |
| contig447_26773442_f2_8.aa | 876 | 4281 | 147 | contig493_5860716_f1_1.aa | 173 | 143 | 74.13% |
| contig447_976577_f2_9.aa | 877 | 4282 | 70 | contig493_11964667_f2_5.aa | 119 | 67 | 52.24% |
| contig447_11128437_f3_13.aa | 878 | 4283 | 70 | contig493_11964667_f2_5.aa | 119 | 36 | 55.56% |
| contig447_391288_f1_6.aa | 879 | 4284 | 368 | contig493_36047176_f1_2.aa | 344 | 344 | 59.30% |
| contig447_5907938_c1_14.aa | 881 | 4286 | 229 | contig323_35742943_c1_21.aa | 229 | 229 | 100.00% |
| contig448_707_f1_1.aa | 883 | 4288 | 910 | contig471_1214057_f2_8.aa | 1095 | 909 | 92.41% |
| contig449_12781712_f2_3.aa | 887 | 4292 | 208 | contig323_24666026_c1_19.aa | 208 | 208 | 100.00% |
| contig45_4806693_c3_5.aa | 888 | 4293 | 222 | contig283_35977142_c3_18.aa | 823 | 216 | 89.35% |
| contig45_24222017_c3_4.aa | 889 | 4294 | 64 | contig324_24265755_c2_13.aa | 64 | 64 | 100.00% |
| contig450_23631561_f2_2.aa | 890 | 4295 | 379 | contig324_26367202_f2_4.aa | 379 | 379 | 100.00% |
| contig450_21650182_c1_7.aa | 893 | 4298 | 82 | contig217_31908561_f1_1.aa | 64 | 23 | 82.61% |
| contig451_16892158_f1_1.aa | 894 | 4299 | 198 | contig157_19719678_f3_3.aa | 246 | 139 | 80.58% |
| contig451_14876507_f2_4.aa | 895 | 4300 | 198 | contig325_34579057_c2_16.aa | 198 | 198 | 100.00% |
| contig451_4901567_c1_9.aa | 896 | 4301 | 184 | contig325_398255_c3_23.aa | 184 | 184 | 100.00% |
| contig451_34023410_c1_8.aa | 897 | 4302 | 184 | contig325_6766877_c1_12.aa | 184 | 184 | 100.00% |
| contig451_5210312_c2_11.aa | 898 | 4303 | 125 | contig441_2242936_f3_15.aa | 648 | 121 | 53.72% |
| contig452_24492188_f1_5.aa | 901 | 4306 | 362 | contig213_16601590_c1_5.aa | 366 | 354 | 78.53% |
| contig453_31648280_f3_3.aa | 903 | 4308 | 562 | contig426_35710433_c3_42.aa | 576 | 556 | 67.63% |
| contig453_821957_f2_2.aa | 905 | 4310 | 823 | contig326_3091317_c3_19.aa | 823 | 823 | 100.00% |
| contig453_24495803_f3_5.aa | 906 | 4311 | 171 | contig443_4010937_c2_14.aa | 295 | 159 | 25.79% |
| contig454_16207963_c2_16.aa | 907 | 4312 | 295 | contig337_2813788_f2_7.aa | 319 | 300 | 31.67% |
| contig454_14455057_c2_14.aa | 910 | 4315 | 274 | contig327_22677202_c2_11.aa | 274 | 274 | 100.00% |
| contig454_24511583_c1_13.aa | 911 | 4316 | 492 | contig327_24651510_c3_12.aa | 492 | 492 | 100.00% |
| contig454_6839061_c1_12.aa | 912 | 4317 | 208 | contig296_21720652_f1_3.aa | 150 | 118 | 86.44% |
| contig454_10574317_c3_17.aa | 913 | 4318 | 303 | contig236_2401702_f2_3.aa | 159 | 161 | 46.58% |
| contig455_22539000_c2_6.aa | 914 | 4319 | 193 | contig328_36132930_c1_17.aa | 193 | 193 | 100.00% |
| contig455_21649067_c3_7.aa | 915 | 4320 | 106 | contig339_5120302_c1_13.aa | 67 | 66 | 86.36% |
| contig457_1057766_c1_17.aa | 926 | 4331 | 538 | contig275_4489213_f1_2.aa | 855 | 512 | 86.52% |
| contig457_32167300_c1_16.aa | 927 | 4332 | 394 | contig275_10289713_f1_1.aa | 661 | 395 | 85.06% |
| contig457_7050056_c1_15.aa | 928 | 4333 | 248 | contig275_10289713_f1_1.aa | 661 | 234 | 85.47% |
| contig458_6344575_f1_1.aa | 929 | 4334 | 211 | contig158_4074027_f2_1.aa | 252 | 204 | 76.96% |
| contig458_10323529_c2_3.aa | 930 | 4335 | 213 | contig501_22460816_c2_51.aa | 400 | 210 | 100.00% |
| contig459_173393_f2_5.aa | 931 | 4336 | 490 | contig330_24414818_c1_12.aa | 490 | 490 | 100.00% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig459__21722512__f1__1.aa | 932 | 4337 | 150 | contig469__25989218__f3__14.aa | 323 | 122 | 55.74% |
| contig459__21679666__f1__2.aa | 933 | 4338 | 304 | contig330__6645051__c3__18.aa | 304 | 304 | 100.00% |
| contig459__9783557__f3__8.aa | 934 | 4339 | 202 | contig330__19784783__f3__9.aa | 202 | 202 | 100.00% |
| contig459__5272650__f1__3.aa | 935 | 4340 | 161 | contig330__211558__f3__10.aa | 161 | 161 | 100.00% |
| contig459__24817576__f2__6.aa | 936 | 4341 | 161 | contig469__34626877__f2__10.aa | 270 | 153 | 74.51% |
| contig459__34609391__f1__4.aa | 937 | 4342 | 327 | contig469__20745312__f3__15.aa | 352 | 323 | 65.02% |
| contig459__24021093__f2__7.aa | 938 | 4343 | 278 | contig66__26375453__f1__1.aa | 237 | 176 | 42.05% |
| contig46__292881__c3__2.aa | 939 | 4344 | 281 | contig231__26365925__c3__4.aa | 339 | 261 | 24.52% |
| contig460__1067677__c3__7.aa | 941 | 4346 | 325 | contig405__34252327__c2__20.aa | 324 | 323 | 81.42% |
| contig460__25521899__c1__5.aa | 942 | 4347 | 263 | contig405__4496068__c3__22.aa | 631 | 263 | 71.10% |
| contig461__2230250__c2__12.aa | 945 | 4350 | 468 | contig332__24822318__f2__5.aa | 468 | 468 | 100.00% |
| contig462__25673905__f2__2.aa | 947 | 4352 | 72 | contig332__16882140__c3__15.aa | 72 | 72 | 100.00% |
| contig462__33382200__f2__3.aa | 949 | 4354 | 557 | contig66__26375453__f1__1.aa | 237 | 239 | 40.17% |
| contig463__26306550__c1__10.aa | 950 | 4355 | 731 | contig306__36210961__c2__24.aa | 679 | 671 | 75.56% |
| contig463__786713__c3__13.aa | 951 | 4356 | 248 | contig306__6648337__c3__28.aa | 191 | 189 | 74.60% |
| contig463__259712__c3__12.aa | 952 | 4357 | 587 | contig333__36226567__c3__29.aa | 587 | 587 | 100.00% |
| contig463__20946443__c2__11.aa | 953 | 4358 | 370 | contig333__32235277__f2__10.aa | 370 | 370 | 100.00% |
| contig464__647150__f3__4.aa | 954 | 4359 | 301 | contig310__6286660__c2__11.aa | 266 | 245 | 35.92% |
| contig464__1194180__f2__2.aa | 955 | 4360 | 66 | contig333__33366436__f1__5.aa | 66 | 66 | 100.00% |
| contig465__1960957__c1__12.aa | 957 | 4362 | 359 | contig381__22462688__c3__29.aa | 879 | 350 | 64.29% |
| contig465__14335942__c3__15.aa | 958 | 4363 | 539 | contig381__22462688__c3__29.aa | 879 | 519 | 75.34% |
| contig466__14932802__f1__3.aa | 959 | 4364 | 776 | contig387__15744031__c1__18.aa | 451 | 426 | 71.36% |
| contig466__15119213__f1__2.aa | 960 | 4365 | 603 | contig387__1665__c2__23.aa | 639 | 595 | 54.96% |
| contig467__22754126__f1__1.aa | 961 | 4366 | 68 | contig335__24298427__f2__4.aa | 68 | 68 | 100.00% |
| contig467__34027217__f2__3.aa | 962 | 4367 | 461 | contig509__23625625__c1__81.aa | 615 | 406 | 21.43% |
| contig467__4884682__f1__2.aa | 963 | 4368 | 163 | contig241__36132765__c2__10.aa | 169 | 144 | 26.39% |
| contig467__4110811__c1__8.aa | 964 | 4369 | 365 | contig415__16492338__c1__19.aa | 345 | 338 | 65.68% |
| contig468__24664807__c2__10.aa | 965 | 4370 | 155 | contig270__21912943__c3__7.aa | 154 | 154 | 81.17% |
| contig468__16675902__c3__14.aa | 966 | 4371 | 681 | contig190__21516680__c3__13.aa | 575 | 557 | 54.04% |
| contig468__34102338__c3__13.aa | 967 | 4372 | 83 | contig190__23633563__c2__11.aa | 82 | 82 | 89.02% |
| contig468__23625327__c2__9.aa | 968 | 4373 | 223 | contig336__34195285__f3__10.aa | 223 | 223 | 100.00% |
| contig469__15832756__f1__1.aa | 970 | 4375 | 549 | contig509__10751561__c2__95.aa | 935 | 543 | 23.94% |
| contig469__277186__f3__7.aa | 971 | 4376 | 138 | contig416__23633250__c3__37.aa | 141 | 109 | 27.52% |
| contig469__24393812__f1__2.aa | 972 | 4377 | 206 | contig337__32070768__f1__1.aa | 79 | 79 | 100.00% |
| contig469__4772187__f3__8.aa | 973 | 4378 | 263 | contig342__24848465__f2__10.aa | 292 | 254 | 38.58% |
| contig469__4567943__f2__5.aa | 974 | 4379 | 228 | contig509__24651587__c2__96.aa | 275 | 216 | 36.11% |
| contig47__25586665__c2__1.aa | 975 | 4380 | 110 | contig490__24432140__c2__72.aa | 196 | 88 | 54.55% |
| contig47__12617343__c3__2.aa | 976 | 4381 | 122 | contig490__24787526__c3__94.aa | 326 | 114 | 75.44% |
| contig470__14181583__c1__8.aa | 977 | 4382 | 402 | contig431__4864703__f3__13.aa | 430 | 388 | 72.17% |
| contig470__6839200__c1__7.aa | 978 | 4383 | 94 | contig337__24408187__f3__11.aa | 94 | 94 | 100.00% |
| contig471__22050037__c1__6.aa | 979 | 4384 | 319 | contig337__2813788__f2__7.aa | 319 | 319 | 100.00% |
| contig472__24647010__c3__7.aa | 981 | 4386 | 262 | contig338__14735817__f1__1.aa | 262 | 262 | 100.00% |
| contig472__5267153__c1__14.aa | 983 | 4388 | 477 | contig357__5111037__c3__25.aa | 549 | 474 | 54.64% |
| contig472__493887__c3__19.aa | 984 | 4389 | 400 | contig510__22844077__c1__84.aa | 555 | 396 | 63.13% |
| contig472__24470343__c2__15.aa | 985 | 4390 | 67 | contig510__22844077__c1__84.aa | 555 | 59 | 69.49% |
| contig472__26602192__c3__18.aa | 986 | 4391 | 101 | contig510__22844077__c1__84.aa | 555 | 90 | 73.33% |
| contig472__657087__c3__17.aa | 987 | 4392 | 486 | contig269__34647787__c3__19.aa | 564 | 448 | 63.17% |
| contig473__14646937__c1__11.aa | 988 | 4393 | 385 | contig292__36126568__c1__18.aa | 576 | 383 | 82.25% |
| contig473__26386087__c2__14.aa | 989 | 4394 | 292 | contig292__31254631__c3__22.aa | 276 | 272 | 60.66% |
| contig473__584657__f3__8.aa | 991 | 4396 | 70 | contig338__34567887__f1__4.aa | 70 | 70 | 100.00% |
| contig473__24646087__f1__2.aa | 992 | 4397 | 230 | contig211__11760452__f1__1.aa | 114 | 112 | 67.86% |
| contig473__29741062__f1__3.aa | 993 | 4398 | 126 | contig338__11797311__c3__34.aa | 126 | 126 | 100.00% |
| contig474__976512__f2__2.aa | 995 | 4400 | 77 | contig338__19532532__f2__9.aa | 77 | 77 | 100.00% |
| contig474__32610887__f2__3.aa | 996 | 4401 | 60 | contig338__26385902__c2__26.aa | 60 | 60 | 100.00% |
| contig474__16532252__c1__10.aa | 997 | 4402 | 124 | contig201__7035933__f1__6.aa | 170 | 123 | 68.29% |
| contig474__819712__f2__4.aa | 998 | 4403 | 65 | contig338__7064077__f3__17.aa | 65 | 65 | 100.00% |
| contig475__16603592__f2__4.aa | 999 | 4404 | 361 | contig458__5199077__c1__29.aa | 327 | 320 | 68.44% |
| contig475__23834631__f3__7.aa | 1000 | 4405 | 262 | contig339__5120302__c1__13.aa | 67 | 67 | 100.00% |
| contig475__22867937__f2__5.aa | 1001 | 4406 | 161 | contig439__35368885__c3__34.aa | 128 | 119 | 39.50% |
| contig475__24664811__f1__3.aa | 1002 | 4407 | 77 | contig468__25500286__c1__39.aa | 87 | 77 | 75.33% |
| contig475__960933__f2__6.aa | 1003 | 4408 | 81 | contig339__3339691__c2__17.aa | 81 | 81 | 100.00% |
| contig476__10804813__f3__5.aa | 1004 | 4409 | 128 | contig339__6150437__f1__2.aa | 128 | 128 | 100.00% |
| contig476__16977015__c2__9.aa | 1006 | 4411 | 248 | contig339__187502__f3__9.aa | 248 | 248 | 100.00% |
| contig477__36211052__f2__3.aa | 1008 | 4413 | 281 | contig330__6645051__c3__18.aa | 304 | 144 | 32.64% |
| contig477__5352188__c2__11.aa | 1010 | 4415 | 141 | contig503__26386088__c1__77.aa | 161 | 134 | 31.34% |
| contig477__4880443__c2__10.aa | 1011 | 4416 | 123 | contig503__26386088__c1__77.aa | 161 | 104 | 25.96% |
| contig477__6837832__f2__6.aa | 1012 | 4417 | 318 | contig466__3959686__c1__33.aa | 324 | 313 | 66.13% |
| contig477__3910150__f1__2.aa | 1013 | 4418 | 70 | contig483__24105467__c2__34.aa | 174 | 46 | 52.17% |
| contig478__10945750__c1__6.aa | 1014 | 4419 | 174 | contig340__157952__f2__6.aa | 174 | 174 | 100.00% |
| contig478__4179211__c3__7.aa | 1015 | 4420 | 905 | contig490__4742968__f1__11.aa | 1027 | 411 | 27.49% |
| contig479__6697186__c1__7.aa | 1018 | 4423 | 457 | contig341__26040962__c3__29.aa | 457 | 457 | 100.00% |
| contig479__29429813__c1__6.aa | 1020 | 4425 | 177 | contig329__24223428__f2__6.aa | 233 | 172 | 27.33% |
| contig411__12109375__c2__2.aa | 1021 | 4426 | 206 | contig341__39818__c2__19.aa | 206 | 206 | 100.00% |
| contig480__4900312__c3__17.aa | 1023 | 4428 | 198 | contig274__26462953__f1__1.aa | 286 | 190 | 33.68% |
| contig480__25663317__c3__15.aa | 1027 | 4432 | 86 | contig305__9847200__c2__17.aa | 457 | 74 | 87.84% |
| contig480__13019439__c1__9.aa | 1028 | 4433 | 353 | contig305__9847200__c2__17.aa | 457 | 349 | 66.76% |
| contig481__19532578__f3__4.aa | 1029 | 4434 | 155 | contig419__16072318__c1__29.aa | 116 | 92 | 30.44% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig481__23628575__f1__1.aa | 1030 | 4435 | 289 | contig342__26804838__f1__4.aa | 289 | 289 | 100.00% |
| contig481__35324037__f3__6.aa | 1031 | 4436 | 351 | contig419__24424182__c3__43.aa | 350 | 332 | 65.96% |
| contig481__25970887__f3__7.aa | 1032 | 4437 | 176 | contig342__24898562__f1__5.aa | 176 | 176 | 100.00% |
| contig482__1285427__f1__1.aa | 1033 | 4438 | 257 | contig459__6914137__f2__7.aa | 362 | 234 | 52.14% |
| contig482__34277067__f3__6.aa | 1034 | 4439 | 321 | contig194__991577__c3__12.aa | 314 | 313 | 85.62% |
| contig482__24853427__f1__4.aa | 1035 | 4440 | 321 | contig194__11176665__c2__10.aa | 346 | 321 | 76.64% |
| contig482__25960937__f2__5.aa | 1036 | 4441 | 316 | contig459__6523285__f1__10.aa | 299 | 283 | 31.10% |
| contig483__10554668__f2__3.aa | 1037 | 4442 | 316 | contig499__34065626__c1__60.aa | 410 | 229 | 26.20% |
| contig483__26773412__f1__1.aa | 1038 | 4443 | 229 | contig497__16838576__f2__19.aa | 280 | 196 | 27.55% |
| contig483__32210953__f3__6.aa | 1039 | 4444 | 349 | contig503__26567250__c3__117.aa | 386 | 341 | 27.86% |
| contig483__15631655__c3__14.aa | 1042 | 4447 | 155 | contig344__14648452__f1__3.aa | 155 | 155 | 100.00% |
| contig483__4964687__f3__7.aa | 1043 | 4448 | 441 | contig344__24406687__f2__4.aa | 441 | 441 | 100.00% |
| contig484__23494156__f3__5.aa | 1044 | 4449 | 316 | contig344__791406__c2__16.aa | 316 | 316 | 100.00% |
| contig484__34651588__f3__6.aa | 1045 | 4450 | 243 | contig345__1067757__f1__1.aa | 243 | 243 | 100.00% |
| contig484__24332327__f2__3.aa | 1046 | 4451 | 65 | contig345__34394687__f2__9.aa | 65 | 65 | 100.00% |
| contig484__23705090__f1__2.aa | 1047 | 4452 | 378 | contig253__34265693__c2__11.aa | 570 | 361 | 34.35% |
| contig484__6928430__f3__7.aa | 1048 | 4453 | 162 | contig373__495677__c3__16.aa | 308 | 106 | 63.21% |
| contig485__24640625__c1__9.aa | 1049 | 4454 | 274 | contig492__19532312__f1__3.aa | 312 | 98 | 38.78% |
| contig485__34585812__f2__2.aa | 1051 | 4456 | 590 | contig389__645635__f2__6.aa | 598 | 583 | 33.45% |
| contig485__7230311__f3__5.aa | 1052 | 4457 | 184 | contig345__26181537__f3__17.aa | 184 | 184 | 100.00% |
| contig486__25976012__c2__7.aa | 1053 | 4458 | 82 | contig346__24429707__c2__23.aa | 82 | 82 | 100.00% |
| contig486__15625702__c3__9.aa | 1054 | 4459 | 303 | contig161__29453433__f1__2.aa | 297 | 278 | 85.61% |
| contig486__6347155__c3__8.aa | 1055 | 4460 | 312 | contig161__34277077__f1__1.aa | 224 | 224 | 81.25% |
| contig487__34385961__f1__6.aa | 1056 | 4461 | 334 | contig509__1177312__f1__39.aa | 603 | 306 | 73.86% |
| contig487__26037500__f1__1.aa | 1057 | 4462 | 281 | contig509__1177312__f2__39.aa | 603 | 271 | 66.42% |
| contig487__24431677__f2__5.aa | 1058 | 4463 | 620 | contig509__29406567__f1__19.aa | 608 | 605 | 67.27% |
| contig487__24415936__c3__12.aa | 1059 | 4464 | 178 | contig509__24222086__c1__69.aa | 186 | 166 | 57.83% |
| contig487__2925192__c2__9.aa | 1061 | 4466 | 120 | contig509__1205302__c2__91.aa | 152 | 118 | 81.36% |
| contig488__5353211__c1__12.aa | 1063 | 4468 | 282 | contig332__26437811__c3__19.aa | 268 | 268 | 69.78% |
| contig488__11751887__c3__17.aa | 1064 | 4469 | 346 | contig332__34421880__c1__12.aa | 331 | 320 | 59.06% |
| contig488__4970075__f3__9.aa | 1065 | 4470 | 396 | contig332__24822318__f2__5.aa | 468 | 385 | 67.79% |
| contig489__24664015__c1__5.aa | 1066 | 4471 | 446 | contig278__24738763__f1__1.aa | 513 | 338 | 57.69% |
| contig489__26192943__c2__7.aa | 1067 | 4472 | 279 | contig327__22677202__c2__11.aa | 274 | 273 | 79.12% |
| contig489__30109437__c3__10.aa | 1068 | 4473 | 102 | contig327__24651510__c3__12.aa | 492 | 69 | 78.26% |
| contig489__26604062__c2__6.aa | 1069 | 4474 | 424 | contig327__24651510__c3__12.aa | 492 | 421 | 88.36% |
| contig49__10753905__f3__1.aa | 1071 | 4476 | 252 | contig443__24667250__c2__15.aa | 476 | 240 | 98.75% |
| contig490__6273349__c1__10.aa | 1078 | 4483 | 317 | contig359__10234432__c3__11.aa | 282 | 273 | 29.30% |
| contig491__23650268__c2__9.aa | 1079 | 4484 | 97 | contig444__23907507__f2__14.aa | 267 | 90 | 56.67% |
| contig491__25587943__f1__1.aa | 1080 | 4485 | 243 | contig444__24414086__c3__36.aa | 254 | 239 | 85.36% |
| contig491__1039502__f2__3.aa | 1081 | 4486 | 497 | contig444__29542525__c2__34.aa | 487 | 494 | 65.79% |
| contig491__26834688__c3__11.aa | 1083 | 4488 | 190 | contig444__20056900__f3__21.aa | 190 | 120 | 32.50% |
| contig491__6423437__c1__5.aa | 1084 | 4489 | 218 | contig497__24259677__f2__7.aa | 459 | 108 | 24.07% |
| contig492__4307330__c2__14.aa | 1087 | 4492 | 326 | contig352__25673512__c3__24.aa | 326 | 326 | 100.00% |
| contig492__10956__c3__15.aa | 1088 | 4493 | 213 | contig352__1172203__f3__11.aa | 213 | 213 | 100.00% |
| contig492__22476703__f3__8.aa | 1090 | 4495 | 294 | contig242__86653__f1__1.aa | 283 | 282 | 69.50% |
| contig492__30303842__c1__9.aa | 1091 | 4496 | 84 | contig242__26442131__c1__9.aa | 200 | 77 | 51.95% |
| contig493__22736042__c2__17.aa | 1092 | 4497 | 242 | contig457__23547827__f2__3.aa | 327 | 238 | 29.83% |
| contig493__24032818__c1__14.aa | 1094 | 4499 | 399 | contig353__22705437__f1__2.aa | 399 | 399 | 100.00% |
| contig494__35985878__f2__4.aa | 1095 | 4500 | 297 | contig353__15720716__f3__7.aa | 297 | 297 | 100.00% |
| contig494__34164201__f1__1.aa | 1096 | 4501 | 174 | contig65__1054667__c2__5.aa | 178 | 179 | 31.84% |
| contig494__4859378__f1__5.aa | 1097 | 4502 | 85 | contig276__5319063__c1__13.aa | 97 | 81 | 64.20% |
| contig494__2835432__c2__11.aa | 1098 | 4503 | 101 | contig353__33984387__f1__3.aa | 101 | 101 | 100.00% |
| contig494__4710877__f1__3.aa | 1099 | 4504 | 404 | contig492__9875217__c1__28.aa | 644 | 374 | 36.36% |
| contig495__14875927__f3__6.aa | 1100 | 4505 | 187 | contig353__12007202__c1__12.aa | 68 | 68 | 100.00% |
| contig495__25586702__f2__4.aa | 1101 | 4506 | 114 | contig354__1343837__f1__1.aa | 114 | 114 | 100.00% |
| contig495__35977155__f2__5.aa | 1103 | 4508 | 218 | contig354__1213188__f1__2.aa | 218 | 218 | 100.00% |
| contig495__34189768__f3__8.aa | 1105 | 4510 | 317 | contig354__13829077__c2__14.aa | 317 | 317 | 100.00% |
| contig495__25630061__f1__9.aa | 1107 | 4512 | 284 | contig355__15125405__f2__5.aa | 284 | 284 | 100.00% |
| contig496__22000192__f3__5.aa | 1110 | 4515 | 517 | contig92__35407805__f2__2.aa | 277 | 270 | 73.70% |
| contig496__26600088__f2__4.aa | 1111 | 4516 | 596 | contig75__11990701__c2__3.aa | 334 | 332 | 84.94% |
| contig496__25558187__f1__3.aa | 1112 | 4517 | 270 | contig444__30339212__c3__41.aa | 255 | 248 | 41.13% |
| contig496__33783330__f3__6.aa | 1113 | 4518 | 212 | contig444__16796885__c1__32.aa | 163 | 160 | 72.50% |
| contig497__26251702__c3__14.aa | 1114 | 4519 | 81 | contig420__20911562__c2__27.aa | 287 | 76 | 73.68% |
| contig497__7038936__c1__10.aa | 1115 | 4520 | 304 | contig420__23829825__c2__26.aa | 289 | 287 | 52.27% |
| contig497__7039817__c2__12.aa | 1116 | 4521 | 757 | contig357__824008__c1__22.aa | 757 | 757 | 100.00% |
| contig497__24628438__c3__13.aa | 1117 | 4522 | 618 | contig420__7081661__c3__31.aa | 628 | 617 | 75.37% |
| contig497__1988304__c2__11.aa | 1118 | 4523 | 161 | contig358__35947011__f2__4.aa | 161 | 161 | 100.00% |
| contig498__30705215__f3__2.aa | 1119 | 4524 | 529 | contig448__1345377__f1__1.aa | 170 | 153 | 35.29% |
| contig498__25667801__f3__3.aa | 1120 | 4525 | 504 | contig377__10289812__f1__4.aa | 522 | 506 | 32.21% |
| contig499__7070212__c1__15.aa | 1123 | 4528 | 192 | contig294__34117967__f1__3.aa | 235 | 182 | 25.82% |
| contig499__24226557__c1__14.aa | 1124 | 4529 | 214 | contig76__25673900__f2__2.aa | 168 | 160 | 65.00% |
| contig499__4179768__c1__13.aa | 1125 | 4530 | 314 | contig452__33683327__c3__38.aa | 328 | 313 | 41.21% |
| contig499__957700__f2__7.aa | 1130 | 4535 | 167 | contig36__24892763__c3__4.aa | 167 | 167 | 100.00% |
| contig499__19631324__c1__11.aa | 1131 | 4536 | 269 | contig505__22681287__f1__8.aa | 349 | 233 | 41.63% |
| contig5__31682253__f1__1.aa | 1132 | 4537 | 182 | contig359__33407912__f3__3.aa | 506 | 182 | 57.14% |
| contig50__24395462__c1__4.aa | 1135 | 4540 | 205 | contig356__5273558__f2__4.aa | 178 | 142 | 38.03% |
| contig500__4102191__f1__2.aa | 1139 | 4544 | 143 | contig345__24899062__f1__4.aa | 168 | 94 | 25.53% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig500__20970882__f1__3.aa | 1141 | 4546 | 368 | contig503__26567250__c3__117.aa | 386 | 356 | 26.40% |
| contig501__4507787__c2__9.aa | 1144 | 4549 | 497 | contig208__16134407__f1__1.aa | 738 | 496 | 84.27% |
| contig501__14742200__c3__10.aa | 1145 | 4550 | 373 | contig208__16134407__f1__1.aa | 738 | 245 | 96.33% |
| contig502__21972626__f1__1.aa | 1146 | 4551 | 76 | contig228__22064788__c3__14.aa | 109 | 17 | 76.47% |
| contig502__34657287__f2__4.aa | 1147 | 4552 | 168 | contig228__5939790__c3__15.aa | 170 | 165 | 56.36% |
| contig502__978412__f2__5.aa | 1148 | 4553 | 142 | contig277__24510787__c1__10.aa | 117 | 111 | 55.86% |
| contig502__9775312__f3__8.aa | 1149 | 4554 | 66 | contig362__28312793__c2__21.aa | 66 | 66 | 100.00% |
| contig502__34650887__f1__2.aa | 1150 | 4555 | 294 | contig228__1188577__c2__13.aa | 289 | 287 | 77.35% |
| contig502__19766583__f2__7.aa | 1151 | 4556 | 276 | contig228__23650402__c3__18.aa | 122 | 119 | 73.11% |
| contig503__117208__f1__1.aa | 1152 | 4557 | 104 | contig491__6054627__c1__49.aa | 119 | 98 | 82.65% |
| contig503__4898518__f1__2.aa | 1154 | 4559 | 545 | contig491__4773518__c3__74.aa | 349 | 342 | 96.78% |
| contig503__24698956__c2__21.aa | 1155 | 4560 | 132 | contig491__24305181__f3__48.aa | 132 | 132 | 85.61% |
| contig503__29407803__f3__7.aa | 1156 | 4561 | 182 | contig420__14877313__c2__24.aa | 246 | 177 | 31.07% |
| contig503__25633432__f2__4.aa | 1157 | 4562 | 266 | contig496__24649055__c1__29.aa | 1044 | 227 | 23.79% |
| contig503__15820967__f1__8.aa | 1158 | 4563 | 519 | contig500__34179817__c2__72.aa | 491 | 413 | 37.05% |
| contig504__24430452__f3__5.aa | 1160 | 4565 | 159 | contig502__35417188__c3__62.aa | 187 | 157 | 87.26% |
| contig504__36538452__f3__6.aa | 1161 | 4566 | 251 | contig284__963942__c2__19.aa | 119 | 119 | 73.95% |
| contig504__30564143__f2__3.aa | 1162 | 4567 | 371 | contig284__31433438__c1__15.aa | 201 | 202 | 80.69% |
| contig504__2933467__f3__7.aa | 1163 | 4568 | 215 | contig284__5120302__c1__16.aa | 212 | 212 | 86.79% |
| contig504__19562563__f1__1.aa | 1164 | 4569 | 241 | contig284__4886592__c2__20.aa | 225 | 224 | 84.38% |
| contig504__9922058__f1__2.aa | 1165 | 4570 | 127 | contig284__5359753__c2__21.aa | 100 | 96 | 65.63% |
| contig504__35401576__f2__4.aa | 1166 | 4571 | 353 | contig363__9267066__c2__20.aa | 353 | 353 | 100.00% |
| contig505__35365937__c3__15.aa | 1170 | 4575 | 314 | contig364__34589553__f3__10.aa | 312 | 312 | 100.00% |
| contig506__30710156__f3__3.aa | 1177 | 4582 | 455 | contig470__16989717__f1__4.aa | 927 | 448 | 70.54% |
| contig506__26376718__f1__1.aa | 1178 | 4583 | 110 | contig470__24408212__f2__14.aa | 115 | 105 | 87.62% |
| contig506__36048577__f1__2.aa | 1179 | 4584 | 482 | contig470__35744062__f3__19.aa | 487 | 447 | 83.89% |
| contig507__13175418__f1__1.aa | 1180 | 4585 | 275 | contig365__34589063__c1__31.aa | 275 | 275 | 100.00% |
| contig507__34117937__c2__11.aa | 1181 | 4586 | 255 | contig365__24095287__c1__30.aa | 255 | 255 | 100.00% |
| contig507__20829692__f1__3.aa | 1183 | 4588 | 449 | contig104__235402__f1__1.aa | 142 | 140 | 35.71% |
| contig507__23673577__f2__4.aa | 1184 | 4589 | 228 | contig1__1526386567__c3__5.aa | 244 | 234 | 35.47% |
| contig507__7320327__f2__5.aa | 1185 | 4590 | 189 | contig69__26179658__f3__2.aa | 158 | 157 | 85.35% |
| contig508__33883591__c3__16.aa | 1186 | 4591 | 292 | contig301__22478183__c1__10.aa | 439 | 233 | 87.98% |
| contig508__33411062__c3__15.aa | 1189 | 4594 | 637 | contig167__31329702__c2__7.aa | 327 | 308 | 79.22% |
| contig509__14930263__f2__3.aa | 1190 | 4595 | 572 | contig495__15791087__f1__9.aa | 857 | 557 | 55.30% |
| contig509__12610937__f3__8.aa | 1191 | 4596 | 148 | contig365__34501568__c3__35.aa | 148 | 148 | 100.00% |
| contig509__20492265__f2__5.aa | 1193 | 4598 | 162 | contig490__36589056__f3__41.aa | 290 | 155 | 32.90% |
| contig509__33373441__f2__7.aa | 1196 | 4601 | 113 | contig366__5209718__f3__12.aa | 113 | 113 | 100.00% |
| contig51__1214082__f2__1.aa | 1197 | 4602 | 250 | contig206__26355087__c1__4.aa | 464 | 226 | 33.19% |
| contig51__33984635__c1__2.aa | 1198 | 4603 | 487 | contig366__24064712__f3__13.aa | 487 | 487 | 100.00% |
| contig510__14647040__c2__13.aa | 1199 | 4604 | 275 | contig510__24801555__c2__105.aa | 497 | 197 | 47.72% |
| contig510__31844750__c3__18.aa | 1200 | 4605 | 745 | contig367__29322150__f1__1.aa | 745 | 745 | 100.00% |
| contig510__893816__c1__10.aa | 1201 | 4606 | 114 | contig367__24254437__f1__2.aa | 114 | 114 | 100.00% |
| contig510__11718766__c3__14.aa | 1202 | 4607 | 158 | contig156__36023462__f3__2.aa | 267 | 158 | 30.38% |
| contig511__555203__f2__4.aa | 1203 | 4603 | 527 | contig367__23634628__c2__15.aa | 527 | 527 | 100.00% |
| contig511__14553953__f2__5.aa | 1205 | 4610 | 304 | contig368__1995327__f3__11.aa | 245 | 245 | 100.00% |
| contig511__21914192__f1__3.aa | 1207 | 4612 | 827 | contig441__36015628__c1__18.aa | 804 | 797 | 57.59% |
| contig511__34164067__f3__8.aa | 1208 | 4613 | 333 | contig165__21640791__f3__7.aa | 200 | 198 | 57.58% |
| contig512__3306562__c1__11.aa | 1211 | 4616 | 142 | contig491__24257712__c1__59.aa | 167 | 138 | 44.20% |
| contig512__16798767__c3__18.aa | 1213 | 4618 | 130 | contig491__35187941__c3__85.aa | 238 | 65 | 49.23% |
| contig512__25417716__c2__14.aa | 1214 | 4619 | 131 | contig506__35187941__c2__76.aa | 192 | 134 | 31.34% |
| contig512__19539077__c3__17.aa | 1215 | 4620 | 543 | contig369__976568__f1__2.aa | 543 | 543 | 100.00% |
| contig512__26054692__c1__10.aa | 1217 | 4622 | 128 | contig508__24415936__c2__65.aa | 114 | 113 | 62.83% |
| contig512__3945906__c2__12.aa | 1219 | 4624 | 125 | contig491__35430443__c2__70.aa | 133 | 133 | 32.33% |
| contig512__14725937__c3__15.aa | 1220 | 4625 | 300 | contig37__24737567__f3__3.aa | 300 | 300 | 100.00% |
| contig513__33476700__c1__16.aa | 1221 | 4626 | 296 | contig488__30157841__c3__55.aa | 470 | 275 | 38.91% |
| contig513__4882887__c2__19.aa | 1225 | 4630 | 359 | contig499__11039067__c2__69.aa | 378 | 331 | 77.95% |
| contig513__6463175__c1__14.aa | 1226 | 4631 | 258 | contig370__10636557__c3__18.aa | 141 | 141 | 100.00% |
| contig513__12596885__c2__18.aa | 1227 | 4632 | 96 | contig499__976577__c3__84.aa | 275 | 46 | 71.74% |
| contig513__20597932__c2__17.aa | 1228 | 4633 | 181 | contig499__34240836__c3__83.aa | 277 | 177 | 88.70% |
| contig514__34554686__c3__17.aa | 1229 | 4634 | 66 | contig508__32210927__c2__62.aa | 356 | 69 | 37.68% |
| contig514__23627202__c2__14.aa | 1230 | 4635 | 118 | contig489__7042212__c1__24.aa | 114 | 117 | 58.97% |
| contig514__26754511__c1__11.aa | 1231 | 4636 | 189 | contig371__6422301__c2__13.aa | 189 | 189 | 100.00% |
| contig514__36135881__c1__10.aa | 1233 | 4638 | 106 | contig489__35992212__c3__47.aa | 103 | 103 | 55.34% |
| contig514__33452__c1__9.aa | 1234 | 4639 | 70 | contig489__26307963__c1__25.aa | 74 | 54 | 31.48% |
| contig514__19737517__c1__8.aa | 1236 | 4641 | 439 | contig489__6923462__c3__45.aa | 447 | 441 | 51.93% |
| contig515__35391575__f2__1.aa | 1237 | 4642 | 259 | contig472__24027217__c3__34.aa | 352 | 239 | 94.56% |
| contig515__6650312__f1__3.aa | 1238 | 4643 | 808 | contig472__34064653__c1__28.aa | 791 | 783 | 72.03% |
| contig515__36225336__c2__11.aa | 1239 | 4644 | 227 | contig442__556578__f3__22.aa | 220 | 207 | 34.30% |
| contig515__34003180__c3__14.aa | 1240 | 4645 | 252 | contig193__399032__c2__13.aa | 279 | 213 | 35.21% |
| contig515__24415932__c3__13.aa | 1241 | 4646 | 276 | contig401__23547180__c1__20.aa | 287 | 283 | 22.97% |
| contig515__25413584__c2__10.aa | 1242 | 4647 | 78 | contig191__23881274__c1__5.aa | 237 | 76 | 53.95% |
| contig516__26367027__f1__1.aa | 1243 | 4648 | 97 | contig462__17010925__f2__15.aa | 67 | 67 | 46.27% |
| contig516__12380131__f3__6.aa | 1244 | 4649 | 507 | contig373__33865965__f2__3.aa | 507 | 507 | 100.00% |
| contig516__24432961__f3__7.aa | 1245 | 4650 | 329 | contig445__24033562__c2__48.aa | 331 | 322 | 52.17% |
| contig516__12614717__f3__8.aa | 1246 | 4651 | 515 | contig445__4898512__c3__61.aa | 519 | 511 | 72.99% |
| contig516__26573911__c1__10.aa | 1247 | 4652 | 342 | contig373__586063__c2__12.aa | 272 | 272 | T00.00% |
| contig516__4886330__c3__17.aa | 1248 | 4653 | 62 | contig457__23547827__f2__3.aa | 327 | 43 | 58.14% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig517__35817756__c3__25.aa | 1249 | 4654 | 285 | contig446__4886713__c2__47.aa | 264 | 260 | 74.23% |
| contig517__3955443__c1__17.aa | 1250 | 4655 | 275 | contig373__495677__c3__16.aa | 308 | 212 | 90.09% |
| contig517__9807178__c3__24.aa | 1251 | 4656 | 244 | contig446__20182688__c3__54.aa | 212 | 230 | 45.22% |
| contig517__22052053__c2__20.aa | 1252 | 4657 | 241 | contig446__31817677__c2__45.aa | 241 | 240 | 60.00% |
| contig517__33799062__c1__14.aa | 1253 | 4658 | 435 | contig446__994013__c1__36.aa | 414 | 413 | 86.20% |
| contig517__993802__c2__18.aa | 1255 | 4660 | 451 | contig446__12149213__c3__53.aa | 446 | 447 | 79.87% |
| contig518__9954413__c1__6.aa | 1259 | 4664 | 92 | contig458__20573500__c1__30.aa | 99 | 90 | 71.11% |
| contig518__10800777__c2__8.aa | 1260 | 4665 | 339 | contig490__24431587__f1__5.aa | 673 | 218 | 27.06% |
| contig519__14642886__f1__1.aa | 1261 | 4666 | 373 | contig412__24353377__f2__9.aa | 396 | 371 | 79.25% |
| contig519__22147187__f2__4.aa | 1262 | 4667 | 225 | contig430__23954437__f2__7.aa | 293 | 201 | 38.81% |
| contig519__24416076__f1__6.aa | 1263 | 4668 | 93 | contig430__23954437__f2__7.aa | 293 | 60 | 45.00% |
| contig52__25578126__c3__2.aa | 1265 | 4670 | 296 | contig317__23600910__c2__18.aa | 485 | 294 | 57.14% |
| contig520__31735778__f1__1.aa | 1266 | 4671 | 344 | contig494__21767962__c1__20.aa | 417 | 322 | 63.67% |
| contig520__4790626__c2__7.aa | 1267 | 4672 | 201 | contig375__4788941__f2__10.aa | 201 | 201 | 100.00% |
| contig520__25959838__f3__5.aa | 1268 | 4673 | 854 | contig484__26852307__c2__49.aa | 855 | 850 | 67.65% |
| contig520__23688175__c3__8.aa | 1269 | 4674 | 119 | contig484__9931575__f3__31.aa | 480 | 119 | 55.46% |
| contig521__22539843__c1__16.aa | 1273 | 4678 | 114 | contig404__25657135__c1__22.aa | 109 | 97 | 58.76% |
| contig521__32470285__c3__23.aa | 1275 | 4680 | 405 | contig470__10814188__f2__16.aa | 412 | 406 | 47.78% |
| contig521__31642313__c3__22.aa | 1276 | 4681 | 73 | contig432__34180312__f1__1.aa | 472 | 58 | 74.14% |
| contig522__22476087__f2__2.aa | 1277 | 4682 | 228 | contig325__25509676__f3__8.aa | 320 | 227 | 85.46% |
| contig522__33412637__f3__7.aa | 1278 | 4683 | 144 | contig325__33480337__f1__3.aa | 138 | 141 | 39.72% |
| contig522__23712802__f2__4.aa | 1279 | 4684 | 743 | contig446__9969092__c2__40.aa | 416 | 412 | 52.43% |
| contig522__34640887__f1__1.aa | 1280 | 4685 | 327 | contig446__24798462__c3__50.aa | 331 | 327 | 72.17% |
| contig522__26734755__f2__5.aa | 1281 | 4686 | 155 | contig446__24648591__c1__34.aa | 455 | 134 | 73.13% |
| contig523__36149007__c3__14.aa | 1282 | 4687 | 317 | contig413__986562__f1__2.aa | 207 | 183 | 80.33% |
| contig523__29306511__c1__10.aa | 1283 | 4688 | 345 | contig358__25585025__f2__11.aa | 326 | 322 | 63.35% |
| contig523__26836062__f3__7.aa | 1284 | 4689 | 302 | contig344__791406__c2__16.aa | 316 | 286 | 25.18% |
| contig523__10942887__c3__12.aa | 1285 | 4690 | 139 | contig373__495677__c3__16.aa | 308 | 139 | 66.19% |
| contig523__14253127__f1__8.aa | 1286 | 4691 | 129 | contig373__15890928__f3__6.aa | 172 | 113 | 63.72% |
| contig524__4689212__f2__3.aa | 1288 | 4693 | 501 | contig510__260942__c3__123.aa | 509 | 500 | 23.20% |
| contig524__22460116__f1__2.aa | 1289 | 4694 | 165 | contig454__22460816__f2__6.aa | 199 | 159 | 98.74% |
| contig525__36133568__f1__1.aa | 1291 | 4696 | 287 | contig502__30078752__c3__55.aa | 235 | 180 | 67.22% |
| contig525__26751302__f1__2.aa | 1292 | 4697 | 471 | contig379__22063441__f2__8.aa | 471 | 471 | 100.00% |
| contig525__5995250__c1__7.aa | 1294 | 4699 | 472 | contig379__14573428__f2__10.aa | 500 | 352 | 100.00% |
| contig526__25526675__f1__1.aa | 1295 | 4700 | 180 | contig79__5937635__c3__3.aa | 328 | 126 | 65.08% |
| contig526__26564012__f2__3.aa | 1296 | 4701 | 251 | contig428__31288253__c2__39.aa | 208 | 199 | 63.82% |
| contig526__36147816__f1__2.aa | 1297 | 4702 | 725 | contig428__30649193__c1__32.aa | 693 | 701 | 56.92% |
| contig526__7086675__f3__8.aa | 1298 | 4703 | 299 | contig428__26679682__c3__47.aa | 303 | 296 | 73.31% |
| contig526__4335938__f2__6.aa | 1299 | 4704 | 229 | contig428__34101713__c3__48.aa | 220 | 218 | 77.98% |
| contig527__2507875__f1__1.aa | 1300 | 4705 | 175 | contig378__16851525__c2__14.aa | 188 | 175 | 99.43% |
| contig527__7070428__f3__2.aa | 1301 | 4706 | 150 | contig378__7070428__c1__10.aa | 150 | 150 | 100.00% |
| cnntig527__6673452__f3__3.aa | 1302 | 4707 | 278 | contig38__26179186__c2__3.aa | 278 | 278 | 100.00% |
| contig527__884505__c2__6.aa | 1303 | 4708 | 235 | contig380__35195218__f1__1.aa | 235 | 235 | 100.00% |
| contig527__641887__c1__4.aa | 1304 | 4709 | 68 | contig378__6369827__c1__13.aa | 198 | 69 | 49.28% |
| contig528__2989063__f2__3.aa | 1305 | 4710 | 426 | contig449__32082162__c3__50.aa | 483 | 426 | 83.33% |
| contig528__21539812__f1__1.aa | 1306 | 4711 | 287 | contig380__16883505__c1__17.aa | 287 | 287 | 100.00% |
| contig528__34195452__f1__5.aa | 1307 | 4712 | 478 | contig449__22152182__c2__42.aa | 528 | 468 | 80.34% |
| contig528__19742827__f1__2.aa | 1308 | 4713 | 132 | contig449__34187875__c1__36.aa | 153 | 130 | 77.69% |
| contig528__4789078__f2__6.aa | 1309 | 4714 | 121 | contig449__6141655__c2__43.aa | 297 | 119 | 62.19% |
| contig529__975092__f3__9.aa | 1310 | 4715 | 526 | contig263__292944__c2__12.aa | 709 | 497 | 31.19% |
| contig529__4687511__f1__1.aa | 1311 | 4716 | 236 | contig410__36125000__c3__23.aa | 283 | 217 | 31.80% |
| contig529__24220463__f1__2.aa | 1312 | 4717 | 352 | contig381__3313510__c3__30.aa | 87 | 87 | 100.00% |
| contig53__30084542__f1__1.aa | 1315 | 4720 | 193 | contig478__24400077__c2__37.aa | 490 | 109 | 26.61% |
| contig530__78262__f2__4.aa | 1316 | 4721 | 299 | contig320__20892590__c3__24.aa | 189 | 182 | 86.81% |
| contig530__33601567__f1__2.aa | 1317 | 4722 | 289 | contig320__33617192__c2__18.aa | 288 | 279 | 68.46% |
| contig530__10444528__f1__3.aa | 1318 | 4723 | 492 | contig382__5870937__f3__13.aa | 492 | 492 | 100.00% |
| contig530__36225000__f3__7.aa | 1319 | 4724 | 294 | contig320__23472002__c2__20.aa | 324 | 285 | 86.32% |
| contig530__30078906__f2__5.aa | 1320 | 4725 | 248 | contig382__430375__c1__21.aa | 248 | 248 | 100.00% |
| contig531__31742135__f3__9.aa | 1321 | 4726 | 250 | contig286__26775050__c3__27.aa | 465 | 220 | 44.09% |
| contig531__4033180__f2__6.aa | 1323 | 4728 | 112 | contig382__24886550__c2__29.aa | 112 | 112 | 100.00% |
| contig531__3945317__c1__14.aa | 1325 | 4730 | 252 | contig462__24875006__f3__35.aa | 257 | 250 | 83.60% |
| contig531__5117168__c1__13.aa | 1326 | 4731 | 267 | contig462__10572836__f2__23.aa | 277 | 264 | 82.20% |
| contig531__34172187__c2__2.aa | 1327 | 4732 | 316 | contig462__33798177__f2__22.aa | 284 | 283 | 80.92% |
| contig531__23912802__c3__20.aa | 1328 | 4733 | 272 | contig462__36148513__f1__34.aa | 285 | 259 | 83.01% |
| contig531__26605194__c2__16.aa | 1330 | 4735 | 155 | contig486__3167677__f3__28.aa | 385 | 146 | 30.14% |
| contig532__36147313__c2__16.aa | 1335 | 4740 | 254 | contig239__33867817__f2__5.aa | 344 | 102 | 31.37% |
| contig533__15862500__c2__19.aa | 1336 | 4741 | 214 | contig485__15115642__f3__22.aa | 439 | 206 | 40.29% |
| contig533__14492943__c1__15.aa | 1337 | 4742 | 106 | contig384__24428150__f1__2.aa | 106 | 106 | 100.00% |
| contig533__26448905__c2__18.aa | 1338 | 4743 | 164 | contig281__4979680__f3__2.aa | 161 | 159 | 67.93% |
| contig533__12144380__f2__8.aa | 1339 | 4744 | 109 | contig384__26757961__f3__16.aa | 109 | 109 | 100.00% |
| contig533__3338142__c3__20.aa | 1340 | 4745 | 141 | contig384__14531515__c2__31.aa | 141 | 141 | 100.00% |
| contig534__792092__c2__9.aa | 1341 | 4746 | 370 | contig365__34074027__c3__36.aa | 418 | 363 | 75.48% |
| contig534__36133417__c1__7.aa | 1342 | 4747 | 341 | contig365__24886086__c2__32.aa | 269 | 206 | 61.65% |
| contig534__1464525__c3__10.aa | 1344 | 4749 | 82 | contig504__26678587__f1__2.aa | 123 | 71 | 97.18% |
| contig535__24120907__f1__1.aa | 1346 | 4751 | 109 | contig384__2037712__f2__13.aa | 109 | 109 | 100.00% |
| contig535__23953503__f3__8.aa | 1347 | 4752 | 305 | contig384__4084568__c1__19.aa | 305 | 305 | 100.00% |
| contig535__24495462__f3__9.aa | 1349 | 4754 | 314 | contig385__23995942__f2__3.aa | 314 | 314 | 100.00% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig535_24431563_f2_5.aa | 1350 | 4755 | 207 | contig385_34571062_f2_4.aa | 207 | 207 | 100.00% |
| contig535_36126328_f2_6.aa | 1351 | 4756 | 170 | contig430_23954437_f2_7.aa | 293 | 166 | 51.81% |
| contig535_34257750_f1_4.aa | 1352 | 4757 | 135 | contig430_23954437_f2_7.aa | 293 | 104 | 39.42% |
| contig535_30526711_f2_7.aa | 1353 | 4758 | 81 | contig385_13808206_c3_29.aa | 81 | 81 | 100.00% |
| contig536_3257705_c3_21.aa | 1354 | 4759 | 120 | contig385_10626637_f2_5.aa | 120 | 120 | 100.00% |
| contig536_14941682_c3_19.aa | 1357 | 4762 | 247 | contig340_22897067_c2_14.aa | 316 | 236 | 49.58% |
| contig537_19665937_f1_10.aa | 1360 | 4765 | 540 | contig253_34265693_c2_11.aa | 570 | 546 | 79.30% |
| contig537_6697186_f1_4.aa | 1361 | 4766 | 394 | contig253_25604715_c3_13.aa | 406 | 391 | 88.49% |
| contig537_24790701_f2_7.aa | 1362 | 4767 | 700 | contig387_24415953_c1_21.aa | 700 | 700 | 100.00% |
| contig538_2822263_c1_10.aa | 1364 | 4769 | 77 | contig356_24023387_c1_11.aa | 88 | 62 | 66.13% |
| contig538_13683462_f3_5.aa | 1365 | 4770 | 348 | contig356_24823376_f1_1.aa | 348 | 340 | 33.53% |
| contig538_14853203_f_36.aa | 1367 | 4772 | 330 | contig356_32620938_f2_3.aa | 473 | 316 | 56.65% |
| contig539_26770302_c2_15.aa | 1369 | 4774 | 388 | contig252_25584676_c1_10.aa | 167 | 147 | 66.67% |
| contig539_22445262_c3_19.aa | 1370 | 4775 | 409 | contig252_33790813_c2_11.aa | 374 | 323 | 89.47% |
| contig539_24649093_c3_18.aa | 1371 | 4776 | 163 | contig252_12696068_c1_8.aa | 179 | 179 | 62.01% |
| contig539_194453_f1_5.aa | 1372 | 4777 | 283 | contig252_21730325_f2_2.aa | 272 | 263 | 71.48% |
| contig539_527358_f2_8.aa | 1373 | 4778 | 160 | contig252_2584411_f2_3.aa | 257 | 117 | 59.83% |
| contig540_24221876_c3_10.aa | 1376 | 4781 | 362 | contig499_10831952_f1_3.aa | 403 | 117 | 93.16% |
| contig540_23445942_f2_4.aa | 1377 | 4782 | 441 | contig429_2751506_f1_1.aa | 318 | 307 | 76.55% |
| contig540_24234425_f1_3.aa | 1378 | 4783 | 170 | contig429_19570327_f2_11.aa | 164 | 156 | 71.80% |
| contig540_33787525_c3_7.aa | 1379 | 4784 | 11 | contig429_20992925_c2_38.aa | 875 | 111 | 81.08% |
| contig540_1416256_c3_6.aa | 1380 | 4785 | 88 | contig429_20992925_c2_38.aa | 875 | 81 | 85.19% |
| contig541_1042337_c2_17.aa | 1381 | 4786 | 103 | contig491_24257712_c1_59.aa | 167 | 96 | 75.00% |
| contig541_25587926_c1_12.aa | 1386 | 4791 | 286 | contig506_21678802_c1_58.aa | 263 | 268 | 33.96% |
| contig541_30269691_c1_11.aa | 1388 | 4793 | 145 | contig506_12687578_c2_73.aa | 228 | 147 | 38.78% |
| contig541_24500327_c2_15.aa | 1389 | 4794 | 72 | contig506_12687578_c2_73.aa | 228 | 58 | 25.86% |
| contig541_33454702_c3_18.aa | 1391 | 4796 | 105 | contig506_24431511_c3_89.aa | 114 | 108 | 26.85% |
| contig542_36195332_c3_14.aa | 1392 | 4797 | 213 | contig219_583285_c2_8.aa | 291 | 192 | 55.21% |
| contig542_34242327_c2_12.aa | 1394 | 4799 | 205 | contig389_34070332_c2_23.aa | 205 | 205 | 100.00% |
| contig542_9765930_f3_8.aa | 1395 | 4800 | 195 | contig389_12688955_f2_9.aa | 195 | 195 | 100.00% |
| contig542_11226567_f1_5.aa | 1396 | 4801 | 367 | contig353_22705437_f1_2.aa | 399 | 354 | 66.95% |
| contig543_24338328_c2_13.aa | 1397 | 4802 | 228 | contig429_26460925_c2_37.aa | 416 | 215 | 80.00% |
| contig543_26756317_c1_10.aa | 1398 | 4803 | 216 | contig429_26460925_c2_37.aa | 416 | 201 | 82.59% |
| contig543_20980325_c2_12.aa | 1399 | 4804 | 378 | contig429_23439818_c3_41.aa | 378 | 372 | 65.32% |
| contig543_4944752_c1_9.aa | 1400 | 4805 | 261 | contig429_34250675_c1_30.aa | 240 | 232 | 59.05% |
| contig543_13025003_c3_15.aa | 1401 | 4806 | 339 | contig127_24851576_c1_4.aa | 237 | 228 | 82.02% |
| contig543_6347040_c3_14.aa | 1402 | 4807 | 509 | contig127_2375253_c3_6.aa | 292 | 204 | 61.77% |
| contig544_29347252_c2_10.aa | 1403 | 4808 | 492 | contig447_10824012_c2_33.aa | 460 | 451 | 66.96% |
| contig544_29312806_c1_8.aa | 1404 | 4809 | 506 | contig447_23832537_c1_27.aa | 482 | 469 | 81.45% |
| contig544_3017176_c3_11.aa | 1405 | 4810 | 608 | contig447_14064838_c1_26.aa | 466 | 425 | 84.47% |
| contig545_24039057_f1_1.aa | 1407 | 4812 | 113 | contig492_22300143_f3_14.aa | 131 | 94 | 28.72% |
| contig545_11730462_c1_13.aa | 1408 | 4813 | 326 | contig284_5120302_c1_16.aa | 212 | 84 | 44.05% |
| contig545_4476713_f3_10.aa | 1409 | 4814 | 87 | contig398_1211592_f3_9.aa | 344 | 78 | 38.46% |
| contig545_23884536_f1_3.aa | 1410 | 4815 | 266 | contig398_1211592_f3_9.aa | 344 | 254 | 35.04% |
| contig545_22549027_f1_4.aa | 1411 | 4816 | 470 | contig439_34274062_c2_27.aa | 480 | 449 | 27.17% |
| contig546_23689050_c2_16.aa | 1413 | 4818 | 375 | contig432_34180312_f1_1.aa | 472 | 367 | 68.39% |
| contig546_4977300_c3_18.aa | 1414 | 4819 | 430 | contig450_25822212_c2_25.aa | 417 | 417 | 34.53% |
| contig546_21657965_c1_12.aa | 1415 | 4820 | 119 | contig470_4376342_f1_5.aa | 146 | 110 | 80.91% |
| contig546_16835967_c3_17.aa | 1416 | 4821 | 110 | contig470_24408212_f2_14.aa | 115 | 105 | 87.62% |
| contig546_7148518_c1_11.aa | 1417 | 4822 | 140 | contig470_4900301_f3_20.aa | 138 | 135 | 58.52% |
| contig546_5273380_c2_13.aa | 1418 | 4823 | 101 | contig392_26801875_f2_6.aa | 101 | 101 | 100.00% |
| contig547_36017262_f2_4.aa | 1419 | 4824 | 443 | contig369_26034686_c2_17.aa | 143 | 142 | 92.25% |
| contig547_964842_f3_9.aa | 1420 | 4825 | 294 | contig369_7303457_c2_18.aa | 300 | 286 | 57.69% |
| contig547_24508337_c2_12.aa | 1422 | 4827 | 548 | contig369_976568_f1_2.aa | 543 | 543 | 89.32% |
| contig547_31416050_f3_10.aa | 1423 | 4828 | 214 | contig370_13943917_c1_14.aa | 957 | 214 | 58.41% |
| contig548_32464192_c2_12.aa | 1424 | 4829 | 147 | contig392_34181528_c3_30.aa | 147 | 147 | 100.00% |
| contig548_16602217_c1_10.aa | 1425 | 4830 | 263 | contig469_2985905_f1_4.aa | 258 | 263 | 39.92% |
| contig548_34492262_c3_14.aa | 1426 | 4831 | 252 | contig469_2985905_f1_4.aa | 258 | 251 | 71.71% |
| contig548_16803140_c1_9.aa | 1427 | 4832 | 129 | contig348_16532250_f1_3.aa | 762 | 62 | 32.26% |
| contig548_1306675_c3_13.aa | 1428 | 4833 | 220 | contig392_14644705_c2_25.aa | 220 | 220 | 100.00% |
| contig549_3203887_f3_8.aa | 1429 | 4834 | 203 | contig474_14647180_c1_26.aa | 291 | 194 | 51.55% |
| contig549_24414818_f3_9.aa | 1430 | 4835 | 204 | contig474_34182687_c2_35.aa | 208 | 203 | 40.89% |
| contig549_22462812_c1_17.aa | 1431 | 4836 | 323 | contig368_9948302_f3_12.aa | 340 | 339 | 32.15% |
| contig549_33210952_c1_16.aa | 1432 | 4837 | 427 | contig379_22063441_f1_8.aa | 471 | 427 | 25.29% |
| contig549_24804082_c1_15.aa | 1433 | 4838 | 236 | contig448_24897342_c2_44.aa | 255 | 220 | 39.55% |
| contig549_275291_c3_20.aa | 1435 | 4840 | 314 | contig393_4902187_c1_33.aa | 167 | 167 | 100.00% |
| contig549_32609456_c1_13.aa | 1436 | 4841 | 129 | contig158_4074027_f2_1.aa | 252 | 95 | 24.21% |
| contig55_11718766_c2_1.aa | 1437 | 4842 | 262 | contig154_31454811_f1_1.aa | 220 | 213 | 57.75% |
| contig550_22400337_c1_15.aa | 1438 | 4843 | 436 | contig393_10585933_c3_44.aa | 543 | 433 | 61.89% |
| contig550_4689027_c1_14.aa | 1439 | 4844 | 99 | contig393_197718_c2_36.aa | 99 | 99 | 100.00% |
| contig550_6837837_c3_17.aa | 1440 | 4845 | 189 | contig334_21929175_c3_14.aa | 203 | 187 | 62.57% |
| contig551_29426556_c3_12.aa | 1441 | 4846 | 379 | contig449_4901711_c1_39.aa | 433 | 360 | 67.22% |
| contig551_15833467_c2_10.aa | 1442 | 4847 | 427 | contig449_32611587_c3_56.aa | 436 | 422 | 59.01% |
| contig551_33599036_f1_1.aa | 1443 | 4848 | 438 | contig394_10829840_c3_23.aa | 438 | 438 | 100.00% |
| contig551_14727217_c3_11.aa | 1444 | 4849 | 243 | contig469_2985905_f1_14.aa | 258 | 266 | 24.44% |
| contig551_16407918_c2_8.aa | 1445 | 4850 | 154 | contig469_2985905_f1_4.aa | 258 | 141 | 26.24% |
| contig552_24611552_c3_13.aa | 1447 | 4852 | 241 | contig394_23704637_c3_21.aa | 241 | 241 | 100.00% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig552_11063187_f3_5.aa | 1448 | 4853 | 190 | contig465_204717_c2_39.aa | 133 | 132 | 95.46% |
| contig552_26756576_c3_12.aa | 1449 | 4854 | 69 | contig465_26365926_f1_11.aa | 69 | 69 | 89.86% |
| contig552_12275257_f1_2.aa | 1450 | 4855 | 652 | contig465_12275257_c3_44.aa | 816 | 651 | 95.08% |
| contig553_10055427_c2_24.aa | 1451 | 4856 | 130 | contig402_24495467_f2_10.aa | 119 | 105 | 32.38% |
| contig553_2187892_c2_23.aa | 1452 | 4857 | 403 | contig232_24507937_f2_3.aa | 294 | 288 | 63.19% |
| contig553_6531587_c3_25.aa | 1454 | 4859 | 419 | contig232_21925337_f2_1.aa | 387 | 394 | 84.77% |
| contig553_6837686_c1_18.aa | 1455 | 4860 | 139 | contig333_33366436_f1_5.aa | 66 | 60 | 90.00% |
| contig553_4882938_c2_21.aa | 1457 | 4862 | 483 | contig333_13865751_f1_4.aa | 484 | 454 | 57.49% |
| contig554_5337953_f1_1.aa | 1459 | 4864 | 638 | contig452_22351578_c2_28.aa | 317 | 321 | 23.68% |
| contig554_29562578_f1_2.aa | 1460 | 4865 | 72 | contig396_24022192_c1_22.aa | 72 | 72 | 100.00% |
| contig554_25680377_f3_5.aa | 1461 | 4866 | 297 | contig396_24806653_c2_28.aa | 297 | 297 | 100.00% |
| contig555_35407183_f3_9.aa | 1464 | 4869 | 188 | contig218_29586637_c1_9.aa | 231 | 156 | 82.05% |
| contig555_31447318_f2_7.aa | 1465 | 4870 | 283 | contig218_14626317_c3_14.aa | 292 | 271 | 76.75% |
| contig555_14899187_f1_3.aa | 1466 | 4871 | 641 | contig396_34173438_c2_26.aa | 641 | 641 | 100.00% |
| contig555_15828436_f1_4.aa | 1467 | 4872 | 144 | contig396_16422552_f2_6.aa | 188 | 143 | 93.01% |
| contig555_16854750_f1_5.aa | 1468 | 4873 | 463 | contig113_13008563_c2_4.aa | 391 | 382 | 73.56% |
| contig556_553550_c1_14.aa | 1470 | 4875 | 259 | contig119_29697217_c2_3.aa | 264 | 137 | 21.90% |
| contig556_36539067_c1_12.aa | 1472 | 4877 | 170 | contig397_7320300_c3_35.aa | 170 | 170 | 100.00% |
| contig556_21484380_f1_1.aa | 1473 | 4878 | 138 | contig397_4773463_f3_16.aa | 138 | 138 | 100.00% |
| contig556_26040927_c2_16.aa | 1474 | 4879 | 178 | contig397_4897707_f1_4.aa | 178 | 178 | 100.00% |
| contig556_3213962_c3_17.aa | 1475 | 4880 | 468 | contig502_14179752_c3_52.aa | 420 | 242 | 42.15% |
| contig557_783385_c2_18.aa | 1477 | 4882 | 278 | contig503_16406327_c2_96.aa | 356 | 267 | 41.95% |
| contig557_36069812_c1_14.aa | 1478 | 4883 | 204 | contig503_24804712_c2_97.aa | 203 | 201 | 34.83% |
| contig557_24648417_c2_16.aa | 1479 | 4884 | 355 | contig490_34178787_f3_30.aa | 598 | 334 | 81.74% |
| contig557_33859692_c1_13.aa | 1480 | 4885 | 305 | contig490_34178787_f3_30.aa | 598 | 288 | 79.51% |
| contig557_287_c2_15.aa | 1481 | 4886 | 500 | contig490_6069180_f3_29.aa | 524 | 485 | 80.83% |
| contig558_34270312_f1_1.aa | 1482 | 4887 | 126 | contig187_14645843_f3_10.aa | 450 | 53 | 28.30% |
| contig558_3995338_f2_4.aa | 1483 | 4888 | 489 | contig411_33828175_c3_12.aa | 358 | 367 | 26.16% |
| contig558_4066025_f2_5.aa | 1484 | 4889 | 179 | contig322_26758418_c2_21.aa | 174 | 174 | 50.00% |
| contig558_34273462_f2_6.aa | 1485 | 4890 | 296 | contig322_26461012_c3_24.aa | 306 | 284 | 36.62% |
| contig558_6501912_f3_8.aa | 1486 | 4891 | 258 | contig324_26367202_f2_4.aa | 379 | 223 | 66.37% |
| contig558_4945375_f2_7.aa | 1487 | 4892 | 176 | contig324_26367202_f2_4.aa | 379 | 156 | 71.80% |
| contig558_34085937_c2_11.aa | 1488 | 4893 | 515 | contig399_34586528_c1_17.aa | 515 | 515 | 100.00% |
| contig559_6336567_f2_2.aa | 1489 | 4894 | 340 | contig399_24664000_f3_14.aa | 340 | 340 | 100.00% |
| contig559_4585937_c1_15.aa | 1490 | 4895 | 102 | contig412_9851582_c1_26.aa | 133 | 98 | 52.04% |
| contig559_51_16592_f1_1.aa | 1491 | 4896 | 236 | contig483_34648457_f3_17.aa | 242 | 227 | 84.14% |
| contig559_26287812_f3_5.aa | 1493 | 4898 | 85 | contig399_14553767_c3_24.aa | 85 | 85 | 100.00% |
| contig559_6537937_c3_21.aa | 1494 | 4899 | 194 | contig399_22036625_f2_10.aa | 194 | 193 | 100.00% |
| contig559_3994143_c1_12.aa | 1495 | 4900 | 286 | contig483_7242052_c2_40.aa | 291 | 284 | 41.90% |
| contig559_24414825_f3_7.aa | 1496 | 4901 | 173 | contig483_13866075_f1_3.aa | 171 | 160 | 68.13% |
| contig559_31366637_c3_19.aa | 1498 | 4903 | 345 | contig397_39818_c1_18.aa | 415 | 339 | 79.06% |
| contig56_23712837_f2_3.aa | 1500 | 4905 | 172 | contig400_6016091_c3_41.aa | 172 | 172 | 100.00% |
| contig56_5894426_c1_4.aa | 1501 | 4906 | 93 | contig400_10430450_c1_32.aa | 93 | 93 | 100.00% |
| contig560_24611401_f3_3.aa | 1502 | 4907 | 111 | contig400_29453328_c2_38.aa | 111 | 111 | 100.00% |
| contig560_22683186_f1_1.aa | 1503 | 4908 | 824 | contig490_15704807_f1_6.aa | 828 | 812 | 86.70% |
| contig560_24417337_c3_14.aa | 1505 | 4910 | 151 | contig279_34178805_f3_7.aa | 312 | 115 | 25.22% |
| contig560_30096075_c2_8.aa | 1507 | 4912 | 78 | contig400_33407566_f1_7.aa | 78 | 78 | 100.00% |
| contig560_2736275_f2_2.aa | 1508 | 4913 | 77 | contig400_1979562_c2_36.aa | 77 | 77 | 100.00% |
| contig561_16845000_f1_1.aa | 1509 | 4914 | 901 | contig400_10752950_c2_35.aa | 901 | 901 | 100.00% |
| contig561_26757062_f2_4.aa | 1510 | 4915 | 242 | contig259_26566012_f2_2.aa | 215 | 213 | 38.03% |
| contig561_2119011_f1_2.aa | 1511 | 4916 | 298 | contig259_24407318_c2_3.aa | 294 | 291 | 55.33% |
| contig561_4877187_f3_8.aa | 1512 | 4917 | 440 | contig394_10829840_c3_23.aa | 438 | 425 | 77.41% |
| contig561_15628_c2_14.aa | 1513 | 4918 | 325 | contig391_11915686_c2_24.aa | 255 | 148 | 27.03% |
| contig561_9789134_c1_10.aa | 1514 | 4919 | 163 | contig402_23525463_f1_1.aa | 155 | 139 | 30.94% |
| contig562_36503966_f2_4.aa | 1515 | 4920 | 235 | contig166_20878791_c1_5.aa | 360 | 232 | 75.43% |
| contig562_34257817_f1_8.aa | 1516 | 4921 | 78 | contig425_194452_f1_9.aa | 85 | 78 | 53.85% |
| contig562_19532203_f3_9.aa | 1517 | 4922 | 354 | contig490_24266577_f1_14.aa | 202 | 188 | 38.83% |
| contig562_3230217_c2_13.aa | 1518 | 4923 | 398 | contig486_7087562_f1_13.aa | 304 | 232 | 24.57% |
| contig562_25547012_c3_16.aa | 1519 | 4924 | 534 | contig363_562637_f1_13.aa | 594 | 327 | 22.63% |
| contig562_33632827_f2_7.aa | 1521 | 4926 | 206 | contig391_11915686_c2_24.aa | 255 | 198 | 54.04% |
| contig563_24225280_c2_18.aa | 1522 | 4927 | 182 | contig267_6533562_c2_17.aa | 373 | 158 | 76.58% |
| contig563_5119575_c1_16.aa | 1523 | 4928 | 234 | contig267_6533562_c2_17.aa | 373 | 210 | 82.86% |
| contig563_34195282_c3_23.aa | 1524 | 4929 | 269 | contig361_23620262_c1_17.aa | 275 | 274 | 80.29% |
| contig563_6640963_c3_22.aa | 1525 | 4930 | 283 | contig361_24433407_c3_24.aa | 246 | 226 | 88.50% |
| contig563_22838916_c3_21.aa | 1526 | 4931 | 365 | contig361_36359576_c2_19.aa | 319 | 307 | 66.45% |
| contig563_1189718_c2_17.aa | 1527 | 4932 | 218 | contig361_30475781_c2_18.aa | 118 | 110 | 75.46% |
| contig563_30109500_c1_14.aa | 1529 | 4934 | 259 | contig406_31641965_c3_43.aa | 225 | 205 | 67.32% |
| contig563_25986083_c3_19.aa | 1530 | 4935 | 65 | contig379_1414061_f1_7.aa | 159 | 63 | 34.92% |
| contig564_4900251_c3_21.aa | 1531 | 4936 | 181 | contig63_26757937_c3_6.aa | 185 | 176 | 65.91% |
| contig564_34187517_f3_7.aa | 1534 | 4939 | 113 | contig402_33838290_f2_9.aa | 113 | 113 | 100.00% |
| contig564_26601558_c3_18.aa | 1535 | 4940 | 136 | contig402_13800781_c3_38.aa | 136 | 136 | 100.00% |
| contig564_34156963_c3_17.aa | 1536 | 4941 | 85 | contig402_3907135_f3_18.aa | 85 | 85 | 100.00% |
| contig564_20754837_c2_12.aa | 1537 | 4942 | 210 | contig322_5134756_c3_23.aa | 108 | 87 | 75.86% |
| contig565_3960877_c1_12.aa | 1539 | 4944 | 449 | contig503_34178266_f3_62.aa | 478 | 448 | 33.26% |
| contig565_34570442_f1_2.aa | 1541 | 4946 | 522 | contig182_11728381_f3_3.aa | 291 | 251 | 26.69% |
| contig565_13706327_f2_9.aa | 1542 | 4947 | 239 | contig235_11901667_c3_13.aa | 215 | 199 | 33.67% |
| contig565_6835927_f1_3.aa | 1543 | 4948 | 502 | contig486_23439137_f1_5.aa | 471 | 453 | 47.02% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig565__36605317__c3__15.aa | 1544 | 4949 | 121 | contig403__4336088__c1__18.aa | 121 | 121 | 100.00% |
| contig566__23547832__c2__15.aa | 1545 | 4950 | 320 | contig124__33673317__f1__1.aa | 264 | 256 | 91.41% |
| contig566__23697811__c1__14.aa | 1546 | 4951 | 282 | contig509__29307838__c1__75.aa | 269 | 244 | 26.23% |
| contig566__5084757__c3__18.aa | 1547 | 4952 | 385 | contig370__4196052__c2__17.aa | 334 | 334 | 85.63% |
| contig566__97268__c3__17.aa | 1548 | 4953 | 197 | contig370__26767767__c2__16.aa | 172 | 159 | 63.52% |
| contig566__6289133__c3__16.aa | 1549 | 4954 | 584 | contig370__13943917__c1__14.aa | 957 | 561 | 57.22% |
| contig567__12195152__f2__5.aa | 1550 | 4955 | 74 | contig299__33828450__f1__1.aa | 154 | 53 | 49.06% |
| contig567__34113442__f1__1.aa | 1551 | 4956 | 366 | contig299__4336082__f3__3.aa | 363 | 357 | 73.95% |
| contig567__16127267__f2__6.aa | 1552 | 4957 | 598 | contig398__33463__f2__4.aa | 337 | 332 | 79.52% |
| contig567__13672262__c2__12.aa | 1554 | 4959 | 199 | contig404__4772213__c1__17.aa | 199 | 199 | 100.00% |
| contig567__22829687__f1__4.aa | 1555 | 4960 | 275 | contig404__5314688__f1__3.aa | 275 | 275 | 100.00% |
| contig567__34179702__f2__8.aa | 1556 | 4961 | 507 | contig490__4742968__f1__11.aa | 1027 | 166 | 41.57% |
| contig568__25431567__f2__3.aa | 1558 | 4963 | 357 | contig285__39818__f1__1.aa | 361 | 342 | 71.05% |
| contig568__25667812__f2__4.aa | 1559 | 4964 | 691 | contig405__235008__c3__21.aa | 691 | 691 | 100.00% |
| contig568__24415936__f3__6.aa | 1560 | 4965 | 278 | contig285__976550__f3__7.aa | 247 | 235 | 66.81% |
| contig568__26756562__f2__5.aa | 1561 | 4966 | 262 | contig486__3167677__f3__28.aa | 385 | 231 | 32.04% |
| contig569__15828390__f3__2.aa | 1562 | 4967 | 241 | contig422__2195337__c2__33.aa | 190 | 187 | 88.77% |
| contig569__30117807__f2__1.aa | 1563 | 4968 | 1247 | contig453__24478402__c2__49.aa | 1231 | 1229 | 79.74% |
| contig570__3947755__f2__5.aa | 1565 | 4970 | 492 | contig406__36210892__c3__40.aa | 492 | 492 | 100.00% |
| contig570__34093830__f1__3.aa | 1568 | 4973 | 242 | contig440__24298827__f3__8.aa | 686 | 198 | 26.26% |
| contig570__4977250__f1__4.aa | 1569 | 4974 | 179 | contig440__24298827__f3__8.aa | 686 | 137 | 25.55% |
| contig570__398577__f2__9.aa | 1571 | 4976 | 173 | contig407__22672893__f2__12.aa | 146 | 146 | 100.00% |
| contig571__14267842__c3__26.aa | 1572 | 4977 | 331 | contig407__25673202__c1__27.aa | 331 | 331 | 100.00% |
| contig571__26439717__c1__19.aa | 1573 | 4978 | 287 | contig481__26026567__c3__42.aa | 306 | 281 | 49.47% |
| contig571__26597816__c3__24.aa | 1574 | 4979 | 170 | contig481__30473461__c1__29.aa | 178 | 169 | 46.75% |
| contig571__34416088__c2__22.aa | 1575 | 4980 | 430 | contig481__788952__c3__41.aa | 431 | 424 | 66.27% |
| contig571__6839090__c2__21.aa | 1576 | 4981 | 375 | contig481__23547162__c3__40.aa | 372 | 366 | 54.65% |
| contig571__26761057__c2__20.aa | 1577 | 4982 | 395 | contig481__23676713__c2__33.aa | 392 | 392 | 78.57% |
| contig571__23703462__c1__18.aa | 1578 | 4983 | 368 | contig481__25600336__c1__27.aa | 267 | 266 | 68.80% |
| contig572__6929707__c3__19.aa | 1580 | 4985 | 364 | contig365__34589063__c1__31.aa | 275 | 269 | 73.98% |
| contig572__994062__c3__18.aa | 1581 | 4986 | 246 | contig365__24095287__c1__30.aa | 255 | 245 | 74.29% |
| contig572__34414061__c3__17.aa | 1582 | 4987 | 315 | contig365__6058387__c2__34.aa | 328 | 306 | 68.63% |
| contig572__5353562__c2__16.aa | 1584 | 4989 | 326 | contig365__4688818__c1__27.aa | 199 | 193 | 59.59% |
| contig572__4007952__c2__15.aa | 1585 | 4990 | 146 | contig365__26366307__c1__26.aa | 161 | 146 | 89.73% |
| contig573__35834377__f3__6.aa | 1586 | 4991 | 157 | contig509__29307838__c1__75.aa | 269 | 151 | 36.42% |
| contig573__24334652__f1__1.aa | 1587 | 4992 | 296 | contig416__22150426__c2__30.aa | 282 | 258 | 39.54% |
| contig573__3914713__f1__2.aa | 1588 | 4993 | 162 | contig370__26767767__c2__16.aa | 172 | 148 | 35.81% |
| contig573__35352137__f2__5.aa | 1589 | 4994 | 290 | contig498__4312818__f3__13.aa | 285 | 276 | 25.36% |
| contig573__14542287__f1__3.aa | 1590 | 4995 | 313 | contig1__1821500050__c3__2.aa | 269 | 263 | 50.95% |
| contig574__6257628__f1__1.aa | 1592 | 4997 | 797 | contig462__29462555__c1__38.aa | 646 | 620 | 64.19% |
| contig574__4335207__c2__20.aa | 1593 | 4998 | 408 | contig408__6136587__c2__44.aa | 408 | 408 | 100.00% |
| contig574__10407557__c1__19.aa | 1594 | 4999 | 826 | contig390__24433188__c3__20.aa | 793 | 729 | 57.75% |
| contig574__16610881__f2__7.aa | 1595 | 5000 | 118 | contig408__13672326__f1__12.aa | 84 | 84 | 100.00% |
| contig574__16448438__c2__18.aa | 1596 | 5001 | 514 | contig408__35314168__c2__42.aa | 514 | 514 | 100.00% |
| contig574__26437805__c2__17.aa | 1597 | 5002 | 417 | contig483__23634662__c1__22.aa | 453 | 394 | 33.00% |
| contig574__6775313__c3__21.aa | 1598 | 5003 | 523 | contig330__24414818__c1__12.aa | 490 | 524 | 33.59% |
| contig575__4334838__f1__1.aa | 1599 | 5004 | 243 | contig285__39818__f1__1.aa | 361 | 236 | 43.22% |
| contig575__16133443__f3__8.aa | 1600 | 5005 | 239 | contig68__26612780__c3__3.aa | 224 | 212 | 31.60% |
| contig575__34176713__f3__9.aa | 1601 | 5006 | 278 | contig285__976550__f3__7.aa | 247 | 226 | 32.74% |
| contig575__15914813__f1__2.aa | 1602 | 5007 | 594 | contig463__29567177__c1__28.aa | 580 | 262 | 27.48% |
| contig575__832702__f2__5.aa | 1603 | 5008 | 242 | contig399__2112655__f2__9.aa | 533 | 119 | 33.61% |
| contig575__24038437__f3__10.aa | 1604 | 5009 | 148 | contig372__24781287__c3__24.aa | 155 | 130 | 20.77% |
| contig576__651055__c3__22.aa | 1605 | 5010 | 345 | contig392__1210966__f2__8.aa | 345 | 244 | 34.84% |
| contig576__6832753__c1__15.aa | 1606 | 5011 | 230 | contig499__34240836__c3__83.aa | 277 | 207 | 26.57% |
| contig577__6754541__c1__16.aa | 1614 | 5019 | 419 | contig410__23907632__f2__6.aa | 419 | 419 | 100.00% |
| contig577__24886263__c2__19.aa | 1615 | 5020 | 130 | contig498__4312818__f3__13.aa | 285 | 116 | 28.45% |
| contig577__890705__f1__1.aa | 1616 | 5021 | 320 | contig342__14626562__f3__11.aa | 241 | 206 | 48.06% |
| contig577__6642842__f1__2.aa | 1617 | 5022 | 337 | contig342__7304700__f3__12.aa | 339 | 326 | 73.93% |
| contig577__34649050__f3__9.aa | 1618 | 5023 | 374 | contig342__24729542__f1__1.aa | 292 | 282 | 67.73% |
| contig577__14742938__f3__10.aa | 1619 | 5024 | 270 | contig342__24848465__f2__10.aa | 292 | 254 | 84.65% |
| contig577__5116660__f3__11.aa | 1620 | 5025 | 239 | contig342__26804838__f1__4.aa | 289 | 239 | 84.10% |
| contig577__26757937__f3__12.aa | 1621 | 5026 | 175 | contig342__24898562__f1__5.aa | 176 | 175 | 88.57% |
| contig578__23986077__c2__19.aa | 1622 | 5027 | 307 | contig203__12575139__c1__4.aa | 294 | 208 | 83.65% |
| contig578__1042337__c2__18.aa | 1623 | 5028 | 345 | contig298__14666007__c1__18.aa | 119 | 111 | 59.46% |
| contig578__24070962__c1__16.aa | 1624 | 5029 | 281 | contig298__33867250__c3__24.aa | 150 | 123 | 52.85% |
| contig578__34038442__c3__20.aa | 1625 | 5030 | 291 | contig412__24407832__c1__28.aa | 291 | 291 | 100.00% |
| contig578__6148466__c1__15.aa | 1626 | 5031 | 200 | contig298__24634687__c1__16.aa | 213 | 193 | 84.97% |
| contig578__16221002__c2__17.aa | 1628 | 5033 | 396 | contig412__24353377__f2__9.aa | 396 | 396 | 100.00% |
| contig578__7319561__c1__14.aa | 1629 | 5034 | 66 | contig181__282253__f1__1.aa | 285 | 44 | 36.36% |
| contig579__162787__c3__20.aa | 1630 | 5035 | 640 | contig283__35977142__c3__18.aa | 823 | 632 | 43.20% |
| contig579__164657__c2__15.aa | 1631 | 5036 | 74 | contig412__26828200__f3__17.aa | 74 | 74 | 100.00% |
| contig579__14666562__f1__2.aa | 1632 | 5037 | 263 | contig412__9455__c1__20.aa | 263 | 263 | 100.00% |
| contig579__36539062__c2__14.aa | 1633 | 5038 | 214 | contig412__25596051__f2__11.aa | 214 | 214 | 100.00% |
| contig579__4484413__c3__17.aa | 1634 | 5039 | 181 | contig424__21520307__f1__1.aa | 384 | 180 | 83.89% |
| contig579__16605338__c3__16.aa | 1635 | 5040 | 141 | contig424__21520307__f1__1.aa | 384 | 142 | 45.07% |
| contig58__24094094__c1__4.aa | 1636 | 5041 | 378 | contig448__5291037__c3__59.aa | 628 | 279 | 24.37% |
| contig580__130326__c2__27.aa | 1637 | 5042 | 145 | contig463__24252188__c3__48.aa | 215 | 121 | 39.67% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig580_24415943_c1_23.aa | 1638 | 5043 | 489 | contig463_975277_c1_27.aa | 495 | 491 | 59.47% |
| contig580_6756718_c2_26.aa | 1639 | 5044 | 223 | contig463_4534441_c3_46.aa | 316 | 222 | 78.38% |
| contig580_33602157_c1_22.aa | 1641 | 5046 | 127 | contig463_4534441_c3_46.aa | 316 | 94 | 56.38% |
| contig580_24332887_c2_25.aa | 1642 | 5047 | 345 | contig463_32226577_c1_25.aa | 315 | 315 | 74.60% |
| contig580_24102191_c1_20.aa | 1645 | 5050 | 280 | contig413_5114455_f1_3.aa | 280 | 280 | 100.00% |
| contig580_13675751_c3_28.aa | 1647 | 5052 | 62 | contig413_33984752_c3_32.aa | 62 | 62 | 100.00% |
| contig581_86038_f2_3.aa | 1648 | 5053 | 252 | contig396_29923412_c2_27.aa | 248 | 242 | 73.97% |
| contig581_14352263_f2_4.aa | 1649 | 5054 | 258 | contig396_21676058_c1_21.aa | 264 | 257 | 82.49% |
| contig581_30667811_f1_8.aa | 1650 | 5055 | 240 | contig414_26854677_c2_25.aa | 240 | 240 | 100.00% |
| contig581_167555_f3_9.aa | 1651 | 5056 | 76 | contig396_24022192_c1_22.aa | 72 | 67 | 79.10% |
| contig581_24495382_f2_6.aa | 1652 | 5057 | 379 | contig396_33835937_c3_32.aa | 376 | 376 | 89.10% |
| contig581_817033_f2_7.aa | 1653 | 5058 | 418 | contig414_34273437_c1_18.aa | 418 | 418 | 100.00% |
| contig582_23636377_f2_3.aa | 1654 | 5059 | 284 | contig508_32210927_c2_62.aa | 356 | 303 | 33.33% |
| contig582_24094175_f1_1.aa | 1656 | 5061 | 557 | contig66_26375453_f1_1.aa | 237 | 228 | 41.67% |
| contig582_35345942_f2_4.aa | 1657 | 5062 | 585 | contig414_18460188_c2_20.aa | 585 | 585 | 100.00% |
| contig582_4969677_c1_8.aa | 1658 | 5063 | 547 | contig415_1205311_f2_5.aa | 547 | 547 | 100.00% |
| contig583_14885936_f1_1.aa | 1659 | 5064 | 286 | contig330_6645051_c3_18.aa | 304 | 144 | 31.94% |
| contig583_34193950_f1_2.aa | 1660 | 5065 | 469 | contig200_33600253_f2_5.aa | 533 | 427 | 27.87% |
| contig583_4882827_f3_5.aa | 1661 | 5066 | 686 | contig432_5132942_f1_2.aa | 702 | 689 | 66.33% |
| contig583_6304572_c1_6.aa | 1662 | 5067 | 211 | contig378_6369827_c1_13.aa | 198 | 197 | 97.97% |
| contig584_6347033_f3_10.aa | 1663 | 5068 | 334 | contig483_36523515_c2_33.aa | 339 | 325 | 65.23% |
| contig584_35962937_f1_1.aa | 1664 | 5069 | 327 | contig290_5859386_c1_7.aa | 356 | 325 | 48.00% |
| contig584_10003756_c3_22.aa | 1665 | 5070 | 530 | contig483_34511067_f2_11.aa | 467 | 533 | 22.33% |
| contig584_15657837_c2_19.aa | 1666 | 5071 | 282 | contig416_22150426_c2_30.aa | 282 | 282 | 100.00% |
| contig584_36573442_c3_21.aa | 1667 | 5072 | 703 | contig360_26839637_f2_5.aa | 293 | 265 | 33.21% |
| contig584_33208176_c2_17.aa | 1668 | 5073 | 155 | contig456_34651428_c3_40.aa | 310 | 148 | 33.11% |
| contig585_22836077_c2_28.aa | 1669 | 5074 | 150 | contig448_4538201_f3_21.aa | 482 | 136 | 30.15% |
| contig585_26386092_c1_23.aa | 1670 | 5075 | 264 | contig175_24805468_c2_8.aa | 100 | 82 | 82.93% |
| contig585_7164812_c1_22.aa | 1671 | 5076 | 230 | contig416_24662501_f3_19.aa | 230 | 230 | 100.00% |
| contig585_960932_c1_21.aa | 1672 | 5077 | 127 | contig175_4023427_c1_6.aa | 133 | 118 | 90.68% |
| contig585_34160912_c2_27.aa | 1673 | 5078 | 378 | contig416_4884687_c3_33.aa | 378 | 378 | 100.00% |
| contig585_14880436_c1_20.aa | 1674 | 5079 | 641 | contig498_5120443_c2_37.aa | 624 | 619 | 44.91% |
| contig585_251567_c3_29.aa | 1676 | 5081 | 351 | contig466_23469667_c3_39.aa | 352 | 132 | 37.88% |
| contig585_34178452_c1_19.aa | 1677 | 5082 | 113 | contig402_24495467_f2_10.aa | 119 | 109 | 29.36% |
| contig585_22923568_c1_18.aa | 1678 | 5083 | 208 | contig510_11931716_c2_93.aa | 198 | 182 | 93.96% |
| contig586_10053418_f1_1.aa | 1679 | 5084 | 234 | contig502_29537665_c1_38.aa | 177 | 169 | 69.23% |
| contig586_25979818_f2_2.aa | 1680 | 5085 | 409 | contig502_14179752_c3_52.aa | 420 | 401 | 77.06% |
| contig586_35350277_f3_4.aa | 1681 | 5086 | 89 | contig417_3367005_f3_17.aa | 89 | 89 | 100.00% |
| contig586_24709530_f2_3.aa | 1682 | 5087 | 295 | contig417_34062925_f2_9.aa | 295 | 295 | 100.00% |
| contig587_16603135_c1_19.aa | 1683 | 5088 | 519 | contig417_24414202_c1_22.aa | 519 | 519 | 100.00% |
| contig587_34182827_f3_12.aa | 1687 | 5092 | 71 | contig419_30664080_c2_38.aa | 155 | 72 | 31.94% |
| contig587_10585337_f2_6.aa | 1689 | 5094 | 715 | contig496_24649055_c1_29.aa | 1044 | 664 | 22.14% |
| contig587_1182925_f3_14.aa | 1692 | 5097 | 414 | contig418_30111036_c1_28.aa | 414 | 414 | 100.00% |
| contig587_15086536_f2_8.aa | 1693 | 5098 | 240 | contig420_20911562_c2_27.aa | 287 | 244 | 27.46% |
| contig587_19720312_f1_3.aa | 1694 | 5099 | 90 | contig418_35196025_c3_41.aa | 90 | 90 | 100.00% |
| contig587_22460816_f2_9.aa | 1696 | 5101 | 499 | contig418_26369068_c3_40.aa | 499 | 499 | 100.00% |
| contig588_13851375_f3_12.aa | 1697 | 5102 | 393 | contig418_1058427_c3_39.aa | 393 | 393 | 100.00% |
| contig588_29928342_f1_1.aa | 1698 | 5103 | 92 | contig227_4797055_f1_1.aa | 111 | 88 | 75.00% |
| contig588_4977187_c1_23.aa | 1699 | 5104 | 236 | contig307_4976687_f1_9.aa | 212 | 207 | 72.95% |
| contig588_16196068_c1_22.aa | 1700 | 5105 | 102 | contig307_3376717_f1_8.aa | 98 | 91 | 48.35% |
| contig588_2932837_c2_27.aa | 1701 | 5106 | 61 | contig419_3125318_c3_45.aa | 61 | 61 | 100.00% |
| contig588_390627_c1_21.aa | 1702 | 5107 | 153 | contig307_24617188_f1_7.aa | 206 | 112 | 66.96% |
| contig588_973452_f2_9.aa | 1703 | 5108 | 226 | contig307_1461636_c3_24.aa | 225 | 221 | 51.58% |
| contig588_14649193_f3_13.aa | 1704 | 5109 | 399 | contig307_4508392_c3_25.aa | 416 | 392 | 82.14% |
| contig588_34173410_f3_14.aa | 1705 | 5110 | 288 | contig459_6812502_c1_17.aa | 301 | 283 | 79.15% |
| contig588_22445187_f1_2.aa | 1706 | 5111 | 186 | contig442_24508437_f2_15.aa | 175 | 171 | 40.35% |
| contig588_23929635_c2_26.aa | 1707 | 5112 | 164 | contig419_4042202_c3_41.aa | 164 | 164 | 100.00% |
| contig588_2855090_c2_25.aa | 1709 | 5114 | 298 | contig215_22368840_c1_7.aa | 222 | 169 | 34.91% |
| contig588_24728412_c2_24.aa | 1710 | 5115 | 395 | contig388_9974030_c1_20.aa | 403 | 397 | 59.70% |
| contig588_897828_c1_16.aa | 1711 | 5116 | 266 | contig388_13712660_c3_28.aa | 285 | 263 | 55.13% |
| contig589_36210450_f1_1.aa | 1713 | 5118 | 63 | contig419_22352000_c2_35.aa | 63 | 63 | 100.00% |
| contig589_4331562_f2_4.aa | 1714 | 5119 | 769 | contig311_34194812_f3_8.aa | 696 | 689 | 78.08% |
| contig589_11128427_f2_5.aa | 1715 | 5120 | 307 | contig457_391575_f3_11.aa | 304 | 304 | 55.26% |
| contig589_4947203_f2_6.aa | 1716 | 5121 | 234 | contig420_15645633_f2_4.aa | 234 | 234 | 100.00% |
| contig59_11991562_f2_1.aa | 1719 | 5124 | 263 | contig289_6697091_c2_12.aa | 428 | 262 | 77.86% |
| contig590_24429768_c3_22.aa | 1720 | 5125 | 209 | contig510_25660952_c1_89.aa | 238 | 202 | 73.27% |
| contig590_24501553_c2_19.aa | 1721 | 5126 | 617 | contig510_23928337_c1_88.aa | 619 | 613 | 63.79% |
| contig590_1039067_c3_21.aa | 1722 | 5127 | 513 | contig510_260942_c3_123.aa | 509 | 510 | 80.20% |
| contig590_31275465_c3_20.aa | 1723 | 5128 | 498 | contig510_34410962_c3_122.aa | 511 | 488 | 35.04% |
| contig590_22712550_c2_18.aa | 1724 | 5129 | 440 | contig510_4977188_c2_106.aa | 436 | 415 | 30.84% |
| contig591_4394591_f1_1.aa | 1725 | 5130 | 1216 | contig490_24431587_f1_5.aa | 673 | 494 | 22.07% |
| contig591_15015941_f2_5.aa | 1726 | 5131 | 206 | contig469_36225691_f1_5.aa | 682 | 137 | 35.04% |
| contig591_157558_f1_3.aa | 1728 | 5133 | 441 | contig421_36570317_f1_2.aa | 441 | 441 | 100.00% |
| contig592_4301537_c2_10.aa | 1731 | 5136 | 158 | contig421_3937562_f3_20.aa | 158 | 158 | 100.00% |
| contig592_24415937_c3_16.aa | 1732 | 5137 | 316 | contig421_24010961_f1_3.aa | 316 | 316 | 100.00% |
| contig592_4400776_c3_15.aa | 1734 | 5139 | 310 | contig497_32208213_f2_18.aa | 376 | 155 | 23.87% |
| contig593_1188760_f2_2.aa | 1736 | 5141 | 510 | contig394_5167752_f1_8.aa | 509 | 505 | 88.32% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig593__24414818__c2__10.aa | 1737 | 5142 | 540 | contig421__26055443__c2__29.aa | 540 | 540 | 100.00% |
| contig593__1053463__c1__7.aa | 1739 | 5144 | 417 | contig394__1053463__c1__14.aa | 425 | 413 | 72.40% |
| contig593__24640832__c3__12.aa | 1740 | 5145 | 231 | contig394__23704637__c3__21.aa | 241 | 230 | 89.57% |
| contig594__26386075__c1__19.aa | 1744 | 5149 | 121 | contig461__25507801__c2__42.aa | 125 | 114 | 75.44% |
| contig594__29502313__c1__18.aa | 1745 | 5150 | 236 | contig422__5189037__c3__43.aa | 236 | 236 | 100.00% |
| contig594__24409661__c1__17.aa | 1746 | 5151 | 112 | contig461__29328567__c3__47.aa | 108 | 99 | 69.70% |
| contig594__14492807__c3__23.aa | 1747 | 5152 | 109 | contig461__26364818__c1__34.aa | 101 | 99 | 85.86% |
| contig595__6335778__f1__1.aa | 1748 | 5153 | 206 | contig72__13104762__f2__1.aa | 186 | 184 | 85.33% |
| contig595__22462812__f1__2.aa | 1750 | 5155 | 275 | contig422__34574062__c3__39.aa | 275 | 275 | 100.00% |
| contig595__1181550__f2__4.aa | 1751 | 5156 | 136 | contig422__36601662__c3__38.aa | 136 | 136 | 100.00% |
| contig595__36126630__c1__15.aa | 1752 | 5157 | 278 | contig423__10426582__f2__8.aa | 278 | 278 | 100.00% |
| contig595__3906643__f3__6.aa | 1753 | 5158 | 545 | contig66__26375453__f1__1.aa | 237 | 230 | 43.04% |
| contig595__4042003__f1__3.aa | 1754 | 5159 | 385 | contig505__26813830__f1__7.aa | 179 | 172 | 34.30% |
| contig595__13861592__c3__18.aa | 1756 | 5161 | 294 | contig259__24407318__f2__3.aa | 294 | 289 | 82.01% |
| contig596__36205015__c3__27.aa | 1759 | 5164 | 467 | contig423__34414628__c3__31.aa | 467 | 467 | 100.00% |
| contig596__26386287__f3__12.aa | 1760 | 5165 | 123 | contig423__20320463__c1__22.aa | 123 | 123 | 100.00% |
| contig596__35198461__c1__21.aa | 1762 | 5167 | 679 | contig465__12275257__c3__44.aa | 816 | 661 | 23.00% |
| contig596__25678513__c2__23.aa | 1766 | 5171 | 134 | contig465__204717__c2__39.aa | 133 | 89 | 30.34% |
| contig596__13869051__c3__24.aa | 1767 | 5172 | 648 | contig424__26382202__f1__3.aa | 648 | 648 | 100.00% |
| contig597__33322837__f3__5.aa | 1768 | 5173 | 372 | contig425__12692965__f3__13.aa | 372 | 372 | 100.00% |
| contig597__4141087__f3__6.aa | 1769 | 5174 | 301 | contig486__24801702__f2__16.aa | 302 | 293 | 37.20% |
| contig597__23682192__f3__7.aa | 1770 | 5175 | 572 | contig509__24667313__c2__104.aa | 564 | 563 | 82.06% |
| contig597__17010927__f1__2.aa | 1771 | 5176 | 466 | contig483__34511067__f2__11.aa | 467 | 461 | 55.32% |
| contig598__23472141__c2__21.aa | 1772 | 5177 | 650 | contig448__24640875__f2__14.aa | 716 | 480 | 32.50% |
| contig598__6430442__c2__20.aa | 1773 | 5178 | 1799 | contig426__132843__c3__44.aa | 1196 | 479 | 24.01% |
| contig599__24509503__f2__2.aa | 1774 | 5179 | 207 | contig503__24640875__c1__78.aa | 228 | 203 | 25.62% |
| contig599__19532010__c1__15.aa | 1775 | 5180 | 318 | contig425__3906313__f2__11.aa | 318 | 318 | 100.00% |
| contig599__13719037__c3__18.aa | 1776 | 5181 | 247 | contig27__29807343__c1__2.aa | 229 | 207 | 52.66% |
| contig599__5256675__c1__13.aa | 1777 | 5182 | 560 | contig51__30336687__f1__2.aa | 288 | 275 | 77.09% |
| contig599__24490881__f2__8.aa | 1778 | 5183 | 159 | contig215__22368840__c1__7.aa | 222 | 49 | 67.35% |
| contig6__29485338__f3__1.aa | 1779 | 5184 | 178 | contig486__14492177__f1__44.aa | 383 | 180 | 52.22% |
| contig60__5960790__f2__2.aa | 1780 | 5185 | 107 | contig470__26756512__c2__32.aa | 515 | 99 | 98.99% |
| contig60__2345958__c3__4.aa | 1781 | 5186 | 153 | contig470__36621093__f3__17.aa | 663 | 142 | 99.30% |
| contig600__29977300__c1__36.aa | 1784 | 5189 | 159 | contig425__23459412__c1__23.aa | 159 | 159 | 100.00% |
| contig600__6021962__f3__23.aa | 1786 | 5191 | 121 | contig378__7070428__c1__10.aa | 150 | 79 | 32.91% |
| contig600__4101718__f3__24.aa | 1787 | 5192 | 67 | contig426__24694075__f1__1.aa | 67 | 67 | 100.00% |
| contig600__5078530__f1__4.aa | 1788 | 5193 | 760 | contig426__21774127__c1__35.aa | 760 | 760 | 100.00% |
| contig600__24484377__f3__26.aa | 1789 | 5194 | 344 | contig494__21767962__c1__20.aa | 417 | 288 | 82.29% |
| contig600__11917811__f1__5.aa | 1790 | 5195 | 137 | contig494__21767962__c1__20.aa | 417 | 117 | 79.49% |
| contig600__547050__c1__35.aa | 1791 | 5196 | 138 | contig426__34667767__c3__45.aa | 138 | 138 | 100.00% |
| contig600__23709453__f3__27.aa | 1792 | 5197 | 282 | contig426__24427317__c2__40.aa | 282 | 282 | 100.00% |
| contig600__24303137__f1__6.aa | 1793 | 5198 | 122 | contig376__36584702__f1__4.aa | 107 | 93 | 26.88% |
| contig600__3399187__f2__15.aa | 1794 | 5199 | 87 | contig510__29301505__c2__95.aa | 438 | 76 | 40.79% |
| contig600__22902165__f1__7.aa | 1795 | 5200 | 160 | contig466__29383441__c1__30.aa | 473 | 137 | 40.88% |
| contig600__4328568__c2__42.aa | 1796 | 5201 | 304 | contig341__26040962__c3__29.aa | 457 | 287 | 74.56% |
| contig600__36214092__f2__17.aa | 1798 | 5203 | 229 | contig100__15117217__f3__2.aa | 202 | 179 | 63.69% |
| contig601__21523963__f3__6.aa | 1802 | 5207 | 333 | contig475__35367155__c2__33.aa | 174 | 178 | 67.42% |
| contig601__34570763__c3__15.aa | 1803 | 5208 | 194 | contig324__23573817__c3__15.aa | 196 | 192 | 55.21% |
| contig601__10557936__c1__7.aa | 1804 | 5209 | 339 | contig324__10414680__c2__9.aa | 351 | 339 | 62.54% |
| contig601__30Q84787__c2__11.aa | 1805 | 5210 | 89 | contig475__23572282__f1__2.aa | 233 | 75 | 72.00% |
| contig601__23525452__c3__14.aa | 1806 | 5211 | 159 | contig475__23572282__f1__2.aa | 233 | 146 | 79.45% |
| contig601__24473137__c2__10.aa | 1807 | 5212 | 465 | contig475__12502180__f3__19.aa | 424 | 422 | 81.28% |
| contig602__12692842__f3__10.aa | 1809 | 5214 | 269 | contig448__1345377__f1__1.aa | 170 | 147 | 65.99% |
| contig602__34508562__f3__11.aa | 1810 | 5215 | 136 | contig448__14664213__f1__2.aa | 136 | 132 | 77.27% |
| contig602__36214082__f3__12.aa | 1811 | 5216 | 302 | contig211__35189757__f1__2.aa | 250 | 249 | 38.55% |
| contig602__51928__c1__19.aa | 1812 | 5217 | 376 | contig330__6645051__c3__18.aa | 304 | 294 | 57.48% |
| contig602__33803178__f3__14.aa | 1813 | 5218 | 213 | contig330__19784783__f3__9.aa | 202 | 186 | 59.68% |
| contig602__4102318__f2__8.aa | 1814 | 5219 | 87 | contig427__3022781__c3__36.aa | 87 | 87 | 100.00% |
| contig602__13850136__c3__23.aa | 1815 | 5220 | 395 | contig319__10238507__c3__23.aa | 399 | 387 | 32.30% |
| contig603__33438760__c1__16.aa | 1818 | 5223 | 264 | contig382__24609427__c2__30.aa | 303 | 220 | 30.46% |
| contig603__35314750__c3__23.aa | 1821 | 5226 | 237 | contig312__23703467__c3__12.aa | 329 | 220 | 29.55% |
| contig603__24416068__c3__22.aa | 1824 | 5229 | 303 | contig428__26679682__c3__47.aa | 303 | 303 | 100.00% |
| contig603__22460816__f2__6.aa | 1825 | 5230 | 172 | contig454__22460816__f2__6.aa | 199 | 172 | 99.42% |
| contig604__2774218__c2__20.aa | 1826 | 5231 | 68 | contig450__25822212__c2__25.aa | 417 | 47 | 48.94% |
| contig604__32500407__f3__10.aa | 1828 | 5233 | 262 | contig509__36210953__c1__74.aa | 146 | 116 | 25.86% |
| contig604__23710942__c2__18.aa | 1830 | 5235 | 228 | contig429__3026702__f3__20.aa | 228 | 228 | 100.00% |
| contig604__14478461__c1__15.aa | 1831 | 5236 | 76 | contig361__23620262__c1__17.aa | 275 | 76 | 81.58% |
| contig604__23439202__c1__14.aa | 1832 | 5237 | 167 | contig361__23620262__c1__17.aa | 275 | 166 | 82.53% |
| contig604__4902212__c2__17.aa | 1833 | 5238 | 284 | contig361__24433407__c3__24.aa | 246 | 226 | 86.28% |
| contig604__13703313__c3__21.aa | 1834 | 5239 | 295 | contig429__13682693__c1__34.aa | 295 | 295 | 100.00% |
| contig605__16441577__c1__23.aa | 1835 | 5240 | 120 | contig423__26343799__c1__21.aa | 104 | 32 | 87.50% |
| contig605__25549143__c1__22.aa | 1836 | 5241 | 360 | contig459__16600202__f2__8.aa | 336 | 334 | 40.12% |
| contig605__26306550__c3__27.aa | 1837 | 5242 | 319 | contig459__24786411__f3__11.aa | 344 | 306 | 79.41% |
| contig605__26594702__c1__20.aa | 1838 | 5243 | 352 | contig459__6914137__f2__7.aa | 362 | 349 | 84.53% |
| contig605__9964030__c1__19.aa | 1839 | 5244 | 362 | contig459__6523285__f3__10.aa | 299 | 274 | 79.93% |
| contig605__16053215__c2__26.aa | 1840 | 5245 | 294 | contig459__6110188__f2__6.aa | 223 | 223 | 82.51% |
| contig605__5860431__c2__24.aa | 1843 | 5248 | 355 | contig430__24428387__f2__5.aa | 355 | 355 | 100.00% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig606_32423135_c2_16.aa | 1845 | 5250 | 157 | contig321_32064597_c3_20.aa | 252 | 134 | 35.82% |
| contig606_9767187_f1_4.aa | 1849 | 5254 | 222 | contig229_16682836_f2_3.aa | 108 | 101 | 50.50% |
| contig606_4891077_f1_5.aa | 1850 | 5255 | 219 | contig229_6657837_f2_4.aa | 241 | 226 | 46.90% |
| contig606_26056507_c3_18.aa | 1851 | 5256 | 604 | contig479_5078380_f3_18.aa | 617 | 601 | 75.71% |
| contig607_3907882_c3_42.aa | 1853 | 5258 | 573 | contig323_2912587_c3_32.aa | 342 | 339 | 56.05% |
| contig607_24230002_c1_32.aa | 1854 | 5259 | 233 | contig323_35742943_c1_21.aa | 229 | 229 | 83.84% |
| contig607_30194036_c2_37.aa | 1855 | 5260 | 305 | contig323_14485937_c2_24.aa | 267 | 251 | 58.17% |
| contig607_4397202_c1_31.aa | 1856 | 5261 | 263 | contig323_14485937_c2_24.aa | 267 | 263 | 82.13% |
| contig607_2620963_c2_36.aa | 1857 | 5262 | 311 | contig432_16830063_f2_7.aa | 311 | 311 | 100.00% |
| contig607_36132765_c3_41.aa | 1858 | 5263 | 326 | contig323_24666026_c1_19.aa | 208 | 148 | 38.51% |
| contig607_11991250_c1_30.aa | 1859 | 5264 | 306 | contig495_24105313_f3_29.aa | 301 | 302 | 56.95% |
| contig607_24302012_c3_40.aa | 1860 | 5265 | 133 | contig379_22063441_f2_8.aa | 471 | 114 | 22.81% |
| contig607_4719136_c3_39.aa | 1862 | 5267 | 305 | contig432_159641_f1_3.aa | 305 | 305 | 100.00% |
| contig607_4082892_c3_38.aa | 1863 | 5268 | 249 | contig298_12506292_c3_22.aa | 381 | 231 | 39.83% |
| contig608_6680437_c2_28.aa | 1865 | 5270 | 814 | contig432_26360427_f2_10.aa | 814 | 814 | 100.00% |
| contig608_24406327_c2_25.aa | 1868 | 5273 | 178 | contig432_15914077_f1_6.aa | 178 | 177 | 100.00% |
| contig608_8462_c2_22.aa | 1872 | 5277 | 365 | contig433_20898462_c3_55.aa | 365 | 365 | 100.00% |
| contig608_5131261_f1_6.aa | 1879 | 5284 | 129 | contig467_19581552_c3_25.aa | 168 | 67 | 38.81% |
| contig609_24490755_f1_1.aa | 1881 | 5286 | 496 | contig18_36462938_f1_1.aa | 73 | 72 | 29.17% |
| contig609_14746002_f3_7.aa | 1882 | 5287 | 203 | contig433_24414717_c3_50.aa | 203 | 203 | 100.00% |
| contig609_1171913_f1_8.aa | 1883 | 5288 | 682 | contig479_36360701_c3_34.aa | 327 | 323 | 95.36% |
| contig609_960017_f2_3.aa | 1884 | 5289 | 668 | contig479_24650313_c3_35.aa | 718 | 612 | 53.76% |
| contig609_21484388_f2_4.aa | 1886 | 5291 | 101 | contig479_24650313_c3_35.aa | 718 | 93 | 56.99% |
| contig609_24428187_c1_12.aa | 1888 | 5293 | 226 | contig319_10238507_c3_23.aa | 399 | 219 | 34.25% |
| contig609_14587808_c1_11.aa | 1889 | 5294 | 167 | contig319_10238507_c3_23.aa | 399 | 164 | 45.73% |
| contig609_29585903_c3_27.aa | 1891 | 5296 | 120 | contig506_6922302_f1_13.aa | 150 | 120 | 31.67% |
| contig61_10742937_c3_1.aa | 1892 | 5297 | 250 | contig466_57_c3_44.aa | 317 | 249 | 26.10% |
| contig610_2777188_f3_9.aa | 1893 | 5298 | 399 | contig492_23557812_c3_45.aa | 412 | 404 | 42.33% |
| contig610_10562550_f2_5.aa | 1894 | 5299 | 191 | contig499_1055442_c3_86.aa | 174 | 143 | 32.17% |
| contig610_26761087_f1_2.aa | 1895 | 5300 | 279 | contig509_29307838_c1_75.aa | 269 | 250 | 34.00% |
| contig610_34651590_f2_6.aa | 1896 | 5301 | 278 | contig416_22150426_c2_30.aa | 282 | 276 | 29.35% |
| contig610_4687578_c2_16.aa | 1898 | 5303 | 197 | contig435_14102312_f3_18.aa | 197 | 197 | 100.00% |
| contig610_25583467_f2_8.aa | 1899 | 5304 | 142 | contig370_4196052_c2_17.aa | 334 | 144 | 29.86% |
| contig610_33464688_f1_4.aa | 1900 | 5305 | 220 | contig361_30475781_c2_18.aa | 118 | 110 | 74.55% |
| contig611_25680333_f2_5.aa | 1902 | 5307 | 305 | contig435_29863586_c2_38.aa | 305 | 305 | 100.00% |
| contig611_34664812_f1_1.aa | 1903 | 5308 | 76 | contig435_34178441_c3_44.aa | 76 | 76 | 100.00% |
| contig611_33204692_f1_10.aa | 1904 | 5309 | 168 | contig509_21619816_c3_110.aa | 173 | 167 | 74.85% |
| contig611_4899187_f3_11.aa | 1905 | 5310 | 268 | contig509_29307838_c1_75.aa | 269 | 268 | 78.36% |
| contig611_14884700_f1_2.aa | 1906 | 5311 | 278 | contig509_24651587_c2_96.aa | 275 | 274 | 79.20% |
| contig611_159825_f2_6.aa | 1907 | 5312 | 134 | contig509_23437568_c3_112.aa | 358 | 131 | 49.62% |
| contig611_10978561_f3_12.aa | 1908 | 5313 | 84 | contig509_23437568_c3_112.aa | 358 | 82 | 39.02% |
| contig611_26367207_f3_13.aa | 1909 | 5314 | 160 | contig509_23437568_c3_112.aa | 358 | 142 | 61.97% |
| contig611_26364637_f2_7.aa | 1910 | 5315 | 257 | contig509_4900463_c3_113.aa | 338 | 237 | 79.33% |
| contig612_4876327_c2_37.aa | 1913 | 5318 | 517 | contig423_24432952_c2_29.aa | 714 | 559 | 25.76% |
| contig612_24257813_c1_26.aa | 1917 | 5322 | 531 | contig483_7242052_c2_40.aa | 291 | 297 | 21.55% |
| contig612_861002_c2_33.aa | 1918 | 5323 | 424 | contig305_270778_c1_13.aa | 326 | 325 | 88.92% |
| contig612_24253582_c2_32.aa | 1919 | 5324 | 315 | contig281_4886088_f3_4.aa | 371 | 303 | 69.64% |
| contig613_5204505_f3_6.aa | 1920 | 5325 | 711 | contig463_5273317_f1_2.aa | 742 | 709 | 67.00% |
| contig613_34257967_c1_9.aa | 1921 | 5326 | 239 | contig436_21681582_f1_2.aa | 239 | 239 | 100.00% |
| contig613_6151890_c2_12.aa | 1922 | 5327 | 211 | contig436_24648381_f1_3.aa | 211 | 211 | 100.00% |
| contig613_11725127_c1_8.aa | 1923 | 5328 | 105 | contig436_26306312_f3_13.aa | 105 | 105 | 100.00% |
| contig614_23831508_c1_21.aa | 1924 | 5329 | 227 | contig436_31282885_f1_4.aa | 227 | 227 | 100.00% |
| contig614_23516080_c3_25.aa | 1925 | 5330 | 234 | contig436_24804700_f1_5.aa | 234 | 234 | 100.00% |
| contig614_784676_c2_23.aa | 1926 | 5331 | 491 | contig344_24406687_f2_4.aa | 441 | 328 | 68.29% |
| contig614_32228441_c1_20.aa | 1927 | 5332 | 321 | contig344_3937577_f3_8.aa | 323 | 320 | 92.19% |
| contig614_34642188_c3_24.aa | 1928 | 5333 | 1126 | contig344_24725002_f1_1.aa | 1114 | 1118 | 59.03% |
| contig615_29880442_f3_8.aa | 1930 | 5335 | 402 | contig273_21541281_c2_12.aa | 449 | 403 | 71.71% |
| contig615_24430427_f3_9.aa | 1931 | 5336 | 82 | contig338_26385902_c2_26.aa | 60 | 58 | 43.10% |
| contig615_12695151_f3_10.aa | 1932 | 5337 | 257 | contig437_33242186_c3_24.aa | 257 | 257 | 100.00% |
| contig615_4881577_f1_2.aa | 1934 | 5339 | 317 | contig312_23703467_c3_12.aa | 329 | 319 | 51.10% |
| contig615_2867077_f1_3.aa | 1935 | 5340 | 505 | contig312_5864155_c1_7.aa | 563 | 509 | 62.28% |
| contig615_5959812_f1_4.aa | 1936 | 5341 | 232 | contig438_24650462_f3_15.aa | 232 | 232 | 100.00% |
| contig615_24228178_f3_11.aa | 1937 | 5342 | 103 | contig402_23525463_f1_1.aa | 155 | 100 | 47.00% |
| contig615_55462_f3_12.aa | 1938 | 5343 | 520 | contig402_25414017_f2_6.aa | 476 | 459 | 60.57% |
| contig615_33397930_f2_7.aa | 1939 | 5344 | 128 | contig439_35368885_c3_34.aa | 128 | 128 | 100.00% |
| contig615_1274192_c2_17.aa | 1940 | 5345 | 201 | contig321_32064597_c3_20.aa | 252 | 198 | 67.68% |
| contig616_4504382_c1_21.aa | 1941 | 5346 | 782 | contig400_10752950_c2_35.aa | 901 | 751 | 62.05% |
| contig616_3166553_f2_10.aa | 1944 | 5349 | 494 | contig503_5867300_c1_82.aa | 536 | 496 | 23.39% |
| contig616_11719813_c2_23.aa | 1945 | 5350 | 197 | contig413_24337567_f3_11.aa | 184 | 116 | 26.72% |
| contig616_34179077_c1_17.aa | 1947 | 5352 | 431 | contig426_132843_c3_44.aa | 1196 | 388 | 23.20% |
| contig617_207068_f1_1.aa | 1948 | 5353 | 80 | contig267_14890705_c2_16.aa | 376 | 61 | 77.05% |
| contig617_24347552_f2_7.aa | 1949 | 5354 | 284 | contig267_14890705_c2_16.aa | 376 | 277 | 93.14% |
| contig617_24890826_c1_15.aa | 1950 | 5355 | 373 | contig361_24803816_f2_7.aa | 361 | 349 | 57.31% |
| contig617_5114677_c3_21.aa | 1951 | 5356 | 370 | contig361_42342_f3_13.aa | 365 | 363 | 72.73% |
| contig617_14317312_c1_14.aa | 1952 | 5357 | 359 | contig361_12535713_f3_12.aa | 329 | 325 | 68.62% |
| contig617_11916394_c2_17.aa | 1953 | 5358 | 686 | contig440_24298827_f3_8.aa | 686 | 686 | 100.00% |
| contig618_21504717_f1_1.aa | 1954 | 5359 | 398 | contig388_24429032_f3_17.aa | 470 | 397 | 74.81% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig618_21617177_c2_15.aa | 1955 | 5360 | 142 | contig213_957811_c1_4.aa | 104 | 83 | 72.29% |
| contig618_30078825_c2_14.aa | 1956 | 5361 | 1053 | contig262_22362827_c1_17.aa | 240 | 220 | 37.27% |
| contig618_23475178_c1_13.aa | 1957 | 5362 | 178 | contig441_4149013_f2_4.aa | 178 | 178 | 100.00% |
| contig618_33408567_f2_9.aa | 1958 | 5363 | 804 | contig441_36015628_c1_18.aa | 804 | 804 | 100.00% |
| contig619_12556693_f2_3.aa | 1961 | 5366 | 304 | contig497_78125_f3_28.aa | 313 | 294 | 69.73% |
| contig619_24645332_c2_15.aa | 1963 | 5368 | 571 | contig347_24645328_f2_5.aa | 577 | 574 | 76.13% |
| contig619_22051018_c1_10.aa | 1964 | 5369 | 373 | contig347_6766691_f1_1.aa | 322 | 313 | 81.15% |
| contig62_161081_f2_2.aa | 1965 | 5370 | 265 | contig451_4494812_c1_29.aa | 775 | 256 | 83.98% |
| contig620_25442152_c3_21.aa | 1967 | 5372 | 262 | contig98_12929663_c2_4.aa | 333 | 185 | 94.05% |
| contig620_25682817_c2_16.aa | 1968 | 5373 | 175 | contig98_12929663_c2_4.aa | 333 | 112 | 79.46% |
| contig620_1042200_c2_15.aa | 1969 | 5374 | 90 | contig442_10289012_c1_35.aa | 90 | 90 | 100.00% |
| contig620_23492342_c1_11.aa | 1970 | 5375 | 416 | contig239_33867817_f2_5.aa | 344 | 309 | 66.67% |
| contig620_6835952_c2_14.aa | 1971 | 5376 | 428 | contig239_34117968_f2_4.aa | 379 | 361 | 73.41% |
| contig620_34414008_c3_19.aa | 1972 | 5377 | 274 | contig239_29970192_f2_3.aa | 192 | 186 | 92.47% |
| contig620_23525317_c3_18.aa | 1974 | 5379 | 186 | contig103_20511432_c2_4.aa | 76 | 55 | 69.09% |
| contig620_26565942_c3_17.aa | 1975 | 5380 | 369 | contig103_35757177_c3_5.aa | 282 | 243 | 90.95% |
| contig621_634687_c2_24.aa | 1976 | 5381 | 217 | contig432_15914077_f1_6.aa | 178 | 157 | 28.66% |
| contig621_33242761_c3_26.aa | 1977 | 5382 | 389 | contig416_4884687_c3_33.aa | 378 | 377 | 64.99% |
| contig621_7291075_c2_22.aa | 1978 | 5383 | 61 | contig389_9922035_f2_7.aa | 179 | 53 | 64.15% |
| contig621_24611586_c1_17.aa | 1979 | 5384 | 141 | contig389_9922035_f2_7.aa | 179 | 108 | 66.67% |
| contig621_676885_c2_20.aa | 1980 | 5385 | 601 | contig389_645635_f2_6.aa | 598 | 598 | 80.94% |
| contig621_4698450_c3_25.aa | 1981 | 5386 | 575 | contig389_13806427_f1_12.aa | 546 | 545 | 81.65% |
| contig622_34187712_f3_12.aa | 1984 | 5389 | 75 | contig339_6150437_f1_2.aa | 128 | 53 | 33.96% |
| contig622_26225187_c1_22.aa | 1985 | 5390 | 351 | contig184_34429715_f3_3.aa | 349 | 344 | 86.92% |
| contig622_976567_f1_2.aa | 1987 | 5392 | 226 | contig474_14647180_c1_26.aa | 291 | 223 | 30.05% |
| contig622_9772763_f3_15.aa | 1988 | 5393 | 128 | contig312_23703467_c3_12.aa | 329 | 107 | 44.86% |
| contig622_12704715_f3_16.aa | 1989 | 5394 | 236 | contig176_14549076_f3_2.aa | 340 | 227 | 82.38% |
| contig622_33478433_f3_17.aa | 1990 | 5395 | 212 | contig176_22837756_f3_3.aa | 165 | 162 | 69.75% |
| contig622_33725676_f2_8.aa | 1991 | 5396 | 379 | contig443_2141250_c1_11.aa | 333 | 333 | 100.00% |
| contig622_23634711_f2_9.aa | 1992 | 5397 | 71 | contig443_19720332_c1_9.aa | 71 | 71 | 100.00% |
| contig622_25673899_c1_18.aa | 1994 | 5399 | 591 | contig400_19743812_c2_37.aa | 345 | 302 | 83.78% |
| contig623_35679675_f3_10.aa | 1995 | 5400 | 163 | contig444_16796885_c1_32.aa | 163 | 163 | 100.00% |
| contig623_4875918_f1_1.aa | 1996 | 5401 | 279 | contig214_4472963_c2_4.aa | 308 | 278 | 61.51% |
| contig623_504838_f1_2.aa | 1997 | 5402 | 401 | contig444_16604813_c3_40.aa | 401 | 401 | 100.00% |
| contig623_26802318_c1_15.aa | 1998 | 5403 | 456 | contig510_24801555_c2_105.aa | 497 | 472 | 50.85% |
| contig623_892332_c2_18.aa | 1999 | 5404 | 459 | contig420_26369063_c3_33.aa | 431 | 426 | 50.24% |
| contig623_13714717_c3_20.aa | 2001 | 5406 | 487 | contig444_29542525_c2_34.aa | 487 | 487 | 100.00% |
| contig623_34375017_f2_9.aa | 2002 | 5407 | 254 | contig444_24414086_c3_36.aa | 254 | 254 | 100.00% |
| contig623_1218831_f1_8.aa | 2003 | 5408 | 140 | contig444_25484692_c2_33.aa | 140 | 140 | 100.00% |
| contig624_15634811_f3_8.aa | 2004 | 5409 | 236 | contig444_23907507_f2_14.aa | 267 | 147 | 77.55% |
| contig624_24804712_f2_5.aa | 2005 | 5410 | 439 | contig267_22828280_c1_15.aa | 256 | 250 | 78.40% |
| contig624_3922338_c3_25.aa | 2006 | 5411 | 293 | contig406_34656686_f1_9.aa | 295 | 289 | 61.59% |
| contig624_1252302_c1_13.aa | 2007 | 5412 | 68 | contig445_401386_f2_12.aa | 68 | 68 | 100.00% |
| contig624_22317130_f1_3.aa | 2008 | 5413 | 511 | contig406_36210892_c3_40.aa | 492 | 482 | 63.69% |
| contig624_23629650_f3_9.aa | 2009 | 5414 | 444 | contig406_34648262_c2_34.aa | 424 | 418 | 76.56% |
| contig624_36213436_f3_10.aa | 2010 | 5415 | 289 | contig406_34642188_c3_41.aa | 288 | 285 | 76.49% |
| contig624_569142_f2_7.aa | 2011 | 5416 | 124 | contig406_259711_c1_30.aa | 126 | 76 | 64.47% |
| contig625_4507943_c1_17.aa | 2012 | 5417 | 119 | contig200_33600253_f2_5.aa | 533 | 96 | 26.04% |
| contig625_4179702_f2_10.aa | 2019 | 5424 | 113 | contig466_20978375_f1_4.aa | 133 | 110 | 51.82% |
| contig626_34492312_c2_15.aa | 2021 | 5426 | 192 | contig383_24820278_c2_27.aa | 193 | 193 | 51.81% |
| contig626_31838313_c2_14.aa | 2022 | 5427 | 719 | contig383_14647752_c2_26.aa | 714 | 723 | 72.20% |
| contig626_24397702_c1_12.aa | 2023 | 5428 | 858 | contig383_24417842_c3_29.aa | 885 | 881 | 78.32% |
| contig626_7228462_c1_11.aa | 2024 | 5429 | 102 | contig446_36209755_c2_46.aa | 102 | 102 | 100.00% |
| contig627_30251308_f2_3.aa | 2025 | 5430 | 279 | contig358_25585025_f2_11.aa | 326 | 273 | 76.56% |
| contig627_25604812_f3_6.aa | 2026 | 5431 | 241 | contig446_31817677_c2_45.aa | 241 | 241 | 100.00% |
| contig627_11039717_c3_18.aa | 2027 | 5432 | 269 | contig504_34273437_c2_40.aa | 416 | 253 | 97.63% |
| contig627_3947263_f3_7.aa | 2028 | 5433 | 215 | contig306_16448437_c3_30.aa | 234 | 215 | 99.54% |
| contig627_13808206_f1_1.aa | 2029 | 5434 | 81 | contig467_13808206_f2_6.aa | 81 | 81 | 98.77% |
| contig627_14578162_f1_2.aa | 2030 | 5435 | 455 | contig446_24648591_c1_34.aa | 455 | 455 | 100.00% |
| contig627_23865952_c3_17.aa | 2031 | 5436 | 66 | contig454_24413400_f3_8.aa | 476 | 56 | 41.07% |
| contig628_6332831_f3_7.aa | 2036 | 5441 | 395 | contig225_12150902_f3_7.aa | 283 | 284 | 60.92% |
| contig628_23706300_f1_1.aa | 2037 | 5442 | 359 | contig377_3917718_f2_6.aa | 369 | 343 | 67.64% |
| contig628_6757825_c3_22.aa | 2038 | 5443 | 803 | contig437_19666088_c1_20.aa | 817 | 813 | 59.41% |
| contig628_9775176_f1_2.aa | 2039 | 5444 | 482 | contig447_23832537_c1_27.aa | 482 | 482 | 100.00% |
| contig628_24413428_c1_16.aa | 2040 | 5445 | 217 | contig447_10557213_c2_32.aa | 217 | 217 | 100.00% |
| contig628_994087_c1_15.aa | 2041 | 5446 | 201 | contig421_23642962_f3_21.aa | 205 | 200 | 64.50% |
| contig628_4882827_c1_14.aa | 2042 | 5447 | 327 | contig421_24010961_f1_3.aa | 316 | 302 | 76.49% |
| contig629_10757836_f1_1.aa | 2044 | 5449 | 395 | contig34_36369827_f1_1.aa | 274 | 274 | 58.39% |
| contig629_24805253_f2_8.aa | 2045 | 5450 | 380 | contig447_12296887_f2_16.aa | 380 | 380 | 100.00% |
| contig629_25428336_f2_9.aa | 2046 | 5451 | 91 | contig433_16695317_c2_44.aa | 90 | 84 | 64.29% |
| contig629_16804702_f2_10.aa | 2047 | 5452 | 224 | contig433_22464427_c3_52.aa | 239 | 220 | 77.27% |
| contig629_24843937_f2_8.aa | 2048 | 5453 | 170 | contig448_1345377_f1_11.aa | 170 | 170 | 100.00% |
| contig629_14962831_f2_11.aa | 2049 | 5454 | 281 | contig433_898452_c3_53.aa | 740 | 278 | 69.42% |
| contig629_954765_f1_3.aa | 2050 | 5455 | 497 | contig433_21694466_c2_46.aa | 498 | 492 | 79.47% |
| contig629_2932812_f2_12.aa | 2051 | 5456 | 351 | contig433_20898462_c3_55.aa | 365 | 343 | 65.02% |
| contig629_3927193_f1_5.aa | 2052 | 5457 | 193 | contig433_34198887_c2_48.aa | 211 | 186 | 61.83% |
| contig629_7070808_f3_15.aa | 2053 | 5458 | 538 | contig433_3401937_c1_42.aa | 517 | 518 | 69.31% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig63__36132250__c3__6.aa | 2054 | 5459 | 83 | contig365__14485910__c2__33.aa | 88 | 81 | 82.72% |
| contig63__16600832__c2__5.aa | 2055 | 5460 | 247 | contig365__24425463__c1__25.aa | 299 | 247 | 76.92% |
| contig630__13789052__f1__7.aa | 2056 | 5461 | 166 | contig413__12116083__c1__17.aa | 156 | 147 | 29.93% |
| contig630__26228381__f2__4.aa | 2057 | 5462 | 82 | contig413__4976587__c2__25.aa | 85 | 77 | 38.96% |
| contig630__24392762__f3__8.aa | 2060 | 5465 | 127 | contig448__26448392__c3__58.aa | 127 | 127 | 100.00% |
| contig630__24508562__c2__15.aa | 2061 | 5466 | 296 | contig448__36067842__c2__42.aa | 296 | 296 | 100.00% |
| contig630__1281577__c3__18.aa | 2062 | 5467 | 157 | contig464__4687827__f3__20.aa | 171 | 157 | 56.69% |
| contig631__34490800__c2__22.aa | 2063 | 5468 | 471 | contig505__24620461__c1__50.aa | 734 | 468 | 79.06% |
| contig631__35207811__f3__11.aa | 2064 | 5469 | 262 | contig505__24648552__f2__18.aa | 266 | 257 | 66.54% |
| contig631__24069087__f1__3.aa | 2065 | 5470 | 711 | contig505__23603327__f3__32.aa | 680 | 696 | 33.33% |
| contig631__33984816__f2__7.aa | 2066 | 5471 | 514 | contig505__4144000__f2__21.aa | 527 | 509 | 59.14% |
| contig631__22117268__f1__4.aa | 2067 | 5472 | 405 | contig505__12509702__f1__6.aa | 401 | 401 | 72.07% |
| contig631__24407802__f3__13.aa | 2069 | 5474 | 436 | contig449__32611587__c3__56.aa | 436 | 436 | 100.00% |
| contig631__24900267__f2__9.aa | 2070 | 5475 | 441 | contig505__6726683__f3__35.aa | 349 | 316 | 48.73% |
| contig632__10598431__c1__14.aa | 2072 | 5477 | 143 | contig449__24845322__c3__55.aa | 143 | 143 | 100.00% |
| contig632__2922200__c2__17.aa | 2073 | 5478 | 575 | contig294__4881452__f1__2.aa | 575 | 575 | 77.91% |
| contig632__4345686__c3__20.aa | 2074 | 5479 | 528 | contig449__22152182__c2__42.aa | 528 | 528 | 100.00% |
| contig632__34398312__c3__19.aa | 2075 | 5480 | 197 | contig442__29922951__c3__45.aa | 217 | 174 | 33.33% |
| contig632__35194712__c2__16.aa | 2076 | 5481 | 489 | contig263__24320877__c1__11.aa | 486 | 465 | 77.42% |
| contig632__193825__c2__15.aa | 2077 | 5482 | 316 | contig263__292944__c2__12.aa | 709 | 317 | 55.21% |
| contig632__79181__f1__6.aa | 2078 | 5483 | 104 | contig491__24305181__f3__48.aa | 132 | 56 | 26.79% |
| contig633__1407037__f3__8.aa | 2079 | 5484 | 184 | contig444__10829218__f3__15.aa | 178 | 166 | 53.01% |
| contig633__29975066__c1__16.aa | 2080 | 5485 | 504 | contig335__6136512__f2__5.aa | 318 | 303 | 44.22% |
| contig633__21671936__c1__15.aa | 2082 | 5487 | 473 | contig317__24814717__c3__22.aa | 471 | 464 | 60.35% |
| contig633__11056562__f1__3.aa | 2083 | 5488 | 319 | contig450__3940875__c2__24.aa | 319 | 319 | 100.00% |
| contig633__31834452__c2__2.aa | 2084 | 5489 | 295 | contig455__24667087__c3__49.aa | 426 | 292 | 56.16% |
| contig634__35335792__c1__19.aa | 2091 | 5496 | 437 | contig451__36524051__c2__37.aa | 437 | 437 | 100.00% |
| contig634__5116632__c1__18.aa | 2092 | 5497 | 73 | contig451__33237517__c1__31.aa | 73 | 73 | 100.00% |
| contig634__36520303__c1__17.aa | 2094 | 5499 | 431 | contig451__6819002__c1__30.aa | 431 | 431 | 100.00% |
| contig634__2345260__f2__12.aa | 2098 | 5503 | 254 | contig451__20963952__c3__39.aa | 254 | 254 | 100.00% |
| contig634__656250__c1__15.aa | 2099 | 5504 | 82 | contig372__34649061__c3__27.aa | 79 | 68 | 27.94% |
| contig635__34648462__c3__19.aa | 2101 | 5506 | 111 | contig483__23634662__c1__22.aa | 453 | 96 | 47.92% |
| contig635__26679803__f2__3.aa | 2102 | 5507 | 158 | contig451__20727324__c1__28.aa | 158 | 158 | 100.00% |
| contig635__25428187__f3__4.aa | 2103 | 5508 | 127 | contig483__5089037__f2__15.aa | 128 | 127 | 50.39% |
| contig636__24414137__c1__14.aa | 2107 | 5512 | 242 | contig359__25580342__c3__12.aa | 246 | 218 | 25.69% |
| contig636__36609387__f1__3.aa | 2109 | 5514 | 310 | contig371__11897656__c3__17.aa | 469 | 303 | 33.33% |
| contig636__16538127__f3__8.aa | 2112 | 5517 | 335 | contig452__4101077__c2__30.aa | 335 | 335 | 100.00% |
| contig636__5917126__c2__18.aa | 2113 | 5518 | 794 | contig379__22063441__f2__8.aa | 471 | 471 | 69.43% |
| contig636__25977328__f1__6.aa | 2114 | 5519 | 169 | contig510__25605092__c2__97.aa | 154 | 148 | 25.68% |
| contig636__23572126__c3__21.aa | 2115 | 5520 | 288 | contig206__30270437__c3__10.aa | 294 | 289 | 33.91% |
| contig636__957275__c3__20.aa | 2116 | 5521 | 451 | contig452__22110918__c3__32.aa | 451 | 451 | 100.00% |
| contig637__19665937__c1__18.aa | 2117 | 5522 | 117 | contig265__5370937__c2__15.aa | 586 | 116 | 84.48% |
| contig637__34074076__c2__24.aa | 2118 | 5523 | 434 | contig147__35674041__f3__1.aa | 324 | 316 | 44.62% |
| contig637__979687__c1__17.aa | 2119 | 5524 | 341 | contig355__32539191__f1__4.aa | 361 | 221 | 83.71% |
| contig637__6907812__c1__15.aa | 2120 | 5525 | 619 | contig355__26367817__f1__3.aa | 650 | 616 | 39.94% |
| contig637__5120217__c3__26.aa | 2121 | 5526 | 118 | contig355__36132837__f2__11.aa | 131 | 117 | 52.99% |
| contig637__27317__c2__22.aa | 2122 | 5527 | 137 | contig355__21730042__f1__2.aa | 152 | 128 | 71.88% |
| contig637__24798577__c2__21.aa | 2123 | 5528 | 323 | contig355__635967__f2__10.aa | 396 | 320 | 78.75% |
| contig637__1428437__c2__20.aa | 2124 | 5529 | 85 | contig355__635967__f2__10.aa | 396 | 73 | 71.23% |
| contig637__24662500__c3__25.aa | 2125 | 5530 | 265 | contig355 35348452__f3__15.aa | 258 | 262 | 46.18% |
| contig637__9767342__c2__19.aa | 2126 | 5531 | 209 | contig355__29503212__f2__7.aa | 201 | 199 | 49.75% |
| contig638__19968768__f2__11.aa | 2127 | 5532 | 275 | contig226__20510953__c3__12.aa | 272 | 256 | 33.59% |
| contig638__23948427__c3__36.aa | 2129 | 5534 | 706 | contig380__24636592__c1__18.aa | 696 | 699 | 71.96% |
| contig638__11754377__c2__32.aa | 2130 | 5535 | 323 | contig380__36134437__c3__22.aa | 312 | 307 | 90.55% |
| contig638__35944827__c1__27.aa | 2131 | 5536 | 97 | contig453__13829077__f3__35.aa | 97 | 97 | 100.00% |
| contig638__20704400__c3__34.aa | 2132 | 5537 | 353 | contig454__21695437__f1__1.aa | 170 | 170 | 100.00% |
| contig638__16830202__c2__31.aa | 2133 | 5538 | 309 | contig454__4073875__f1__7.aa | 309 | 309 | 100.00% |
| contig638__16425759__c2__30.aa | 2135 | 5540 | 702 | contig286__22845463__f1__4.aa | 319 | 260 | 58.85% |
| contig639__1429217__f2__4.aa | 2136 | 5541 | 472 | contig221__20707025__f1__1.aa | 346 | 322 | 75.16% |
| contig639__21725430__c3__12.aa | 2137 | 5542 | 1199 | contig453__24478402__c2__49.aa | 1231 | 1179 | 70.14% |
| contig639__30739712__c1__8.aa | 2138 | 5543 | 478 | contig253__25604715__c3__13.aa | 406 | 343 | 25.36% |
| contig64__30125205__f1__1.aa | 2139 | 5544 | 98 | contig469__4023593__f3__16.aa | 415 | 62 | 51.61% |
| contig64__23962762__f2__3.aa | 2140 | 5545 | 165 | contig469__4023593__f3__16.aa | 415 | 166 | 40.96% |
| contig64__9803925__f1__2.aa | 2141 | 5546 | 60 | contig455__36386505__c2__48.aa | 60 | 60 | 100.00% |
| contig640__26617692__c3__30.aa | 2142 | 5547 | 493 | contig150__34640906__f3__1.aa | 449 | 406 | 45.81% |
| contig640__24635962__c3__29.aa | 2144 | 5549 | 106 | contig455__23478433__c2__46.aa | 106 | 106 | 100.00% |
| contig640__1039077__c1__22.aa | 2148 | 5553 | 477 | contig284__31433438__c1__15.aa | 201 | 193 | 25.39% |
| contig640__36520462__c1__21.aa | 2149 | 5554 | 197 | contig284__5120302__c1__16.aa | 212 | 194 | 26.80% |
| contig641__6345280__f3__11.aa | 2151 | 5556 | 140 | contig447__36585942__c3__35.aa | 336 | 132 | 87.12% |
| contig641__24409376__f2__6.aa | 2152 | 5557 | 62 | contig209__13829688__c3__9.aa | 417 | 36 | 63.89% |
| contig641__7057325__f3__12.aa | 2153 | 5558 | 419 | contig209__13829688__c3__9.aa | 417 | 381 | 66.40% |
| contig641__24422827__f3__13.aa | 2156 | 5561 | 322 | contig419__11377__c2__36.aa | 339 | 302 | 50.99% |
| contig641__35417813__f1__1.aa | 2157 | 5562 | 353 | contig419__35329687__c3__40.aa | 356 | 354 | 31.92% |
| contig641__19705332__f3__15.aa | 2159 | 5564 | 157 | contig456__23604837__c2__33.aa | 157 | 157 | 100.00% |
| contig641__33863802__f2__7.aa | 2160 | 5565 | 172 | contig419__4042202__c3__41.aa | 164 | 83 | 33.74% |
| contig641__5860633__c2__27.aa | 2161 | 5566 | 398 | contig506__20709525__f3__50.aa | 391 | 392 | 26.02% |
| contig641__5087517__c2__26.aa | 2163 | 5568 | 218 | contig506__30567812__f1__14.aa | 181 | 87 | 40.23% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig641_20314203_c2_25.aa | 2165 | 5570 | 287 | contig456_23470688_f3_16.aa | 287 | 287 | 100.00% |
| contig641_970000_f1_4.aa | 2166 | 5571 | 82 | contig491_25580017_c2_63.aa | 107 | 60 | 35.00% |
| contig641_1227302_f3_17.aa | 2167 | 5572 | 74 | contig456_24500300_c3_37.aa | 74 | 74 | 100.00% |
| contig641_5359652_f1_5.aa | 2168 | 5573 | 62 | contig456_14536500_c1_20.aa | 62 | 62 | 100.00% |
| contig642_14626378_c1_15.aa | 2172 | 5577 | 327 | contig457_23547827_c2_3.aa | 327 | 327 | 100.00% |
| contig642_34417182_c1_14.aa | 2173 | 5578 | 944 | contig472_24664692_c2_31.aa | 1242 | 932 | 62.55% |
| contig642_24073342_c3_18.aa | 2174 | 5579 | 1206 | contig472_34183467_c3_33.aa | 1179 | 1194 | 49.33% |
| contig642_7220263_c1_13.aa | 2175 | 5580 | 189 | contig413_24337567_f3_11.aa | 184 | 178 | 45.51% |
| contig643_1304837_f1_1.aa | 2177 | 5582 | 64 | contig457_16598428_c1_19.aa | 64 | 64 | 100.00% |
| contig643_3365965_f2_5.aa | 2178 | 5583 | 304 | contig457_391575_f3_11.aa | 304 | 304 | 100.00% |
| contig643_25913143_f1_2.aa | 2179 | 5584 | 939 | contig300_24609767_c3_12.aa | 556 | 353 | 28.05% |
| contig644_35423311_f1_1.aa | 2188 | 5593 | 378 | contig341_12204162_f1_1.aa | 626 | 368 | 70.65% |
| contig644_34570312_c1_16.aa | 2189 | 5594 | 258 | contig454_4073875_f3_7.aa | 309 | 164 | 31.10% |
| contig644_10625061_f2_5.aa | 2190 | 5595 | 307 | contig458_34413912_c1_33.aa | 307 | 307 | 100.00% |
| contig644_642268_f2_6.aa | 2191 | 5596 | 487 | contig495_11113582_f1_1.aa | 582 | 484 | 73.55% |
| contig644_6851637_f1_4.aa | 2193 | 5598 | 316 | contig172_10664058_f1_1.aa | 173 | 167 | 74.25% |
| contig644_26360375_f2_8.aa | 2194 | 5599 | 818 | contig366_14644442_f2_6.aa | 800 | 729 | 82.44% |
| contig645_30277177_c2_13.aa | 2195 | 5600 | 1059 | contig112_32667500_f2_1.aa | 308 | 306 | 87.91% |
| contig646_24710962_f1_10.aa | 2198 | 5603 | 234 | contig419_7081936_c2_32.aa | 286 | 229 | 60.70% |
| contig646_4976587_f1_11.aa | 2199 | 5604 | 327 | contig458_5199077_c1_29.aa | 327 | 327 | 100.00% |
| contig646_36148462_c3_44.aa | 2201 | 5606 | 223 | contig459_6110188_f2_6.aa | 223 | 223 | 100.00% |
| contig646_22266437_f3_13.aa | 2202 | 5607 | 362 | contig459_6914137_f2_7.aa | 362 | 362 | 100.00% |
| contig646_34565692_f1_2.aa | 2203 | 5608 | 344 | contig459_24786411_f1_11.aa | 344 | 344 | 100.00% |
| contig646_6913925_f1_3.aa | 2204 | 5609 | 231 | contig416_24392182_c2_29.aa | 498 | 231 | 80.52% |
| contig646_35945461_f3_15.aa | 2205 | 5610 | 160 | contig416_10739667_c1_25.aa | 168 | 150 | 59.33% |
| contig646_34640930_f2_8.aa | 2206 | 5611 | 332 | contig450_26181542_c2_23.aa | 332 | 326 | 62.27% |
| contig646_13676886_f1_4.aa | 2207 | 5612 | 189 | contig388_15683443_c1_21.aa | 181 | 177 | 88.70% |
| contig646_33209880_c1_20.aa | 2209 | 5614 | 74 | contig459_3909802_f1_4.aa | 74 | 74 | 100.00% |
| contig646_4301313_c2_28.aa | 2210 | 5615 | 79 | contig388_6837782_f2_10.aa | 145 | 54 | 48.15% |
| contig646_36620951_f1_5.aa | 2211 | 5616 | 151 | contig388_6662760_c3_30.aa | 373 | 138 | 63.04% |
| contig646_23830251_f3_18.aa | 2213 | 5618 | 222 | contig388_6662760_c3_30.aa | 373 | 162 | 81.48% |
| contig646_1189450_f3_19.aa | 2214 | 5619 | 361 | contig90_24895642_f1_1.aa | 292 | 241 | 76.35% |
| contig646_31679937_f1_6.aa | 2215 | 5620 | 451 | contig460_38592_f1_1.aa | 451 | 451 | 100.00% |
| contig647_22308213_c2_24.aa | 2216 | 5621 | 182 | contig439_24336088_c1_19.aa | 189 | 180 | 61.11% |
| contig647_23473217_c1_19.aa | 2217 | 5622 | 237 | contig260_34641878_c3_28.aa | 194 | 191 | 24.61% |
| contig647_24412580_c2_22.aa | 2220 | 5625 | 264 | contig460_1267216_f3_14.aa | 264 | 264 | 100.00% |
| contig647_4885875_c1_17.aa | 2222 | 5627 | 598 | contig460_33829037_f2_10.aa | 598 | 598 | 100.00% |
| contig647_36209628_c1_16.aa | 2226 | 5631 | 720 | contig460_33829037_f2_10.aa | 598 | 563 | 25.58% |
| contig648_9776700_f2_7.aa | 2230 | 5635 | 217 | contig265_21484453_c3_19.aa | 204 | 188 | 71.29% |
| contig648_5275282_f3_9.aa | 2231 | 5636 | 150 | contig462_26839688_f3_27.aa | 150 | 150 | 100.00% |
| contig648_2760458_f1_1.aa | 2232 | 5637 | 96 | contig462_26761300_f2_11.aa | 96 | 96 | 100.00% |
| contig648_24886502_f1_12.aa | 2233 | 5638 | 284 | contig505_5355305_f2_13.aa | 279 | 269 | 73.23% |
| contig648_10946028_f1_2.aa | 2234 | 5639 | 151 | contig505_34564202_f3_29.aa | 115 | 115 | 73.04% |
| contig648_25819461_f1_3.aa | 2235 | 5640 | 313 | contig505_23603461_f2_14.aa | 291 | 291 | 62.89% |
| contig648_865942_f3_11.aa | 2236 | 5641 | 231 | contig312_23703467_c3_12.aa | 329 | 232 | 33.62% |
| contig648_14647805_f1_13.aa | 2238 | 5643 | 422 | contig505_5353588_f2_15.aa | 376 | 372 | 80.91% |
| contig648_54812_c3_29.aa | 2239 | 5644 | 203 | contig505_25584407_c1_51.aa | 208 | 198 | 76.26% |
| contig648_25510192_c1_16.aa | 2240 | 5645 | 295 | contig505_24620461_c1_50.aa | 734 | 293 | 86.01% |
| contig649_25589202_f2_6.aa | 2248 | 5653 | 284 | contig462_33798177_f2_22.aa | 284 | 284 | 100.00% |
| contig65_24251887_f2_2.aa | 2252 | 5657 | 100 | contig77_29959837_f3_5.aa | 102 | 92 | 81.52% |
| contig65_34267012_f1_1.aa | 2253 | 5658 | 158 | contig77_34267013_f2_3.aa | 160 | 154 | 72.08% |
| contig650_24391927_c1_17.aa | 2257 | 5662 | 336 | contig480_24335952_f2_6.aa | 316 | 231 | 26.41% |
| contig650_35960187_f1_4.aa | 2258 | 5663 | 500 | contig420_7081661_c3_31.aa | 628 | 235 | 34.89% |
| contig650_12697187_f3_15.aa | 2259 | 5664 | 231 | contig495_4882827_c1_36.aa | 234 | 231 | 41.56% |
| contig650_19572186_c2_20.aa | 2260 | 5665 | 382 | contig408_6835917_c2_43.aa | 435 | 381 | 77.95% |
| contig651_14897050_c1_22.aa | 2262 | 5667 | 496 | contig463_15089663_c3_49.aa | 496 | 496 | 100.00% |
| contig651_19689416_c1_21.aa | 2265 | 5670 | 215 | contig463_24252188_c3_48.aa | 215 | 215 | 100.00% |
| contig651_13867952_c3_31.aa | 2267 | 5672 | 495 | contig463_975277_c1_27.aa | 495 | 495 | 100.00% |
| contig651_24875635_c3_29.aa | 2269 | 5674 | 194 | contig490_24431587_f1_5.aa | 673 | 190 | 22.63% |
| contig651_34651525_c1_20.aa | 2270 | 5675 | 1729 | contig500_34179817_c2_72.aa | 491 | 361 | 25.76% |
| contig652_2734502_f2_8.aa | 2272 | 5677 | 312 | contig463_5364593_c3_43.aa | 312 | 312 | 100.00% |
| contig652_33411713_c3_30.aa | 2273 | 5678 | 86 | contig482_24258262_c3_51.aa | 106 | 73 | 50.69% |
| contig652_34414067_c1_17.aa | 2274 | 5679 | 61 | contig486_16679668_f2_22.aa | 76 | 56 | 26.79% |
| contig652_26563752_c3_28.aa | 2275 | 5680 | 203 | contig382_4494030_c2_32.aa | 149 | 146 | 69.18% |
| contig652_390655_f1_2.aa | 2276 | 5681 | 123 | contig455_16604687_c1_35.aa | 123 | 111 | 30.63% |
| contig652_3916587_f2_9.aa | 2277 | 5682 | 662 | contig455_3929712_c2_44.aa | 670 | 665 | 49.17% |
| contig652_19562812_f2_10.aa | 2278 | 5683 | 166 | contig455_214200_c2_45.aa | 162 | 155 | 89.03% |
| contig652_30349193_f3_14.aa | 2279 | 5684 | 197 | contig455_26022162_c1_37.aa | 219 | 198 | 39.39% |
| contig652_585961_f1_6.aa | 2280 | 5685 | 345 | contig455_10723763_c3_53.aa | 341 | 325 | 52.92% |
| contig652_26651875_f2_11.aa | 2281 | 5686 | 171 | contig464_4687827_f3_20.aa | 171 | 171 | 100.00% |
| contig652_29489687_f1_7.aa | 2282 | 5687 | 729 | contig464_13723507_f2_16.aa | 729 | 729 | 100.00% |
| contig652_23478441_f2_13.aa | 2283 | 5688 | 300 | contig455_282903_c3_55.aa | 369 | 202 | 81.68% |
| contig653_33212875_f2_5.aa | 2284 | 5689 | 66 | contig465_25880217_c2_41.aa | 66 | 66 | 100.00% |
| contig653_679692_c1_15.aa | 2285 | 5690 | 77 | contig465_17036301_f2_18.aa | 77 | 77 | 100.00% |
| contig653_4885941_f1_8.aa | 2286 | 5691 | 60 | contig465_33291375_f1_1.aa | 60 | 60 | 100.00% |
| c00tig653_24492937_f3_9.aa | 2287 | 5692 | 101 | contig465_20098513_f3_27.aa | 101 | 101 | 100.00% |
| contig653_6930387_f1_2.aa | 2289 | 5694 | 600 | contig425_3906313_f2_11.aa | 318 | 293 | 47.10% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig653_1461567_f2_7.aa | 2290 | 5695 | 141 | contig510_21751425_c3_113.aa | 214 | 59 | 37.29% |
| contig653_20351713_f1_3.aa | 2291 | 5696 | 70 | contig458_20573500_c1_30.aa | 99 | 68 | 85.29% |
| contig653_14850326_f1_4.aa | 2292 | 5697 | 456 | contig322_34094062_c3_26.aa | 453 | 454 | 63.22% |
| contig654_32239437_f3_10.aa | 2293 | 5698 | 108 | contig409_32239437_f2_10.aa | 108 | 108 | 100.00% |
| contig654_23947182_f3_11.aa | 2294 | 5699 | 66 | contig465_4329201_f1_6.aa | 66 | 66 | 100.00% |
| contig654_9820327_c3_22.aa | 2295 | 5700 | 165 | contig501_9820327_c1_46.aa | 165 | 165 | 100.00% |
| contig654_36113801_c2_18.aa | 2296 | 5701 | 342 | contig505_22681287_f1_8.aa | 349 | 338 | 80.47% |
| contig654_19781402_c3_21.aa | 2297 | 5702 | 290 | contig505_36531277_f3_38.aa | 253 | 252 | 73.81% |
| contig654_276577_c2_17.aa | 2298 | 5703 | 263 | contig505_23634677_f1_37.aa | 225 | 229 | 36.68% |
| contig654_11262_c3_20.aa | 2300 | 5705 | 369 | contig505_26813830_f1_7.aa | 179 | 168 | 83.93% |
| contig655_23632837_c2_15.aa | 2301 | 5706 | 254 | contig345_1067757_f1_1.aa | 243 | 145 | 38.62% |
| contig655_3912678_c1_11.aa | 2302 | 5707 | 1163 | contig255_23626253_f3_5.aa | 973 | 965 | 82.49% |
| contig655_24321883_c2_14.aa | 2303 | 5708 | 403 | contig255_12504386_f2_4.aa | 172 | 168 | 72.62% |
| contig655_5939818_c2_13.aa | 2304 | 5709 | 106 | contig316_26604558_f3_7.aa | 102 | 101 | 70.30% |
| contig655_908452_c2_12.aa | 2305 | 5710 | 589 | contig316_9814013_f1_1.aa | 616 | 581 | 60.76% |
| contig655_10058593_c1_10.aa | 2306 | 5711 | 271 | contig316_26182638_f2_4.aa | 452 | 259 | 91.89% |
| contig656_22870316_f3_16.aa | 2307 | 5712 | 399 | contig351_25984702_f1_1.aa | 424 | 390 | 55.39% |
| contig656_34430313_c2_28.aa | 2308 | 5713 | 133 | contig466_20978375_f1_4.aa | 133 | 133 | 100.00% |
| contig656_24806686_c3_32.aa | 2309 | 5714 | 450 | contig428_24416067_c1_35.aa | 525 | 514 | 38.72% |
| contig656_24431693_c2_27.aa | 2313 | 5718 | 411 | contig279_24423588_f3_9.aa | 430 | 418 | 20.57% |
| contig657_13832950_f2_5.aa | 2317 | 5722 | 246 | contig464_24870942_f1_1.aa | 223 | 220 | 79.09% |
| contig657_6287752_f1_1.aa | 2318 | 5723 | 293 | contig466_16881680_f2_17.aa | 130 | 130 | 100.00% |
| contig657_26574068_f2_6.aa | 2320 | 5725 | 676 | contig466_33791088_c2_36.aa | 676 | 676 | 100.00% |
| contig657_3004680_c3_20.aa | 2321 | 5726 | 334 | contig464_1989717_c3_35.aa | 325 | 318 | 93.08% |
| contig657_979715_c1_13.aa | 2322 | 5727 | 352 | contig466_23469667_c3_39.aa | 352 | 352 | 100.00% |
| contig657_3360912_c3_19.aa | 2323 | 5728 | 131 | contig382_4494030_c2_32.aa | 149 | 145 | 32.41% |
| contig657_33313752_c2_17.aa | 2324 | 5729 | 88 | contig464_1181265_c3_34.aa | 101 | 79 | 79.75% |
| contig658_14269013_f2_6.aa | 2325 | 5730 | 158 | contig467_13792813_f1_2.aa | 158 | 158 | 100.00% |
| contig658_21900800_f3_10.aa | 2326 | 5731 | 65 | contig467_24429068_f3_11.aa | 65 | 65 | 100.00% |
| contig658_16878375_c2_16.aa | 2327 | 5732 | 231 | contig241_24406952_c2_9.aa | 200 | 200 | 61.00% |
| contig658_23593750_c1_12.aa | 2328 | 5733 | 863 | contig462_29462555_c1_38.aa | 646 | 568 | 25.00% |
| contig658_23595876_f3_11.aa | 2330 | 5735 | 453 | contig408_10236387_c3_46.aa | 469 | 443 | 65.91% |
| contig658_24407762_f2_9.aa | 2332 | 5737 | 64 | contig408_6071062_c1_41.aa | 235 | 43 | 48.84% |
| contig659_10970142_f1_1.aa | 2333 | 5738 | 234 | contig473_16448437_f2_4.aa | 234 | 234 | 100.00% |
| contig659_22854686_f1_2.aa | 2334 | 5739 | 370 | contig322_24273303_c2_22.aa | 309 | 263 | 40.30% |
| contig659_19932800_f3_6.aa | 2335 | 5740 | 78 | contig445_4898512_c3_61.aa | 519 | 59 | 76.27% |
| contig659_6914002_f2_4.aa | 2336 | 5741 | 153 | contig445_4898512_c3_61.aa | 519 | 151 | 88.74% |
| contig659_11720888_f1_3.aa | 2337 | 5742 | 162 | contig445_9959767_c1_43.aa | 549 | 148 | 71.62% |
| contig659_23988452_f2_5.aa | 2338 | 5743 | 319 | contig502_23988452_f1_6.aa | 319 | 319 | 98.43% |
| contig659_32519551_c3_11.aa | 2339 | 5744 | 139 | contig9_34527343_f2_2.aa | 161 | 128 | 99.22% |
| contig66_4791251_f1_1.aa | 2340 | 5745 | 227 | contig210_2166076_c2_9.aa | 599 | 164 | 38.42% |
| contig660_33783425_c2_20.aa | 2342 | 5747 | 176 | contig468_4414561_c1_42.aa | 176 | 176 | 100.00% |
| contig660_4902203_c1_16.aa | 2344 | 5749 | 842 | contig502_34432800_c1_41.aa | 327 | 295 | 28.81% |
| contig660_36222937_c1_15.aa | 2345 | 5750 | 101 | contig468_26369702_c1_40.aa | 101 | 101 | 100.00% |
| contig660_9953467_c1_14.aa | 2346 | 5751 | 306 | contig468_23678437_c2_46.aa | 306 | 306 | 100.00% |
| contig661_32664681_c1_19.aa | 2349 | 5754 | 464 | contig426_26753802_c1_34.aa | 214 | 211 | 90.05% |
| contig661_34117306_c2_22.aa | 2350 | 5755 | 283 | contig426_24427317_c2_40.aa | 282 | 279 | 65.23% |
| contig661_25505458_c2_21.aa | 2351 | 5756 | 1208 | contig426_132843_c3_44.aa | 1196 | 1192 | 61.33% |
| contig662_792827_c3_47.aa | 2352 | 5757 | 73 | contig471_1056515_f3_19.aa | 145 | 69 | 91.30% |
| contig662_5176887_c3_45.aa | 2355 | 5760 | 466 | contig471_35188262_f2_9.aa | 352 | 342 | 85.67% |
| contig662_4182828_c2_40.aa | 2356 | 5761 | 117 | contig471_3948453_f3_16.aa | 117 | 117 | 76.07% |
| contig662_24407963_c2_39.aa | 2357 | 5762 | 127 | contig471_24804838_f3_15.aa | 128 | 128 | 92.19% |
| contig662_24432937_c2_38.aa | 2358 | 5763 | 109 | contig471_24432937_f3_14.aa | 109 | 109 | 95.41% |
| contig662_15046932_c1_30.aa | 2359 | 5764 | 1096 | contig471_1214057_f2_8.aa | 1095 | 1093 | 82.16% |
| contig662_5187502_c3_44.aa | 2360 | 5765 | 61 | contig454_4073875_f1_7.aa | 309 | 38 | 39.47% |
| contig662_127318_c2_33.aa | 2363 | 5768 | 314 | contig499_55443_f1_45.aa | 274 | 110 | 36.36% |
| contig662_281344_c2_32.aa | 2365 | 5770 | 267 | contig499_10831952_f1_3.aa | 403 | 264 | 93.18% |
| contig663_4876652_f1_2.aa | 2367 | 5772 | 380 | contig141_24648452_f1_1.aa | 257 | 249 | 86.35% |
| contig663_19923467_f3_11.aa | 2368 | 5773 | 565 | contig470_36621093_f3_17.aa | 663 | 567 | 85.89% |
| contig663_4710943_c2_23.aa | 2369 | 5774 | 510 | contig470_26756512_c2_32.aa | 515 | 507 | 79.09% |
| contig663_36225092_c2_22.aa | 2371 | 5776 | 128 | contig470_205342_c3_45.aa | 117 | 116 | 37.07% |
| contig663_6823387_c1_17.aa | 2372 | 5777 | 364 | contig469_125136_c2_28.aa | 364 | 364 | 100.00% |
| contig663_26350950_f3_12.aa | 2373 | 5778 | 272 | contig470_26682212_f2_9.aa | 219 | 216 | 57.41% |
| contig663_24410927_f3_13.aa | 2374 | 5779 | 341 | contig470_23726687_f2_10.aa | 261 | 254 | 74.02% |
| contig663_24027188_f2_10.aa | 2375 | 5780 | 437 | contig470_8443_f2_11.aa | 429 | 430 | 53.26% |
| contig663_4898542_f1_6.aa | 2376 | 5781 | 490 | contig470_16989717_f1_4.aa | 927 | 473 | 74.42% |
| contig664_6328431_f1_1.aa | 2377 | 5782 | 117 | contig470_205342_c3_45.aa | 117 | 117 | 100.00% |
| contig664_13869057_c1_17.aa | 2379 | 5784 | 335 | contig472_31461666_f2_12.aa | 330 | 328 | 84.15% |
| contig664_34611257_c2_18.aa | 2380 | 5785 | 219 | contig470_26682812_f2_9.aa | 219 | 219 | 100.00% |
| contig665_14667875_f2_10.aa | 2381 | 5786 | 360 | contig425 13915882_c1_24.aa | 325 | 339 | 26.25% |
| contig665_24240962_c3_44.aa | 2382 | 5787 | 226 | contig421_26298501_f2_13.aa | 251 | 227 | 58.15% |
| contig665_2914087_c3_43.aa | 2383 | 5788 | 411 | contig417_24414202_c1_22.aa | 519 | 344 | 21.51% |
| contig665_10019677_f1_3.aa | 2384 | 5789 | 927 | contig470_16989717_f1_4.aa | 927 | 927 | 100.00% |
| contig665_24228452_c1_30.aa | 2385 | 5790 | 552 | contig336_16431510_c3_17.aa | 140 | 131 | 27.48% |
| contig665_34189517_f2_12.aa | 2386 | 5791 | 115 | contig470_24408212_f2_14.aa | 115 | 115 | 100.00% |
| contig665_14884402_f1_5.aa | 2388 | 5793 | 487 | contig470_35744062_f3_19.aa | 487 | 487 | 100.00% |
| contig665_2929500_f3_24.aa | 2392 | 5797 | 138 | contig470_4900301_f1_20.aa | 138 | 138 | 100.00% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig665_21884561_c3_41.aa | 2393 | 5798 | 412 | contig470_10814188_f2_16.aa | 412 | 412 | 100.00% |
| contig665_20083462_f3_26.aa | 2395 | 5800 | 98 | contig471_4823576_c1_32.aa | 98 | 98 | 100.00% |
| contig666_9805325_c1_34.aa | 2396 | 5801 | 310 | contig471_5352188_c3_47.aa | 310 | 310 | 100.00% |
| contig666_10265643_c1_33.aa | 2397 | 5802 | 240 | contig462_10253143_f2_19.aa | 231 | 234 | 81.62% |
| contig666_3315700_c2_43.aa | 2398 | 5803 | 432 | contig462_30708542_f2_18.aa | 345 | 335 | 75.82% |
| contig666_23955443_c2_42.aa | 2399 | 5804 | 151 | contig462_23955443_f3_30.aa | 151 | 151 | 94.04% |
| contig666_34251902_c3_47.aa | 2400 | 5805 | 72 | contig462_31437817_f2_17.aa | 69 | 69 | 78.26% |
| contig666_33323812_c1_31.aa | 2401 | 5806 | 179 | contig462_32505042_f3_29.aa | 183 | 179 | 96.65% |
| contig666_7242152_c2_41.aa | 2402 | 5807 | 124 | contig462_24407785_f1_4.aa | 127 | 123 | 92.68% |
| contig666_4161578_c1_30.aa | 2403 | 5808 | 117 | contig471_3948453_f1_16.aa | 117 | 117 | 100.00% |
| contig666_24255132_c3_46.aa | 2404 | 5809 | 352 | contig471_35188262_f2_9.aa | 352 | 352 | 100.00% |
| contig666_17010885_c1_29.aa | 2405 | 5810 | 67 | contig462_17010925_f2_15.aa | 67 | 66 | 98.49% |
| contig666_2598452_c1_28.aa | 2406 | 5811 | 179 | contig462_2598452_f2_14.aa | 179 | 179 | 95.53% |
| contig666_26027217_c3_45.aa | 2407 | 5812 | 109 | contig462_21641538_f2_13.aa | 112 | 109 | 88.99% |
| contig666_10741542_c1_27.aa | 2408 | 5813 | 132 | contig462_42286_f2_12.aa | 140 | 132 | 93.94% |
| contig666_26615926_c1_26.aa | 2409 | 5814 | 97 | contig462_26761300_f2_11.aa | 96 | 89 | 94.38% |
| contig666_24884787_c2_39.aa | 2410 | 5815 | 65 | contig471_35990893_f3_18.aa | 65 | 65 | 100.00% |
| contig666_26839688_c1_25.aa | 2411 | 5816 | 145 | contig471_1056515_f3_19.aa | 145 | 145 | 100.00% |
| contig666_22557963_c2_38.aa | 2412 | 5817 | 235 | contig471_10343953_f3_20.aa | 235 | 235 | 100.00% |
| contig666_23439687_c2_37.aa | 2413 | 5818 | 63 | contig462_25579827_f3_25.aa | 114 | 52 | 90.39% |
| contig666_5203543_c2_35.aa | 2415 | 5820 | 277 | contig25_24899175_c1_4.aa | 244 | 231 | 91.78% |
| contig667_33986643_f2_7.aa | 2417 | 5822 | 496 | contig263_292944_c2_12.aa | 709 | 502 | 33.47% |
| contig667_22460816_f3_13.aa | 2422 | 5827 | 400 | contig501_22460816_c2_51.aa | 400 | 400 | 100.00% |
| contig667_22558437_c2_23.aa | 2425 | 5830 | 307 | contig465_36210963_c3_46.aa | 309 | 305 | 62.30% |
| contig667_21490686_c3_27.aa | 2426 | 5831 | 264 | contig465_24648438_c3_45.aa | 336 | 257 | 86.77% |
| contig667_14880385_c2_22.aa | 2427 | 5832 | 96 | contig465_24648438_c3_45.aa | 336 | 86 | 60.47% |
| contig667_14166285_c3_26.aa | 2428 | 5833 | 717 | contig465_33605083_c1_35.aa | 736 | 707 | 73.41% |
| contig667_10584692_c1_17.aa | 2430 | 5835 | 82 | contig465_12275257_c3_44.aa | 816 | 78 | 98.72% |
| contig668_24609568_f1_1.aa | 2431 | 5836 | 424 | contig410_6542894_c2_14.aa | 412 | 396 | 44.70% |
| contig668_34424091_f1_2.aa | 2432 | 5837 | 368 | contig277_5323390_c3_15.aa | 379 | 359 | 46.80% |
| contig668_24485627_f3_9.aa | 2433 | 5838 | 354 | contig295_10759682_c3_10.aa | 362 | 334 | 72.16% |
| contig668_24104681_f1_3.aa | 2434 | 5839 | 384 | contig295_24026551_c1_6.aa | 379 | 378 | 80.42% |
| contig668_869028_f1_4.aa | 2435 | 5840 | 248 | contig295_23438588_c1_7.aa | 250 | 246 | 81.30% |
| contig668_5272953_f1_5.aa | 2436 | 5841 | 339 | contig361_36359576_c2_19.aa | 319 | 307 | 30.29% |
| contig668_14664050_f1_6.aa | 2438 | 5843 | 353 | contig283_11910400_c1_16.aa | 237 | 205 | 24.39% |
| contig668_39077_f3_10.aa | 2439 | 5844 | 148 | contig333_4328201_f2_7.aa | 156 | 140 | 63.57% |
| contig668_22848588_f2_8.aa | 2440 | 5845 | 298 | contig333_32235277_f2_10.aa | 370 | 291 | 76.63% |
| contig669_6851692_f1_1.aa | 2441 | 5846 | 389 | contig235_32047676_f1_1.aa | 193 | 186 | 33.87% |
| contig669_23526582_f1_2.aa | 2442 | 5847 | 265 | contig509_29307838_c1_75.aa | 269 | 261 | 36.02% |
| contig669_963201_f2_11.aa | 2443 | 5848 | 300 | contig509_24651587_c2_96.aa | 275 | 271 | 38.01% |
| contig669_789087_c1_31.aa | 2444 | 5849 | 280 | contig474_34164188_c1_29.aa | 280 | 280 | 100.00% |
| contig669_30602312_c3_44.aa | 2445 | 5850 | 556 | contig66_26375453_f1_1.aa | 237 | 228 | 63.16% |
| contig669_937_c3_43.aa | 2446 | 5851 | 147 | contig273_34259811_f1_1.aa | 125 | 119 | 63.03% |
| contig669_35212541_f2_12.aa | 2447 | 5852 | 91 | contig474_24892887_f2_15.aa | 91 | 91 | 100.00% |
| contig669_13089055_f1_6.aa | 2449 | 5854 | 166 | contig358_35947011_f2_4.aa | 161 | 157 | 56.05% |
| contig669_5086438_f2_14.aa | 2450 | 5855 | 208 | contig474_34182687_c2_35.aa | 208 | 208 | 100.00% |
| contig669_7245302_f1_7.aa | 2451 | 5856 | 142 | contig499_5129627_c1_54.aa | 168 | 149 | 31.54% |
| contig669_36225125_f3_23.aa | 2452 | 5857 | 424 | contig475_12502180_f3_19.aa | 424 | 424 | 100.00% |
| contig669_14898577_f2_16.aa | 2455 | 5860 | 256 | contig509_29307838_c1_75.aa | 269 | 236 | 41.53% |
| contig669_23884703_f3_25.aa | 2456 | 5861 | 284 | contig509_24651587_c2_96.aa | 275 | 270 | 49.63% |
| contig669_194376_f1_9.aa | 2457 | 5862 | 86 | contig358_24350652_f2_5.aa | 211 | 70 | 54.29% |
| contig67_22439777_c2_2.aa | 2458 | 5863 | 243 | contig475_242750_f3_21.aa | 243 | 243 | 100.00% |
| contig670_21972660_f3_8.aa | 2459 | 5864 | 451 | contig396_23445431_c1_17.aa | 502 | 449 | 82.63% |
| contig670_15032813_f1_1.aa | 2460 | 5865 | 641 | contig396_34173438_c2_26.aa | 641 | 639 | 88.11% |
| contig670_22458337_f1_2.aa | 2461 | 5866 | 276 | contig407_34257813_c2_29.aa | 274 | 267 | 74.16% |
| contig670_6666577_f1_3.aa | 2462 | 5867 | 620 | contig407_36615967_c2_30.aa | 628 | 594 | 45.96% |
| contig670_15837942_f3_10.aa | 2463 | 5868 | 171 | contig407_24273430_c3_33.aa | 171 | 161 | 50.31% |
| contig670_24022767_f2_6.aa | 2464 | 5869 | 379 | contig475_12709455_c3_39.aa | 379 | 379 | 100.00% |
| contig670_30493817_f1_11.aa | 2465 | 5870 | 342 | contig407_25673202_c1_27.aa | 331 | 330 | 82.12% |
| contig670_312_f3_12.aa | 2466 | 5871 | 126 | contig498_4110932_c2_38.aa | 142 | 124 | 56.45% |
| contig670_994087_f3_13.aa | 2467 | 5872 | 226 | contig498_22558438_c3_47.aa | 249 | 224 | 58.48% |
| contig671_5289005_f3_9.aa | 2470 | 5875 | 83 | contig510_23594018_c2_110.aa | 107 | 65 | 61.54% |
| contig671_5898452_f3_10.aa | 2471 | 5876 | 549 | contig492_32204785_f3_23.aa | 547 | 533 | 42.78% |
| contig671_23603437_f1_1.aa | 2472 | 5877 | 100 | contig355_21730042_f1_2.aa | 152 | 91 | 34.07% |
| contig671_5116451_f2_8.aa | 2474 | 5879 | 226 | contig505_24648552_f2_13.aa | 266 | 224 | 43.30% |
| contig671_210965_f1_3.aa | 2475 | 5880 | 411 | contig379_22063441_f2_8.aa | 471 | 370 | 25.68% |
| contig671_30745885_f3_12.aa | 2477 | 5882 | 105 | contig442_30473457_f2_12.aa | 497 | 96 | 43.75% |
| contig672_5879683_cf 25.aa | 2478 | 5883 | 194 | contig249_29898587_f3_6.aa | 192 | 181 | 66.85% |
| contig672_4744217_c1_24.aa | 2479 | 5884 | 352 | contig249_24884838_f3_5.aa | 351 | 348 | 67.24% |
| contig672_4714162_c3_34.aa | 2480 | 5885 | 397 | contig249_4882877_f1_1.aa | 252 | 250 | 72.00% |
| contig672_26601587_c3_33.aa | 2481 | 5886 | 888 | contig432_26360427_f2_10.aa | 814 | 785 | 57.07% |
| contig672_22085880_f1_6.aa | 2482 | 5887 | 318 | contig330_6645051_c3_18.aa | 304 | 224 | 26.79% |
| contig672_1272792_f3_21.aa | 2483 | 5888 | 317 | contig330_6645051_c3_18.aa | 304 | 228 | 27.19% |
| contig672_13862952_c1_23.aa | 2484 | 5889 | 382 | contig395_15836693_c2_15.aa | 391 | 380 | 29.21% |
| contig672_26367300_c3_30.aa | 2485 | 5890 | 399 | contig395_15836693_c2_15.aa | 391 | 373 | 46.38% |
| contig673_13830318_f1_1.aa | 2489 | 5894 | 212 | contig434_16601506_f2_7.aa | 177 | 178 | 49.44% |
| contig673_4726693_f3_14.aa | 2490 | 5895 | 792 | contig434_4100318_f1_1.aa | 788 | 791 | 74.46% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig673_3214717_f3_15.aa | 2491 | 5896 | 158 | contig434_26573512_f1_2.aa | 161 | 154 | 85.71% |
| contig673_26564127_f2_7.aa | 2492 | 5897 | 241 | contig434_26571012_f2_9.aa | 241 | 239 | 70.29% |
| contig673_13867805_f2_8.aa | 2493 | 5898 | 173 | contig478_395962_f2_12.aa | 173 | 173 | 100.00% |
| contig673_3159413_f1_5.aa | 2494 | 5899 | 178 | contig434_6850187_f3_17.aa | 186 | 175 | 63.43% |
| contig673_4870303_f2_9.aa | 2495 | 5900 | 183 | contig434_4859503_f1_4.aa | 183 | 181 | 62.98% |
| contig673_23860452_f3_16.aa | 2496 | 5901 | 518 | contig434_4939078_f2_11.aa | 521 | 518 | 88.22% |
| contig673_36335333_f3_17.aa | 2497 | 5902 | 270 | contig478_3126885_c1_28.aa | 270 | 270 | 100.00% |
| contig673_26376251_f1_6.aa | 2498 | 5903 | 477 | contig434_25424012_f1_5.aa | 477 | 468 | 94.02% |
| contig673_24485257_f2_11.aa | 2499 | 5904 | 64 | contig434_24485258_f2_13.aa | 147 | 47 | 59.57% |
| contig674_6678588_f2_6.aa | 2500 | 5905 | 354 | contig479_16187501_f2_7.aa | 354 | 354 | 100.00% |
| contig674_35395677_f1_1.aa | 2501 | 5906 | 90 | contig445_9959767_c1_43.aa | 549 | 85 | 56.47% |
| contig674_36220300_f2_7.aa | 2502 | 5907 | 361 | contig439_10241011_c2_26.aa | 223 | 188 | 24.47% |
| contig674_24431552_f2_8.aa | 2504 | 5909 | 378 | contig483_36523515_c2_33.aa | 339 | 107 | 30.84% |
| contig674_26250625_c3_30.aa | 2506 | 5911 | 112 | contig507_24406387_f2_37.aa | 304 | 119 | 44.54% |
| contig674_24407268_c3_29.aa | 2507 | 5912 | 102 | contig510_19805317_f2_50.aa | 311 | 103 | 25.24% |
| contig674_34589000_c2_26.aa | 2509 | 5914 | 249 | contig480_32245388_f3_8.aa | 249 | 249 | 100.00% |
| contig674_977318_f1_4.aa | 2512 | 5917 | 265 | contig509_29307838_c1_75.aa | 269 | 258 | 31.01% |
| contig674_9929676_c2_25.aa | 2513 | 5918 | 264 | contig480_6329692_f1_2.aa | 264 | 264 | 100.00% |
| contig674_30371086_f2_12.aa | 2514 | 5919 | 70 | contig480_4885936_f3_9.aa | 70 | 70 | 100.00% |
| contig674_30079637_f2_13.aa | 2515 | 5920 | 168 | contig370_26767767_c2_16.aa | 172 | 151 | 34.44% |
| contig674_4812_f1_5.aa | 2516 | 5921 | 148 | contig416_23633250_c3_37.aa | 141 | 137 | 36.50% |
| contig675_5189077_c2_28.aa | 2518 | 5923 | 135 | contig474_1408437_f2_14.aa | 471 | 129 | 34.11% |
| contig675_30162691_c1_21.aa | 2520 | 5925 | 140 | contig474_24429838_f2_13.aa | 103 | 99 | 26.26% |
| contig675_26359635_c3_37.aa | 2521 | 5926 | 172 | contig474_970287_f2_12.aa | 166 | 138 | 28.99% |
| contig675_3908135_f2_6.aa | 2522 | 5927 | 173 | contig302_23884838_c3_15.aa | 145 | 142 | 64.09% |
| contig675_34273385_f3_10.aa | 2523 | 5928 | 177 | contig302_4962818_c1_11.aa | 72 | 68 | 79.41% |
| contig675_26449063_f3_11.aa | 2525 | 5930 | 148 | contig370_4196052_c2_17.aa | 334 | 130 | 26.92% |
| contig675_2117942_f2_7.aa | 2526 | 5931 | 67 | contig481_25975427_c2_38.aa | 67 | 67 | 100.00% |
| contig675_34589187_f2_8.aa | 2527 | 5932 | 339 | contig481_5879557_f1_3.aa | 339 | 339 | 100.00% |
| contig675_14648282_f2_9.aa | 2528 | 5933 | 583 | contig481_29301592_f1_18.aa | 583 | 583 | 100.00% |
| contig675_3339050_c1_15.aa | 2529 | 5934 | 306 | contig481_26026567_c3_42.aa | 306 | 306 | 100.00% |
| contig675_24022818_f1_12.aa | 2531 | 5936 | 109 | contig497_24427137_f3_30.aa | 160 | 108 | 30.56% |
| contig675_972252_f1_5.aa | 2532 | 5937 | 375 | contig368_9948302_f1_12.aa | 340 | 365 | 23.29% |
| contig676_29541405_f3_9.aa | 2535 | 5940 | 373 | contig193_399032_c2_13.aa | 279 | 251 | 39.84% |
| contig676_35289127_f1_1.aa | 2536 | 5941 | 217 | contig191_23881274_c1_5.aa | 237 | 217 | 66.36% |
| contig676_12633562_f1_2.aa | 2537 | 5942 | 389 | contig346_24038892_c1_20.aa | 411 | 399 | 32.58% |
| contig676_24117937_c2_24.aa | 2538 | 5943 | 91 | contig482_4578937_c2_45.aa | 91 | 91 | 100.00% |
| contig676_24900462_c2_23.aa | 2539 | 5944 | 147 | contig482_6834537_c3_53.aa | 147 | 147 | 100.00% |
| contig676_29895062_c1_18.aa | 2540 | 5945 | 61 | contig482_6917337_c1_38.aa | 61 | 61 | 100.00% |
| contig676_22539818_c3_31.aa | 2542 | 5947 | 424 | contig421_36570317_f1_2.aa | 441 | 437 | 26.55% |
| contig677_22691312_c1_24.aa | 2546 | 5951 | 363 | contig408_6136587_c2_44.aa | 408 | 358 | 72.35% |
| contig677_24851502_c3_42.aa | 2547 | 5952 | 70 | contig510_3298262_c1_83.aa | 128 | 70 | 84.29% |
| contig677_36225002_c3_41.aa | 2548 | 5953 | 346 | contig510_213140_c3_115.aa | 398 | 345 | 84.93% |
| contig677_19652265_c3_40.aa | 2550 | 5955 | 765 | contig482_10744042_c3_49.aa | 765 | 765 | 100.00% |
| contig677_29494001_c3_39.aa | 2551 | 5956 | 805 | contig482_4023427_c2_39.aa | 805 | 805 | 100.00% |
| contig677_35273453_c2_29.aa | 2555 | 5960 | 67 | contig179_33207930_f3_5.aa | 86 | 61 | 50.82% |
| contig677_32222803_c3_33.aa | 2562 | 5967 | 115 | contig483_803393_f1_4.aa | 115 | 115 | 100.00% |
| contig677_4181312_c2_25.aa | 2563 | 5968 | 795 | contig444_30339212_c3_41.aa | 255 | 86 | 33.72% |
| contig678_24423558_f2_10.aa | 2565 | 5970 | 254 | contig483_23598577_f3_20.aa | 254 | 254 | 100.00% |
| contig678_26775450_c3_33.aa | 2566 | 5971 | 425 | contig353_4148593_f1_4.aa | 408 | 407 | 23.34% |
| contig678_4015968_c3_32.aa | 2568 | 5973 | 405 | contig398_3913180_c3_22.aa | 389 | 370 | 24.60% |
| contig678_36133388_c3_31.aa | 2570 | 5975 | 453 | contig483_23634662_c1_22.aa | 453 | 453 | 100.00% |
| contig678_26304577_c2_26.aa | 2572 | 5977 | 454 | contig279_24423588_f3_9.aa | 430 | 448 | 25.67% |
| contig678_26462825_c2_24.aa | 2574 | 5979 | 171 | contig510_16617337_c2_98.aa | 177 | 168 | 51.79% |
| contig678_32934_c2_23.aa | 2575 | 5980 | 148 | contig510_25605092_c2_97.aa | 154 | 148 | 70.95% |
| contig679_29336088_c3_38.aa | 2576 | 5981 | 113 | contig484_6117308_c3_59.aa | 113 | 113 | 100.00% |
| contig679_20894063_c3_37.aa | 2578 | 5983 | 223 | contig277_2421928_f1_3.aa | 274 | 99 | 32.32% |
| contig679_35367967_c2_34.aa | 2579 | 5984 | 310 | contig484_15703430_f3_29.aa | 310 | 310 | 100.00% |
| contig679_34172160_f2_11.aa | 2580 | 5985 | 251 | contig508_54688_c1_48.aa | 236 | 232 | 31.03% |
| contig679_32208317_f1_4.aa | 2581 | 5986 | 67 | contig484_10586391_c3_57.aa | 67 | 67 | 100.00% |
| contig679_7078537_c3_36.aa | 2583 | 5988 | 158 | contig314_36131455_f1_4.aa | 167 | 143 | 53.15% |
| contig679_22298217_c2_33.aa | 2584 | 5989 | 855 | contig484_26852307_c2_49.aa | 855 | 855 | 100.00% |
| contig679_24412802_c2_32.aa | 2585 | 5990 | 497 | contig428_24416067_c1_35.aa | 525 | 526 | 37.26% |
| contig679_35782882_c3_35.aa | 2586 | 5991 | 110 | contig484_4296961_f1_8.aa | 110 | 110 | 100.00% |
| contig679_25631642_c1_26.aa | 2587 | 5992 | 195 | contig428_24619030_c2_44.aa | 170 | 167 | 53.29% |
| contig679_35422180_c2_31.aa | 2588 | 5993 | 304 | contig428_36187800_c1_33.aa | 208 | 204 | 68.63% |
| contig679_4961592_c1_25.aa | 2589 | 5994 | 708 | contig276_31648428_c2_14.aa | 750 | 705 | 89.08% |
| contig679_35400018_c1_24.aa | 2590 | 5995 | 121 | contig276_7242205_c1_10.aa | 95 | 94 | 86.17% |
| contig68_12219530_f3_2.aa | 2591 | 5996 | 271 | contig352_25597839_c2_15.aa | 359 | 265 | 64.53% |
| contig680_30564025_f2_3.aa | 2592 | 5997 | 255 | contig484_6929813_c3_62.aa | 134 | 117 | 46.15% |
| contig680_4714093_f3_5.aa | 2594 | 5999 | 1747 | contig340_40932_c1_11.aa | 669 | 600 | 21.00% |
| contig681_25673905_f3_17.aa | 2595 | 6000 | 365 | contig245_12113530_f2_3.aa | 354 | 333 | 24.63% |
| contig681_24010937_f2_9.aa | 2596 | 6001 | 487 | contig435_4822197_c2_35.aa | 423 | 419 | 77.57% |
| contig681_24804662_f2_10.aa | 2597 | 6002 | 229 | contig435_16601592_c2_36.aa | 235 | 227 | 75.33% |
| contig681_1962561_f3_18.aa | 2598 | 6003 | 89 | contig485_10745286_f1_5.aa | 89 | 89 | 100.00% |
| contig681_31251093_f2_11.aa | 2599 | 6004 | 84 | contig485_29299087_f2_15.aa | 84 | 84 | 100.00% |
| contig681_20500075_f1_4.aa | 2600 | 6005 | 375 | contig435_24415701_c3_40.aa | 374 | 375 | 61.33% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig681_21571907_f2_13.aa | 2601 | 6006 | 523 | contig435_35947562_c1_30.aa | 528 | 512 | 81.45% |
| contig681_24667092_f3_20.aa | 2602 | 6007 | 382 | contig435_3417812_c2_37.aa | 383 | 382 | 64.92% |
| contig681_33724167_f2_14.aa | 2603 | 6008 | 60 | contig485_24022900_f2_16.aa | 60 | 60 | 100.00% |
| contig681_7033157_c2_39.aa | 2604 | 6009 | 561 | contig485_16214088_f3_27.aa | 561 | 561 | 100.00% |
| contig681_211_f1_6.aa | 2605 | 6010 | 223 | contig485_26695887_f2_11.aa | 201 | 185 | 35.68% |
| contig681_4726516_f2_15.aa | 2606 | 6011 | 406 | contig435_29863586_c2_38.aa | 305 | 303 | 85.48% |
| contig681_23985902_f3_21.aa | 2607 | 6012 | 215 | contig486_19691017_f3_24.aa | 215 | 215 | 100.00% |
| contig681_34414657_f2_16.aa | 2608 | 6013 | 237 | contig435_23673136_c2_39.aa | 244 | 235 | 74.47% |
| contig682_808587_c1_27.aa | 2614 | 6019 | 399 | contig377_2039178_c1_13.aa | 448 | 167 | 23.95% |
| contig682_33306556_c1_26.aa | 2617 | 6022 | 268 | contig486_30359425_f2_20.aa | 268 | 268 | 100.00% |
| contig682_23682963_c1_25.aa | 2619 | 6024 | 116 | contig486_34459816_c3_72.aa | 116 | 116 | 100.00% |
| contig682_2049068_c3_31.aa | 2620 | 6025 | 103 | contig486_14140681_c3_71.aa | 103 | 103 | 100.00% |
| contig682_4788941_f1_8.aa | 2621 | 6026 | 202 | contig476_4788941_c1_8.aa | 403 | 203 | 96.55% |
| contig683_31741033_f1_1.aa | 2622 | 6027 | 379 | contig398_34257805_f3_8.aa | 417 | 376 | 49.73% |
| contig683_24219442_f3_5.aa | 2623 | 6028 | 352 | contig398_1211592_f3_9.aa | 344 | 337 | 81.60% |
| contig683_12359450_f3_6.aa | 2624 | 6029 | 334 | contig398_14101593_f3_10.aa | 339 | 310 | 65.48% |
| contig683_834642_f3_7.aa | 2625 | 6030 | 305 | contig486_26214818_f3_36.aa | 305 | 305 | 100.00% |
| contig683_16829837_f2_3.aa | 2626 | 6031 | 485 | contig189_33239012_c1_5.aa | 321 | 299 | 42.81% |
| contig683_14547808_c3_18.aa | 2627 | 6032 | 245 | contig510_35370437_c3_121.aa | 230 | 229 | 41.92% |
| contig683_12707562_c1_12.aa | 2628 | 6033 | 120 | contig59_4728568_c1_2.aa | 105 | 95 | 29.47% |
| contig683_24886062_f3_8.aa | 2629 | 6034 | 346 | contig368_9948302_f3_12.aa | 340 | 350 | 32.29% |
| contig683_34172677_c3_16.aa | 2632 | 6037 | 174 | contig378_16851525_c2_14.aa | 188 | 164 | 98.17% |
| contig684_36423427_c1_30.aa | 2633 | 6038 | 386 | contig503_24640875_c1_78.aa | 228 | 232 | 28.02% |
| contig684_25582175_c1_29.aa | 2636 | 6041 | 748 | contig469_2985905_f1_4.aa | 258 | 179 | 27.93% |
| contig684_2869687_c1_28.aa | 2637 | 6042 | 306 | contig487_2930280_c3_59.aa | 338 | 82 | 51.22% |
| contig684_32656705_c3_38.aa | 2638 | 6043 | 1278 | contig469_2985905_f1_4.aa | 258 | 188 | 26.60% |
| contig684_4971041_c2_31.aa | 2640 | 6045 | 283 | contig305_14709818_f2_9.aa | 321 | 279 | 66.67% |
| contig685_24804700_f3_26.aa | 2642 | 6047 | 324 | contig203_30744010_c3_6.aa | 332 | 241 | 20.75% |
| contig685_29480061_c1_37.aa | 2643 | 6048 | 467 | contig466_29383441_c1_30.aa | 473 | 462 | 81.39% |
| contig685_24636465_c2_43.aa | 2644 | 6049 | 118 | contig466_15057813_c3_40.aa | 100 | 97 | 64.95% |
| contig685_17010800_c1_36.aa | 2645 | 6050 | 676 | contig466_33791088_c2_36.aa | 676 | 679 | 50.07% |
| contig685_4867338_c1_34.aa | 2647 | 6052 | 381 | contig503_26567250_c3_117.aa | 386 | 352 | 28.13% |
| contig685_23602181_c1_33.aa | 2648 | 6053 | 237 | contig497_16838576_f2_19.aa | 280 | 260 | 26.54% |
| contig685_4726393_c2_41.aa | 2649 | 6054 | 326 | contig398_34257805_f3_8.aa | 417 | 324 | 23.15% |
| contig685_25660302_c2_39.aa | 2651 | 6056 | 711 | contig510_19562658_c3_127.aa | 507 | 484 | 65.91% |
| contig685_26344125_c1_32.aa | 2652 | 6057 | 143 | contig295_23438588_c1_7.aa | 250 | 140 | 70.00% |
| contig686_6035151_f1_1.aa | 2653 | 6058 | 113 | contig455_35938380_f1_7.aa | 246 | 102 | 48.04% |
| contig686_25640700_c2_47.aa | 2654 | 6059 | 298 | contig412_24407832_c1_28.aa | 291 | 290 | 46.55% |
| contig686_34172760_f3_26.aa | 2656 | 6061 | 319 | contig274_35172062_c3_11.aa | 323 | 315 | 67.62% |
| contig686_395317_c3_54.aa | 2657 | 6062 | 307 | contig488_34183130_c3_52.aa | 307 | 307 | 100.00% |
| contig686_20442325_c3_53.aa | 2658 | 6063 | 233 | contig486_29314080_f3_25.aa | 267 | 233 | 60.09% |
| contig686_24484692_c1_40.aa | 2659 | 6064 | 171 | contig274_35352137_f2_4.aa | 173 | 164 | 64.63% |
| contig686_7277211_c3_52.aa | 2660 | 6065 | 241 | contig431_16824092_c2_29.aa | 241 | 241 | 68.05% |
| contig686_32228826_c2_46.aa | 2661 | 6066 | 332 | contig431_24010217_c1_25.aa | 303 | 297 | 59.93% |
| contig686_24400140_c1_39.aa | 2662 | 6067 | 237 | contig431_7085912_c3_37.aa | 226 | 224 | 69.20% |
| contig686_34062812_c3_51.aa | 2663 | 6068 | 110 | contig431_14254800_c1_24.aa | 109 | 100 | 84.00% |
| contig686_10742343_c1_38.aa | 2664 | 6069 | 103 | contig489_35992212_c3_47.aa | 103 | 103 | 100.00% |
| contig686_9800910_c1_37.aa | 2665 | 6070 | 166 | contig431_9816535_c3_32.aa | 167 | 166 | 61.45% |
| contig686_22381542_c2_45.aa | 2666 | 6071 | 367 | contig431_1041259_c1_22.aa | 270 | 262 | 82.44% |
| contig686_20714717_f1_7.aa | 2667 | 6072 | 259 | contig410_10735930_f3_9.aa | 271 | 254 | 66.14% |
| contig686_32228213_c1_36.aa | 2668 | 6073 | 174 | contig274_167702_f1_2.aa | 172 | 170 | 55.88% |
| contig686_24726713_c1_35.aa | 2669 | 6074 | 208 | contig489_30204550_c2_36.aa | 208 | 208 | 100.00% |
| contig686_16594063_c3_49.aa | 2670 | 6075 | 164 | contig489_4068750_c3_43.aa | 164 | 164 | 100.00% |
| contig686_34648325_f2_25.aa | 2673 | 6078 | 124 | contig191_23881274_c1_5.aa | 237 | 107 | 42.99% |
| contig687_22851577_f3_16.aa | 2677 | 6082 | 310 | contig321_32064597_c3_20.aa | 252 | 261 | 36.78% |
| contig687_19727318_f1_3.aa | 2679 | 6084 | 182 | contig279_34177136_f1_1.aa | 178 | 173 | 86.71% |
| contig687_10947807_f2_10.aa | 2680 | 6085 | 428 | contig279_34178805_f1_7.aa | 312 | 309 | 85.76% |
| contig687_24863750_f3_17.aa | 2681 | 6086 | 324 | contig279_4492943_f3_8.aa | 312 | 308 | 86.69% |
| contig687_19549091_f2_11.aa | 2682 | 6087 | 114 | contig489_7042212_c1_24.aa | 114 | 114 | 100.00% |
| contig687_33239716_f1_4.aa | 2684 | 6089 | 371 | contig279_22478462_f2_5.aa | 351 | 333 | 87.09% |
| contig687_35312816_f3_18.aa | 2685 | 6090 | 1074 | contig436_35585387_f1_1.aa | 835 | 835 | 82.64% |
| contig687_5100342_f2_12.aa | 2686 | 6091 | 86 | contig49_26740942_c2_6.aa | 86 | 86 | 100.00% |
| contig687_3923143_f1_7.aa | 2687 | 6092 | 493 | contig436_36214637_f2_9.aa | 316 | 309 | 86.73% |
| contig687_33886588_f2_13.aa | 2688 | 6093 | 184 | contig436_21681582_f1_2.aa | 239 | 181 | 69.06% |
| contig687_24019703_f3_20.aa | 2689 | 6094 | 257 | contig436_24648381_f1_3.aa | 211 | 205 | 82.93% |
| contig687_25490628_f2_14.aa | 2690 | 6095 | 126 | contig436_24804700_f1_5.aa | 234 | 106 | 53.77% |
| contig687_4381581_f1_21.aa | 2691 | 6096 | 123 | contig436_24804700_f1_5.aa | 234 | 108 | 33.33% |
| contig688_24485950_c1_35.aa | 2699 | 6104 | 326 | contig490_24787526_c3_94.aa | 326 | 326 | 100.00% |
| contig688_36542177_c3_50.aa | 2701 | 6106 | 673 | contig490_24431587_f1_5.aa | 673 | 673 | 100.00% |
| contig688_32062811_c1_33.aa | 2702 | 6107 | 65 | contig490_4737783_c2_70.aa | 65 | 65 | 100.00% |
| contig688_36147285_c1_31.aa | 2704 | 6109 | 828 | contig490_15704807_f1_6.aa | 828 | 828 | 100.00% |
| contig688_11773436_f3_24.aa | 2705 | 6110 | 522 | contig490_34589063_f3_35.aa | 522 | 522 | 100.00% |
| contig688_6855067_f2_11.aa | 2706 | 6111 | 155 | contig339_24641250_f1_3.aa | 144 | 124 | 33.07% |
| contig688_22273377_f3_25.aa | 2707 | 6112 | 543 | contig490_24395078_c1_49.aa | 543 | 543 | 100.00% |
| contig688_25865687_f3_26.aa | 2708 | 6113 | 388 | contig506_20709525_f3_50.aa | 391 | 392 | 26.28% |
| contig688_26183467_c3_44.aa | 2710 | 6115 | 325 | contig116_29802163_c1_1.aa | 202 | 201 | 26.87% |
| contig689_19720380_c1_17.aa | 2716 | 6121 | 517 | contig375_7304712_c1_19.aa | 428 | 479 | 46.14% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig689_21521951_f1_2.aa | 2717 | 6122 | 1154 | contig248_20759716_c2_13.aa | 628 | 624 | 62.66% |
| contig689_24415930_f1_3.aa | 2718 | 6123 | 477 | contig310_4949052_f1_1.aa | 446 | 445 | 49.66% |
| contig689_19932192_f3_10.aa | 2719 | 6124 | 659 | contig310_9800706_f3_7.aa | 392 | 363 | 72.45% |
| contig689_10678250_f3_11.aa | 2720 | 6125 | 315 | contig310_29900200_f2_6.aa | 325 | 284 | 65.49% |
| contig689_24037942_c1_13.aa | 2721 | 6126 | 105 | contig491_29876292_c3_90.aa | 105 | 105 | 100.00% |
| contig689_23635927_f1_4.aa | 2722 | 6127 | 89 | contig491_4094061_f2_17.aa | 89 | 89 | 100.00% |
| contig69_19925182_c3_3.aa | 2724 | 6129 | 257 | contig414_26854677_c2_25.aa | 240 | 225 | 20.89% |
| contig690_23694503_c2_23.aa | 2730 | 6135 | 133 | contig491_35430443_c2_70.aa | 133 | 133 | 100.00% |
| contig690_16881881_f2_9.aa | 2731 | 6136 | 82 | contig491_4300040_c3_86.aa | 82 | 82 | 100.00% |
| contig691_33632952_f1_1.aa | 2732 | 6137 | 117 | contig491_5085837_c1_57.aa | 117 | 117 | 100.00% |
| contig691_24432937_f2_9.aa | 2733 | 6138 | 238 | contig491_35187941_c3_85.aa | 238 | 238 | 100.00% |
| contig691_24804838_f2_10.aa | 2734 | 6139 | 128 | contig471_24804838_f3_15.aa | 128 | 128 | 96.09% |
| contig691_3948453_f2_11.aa | 2735 | 6140 | 62 | contig491_22477250_c2_69.aa | 62 | 62 | 100.00% |
| contig691_26620455_f2_12.aa | 2736 | 6141 | 109 | contig491_36227013_c3_84.aa | 109 | 109 | 100.00% |
| contig691_4688778_f1_2.aa | 2738 | 6143 | 122 | contig491_31442937_c2_68.aa | 122 | 122 | 100.00% |
| contig691_35585832_f1_17.aa | 2739 | 6144 | 278 | contig471_4688778_f1_3.aa | 629 | 264 | 95.83% |
| contig691_14959452_f2_13.aa | 2741 | 6146 | 100 | contig491_34175307_c2_67.aa | 100 | 100 | 100.00% |
| contig691_36501967_f1_3.aa | 2742 | 6147 | 285 | contig491_16803437_c3_82.aa | 285 | 285 | 100.00% |
| contig691_10723761_f3_18.aa | 2743 | 6148 | 178 | contig491_24616302_c3_81.aa | 178 | 178 | 100.00% |
| contig691_984536_f3_19.aa | 2744 | 6149 | 402 | contig471_984536_f1_6.aa | 389 | 378 | 95.77% |
| contig691_4120650_c1_25.aa | 2745 | 6150 | 437 | contig498_30480333_f1_30.aa | 446 | 438 | 62.33% |
| contig691_21500087_f1_5.aa | 2747 | 6152 | 86 | contig465_16197587_c3_42.aa | 90 | 68 | 95.59% |
| contig691_14117943_f1_6.aa | 2748 | 6153 | 171 | contig465_14336718_c3_43.aa | 171 | 168 | 87.50% |
| contig691_31916062_f2_15.aa | 2751 | 6156 | 135 | contig465_204717_c2_39.aa | 133 | 129 | 97.67% |
| contig691_12275257_f3_20.aa | 2752 | 6157 | 816 | contig465_12275257_c3_44.aa | 816 | 816 | 97.43% |
| contig691_33605083_f1_8.aa | 2753 | 6158 | 195 | contig465_33605083_c1_35.aa | 736 | 188 | 96.28% |
| contig692_6648582_f2_6.aa | 2754 | 6159 | 666 | contig475_20511092_c1_26.aa | 682 | 665 | 60.60% |
| contig692_25400338_f3_11.aa | 2755 | 6160 | 145 | contig475_36142192_c2_36.aa | 152 | 142 | 54.23% |
| contig692_13922561_f1_2.aa | 2756 | 6161 | 676 | contig475_2148910_c1_30.aa | 631 | 632 | 74.05% |
| contig692_283412_f3_14.aa | 2757 | 6162 | 161 | contig475_31454025_c3_45.aa | 196 | 151 | 78.81% |
| contig692_23633442_f2_8.aa | 2758 | 6163 | 400 | contig475_24495443_c3_46.aa | 387 | 388 | 75.00% |
| contig692_10187936_c3_42.aa | 2759 | 6164 | 216 | contig491_23992067_c2_61.aa | 216 | 216 | 100.00% |
| contig692_4422093_c3_41.aa | 2760 | 6165 | 215 | contig364_34646938_f1_2.aa | 349 | 213 | 19.72% |
| contig692_5083588_f1_4.aa | 2762 | 6167 | 239 | contig505_24648552_f2_18.aa | 266 | 229 | 39.74% |
| contig692_23562827_f3_15.aa | 2763 | 6168 | 409 | contig379_22063441_f2_8.aa | 471 | 306 | 23.20% |
| contig692_30736568_c2_26.aa | 2764 | 6169 | 241 | contig379_3947165_c3_35.aa | 237 | 235 | 45.11% |
| contig692_962800_c3_37.aa | 2765 | 6170 | 506 | contig379_24740936_c1_19.aa | 512 | 485 | 78.97% |
| contig693_19558192_f3_8.aa | 2766 | 6171 | 506 | contig430_15056577_f2_6.aa | 510 | 502 | 71.32% |
| contig693_24642808_f2_3.aa | 2767 | 6172 | 234 | contig464_24870942_f1_1.aa | 223 | 215 | 30.70% |
| contig693_24486582_c1_19.aa | 2769 | 6174 | 282 | contig412_9455_c1_20.aa | 263 | 110 | 30.91% |
| contig693_31305215_c2_24.aa | 2770 | 6175 | 631 | contig369_10972787_f3_9.aa | 578 | 579 | 22.28% |
| contig693_32462951_c1_15.aa | 2772 | 6177 | 523 | contig505_4144000_f2_21.aa | 527 | 502 | 26.89% |
| contig694_4105463_c3_51.aa | 2776 | 6181 | 331 | contig465_36210963_c3_46.aa | 309 | 318 | 23.59% |
| contig694_24415925_c2_46.aa | 2779 | 6184 | 243 | contig508_54688_c1_48.aa | 236 | 254 | 25.98% |
| contig694_24410662_c2_45.aa | 2780 | 6185 | 669 | contig508_26852187_c3_75.aa | 702 | 669 | 24.37% |
| contig694_4470642_c2_44.aa | 2783 | 6188 | 439 | contig427_25587817_f1_8.aa | 405 | 396 | 31.06% |
| contig694_4886328_c1_35.aa | 2784 | 6189 | 318 | contig493_4870462_c2_34.aa | 318 | 318 | 100.00% |
| contig694_34181686_c2_42.aa | 2787 | 6192 | 390 | contig471_35188262_f2_9.aa | 352 | 222 | 36.49% |
| contig694_5117677_c1_33.aa | 2790 | 6195 | 289 | contig493_21673127_c1_25.aa | 289 | 289 | 100.00% |
| contig694_24507875_c1_32.aa | 2791 | 6196 | 294 | contig494_24484390_c1_23.aa | 294 | 294 | 100.00% |
| contig694_24299078_c2_39.aa | 2792 | 6197 | 275 | contig494_13867202_c2_30.aa | 275 | 275 | 100.00% |
| contig694_31447212_c1_31.aa | 2793 | 6198 | 290 | contig494_395130_c3_38.aa | 290 | 290 | 100.00% |
| contig695_34570375_c3_54.aa | 2795 | 6200 | 234 | contig510_10190844_c2_92.aa | 114 | 102 | 56.86% |
| contig695_1040932_c1_37.aa | 2796 | 6201 | 261 | contig341_33469050_f2_5.aa | 248 | 239 | 56.49% |
| contig695_6728378_f1_3.aa | 2797 | 6202 | 203 | contig341_39818_c2_19.aa | 206 | 201 | 65.67% |
| contig695_24410928_f3_25.aa | 2798 | 6203 | 258 | contig494_2049068_c2_29.aa | 258 | 258 | 100.00% |
| contig695_633336_c3_50.aa | 2800 | 6205 | 296 | contig416_22150426_c2_30.aa | 282 | 272 | 44.12% |
| contig695_9804838_c2_41.aa | 2801 | 6206 | 267 | contig509_29307838_c1_75.aa | 269 | 252 | 30.16% |
| contig695_980443_c2_40.aa | 2802 | 6207 | 312 | contig509_21619816_c3_110.aa | 173 | 154 | 33.77% |
| contig695_24117887_f2_17.aa | 2803 | 6208 | 240 | contig450_2834687_c2_21.aa | 262 | 234 | 28.21% |
| contig695_26603568_c3_48.aa | 2805 | 6210 | 391 | contig492_23557812_c3_45.aa | 412 | 383 | 39.43% |
| contig695_578386_f2_20.aa | 2806 | 6211 | 232 | contig494_24260902_c3_36.aa | 232 | 232 | 100.00% |
| contig695_34105302_c2_38.aa | 2808 | 6213 | 231 | contig492_9875217_c1_28.aa | 644 | 138 | 29.71% |
| contig696_24806678_f3_15.aa | 2809 | 6214 | 276 | contig226_20510953_c3_12.aa | 272 | 273 | 78.02% |
| contig696_26835938_f2_7.aa | 2810 | 6215 | 915 | contig494_10585375_f1_6.aa | 915 | 915 | 100.00% |
| contig696_35989192_f2_8.aa | 2812 | 6217 | 582 | contig495_11113582_f1_1.aa | 582 | 582 | 100.00% |
| contig696_34642662_c1_28.aa | 2813 | 6218 | 251 | contig423_23859827_f3_13.aa | 228 | 187 | 27.81% |
| contig696_24396916_c3_55.aa | 2814 | 6219 | 357 | contig495_24431552_c3_75.aa | 357 | 357 | 100.00% |
| contig696_26366325_f1_2.aa | 2816 | 6221 | 70 | contig495_9945936_f1_5.aa | 70 | 70 | 100.00% |
| contig696_6854813_f3_21.aa | 2817 | 6222 | 377 | contig443_15895263_c1_12.aa | 234 | 200 | 22.50% |
| contig696_26756562_f2_12.aa | 2818 | 6223 | 125 | contig495_24625702_c3_73.aa | 125 | 125 | 100.00% |
| contig696_6929825_f3_22.aa | 2820 | 6225 | 178 | contig495_29492212_f2_19.aa | 178 | 178 | 100.00% |
| contig696_31798377_f2_14.aa | 2821 | 6226 | 519 | contig358_26776700_c1_17.aa | 434 | 166 | 25.90% |
| contig696_20947200_f3_23.aa | 2822 | 6227 | 857 | contig495_15791087_f1_9.aa | 857 | 857 | 100.00% |
| contig696_34648536_f1_4.aa | 2823 | 6228 | 471 | contig255_23626253_f3_5.aa | 973 | 435 | 36.32% |
| contig696_23837591_f1_5.aa | 2824 | 6229 | 400 | contig503_867338_f3_61.aa | 550 | 351 | 25.07% |
| contig697_16837715_c3_58.aa | 2825 | 6230 | 585 | contig495_14741253_c3_66.aa | 585 | 585 | 100.00% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig697__1230342__c2__47.aa | 2826 | 6231 | 151 | contig503__24487812__c1__73.aa | 153 | 147 | 53.74% |
| contig697__16211012__c3__56.aa | 2828 | 6233 | 178 | contig388__6837782__f2__10.aa | 145 | 117 | 30.77% |
| contig697__650203__c1__39.aa | 2829 | 6234 | 139 | contig495__7240812__f3__33.aa | 118 | 118 | 100.00% |
| contig697__585836__c1__38.aa | 2830 | 6235 | 269 | contig495__16517552__f2__23.aa | 269 | 269 | 100.00% |
| contig697__34432875__c1__37.aa | 2831 | 6236 | 336 | contig219__24414207__c1__6.aa | 334 | 331 | 54.68% |
| contig697__22477302__c1__36.aa | 2832 | 6237 | 251 | contig496__29339680__f3__17.aa | 251 | 251 | 100.00% |
| contig697__31952__c2__44.aa | 2833 | 6238 | 66 | contig496__29505317__c1__31.aa | 66 | 66 | 100.00% |
| contig697__1042337__c2__43.aa | 2834 | 6239 | 1070 | contig496__1058562__c1__30.aa | 1070 | 1070 | 100.00% |
| contig697__1366557__f3__26.aa | 2836 | 6241 | 362 | contig448__24797258__c3__60.aa | 369 | 349 | 46.13% |
| contig697__19926463__f1__5.aa | 2837 | 6242 | 72 | contig423__23625127__f3__12.aa | 83 | 55 | 43.64% |
| contig697__19661592__f1__6.aa | 2838 | 6243 | 216 | contig205__3948338__f3__4.aa | 283 | 182 | 43.41% |
| contig697__34432837__c3__53.aa | 2839 | 6244 | 100 | contig496__3204549__c2__33.aa | 100 | 100 | 100.00% |
| contig697__21907902__c3__51.aa | 2841 | 6246 | 221 | contig497__4726588__f3__21.aa | 221 | 221 | 100.00% |
| contig697__24298917__c3__50.aa | 2842 | 6247 | 459 | contig497__24259677__f2__7.aa | 459 | 459 | 100.00% |
| contig697__36142200__c1__33.aa | 2843 | 6248 | 450 | contig497__2381931__f2__8.aa | 161 | 161 | 100.00% |
| contig697__5367887__c1__32.aa | 2844 | 6249 | 558 | contig66__26375453__f1__1.aa | 237 | 232 | 42.24% |
| contig697__661556__c3__48.aa | 2847 | 6252 | 539 | contig497__7086593__f2__10.aa | 539 | 539 | 100.00% |
| contig697__978427__c1__31.aa | 2848 | 6253 | 142 | contig338__26757837__f1__3.aa | 151 | 142 | 30.99% |
| contig697__19628761__c2__40.aa | 2849 | 6254 | 325 | contig297__9949218__f3__5.aa | 532 | 231 | 67.97% |
| contig698__36140907__c3__79.aa | 2850 | 6255 | 159 | contig497__1344180__f2__12.aa | 159 | 159 | 100.00% |
| contig698__2110751__c1__54.aa | 2851 | 6256 | 190 | contig474__1408437__f2__14.aa | 471 | 156 | 25.00% |
| contig698__36128451__c3__78.aa | 2853 | 6258 | 303 | contig497__34179702__c3__15.aa | 303 | 303 | 100.00% |
| contig698__26776510__c3__77.aa | 2854 | 6259 | 98 | contig474__24429838__f2__13.aa | 103 | 103 | 28.16% |
| contig698__34430427__c3__76.aa | 2855 | 6260 | 157 | contig474__970287__f3__12.aa | 166 | 156 | 27.56% |
| contig698__2164038__c1__53.aa | 2856 | 6261 | 313 | contig497__78125__f3__28.aa | 313 | 313 | 100.00% |
| contig698__35625212__c3__75.aa | 2857 | 6262 | 60 | contig497__165887__c1__37.aa | 60 | 60 | 100.00% |
| contig698__208562__c2__63.aa | 2858 | 6263 | 414 | contig414__34273437__c1__18.aa | 418 | 382 | 99.22% |
| contig698__14540887__c3__72.aa | 2859 | 6264 | 195 | contig507__7226411__c1__66.aa | 635 | 105 | 37.14% |
| contig698__21525463__c3__71.aa | 2860 | 6265 | 160 | contig497__24427137__f3__30.aa | 160 | 160 | 100.00% |
| contig698__23988452__f3__37.aa | 2861 | 6266 | 194 | contig502__23988452__f1__6.aa | 319 | 159 | 98.74% |
| contig698__34183201__f1__4.aa | 2862 | 6267 | 96 | contig502__23988452__f1__6.aa | 319 | 94 | 94.68% |
| contig698__32073575__c3__70.aa | 2863 | 6268 | 130 | contig465__204717__c2__39.aa | 133 | 99 | 32.32% |
| contig698__34069068__c2__62.aa | 2864 | 6269 | 102 | contig465__16197587__c3__42.aa | 90 | 61 | 26.23% |
| contig698__7035717__c2__61.aa | 2865 | 6270 | 285 | contig498__4312818__f3__13.aa | 285 | 285 | 100.00% |
| contig698__21526068__c3__69.aa | 2866 | 6271 | 330 | contig332__34421880__c1__12.aa | 331 | 326 | 32.52% |
| contig698__14665930__c3__67.aa | 2868 | 6273 | 398 | contig498__36501653__c1__36.aa | 398 | 398 | 100.00% |
| contig698__10937__c2__57.aa | 2869 | 6274 | 251 | contig498__24664812__c2__43.aa | 251 | 251 | 100.00% |
| contig698__24315762__f1__43.aa | 2870 | 6275 | 183 | contig498__13867802__c3__52.aa | 183 | 183 | 100.00% |
| contig698__4781325__f2__23.aa | 2871 | 6276 | 151 | contig498__26775051__f2__9.aa | 151 | 151 | 100.00% |
| contig698__15667875__f2__24.aa | 2872 | 6277 | 391 | contig498__19726555__c2__42.aa | 391 | 391 | 100.00% |
| contig698__22460816__f3__46.aa | 2876 | 6281 | 149 | contig454__22460816__f2__6.aa | 199 | 149 | 94.63% |
| contig698__24409642__f2__25.aa | 2877 | 6282 | 280 | contig498__33634712__c3__48.aa | 280 | 280 | 100.00% |
| contig698__24221913__c3__65.aa | 2878 | 6283 | 302 | contig498__23437882__f3__28.aa | 302 | 302 | 100.00% |
| contig699__11910468__f3__16.aa | 2879 | 6284 | 259 | contig487__4491683__c1__35.aa | 335 | 217 | 34.10% |
| contig699__26851457__f1__1.aa | 2880 | 6285 | 341 | contig487__22463937__f3__31.aa | 304 | 308 | 39.94% |
| contig699__10001262__f3__17.aa | 2881 | 6286 | 600 | contig487__977217__c2__45.aa | 506 | 534 | 22.66% |
| contig699__26774053__f2__8.aa | 2882 | 6287 | 217 | contig463__24252188__c3__48.aa | 215 | 207 | 25.12% |
| contig699__35994030__f1__5.aa | 2887 | 6292 | 322 | contig460__25586092__f3__12.aa | 292 | 288 | 30.90% |
| contig699__2074092__c2__33.aa | 2889 | 6294 | 125 | contig499__22697590__f2__21.aa | 125 | 125 | 100.00% |
| contig699__26367786__f2__13.aa | 2890 | 6295 | 485 | contig401__24007952__c2__26.aa | 478 | 475 | 77.26% |
| contig699__6135938__f2__14.aa | 2891 | 6296 | 355 | contig466__23469667__c3__39.aa | 352 | 325 | 38.77% |
| contig699__26370887__f2__15.aa | 2893 | 6298 | 172 | contig441__162818__f2__8.aa | 155 | 147 | 64.63% |
| contig699__103825__c1__21.aa | 2894 | 6299 | 390 | contig499__1712__c1__61.aa | 390 | 390 | 100.00% |
| contig699__5362937__c3__42.aa | 2895 | 6300 | 410 | contig499__34065626__c1__60.aa | 410 | 410 | 100.00% |
| contig7__28384812__c1__3.aa | 2896 | 6301 | 264 | contig6__6070338__f2__1.aa | 192 | 190 | 74.21% |
| contig70__12118765__f3__1.aa | 2897 | 6302 | 261 | contig291__36203136__c1__18.aa | 483 | 248 | 91.13% |
| contig700__23546952__c3__53.aa | 2898 | 6303 | 223 | contig360__25585900__f1__3.aa | 247 | 159 | 25.79% |
| contig700__14539202__c3__52.aa | 2899 | 6304 | 77 | contig499__196890__c3__91.aa | 77 | 77 | 100.00% |
| contig700__4798461__c1__39.aa | 2900 | 6305 | 304 | contig456__34651428__c3__40.aa | 310 | 283 | 43.11% |
| contig700__7244802__c1__38.aa | 2902 | 6307 | 392 | contig499__24414160__c2__74.aa | 392 | 392 | 100.00% |
| contig700__20511093__c3__51.aa | 2903 | 6308 | 385 | contig492__23557812__c3__45.aa | 412 | 339 | 47.49% |
| contig700__34429700__c3__50.aa | 2904 | 6309 | 281 | contig499__36211556__c1__55.aa | 281 | 281 | 100.00% |
| contig700__24273437__f1__4.aa | 2906 | 6311 | 341 | contig219__24414207__c1__6.aa | 334 | 307 | 37.46% |
| contig700__24628217__f1__13.aa | 2907 | 6312 | 73 | contig219__24414207__c1__6.aa | 334 | 48 | 37.50% |
| contig700__13689692__c3__48.aa | 2909 | 6314 | 899 | contig499__20525062__c3__85.aa | 899 | 899 | 100.00% |
| contig700__16525213__c1__35.aa | 2910 | 6315 | 71 | contig499__26210313__c2__78.aa | 87 | 75 | 32.00% |
| contig700__5132812__c1__33.aa | 2911 | 6316 | 74 | contig500__11990877__f2__44.aa | 73 | 73 | 47.95% |
| contig700__35189213__c1__32.aa | 2913 | 6318 | 163 | contig500__26600027__f2__43.aa | 136 | 139 | 30.94% |
| contig700__195258__c3__46.aa | 2914 | 6319 | 62 | contig499__422550__c2__67.aa | 62 | 62 | 100.00% |
| contig700__2109385__c1__31.aa | 2915 | 6320 | 101 | contig499__35362890__c1__52.aa | 101 | 101 | 100.00% |
| contig700__35972785__c3__45.aa | 2916 | 6321 | 152 | contig5__7082011__f3__3.aa | 190 | 94 | 84.04% |
| contig700__24415925__c1__30.aa | 2917 | 6322 | 141 | contig50__995328__c2__5.aa | 141 | 141 | 100.00% |
| contig700__35737937__c1__29.aa | 2918 | 6323 | 88 | contig50__239653__f1__1.aa | 88 | 88 | 100.00% |
| contig700__13675828__c1__28.aa | 2919 | 6324 | 535 | contig50__22468765__c2__4.aa | 144 | 144 | 100.00% |
| contig701__4023910__f2__15.aa | 2920 | 6325 | 76 | contig332__24822318__f2__5.aa | 468 | 63 | 57.14% |
| contig701__26367958__c3__66.aa | 2924 | 6329 | 69 | contig500__24257628__c2__74.aa | 69 | 69 | 100.00% |
| contig701__13907687__c2__60.aa | 2925 | 6330 | 226 | contig500__25428212__c2__73.aa | 226 | 226 | 100.00% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig701_22460816_f1_6.aa | 2926 | 6331 | 400 | contig501_22460816_c2_51.aa | 400 | 400 | 100.00% |
| contig701_1376262_f1_7.aa | 2928 | 6333 | 257 | contig508_12760452_c1_47.aa | 77 | 75 | 36.00% |
| contig701_24789212_f1_9.aa | 2930 | 6335 | 591 | contig500_33259677_c2_70.aa | 591 | 591 | 100.00% |
| contig701_6843752_f2_21.aa | 2932 | 6337 | 158 | contig500_9804090_c1_64.aa | 158 | 158 | 100.00% |
| contig701_4695318_f1_10.aa | 2934 | 6339 | 136 | contig500_26600027_f2_43.aa | 136 | 136 | 100.00% |
| contig701_3945327_f2_23.aa | 2935 | 6340 | 73 | contig500_11990877_f2_44.aa | 73 | 73 | 100.00% |
| contig701_14570967_f1_11.aa | 2936 | 6341 | 112 | contig500_34381382_f2_45.aa | 112 | 112 | 100.00% |
| contig701_26620430_f3_35.aa | 2937 | 6342 | 71 | contig500_34172832_f1_21.aa | 71 | 71 | 100.00% |
| contig701_29297578_f1_12.aa | 2938 | 6343 | 65 | contig500_5268765_f2_46.aa | 65 | 65 | 100.00% |
| contig701_14237583_f3_36.aa | 2939 | 6344 | 133 | contig500_24417543_f2_47.aa | 164 | 45 | 93.33% |
| contig701_24412786_f1_13.aa | 2940 | 6345 | 135 | contig500_16875000_f2_48.aa | 135 | 135 | 100.00% |
| contig701_9960013_c1_41.aa | 2941 | 6346 | 438 | contig500_156588_c3_75.aa | 438 | 438 | 100.00% |
| contig701_22087811_f3_37.aa | 2944 | 6349 | 165 | contig501_9820452_c1_46.aa | 165 | 165 | 100.00% |
| contig701_4105452_f1_14.aa | 2945 | 6350 | 311 | contig501_24226417_c1_45.aa | 311 | 311 | 100.00% |
| contig702_24853530_f3_16.aa | 2947 | 6352 | 400 | contig501_22460816_c2_51.aa | 400 | 400 | 100.00% |
| contig702_26641562_f2_5.aa | 2948 | 6353 | 335 | contig501_5085937_c1_44.aa | 335 | 335 | 100.00% |
| contig702_24406251_f2_6.aa | 2949 | 6354 | 385 | contig501_34414057_c3_57.aa | 385 | 385 | 100.00% |
| contig702_2460941_f3_17.aa | 2950 | 6355 | 482 | contig501_29298437_c1_43.aa | 482 | 482 | 100.00% |
| contig702_34252126_f1_1.aa | 2951 | 6356 | 1073 | contig496_1058562_c1_30.aa | 1070 | 1066 | 62.01% |
| contig702_19615825_f2_8.aa | 2952 | 6357 | 405 | contig501_36377267_c3_56.aa | 405 | 405 | 100.00% |
| contig702_20508425_f2_9.aa | 2954 | 6359 | 383 | contig501_30117882_c1_41.aa | 383 | 383 | 100.00% |
| contig702_2228593_f2_10.aa | 2955 | 6360 | 346 | contig501_25667765_c2_50.aa | 346 | 346 | 100.00% |
| contig702_34195312_f3_19.aa | 2956 | 6361 | 268 | contig497_16838576_f2_19.aa | 280 | 282 | 35.46% |
| contig702_34649087_f3_20.aa | 2957 | 6362 | 315 | contig501_32680212_c3_54.aa | 315 | 315 | 100.00% |
| contig702_24648542_f2_11.aa | 2958 | 6363 | 235 | contig501_11016590_c1_39.aa | 235 | 235 | 100.00% |
| contig702_4414702_c2_41.aa | 2959 | 6364 | 618 | contig501_34258437_c3_53.aa | 618 | 618 | 100.00% |
| contig702_6038427_f2_12.aa | 2960 | 6365 | 97 | contig501_10000308_f3_35.aa | 97 | 97 | 100.00% |
| contig702_1203568_f3_22.aa | 2961 | 6366 | 263 | contig501_34178438_c2_48.aa | 263 | 263 | 100.00% |
| contig702_191590_c2_40.aa | 2962 | 6367 | 224 | contig501_14629183_c2_47.aa | 224 | 224 | 100.00% |
| contig703_10827_c1_43.aa | 2964 | 6369 | 187 | contig502_35417188_c3_62.aa | 187 | 187 | 100.00% |
| contig703_6814062_f3_24.aa | 2965 | 6370 | 395 | contig502_5914818_c3_61.aa | 395 | 395 | 100.00% |
| contig703_23439217_c1_42.aa | 2966 | 6371 | 63 | contig502_34178780_c1_46.aa | 63 | 63 | 100.00% |
| contig703_20510950_c2_52.aa | 2967 | 6372 | 390 | contig502_23446063_f1_2.aa | 390 | 390 | 100.00% |
| contig703_3167950_c3_58.aa | 2968 | 6373 | 329 | contig502_6640276_c1_44.aa | 329 | 329 | 100.00% |
| contig703_35367750_c2_51.aa | 2969 | 6374 | 472 | contig502_15118812_c2_50.aa | 472 | 472 | 100.00% |
| contig703_24495913_c3_56.aa | 2970 | 6375 | 140 | contig416_23633250_c3_37.aa | 141 | 135 | 56.30% |
| contig703_36383275_c2_50.aa | 2972 | 6377 | 291 | contig416_22150426_c2_30.aa | 282 | 277 | 88.09% |
| contig703_34642186_c1_40.aa | 2973 | 6378 | 306 | contig509_29307838_c1_75.aa | 269 | 253 | 31.23% |
| contig703_34189067_c3_54.aa | 2974 | 6379 | 327 | contig502_34432800_c1_41.aa | 327 | 327 | 100.00% |
| contig703_667177_c1_39.aa | 2975 | 6380 | 356 | contig502_14884712_c3_56.aa | 356 | 356 | 100.00% |
| contig703_4586700_c2_49.aa | 2976 | 6381 | 238 | contig502_24489717_c2_49.aa | 238 | 238 | 100.00% |
| contig703_14875066_c2_48.aa | 2977 | 6382 | 376 | contig502_30078752_c3_55.aa | 235 | 235 | 100.00% |
| contig703_1383550_c1_38.aa | 2978 | 6383 | 395 | contig450_24508502_c2_22.aa | 394 | 396 | 62.37% |
| contig703_7297306_c2_47.aa | 2979 | 6384 | 251 | contig450_2834687_c2_21.aa | 262 | 246 | 65.45% |
| contig703_4898328_c1_37.aa | 2980 | 6385 | 303 | contig458_4774083_c2_39.aa | 303 | 295 | 66.44% |
| contig703_6917837_c3_53.aa | 2981 | 6386 | 319 | contig502_23988452_f1_6.aa | 319 | 319 | 100.00% |
| contig703_22460816_f3_36.aa | 2982 | 6387 | 165 | contig378_22460816_c3_16.aa | 226 | 167 | 92.81% |
| contig704_22839077_c2_41.aa | 2983 | 6388 | 159 | contig364_21614376_f3_13.aa | 248 | 123 | 32.52% |
| contig704_4095963_c2_40.aa | 2984 | 6389 | 278 | contig502_23938376_c2_48.aa | 129 | 88 | 36.36% |
| contig704_4120450_c1_33.aa | 2986 | 6391 | 646 | contig503_35448508_c2_103.aa | 646 | 646 | 100.00% |
| contig704_26694212_c3_53.aa | 2987 | 6392 | 330 | contig502_24429677_c3_57.aa | 333 | 323 | 52.94% |
| contig704_13886590_c2_38.aa | 2989 | 6394 | 356 | contig502_14884712_c3_56.aa | 356 | 348 | 58.05% |
| contig704_26437926_c3_51.aa | 2990 | 6395 | 216 | contig502_24489717_c2_49.aa | 238 | 208 | 74.52% |
| contig704_2734702_f3_19.aa | 2991 | 6396 | 201 | contig476_4788941_c1_8.aa | 403 | 183 | 98.91% |
| contig704_12691037_f1_4.aa | 2992 | 6397 | 223 | contig215_45562718_c2_8.aa | 234 | 219 | 99.54% |
| contig704_788377_c1_32.aa | 2993 | 6398 | 125 | contig408_6071062_c1_41.aa | 235 | 108 | 39.82% |
| contig704_12681625_c1_31.aa | 2994 | 6399 | 324 | contig503_34182187_f3_53.aa | 324 | 324 | 100.00% |
| contig704_26353427_c2_37.aa | 2995 | 6400 | 306 | contig503_4960088_c2_98.aa | 306 | 306 | 100.00% |
| contig704_20742090_c3_49.aa | 2996 | 6401 | 209 | contig454_4100078_f1_3.aa | 206 | 205 | 41.46% |
| contig704_4195137_c3_47.aa | 2998 | 6403 | 356 | contig503_16406327_c2_96.aa | 356 | 356 | 100.00% |
| contig704_16448437_c1_30.aa | 2999 | 6404 | 455 | contig503_4884662_c3_119.aa | 455 | 455 | 100.00% |
| contig704_13808206_c2_36.aa | 3000 | 6405 | 81 | contig467_13808206_f2_6.aa | 81 | 81 | 100.00% |
| contig704_16448437_f1_5.aa | 3002 | 6407 | 234 | contig306_16448437_c3_30.aa | 234 | 234 | 100.00% |
| contig704_13808206_c2_15.aa | 3003 | 6408 | 81 | contig467_13808206_f2_6.aa | 81 | 81 | 100.00% |
| contig704_34015677_f3_22.aa | 3004 | 6409 | 234 | contig329_24223428_f2_6.aa | 233 | 212 | 28.30% |
| contig704_14632840_f1_7.aa | 3005 | 6410 | 197 | contig503_24640875_c1_78.aa | 228 | 63 | 98.41% |
| contig704_16447186_f3_23.aa | 3006 | 6411 | 64 | contig503_20703156_f3_59.aa | 64 | 64 | 100.00% |
| contig704_24805312_f3_24.aa | 3007 | 6412 | 345 | contig503_3385062_c3_116.aa | 345 | 345 | 100.00% |
| contig704_36141037_c1_27.aa | 3008 | 6413 | 161 | contig503_26386088_c1_77.aa | 161 | 161 | 100.00% |
| contig704_15117276_f1_8.aa | 3010 | 6415 | 205 | contig489_6923462_c3_45.aa | 447 | 195 | 56.92% |
| contig704_13130311_f2_17.aa | 3011 | 6416 | 478 | contig503_34178266_f3_62.aa | 478 | 478 | 100.00% |
| contig704_24806561_f2_18.aa | 3012 | 6417 | 119 | contig503_24487812_c1_73.aa | 153 | 61 | 81.97% |
| contig705_33400927_c2_34.aa | 3013 | 6418 | 285 | contig503_34195932_c3_111.aa | 285 | 285 | 100.00% |
| contig705_30274012_c3_45.aa | 3014 | 6419 | 214 | contig503_36210900_c3_110.aa | 214 | 214 | 100.00% |
| contig705_15818_f3_16.aa | 3015 | 6420 | 322 | contig488_6839077_c2_47.aa | 341 | 195 | 28.72% |
| contig705_35744063_c3_42.aa | 3016 | 6421 | 451 | contig346_34064067_c1_21.aa | 443 | 450 | 74.89% |
| contig705_10598452_c2_33.aa | 3017 | 6422 | 515 | contig503_24879712_c1_72.aa | 515 | 515 | 100.00% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig705_34038288_c3_40.aa | 3018 | 6423 | 179 | contig346_24649187_c2_22.aa | 177 | 164 | 53.66% |
| contig705_6539077_c3_39.aa | 3019 | 6424 | 929 | contig346_11726593_c1_18.aa | 769 | 725 | 50.90% |
| contig705_667202_c1_27.aa | 3021 | 6426 | 499 | contig439_34274062_c2_27.aa | 480 | 479 | 24.64% |
| contig705_21542337_c3_36.aa | 3022 | 6427 | 1456 | contig292_4114041_c2_21.aa | 589 | 583 | 82.16% |
| contig706_4694063_c2_50.aa | 3023 | 6428 | 137 | contig266_12890943_c1_5.aa | 408 | 128 | 47.66% |
| contig706_2942202_c1_40.aa | 3024 | 6429 | 287 | contig504_26423152_f1_1.aa | 319 | 197 | 100.00% |
| contig706_3133325_c2_49.aa | 3025 | 6430 | 310 | contig504_23931503_f2_8.aa | 63 | 63 | 100.00% |
| contig706_33317042_c3_64.aa | 3026 | 6431 | 81 | contig504_9875327_f3_16.aa | 81 | 81 | 100.00% |
| contig706_4891943_c1_39.aa | 3027 | 6432 | 228 | contig504_4099077_f3_17.aa | 228 | 228 | 100.00% |
| contig706_29328415_f1_3.aa | 3028 | 6433 | 297 | contig499_55443_f3_45.aa | 274 | 259 | 26.26% |
| contig706_24426577_f3_22.aa | 3030 | 6435 | 61 | contig504_32213278_f1_10.aa | 61 | 61 | 100.00% |
| contig706_4788941_c2_46.aa | 3031 | 6436 | 432 | contig476_4788941_c1_8.aa | 403 | 350 | 99.43% |
| contig706_1461502_f1_5.aa | 3034 | 6439 | 276 | contig504_16593760_c1_25.aa | 305 | 138 | 96.38% |
| contig706_34585751_f3_24.aa | 3036 | 6441 | 740 | contig275_10289713_f1_1.aa | 661 | 245 | 20.41% |
| contig706_22447281_c1_33.aa | 3038 | 6443 | 129 | contig504_23835902_c2_41.aa | 129 | 129 | 100.00% |
| contig706_650277_c3_58.aa | 3039 | 6444 | 78 | contig507_22070443_c1_64.aa | 708 | 68 | 51.47% |
| contig706_26042092_c3_57.aa | 3040 | 6445 | 288 | contig507_1071067_c2_75.aa | 227 | 227 | 88.55% |
| contig706_23476713_c3_54.aa | 3042 | 6447 | 167 | contig499_1055442_c3_86.aa | 174 | 159 | 47.80% |
| contig706_34062932_c3_53.aa | 3043 | 6448 | 171 | contig499_5129627_c1_54.aa | 168 | 169 | 39.05% |
| contig706_32042318_f1_8.aa | 3044 | 6449 | 315 | contig362_15819827_c3_27.aa | 291 | 291 | 84.54% |
| contig706_34475067_f2_21.aa | 3045 | 6450 | 76 | contig504_23988452_c3_54.aa | 76 | 76 | 100.00% |
| contig707_26256507_c2_69.aa | 3046 | 6451 | 312 | contig504_2931500_f1_7.aa | 312 | 312 | 100.00% |
| contig707_30366567_c2_68.aa | 3047 | 6452 | 313 | contig505_21681508_f3_28.aa | 313 | 313 | 100.00% |
| contig707_36148562_c3_80.aa | 3049 | 6454 | 115 | contig505_34564202_f3_9.aa | 115 | 115 | 100.00% |
| contig707_4820393_c1_54.aa | 3051 | 6456 | 317 | contig398_14101593_f3_10.aa | 339 | 314 | 51.27% |
| contig707_1252250_c1_53.aa | 3052 | 6457 | 428 | contig279_4492943_f3_8.aa | 312 | 181 | 30.39% |
| contig707_35714457_c2_65.aa | 3053 | 6458 | 734 | contig505_24620461_c1_50.aa | 734 | 734 | 100.00% |
| contig707_3907812_c1_52.aa | 3054 | 6459 | 266 | contig505_24648552_f2_18.aa | 266 | 266 | 100.00% |
| contig707_1985077_c3_76.aa | 3056 | 6461 | 457 | contig279_24423588_f3_9.aa | 430 | 447 | 27.52% |
| contig707_6929677_c1_50.aa | 3057 | 6462 | 527 | contig505_4144000_f2_21.aa | 527 | 527 | 100.00% |
| contig707_397261_f1_11.aa | 3059 | 6464 | 93 | contig505_33400926_f3_34.aa | 93 | 93 | 100.00% |
| contig707_6663937_c3_74.aa | 3061 | 6466 | 349 | contig505_6726683_f3_35.aa | 349 | 349 | 100.00% |
| contig707_5257838_f1_12.aa | 3062 | 6467 | 103 | contig505_10631562_c1_43.aa | 103 | 103 | 100.00% |
| contig707_25556337_f1_13.aa | 3063 | 6468 | 115 | contig505_25554555_f2_24.aa | 115 | 115 | 100.00% |
| contig707_25588577_c1_47.aa | 3064 | 6469 | 150 | contig426_5117825_f3_19.aa | 194 | 150 | 56.00% |
| contig707_277062_f2_31.aa | 3065 | 6470 | 225 | contig505_23634677_f3_37.aa | 225 | 225 | 100.00% |
| contig708_4876563_f3_27.aa | 3066 | 6471 | 65 | contig505_31256_f2_26.aa | 65 | 65 | 100.00% |
| contig708_472176_c1_57.aa | 3068 | 6473 | 349 | contig505_22681287_f1_8.aa | 349 | 349 | 100.00% |
| contig708_961077_f2_16.aa | 3069 | 6474 | 439 | contig505_34579057_c2_59.aa | 439 | 439 | 100.00% |
| contig708_34027337_f3_30.aa | 3072 | 6477 | 174 | contig505_546887_f1_11.aa | 174 | 174 | 100.00% |
| contig708_20181552_f2_18.aa | 3073 | 6478 | 96 | contig506_424092_c3_100.aa | 96 | 96 | 100.00% |
| contig708_14181562_f1_4.aa | 3074 | 6479 | 1057 | contig506_23572187_c1_69.aa | 1057 | 1057 | 100.00% |
| contig708_25431537_f3_32.aa | 3075 | 6480 | 576 | contig503_12773907_c2_90.aa | 575 | 553 | 24.41% |
| contig708_7089217_f1_6.aa | 3077 | 6482 | 135 | contig506_13147061_c1_68.aa | 135 | 135 | 100.00% |
| contig708_12926525_f3_34.aa | 3080 | 6485 | 160 | contig506_30131580_c3_97.aa | 160 | 160 | 100.00% |
| contig708_25548437_f1_9.aa | 3083 | 6488 | 294 | contig506_4956578_c2_82.aa | 294 | 294 | 100.00% |
| contig708_24406442_f2_21.aa | 3085 | 6490 | 214 | contig506_4804676_c2_80.aa | 214 | 214 | 100.00% |
| contig708_16292813_f2_22.aa | 3086 | 6491 | 772 | contig506_23572187_c1_69.aa | 1057 | 694 | 19.74% |
| contig708_833338_f3_37.aa | 3088 | 6493 | 935 | contig300_24609767_c3_12.aa | 556 | 299 | 30.10% |
| contig708_26776691_f3_38.aa | 3089 | 6494 | 308 | contig300_33860452_c2_10.aa | 708 | 173 | 20.81% |
| contig708_25447182_f1_11.aa | 3090 | 6495 | 121 | contig506_34192513_c1_64.aa | 121 | 121 | 100.00% |
| contig708_16834792_f1_12.aa | 3092 | 6497 | 185 | contig349_14926253_c2_14.aa | 358 | 135 | 23.70% |
| contig708_26617927_f3_39.aa | 3093 | 6498 | 130 | contig339_24797800_c2_18.aa | 174 | 133 | 38.35% |
| contig708_26454842_f3_40.aa | 3094 | 6499 | 98 | contig506_6073412_f1_27.aa | 98 | 98 | 100.00% |
| contig708_29461467_f2_25.aa | 3095 | 6500 | 78 | contig506_2866682_c1_63.aa | 78 | 78 | 100.00% |
| contig708_22539000_f1_13.aa | 3096 | 6501 | 441 | contig490_24431587_f1_5.aa | 673 | 248 | 26.61% |
| contig708_22460816_f1_41.aa | 3097 | 6502 | 154 | contig454_22460816_f2_6.aa | 199 | 154 | 100.00% |
| contig708_16839056_f1_15.aa | 3098 | 6503 | 192 | contig506_35187941_c2_76.aa | 192 | 192 | 100.00% |
| contig709_1222561_f1_32.aa | 3099 | 6504 | 146 | contig506_36194062_c3_93.aa | 146 | 146 | 100.00% |
| contig709_197187_f2_13.aa | 3100 | 6505 | 85 | contig506_22836693_c1_61.aa | 85 | 85 | 100.00% |
| contig709_36210963_f2_14.aa | 3101 | 6506 | 124 | contig506_36220678_c3_92.aa | 124 | 124 | 100.00% |
| contig709_34195312_c1_68.aa | 3102 | 6507 | 123 | contig506_24817912_c1_60.aa | 123 | 123 | 100.00% |
| contig709_24103385_c3_111.aa | 3104 | 6509 | 80 | contig506_24319011_c2_75.aa | 80 | 80 | 100.00% |
| contig709_33447337_f2_15.aa | 3105 | 6510 | 100 | contig506_34175307_c1_59.aa | 100 | 100 | 100.00% |
| contig709_36338958_f3_36.aa | 3106 | 6511 | 230 | contig204_33447337_f2_2.aa | 184 | 130 | 100.00% |
| contig709_4460937_f2_16.aa | 3107 | 6512 | 225 | contig204_4460937_f1_1.aa | 213 | 181 | 99.45% |
| contig709_20707510_f3_38.aa | 3109 | 6514 | 168 | contig506_2037825_c1_57.aa | 168 | 168 | 100.00% |
| contig709_24225925_c3_107.aa | 3110 | 6515 | 114 | contig506_24431511_c3_89.aa | 114 | 114 | 100.00% |
| contig709_6696067_f3_39.aa | 3111 | 6516 | 241 | contig506_24319002_c3_88.aa | 241 | 241 | 100.00% |
| contig709_4726588_f3_40.aa | 3112 | 6517 | 221 | contig497_4726588_f3_21.aa | 221 | 221 | 100.00% |
| contig709_24259677_f2_18.aa | 3113 | 6518 | 405 | contig497_24259677_f2_7.aa | 459 | 405 | 98.77% |
| contig709_22947328_f3_41.aa | 3114 | 6519 | 264 | contig506_4976587_c1_53.aa | 264 | 264 | 100.00% |
| contig709_35585752_c1_63.aa | 3116 | 6521 | 294 | contig506_6922302_f1_13.aa | 150 | 150 | 100.00% |
| contig709_20352187_c2_84.aa | 3117 | 6522 | 181 | contig506_30567812_f1_14.aa | 181 | 181 | 100.00% |
| contig709_20370453_f1_4.aa | 3118 | 6523 | 221 | contig392_20370453_f2_12.aa | 221 | 221 | 100.00% |
| contig709_24821002_f3_43.aa | 3119 | 6524 | 191 | contig392_24821002_f1_5.aa | 231 | 136 | 97.06% |
| contig709_11077_f2_19.aa | 3120 | 6525 | 254 | contig494_2049068_c2_29.aa | 258 | 229 | 97.38% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig709__4148450__c3__100.aa | 3121 | 6526 | 340 | contig494__1957963__f2__9.aa | 393 | 335 | 94.63% |
| contig709__395130__f1__5.aa | 3122 | 6527 | 103 | contig507__32553167__f1__1.aa | 103 | 103 | 100.00% |
| contig709__13867202__f3__44.aa | 3123 | 6528 | 185 | contig507__585000__c2__84.aa | 185 | 185 | 100.00% |
| contig709__24484390__f2__21.aa | 3124 | 6529 | 238 | contig507__25429640__c1__73.aa | 238 | 238 | 100.00% |
| contig709__4719843__f2__22.aa | 3125 | 6530 | 135 | contig375__1415782__c3__22.aa | 90 | 85 | 92.94% |
| contig709__24860913__c1__57.aa | 3126 | 6531 | 89 | contig507__24406387__f2__37.aa | 304 | 75 | 36.00% |
| contig709__16593760__c2__80.aa | 3127 | 6532 | 305 | contig504__16593760__c1__25.aa | 305 | 305 | 99.02% |
| contig709__24489176__c3__97.aa | 3128 | 6533 | 150 | contig507__4428777__f1__3.aa | 89 | 89 | 100.00% |
| contig709__23438762__f3__46.aa | 3129 | 6534 | 102 | contig343__23438762__f3__3.aa | 102 | 102 | 95.10% |
| contig709__2381306__f3__47.aa | 3130 | 6535 | 312 | contig507__4414077__c1__71.aa | 312 | 312 | 100.00% |
| contig709__9791677__f2__24.aa | 3131 | 6536 | 433 | contig470__35744062__f3__19.aa | 487 | 419 | 39.14% |
| contig709__33984711__f3__48.aa | 3132 | 6537 | 60 | contig470__35744062__f3__19.aa | 487 | 55 | 50.91% |
| contig709__817842__f2__27.aa | 3134 | 6539 | 138 | contig413__12116083__c1__17.aa | 156 | 125 | 28.80% |
| contig709__24422182__f1__8.aa | 3135 | 6540 | 1067 | contig507__24476592__c2__82.aa | 1067 | 1067 | 100.00% |
| contig709__4101702__f1__10.aa | 3137 | 6542 | 392 | contig339__36135262__f3__10.aa | 414 | 376 | 26.06% |
| contig709__4727262__f3__49.aa | 3138 | 6543 | 204 | contig507__22926693__c1__67.aa | 204 | 204 | 100.00% |
| contig709__25469025__f2__29.aa | 3139 | 6544 | 635 | contig507__7226411__c1__66.aa | 635 | 635 | 100.00% |
| contig709__4721883__c3__90.aa | 3141 | 6546 | 273 | contig507__24406387__f2__37.aa | 304 | 144 | 87.50% |
| contig709__34651556__c2__74.aa | 3142 | 6547 | 136 | contig322__24273303__c2__22.aa | 309 | 139 | 25.90% |
| contig709__33785837__f2__31.aa | 3144 | 6549 | 81 | contig467__13808206__f2__6.aa | 81 | 81 | 100.00% |
| contig71__25507180__f2__2.aa | 3145 | 6550 | 151 | contig507__4195137__f3__54.aa | 151 | 151 | 100.00% |
| contig710__10346942__c3__21.aa | 3148 | 6553 | 82 | contig217__31908561__f1__1.aa | 64 | 23 | 82.61% |
| contig710__627181__f3__14.aa | 3149 | 6554 | 177 | contig507__5117775__f1__19.aa | 177 | 177 | 100.00% |
| contig710__26678587__c3__20.aa | 3150 | 6555 | 192 | contig504__26678587__f1__2.aa | 123 | 123 | 100.00% |
| contig710__23723842__c3__19.aa | 3151 | 6556 | 88 | contig507__11925763__f3__58.aa | 88 | 88 | 100.00% |
| contig711__6464751__c1__35.aa | 3152 | 6557 | 468 | contig490__24431587__f1__5.aa | 673 | 295 | 55.93% |
| contig711__22460816__c1__34.aa | 3153 | 6558 | 143 | contig507__24354550__c3__85.aa | 143 | 143 | 100.00% |
| contig711__26376277__c1__33.aa | 3154 | 6559 | 238 | contig507__16448437__f1__17.aa | 234 | 231 | 48.92% |
| contig711__24487812__c1__32.aa | 3157 | 6562 | 198 | contig508__7063140__c3__82.aa | 142 | 142 | 100.00% |
| contig711__3957818__c2__37.aa | 3159 | 6564 | 283 | contig508__26751552__c3__81.aa | 97 | 97 | 100.00% |
| contig711__34407587__c3__41.aa | 3160 | 6565 | 361 | contig508__19933518__c2__72.aa | 361 | 361 | 100.00% |
| contig711__25470661__f1__5.aa | 3162 | 6567 | 219 | contig508__24495902__c3__79.aa | 219 | 219 | 100.00% |
| contig711__34430450__c3__39.aa | 3163 | 6568 | 405 | contig508__4886590__c3__78.aa | 405 | 405 | 100.00% |
| contig711__11915936__c1__27.aa | 3164 | 6569 | 676 | contig508__1207576__c1__57.aa | 676 | 676 | 100.00% |
| contig711__24422127__c1__26.aa | 3165 | 6570 | 127 | contig508__23988587__c1__55.aa | 127 | 127 | 100.00% |
| contig711__6270288__c2__36.aa | 3166 | 6571 | 795 | contig508__25677312__c1__54.aa | 795 | 795 | 100.00% |
| contig712__7228468__c3__59.aa | 3168 | 6573 | 72 | contig508__5314377__f1__7.aa | 72 | 72 | 100.00% |
| contig712__23682952__c3__58.aa | 3170 | 6575 | 108 | contig508__36131432__c3__76.aa | 108 | 108 | 100.00% |
| contig712__23712837__c2__50.aa | 3171 | 6576 | 81 | contig508__15666066__c1__53.aa | 81 | 81 | 100.00% |
| contig712__22693817__c1__41.aa | 3172 | 6577 | 161 | contig508__34192187__c2__68.aa | 161 | 161 | 100.00% |
| contig712__34063750__c1__39.aa | 3174 | 6579 | 256 | contig508__14511592__c1__51.aa | 256 | 256 | 100.00% |
| contig712__31848465__c1__38.aa | 3178 | 6583 | 306 | contig377__2039178__c1__13.aa | 448 | 322 | 25.16% |
| contig712__22384540__c2__47.aa | 3180 | 6585 | 75 | contig508__6132812__c3__74.aa | 75 | 75 | 100.00% |
| contig712__15057803__c1__37.aa | 3181 | 6586 | 77 | contig508__12760452__c1__47.aa | 77 | 77 | 100.00% |
| contig712__21681535__c3__54.aa | 3183 | 6588 | 114 | contig508__24415936__c2__65.aa | 114 | 114 | 100.00% |
| contig712__84687__c2__44.aa | 3184 | 6589 | 99 | contig508__5112701__f1__13.aa | 72 | 72 | 100.00% |
| contig712__32600186__c1__35.aa | 3185 | 6590 | 928 | contig426__132843__c3__44.aa | 1196 | 878 | 24.26% |
| contig713__24406568__c1__53.aa | 3188 | 6593 | 372 | contig474__22546908__f1__2.aa | 333 | 228 | 25.88% |
| contig713__31656562__f3__19.aa | 3189 | 6594 | 454 | contig509__24860083__c2__106.aa | 454 | 454 | 100.00% |
| contig713__14492943__f3__20.aa | 3190 | 6595 | 227 | contig509__4884637__c1__86.aa | 227 | 227 | 100.00% |
| contig713__3164143__f2__10.aa | 3192 | 6597 | 65 | contig509__2000005__f2__24.aa | 65 | 65 | 100.00% |
| contig713__4121087__f2__12.aa | 3194 | 6599 | 514 | contig509__19691003__f1__5.aa | 514 | 514 | 100.00% |
| contig713__24805302__c1__45.aa | 3195 | 6600 | 238 | contig353__24219187__c1__13.aa | 237 | 213 | 63.38% |
| contig713__33470268__f3__25.aa | 3196 | 6601 | 306 | contig458__10393837__c3__42.aa | 355 | 297 | 79.80% |
| contig713__10008588__f1__26.aa | 3197 | 6602 | 194 | contig260__34641878__c3__28.aa | 194 | 193 | 33.16% |
| contig713__16797338__f3__28.aa | 3199 | 6604 | 174 | contig439__24336088__c1__19.aa | 189 | 173 | 67.05% |
| contig713__23712782__f1__2.aa | 3200 | 6605 | 417 | contig509__31410067__c1__82.aa | 417 | 417 | 100.00% |
| contig713__14667342__f3__29.aa | 3201 | 6606 | 615 | contig509__23625625__c1__81.aa | 615 | 615 | 100.00% |
| contig713__4879561__f1__30.aa | 3202 | 6607 | 90 | contig509__25408415__c2__100.aa | 90 | 90 | 100.00% |
| contig713__33620807__f2__16.aa | 3203 | 6608 | 204 | contig509__30080327__c3__115.aa | 204 | 204 | 100.00% |
| contig713__36572877__c2__65.aa | 3205 | 6610 | 378 | contig498__19726555__c2__42.aa | 391 | 226 | 26.11% |
| contig713__24484681__c3__83.aa | 3206 | 6611 | 356 | contig509__13837813__c2__98.aa | 356 | 356 | 100.00% |
| contig713__976512__f3__32.aa | 3207 | 6612 | 2054 | contig490__36589056__f3__41.aa | 290 | 263 | 37.64% |
| contig713__26766942__f1__5.aa | 3208 | 6613 | 309 | contig429__24431567__c1__33.aa | 303 | 298 | 51.01% |
| contig713__30275432__f1__6.aa | 3209 | 6614 | 502 | contig372__24883387__c3__26.aa | 561 | 507 | 24.06% |
| contig714__29584838__c3__142.aa | 3214 | 6619 | 269 | contig509__29307838__c1__75.aa | 269 | 269 | 100.00% |
| contig714__4691018__c3__141.aa | 3215 | 6620 | 1052 | contig506__23572187__c1__69.aa | 1057 | 1001 | 24.38% |
| contig714__19666567__c2__116.aa | 3218 | 6623 | 80 | contig509__25552318__f1__16.aa | 80 | 80 | 100.00% |
| contig714__26384703__c1__97.aa | 3220 | 6625 | 608 | contig509__29406567__f1__19.aa | 608 | 608 | 100.00% |
| contig714__161517__c1__94.aa | 3224 | 6629 | 122 | contig509__1205302__c2__91.aa | 152 | 30 | 60.00% |
| contig714__995450__c2__113.aa | 3225 | 6630 | 352 | contig509__23625427__f1__20.aa | 382 | 333 | 36.04% |
| contig714__26604062__c2__112.aa | 3226 | 6631 | 288 | contig51__30336687__f3__2.aa | 288 | 288 | 100.00% |
| contig714__4397536__c1__93.aa | 3227 | 6632 | 66 | contig51__910030__f1__1.aa | 66 | 66 | 100.00% |
| contig714__24611575__c2__110.aa | 3234 | 6639 | 459 | contig496__1058562__c1__30.aa | 1070 | 459 | 24.40% |
| contig714__33536__c2__109.aa | 3235 | 6640 | 619 | contig510__23928337__c1__88.aa | 619 | 619 | 100.00% |
| contig714__3010911__c1__84.aa | 3236 | 6641 | 509 | contig510__260942__c3__123.aa | 509 | 509 | 100.00% |
| contig714__4875063__c2__106.aa | 3243 | 6648 | 157 | contig510__20085062__c3__120.aa | 157 | 157 | 100.00% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig714__26853587__c3__128.aa | 3244 | 6649 | 80 | contig510__34425463__f1__15.aa | 89 | 89 | 100.00% |
| contig714__6924217__c3__127.aa | 3245 | 6650 | 497 | contig510__24801555__c2__105.aa | 497 | 497 | 100.00% |
| contig714__24353437__c2__105.aa | 3247 | 6652 | 605 | contig510__34110032__c3__116.aa | 605 | 605 | 100.00% |
| contig714__36132911__c3__126.aa | 3250 | 6655 | 555 | contig510__22844077__c1__84.aa | 555 | 555 | 100.00% |
| contig714__25628216__c2__103.aa | 3253 | 6658 | 79 | contig510__24508562__c2__99.aa | 79 | 79 | 100.00% |
| contig714__15807063__c3__123.aa | 3254 | 6659 | 153 | contig510__24303552__c1__82.aa | 153 | 153 | 100.00% |
| contig714__34042963__c2__102.aa | 3255 | 6660 | 255 | contig510__33788280__c1__81.aa | 255 | 255 | 100.00% |
| contig714__20119062__c3__122.aa | 3256 | 6661 | 118 | contig506__36220678__c3__92.aa | 124 | 98 | 26.53% |
| contig714__26461577__c3__121.aa | 3257 | 6662 | 76 | contig224__12925307__f2__3.aa | 123 | 48 | 39.58% |
| contig714__23442842__f1__21.aa | 3258 | 6663 | 124 | contig339__6150437__f1__2.aa | 128 | 125 | 31.20% |
| contig714__34257902__f1__22.aa | 3260 | 6665 | 210 | contig510__25584688__c1__79.aa | 210 | 210 | 100.00% |
| contig714__24253878__f3__75.aa | 3261 | 6666 | 412 | contig491__24228463__f2__28.aa | 383 | 414 | 29.23% |
| contig715__884505__f2__13.aa | 3263 | 6668 | 152 | contig416__33238500__c3__31.aa | 151 | 149 | 99.33% |
| contig715__5113757__c1__58.aa | 3264 | 6669 | 438 | contig510__29301505__c2__95.aa | 438 | 438 | 100.00% |
| contig715__22853150__f3__27.aa | 3265 | 6670 | 1306 | contig428__24416067__c1__35.aa | 525 | 143 | 25.87% |
| contig715__23678287__f3__29.aa | 3270 | 6675 | 114 | contig510__10190844__c2__92.aa | 114 | 114 | 100.00% |
| contig715__4408338__f2__16.aa | 3273 | 6678 | 342 | contig511__23703840__c1__65.aa | 342 | 342 | 100.00% |
| contig715__34063750__f1__4.aa | 3274 | 6679 | 86 | contig511__22475327__c1__64.aa | 86 | 86 | 100.00% |
| contig715__22693817__f1__5.aa | 3276 | 6681 | 609 | contig511__20056587__c1__63.aa | 609 | 609 | 100.00% |
| contig715__6836062__f2__18.aa | 3277 | 6682 | 327 | contig465__36210963__c3__46.aa | 309 | 239 | 20.92% |
| contig715__23682952__f3__30.aa | 3278 | 6683 | 71 | contig511__37760__f1__2.aa | 71 | 71 | 100.00% |
| contig715__20939062__f2__19.aa | 3279 | 6684 | 90 | contig511__4110943__c3__94.aa | 90 | 90 | 100.00% |
| contig715__4726713__f2__20.aa | 3280 | 6685 | 165 | contig190__14726530__c1__9.aa | 177 | 172 | 66.28% |
| contig715__24410927__f2__21.aa | 3282 | 6687 | 155 | contig511__12270327__c2__83.aa | 155 | 155 | 100.00% |
| contig715__4882827__c3__32.aa | 3283 | 6688 | 106 | contig511__25417062__c3__93.aa | 106 | 106 | 100.00% |
| contig715__13877317__f1__9.aa | 3285 | 6690 | 304 | contig511__7236512__c2__81.aa | 304 | 304 | 100.00% |
| contig715__6270288__f2__23.aa | 3286 | 6691 | 216 | contig511__34562827__c1__61.aa | 216 | 216 | 100.00% |
| contig715__25676937__f2__24.aa | 3287 | 6692 | 384 | contig511__7244437__c2__80.aa | 384 | 384 | 100.00% |
| contig715__34430450__f1__10.aa | 3288 | 6693 | 656 | contig511__992937__c2__79.aa | 656 | 656 | 100.00% |
| contig715__14734687__f3__35.aa | 3290 | 6695 | 206 | contig511__5900252__c2__77.aa | 206 | 206 | 100.00% |
| contig715__1047187__f3__37.aa | 3292 | 6697 | 901 | contig511__34177133__c1__60.aa | 901 | 901 | 100.00% |
| contig715__34187752__f1__12.aa | 3294 | 6699 | 242 | contig511__26680342__c2__74.aa | 242 | 242 | 100.00% |
| contig716__24814793__f2__31.aa | 3296 | 6701 | 388 | contig409__34196061__c1__16.aa | 538 | 408 | 38.73% |
| contig716__34379002__f3__60.aa | 3297 | 6702 | 79 | contig511__36225387__c2__71.aa | 79 | 79 | 100.00% |
| contig716__7308311__f1__1.aa | 3298 | 6703 | 130 | contig511__4823751__c2__70.aa | 130 | 130 | 100.00% |
| contig716__13808206__f2__32.aa | 3300 | 6705 | 81 | contig467__13808206__f2__6.aa | 81 | 81 | 100.00% |
| contig716__20969002__c3__159.aa | 3301 | 6706 | 73 | contig467__19581552__c3__25.aa | 168 | 32 | 40.63% |
| contig716__2744553__c1__109.aa | 3302 | 6707 | 438 | contig511__6118762__c2__90.aa | 472 | 385 | 97.14% |
| contig716__165751__c3__158.aa | 3303 | 6708 | 260 | contig209__24027215__c3__12.aa | 89 | 50 | 40.00% |
| contig716__4876077__c3__157.aa | 3304 | 6709 | 264 | contig378__6673452__c1__11.aa | 479 | 263 | 24.34% |
| contig716__19534635__c1__108.aa | 3305 | 6710 | 86 | contig199__26015691__f2__2.aa | 205 | 76 | 35.53% |
| contig716__26445885__c3__156.aa | 3306 | 6711 | 108 | contig511__34118826__c3__88.aa | 108 | 108 | 100.00% |
| contig716__26258452__c1__107.aa | 3307 | 6712 | 149 | contig511__22687801__c3__87.aa | 149 | 149 | 100.00% |
| contig716__6917832__c2__135.aa | 3308 | 6713 | 249 | contig298__9804628__f3__13.aa | 212 | 171 | 25.15% |
| contig716__26756566__c1__106.aa | 3309 | 6714 | 102 | contig511__4026518__c1__55.aa | 102 | 102 | 100.00% |
| contig716__30745632__c2__134.aa | 3310 | 6715 | 79 | contig385__30745632__f3__8.aa | 78 | 78 | 97.44% |
| contig716__24885437__c1__105.aa | 3311 | 6716 | 291 | contig511__34175252__c2__67.aa | 291 | 291 | 100.00% |
| contig716__4069827__c3__155.aa | 3312 | 6717 | 68 | contig52__10739052__c1__3.aa | 68 | 68 | 100.00% |
| contig716__13947175__c2__133.aa | 3315 | 6720 | 231 | contig504__22147812__c3__55.aa | 239 | 217 | 94.93% |
| contig716__19812826__c2__132.aa | 3316 | 6721 | 215 | contig504__23835902__c2__41.aa | 129 | 121 | 90.08% |
| contig716__4540637__c3__151.aa | 3318 | 6723 | 99 | contig56__21675827__c3__3.aa | 99 | 99 | 100.00% |
| contig716__4902217__c2__131.aa | 3319 | 6724 | 192 | contig58__3126033__f2__3.aa | 192 | 192 | 100.00% |
| contig716__25603436__c3__150.aa | 3320 | 6725 | 78 | contig58__25470090__f2__4.aa | 78 | 77 | 100.00% |
| contig716__26367812__c1__102.aa | 3321 | 6726 | 120 | contig59__14093787__c3__3.aa | 120 | 120 | 100.00% |
| contig716__29929702__c2__129.aa | 3322 | 6727 | 105 | contig59__4728568__c1__2.aa | 105 | 105 | 100.00% |
| contig716__6015675__c1__100.aa | 3323 | 6728 | 192 | contig6__6070338__f2__1.aa | 192 | 192 | 100.00% |
| contig716__3907893__c2__128.aa | 3324 | 6729 | 86 | contig60__20595840__f3__1.aa | 86 | 85 | 100.00% |
| contig716__23848262__f2__46.aa | 3325 | 6730 | 176 | contig61__589126__c2__3.aa | 176 | 176 | 100.00% |
| contig716__11740677__c1__98.aa | 3326 | 6731 | 177 | contig62__33484632__c2__1.aa | 177 | 177 | 100.00% |
| contig716__5321062__c1__97.aa | 3327 | 6732 | 185 | contig63__26757937__c3__6.aa | 185 | 185 | 100.00% |
| contig716__34037817__c3__148.aa | 3328 | 6733 | 228 | contig482__26306562__c2__46.aa | 78 | 74 | 62.16% |
| contig716__24406566__c1__96.aa | 3330 | 6735 | 178 | contig65__1054667__c2__5.aa | 178 | 178 | 100.00% |
| contig716__24415628__c1__95.aa | 3331 | 6736 | 289 | contig66__26375453__f1__1.aa | 237 | 236 | 100.00% |
| contig716__16448437__c3__147.aa | 3332 | 6737 | 234 | contig306__16448437__c3__30.aa | 234 | 234 | 100.00% |
| contig716__13808206__c1__93.aa | 3333 | 6738 | 81 | contig467__13808206__f2__6.aa | 81 | 81 | 100.00% |
| contig716__7320437__c2__125.aa | 3334 | 6739 | 354 | contig489__6923462__c3__45.aa | 447 | 343 | 95.63% |
| contig716__3915955__c1__92.aa | 3335 | 6740 | 1467 | contig508__24408438__c3__77.aa | 710 | 279 | 23.66% |
| contig716__4788941__f2__56.aa | 3337 | 6742 | 403 | contig476__4788941__c1__8.aa | 403 | 403 | 100.00% |
| contig716__5370313__c1__90.aa | 3340 | 6745 | 194 | contig71__21491256__f2__1.aa | 194 | 194 | 100.00% |
| contig716__21647338__c2__120.aa | 3342 | 6747 | 158 | contig73__22000318__f3__1.aa | 158 | 158 | 100.00% |
| contig716__24241702__c2__119.aa | 3343 | 6748 | 76 | contig73__34193751__f3__2.aa | 76 | 76 | 100.00% |
| contig716__10819003__f2__116.aa | 3347 | 6752 | 356 | contig323__2912589__c3__32.aa | 342 | 151 | 27.82% |
| contig716__9961693__c1__88.aa | 3352 | 6757 | 97 | contig77__24392882__f1__1.aa | 97 | 97 | 100.00% |
| contig716__14656952__c2__112.aa | 3353 | 6758 | 102 | contig77__29959837__f3__5.aa | 102 | 102 | 100.00% |
| contig716__7204442__c2__111.aa | 3355 | 6760 | 182 | contig77__26837591__f1__2.aa | 131 | 131 | 100.00% |
| contig716__34271887__c1__86.aa | 3356 | 6761 | 330 | contig78__21542550__f1__1.aa | 330 | 330 | 100.00% |
| contig72__426099__c1__5.aa | 3357 | 6762 | 64 | contig57__26598125__c1__2.aa | 64 | 64 | 100.00% |

TABLE 3-continued

| E. faccalis ORF Name | ntSeqID | aaSeqID | Length | E. faccium ORF Name | Length | Overlap | Precent ID |
|---|---|---|---|---|---|---|---|
| contig72__7032011__f2__1.aa | 3358 | 6763 | 328 | contig79__5937635__c3__3.aa | 328 | 328 | 100.00% |
| contig73__25192__f2__1.aa | 3359 | 6764 | 234 | contig277__2421928__f1__3.aa | 274 | 236 | 63.14% |
| contig74__4883438__c2__5.aa | 3360 | 6765 | 82 | contig391__4898452__c1__21.aa | 206 | 36 | 63.89% |
| contig74__15787525__c2__4.aa | 3361 | 6766 | 274 | contig80__7078912__f1__1.aa | 274 | 274 | 100.00% |
| contig75__26067717__f3__1.aa | 3362 | 6767 | 183 | contig81__3322302__f3__2.aa | 183 | 183 | 100.00% |
| contig76__34273407__f1__3.aa | 3363 | 6768 | 91 | contig81__25571062__f1__1.aa | 91 | 91 | 100.00% |
| contig76__5406__c2__5.aa | 3364 | 6769 | 217 | contig82__23647842__f2__1.aa | 217 | 217 | 100.00% |
| contig77__31750785__f2__1.aa | 3366 | 6771 | 283 | contig83__15719142__f2__1.aa | 283 | 283 | 100.00% |
| contig78__1269680__f3__1.aa | 3367 | 6772 | 203 | contig165__13860131__c3__12.aa | 304 | 196 | 57.65% |
| contig8__4898461__f2__1.aa | 3369 | 6774 | 143 | contig466__33791088__c2__36.aa | 676 | 142 | 98.59% |
| contig80__23445462__f3__1.aa | 3370 | 6775 | 184 | contig41__14745905__f2__1.aa | 92 | 54 | 64.82% |
| contig81__31726407__c3__2.aa | 3371 | 6776 | 175 | contig268__24081436__f1__2.aa | 166 | 155 | 40.00% |
| contig82__14894567__f2__1.aa | 3372 | 6777 | 111 | contig86__23632211__f3__4.aa | 111 | 111 | 100.00% |
| contig83__24511017__c3__4.aa | 3373 | 6778 | 247 | contig87__13703181__c2__3.aa | 247 | 247 | 100.00% |
| contig84__20714557__c3__3.aa | 3376 | 6781 | 249 | contig434__25424012__f1__5.aa | 477 | 232 | 26.72% |
| contig85__5292176__f2__1.aa | 3378 | 6783 | 77 | contig89__35351531__f3__4.aa | 77 | 77 | 100.00% |
| contig86__34190928__f2__1.aa | 3379 | 6784 | 161 | contig9__34527343__f2__2.aa | 161 | 161 | 100.00% |
| contig87__4070275__c1__2.aa | 3382 | 6787 | 167 | contig119__29697217__c2__3.aa | 264 | 116 | 37.07% |
| contig88__781528__f2__4.aa | 3383 | 6788 | 256 | contig386__19796941__c1__5.aa | 135 | 133 | 78.95% |
| contig89__22322788__f2__1.aa | 3384 | 6789 | 206 | contig457__24000262__c2__28.aa | 255 | 203 | 65.52% |
| contig9__30724631__f1__1.aa | 3385 | 6790 | 229 | contig66__26375453__f1__1.aa | 237 | 214 | 71.96% |
| contig90__22011551__f2__2.aa | 3386 | 6791 | 219 | contig309__4899140__f2__6.aa | 227 | 153 | 71.90% |
| contig91__36443953__c1__4.aa | 3387 | 6792 | 257 | contig432__26360427__f2__10.aa | 814 | 224 | 54.46% |
| contig92__6273282__f2__1.aa | 3389 | 6794 | 243 | contig412__24407832__c1__28.aa | 291 | 243 | 44.86% |
| contig93__30359687__f2__1.aa | 3391 | 6796 | 71 | contig320__29584812__f2__7.aa | 318 | 69 | 60.87% |
| contig93__10548751__f3__2.aa | 3392 | 6797 | 210 | contig320__29584812__f2__7.aa | 318 | 189 | 61.38% |
| contig94__2931568__c1__1.aa | 3393 | 6798 | 218 | contig354__1077__f2__7.aa | 252 | 194 | 35.05% |
| contig95__11885082__f1__1.aa | 3394 | 6799 | 245 | contig96__23929703__c1__3.aa | 245 | 245 | 100.00% |
| contig95__34180342__f3__2.aa | 3395 | 6800 | 68 | contig443__24667250__c2__15.aa | 476 | 28 | 53.57% |
| contig97__30713280__f3__4.aa | 3397 | 6802 | 333 | contig98__12929663__c2__4.aa | 333 | 333 | 100.00% |
| contig97__20007188__c3__6.aa | 3398 | 6803 | 266 | contig99__11911092__f3__1.aa | 266 | 266 | 100.00% |
| contig98__976626__f2__2.aa | 3401 | 6806 | 188 | contig36__123620262__c1__17.aa | 275 | 187 | 25.13% |
| contig99__21759558__f1__1.aa | 3402 | 6807 | 108 | contig468__24687551__c2__43.aa | 209 | 88 | 36.36% |
| contig99__22460893__c2__4.aa | 3403 | 6808 | 142 | contig314__14252175__f3__8.aa | 137 | 105 | 35.24% |

SEQUENCE LISTING

The patent contains a lengthy "Sequence Listing" section. A copy of the "Sequence Listing" is available in electronic form from the USPTO web site (http://seqdata.uspto.gov/sequence.html?DocID=6617156B1). An electronic copy of the "Sequence Listing" will also be available from the USPTO upon request and payment of the fee set forth in 37 CFR 1.19(b)(3).

What is claimed is:

1. An isolated nucleic acid comprising a nucleotide sequence encoding an E. faecalis polypeptide selected from the group consisting of SEQ ID NO:5177, SEQ ID NO:4597, SEQ ID NO:6122, and SEQ ID NO:4420.

2. A recombinant expression vector comprising the nucleic acid of claim 1 operably linked to a transcription regulatory element.

3. A cell comprising a recombinant expression vector of claim 2.

4. A method for producing an E. faecalis polypeptide comprising culturing a cell of claim 3 under conditions that permit expression of the polypeptide.

5. An isolated nucleic acid comprising a nucleotide sequence selected from the group consisting of SEQ ID NO:1772, SEQ ID NO:2248, SEQ ID NO:93, SEQ ID NO:1192, SEQ ID NO:1645, SEQ ID NO:1773, SEQ ID NO:2717, SEQ ID NO:2917, and SEQ ID NO:1015.

6. A recombinant vector comprising the nucleic acid of claim 5.

7. A cell comprising the recombinant vector of claim 6.

8. An isolated nucleic acid comprising a nucleotide sequence which can be used to detect the presence of E. faecalis in a sample, wherein said nucleic acid shares at least 90% homology to a sequence selected from the group consisting of SEQ ID NO:93, SEQ ID NO:1645, SEQ ID NO:1773, SEQ ID NO:2917, and SEQ ID NO:1015.

9. A recombinant vector comprising the nucleic acid of claim 8.

10. A cell comprising the recombinant vector of claim 9.

11. An isolated nucleic acid comprising a nucleotide sequence which can be used to detect the presence of E. faecalis in a sample, wherein said nucleic acid shares at least 95% homology to a sequence selected from the group consisting of SEQ ID NO:93, SEQ ID NO:1645, SEQ ID NO:1773, SEQ ID NO:2917, and SEQ ID N:1015.

12. A recombinant vector comprising the nucleic acid of claim 11.

13. A cell comprising the recombinant vector of claim 12.

14. An isolated nucleic acid comprising SEQ ID NO:2594.

15. A recombinant vector comprising the nucleic acid of claim 14.

16. A cell comprising the recombinant vector of claim 15.

17. An isolated nucleic acid comprising a nucleotide sequence which can be used to detect the presence of *E. faecalis* in a sample, wherein said nucleic acid shares at least 95% homology to SEQ ID NO:2594.

18. A recombinant vector comprising the nucleic acid of claim 17.

19. A cell comprising the recombinant vector of claim 18.

* * * * *